US006184344B1

(12) United States Patent
Kent et al.

(10) Patent No.: US 6,184,344 B1
(45) Date of Patent: Feb. 6, 2001

(54) SYNTHESIS OF PROTEINS BY NATIVE CHEMICAL LIGATION

(75) Inventors: Stephen B. H. Kent, San Francisco, CA (US); Tom W. Muir, New York, NY (US); Philip E. Dawson, Solana Beach, CA (US)

(73) Assignee: The Scripps Research Institute, La Jolla, CA (US)

( * ) Notice: Under 35 U.S.C. 154(b), the term of this patent shall be extended for 0 days.

(21) Appl. No.: 08/945,997

(22) PCT Filed: May 4, 1995

(86) PCT No.: PCT/US95/05668

§ 371 Date: Feb. 12, 1998

§ 102(e) Date: Feb. 12, 1998

(87) PCT Pub. No.: WO96/34878

PCT Pub. Date: Nov. 7, 1996

(51) Int. Cl.[7] .............................. C07K 1/02; C07K 1/04

(52) U.S. Cl. .............................. 530/323; 530/334; 530/339

(58) Field of Search .............................. 558/253; 525/54.1, 525/54.11; 530/816, 323, 333, 334, 338, 339

(56) References Cited

U.S. PATENT DOCUMENTS 4,910,222 * 3/1990 Puricelli .............................. 514/513
5,399,501 * 3/1995 Pope et al. .............................. 436/532

OTHER PUBLICATIONS

Abbott et al, Intrahepatic Transport and Utilization . . . , PNAS USA, vol. 83, pp. 1246–1250, Mar. 1986.*

Canne et al, A General Method for the Synthesis of Thioester . . . , Tetrahedron Lett, vol. 36, No. 8 pp. 1217–1220, 1995.*

Schnolzer et al, Constructing Proteins by Dovetailing . . . Science, vol. 256, pp. 221–225, Apr. 10, 1992.*

Baca, et al., "Chemical Ligation of Cysteine–Containing Peptides: Synthesis of a 22 kDa Tethered Dimer of HIV–1 Protease", *J. Am. Chem. Soc. 117:* 1881–1887 (1995).

Canne, et al., "Total Chemical Synthesis of a Unique Transcription Factor–Related Protein: cMyc–Max", *J. Am. Chem. Soc. 117:* 2998–3007 (1995).

Clark–Lewis, et al., "Chemical Synthesis, Purification, and Characterization of Two Inflammatory Proteins, Neutrophil Activating Peptide 1 (Interleukin–8) and Neutrophil Activating Peptide 2", *Biochemistry 30:* 3128–3135 (1991).

Clark–Lewis, et al., "Structural Requirements for Interleukin–8 Function Identified by Design of Analogs and CXC Chemokine Hybrids", *The Journal of Biological Chemistry 269* (23): 16075–16081 (1994).

D'Andrea, et al., "A Mutation of the Common Receptor Subunit for Interleukin–3 (IL–3), Granulocyte–Macrophage Colony–Stimulating Factor, and IL–5 That Leads to Ligand Independence and Tumorigenicity", *Blood 83* (10): 2802–2808 (1994).

(List continued on next page.)

*Primary Examiner*—Jeffrey E Russel
(74) *Attorney, Agent, or Firm*—Donald G. Lewis

(57) ABSTRACT

Proteins of moderate size having native peptide backbones are produced by a method of native chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. The technique of native chemical ligation is employable for chemically synthesizing full length proteins.

7 Claims, 10 Drawing Sheets

OTHER PUBLICATIONS

Dawson, et al., "Synthesis of Proteins by Native Chemical Ligation", *Science 266:* 776–779 (1994).

Yamashiro, et al., "New segment synthesis of α–inhibin–92 by the acyl disulfide method", *Int. J. Peptide Protein Res. 31:* 322–334 (1988).

Schnölzer, et al., "In situ neutralization in Boc–chemistry solid phase peptide synthesis", *Int. J. Peptide Res. 40:* 180–193 (1992).

* cited by examiner

2

3

1

Analysis: Channel A

| Peak No. | Time | Type | Height(μV) | Area(μV-sec) | Area% |
|---|---|---|---|---|---|
| 1 | 1.506 | N1 | 3161 | 10542 | 0.194 |
| 2 | 1.603 | N2 | 9956 | 54777 | 1.011 |
| 3 | 2.230 | N3 | 1485 | 14875 | 0.274 |
| 4 | 2.833 | N | 5628 | 53493 | 0.987 |
| 5 | 10.276 | N1 | 10621 | 48495 | 0.895 |
| 6 | 10.416 | N2 | 177905 | 958119 | 17.689 |
| 7 | 11.310 | N | 27080 | 145916 | 2.693 |
| 8 | 12.186 | N1 | 5217 | 29312 | 0.541 |
| 9 | 12.376 | N2 | 2379 | 13576 | 0.250 |
| 10 | 12.546 | N3 | 127436 | 729096 | 13.460 |
| 11 | 13.076 | N | 2349 | 12443 | 0.229 |
| 12 | 13.466 | N1 | 369155 | 2324707 | 42.919 |

SYNTHESIS OF PROTEINS BY NATIVE CHEMICAL LIGATION

GOVERNMENT RIGHTS

The invention disclosed herein was supported in part by Grants Number R01 GM 48897 and P01 GM 48870 from the National Institutes of Health. The United States government may have certain rights to this invention.

FIELD OF INVENTION

The invention relates to methods and intermediates for chemically ligating two oligopeptides end to end with an amide bond. More particularly, the invention relates to methods and intermediates for chemically ligating oligopeptides wherein an unoxidized N-terminal cysteine of a first oligopeptide condenses with a C-terminal thioester of a second oligopeptide to form a β-aminothioester intermediate which spontaneously rearranges intramolecularly to form an amide bond and the ligation product.

BACKGROUND

Proteins may be synthesized chemically, ribosomally in a cell free system, or ribosomally within a cell. Advances in each of these areas have significantly improved access to many proteins but have also stimulated demand for yet further improvements.

Proteins owe their diverse properties to the precisely folded three dimensional structures of their polypeptide chains. The three dimensional structure of a protein determines its functional attributes. However, at present, it is difficult to predict and/or fully explain the biological properties of a protein from its three dimensional structure alone. A better understanding of how structure determines the biological properties of a protein can be achieved by systematically varying the covalent structure of the molecule and correlating the effects with the folded structure and biological function. Accordingly, there is an increased demand for enhanced synthetic techniques for synthesizing new proteins and protein analogs.

Techniques derived from recombinant DNA-based molecular biology can be employed to facilitate the expression of proteins in genetically engineered micro-organisms. The use of site-directed mutagenesis, as disclosed by M. Smith (*Angew. Chem. Int. Ed. Engl.* (1994): vol. 33, p 1214), enables the preparation of large numbers of modified proteins in useful amounts for systematic study, e.g., C. Eigenbrot and A. Kossiakoff, *Current Opinion in Biotechnology* (1992): vol. 3, p 333. The use of innovative approaches increases the range of amino acids that can be incorporated in expression systems and promises to significantly extend the utility of biosynthetic modification of the covalent structure of proteins. (C. J. Noren et al., *Science* (1989): vol. 244, p 182 (1989); J. A. Ellman et al., *Science* (1992): vol. 255, p 197.) However, there appear to be limitations inherent to the nature of ribosomal protein synthesis. (v. w. Cornish, et al., *Proc. Natl. Acad. Sci. USA* (1994): vol. 91, p 2910.)

Chemical synthesis of proteins has also contributed to the exploration of the relationship of protein structure to function. Stepwise solid phase synthesis has permitted the de novo preparation of small proteins. (T. W. Muir et al., *Curr. Opin. Biotech.* (1993): vol. 4, p 420.) There are also several examples of the use of stepwise solid phase synthesis of whole proteins to explore the molecular basis of biological function. (M. Miller, et al., *Science* (1989): vol. 246, p 1149; A. Wlodawer, et al., *Science* (1989): vol. 245, p 616; L. H.

Huang, et al., Biochemistry (1991): vol. 30, p 7402; and K. Rajarathnam, et al., *Science* (1994): vol. 264, p 90.)

Semi-synthesis through the conformationally-assisted religation of peptide fragments can also be employed, in special instances, to study of the structure/function relationship of proteins. (R. E. Offord, "Chemical Approaches to Protein Engineering", in *Protein Design and the Development of New therapeutics and Vaccines*, J. B. Hook, G. Poste, Eds., (Plenum Press, New York, 1990) pp. 253–282; C. J. A. Wallace, et al., J. *Biol. Chem.* (1992): vol. 267, p 3852. An important extension of the semisynthesis approach is the use of enzymatic ligation of cloned or synthetic peptide segments. (L. Abrahmsen, et al., *Biochemistry* (1991): vol. 30, p 4151; T. K. Chang, et al., *Proc. Natl. Acad. Sci. USA* (1994): in press.) Although the above methodologies have been successfully applied to the synthesis of proteins and protein analogs, T. W. Muir et al., report that there is a continued interest in the wider application of the tools of organic chemistry to the study of proteins *(Curr. Opin. Biotech.* (1993): vol. 4, p 420.)

Stephen Kent et al. recently introduced the chemical ligation of unprotected peptide segments as an improved route to the total synthesis of proteins. (M. Schnlzer, et al., *Science* (1992): vol., 3256, p 221.) Chemical ligation involves the chemoselective reaction of unprotected peptides to give a product with an unnatural backbone structure at the ligation site. Use of unprotected peptides circumvented the difficulties inherent to classical chemical synthesis, viz complex combinations of protecting groups that lead to limited solubility of many synthetic intermediates, e.g. K.

Akaji, et al., *Chem. Pharm. Bull.* (Tokyo) (1985): vol. 33, p 184. In contrast, the chemical ligation technique has allowed us to make good use of the ability to routinely make, purify, and characterize unprotected peptides 50 or more residues in length. Using optimized stepwise solid phase methods the preparation in good yield and high purity of peptides up to 60 residues is routine. In favorable cases, peptides of 80+ residues can be prepared. (M. Schnolzer, et al., *Int. J. Pept. Prot. Res.* (1992): vol. 40, p 180–193.)

The key aspect of the above approach to chemical ligation is the use of a chemoselective reaction to specifically and unambiguously join peptides by formation of an unnatural (i.e. non-peptide) backbone structure at the ligation site. It has permitted the facile preparation of a wide range of backbone-modified proteins, including analogues of protein domains, e.g., ligated 10F3, the integrin-binding module of fibronectin: 95 residues (M. Williams, et al., *J. Am. Chem. Soc.* (1994): in press.) The catalytic contribution of flap-substrate hydrogen bonds in HIV-1 protease has been elucidated by the chemical synthesis of a homodimer of 99 residue subunits of this protein by chemical ligation. (M. Baca, et al., *Proc. Natl. Acad. Sci. U.S.*, (1993): vol. 90, p 11638.) Chemical ligation has also proven to be useful for the routine, reproducible synthesis of large amounts of proteins in high purity with full biological activity (20). (R. C. deLisle Milton, et al., "Synthesis of Proteins by Chemical Ligation of Unprotected Peptide Segments: Mirror-Image Enzyme Molecules, D- & L-HIV Protease Analogs," in *Techniques in Protein Chemistry IV*, Academic Press, New York, pp. 257–267 (1992).)

Chemical ligation can also be employed for the straightforward production of protein-like molecules of unusual topology, e.g., four-helix bundle template-assembled synthetic protein (MW 6647 Da) (P. E. Dawson, et al., *J. Am. Chem. Soc.* (1993): vol. 115, p 7263); homogeneous multivalent artificial protein (MW 19,916 Da) (K. Rose, *J. Am. Chem. Soc.* (1994): vol. 3116, p 30); artificial neoprotein mimic of the cytoplasmic domains of a multichain integrin receptor (MW 14,194 Da) (T. W. Muir, et al., *Biochemistry*, (1994): vol. 33, pp 7701–7708; and peptide dendrimer (MW 24,205 Da) (C. Rao, et al., *J. Am. Chem. Soc.* (1994): vol. 116, p 6975. The range of proteins accessible by this technique is limited by the size of the synthetic peptide segments.

A useful extension would occur if one had direct synthetic access to native backbone polypeptide chains up to the size of typical protein domains. (A. L. Berman, et al., *Proc. Natl. Acad. Sci. USA* (1994): vol. 91, p 4044.) Chemical ligation would then be employed to string these domains together to explore the world of proteins in a general fashion.

A modular strategy for the total synthesis of proteins has been developed, based on the convergent chemical ligation of unprotected peptides has been disclosed by L. E. Canne, et al. (presented at the Annual Meeting of the Protein Society, San Diego, July 1994). Protein domains (modules) were prepared by chemical ligation of 50–70 residue segments; these domains were then stitched together to give the target protein. Mutually compatible ligation chemistries are required: intra-domain ligation should optimally yield a stable, peptide-like bond; inter-domain ligation will tolerate a wider variation of properties of the structure formed at the ligation site.

Straightforward total chemical synthesis of proteins represents the realization of an important objective of organic chemistry. It raises the exciting prospect of unrestricted variation of protein covalent structure made possible by general synthetic access, and will give new impetus to exploration of the structural basis of properties such as folding, stability, catalytic activity, binding, and biological action.

What is needed is a technique of native chemical ligation which combines the formation of a native peptide bond at the ligation site with the advantages of chemoselective reaction of unprotected peptides. This second generation ligation chemistry would significantly increase the size of native backbone polypeptides directly accessible by total chemical synthesis. It could be usefully applied to a wide range of synthetic targets, including proteins of moderate size, and it allows direct access to protein functional domains. Native chemical ligation is a foundation stone of a general modular approach to the total chemical synthesis of proteins. Furthermore, it is compatible with the use of both chemically synthesized peptides and peptide segments derived from other sources.

SUMMARY

One aspect of the invention is directed to a method of native chemical ligation. The method of native chemical ligation facilitates the chemical synthesis of proteins and large oligopeptide. The principle of 'native chemical ligation' is shown in FIG. 1. The first step is the chemoselective reaction of an unprotected synthetic peptide-α-thioester with another unprotected peptide segment containing an N-terminal Cys residue, to give a thioester-linked intermediate as the initial covalent product. Without change in the reaction conditions, this intermediate undergoes spontaneous, rapid intramolecular reaction to form a native peptide bond at the ligation site. The target full length polypeptide product is obtained in the desired final form without further manipulation. The general synthetic access provided by the method of native chemical ligation greatly expands the scope of variation of the covalent structure of the protein molecule.

One embodiment of the invention provides a method for ligating a first oligopeptide with a second oligopeptide end to end for producing an oligopeptide product. The first and second oligopeptides are admixed in a reaction solution including a catalytic thiol. The catalytic thiol may be an unconjugated mercaptan or a conjugated thiol. Preferred catalytic thiols include benzyl mercaptan, thiophenol, 1-thio-2-nitrophenol, 2-thio-benzoic acid, 2-thio-pyridine, 4-thio-2-pyridinecarboxylic acid, and 4-thio-2-nitropyridine. The first oligopeptide includes a C-terminal thioester. The second oligopeptide includes an N-terminal cysteine having an unoxidized sulfhydryl side chain. The unoxidized sulfhydryl side chain of the N-terminal cysteine is then condensed with the C-terminal thioester to produce an intermediate oligopeptide which links the first and second oligopeptides with a β-aminothioester bond. The β-aminothioester bond of the intermediate oligopeptide then undergoes an intramolecular rearrangement to produce the oligopeptide product which links the first and second oligopeptides with an amide bond.

Another aspect of the invention is directed to an oligopeptide intermediate which comprises a first oligopeptide segment having a C-terminal thioester, a second oligopeptide segment having a N-terminal cysteine, and a β-aminothioester linkage unit which links the C-terminal thioester and the N-terminal cysteine. The β-aminothioester linkage unit spontaneously rearranges intramolecularly to form an amide bond linking the first and second oligopeptides segments end to end.

Another aspect of the invention is directed to a method for producing an oligopeptide having a C-terminal thioester. The method admixes a resin having a linker with an unoxidized thiol with a Boc-amino acid succinimide ester under reaction conditions to produce a Boc-amino thioester-resin. An oligopeptide is then assembled onto the Boc-amino thioester-resin by stepwise solid phase peptide synthesis. When the oligopeptide is complete, the Boc-amino thioester-resin is cleaved with HS to produce an oligopeptide having a C-terminal thiol. The C-terminal thiol is then converted to an oligopeptide having a C-terminal thioester.

The oligopeptide thioester (α-COSR moiety) of FIG. 1 can be readily generated from a corresponding oligopeptide thiol (αCOSH) prepared by highly optimized stepwise SPPS on a thioester resin. The thioester resin was prepared by the method of L. E. Canne et al., *Tetrahedron Letters* (1995): vol. 36, pp. 1217–1220, incorporated herein by reference. The method of Canne employs the thioester resin disclosed by Blake and Yamashiro (J. Blake, *Int. J. Pept. Protein Res.* (1981): vol. 17, p 273; D. Yamashiro, et al., *Int. J. Pept. Protein Res.* (1988): vol. 31, p 322). Peptide products were cleaved, purified, and characterized by conventional methods. (M. Schnolzer, et al., *Int. J. Pept. Protein Res.*,(1992): vol. 40, pp 180–193.)

The Yamashiro methodology activates a thiocarboxyl group on a protected oligopeptide with diaryl disulfides to give acyl disulfides (Yamashiro et. al. *Int. J. Peptide Protein Res.* (1922): vol. 31, pp 322–334). These C-terminal-peptide-acyl-disulfides are highly reactive electrophilic intermediates which are attacked and subsequently coupled with an a-amino group on the N-terminus of a second peptide to form native peptide bonds. The reported coupling yields using 2,2'-dipyridyl disulfide as the activator of the thiocarboxyl group afford the desired α-IB-92 product in 45% yield. Overall yields based on the starting resin for a 3-segment synthesis of α-IB-92 are reported as 8%, while a 2-segment synthesis gave 11%.

Due to the high reactivity of the diaryl disulfide bond, the Yamashiro approach requires extensive protection and deprotection of amino acid residues present in the peptide molecule. The lysine group for example is protected as a citraconyl derivative because of the reactive amine functionality. Additionally, an Msc group or tBOC group is used to protect any terminal amine functionalities present in the molecule.

The invention stated herein does not require the use of any protecting groups for the coupling of two oligopeptides because a less reactive (and thus more chemoselective) thioester electrophile is used instead of the acyl disulfide moiety (Yamashiro's approach). In the intermolecular coupling step, this thioester electrophile requires a more nucleophilic sulfhydryl moiety rather than a free amine. The nucleophilic sulfhydryl moiety can be found on cysteine residues. Since the amino and hydroxyl functionalities are relatively unreactive to the thioester electrophile, a selective coupling of the two unprotected oligopeptides is achieved with the cysteine sulfhydryl moiety. The sulfhydryl group on the cysteine of peptide 2 will first attack the thioester of peptide 1 and form a coupled thioester intermediate. This coupled thioester intermediate is concomitantly attacked by the free α-amino moiety from the cysteine and spontaneously rearranges to form the native peptide bond. Yields are therefore increased by eliminating protection and deprotection steps, since side undesired reactions are reduced (FIG. 1).

The thioester moiety is prepared from a precursor thioacid which is obtained by optimized stepwise solid-phase peptide synthesis on a aminomethyl resin support equipped with a thioester resin linker. The precursor thioacid is subsequently generated in liquid HF at 0° C. in 1 hour (Yamashiro et. al. *Int. J. Pept. Protein Res.* (1988): vol. 31, p 322).

A procedure for the synthesis of the thioester linker with use of a stepwise solid phase peptide synthesis has been reported by Blake (Blake et. al. *Proc. Natl. Acad. Sci. USA* (1981): vol. 78, 4055) and Yamashiro (Yamashiro et. al. *Int. J. Pept. Protein Res.* (1988): vol. 31, p 322). This method is undesirable, however, because it requires the conversion of Boc-amino acid succinimide esters to the corresponding Boc-amino thioacids with hydrogen sulfide. An improved methodology reported herein, utilizes the Boc-amino acid succinimide ester directly and therefore avoids the inconvenience and hazards of hydrogen sulfide gas (Kent et. al. *Tetrahedron Lett.* (1995): vol. 36, p 1217).

In this method (FIG. 2), thiol 3 is generated from the reaction of chloride 2 (Yamashiro et. al. *Int. J. Pept. Protein Res.* (1988): vol. 31, p 322) with thiourea, followed by hydrolysis of the resulting thiouronium salt in aqueous base. Thiol 3 is a general intermediate which can be reacted with a wide range of commercially available Boc-amino acid succinimide esters to produce the desired thioester linker 1 which is conveniently isolated as the dicyclohexylamine (DCHA) salt.

Model studies were undertaken with small peptides to investigate the native chemical ligation approach. To help explore the mechanism of the reaction, the peptide Leu-Tyr-Arg-Ala-Gly-α-COSBzl (Sequence No.: 3) was reacted with Ac-Cys. The exact mass of the resulting ligation product was determined by electrospray mass spectrometry, and was consistent with a thioester-linked peptide as the ligation product generated by nucleophilic attack of the Ac-Cys side chain on the a-thioester moiety of the peptide. Reaction of Leu-Tyr-Arg-Ala-Gly-α-COSBzl (Sequence No.: 3) with H-Cys-Arg-Ala-Glu-Tyr-Ser (Sequence No.: 2) (containing an unblocked a-NH2 functional group) proceeded rapidly at pH 6.8 (below pH 6 the reaction proceeded very slowly, suggesting the involvement of the ionized thiolate form of the cys side chain), and gave a single product of the expected mass. This product lacked susceptibility to nucleophiles, and had the ability to form disulfide-linked dimeric peptides, indicating unambiguously the formation of a native amide bond at the ligation site. These studies were consistent with the mechanism shown in FIG. 1, in which the initial thioester ligation product was not observed as a discrete intermediate because of the rapid rearrangement to form a stable peptide bond. Facile intramolecular reaction results from the favorable geometric arrangement of the α-$NH_2$ moiety with respect to the thioester formed in the initial chemoselective ligation reaction. Use of such 'entropy activation' for peptide bond formation is based on principles enunciated by Brenner. (M. Brenner, in *Peptides. Proceedings of the Eighth European Peptide Symposium* H. C. Beyerman, Eds. (North Holland, Amsterdam, 1967) pp. 1–7.) The concept of 'entropy activation' for peptide bond formation has been more recently adopted by D. S. Kemp et al. (*J. Org. Chem.* (1993): vol. 58, p 2216) and by C.-F. Liu, et al. (*J. Am. Chem. Soc.* (1994): vol. 116, p 4149).

Several model peptides have been synthesized by the method of native chemical ligation. The successful synthesis of these model peptides establish that native chemical ligation is generally applicable to peptides containing the full range of functional groups normally found in proteins. Even free internal Cys residues may be present in either of the reacting segments. Internal Cys residues can undergo ester exchange with the peptide-a-thioester component; however, this reaction is unproductive because no rearrangement to the amide bond can occur; the thioester formed is readily reversible and remains a productive part of the reacting system. As disclosed herein, native chemical ligation is limited to reaction at an N-terminal Cys residue. It is important to prevent the side chain thiol of this Cys from oxidizing to form a disulfide linked dimer, because this is unreactive in the ligation. An excess of thiol corresponding to the thioester leaving group was used to keep the Cys residues in reduced form without interfering with the ligation reaction. The amino-terminal peptide segment must be prepared by chemical synthesis to equip it with the necessary α-COSR functionality. Furthermore, for optimal ligation, this component should have an unhindered (i.e. non β-branched) C-terminal amino acid. Solubilizing agents such as urea or guanidine hydrochloride did not interfere with the ligation and could be used to enhance the concentration of peptide segments, and thus increase the reaction rate.

Further model reactions demonstrate that the use of better thioester leaving groups results in faster ligation reactions. We applied this observation to the native chemical ligation of peptides from the extracellular domain of a human cytokine receptor (R. D'Andrea, et al., *Blood*, (1994): vol. 83, p 2802.) as shown in FIG. 5. Use of the 5-thio-2-nitrobenzoic acid (-SNB) leaving group, corresponding to the reduced form of Elman's reagent, gave rapid high yield reaction. As described below in connection with FIG. 5, the reaction between the peptide segments was observed to have gone essentially to completion in less than 5 minutes, giving the 50 residue product with a native peptide bond at the site of ligation. Thus, rapid native chemical ligation can be achieved by use of a thioester leaving group with suitably tuned properties.

Application of the native chemical ligation method to the total synthesis of a protein molecule was illustrated by the preparation of human interleukin 8 (IL-8). (M. Baggiolini, et al., *FEBS Lett.* (1989): vol. 307, p 97; I. Clark-Lewis, et al., *J. Biol. Chem.* (1994): vol. 269, p 16075 (1994); I. Clark-Lewis, *Biochemistry* (1991): vol. 30, p 3128; and K. Rajarathnam, et al., (1994): *Biochemistry*, (1994): vol. 29, p 1689.) The 72 amino acid polypeptide chain contains four Cys residues, which form two functionally critical disulfide bridges in the native protein molecule. The total synthesis of IL-8 is shown in FIG. 7. The two unprotected synthetic peptide segments reacted cleanly to give the full length polypeptide chain in reduced form without further chemical manipulation (9). This successful ligation was particularly significant because the 33- and 39-residue IL-8 segments each contained two Cys residues, and together encompassed 18 of the 20 genetically encoded amino acids found in proteins. The purified product was folded and oxidized as previously described, to give IL-8 with a mass precisely 4 daltons less than that of the original ligation product, indicating the formation of two disulfide bonds. The properties of this folded product were identical to those of previously studied authentic IL-8 samples. Titration in an assay for neutrophil elastase release demonstrated that the potencies (ED50=0.3nM) and maximal responses of the folded, ligated [Ala33]IL-8 and the corresponding molecule obtained by conventional synthesis were indistinguishable and identical to native sequence IL-8. This result unambiguously confirmed the formation of a peptide bond at the ligation site, because the thioester-to-amide rearrangement must have taken place to give the free $Cys^{34}$ side chain that formed the native disulfide bond (see FIG. 7).

Proteins are usually studied by expression in genetically engineered micro-organisms using the methods of recombinant DNA-based molecular biology. Methods such as site-directed mutagenesis have had a major impact on the ability to prepare large numbers of modified proteins in useful amounts for systematic study. Innovative approaches have increased the range of amino acids that can be incorporated in expression systems and promise to significantly extend the utility of biosynthetic modification of the covalent structure of proteins. However, there appear to be limitations inherent to the nature of ribosomal protein synthesis.

Wieland discloses a method for synthesizing dipeptides using a thioester intermediate. (Wieland et. al. *Liebigs Ann. Chem.* (1953): vol. 580, p 159.) Wieland utilizes the reaction of S-glycyl-(or other un-branched aminoacyl-) thiophenols with cysteine. Thus, the sulfhydryl group on the cysteine residue first attacks the thioester of the S-glycyl-thiophenol and forms a coupled thioester intermediate. This coupled thioester intermediate is concomitantly attacked by the free α-amino moiety from the cysteine and spontaneously rearranges to form the native peptide bond.

A limitation of the Wieland approach is the size of the molecules utilized (only mono-amino acids are coupled to cysteine) and stems from the methodology used for the synthesis of the thioester. To form the thioester, Wieland's approach requires the activation of the terminal carboxylic acid as a mixed anhydride, acid chloride or thioacid. A problem arises if an acidic moiety is present in an amino acid residue such as Asp(D) and Glu(E). In these cases, the Wieland produces an undesired side reaction and therefore requires a complex protecting group strategy, particularly if oligopeptides are synthesized.

The invention described herein eliminates the need for an elaborate protecting group strategy since the oligopeptide-thioester moiety is derived from a precursor thioacid. This precursor thioacid (peptide-α-COSH) is synthesized by a standard stepwise solid-phase peptide synthesis on an aminomethyl resin support, equipped with a thioester resin linker. The precursor thioacid is cleaved from the linker/resin almost quantitatively (99%) in liquid HF at 0° C. for 1 hour.

The thioester peptide (peptide-α-COSR) can be synthesized in two general ways:

(1) Reaction of a crude lyophilized thioacid peptide (peptide-α-COSH) with Ellman's reagent (5,5'-dithiobis-2-nitrobenzoic acid, available from Aldrich company) at pH 5.5 (2.0 equivalents), 6M Guanidine in 100mM Na acetate buffer. This gives the SNB-thioester peptide (peptide-α-COSNB) which is subsequently purified by reversed phase high performance liquid chromatography (RPHPLC).

(2) Reaction of a crude lyophilized thioacid peptide (peptide-α-COSH) with benzyl bromide at pH 4.0, 6M guanidine and 100 mM Na acetate buffer. The benzyl thioester (peptide-α-COSBn) is then purified by RPHPLC.

The conditions stated above, permit the formation of an unprotected oligonucleotide which is equipped with the activated thioester. Subsequent reaction with a second peptide containing a terminal cysteine residue, permits a facile coupling with the formation of a native peptide bond and can generate oligopeptide chains of 100 or more amino acid residues (FIG. 1).

In favorable cases, chemical synthesis has already made important contributions to the exploration of the relationship of protein structure to function. Stepwise solid phase synthesis has permitted the de novo preparation of small proteins (14) and there have been several notable examples of the use of this method of total protein synthesis to explore the molecular basis of biological function. Another method that has in special instances allowed chemistry to be applied to the study of proteins is semi-synthesis through the conformationally-assisted religation of peptide fragments. An important extension of the semisynthesis approach is the use of enzymatic ligation of cloned or synthetic peptide segments. Although these methods currently have severe limitations, there continues to be serious interest in the wider application of the tools of organic chemistry to the study of proteins.

Native chemical ligation provides precisely that capability. It combines the formation of a native peptide bond at the ligation site with the advantages of chemoselective reaction of unprotected peptides. This second generation ligation chemistry dramatically increases the size of native backbone polypeptides directly accessible by total chemical synthesis. It can be usefully applied to a wide range of synthetic targets, including proteins of moderate size, and it allows direct access to protein functional domains. Native chemical ligation is a foundation stone of a general modular approach to the total chemical synthesis of proteins. Furthermore, it is compatible with the use of both chemically synthesized peptides and peptide segments derived from other sources.

Straightforward total chemical synthesis of proteins represents the realization of an important objective of organic chemistry. It provides for unrestricted variation of protein covalent structure made possible by general synthetic access, and provides new impetus to exploration of the structural basis of properties such as folding, stability, catalytic activity, binding, and biological action.

In an alternative embodiment, the carboxy-terminal peptide segment or protein module can be expressed by standard recDNA means; provided the product contained an N-terminal Cys residue, it could be reacted with the synthetic amino-terminal peptide-α-COSR using the native chemical ligation described here to give a product in which part of the protein had derived from chemical synthesis and part from ribosomal synthesis.

BRIEF DESCRIPTION OF DRAWINGS

FIG. 8(A) illustrates the unreacted IL-8 peptides (1–33)-SBenzyl (Sequence No. 8) and IL-8 34–72 (Sequence No. 9) prior to ligation; FIG. 8(B) illustrates the unfolded IL-8 ligation product, Sequence No. 10; and FIG. 8(C) illustrates the folded IL-8 ligation product, Sequence No. 10.

DETAILED DESCRIPTION

Peptide-α-thioacid Formation

A typical procedure for the formation and utilization of the thioester resin linker for use in the solid phase synthesis of peptide-a-thioacids is as follows: (Kent et. al. *Tetrahedron Lett.* (1995): vol. 36, p 1217).

Figure 2:
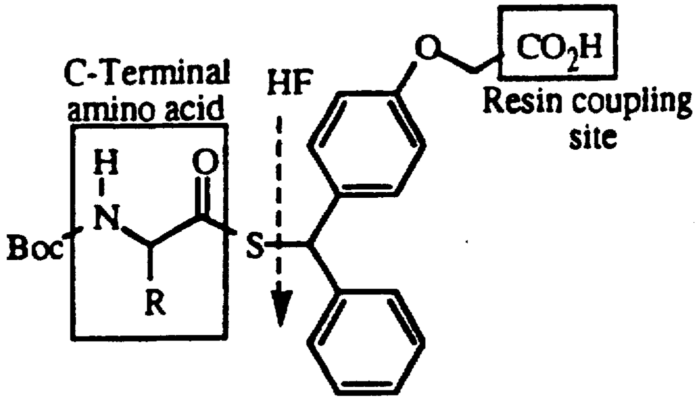
FIG. 2 illustrates a general synthesis of Boc-amino thioester linker (1), dicyclohexylamine salt.
Figure 2:
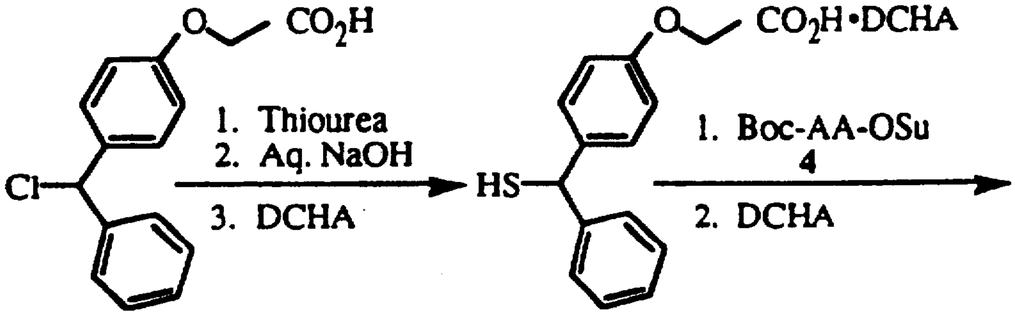
Figure 2:
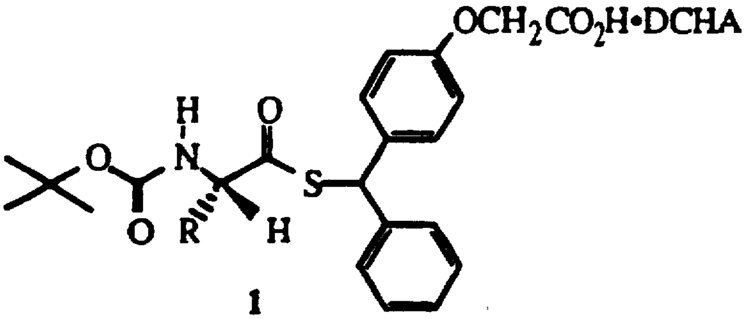

4-(α-Mercaptobenzyl)phenoxyacetic acid, dicyclohexylamine (3) FIG. 2. A mixture of 2, formed using the conditions as established by Yamashiro et. al. *Int. J. Pept. Protein Res.* (1988): vol. 31, pp 322–334, (7.5 grams, 27 mmol), thiourea (2.3 g, 30 mmol), and ethanol (100 mL) were heated to reflux (conditions as reported by Koenig et al *J. Org. Chem.* (1958): vol. 23, pp 1525–1530). After 4 hours, conversion to the thiouronium salt was essentially complete as shown by TLC (90:5:5 chloroform:Methanol:Acetic acid). 10N NaOH (30 ml) was added and the reflux continued for 2–3 hours. After cooling to room temperature, the reaction mixture was concentrated in vacuo to approximately half the original volume, acidified with concentrated HCl (to pH 2.0), and extracted with ethylacetate (4×30 mL). The combined ethylacetate extracts were washed with saturated NaCl (1×30 mL) and dried over $MgSO_4$. The volatile materials were removed in vacuo. The resulting oil was dissolved in ethylacetate (100 mL) and any insoluble material filtered. DCHA (dicyclohexylamine—available from Aldrich company), (6.0 mL, 30 mmol) was added to the filtrate with stirring. Within a few minutes, a white solid began to precipitate. Diethylether (150 mL) was added and the suspension cooled at −20° C. for several hours. The resulting white solid was filtered, washed with Diethylether, and dried under vacuum to give 3 (10.3 g, 23 mmol, 84%): $^1$H NMR ($CDCl_3$): δ 5 7.30 (m, 7H), 6.82 (d, 2H, J=8.7 Hz), 5.39 (br s, 1H), 4.40 (s, 2H), 2.81 (m, 2H), 2.23 (br s, 1H, ex $D_2O$), 1.88–1.02 (comp m, 20H); FAB MS (cesium ion): calc for [$C_{27}H_{37}NO_3S$, $H^+$] 456.2572, found 456.2572. Anal. Calcd for $C_{27}H_{37}NO_3S$: C, 71.17; H, 8.18; N, 3.07; S, 7.04. Found: C, 71.11; H, 8.41; N, 3.08; S, 7.09.

General Synthesis of Boc-amino thioester linker (1), dicyclohexylamine salt (FIG. 2). A mixture of 3 (3.67 mmol), Boc-Ala-OSu (available from Novabiochem Corp.) (3.68 mmol), DIEA (diisopropylethylamine-5.74 mmol), dimethylformamide (35 mL) and methylene chloride (4 mL) was stirred at room temperature. After several hours, the initial white suspension completely dissolved to give a clear, colorless solution. After 24 hours, the reaction mixture was poured into 1N HCl (150 mL) and extracted with ethylacetate (4×35 mL). The combined ethylacetate extracts were washed with 1N HCl (2×30 mL), $H_2O$ (1×30 mL), saturated NaCl (1×30 mL) and dried over $MgSO_4$. Volatiles were removed in vacuo. The resulting oil was purified by flash chromatography (925:50:25 Chloroform:MeOH:acetic acid) to give an oil contaminated with Acetic acid. To remove residual Acetic acid, the oil was dissolved in Chloroform (40 mL) and washed with 0.1 N HCl (7×10 mL), saturated NaCl (1×10 mL) and dried over $MgSO_4$. Volatiles were removed in vacuo to give 1 as an oil. This oil was dissolved in diethylether (10 mL) to which was added dicyclohexylamine (1 equivalents). Hexane (100 mL) was added with stirring to separate the dicyclohexylamine salt of 1 as a thick oil from any unreacted dicyclohexylamine. Solvents were decanted from the oil and the oil dissolved in $CH_2Cl_2$ (30–40 mL). The resulting solution was concentrated in vacuo to give the dicyclohexylamine salt 1 as a white foamy solid (FIG. 2).

An example of the linkage and synthesis on the resin is as follows: 4-[a-(Boc-Ala-S)benzyl]phenoxyacetic acid (0.80 mmol) is added in 9 ml methylene chloride to 1.00 g aminomethyl-resin (0.40 mmol) and treated at 0° C. with 1.33 mL 0.6 M DCCI (dicyclohexylcarbodiimide) in methylene chloride for 15 min and at 24° C. for 30 minutes. The product is then subjected to standard solid-phase peptide synthesis conditions (Kent et. al. *Tetrahedron Letters* (1995): vol. 36, p 1217; J. Blake, *Int. J. Pept. Protein Res.* (1981): vol. 17, p 273). Once the desired chain is synthesized, the peptide resin (approx. 45 μmol original load) is treated in 8 mL liquid HF (0.8 mL anisole) at 0° C. for 1 hour. After evaporation with nitrogen, the residue is washed with ethyl acetate. The solid is subsequently stirred in water (approx. 15 mL) at 0° C. while adjusting the pH to 6.0 with solid ammonium bicarbonate. Filtration and lyophilization gives the crude thioacid product which can be further purified by preparative HPLC in 30 mg batches.

Preparation of the Thioester Terminal Peptide Segment

The α-COSR thioester peptide can be synthesized in two general ways:

(1) Reaction of a crude lyophilized thioacid peptide with Ellman's reagent (5,5'-dithiobis-2-nitrobenzoic acid, available from Aldrich company) at pH 5.5 (2.0 equivalents), 6M Guanidine in 100 mM Na acetate buffer. This gives the SNB-thioester peptide which is subsequently purified by reversed phase high performance liquid chromatography (RPHPLC).

(2) Reaction of a crude lyophilized thioacid peptide with benzyl bromide at pH 4.0, 6M guanidine and 100 mM Na acetate buffer. The benzyl thioester is then purified by RPHPLC.

Figure 1:
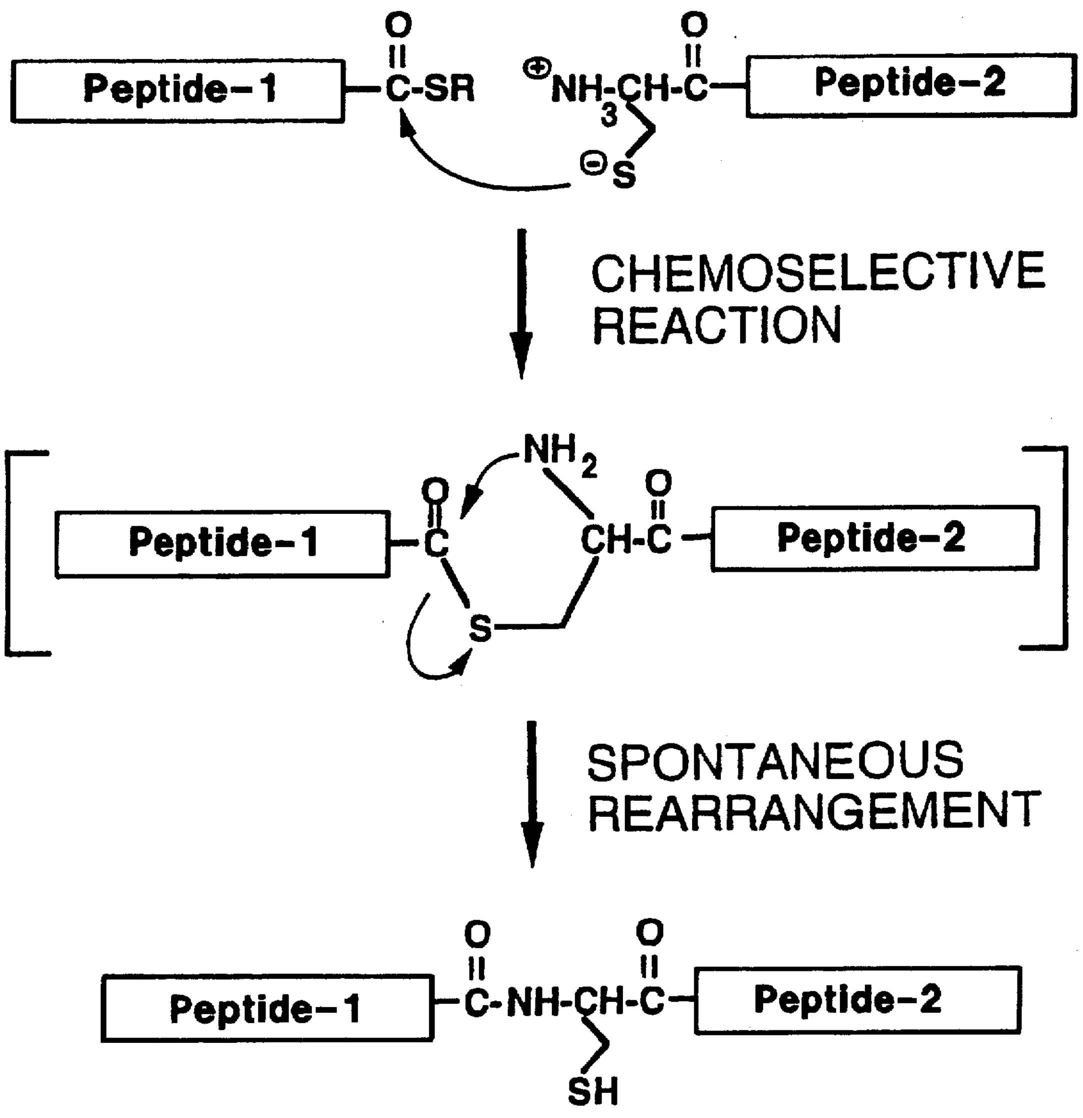
FIG. 1 illustrates the overall principle of 'native chemical ligation.'

The conditions stated above, permit the formation of an unprotected oligonucleotide which is equipped with the activated thioester. Subsequent reaction with a second peptide containing a terminal cysteine residue, permits a facile coupling with the formation of a native peptide bond and can generate oligopeptide chains of 100 or more amino acid residues (FIG. 1).

EXAMPLES

Example 1

The model peptide Leu-Tyr-Arg-Ala-Gly-αCOSH (Sequence No.: 1) is prepared by optimized stepwise solid-phase peptide synthesis on an aminomethyl resin. The thioester resin linker is prepared by a generalized version as adopted from Kent et. al. *Tetrahedron Letters*, (1995): vol. 36, p 1217; J. Blake, *Int. J. Pept. Protein Res.* (1981): vol. 17, p 273; D. Yamashiro and C. H. *Li, ibid.* (1988): vol. 31, p 322. Once the desired chain is synthesized, the peptide resin (approx. 45 μmol original load) is treated in 8 mL liquid HF (0.8 mL anisole) at 0° C. for 1 hour. After evaporation with nitrogen, the residue is washed with ethyl acetate. The solid is subsequently stirred in water (approx. 15 mL) at 0° C. while adjusting the pH to 6.0 with solid ammonium bicarbonate. Filtration and lyophilization gives the crude thioacid product which can be further purified by preparative HPLC in 30 mg batches.

The thioester terminal peptide segment is subsequently prepared from the thioacid fragment by chemical synthesis to equip it with the necessary α-COSR functionality where R is an alkyl group such as benzyl, 5-thio-2-nitrobenzoic acid (-SNB), thiophenol, etc. The use of better thioester leaving groups resulted in faster ligation reactions. Thus, the model peptide Leu-Tyr-Arg-Ala-Gly-αCOSH (Sequence No.: 1) is first converted to the thiobenzylester by reaction with benzyl bromide (15 equivalents) in 6.0 M guanidine-HCl, pH 4.6, sodium acetate buffer to form Leu-Tyr-Arg-Ala-Gly-αCOSBn (Sequence No.: 3). The resulting peptide is purified under standard reversed-phase high-performance liquid chromatography (HPLC) conditions using approximately 20–45% acetonitrile at 1% per minute; monitored at 214 nm.

For the peptide H-Cys-Arg-Ala-Glu-u-Tyr-Ser (Sequence No.: 2), solid phase methods allow the preparation of peptides of up to 60 residues in good yield and high purity as described in M. Schnolzer, P. Alewood, D. Alewood, S. B. H. Kent, *Int. J. Pept. Protein Res.* (1992): vol. 40, 180.

First, to explore the mechanism of the reaction, the peptide Leu-Tyr-Arg-Ala-Gly-αCOSBn (Bn, benzyl; sequence No.: 3) was reacted with Ac-Cys (containing a blocked α-$NH_2$ functional group—commercially available from Novabiochem corp.). The exact mass of the resulting ligation product, Leu-Tyr-Arg-Ala-Gly-αCOS-$CH_2C(NHAc)CO_2H$ (Sequence No.: 4), was determined by electrospray mass spectrometry and was consistent with a thioester-linked peptide as the ligation product generated by nucleophilic attack of the Ac-Cys side chain on the α-thioester moiety of the peptide.

Figure 3A:
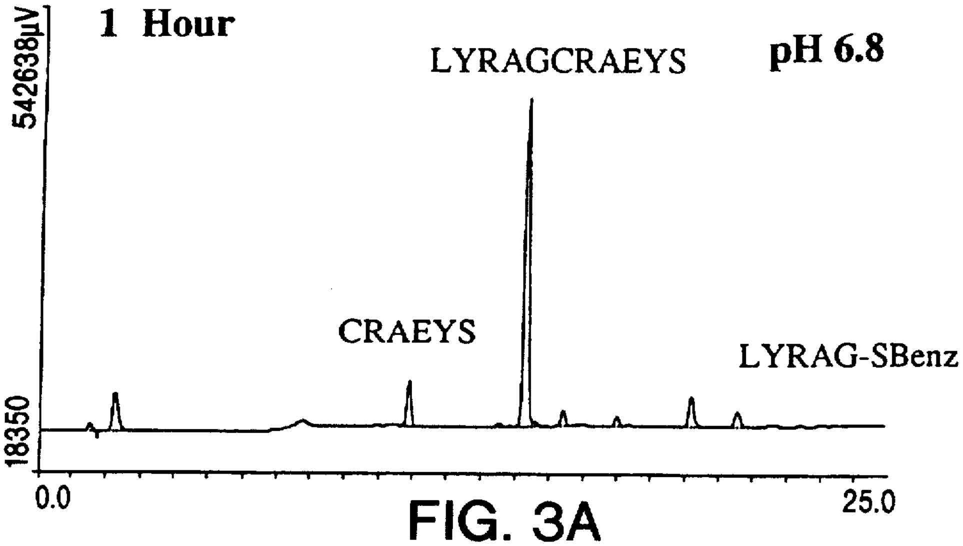
FIG. 3 illustrates the progress of a first native chemical ligation reaction for the production of model peptide (Sequence No. 5) of Example 1 using a first peptide segment (Sequence No. 2) and a second peptide seguement (Sequence No. 3) having a S-benzyl derivative, as monitored by HPLC.
Figure 3B:
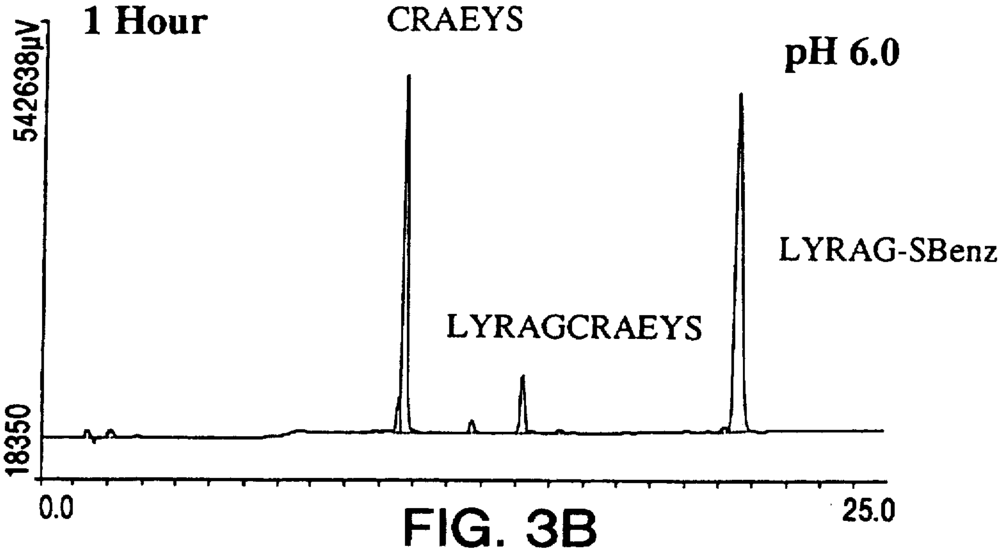
Figure 3C:
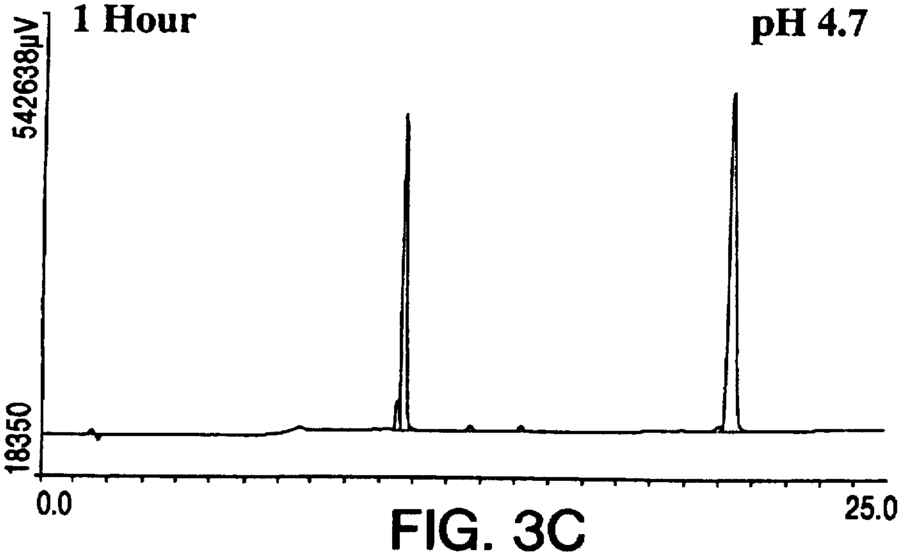

Finally, the reaction of Leu-Tyr-Arg-Ala-Gly-αCOSBn (Sequence No.: 3) with Cys-Arg-Ala-Glu-Tyr-Ser (Sequence No.: 2, containing an unblocked α-$NH_2$ functional group) proceeded rapidly at pH 6.8 (below pH 6.0, the reaction proceeded very slowly, suggesting the involvement of the ionized thiolate of the Cys side chain at pH 6.8; FIG. 3) and gave a single product of the expected mass. The peptides Leu-Tyr-Arg-Ala-Gly-αCOSBn SEQ ID No: 3+Cys-Arg-Ala-Glu-Tyr-Ser SEQ ID No: 2 were reacted in 0.1 M phosphate buffer at pH 6.8, 6.0 and 4.7 at 25° C. After 1 hour, the reactions had proceeded as follows: at pH 6.8 >95%; at pH 6.0 approximately 10%; and at pH 4.7, approximately 1.0% of ligated product Leu-Tyr-Arg-Ala-Gly-Cys-Arg-Ala-Glu-Tyr-Ser (Sequence No.: 5). As observed by HPLC, FIG. 3 shows the pH dependence of the reaction after 1 hour and at 25° C. This product lacked susceptibility to nucleophiles and had the ability to form disulfide-linked dimeric peptides, indicating unambiguously the formation of a native amide bond at the ligation site.

Figure 4:
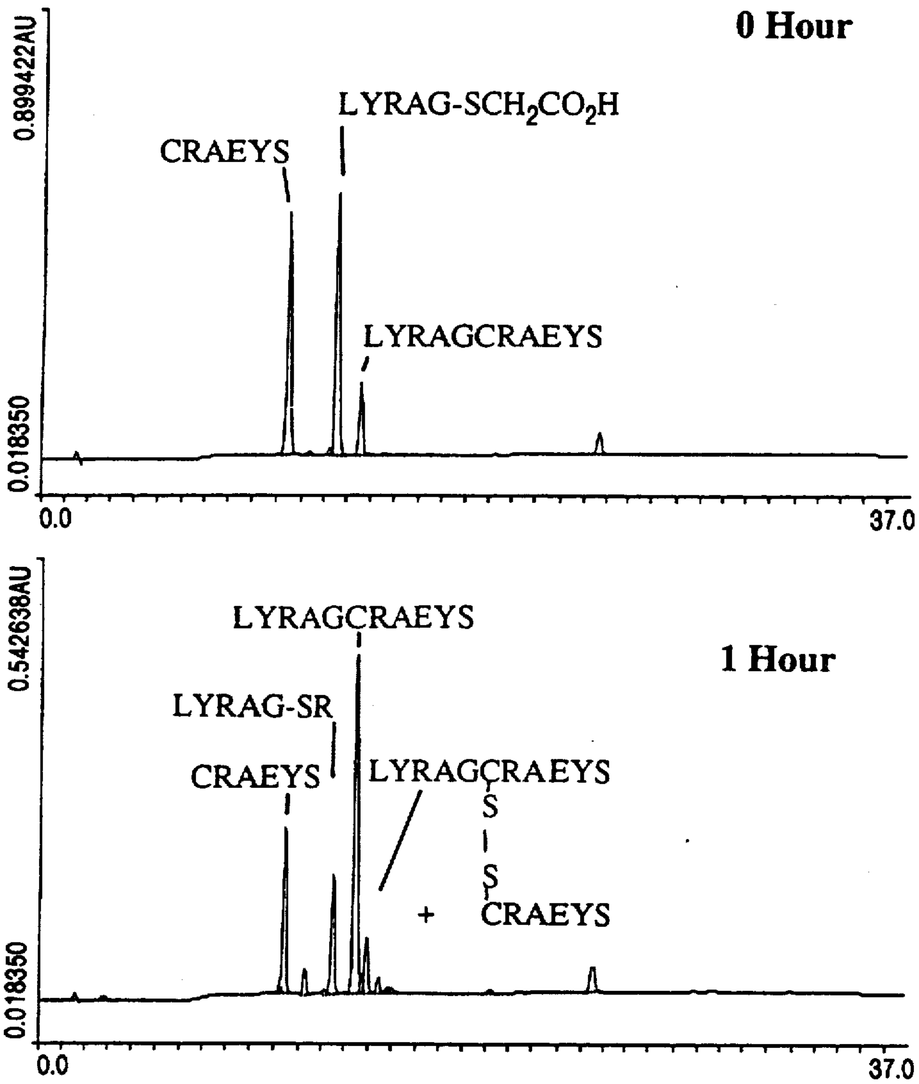
FIG. 4 illustrates the progress of a second native chemical ligation reaction for the production of model peptide (Sequence No. 5) of Example 1 using a first peptide segment (Sequence No. 2) and a second peptide seguement (Sequence No. 6) having a thioacetic acid derivative, as monitored by HPLC.

Another, unpublished model using the 2-thioacetic acid derivative Leu-Tyr-Arg-Ala-Gly-$SCH_2COOH$ (Sequence No.: 6- formed from attack of the thioacid Leu-Tyr-Arg-Ala-Gly-SH (Sequence No.: 1), onto 2-bromoacetic acid in methylene chloride)+Cys-Arg-A-la-Glu-Tyr-Ser (Sequence No.: 2) was ligated at pH 6.8 in 0.2 M phosphate buffer, at 45° C. After 1.0 hour the reaction had proceeded to 80% as observed in FIG. 4 by HPLC. The isolation of oxidation products from the ligated Leu-Tyr-Arg-Ala-Gly-Cys-Arg-Ala-Glu-Tyr-Ser (Sequence No.: 5) and unreacted Cys-Arg-Ala-Glu-Tyr-Ser (Sequence No.: 2 demonstrated the presence of a free thiol ligation product.

The native chemical ligation procedure is generally applicable to peptides containing the full range of functional groups, normally found in proteins. Even free internal Cys residues may be present in either of the reacting segments. Internal Cys residues can undergo ester exchange with the peptide-α-thioester component; however, this reaction is unproductive because no rearrangement to the amide bond can occur, the thioester formed is readily reversible and remains a productive part of the reacting system.

The native chemical ligation procedure is limited to reaction at an amino-terminal Cys residue. To prevent the side chain thiol of this Cys from oxidizing to form a disulfide-linked dimer, an excess of thiol corresponding to the thioester leaving group is used to keep the Cys residues in reduced form without interfering with the ligation reaction. In addition, small amounts of low molecular weight thiols such as benzyl mercaptan or thiophenol are added to the coupling reaction mixture to maintain a reducing environment.

The addition of thiols increases the reactivity of the thioester, particularly if the added thiol is a better leaving group than the pre-formed thioester. An example of this observation is when the benzyl ester is converted to a phenyl ester by addition of thiophenol to reaction. Reaction yields and rates are substantially increased. For example, after 7 hours with benzyl mercaptan, the Barnase reaction yielded 25%, while the thiophenol treatment to the same reaction mixture yielded 90%).

Addition of thiols to the ligation mixture also keeps the reaction mixture in a reduced form. This prevents oxidation of the reactive N-terminal Cys residues and when internal Cys residues are present, the thiols reduce the formation of intramolecular disulfide bonds. Additionally, the reducing environment increases the stability of the thioester segment (ligation reactions can proceed overnight with little or no hydrolysis at pH 7.5).

Example 2

A rapid native chemical ligation is illustrated by the synthesis of a peptide segment corresponding to residues 46 to 95 from the external domain of the human IL-3 receptor β-subunit incorporated herein: R.D'Andrea et. al., *Blood* (1994): vol. 83, p 2802.

Crude synthetic IL-3 Msc(46–76)αCOSH was converted to the 5 thio-2-nitrobenzoic acid ester (-COSNB) by treatment with 5,5'-dithio-bis(2-nitrobenzoic acid) [10 equivalents (eq)] in 8 M urea, pH 4.0, 50 mM ammonium acetate buffer [Msc, 2 (methyl-sulfonyl)-ethyloxy-carbonyl (Fluka #69227) protecting group is placed on the N-terminus using 1.1 equivalents (eq.) 2-(methylsulfonyl)ethyl 4-nitrophenyl carbonate, 1.1 eq. diisopropylethylamine, and 0.5 M dimethylformamide]. This thioester-containing material was found to be completely stable below pH 6.0, and was readily purified under standard reversed-phase HPLC conditions using approximately 20–45% acetonitrile at 1% per minute and monitored at 214 nm.

Figure 5:
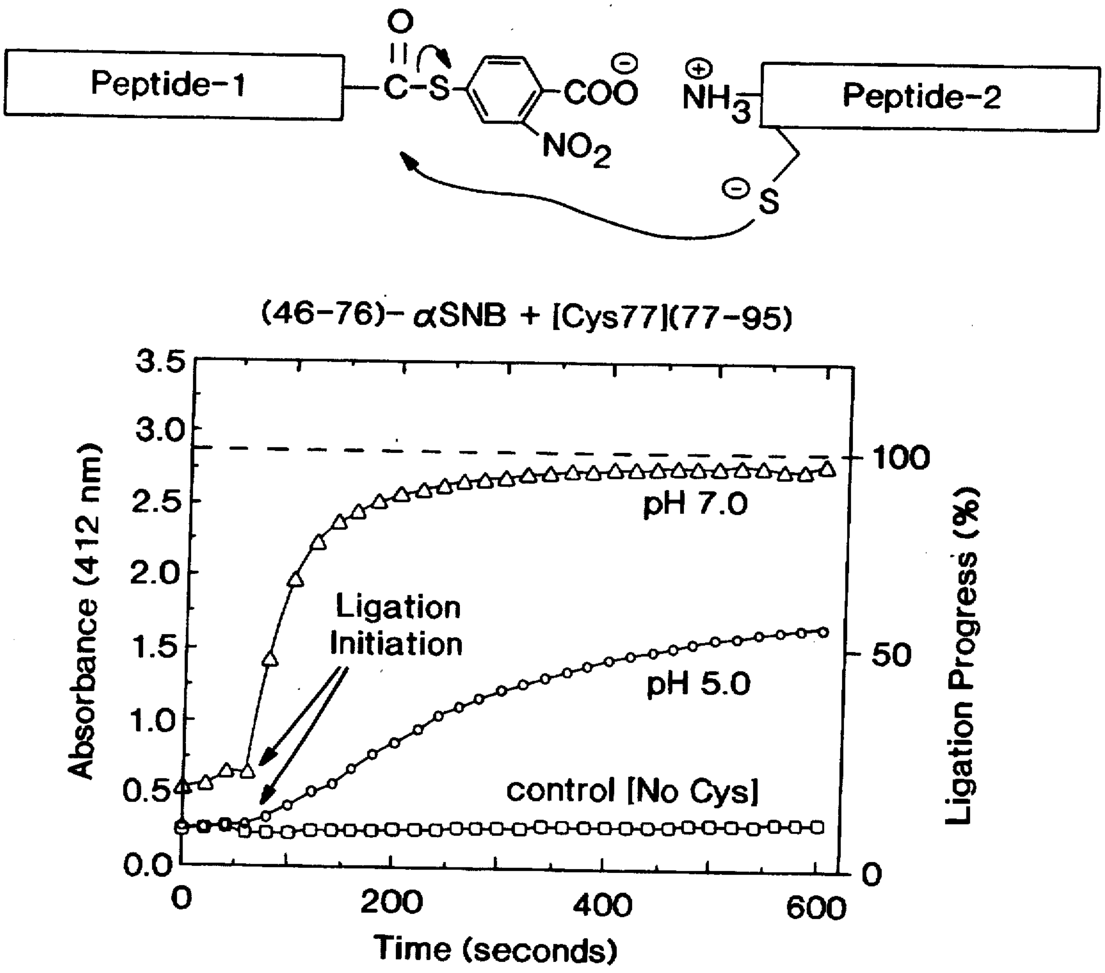
FIG. 5 illustrates the kinetics of the native chemical ligation reaction of Example 2 with respect to the linkage of peptide segments 46–76 and 77–95 for producing IL-3 receptor β-subunit.

As shown in FIG. 5, ligation is initiated by adding IL-3 [Cys77](77–95) (prepared by standard solid phase methods Kent et al., *Int. J. Pept. Protein Res.* (1992): vol. 40, 180) to purified IL-3 Msc(46–76)αCOSNB at the stated pH and the reaction is monitored by UV [the substituted aryl thiolate leaving group has a characteristic UV absorbtion at 412 nm ($\epsilon_{TNB,\ 412\ nm}$=13, 700 $dm^3 mol\ cm^{-1}$)]. At pH 7.0, the reaction is essentially complete within 5 min. No reaction is observed when Msc(46–76)αCOSNB is exposed to a 10-fold molar excess of Leu-enkephalin (amino-terminal residue, Tyr) at pH 5.0. This control experiment confirms the absolute requirement for an amino-terminal Cys residue at the site of ligation (FIG. 5).

Figure 6:
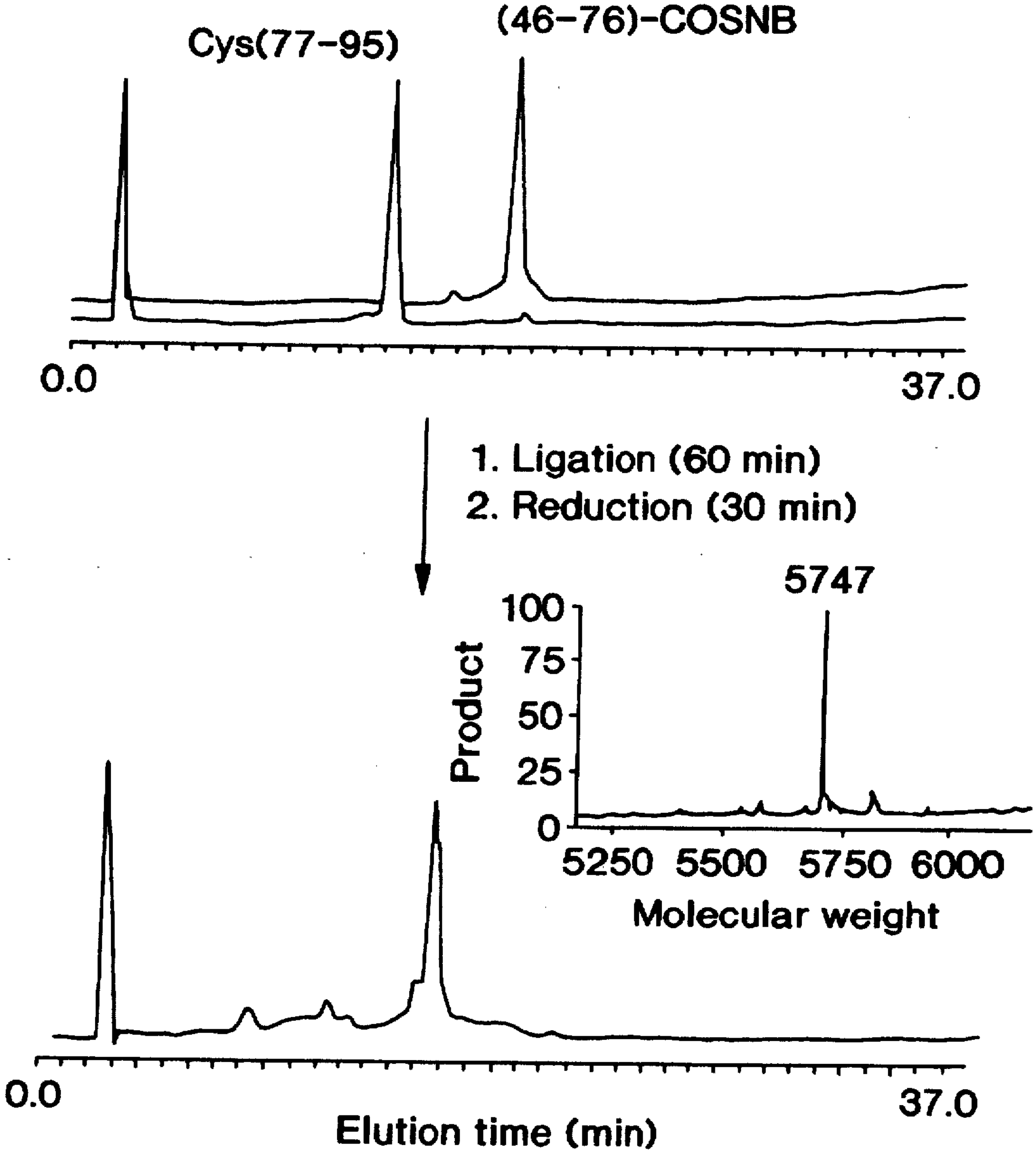
FIG. 6 illustrates the reversed-phase HPLC purification and electrospray mass spectroscopy of unreacted IL-3 peptide segments (46–76) and (77–95) of IL-3 receptor β-subunit and of their native chemical ligation product as detailed in Example 2.

Purified IL-3 [Cys77](77–95) (0.98 mM) and IL-3 (46–76)αCOSNB (0.9 mM) were reacted in 8 M urea, pH 5.0, 50 mM ammonium acetate buffer at 23° C. (monitored by analytical HPLC 9C18 reversed phase 22.5 to 45% acetonitrile at 0.7% per minute; 214 nm). After 1 hour, the ligation solution is exposed to the reducing agent tris(2-carboxyethyl)phosphine (TCEP) at pH 9.0 and subsequently raised to pH 13.0 to remove the Msc protecting group (Treatment with TCEP was found to aid in the purification and analysis of product by reducing the thiophenol and benzyl mercaptan disulfide products which had a tendency to co-elute with the peptide products). FIG. 6 shows the progress of the reaction by HPLC; conversion of the starting peptides to the crude product is shown (FIG. 6). The 50 residue product has the expected molecular mass by electrospray mass spectrometry [observed, 5747.0 daltons; calculated (average isotope composition), 5747.4 daltons]. The ligation product is shown to be stable at high pH, reducing conditions, and forms an intramolecular disulfide bond. These observations are consistent with the presence of a native peptide bond at the site of ligation.

Analogous methods have required removal of protecting groups (J. Blake et. al., *Int. J. Pept. Protein Res.* (1981): vol. 17, p 273; Kemp et. al. *J. Org. Chem.* (1993): vol. 58, p 2216; Liu et. al. *J. Am. Chem. Soc.* (1994): vol. 116, 4149) or conversion of intermediates to the final form, or both steps. No previous method has allowed the chemical reaction of unprotected peptide segments to directly yield a native backbone final product.

Example 3

The IL-8(34–72) segment (Sequence No. 9) is prepared by optimized stepwise solid-phase methods as described by Kent et al., *Int. J. Pept. Protein Res.* (1992): vol. 40, 180 and yield peptides from 60–80 residues in good yields and high purities. The peptide-αCOSH is prepared by optimized stepwise solid-phase peptide synthesis on a aminomethyl resin with a thioester linker. The thioester linker is prepared by a generalized version as adopted from J. Blake, *Int. J. Pept. Protein Res.* (1981): vol. 17, p 273; D. Yamashiro and C. H. Li, ibid. vol. 31, 322 (1988). Products are subsequently purified by standard reversed-phase HPLC conditions and characterized by standard methods which include electrospray mass spectrometry.

Figure 7:
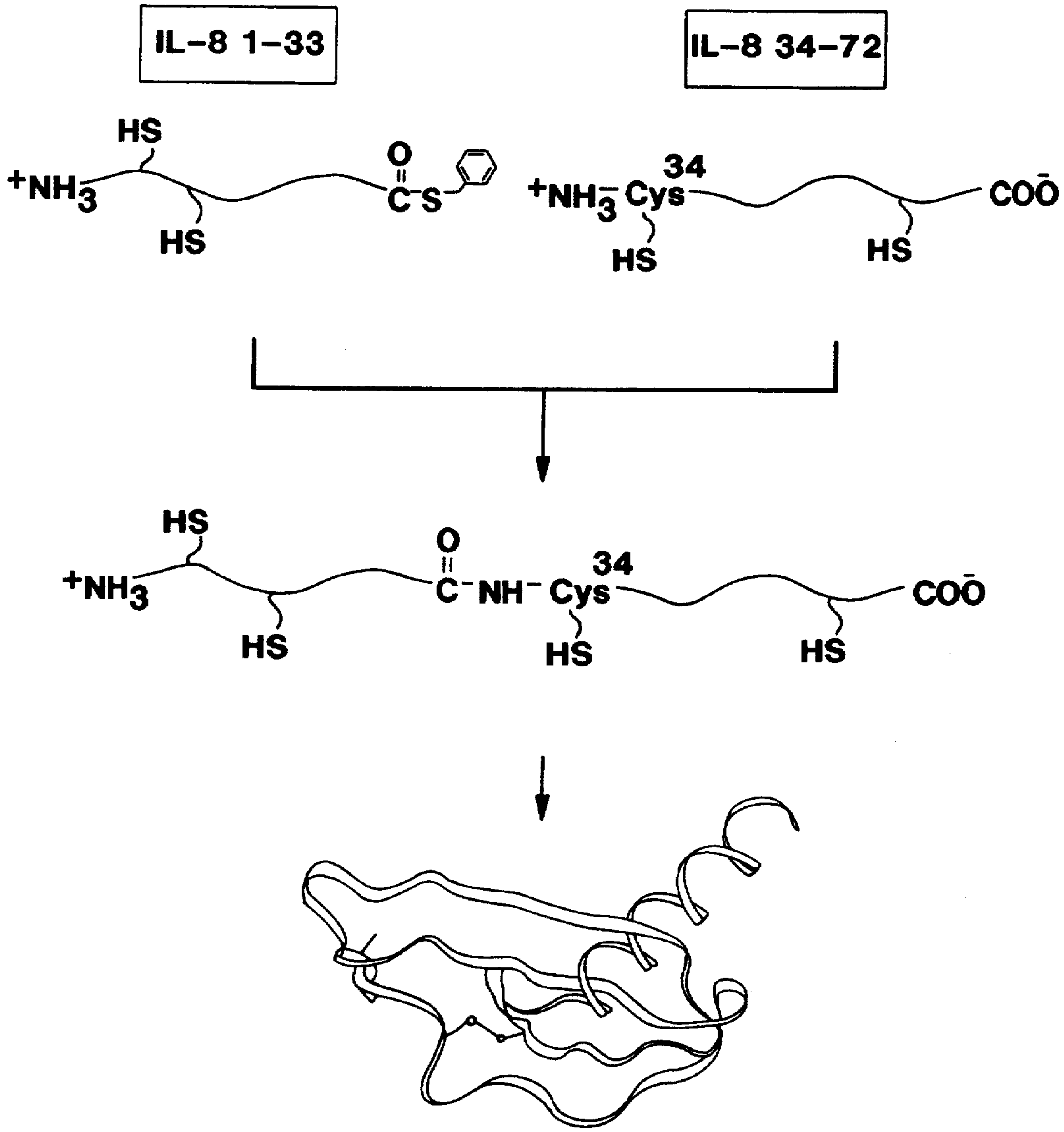
FIG. 7 illustrates a native chemical ligation scheme for producing LI-8 as detailed in Example 3.

Crude synthetic segment IL-8(1–33)αCOSH (Sequence No.: 7) is converted to the thiobenzyl ester by reaction with benzyl bromide (15 equivalents) in 6 M guanidine-HCl at pH 4.6 in 100 mM sodium acetate buffer. The reaction mixture is purified under standard reversed-phase HPLC conditions and forms the thiobenzyl ester, IL-8(1–33) αCOSBn (Sequence No.: 8), (FIG. 7).

The segments IL-8(1–33)αCOSBn (Sequence No.: 8), (5.0 mg, 1.3 μmol) and IL-8(34–72) (Sequence No. 9), (4.8 mg, 1.1 mmol) were reacted in 0.5 ml 6.0 M guanidine-HCl, pH 7.6, phosphate buffer at 23° C. in the presence of benzyl mercaptan (5 ml). After suitable reaction time (48 to 72 hours), a ligation yield of approximately 60% was obtained. The product was purified by standard reversed-phase HPLC as described via supra and characterized by electrospray mass spectroscopy.

Figure 8A:
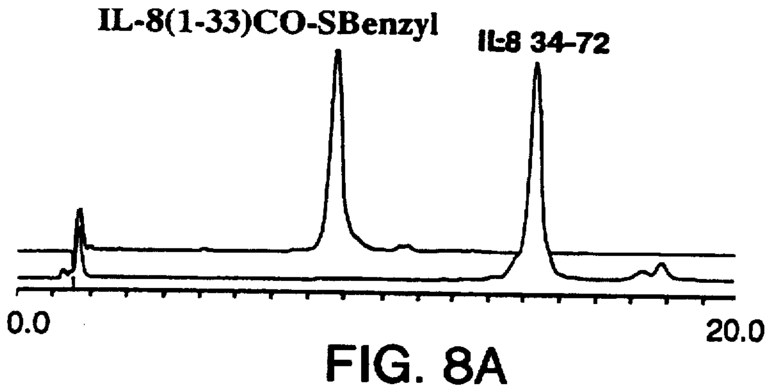
FIG. 8(A)–(C) illustrates the reversed-phase HPLC purification and electrospray mass spectroscopy of IL-8 (Sequence No.: 10) as formed by a native chemical ligation of peptides Sequence No.'s 8 and 9 in Example 3.
Figure 8B:
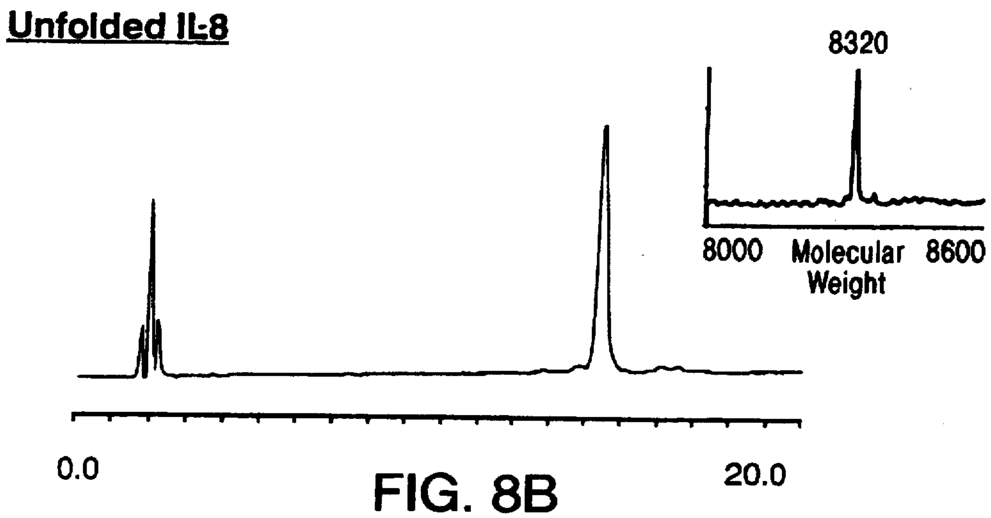

As shown in FIG. 8B, an analytical HPLC spectrum ($C_{18}$reversed phase; 25 to 45% acetonitrile at 1% per minute; monitored at 214 nm) is shown before the reaction of the synthetic peptide segments IL-8(1–33)αCOSBzl and IL-8(34–72).

Figure 8C:
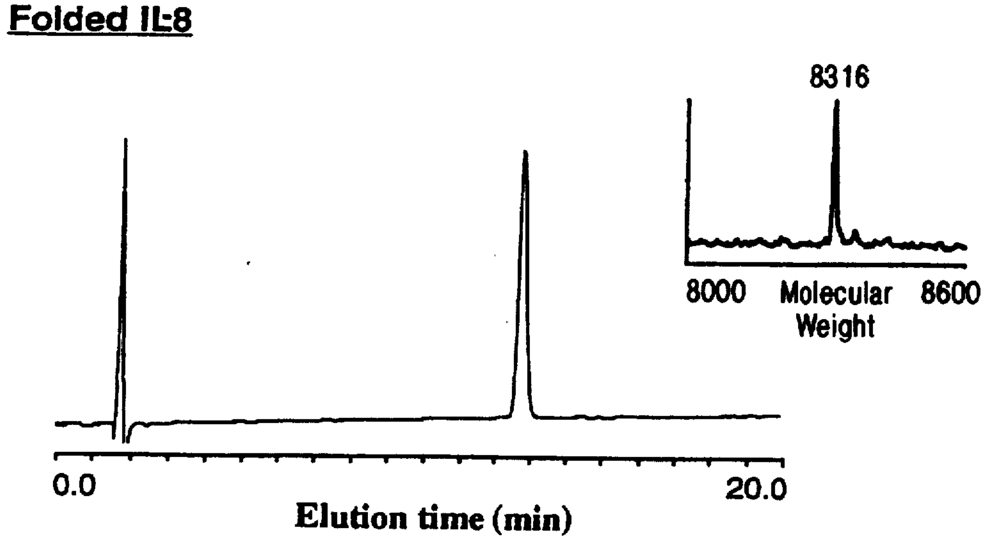

As shown in FIG. 8C, an analytical HPLC spectrum ($C_{18}$ reversed phase; 25 to 45% acetonitrile at 1% per minute; monitored at 214 nm) of the purified ligation product, IL-8(1–72)$(SH)_4$ (Sequence No.: 10), in fully reduced form. (Inset) Electrospray mass spectrum (raw data displayed as a single charge state): observed molecular mass 8319.8 daltons; calculated molecular mass (average isotope composition), 8319.8 daltons.

As shown in FIG. 8D, air oxidation of the purified 1–72 ligation product forms the folded $[Ala^{33}]$IL-8 molecule, shown after HPLC purification. The earlier elution of the folded, disulfide cross-linked native protein compared with the reduced polypeptide is typical (see Lewis et. al *FEB Lett.* (1989): vol. 307, p 97; Lewis et al *J. Biol Chem.* : vol. 269, p 16075; Lewis et. al *Biochemistry* (1991): vol. 30, 3128).

Folding and oxidation conditions: polypeptide at 0.2 mg/ml, 1M guanidine-HCl, pH 8.5 tris buffer, and vigorous stirring in air at ambient temperature (inset). Electrospray mass spectrometry of the oxidized and folded synthetic IL-8 (raw data displayed as a single charge state). Observed molecular mass, 8315.6 daltons; calculated molecular mass (average isotope composition), 8315.8 daltons. (FIG. 8).

Example 4

HIV-1 K41 Protease (unpublished conditions)

Ligation reactions are performed in several ways. An optimized procedure for a ligation reaction involving a (5-thio-2-nitrobenzoic acid) SNB thioester is to weigh the two peptides, HIV (1–40)-COSNB (Sequence No.: 11, formed from standard conditions stated herein) and HIV (41–99) (Sequence No.: 12, formed from standard conditions stated herein), as solids in the same reaction vessel and add 6.0 M guanidine HCl pH 6.5 with 100 mM Na acetate (the approximate peptide concentration is 7–13 mg/mL of each peptide).

After 5 min, approx. 2.0% thiol is added. Two thiol catalysts have been used, viz. benzyl mercaptan (forms the benzyl thioester insitu; Sequence No.: 13) and thiophenol (forms the phenyl thioester insitu; sequence No.: 14). In the ligation of HIV PR, reaction with benzyl mercaptan gave greater than 60% product yield in 40 hours while the thiophenol gave greater than 80% product yield in 10 hours to form HIV-1 K41 protease (Sequence No.: 15).

Figure 9:
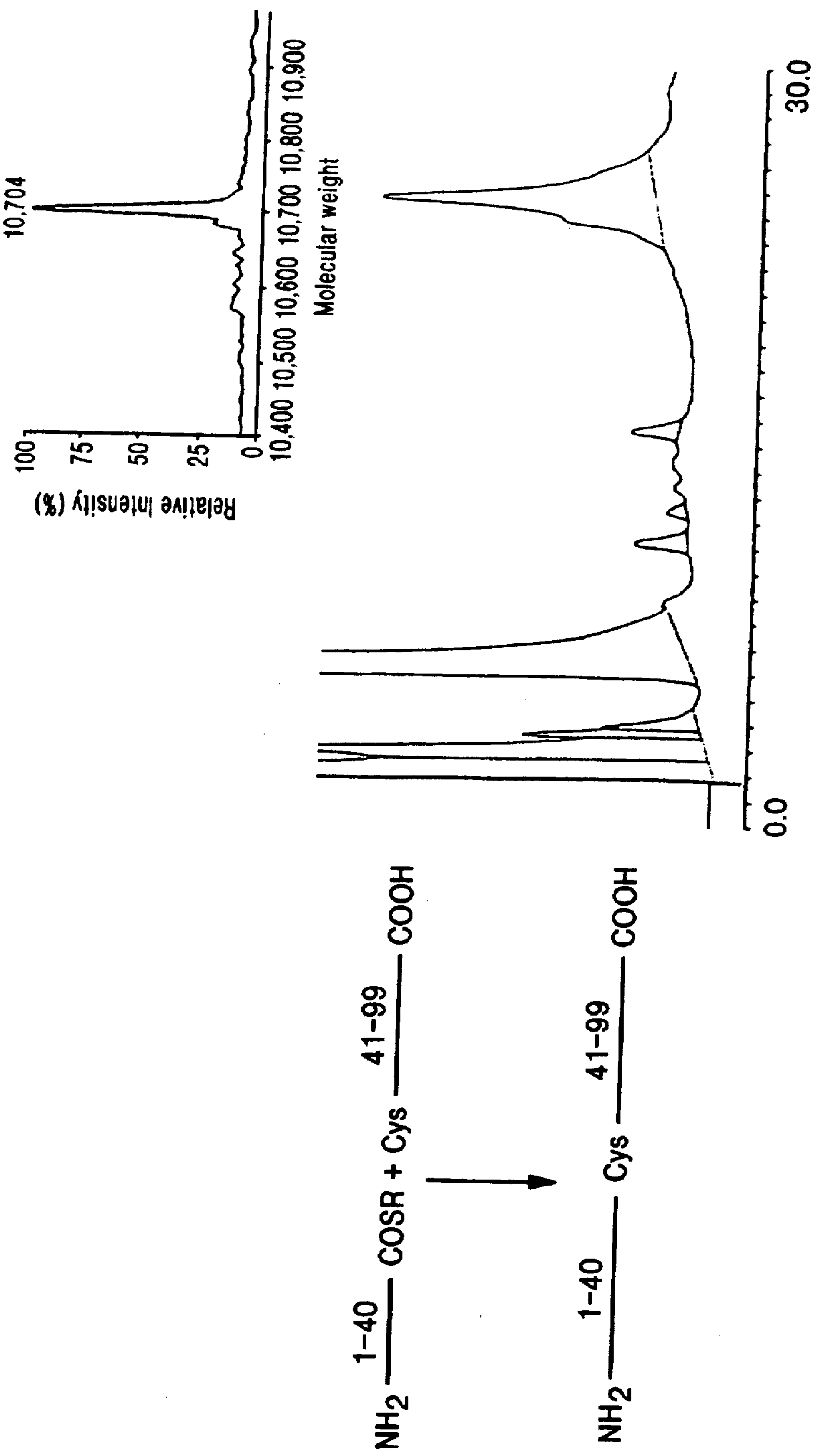
FIG. 9 illustrates the reversed-phase HPLC purification and electrospray mass spectroscopy of HIV-1 K41 protease (Sequence No.: 15) as formed by native chemical ligation of peptides Sequence No.'s 11 and 12 in Example 4.

Subsequent treatment with TCEP was found to aid in the purification and analysis of product by reducing the thiophenol and benzyl mercaptan disulfide products which tend to co-elute with peptide products. The product was purified by standard reversed-phase HPLC as described via supra and characterized by electrospray mass spectroscopy (FIG. 9).

Example 5

Barnase Example (unpublished conditions)

Figure 10A:
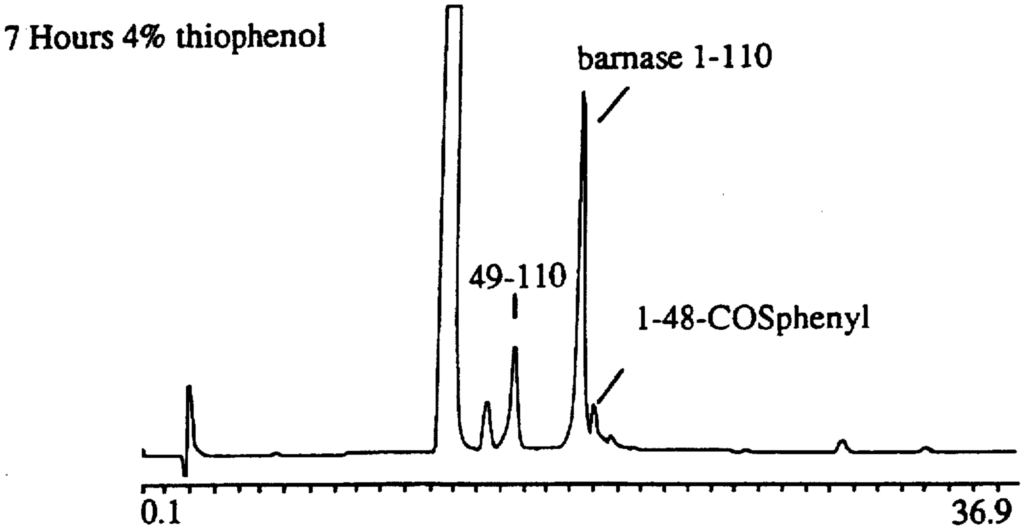
FIG. 10 illustrates the reversed-phase HPLC purification of Barnase K39 (Sequence No.: 20) as formed by native chemical ligation of peptide Sequence No's. 17 and 18 in Example 5.
Figure 10B:
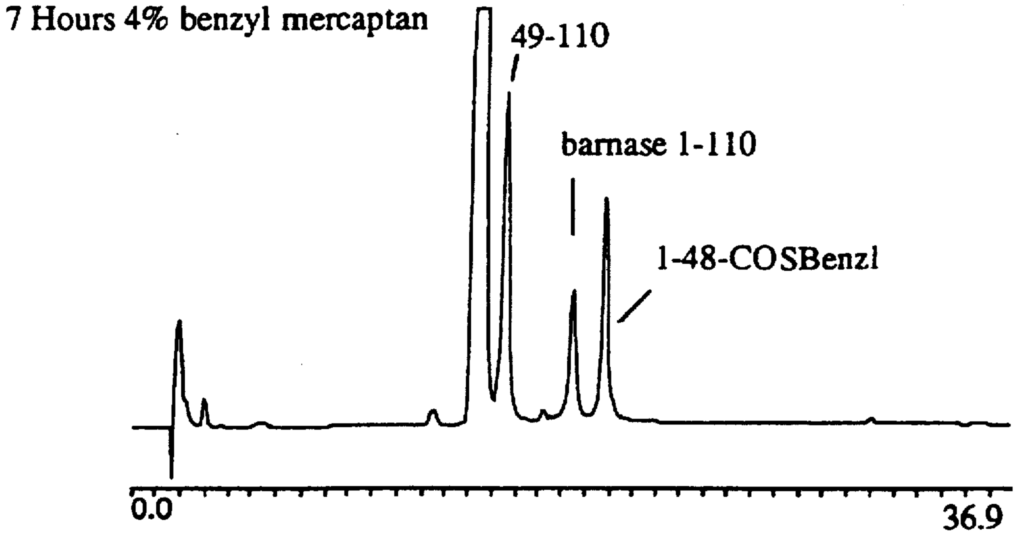

The two peptides Barnase(1–48)-SNB (Sequence No.: 16, formed from standard conditions stated herein) and Barnase (49–110), (Sequence No.: 17, formed from standard conditions stated herein) were weighed as solids in the same reaction vessel and dissolved in pH 7.5 buffer (6M Guanidine 100 mM phosphate). Immediately upon dissolving the peptides, 2% benzyl mercaptan (forms the benzyl thioester insitu; Sequence No.: 18) or 4% thiophenol (forms the phenyl thioester insitu; Sequence No.: 19) was added. After 7 hours, the benzyl mercaptan reaction proceeded 25% and the thiophenol reaction proceeded to >90% to form Barnase (1–110) (Sequence No.: 20). The product was purified by standard reversed-phase HPLC as described via supra (FIG. 10).

The addition of thiols increases the reactivity of the thioester, particularly if the added thiol is a better leaving group than the pre-formed thioester. An example of this observation is when the benzyl ester is converted to a phenyl ester by addition of thiophenol to reaction. Reaction yields and rates are substantially increased. For example, after 7 hours with benzyl mercaptan, the Barnase reaction yielded 25%, while the thiophenol treatment to the same reaction mixture yielded 90% to form Barnase (1–110) (Sequence No.: 20).

Addition of thiols to the ligation mixture also keeps the reaction mixture in a reduced form. This prevents oxidation of the reactive N-terminal Cys residues and when internal Cys residues are present, the thiols reduce the formation of intramolecular disulfide bonds. Additionally, the reducing environment increases the stability of the thioester segment (ligation reactions can proceed overnight with little or no hydrolysis at pH 7.5).

What is claimed is:

1. A method for ligating a first oligopeptide with a second oligopeptide end to end for producing an oligopeptide product, the method comprising the following steps:

Step A: admixing the first and second oligopeptides in a reaction solution including a catalytic thiol, the first oligopeptide including a C-terminal thioester, the second oligopeptide including an N-terminal cysteine having an unoxidized sulfhydryl side chain; then Step B: condensing the unoxidized sulfhydryl side chain of the N-terminal cysteine with the C-terminal thioester for producing an intermediate oligopeptide linking the first and second oligopeptides with a β-aminothioester bond; and then Step C: rearranging the β-aminothioester bond of the intermedite oligopeptide of said Step B for producing the oligopeptide product linking the first and second oligopeptides with an amide bond.

2. A method as described in claim 1 wherein, in said step A, the catalytic thiol is selected from the group consisting of unconjugated mercaptans and conjugated thiols.

3. A method as described in claim 2 wherein, in said step A, the catalytic thiol is benzyl mercaptan.

4. A method as described in claim 2 wherein, in said step A, the catalytic thiol is a conjugated thiol selected from the group consisting of thiophenol, 1-thio-2-nitrophenol, 2-thio-benzoic acid, 2-thio-pyridine, 4-thio-2-pyridinecarboxylic acid, and 4-thio-2-nitro-pyridine.

5. A method as described in claim 4 wherein, in said step A, the conjugated thiol is thiophenol.

6. An oligopeptide intermediate comprising:

a first oligopeptide segment having a C-terminal thioester, a second oligopeptide segment having a N-terminal cysteine, and a β-aminothioester linkage unit linking the C-terminal thioester and the N-terminal cysteine, said β-aminothioester linkage unit spontaneously rearranging intramolecularly to form an amide bond linking said first and second oligopeptides segments end to end.

7. A method for producing an oligopeptide having a C-terminal thioester, the method comprising the following steps:

Step A: providing a resin having a linker with an unoxidized thiol;

Step B: providing a Boc-amino acid succinimide ester; then

Step C: admixing the resin of said Step A and the Boc-amino acid succinimide ester of said Step B under reaction conditions for producing a Boc-amino thioester-resin; then Step D: assembling an oligopeptide onto the Boc-amino thioester-resin by stepwise solid phase peptide synthesis; then Step E: cleaving the Boc-amino thioester-resin of said Step D with HF for producing an oligopeptide having a C-terminal thiol; and then Step F: converting the oligopeptide having a C-terminal thiol of said Step E to the oligopeptide having a C-terminal thioester.

* * * * *

UNITED STATES PATENT AND TRADEMARK OFFICE

CERTIFICATE OF CORRECTION

PATENT NO. : 6,184,344
DATED : November 14, 2000
INVENTOR(S) : Bi

It is certified that error appears in the above-identified patent and that said Letters Patent is hereby corrected as shown below:

Please add the attached appendix after column 58, line 8.

Signed and Sealed this

Fifth Day of February, 2002

*Attest:*

JAMES E. ROGAN

*Attesting Officer*

*Director of the United States Patent and Trademark Office*

APPENDIX

```
Copr. 1995 Zenith Data Systems Corp
#include "sr.h"
#include "sio.h"
#include "spawn.h"
#include "frame.h"
#include "sm.h"
#include "sl.h"

#if defined( _MSC_VER )
#pragma warning( disable : 4704 )
#endif

static char szPrompt[] = STR_PROMPT;
static char szLSLProg[] = STR_LSL;
static char szLSLProgParm[
SL_LSL_CMD_LENGTH ];
static char szIPXODIProg[] = STR_IPXODI;
static char szProximProg[] = STR_PROXIM;
static char szSMANProg[] =
STR_SMANPROGNAME;
static char szSViewProg[] =
STR_SVIEWPROGNAME;
static char szSViewParm[] =
STR_WELCOMESCREEN;
static char szPenDrvProg[] =
STR_PDRVPROGNAME;
static char szSDrvNetProg[] =
STR_SDRVNETPROGNAME;
static char szRWinProg[] = STR_RWINPROGNAME;
static char szCommandProg[] =
STR_COMMANDPROGNAME;
static char szCommandParm[] =
STR_COMMANDPARM;
static char szCommandDir[] = STR_COMMANDDIR;
static char szFormatPrompt[ 10 ];
static char szCommandLine[ 90 ];
static char szNullStr[] = "\0";
static char szOutStr[ 80 ];
static char szProgParmStr[ 80 ];

static BOOL fExit, fNextCommand, fAutoStart =
FALSE, fError =
FALSE;
static BYTE fVIDRedir = FALSE, fTitleScreen =
FALSE, fLoadSMLow =
FALSE,
        fAllowAbort = FALSE;
static char *sToken, *szProgName, *szProgParms;

static int iErrorCode = ERR_SUCCESS;
static int iCol;
static WORD wParms;
static word stsStack[ MAX_STACKSIZE + 1 ];

static GENERALSTATEIDXS iGeneralState;
static COMMANDSTATEIDXS iCommandState;
static TRAPREC VIDTrapRec;
static TRAPREC SMTrapRec;

void main()
{
  int iCmdLineIdx;
  BYTE nLenCmdLine;

  sprintf( szFormatPrompt, "\n%s", szPrompt );

  chk_video();
  get_crs();
  crs_x = bare_x;
  crs_y = bare_y;
  mv_crs();

  fExit = FALSE;

  iCmdLineIdx = str_pos( '-', cmd_line );
  nLenCmdLine = str_len( cmd_line );

  while ( iCmdLineIdx > 0 && iCmdLineIdx <
nLenCmdLine )
  {
    switch ( cmd_line[ iCmdLineIdx ] | 0x20 )
    {
      case 'y':
        fAutoStart = TRUE;

        if ( ( ( cmd_line[ iCmdLineIdx + 1 ] | 0x20 ) ==
't' ) )
        {
          fTitleScreen = TRUE;
          fVIDRedir = TRUE;
        }
        break;

      case 'l':
        fLoadSMLow = TRUE;
        break;

      case 'a':
        fAllowAbort = TRUE;
        break;

      default:
        printf( "\nERROR: invalid parameter\n" );
        break;
    }

    *( cmd_line + iCmdLineIdx - 1 ) = ' ';

    iCmdLineIdx = str_pos( '-', cmd_line );
  }

  if( fVIDRedir )
  {
    printf( "Servlogs Loader, Copyright (c) 1994-1995
Zenith Data
Systems\n" );
    printf( "Mobile Systems Engineering. Version
1.1\n" );
  }

  if( fAutoStart )
  {
    clr_scr();

    crs_x = 0;
    crs_y = 0;
    mv_crs();

    if( fTitleScreen )
    {
      RunProgram( szSViewProg, szSViewParm );
    }

    if ( KeyPressed( 2 ) )
    {
      switch( GetActionKey() )
      {
        case KBD_DIAG:
          change_dir( szCommandDir );
          RunProgram( szCommandProg,
szCommandParm );
          DoExit( 1 );
          break;

        case KBD_ABORTLOAD:
          if ( fAllowAbort )
            DoExit( 1 );
          break;
      }
    }
  }

  do
  {
    iCol = 0;

    if( fError )
      fil_chr( szCommandLine, 0, sizeof(
szCommandLine ) );
    else
      fError = FALSE;

    if ( fAutoStart )
    {
      printf( szFormatPrompt );
      edit_str( szCommandLine,
MAX_WIDTHOFSCREEN - sizeof(
szPrompt ), &iCol, pstay );
      up_case( szCommandLine );
    }
    else
    {
      szCommandLine[0] = 'C';
      szCommandLine[1] = 'W';
      fAutoStart = FALSE;
    }

    sToken = szCommandLine;
    iGeneralState = STM_COMMAND;
    iCommandState = COM_UNKNOWN;
    fNextCommand = FALSE;

    while ( *sToken != NULL && !fNextCommand &&
!fExit )
    {
      if ( iGeneralState > STM_UNKNOWN )
        iGeneralState = STM_UNKNOWN;

      if ( ( iErrorCode = ( *fnStateTableProcs[
iGeneralState ]
)() ) == ERR_INTERNAL )
        fExit = TRUE;
    }
  } while ( !fExit );

  DoExit( 0 );
}

void DoExit( int iStatus )
{
  RemoveVidTrap();
  SetVideoMode( SM_TEXTVIDMODE | 0x80 );

  exit( iStatus );
}

int ProcessIdle( void )
{
  return ( ERR_SUCCESS );
}

int ParseCommand( void )
{
  switch ( *sToken )
  {
    case 'R':
      if ( *( sToken + 1 ) == VAL_SPACE )
      {
        iGeneralState = STM_PARM;
        iCommandState = COM_RUNPROG;
        sToken += 2;
      }
      else if ( *( sToken + 1 ) == NULL )
      {
        iGeneralState = STM_EXECUTE;
        iCommandState = COM_RUNSM;
      }
      else
        goto com_unknown;
      break;

    case 'C':
      if ( *( sToken + 2 ) == NULL )
      {
        iGeneralState = STM_EXECUTE;

        if ( *( sToken + 1 ) == 'D' )
          iCommandState = COM_RUNDOSCOS;
        else if ( *( sToken + 1 ) == 'W' )
          iCommandState = COM_RUNWINCOS;
        else
          goto com_unknown;
      }
      else
        goto com_unknown;
      break;

    case 'X':
      if ( *( sToken + 1 ) == 'X' )
        iGeneralState = STM_EXIT;
      else
        goto com_unknown;
      break;

    default:
com_unknown:
      printf( "\nERROR: command unknown" );
      fError = fNextCommand = TRUE;
  }

  return ( ERR_SUCCESS );
}

int ParseParameters( void )
{
  switch ( iCommandState )
  {
    case COM_RUNPROG:
      if ( ( wParms = str_pos( VAL_SPACE, sToken )
) > 0 )
      {
        *( sToken + ( wParms - 1 ) ) = NULL;
        szProgName = sToken;
        sToken += wParms;
        sprintf( szProgParmsStr, " %s\r", sToken );
        szProgParms = szProgParmsStr;
      }
      else
      {
        szProgName = sToken;
        szProgParms = szNullStr;
      }

      iGeneralState = STM_EXECUTE;
      break;

    default:
      fError = TRUE;
      printf( "\nERROR: unknown command in the
parse parameter
state" );
      break;
  }

  return ( ERR_SUCCESS );
}

int ExecuteCommand( void )
{
  if ( fVIDRedir )
    printf( "\n" );

  switch ( iCommandState )
  {
    case COM_RUNSM:
      fNextCommand = TRUE;
      RunProgram( szSMANProg, szNullStr );
      break;

    case COM_RUNDOSCOS:
    case COM_RUNWINCOS:
      fNextCommand = TRUE;

      if( fVIDRedir )
        InitTraps( ITR_SETVIDTRAP );
      else
        InitTraps( ITR_NOSETVIDTRAP );

      if( LoadSM( fLoadSMLow ?
SMD_ALLOCFIRSTFIT :
SMD_ALLOCBESTFIT ) != ERR_SUCCESS )
        break;

      strcpy( szLSLProgParm, " " );

      switch ( GetFrameType() )
      {
        case SL_FT_E802_2:
          strcat( szLSLProgParm,
SL_LSL_CMD_E802_2 );
          break;

        case SL_FT_EII:
          strcat( szLSLProgParm, SL_LSL_CMD_EII );
          break;

        case SL_FT_ESNAP:
          strcat( szLSLProgParm,
SL_LSL_CMD_ESNAP );
          break;

        case SL_FT_E802_3:
          strcat( szLSLProgParm,
SL_LSL_CMD_E802_3 );
          break;

        default:
          if ( fVIDRedir )
            printf( "ERROR: invalid Frame Type
detected. The
default Frame Type 802.3 will be used.\n" );
          strcat( szLSLProgParm,
SL_LSL_CMD_E802_3 );
          break;
      }

      if (
#if defined( MOUSE )
          RunProgram( "mouse.com", szNullStr ) !=
ERR_SUCCESS
||
#else
          RunProgram( szPenDrvProg, szNullStr ) !=
ERR_SUCCESS
||
#endif
          LoadNetwork() != ERR_SUCCESS ||
          RunProgram( szSDrvNetProg, " -M1
-C0848 -INT20\r" ) !=
ERR_SUCCESS )
        break;

      if ( iCommandState == COM_RUNWINCOS )
        RunProgram( szRWinProg, szNullStr );

      iGetSUI();
      break;

    case COM_RUNPROG:
      fNextCommand = TRUE;
      RunProgram( szProgName, szProgParms );
      break;

    default:
      fError = TRUE;
```

```
    printf( "\nERROR: unknown command in the
execution state" );
  }
    break;
  }

  return ( ERR_SUCCESS );
}

int ProcessSLExit( void )
{
  fExit = TRUE;

  return ( ERR_SUCCESS );
}

int ProcessStateUnknown( void )
{
  printf( "\nERROR: unknown state" );

  return ( ERR_INTERNAL );
}

int RunProgram( char *szProgName, char
*szProgParms )
{
  int iSpawnReturn;

  if ( ( iSpawnReturn = spawn_w( szProgName,
szProgParms ) ) ==
0 )
    iSpawnReturn = ERR_SUCCESS;
  else
  {
    if ( fVIDRedir )
      printf( "\nERROR: %s, spawn error %d",
szProgName,
      iSpawnReturn );
    fError = TRUE;
  }

  return ( iSpawnReturn );
}

int LoadMLID( char *szProgName )
{
  int iLoadIdx;

  for ( iLoadIdx = 0; iLoadIdx <
MAX_MLIDLOADRETRY; ++iLoadIdx )
  {
    if ( RunProgram( szProgName, szNullStr ) !=
ERR_SUCCESS )
      return ( ERR_INTERNAL );

    if ( GetMLIDStatus() == TRUE )
      return ( ERR_SUCCESS );
  }

  sprintf( szOutStr,
      "\nERROR: The load sequence was aborted
due to a
failure in the loading of %s.\n",
      szProximProg );

  DisplayError( szOutStr );

  return ( ERR_INTERNAL );
}

int EnableKbd( void )
{
  REG_W InArgs, OutArgs;

  fl_chr( &InArgs, 0, sizeof( InArgs ) );

  InArgs.ax = SM_SLENABLEKBD;

  intw( &InArgs, &OutArgs, SM_SCSINTNUM );

  return ( 0 );
}

int GetFrameType( void )
{
  REG_W InArgs, OutArgs;

  fl_chr( &InArgs, 0, sizeof( InArgs ) );

  InArgs.ax = SM_SLGETFRAMETYPE;

  intw( &InArgs, &OutArgs, SM_SCSINTNUM );

  return ( OutArgs.ax );
}

int GetMLIDStatus( void )
{
  REG_W InArgs, OutArgs;

  fl_chr( &InArgs, 0, sizeof( InArgs ) );

  InArgs.ax = SM_SLGETMLIDSTATUS;

  intw( &InArgs, &OutArgs, SM_SCSINTNUM );

  return ( OutArgs.ax );
}

void SetOldVidVector( LONG lOldVidVector )
{
  REG_W InArgs, OutArgs;

  fl_chr( &InArgs, 0, sizeof( InArgs ) );

  InArgs.ax = SM_SLSETOLDVIDVECTOR;
  InArgs.bx = OFF( lOldVidVector );
  InArgs.dx = SEG( lOldVidVector );
  intw( &InArgs, &OutArgs, SM_SCSINTNUM );
}

int ExitSM( void )
{
  REG_W InArgs, OutArgs;

  RemoveVidTrap();

  fl_chr( &InArgs, 0, sizeof( InArgs ) );

  InArgs.ax = SM_SLLOADSM;

  intw( &InArgs, &OutArgs, SM_SCSINTNUM );

  EnableKbd();

  return ( 0 );
}

int LoadSM( int iMemStrategy )
{
  int iRunStatus;

  if ( iMemStrategy != SMO_ALLOCFIRSTFIT )
  {
    PatchMCB();
    SetMemStrategy( iMemStrategy );
  }

  iRunStatus = RunProgram( szSMANProg
szNullStr );

  SetMemStrategy( SMO_ALLOCFIRSTFIT );

  return ( iRunStatus );
}

int LoadNetwork( void )
{
  if ( RunProgram( szLSLProg, szLSLProgParm ) !=
ERR_SUCCESS ||
      LoadMLID( szProximProg )        !=
ERR_SUCCESS ||
      RunProgram( szIPXODIProg, szNullStr ) !=
ERR_SUCCESS )
    return ( ERR_INTERNAL );

  return ( ERR_SUCCESS );
}

int KeyProcessIn( int iDelay )
{
  int iTickCount;
  long lSyncCount;

  bfFlag = 0;

  if ( fVIDRedir )
  {
    if ( fAllowAbort )
      printf( "\n[CTRL]+[ALT]+A to abort load
sequence or
[CTRL]+[ALT]+D to load diagnostic...\n" );
    else
      printf( "\n[CTRL]+[ALT]+D to load
diagnostic...\n" );
  }

  for ( iTickCount = 0; iTickCount < iDelay;
++iTickCount )
  {
    lSyncCount = sync_tick();

    while ( TRUE )
    {
      if ( sync_tick() - lSyncCount >= 20 )
        break;

      if ( anykey() )
        return ( TRUE );
    }
  }

  return ( FALSE );
}

ACTIONKEYS GetActionKey( void )
{
  WORD wKey;

  if ( anykey() )
  {
    wKey = getkey();

    if ( bfFlag & KBD_CTRLMASK &&
        bfFlag & KBD_ALTMASK )
    {
      switch( wKey )
      {
        case KBD_DSCAN:
          return ( KBD_DIAG );

        case KBD_ASCAN:
          return ( KBD_ABORTLOAD );
      }
    }
  }

  return ( KBD_NOACTIONKEY );
}

void InitTraps( BYTE nVidTrapStatus )
{
  install_trap( ( lb )TrapService, MAX_STACKSIZE *
sizeof ( int
), SMD_FULLREENTER );
  enable_ter( starStack, MAX_STACKSIZE * sizeof (
int ) );

  if ( nVidTrapStatus == ITR_SETVIDTRAP )
  {
    VIDTrapRec.tr_int = SSS_VIDINTNUM;
    VIDTrapRec.tr_sem_srv =
CRU_ONBUSYOLDINT;

    add_trap( &VIDTrapRec );

    fVIDRedir = TRUE;
  }

  SMTrapRec.tr_int = SSS_SLINTNUM;
  SMTrapRec.tr_sem_srv = CRU_ONBUSYOLDINT;

  add_trap( &SMTrapRec );
}

BOOL RemoveVidTrap( void )
{
  BOOL fReturn = FALSE;
  DWORD dwCurrVidTrap;
  DWORD dwOldVidTrap = VIDTrapRec.tr_old_int;

  PCS_BEGINCRITICAL;

  if ( VIDTrapRec.tr_int != 0 )
  {
    SetOldVidVector( dwOldVidTrap );
    if ( ( dwCurrVidTrap = clr_trap( &VIDTrapRec ) )
!=
dwOldVidTrap )
      set_int_vec( SSS_VIDINTNUM, dwCurrVidTrap
);

    VIDTrapRec.tr_int = 0;

    fReturn = TRUE;
    fVIDRedir = FALSE;
  }

  PCS_ENDCRITICAL;

  return ( fReturn );
}

void DisplayError( char *szErrStr )
{
  RemoveVidTrap();
  SetVideoMode( SM_TEXTVIDMODE | 0x80 );

  printf( szErrStr );
}

WORD TrapService( struct trap_rec *CurrTrapRec )
{
  struct REGW InRegs, OutRegs;
  WORD wFlags;

  GetForegroundRegs( &InRegs );

  switch ( CurrTrapRec->tr_int )
  {
    case SSS_VIDINTNUM:
      switch ( HIBYTE( InRegs.ax ) )
      {
        case SSS_TELETYPE:
          break;

        case SSS_RELOCATEDSCRADD:

          wFlags = intw( &InRegs, &OutRegs,
SSS_VIDINTNUM );
          SetForegroundRegsFlags( &OutRegs,
SFR_SETFLAGS, wFlags
);
          SetVideoMode( SM_INITIALVIDMODE );

          break;

        default:
          return ( ( WORD )CurrTrapRec );
      }
      break;

    case SSS_SLINTNUM:
      wFlags = intw( &InRegs, &OutRegs,
SSS_INTNUM );
      SetForegroundRegsFlags( &OutRegs,
SFR_SETFLAGS, wFlags );
      break;

    default:
      return ( ( WORD )CurrTrapRec );
  }

  return ( 0 );
}

void GetForegroundRegs( struct REGW *InRegs )
{
  register struct sreg *s;
  register struct REGW *r;
  struct glob_stk far *p;

  r = InRegs;
  s = _int_frame;

  r->es = s->es;
  r->bp = s->bp;
  r->di = s->di;
  r->si = s->si;
  r->ax = s->ax;

  *(word*)&p = s->saved_sp;
  *((word*)&p+1) = s->saved_ss;

  r->ds = p->ds;
  r->dx = p->dx;
  r->bx = p->bx;
  r->cx = p->cx;
}

void SetForegroundRegsFlags( struct REGW
*OutRegs, BYTE
fSetFlags, WORD wFlags )
{
  struct sreg *s;
  struct REGW *r;
  struct glob_stk far *p;

  r = OutRegs;
  s = _int_frame;

  s->es = r->es;
  s->bp = r->bp;
  s->di = r->di;
  s->si = r->si;
  s->ax = r->ax;

  p = ( struct glob_stk far * )MK_FP( s->saved_ss,
s->saved_sp );

  p->ds = r->ds;
  p->dx = r->dx;
  p->bx = r->bx;
  p->cx = r->cx;

  if ( fSetFlags == SFR_SETFLAGS )
    p->Flags = wFlags;
}

WORD SetVideoMode( BYTE nRequestedMode )
{
  int AX;

  AX = MAKEWORD( nRequestedMode, 0 );
```

```
    int16( AX );

    return ( 0 );
}

#if defined( _MSC_VER )
#pragma warning( default : 4704 )
#endif
Copr 1995 Zenith Data Systems Corp.

#include "xr.h"
#include "xio.h"
#include "xpmem.h"
#include "frame.h"
#include "sm.h"

#define MCB_TARGETSEGMENT 0xC300
#define MCB_TARGETSEGSIZE 0x1000
#define MCB_OWNERDOS 0x0008

MCB far *GetFirstMCB( void );
MCB far *GetNextMCB( MCB far *lpCurrMCB );
MCB far *GetLastMCB( void );

int PatchMCB( void )
{
  MCB far *lpLastMCB,
  MCB far *lpBeyondLastMCB,
  MCB far *lpTargetMCB.

  PCS_BEGINCRITICAL

  if ( ( lpLastMCB = GetLastMCB() ) == NULL )
    return ( ERR_INTERNAL );

  lpLastMCB->cType = 'M';
  lpLastMCB->wSize -= 1;

  if ( ( lpBeyondLastMCB = GetNextMCB(
lpLastMCB ) ) == NULL )
    return ( ERR_INTERNAL );

  lpBeyondLastMCB->cType = 'M'.
  lpBeyondLastMCB->wSize =
MCB_TARGETSEGMENT - SEG(
lpBeyondLastMCB ) - 1;
  lpBeyondLastMCB->wOwner =
MCB_OWNERDOS.

  lpTargetMCB = ( MCB far * )MK_FP(
MCB_TARGETSEGMENT, 0 );
  lpTargetMCB->cType = 'Z';
  lpTargetMCB->wOwner = 0;
  lpTargetMCB->wSize = ( WORD
)MCB_TARGETSEGSIZE - 1;

  return ( ERR_SUCCESS );
}

int SetMemStrategy( int iStratCode )
{
  REG_W InRegs, OutRegs,
  WORD wFlags;

  _fmemset( ( NPSTR )&InRegs, 0, sizeof( REG_W ) );

  InRegs.ax = SMO_GETSETALLOCSTRAT |
SMO_SETALLOCSTRAT;
  InRegs.bx = iStratCode.

  wFlags = intx( &InRegs, &OutRegs, SMO_DOSINT
);

  if ( !( wFlags & GEN_CARRYFLAG ) )
    return ( ERR_SUCCESS );
  else
    return ( ERR_INTERNAL );
}

MCB far *GetFirstMCB( void )
{
  REG_W InRegs, OutRegs;
  WORD wFlags;
  unsigned far *lpListOfLists;

  _fmemset( ( NPSTR )&InRegs, 0, sizeof( REG_W ) );

  InRegs.ax = SMO_GETLISTOFLISTS;

  wFlags = intx( &InRegs, &OutRegs, SMO_DOSINT
);

  if ( !( wFlags & GEN_CARRYFLAG ) )
  {
    lpListOfLists = ( unsigned far * ) MK_FP(
OutRegs.es.
OutRegs.bx - 2 );
    return ( ( MCB far * ) MK_FP( *lpListOfLists, 0 ) );
  }
  else
    return ( NULL );
}

MCB far *GetNextMCB( MCB far *lpCurrMCB )
{
  return ( MK_FP( SEG( lpCurrMCB ) +
lpCurrMCB->wSize + 1, 0 ) );

}

MCB far *GetLastMCB( void )
{
  MCB far *lpLastMCB = GetFirstMCB();

  while ( TRUE )
  {
    if ( lpLastMCB == NULL )
      return ( NULL );

    lpLastMCB = GetNextMCB( lpLastMCB );

    if ( lpLastMCB->cType == 'Z' )
      return ( lpLastMCB );
  }
}


Copr. 1995 Zenith Data Systems Corp.

#include "xr.h"
#include "xpmem.h"
#include "sm.h"
#include "fm.h"

BOOL f2MegFlash = FALSE;
static BYTE nCurrVidPalette = 0;
static BYTE nCurrSpeakerState = FON;
static BYTE nCurrRightMouseButton = FOFF;
static BYTE fSuspendInProgress = FOFF;

BYTE aBrightValues[] =
{
0,
3,
6,
9,
19,
21,
25,
27,
29,
31,
33
35,
37,
39,
41,
43,
45,
47,
49,
51,
53,
55,
57,
59,
};

BYTE aContrastValues[] =
{
25,
27,
28,
29,
30,
31,
32,
34,
36,
38,
39,
40,
41,
42,
43,
44,
45,
46,
47,
48,
49,
50,
51,
52,
};

int SetContrast( BYTE nContrastIdx )
{
  REG_W InRegs, OutRegs,
  WORD wFlags,

  _fmemset( ( NPSTR )&InRegs, 0, sizeof( REG_W ) );

  InRegs.ax = SSS_SARATOGAFUNC;
  InRegs.bx = SSS_ADJUSTCONTRAST;
  InRegs.cx |= aContrastValues[ nContrastIdx ];

#if defined( NOINT15 )
  wFlags = intx( &InRegs, &OutRegs,
SSS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

int SetBrightness( BYTE nBrightnessIdx )
{
  REG_W InRegs, OutRegs;
  WORD wFlags;

  _fmemset( ( NPSTR )&InRegs, 0, sizeof( REG_W ) );

  InRegs.ax = SSS_SARATOGAFUNC;
  InRegs.bx = SSS_ADJUSTBRIGHTNESS,
  InRegs.cx |= aBrightValues[ nBrightnessIdx ];

#if defined( NOINT15 )
  wFlags = intx( &InRegs, &OutRegs,
SSS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

int SetPowerEnable( BYTE nPowerMode )
{
  REG_W InRegs, OutRegs,
  WORD wFlags;

  _fmemset( ( NPSTR )&InRegs, 0, sizeof( REG_W ) );

  InRegs.ax = SSS_SARATOGAFUNC;
  InRegs.bx = SSS_SETPOWERENABLE,
  InRegs.cx |= ( WORD )nPowerMode;


#if defined( NOINT15 )
  wFlags = intx( &InRegs, &OutRegs,
SSS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

int SetDozeTimeout( BYTE nDozeIdx )
{
  REG_W InRegs, OutRegs;
  WORD wFlags;

  _fmemset( ( NPSTR )&InRegs, 0, sizeof( REG_W ) );

  InRegs.ax = SSS_SARATOGAFUNC;
  InRegs.bx = SSS_SETDOZETIMEOUT;
  InRegs.cx |= ( WORD )nDozeIdx;

#if defined( NOINT15 )
  wFlags = intx( &InRegs, &OutRegs,
SSS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

int SetSleepTimeout( BYTE nSleepIdx )
{
  REG_W InRegs, OutRegs;
  WORD wFlags;

  _fmemset( ( NPSTR )&InRegs, 0, sizeof( REG_W ) );

  InRegs.ax = SSS_SARATOGAFUNC;
  InRegs.bx = SSS_SETSLEEPTIMEOUT;
  InRegs.cx |= nSleepIdx;

#if defined( NOINT15 )
  wFlags = intx( &InRegs, &OutRegs,
SSS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

int SetSuspendTimeout( BYTE nSuspendIdx )
{
  REG_W InRegs, OutRegs;
  WORD wFlags;

  _fmemset( ( NPSTR )&InRegs, 0, sizeof( REG_W ) );

  InRegs.ax = SSS_SARATOGAFUNC;
  InRegs.bx = SSS_SETSUSPENDTIMEOUT;
  InRegs.cx |= nSuspendIdx;

#if defined( NOINT15 )
  wFlags = intx( &InRegs, &OutRegs,
SSS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

void Set2MegFlash( BOOL fNew2MegFlash )
{
  f2MegFlash = fNew2MegFlash;
}

BOOL IsFlashSupported( void )
{
  REG_W InRegs, OutRegs,

  _fmemset( ( NPSTR )&InRegs, 0, sizeof( InRegs ) );

  InRegs.ax  = SSS_SARATOGAFLASH;
  InRegs.cx |= SSS_FLASHAVAILABLE;

#if defined( FLASHTEST )
  intx( &InRegs, &OutRegs, SSS_SLINTNUM );
#else
  return ( TRUE );
#endif

  return ( OutRegs.ax ==
SSS_FLASHAVAILRETCODE );
}

int FlashSector( LPSTR sFlashImageBuff, int
iCurrFlashFile )
{
  REG_W InRegs, OutRegs;
  int iFlashSector, iReturn;
  WORD wFlags;
  LONG l20BitAddr;

  if ( iCurrFlashFile == 0 || sFlashImageBuff ==
NULL )
    return ( ERR_INVALIDPARM );

  if ( EnableFlashWrite( TRUE ) != ERR_SUCCESS
)
    return ( ERR_INTERNAL );

  _fmemset( &InRegs, 0, sizeof ( InRegs ) );

  if ( f2MegFlash )
    iFlashSector = SSS_2MEGBASESECTOR + (
iCurrFlashFile - 1 );
  else
    iFlashSector = SSS_1MEGBASESECTOR + (
iCurrFlashFile - 1 );

  l20BitAddr = ( ( LONG )SEG( sFlashImageBuff )
* 16 ) + OFF(
sFlashImageBuff );
```

```
  InRegs.ax = MAKEWORD( SBS_FLASHNOTEXT,
HIBYTE(
SBS_SARATOGAFLASH ) );
  InRegs.bx = MAKEWORD( LOBYTE( HIWORD(
l2ndEAdd ) ),
                 LOBYTE( lFlashSector ) );
  InRegs.di = LOWORD( l2ndEAdd );

#if defined( FLASHTEST )
  wFlags = Intx( &InRegs, &OutRegs,
SBS_SLINTNUM );
#else
  wFlags = 0;
#endif

  if ( !( wFlags & GEN_CARRYFLAG ) )
    iReturn = SBS_FLASHSUCCESS;
  else
    iReturn = HIBYTE( OutRegs.ax );

  EnableFlashWrite( FALSE );

  return ( iReturn );
}

int EnableFlashWrite( BOOL fEnable )
{
  REG_W InRegs, OutRegs;
  WORD wFlags;

  fl_str( &InRegs, 0, sizeof( InRegs ) );

  InRegs.ax = MAKEWORD( LOBYTE( fEnable ?
SBS_ENABLEWRITE :
SBS_DISABLEWRITE ) ),
                 HIBYTE( SBS_SARATOGAFUNC
) );
  InRegs.bx = SBS_ENABLEDISABLEWRITE;

#if defined( FLASHTEST )
  wFlags = Intx( &InRegs, &OutRegs,
SBS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

int RotatePalette( void )
{
  REG_W InRegs, OutRegs;
  int iCurrVideoMode = GetCurrVidMode();
  BYTE nNewVidPalette;

  fl_str( ( NPSTR )&InRegs, 0, sizeof( REG_W ) );

  if ( iCurrVideoMode == SUI_INITIALVIDMODE )
  {
    if ( nCurrVidPalette != SBS_INVVIDPALLETTE )
      nNewVidPalette = SBS_INVVIDPALLETTE;
    else
      nNewVidPalette = SBS_DEFVIDPALLETTE;
  }
  else
  {
    if ( ( nNewVidPalette = nCurrVidPalette + 1 ) >
      SBS_MAXNUMVIDPAL )
      nNewVidPalette = SBS_DEFVIDPALLETTE;
  }

  InRegs.ax = ( WORD )( SBS_VIDEO |
nNewVidPalette );
  InRegs.bx = ( WORD )( SBS_VIDEOPALLETTE );

#if defined( NOINT15 )
  Intx( &InRegs, &OutRegs, SBS_VIDINTNUM );
#else
#endif

  nCurrVidPalette = nNewVidPalette;

  return ( ERR_SUCCESS );
}

int ToggleSpeaker( void )
{
  REG_W InRegs, OutRegs;
  WORD wFlags;
  BYTE nNewSpeakerState;

  fl_str( ( NPSTR )&InRegs, 0, sizeof( REG_W ) );

  if ( nCurrSpeakerState == FON )
    nNewSpeakerState = FOFF;
  else
    nNewSpeakerState = FON;

  InRegs.ax = SBS_SARATOGAFUNC |
nNewSpeakerState;
  InRegs.bx = SBS_ENADISSPEAKER;

#if defined( NOINT15 )
  wFlags = Intx( &InRegs, &OutRegs,
SBS_SLINTNUM );
#else
  wFlags = 0;
#endif

  if ( !( wFlags & GEN_CARRYFLAG ) )
  {
    nCurrSpeakerState = nNewSpeakerState;
    return ( ERR_SUCCESS );
  }
  else
    return ( ERR_INTERNAL );
}

BYTE GetRightMouseButton( void )
{
  return ( nCurrRightMouseButton );
}

int EnableRightMouseButton( BYTE
nNewRightMouseButton )
{
  REG_W InRegs, OutRegs;
  WORD wFlags;

  fl_str( ( NPSTR )&InRegs, 0, sizeof( REG_W ) );

  InRegs.ax = SBS_SARATOGAFUNC |
nNewRightMouseButton;
  InRegs.bx = SBS_ENADISRIGHTMOUSE;

#if defined( NOINT15 )
  wFlags = Intx( &InRegs, &OutRegs,
SBS_SLINTNUM );
#else
  wFlags = 0;
#endif

  if ( !( wFlags & GEN_CARRYFLAG ) )
  {
    nCurrRightMouseButton =
nNewRightMouseButton;
    return ( ERR_SUCCESS );
  }
  else
    return ( ERR_INTERNAL );
}

int SetTowerIcon( BYTE nTowerStatus, BYTE
nMovesStatus )
{
  REG_W InRegs, OutRegs;
  WORD wFlags;

  fl_str( ( NPSTR )&InRegs, 0, sizeof( REG_W ) );

  InRegs.ax = SBS_SARATOGAFUNC |
nTowerStatus;
  InRegs.bx = SBS_TOWERWINVESICON;
  InRegs.cx = ( WORD )nMovesStatus;

#if defined( NOINT15 )
  wFlags = Intx( &InRegs, &OutRegs,
SBS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

int DoSleep( void )
{
  REG_W InRegs, OutRegs;
  WORD wFlags;

  fl_str( ( NPSTR )&InRegs, 0, sizeof( REG_W ) );

  InRegs.ax = SBS_SARATOGAFUNC;
  InRegs.bx = SBS_GOTOSLEEP;

#if defined( NOINT15 )
  wFlags = Intx( &InRegs, &OutRegs,
SBS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

int DoSuspend( BOOL fSaveEEROMData )
{
  REG_W InRegs, OutRegs;

  fl_str( ( NPSTR )&InRegs, 0, sizeof( REG_W ) );

  if ( fSaveEEROMData )
    SetEEVData();

  InRegs.ax = SBS_SARATOGAFUNC;
  InRegs.bx = SBS_GOTOSUSPEND;

#if defined( NOINT15 )
  Intx( &InRegs, &OutRegs, SBS_SLINTNUM );
#else
#endif

  return ( ERR_INTERNAL );
}

int SetSuspendFlagPointer( void )
{
  REG_W InRegs, OutRegs;
  WORD wFlags;

  fl_str( ( NPSTR )&InRegs, 0, sizeof( REG_W ) );

  InRegs.ax = SBS_SARATOGAFUNC;
  InRegs.bx = SBS_SUSPENDFLAGPTR;
  InRegs.es = SEG( &fSuspendInProgress );
  InRegs.dx = OFF( &fSuspendInProgress );

#if defined( NOINT15 )
  wFlags = Intx( &InRegs, &OutRegs,
SBS_SLINTNUM );
#else
  wFlags = 0;
#endif

  if ( !( wFlags & GEN_CARRYFLAG ) )
  {
    SetSuspendFlag( FOFF );
    return ( ERR_SUCCESS );
  }
  else
    return ( ERR_INTERNAL );
}

void SetSuspendFlag( BOOL fStatus )
{
  PCS_BEGINCRITICAL;
  fSuspendInProgress = LOBYTE( fStatus );
  PCS_ENDCRITICAL;
}

BOOL GetSuspendFlag( void )
{
  BOOL fReturn;

  PCS_BEGINCRITICAL;
  fReturn = fSuspendInProgress;
  PCS_ENDCRITICAL;

  return ( fReturn );
}

int GetSystemResumeBit( void )
{
  REG_W InRegs, OutRegs;
  WORD wFlags;

  fl_str( ( NPSTR )&InRegs, 0, sizeof( REG_W ) );

  InRegs.ax = SBS_SARATOGAFUNC;
  InRegs.bx = SBS_GETSYSRESUMEBIT;

#if defined( NOINT15 )
  wFlags = Intx( &InRegs, &OutRegs,
SBS_SLINTNUM );
#else
  wFlags = 0;
#endif

  if ( !( wFlags & GEN_CARRYFLAG ) )
    return ( OutRegs.ax & 0x00FF );
  else
    return ( ERR_INTERNAL );
}

int ClearSystemResumeBit( void )
{
  REG_W InRegs, OutRegs;
  WORD wFlags;

  fl_str( ( NPSTR )&InRegs, 0, sizeof( REG_W ) );

  InRegs.ax = SBS_SARATOGAFUNC;
  InRegs.bx = SBS_CLEARSYSRESUMEBIT;

#if defined( NOINT15 )
  wFlags = Intx( &InRegs, &OutRegs,
SBS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

int SetWellingtons( BYTE nWellingtonStatus, BYTE
fBusyCursor )
{
  REG_W InRegs, OutRegs;
  WORD wFlags;

  fl_str( ( NPSTR )&InRegs, 0, sizeof( REG_W ) );

  InRegs.ax = SBS_SARATOGAFUNC;
  InRegs.bx = SBS_WAITINGICON;
  InRegs.cx |= nWellingtonStatus;

#if defined( NOINT15 )
  wFlags = Intx( &InRegs, &OutRegs,
SBS_SLINTNUM );
#else
  wFlags = 0;
#endif

  if ( nWellingtonStatus ==
SBS_WAITINGICONOFF )
  {
    if ( fBusyCursor )
      EnableBusyCursor( SUI_BUSYCURSOROFF );

    GetStatIcon();
  }
  else
  {
    if ( fBusyCursor )
      EnableBusyCursor( SUI_BUSYCURSORON );

  }

  if ( !( wFlags & GEN_CARRYFLAG ) )
    return ( ERR_SUCCESS );
  else
    return ( ERR_INTERNAL );
}

int EnableKbdAfterBoot( void )
{
  REG_W InRegs, OutRegs;
  WORD wFlags;

  fl_str( ( NPSTR )&InRegs, 0, sizeof( REG_W ) );

  InRegs.ax = SBS_SARATOGAFUNC;
  InRegs.bx = SBS_ENABLEKBD;

#if defined( NOINT15 )
  wFlags = Intx( &InRegs, &OutRegs,
SBS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

LONG GetBatteryInfo( void )
{
  REG_W InRegs, OutRegs;
  WORD wFlags;

  fl_str( ( NPSTR )&InRegs, 0, sizeof( REG_W ) );

  InRegs.ax = SBS_SARATOGAFUNC;
  InRegs.bx = SBS_GETBATTERYINFO;

#if defined( NOINT15 )
  wFlags = Intx( &InRegs, &OutRegs,
SBS_SLINTNUM );
#else
  wFlags = 0;
#endif
```

```
  if ( !( wFlags & GEN_CARRYFLAG ) )
#if !defined( NOINT15 )
    return ( MAKELONG( OutRegs.ax, OutRegs.bx )
);
#else
    return ( SBS_NOINT15BATTERYINFO );
#endif
  else
    return ( SBS_GETBATTERYINFOERROR );

}

WORD GetSizeOfExtendedMem( void )
{
  BYTE nExtMemHigh, nExtMemLow;

  PCS_BEGINCRITICAL

  outp( SBS_CMOSPORT,
SBS_CMOSREADHIGHBYTE );
  nExtMemHigh = inp(
SBS_CMOSEXTENDEDMEM );
  outp( SBS_CMOSPORT,
SBS_CMOSREADLOWBYTE );
  nExtMemLow = inp(
SBS_CMOSEXTENDEDMEM );

  PCS_ENDCRITICAL

  return ( MAKEWORD( nExtMemLow,
nExtMemHigh ) );
}

int GetBIOSVersion( void )
{
  REG_W InRegs, OutRegs;
  WORD wFlags;

  fl_clr( ( NPSTR )&InRegs, 0, sizeof( REG_W ) );

  InRegs.ax = SBS_SARATOGAFUNC;
  InRegs.bx = SBS_GETBIOSVERSION;

#if !defined( NOINT15 )
  wFlags = int( &InRegs, &OutRegs,
SBS_SLINTNUM );
#else
  wFlags = 0;
#endif

  if ( !( wFlags & GEN_CARRYFLAG ) )
#if !defined( NOINT15 )
    return ( OutRegs.ax );
#else
    return ( 0 );
#endif
  else
    return ( 0 );
}
Copr. 1995 Zenith Data Systems Corp.

#include "pr.h"
#include "sio.h"
#include "smem.h"
#include "sm.h"

#define SMD_MAXBEARIMAGES 8

#if defined( _MSC_VER )
#pragma warning( disable : 4704 )
#endif

static char aBearImages[] = { "|-\-" };

static BYTE nClockReenterCount = 0;
static WORD wLastKey;
static BOOL fDispatchActive = FALSE;
static BOOL fRecsInstalled = FALSE;
static int aEventStack[ SMD_EVENTSTACKLIMIT ];
static int iEventStackPtr =
SMD_EVENTSTACKLIMIT - 1;
static int iTempThreadIdx = -1;

EVENT EventQueue[ SMD_MAXTHREADS ];

int AddThread( int iIdx, NEARPROC lpThread,
APIFUNC
pAPIFuncTable[],
            THREADTYPEID ThreadTypeId, BOOL
fReentrant, LONG
lTimeLimit,
            int iRetryLimit )
{
  if ( iIdx >= SMD_MAXTHREADS )
    return ( ERR_INTERNAL );

  PCS_BEGINCRITICAL
  EventQueue[ iIdx ].lpThread = lpThread;
  EventQueue[ iIdx ].pAPIFuncTable =
pAPIFuncTable;
  EventQueue[ iIdx ].ThreadTypeId = ThreadTypeId;
  EventQueue[ iIdx ].lTimeLimit = lTimeLimit;
  EventQueue[ iIdx ].lTimeCurrent = 0L;
  EventQueue[ iIdx ].iRetryLimit = iRetryLimit;
  EventQueue[ iIdx ].iInitRetryLimit = iRetryLimit;
  EventQueue[ iIdx ].nReenterCount = 0;
  EventQueue[ iIdx ].bReentrant = fReentrant;
  PCS_ENDCRITICAL

  return ( ERR_SUCCESS );
}

BYTE IsThreadActive( int iIdx )
{
  BYTE fThreadStatus;
  NEARPROC lpThread;

  if ( iIdx >= SMD_MAXTHREADS )
    return ( FALSE );

  lpThread = EventQueue[ iIdx ].lpThread;

  PCS_BEGINCRITICAL

  fThreadStatus = ( lpThread != NULL && lpThread
!= ( NEARPROC
)SMD_THREADACTIVE );

  PCS_ENDCRITICAL

  return ( fThreadStatus );
}

void ResetTime( int iIdx )
{
  if ( iIdx >= SMD_MAXTHREADS )
    return;

  EventQueue[ iIdx ].lTimeCurrent = 0;
}

int SetRetryLimit( int iIdx, int iNewRetryLimit )
{
  if ( iIdx >= SMD_MAXTHREADS )
    return ( ERR_INTERNAL );

  PCS_BEGINCRITICAL
  EventQueue[ iIdx ].iRetryLimit = iNewRetryLimit;
  EventQueue[ iIdx ].lTimeCurrent = 0;
  PCS_ENDCRITICAL

  return ( ERR_SUCCESS );
}

BYTE GetRetryLimit( int iIdx )
{
  int iReturn;

  if ( iIdx >= SMD_MAXTHREADS )
    return ( 0 );

  if ( ( iReturn = EventQueue[ iIdx ].iRetryLimit ) < 0
)
    iReturn = 0;

  return ( iReturn );
}

BYTE GetInitRetryLimit( int iIdx )
{
  int iReturn;

  if ( iIdx >= SMD_MAXTHREADS )
    return ( 0 );

  if ( ( iReturn = EventQueue[ iIdx ].iInitRetryLimit ) <
0 )
    iReturn = 0;

  return ( iReturn );
}

int ResetRetryLimit( int iIdx )
{
  if ( iIdx >= SMD_MAXTHREADS )
    return ( ERR_INTERNAL );

  PCS_BEGINCRITICAL
  EventQueue[ iIdx ].iRetryLimit = EventQueue[ iIdx
].iInitRetryLimit;
  EventQueue[ iIdx ].lTimeCurrent = 0;
  PCS_ENDCRITICAL

  return ( ERR_SUCCESS );
}

int SetTimeLimit( int iIdx, LONG lNewTimeLimit )
{
  if ( iIdx >= SMD_MAXTHREADS )
    return ( ERR_INTERNAL );

  PCS_BEGINCRITICAL
  EventQueue[ iIdx ].lTimeLimit = lNewTimeLimit;
  PCS_ENDCRITICAL

  return ( ERR_SUCCESS );
}

THREADTYPEID GetThreadType( int iIdx )
{
  if ( iIdx >= SMD_MAXTHREADS )
    return ( ERR_INTERNAL );

  return ( EventQueue[ iIdx ].ThreadTypeId );
}

NEARPROC GetThreadAddress( int iIdx )
{
  if ( iIdx >= SMD_MAXTHREADS )
    return ( ( NEARPROC )NULL );

  return ( EventQueue[ iIdx ].lpThread );
}

int DelThread( int iIdx )
{
  int iReturn = 0;

  if ( iIdx >= SMD_MAXTHREADS || iIdx < 0 )
  {
    TRACE( "ERROR: Invalid thread ID passed to
DelThread()\n" );
    return ( ERR_INTERNAL );
  }

  PCS_BEGINCRITICAL
  EventQueue[ iIdx ].lpThread = NULL;
  PCS_ENDCRITICAL

#if !defined( PROD )
  sprintf( szTempStr, "NOTICE: Temp thread
deallocated - %d\n",
iIdx );
  TRACE( szTempStr );
#endif

  return ( iReturn );
}

int InitDispatcher( void )
{
  iTempThreadIdx = GetTempEventNum();

  if ( iTempThreadIdx < 0 )
    return ( ERR_INTERNAL );

  fl_clr( ( NPSTR )EventQueue, 0, sizeof(
EventQueue ) );

  AddThread( iTempThreadIdx, InstallRecs, NULL,
SMD_ONETIME,
FALSE, SM_POLLFREQ,
            0 );

  InitVIDTrapRec();
  add_trap( GetVIDTrapRec() );

  InitPNDTrapRec();
  add_trap( GetPNDTrapRec() );

  InitSCSTrapRec();
  add_trap( GetSCSTrapRec() );

  InitPRXTrapRec();
  add_trap( GetPRXTrapRec() );

  AddThread( SM_PNDEVENTNUM, NULL,
GetPNDFuncTable(),
SMD_ONDEMAND, FALSE,
            SM_PNDPOLLFREQ, 0 );
  AddThread( SM_SUIEVENTNUM, NULL,
GetSUIFuncTable(),
SMD_ONDEMAND, FALSE,
            SM_SUIPOLLFREQ, 0 );
  AddThread( SM_SCSEVENTNUM, NULL,
GetSCSFuncTable(),
SMD_ONDEMAND, TRUE,
            SM_SCSPOLLFREQ, 0 );
  AddThread( SM_PRXEVENTNUM, NULL,
GetPRXFuncTable(),
SMD_ONDEMAND, FALSE,
            SM_PRXPOLLFREQ, 0 );
}

int ShutDownDispatcher( void )
{
  RestoreOldSUIIntVec();
  return ( 0 );
}

void InstallRecs( void )
{
  DelThread( iTempThreadIdx );

  AddThread( PND_EVENTNUM, CheckPenDriver,
NULL, SMD_POLLED,
FALSE,
            PND_POLLFREQ, 0 );
  AddThread( PRX_EVENTNUM, CheckSystem,
NULL, SMD_POLLED,
            FALSE, PRX_POLLFREQ, 0 );

  InitSUICallRec();
  InitSCSCallRec();

  SetSuspendFlagPointer();
  add_trap( GetSUIMouseTrapRec() );

  fRecsInstalled = TRUE;
}

void Dispatch( THREADTYPEID ActiveThreadId, int
iEventThreadIdx )
{
  int iThreadIdx,
  BOOL fFirstEntry = FALSE;
  EVENT *ev;
  NEARPROC lpOriginalThread = NULL;

  struct REGW Regs;

  if ( iEventThreadIdx >= SMD_MAXTHREADS )
    goto Exit;

  SetDispatchActive( TRUE );

  ev = &EventQueue[ iEventThreadIdx ];

  if ( ActiveThreadId == SMD_ONDEMAND )
  {
    if ( ev->bReentrant || ev->nReenterCount == 0 )
    {
      PCS_BEGINCRITICAL
      ++ev->nReenterCount;
      PCS_ENDCRITICAL

      if ( ev->pAPIFuncTable != NULL )
        CallAPIFunction( ev->pAPIFuncTable );
      else
        TRACE( "ERROR: Function table is NULL in
dispatcher" );

      PCS_BEGINCRITICAL
      --ev->nReenterCount;
      PCS_ENDCRITICAL
    }
    else
    {
      GetForegroundRegs( &Regs );
      Regs.ax = ( WORD )ERR_INTERNAL;
      SetForegroundRegs( &Regs );
    }

    goto Exit;
  }

  for ( iThreadIdx = 0; iThreadIdx <
SMD_MAXTHREADS; ++iThreadIdx
)
  {
    ev = &EventQueue[ iThreadIdx ];

    if ( ev->lpThread != NULL )
    {
      if ( ev->ThreadTypeId == ActiveThreadId ||
          ActiveThreadId ==
SMD_ALLTHREADTYPES )
      {
```

```
    if ( ev->bReentrant || ev->nReenterCount == 0
)
    {
      PCS_BEGINCRITICAL
      ++ev->nReenterCount;
      PCS_ENDCRITICAL
    }
    else
    {
#if !defined( PROD )
      sprintf( szTempStr, "NOTICE: Thread #%d
reentered, but
returned\n", iThreadIdx );
      TRACE( szTempStr );
#endif
      goto Exit;
    }

    switch ( ev->ThreadTypeId )
    {
      case SMD_ONETIME:
        if ( ev->iTimeCurrent >= 0 )
        {
          if ( ++ev->iTimeCurrent >= ev->iTimeLimit
)
          {
            ev->iTimeCurrent = -1;
            TRACE( "NOTICE: ONETIME thread
expired\n" );
          }
          else
            fNextEntry = TRUE;
        }
        else
          fNextEntry = TRUE;
        break;

      case SMD_MANYTIMES:
        if ( ev->iTimeCurrent >= 0 )
        {
          if ( ++ev->iTimeCurrent >= ev->iTimeLimit
)
          {
            if ( --ev->iRetryLimit <= 0 )
            {
              ev->iTimeCurrent = -1;
              TRACE( "NOTICE: MANYTIMES
thread expired\n" );
            }
            else
              ev->iTimeCurrent = 0;
          }
          else
            fNextEntry = TRUE;
        }
        else
          fNextEntry = TRUE;
        break;

      case SMD_POLLED:
        if ( ++ev->iTimeCurrent >= ev->iTimeLimit )
          ev->iTimeCurrent = 0;
        else
          fNextEntry = TRUE;
        break;

      default:
        fNextEntry = TRUE;
        break;
    }
  }
  else
    fNextEntry = TRUE;

  if ( fNextEntry )
  {
    fNextEntry = FALSE;
    PCS_BEGINCRITICAL
    --ev->nReenterCount;
    PCS_ENDCRITICAL
  }
  else
  {
    if ( ev->lpThread != NULL && ev->lpThread !=
( NEARPROC
)SMD_THREADACTIVE )
    {
      lpOriginalThread = ev->lpThread;
      ( *ev->lpThread )();

      PCS_BEGINCRITICAL
      if ( lpOriginalThread == ev->lpThread &&
          ( WORD )( ev->nReenterCount - 1 ) <
          ( WORD )ev->nReenterCount )
        --ev->nReenterCount;
      PCS_ENDCRITICAL
    }
  }
}

Exit:
  SetDispatchActive( FALSE );
}

WORD TrapService( struct trap_rec *CurTrapRec )
{
  REG_W Regs;
  IntEG MinArgs;
  WORD wReturn = 0;

  switch ( CurTrapRec->tr_int )
  {
    case SM_SUINTNUM:
      Dispatch( SMD_ONDEMAND,
SM_SUIEVENTNUM );
      break;

    case SM_SCSINTNUM:
      Dispatch( SMD_ONDEMAND,
SM_SCSEVENTNUM );
      break;

    case SM_PNDINTNUM:
      Dispatch( SMD_ONDEMAND,
SM_PNDEVENTNUM );
      break;

    case SM_PRXINTNUM:
      Dispatch( SMD_ONDEMAND,
SM_PRXEVENTNUM );
      break;

    case SSS_VIDINTNUM:
      VIDTrapService();
      return ( ( WORD )CurTrapRec );
      break;

    case PND_INTNUM:
      GetForegroundRegs( &Regs );

      if ( Regs.ax == PND_SETEVENTHANDLER &&
!GetPNDActiveStatus() )
      {
        MinArgs.ax = 0x350C;
        MinArgs.es = Regs.es;
        MinArgs.dx = Regs.dx;
        MinArgs.cx = Regs.cx;

        mouse( &MinArgs, &MExtendOutArgs );
      }
      else
        return ( ( WORD )CurTrapRec );

    default:
      return ( ( WORD )CurTrapRec );
  }
  return ( wReturn );
}

void FCallService( WORD wAX )
{
  switch ( PopEventNum() )
  {
    case SM_SUIEVENTNUM:
      Dispatch( SMD_ONDEMAND,
SM_SUIEVENTNUM );
      break;

    case SM_SCSEVENTNUM:
      Dispatch( SMD_ONDEMAND,
SM_SCSEVENTNUM );
      break;



  }
}

void ClockTick( void )
{


  add_isa_event( SMD_DISPATFREQ );



  Dispatch( SMD_ALLTHREADTYPES, 0 );

}

void DecClockReCount( void )
{
  PCS_BEGINCRITICAL;
  --nClockReenterCount;
  PCS_ENDCRITICAL;
}

#if !defined( NODEBUG )
void KbdService( WORD wHotKey )
{

  wLastKey = wHotKey;

}

WORD GetLastKey( void )
{
  WORD wTempLastKey = wLastKey;
  wLastKey = 0;

  return ( wTempLastKey );
}
#endif

void SetDispatchActive( BOOL bNewDispatchActive
)
{
  PCS_BEGINCRITICAL
  fDispatchActive = bNewDispatchActive;
  PCS_ENDCRITICAL
}

BOOL GetDispatchActive( void )
{
  BOOL fCurrentDisActive;

  PCS_BEGINCRITICAL
  fCurrentDisActive = fDispatchActive;
  PCS_ENDCRITICAL

  return ( fCurrentDisActive );
}

void CrankGear( BYTE *bGearIdx, char *szLabel )
{
  BYTE bNewGearIdx = *bGearIdx;
  if ( ++bNewGearIdx == SMD_MAXGEARIMAGES )
    bNewGearIdx = 0;

  ++ram_x;

  *bGearIdx = bNewGearIdx;
}

void PushEventNum( int iEventNum )
{
  aEventStack[ iEventStackPtr ] = iEventNum;
  iEventStackPtr = iEventStackPtr > 0 ?
iEventStackPtr - 1 :
iEventStackPtr;
}

int PopEventNum( void )
{
  int iReturn;

  PCS_BEGINCRITICAL
  iEventStackPtr = iEventStackPtr <
SMD_EVENTSTACKLIMIT - 1 ?
iEventStackPtr + 1 : iEventStackPtr;
  iReturn = aEventStack[ iEventStackPtr ];
  PCS_ENDCRITICAL

  return ( iReturn );
}

int GetTempEventNum( void )
{
  register int iThreadIdx;
  int iReturn = ERR_INTERNAL;

  PCS_BEGINCRITICAL

  for ( iThreadIdx = SMD_REUSETHREADS - 1;
iThreadIdx <
SMD_MAXTHREADS;
        ++iThreadIdx )
  {
    if ( EventQueue[ iThreadIdx ].lpThread == NULL )

    {
#if !defined( PROD )
      sprintf( szTempStr, "NOTICE: Temp thread
allocated - %d\n",
iThreadIdx );
      TRACE( szTempStr );
#endif
      iReturn = iThreadIdx;
      EventQueue[ iThreadIdx ].lpThread = (
NEARPROC
)SMD_THREADACTIVE;
      break;
    }
  }
  PCS_ENDCRITICAL

#if !defined( PROD )
  if ( iReturn == ERR_INTERNAL )
    TRACE( "ERROR: Out of temporary threads" );
#endif

  return ( iReturn );
}

#if defined( _MSC_VER )
#pragma warning( default : 4704 )
#endif
Copr. 1995 Zenith Data Systems Corp.

#include "sr.h"
#include "sio.h"
#include "sposm.h"
#include "t2.h"
#include "frame.h"
#include "sm.h"

#if defined( _MSC_VER )
#pragma warning( disable : 4704 )
#endif

THREADTYPEID ActiveThreadType =
SMD_NOTHREAD;

char          szSMSignature[] =
SM_SMSIGNATURE;
char          szSMVersionName[] =
STR_SMVERSIONNAME;
char          szSMVersionNum[] =
STR_SMVERSIONNUM;
char          szSMModuleName[] =
STR_SMMODULENAME;
char          szSUIExecName[] = SUI_EXECNAME;
char          szSCSAbortConn[] =
SM_SCSABORTCONN;
char          szTempStr[ GEN_MAXLENTEMPSTR ];
char          szTempMsgStr[
GEN_MAXLENTEMPSTR * 2 ];
char          szNullMsg[] = "\0";
SCANCODE      aUGNoticon1Def[] =
SUI_UGNOTICON1DEF;
char          szPassword[ SUI_MAXLENPASSWORD
+ 1 ];
char          nRLUNetState = 0;
char          fEEPROMInited = FALSE;
WORD            wScreenCode = SUI_NOSCREEN;
WORD            wOldScreenCode =
SUI_NOSCREEN;
MREG          MEventOutArgs;
FARCALLENTRY  lpfnFarCallEntry = NULL;
SUICB         lpfnSUICallBack = NULL;
UICONFIGDATA  UIConfigData;
LISTBOXENTRY  ListBoxEntry;
MSGBOXBUFF    MsgBoxBuff[
SM_SUIMAXMSGBOXLINES ];
BUFFHEADER    BuffHead;

BOOL fConnectRequested = FALSE;

char GetEEPROMInited( void )
{
  return ( fEEPROMInited );
}

void InitUIConfigData( void )
{
  if ( GetEEUIData( &UIConfigData ) ==
ERR_SUCCESS )
  {
    if ( UIConfigData.nMajorVersionNum ==
GEN_SMMAJORVERSIONNUM
&&
        UIConfigData.nMinorVersionNum ==
GEN_SMMINORVERSIONNUM )
    {
      if ( ( ( int )UIConfigData.wXLowerPenCalib -
             ( int )UIConfigData.wXUpperPenCalib ) >=
200 )
      {
        if ( UIConfigData.wXUpperPenCalib ==
PND_XUPPERPENCALIB
&&
            UIConfigData.wYUpperPenCalib ==
PND_YUPPERPENCALIB
&&
            UIConfigData.wXLowerPenCalib ==
PND_XLOWERPENCALIB
&&
            UIConfigData.wYLowerPenCalib ==
PND_YLOWERPENCALIB )
          InitEEPROM();
      }
      else
```

```
      InitEEPROM();

    }
    else
      InitEEPROM();
  }
  else
    InitEEPROM();

  fl_clr( &MEventOutArgs, 0, sizeof( MREG ) );
  lpfnPenCallEntry = MK_FP( _csedo, _fnoll_entry );
}

void InitEEPROM( void )
{
  TRACE( "ERROR: Invalid values or unable to read
from EEPROM\n"
);

  fl_clr( &UIConfigData, 0, sizeof( UICONFIGDATA
) );

  UIConfigData.wBufLen          = sizeof(
UICONFIGDATA );
  UIConfigData.nMajorVersionNum =
GEN_SWMAJORVERSIONNUM;
  UIConfigData.nMinorVersionNum =
GEN_SWMINORVERSIONNUM;
  UIConfigData.bConnectType    =
SM_NETWORKCONNECT;
  UIConfigData.nDomainID       = PRX_DOMAIN0;

  UIConfigData.nContrastIdx    =
SHC_DEFCONTRASTIDX;
  UIConfigData.nBrightnessIdx  =
SHC_DEFBRIGHTNESSIDX;

  UIConfigData.nSleepTimeIdx   =
SSS_SLEEPDISABLED;
  UIConfigData.bAutoShutoff    = FALSE;

  UIConfigData.wUILanguage     =
SM_UILENGLISH;
  UIConfigData.nFrameType      =
PRX_FRAME8023;

  UIConfigData.nLastOSKScreen      =
SUI_BIGALPHA;
  UIConfigData.nLastOSKDigScreen   =
SUI_BIGALPHA;
  UIConfigData.nLastSetupDigScreen =
SUI_HOSTSELECTION;

  UIConfigData.xPenLastOSKScreen =
SUI_XULBIGALPHA;
  UIConfigData.yPenLastOSKScreen =
SUI_YULBIGALPHA;

  mem_cpy( szUIDHotIcon1Def,
UIConfigData.szUIDHotIcon1,
SUI_MAXLENDEFHOTICON );

  TRACE( "NOTICE: Using pen calibration values
set to zero.\n" );

  UIConfigData.wXUpperPenCalib =
PHS_XUPPERPENCALIB;
  UIConfigData.wYUpperPenCalib =
PHS_YUPPERPENCALIB;
  UIConfigData.wXLowerPenCalib =
PHS_XLOWERPENCALIB;
  UIConfigData.wYLowerPenCalib =
PHS_YLOWERPENCALIB;

  fEEPROMValid = TRUE;

  SetEEUIData();

  SetContrast( UIConfigData.nContrastIdx );
  SetBrightness( UIConfigData.nBrightnessIdx );
}

void InitSUI( void )
{
  SetDomainWarning( FALSE );
  SetSecurityWarning( FALSE );
}

void InitSaratoga( BYTE nInitType )
{
  if ( nInitType == SSS_DRIVERSLOADING )
  {
    TRACE( "NOTICE: Power management disabled
for driver load
sequence\n" );
    SetPowerEnable( SSS_POWERMANDISABLED
);
  }
  else if ( nInitType == SSS_SUILOADING )
  {
    if ( SetSleepTimeout(
UIConfigData.nSleepTimeIdx ) ==
ERR_SUCCESS )
    {
      if ( UIConfigData.nSleepTimeIdx ==
SSS_SLEEPDISABLED )
      {
        TRACE( "NOTICE: Power management now
disabled, DOZE
disabled\n" );
        SetPowerEnable(
SSS_POWERMANDISABLED );
        SetDozeTimeout( SSS_DOZEDISABLED );
      }
      else
      {
        TRACE( "NOTICE: Power management now
enabled, DOZE
disabled\n" );
        SetPowerEnable(
SSS_POWERMANENABLED );
        SetDozeTimeout( SSS_DOZEDISABLED );

      }

      if ( UIConfigData.bAutoShutoff )
      {
        TRACE( "NOTICE: Suspend after 60 minutes
enabled\n" );
        SetSuspendTimeout( SSS_SUSPENDAFTER60MIN
);
      }
      else
      {
        TRACE( "NOTICE: Suspend disabled\n" );
        SetSuspendTimeout(
SSS_SUSPENDDISABLED );
      }
    }
  }

}

int GetEEMouseConfig( void )
{
  REG_W InRegs, OutRegs;
  PENCALIB pc;
  WORD wFlags;

  fl_clr( &InRegs, 0, sizeof( REG_W ) );
  fl_clr( &pc, 0, sizeof( PENCALIB ) );

  InRegs.ax = SSS_SARATOGAFUNC;
  InRegs.bx = SSS_EEPROMTOMEMORY;
  InRegs.cx = SSS_LENMOUSECFGDATA;
  InRegs.dx = PHO_OFFCALIB;

  InRegs.es = SEG( &pc );
  InRegs.di = OFF( &pc );

#if defined( NOINT15 )
  wFlags = intx( &InRegs, &OutRegs
SSS_SLINTNUM );
#else
  wFlags = 0;
#endif

  if ( !( wFlags & GEN_CARRYFLAG ) )
  {
    UIConfigData.wXUpperPenCalib =
pc.wXUpperPenCalib;
    UIConfigData.wYUpperPenCalib =
pc.wYUpperPenCalib;
    UIConfigData.wXLowerPenCalib =
pc.wXLowerPenCalib;
    UIConfigData.wYLowerPenCalib =
pc.wYLowerPenCalib;

    return ( ERR_SUCCESS );
  }
  else
    return ( ERR_INTERNAL );
}

int SetEEMouseConfig( PENCALIB *pc )
{
  UIConfigData.wXUpperPenCalib =
pc->wXUpperPenCalib;
  UIConfigData.wYUpperPenCalib =
pc->wYUpperPenCalib;
  UIConfigData.wXLowerPenCalib =
pc->wXLowerPenCalib;
  UIConfigData.wYLowerPenCalib =
pc->wYLowerPenCalib;

  return ( SetEEUIData() );
}

int SetEEUIData( void )
{
  REG_W InRegs, OutRegs;
  WORD wFlags;
  UICONFIGDATA ChkUIConfigData;
  int iReturn = ERR_SUCCESS;

  fl_clr( &ChkUIConfigData, 0, sizeof(
UICONFIGDATA ) );

  if ( GetEEUIData( &ChkUIConfigData ) ==
ERR_SUCCESS )
  {
    if ( mem_cmp( ( NPSTR )&ChkUIConfigData, (
NPSTR
)&UIConfigData,
          sizeof( UICONFIGDATA ) ) != sizeof(
UICONFIGDATA ) )

    {
      fl_clr( &InRegs, 0, sizeof( REG_W ) );

      InRegs.ax = SSS_SARATOGAFUNC;
      InRegs.bx = SSS_MEMORYTOEEPROM;
      InRegs.cx = sizeof( UICONFIGDATA );
      InRegs.dx = SSS_OFFUICFGDATA;
      InRegs.es = SEG( &UIConfigData );
      InRegs.di = OFF( &UIConfigData );

#if defined( NOINT15 )
      PCS_BEGINCRITICAL
      wFlags = intx( &InRegs, &OutRegs,
SSS_SLINTNUM );
      PCS_ENDCRITICAL
#else
      wFlags = 0;
#endif
      if ( !( wFlags & GEN_CARRYFLAG ) )
        iReturn = ERR_SUCCESS;
      else
        iReturn = ERR_INTERNAL;
    }
  }
  else
    iReturn = ERR_INTERNAL;

#if defined( PROS )
  if ( iReturn == ERR_INTERNAL )
    TRACE( "ERROR: SetEEUIData() error returned
from extended
BIOS call to save EEPROM data\n" );
#endif

  return ( iReturn );
}

int GetEEUIData( UICONFIGDATA
*CurrUIConfigData )
{
  REG_W InRegs, OutRegs;
  WORD wFlags;
  UICONFIGDATA TempUIConfigData;

  fl_clr( &InRegs, 0, sizeof( REG_W ) );

  InRegs.ax = SSS_SARATOGAFUNC;
  InRegs.bx = SSS_EEPROMTOMEMORY;
  InRegs.cx = sizeof( UICONFIGDATA );
  InRegs.dx = SSS_OFFUICFGDATA;
  InRegs.es = SEG( &TempUIConfigData );
  InRegs.di = OFF( &TempUIConfigData );

#if defined( NOINT15 )
  PCS_BEGINCRITICAL
  wFlags = intx( &InRegs, &OutRegs,
SSS_SLINTNUM );
  PCS_ENDCRITICAL
#else
  wFlags = 0;
#endif

  if ( !( wFlags & GEN_CARRYFLAG ) )
  {
    *CurrUIConfigData = TempUIConfigData;

    return ( ERR_SUCCESS );
  }
  else
    return ( ERR_INTERNAL );
}

int ClearEEPROM( void )
{
  REG_W InRegs, OutRegs;
  WORD wFlags;
  UICONFIGDATA UINullData;

  fl_clr( &InRegs, 0, sizeof( InRegs ) );
  fl_clr( &UINullData, 0, sizeof( UINullData ) );

    InRegs.ax = SSS_SARATOGAFUNC;
    InRegs.bx = SSS_MEMORYTOEEPROM;
    InRegs.cx = sizeof( UICONFIGDATA );
    InRegs.dx = SSS_OFFUICFGDATA;
    InRegs.es = SEG( &UINullData );
    InRegs.di = OFF( &UINullData );

#if defined( FLASHTEST )
  wFlags = intx( &InRegs, &OutRegs,
SSS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

#if defined( _MSC_VER )
#pragma warning( default : 4704 )
#endif
Copr. 1995 Zenith Data Systems Corp.

#include "sr.h"
#include "wpsum.h"
#include "ic2.h"
#include "sis.h"
#include "sm.h"

#if defined( _MSC_VER )
#pragma warning( disable : 4704 )
#endif

HOSTLISTENTRIES HostListEntries = { 0, 0 };
static HOSTLISTENTRIES BroadcastHLEntries = {
0, 0 };
static int          iHLStatus = SM_BLANK;
static int          iHLThreadId = -1;
static int          iHostFetchThreadIdx;
static int          iLBCurrHost = 0;
static int          iLBCurrGroup = 0;
static int          iCurrGroupIdx = 0;
static int          iNumGroups = 0;
static char         szWorkAroundNodeAdd[
SCS_MAXLENNODEADD ];
static char         szSerialDup[
SCS_MAXLENSERIALNUM ];
static char         szCurrHostName[
SCS_MAXLENHOSTNAME + 1 ];

static char         fRequestHostList = FALSE;

void SetCurrHostName( char *szNewCurrHostName
)
{
  strcpy( szCurrHostName, szNewCurrHostName );
}

char *GetCurrHostName( void )
{
  return ( szCurrHostName );
}

int GetLBCurrHost( void )
{
  return ( iLBCurrHost );
}

void SetLBCurrHost( int iNewLBCurrHost )
{
  iLBCurrHost = iNewLBCurrHost;
}

char GetRequestHostList( void )
{
  return ( fRequestHostList );
}

void SetRequestHostList( int iNewRequestHostList )
{
  PCS_BEGINCRITICAL;
  fRequestHostList = LOBYTE( iNewRequestHostList
);
  PCS_ENDCRITICAL;
}

int GetLBCurrGroup( void )
{
  return ( iLBCurrGroup );
}

void SetLBCurrGroup( int iNewLBCurrGroup )
{
  if ( iLBCurrGroup != iNewLBCurrGroup )
    iCurrGroupIdx = GetGroupIdx( iNewLBCurrGroup
);
```

```
  nLBCurrGroup = iNewLBCurrGroup;
}

char *GetLBGroup( int iGroupNum )
{
  int iUseGroup;
  char *szReturn;
  int iLBGroupIdx;

  if ( iHLStatus != SHI_AVAILABLE ||
HostListEntries.iNumEntries
== 0 )
    return ( szNullStr );

  iUseGroup = ( iGroupNum ==
SUI_LSCURRENTRY ? nLBCurrGroup :
iGroupNum );

  iLBGroupIdx = GetGroupIdx( iUseGroup );

  szReturn = HostListEntries.aHostListBuff[
iLBGroupIdx
].HostDataBuff.szGroupName;

  return ( szReturn == NULL ? szNullStr : szReturn
);
}

char *GetLBHost( int iHostNum )
{
  char *szReturn;

  if ( GetCurrActionCode() ==
SUI_LASTCONNECTION )
    return ( UIConfigData.szLastHostName );

  if ( iHLStatus != SHI_AVAILABLE ||
HostListEntries.iNumEntries
== 0 )
    return ( szNullStr );

  szReturn = HostListEntries.aHostListBuff[
GetHostIdx( iHostNum
) ].HostDataBuff.szHostName;

  return ( szReturn == NULL ? szNullStr : szReturn
);
}

int GetLBHostStatus( int iHostNum )
{
  int iReturn;

  if ( iHLStatus != SHI_AVAILABLE ||
HostListEntries.iNumEntries
== 0 )
    return ( SUI_LSENTRYENABLED );

  iReturn = HostListEntries.aHostListBuff[
GetHostIdx( iHostNum )
].HostDataBuff.nHostStatus;

  if ( iReturn == SCS_HOSTAVAILABLE )
    iReturn = SUI_LSENTRYENABLED;
  else
    iReturn = SUI_LSENTRYDISABLED;

  return ( iReturn );
}

int SetLBHostStatus( int iHostNum, BYTE
nNewHostStatus )
{
  if ( iHLStatus != SHI_AVAILABLE ||
HostListEntries.iNumEntries
== 0 )
    return ( ERR_INTERNAL );

  HostListEntries.aHostListBuff[ GetHostIdx(
iHostNum )
].HostDataBuff.nHostStatus = nNewHostStatus;

  return ( ERR_SUCCESS );
}

char *GetCurrNodeAddress( void )
{
  int iHostIdx;
  char *szReturn = NULL;

  if ( GetCurrActionCode() ==
SUI_LASTCONNECTION )
    return ( UIConfigData.szLastNodeAddress );

  if ( iHLStatus != SHI_AVAILABLE ||
HostListEntries.iNumEntries
== 0 )
    return ( szNullStr );

  if ( nLBCurrHost > 0 )
  {
    iHostIdx = GetGroupIdx( nLBCurrGroup ) + (
nLBCurrHost - 1 );
    szReturn = HostListEntries.aHostListBuff[
iHostIdx
].szNodeAddress;
  }

  return ( szReturn == NULL ? szNullStr : szReturn
);
}

WORD GetCurrHostVersionNum( void )
{
  int iHostIdx;
  BYTE nMinorVersion;
  BYTE nMajorVersion;

  if ( iHLStatus != SHI_AVAILABLE ||
HostListEntries.iNumEntries
== 0 )
    return ( 0 );

  if ( nLBCurrHost > 0 )
    iHostIdx = GetHostIdx( SUI_LSCURRENTRY );
  else
    return ( 0 );

  nMinorVersion = HostListEntries.aHostListBuff[
iHostIdx
].HostDataBuff.nMinorVersion;
  nMajorVersion = HostListEntries.aHostListBuff[
iHostIdx
].HostDataBuff.nMajorVersion;

  return ( MAKEWORD( nMinorVersion,
nMajorVersion ) );
}

BOOL IsPWRequired( void )
{
  BOOL fReturn = FALSE;

  if ( GetCurrActionCode() ==
SUI_LASTCONNECTION )
    return ( UIConfigData.bLastConnPassword );

  if ( iHLStatus != SHI_AVAILABLE ||
HostListEntries.iNumEntries
== 0 )
    return ( FALSE );

  if ( nLBCurrHost > 0 )
    fReturn = HostListEntries.aHostListBuff[
GetHostIdx(
SUI_LSCURRENTRY ) ].HostDataBuff.
          bPasswordProtect;

  return ( fReturn );
}

int GetNumHostEntries( void )
{
  int iNextGroupIdx;

  if ( iHLStatus != SHI_AVAILABLE )
    return ( ERR_INTERNAL );

  if ( ( iNextGroupIdx = GetGroupIdx( nLBCurrGroup
+ 1 ) ) >= 0 )
    return ( iNextGroupIdx - iCurrGroupIdx );
  else
    return ( HostListEntries.iNumEntries -
iCurrGroupIdx );
}

int GetNumGroupEntries( void )
{
  if ( iHLStatus != SHI_AVAILABLE )
    return ( ERR_INTERNAL );

  return ( iNumGroups );
}

int GetGroupIdx( int iGroupNum )
{
  LONG lGroupIdx;

  lGroupIdx = GetEntryOffset(
HostListEntries.iNumEntries,
            sizeof ( HOSTLISTBUFF ),
SCS_MAXLENNODEADD,
            iGroupNum, ( NPSTR
)HostListEntries.aHostListBuff );

  if ( lGroupIdx >= 0 )
    return ( ( int )lGroupIdx / sizeof (
HOSTLISTBUFF ) );
  else
    return ( ERR_INTERNAL );
}

int GetGroupNum( int iHostIdx )
{
  LONG lLowGroupIdx = 0L;
  LONG lHighGroupIdx = 0L;
  int iGroupNum;

  for ( iGroupNum = 1; lHighGroupIdx >= 0;
++iGroupNum )
  {
    lLowGroupIdx = lHighGroupIdx;
    lHighGroupIdx = GetEntryOffset(
HostListEntries.iNumEntries,
                  sizeof ( HOSTLISTBUFF
),
SCS_MAXLENNODEADD,
                  iGroupNum, ( NPSTR
)HostListEntries.aHostListBuff );
    lHighGroupIdx /= sizeof ( HOSTLISTBUFF );

    if ( ( LONG )iHostIdx >= lLowGroupIdx && (
LONG )iHostIdx <
lHighGroupIdx )
      return ( iGroupNum );
  }

  return ( HLD_NOTINGROUP );
}

int GetHostIdx( int iHostNum )
{
  int iUseHost;
  int iHostIdx;

  iUseHost = ( iHostNum == SUI_LSCURRENTRY ?
nLBCurrHost :
iHostNum );
  iHostIdx = iCurrGroupIdx + ( iUseHost - 1 );

  return ( iHostIdx );
}

int SortGroupHost( void )
{
  int iGroupNum;
  int iSortStatus;

  iSortStatus =
    SortList( HostListEntries.iNumEntries, sizeof (
HOSTLISTBUFF
),
          SCS_OFFGROUPKEY,
SCS_OFFHOSTKEY,
          ( NPSTR )HostListEntries.aHostListBuff );

  if ( iSortStatus == ERR_SUCCESS )
  {
    for ( iNumGroups = 0, iGroupNum = 1;
iGroupNum <=
HostListEntries.iNumEntries;
        ++iGroupNum )
    {
      if ( GetGroupIdx( iGroupNum ) >= 0 )
        iNumGroups++;
    }
  }

  return ( iSortStatus );
}

int SortSerialNums( void )
{
  int iEntryIdx;

  if ( HostListEntries.aHostListBuff == NULL ||
HostListEntries.iNumEntries <= 0 )
    return ( ERR_INTERNAL );

  for ( iEntryIdx = 0; iEntryIdx <
HostListEntries.iNumEntries;
++iEntryIdx )
    HostListEntries.aHostListBuff[ iEntryIdx ].
      HostDataBuff.szHostSerial[
SCS_MAXLENSERIALNUM - 1 ] = 0;

  return ( SortList( HostListEntries.iNumEntries,
sizeof (
HOSTLISTBUFF ),
        SCS_OFFSERIALNUM, NULL, ( NPSTR
)HostListEntries.aHostListBuff ) );
}

int ValidateSerialNums( void )
{
  int iEntryIdx, iNextEntryIdx;
  int iSerialStatus = HLD_VALIDSERIALS;

  szSerialDup[0] = '\0';

  if ( SortSerialNums() != ERR_SUCCESS )
    return ( FALSE );

  for ( iEntryIdx = 0; iEntryIdx <
HostListEntries.iNumEntries;
++iEntryIdx )
  {
    if ( IsZeroString( HostListEntries.aHostListBuff[
iEntryIdx
].
                HostDataBuff.szHostSerial ) )
      iSerialStatus = HLD_INVALIDSERIALS;
    else
    {
      if ( ( iNextEntryIdx = iEntryIdx + 1 ) <
HostListEntries.iNumEntries )
      {
        if ( lstrcmp( HostListEntries.aHostListBuff[
iEntryIdx
].HostDataBuff.szHostSerial,
                HostListEntries.aHostListBuff[
iNextEntryIdx ].
                HostDataBuff.szHostSerial ) )
          iSerialStatus = HLD_DUPLICATESERIALS;
      }
    }

    if ( iSerialStatus != HLD_VALIDSERIALS )

    {
      strcpy( szSerialDup,
HostListEntries.aHostListBuff[
iEntryIdx ].
                HostDataBuff.szHostSerial );
      break;
    }
  }

  return ( iSerialStatus );
}

int RequestHostList( void )
{
  SetRequestHostList( TRUE );

  if ( !GetICSActiveStatus() )
    return ( ERR_INTERNAL );

  if ( ( AllocHLMem( &HostListEntries,
HLD_MAXIMUMHOSTENTRIES ) )
!= ERR_SUCCESS )
    return ( ERR_OUTOFMEM );

  if ( ( AllocHLMem( &BroadcastHLEntries,
HLD_MAXIMUMHOSTENTRIES )
) != ERR_SUCCESS )
    return ( ERR_OUTOFMEM );

  HostListEntries.iNumEntries = 0;
  nLBCurrHost = nLBCurrGroup = 0;

  if ( ( SendRequestHostList() == ERR_SUCCESS )
&&
      ( ( iWaitForHLThreadIdx =
GetTempEventNum() ) >= 0 ) )
  {
    AddThread( iWaitForHLThreadIdx, WaitForHLD,
NULL,
SMD_MANYTIMES, FALSE,
          HLD_POLLFREQ, HLD_MAXRETRIES );

    SetStatusHLInMem( SHI_INPROGRESS );
  }
  else
  {
    FreeHLMem( &HostListEntries );
    FreeHLMem( &BroadcastHLEntries );
    SetStatusHLInMem( SHI_AVAILABLE );
    return ( ERR_INTERNAL );
  }

  return ( ERR_SUCCESS );
}

void WaitForHLD( void )
{
  int iNumEntries;
  int iSerialStatus;
  LONG lGroupHostNums;
  int iHostConnectIdx;

  CancelRequestHostList();
```

```
    if ( ( NumEntries = *( int *
)BroadcastHLEntries.aHostListBuff
) > 0 )
    {
      BroadcastHLEntries.NumEntries = NumEntries;

      mem_mv( ( PVOID )( ( BYTE * )(
BroadcastHLEntries.aHostListBuff ) +
SCS_HOSTLISTNUMOFFSET ),
          ( PVOID )(
BroadcastHLEntries.aHostListBuff ),
NumEntries *
          sizeof ( HOSTLISTBUFF ) + sizeof ( int ) );

      SaveNewHosts();
    }

    if ( SetRetryLimit( WaitForHLThreadIdx ) > 0 &&
SendRequestHostList() == ERR_SUCCESS )
    {
      SetStatusHLInitem( SM_INPROGRESS );
    }
    else
    {
      DelThread( WaitForHLThreadIdx );

      if ( HostListEntries.NumEntries > 0 )
      {
        AllocHLMem( &HostListEntries,
HostListEntries.NumEntries
);

        if ( ( iSerialStatus = ValidateSerialNums() ) !=
HLD_VALIDSERIALS )
        {
          if ( iSerialStatus == HLD_INVALIDSERIALS )
            OpenMessageBox(
STR_HLDINVSERIALNUMS, 0,
SUI_LEFTJUSTIFIED, SUI_OK );
          else
            OpenMessageBox(
STR_HLDDUPSERIALNUMS, 0,
SUI_LEFTJUSTIFIED, SUI_OK );
        }

        SortGroupHost();

        if ( GetSCSCallProgress() !=
SM_SCSDISCONNECTED )
        {
          if ( ( iHostConnectIdx = FindNodeAddress(
&HostListEntries,

UIConfigData.szLastNodeAddress )
) != FNA_NOTFOUND )
            HostListEntries.aHostListBuff[
iHostConnectIdx ].
                    HostDataBuff.aHostStatus =
SCS_HOSTAVAILABLE;
        }

        if ( ( lGroupHostNums = FindFirstAvailHost(
&HostListEntries ) ) != HLD_NOHOSTAVAIL )
        {
          iLSCurrGroup = HIWORD( lGroupHostNums );
          iLSCurrHost = LOWORD( lGroupHostNums );
        }
        else
        {
          iLSCurrGroup = iNumGroups > 0 ? 1 : 0;
          iLSCurrHost = 0;
        }
      }
      else
      {
        FreeHLMem( &HostListEntries );
        iLSCurrGroup = 1;
        iLSCurrHost = 0;
      }

      FreeHLMem( &BroadcastHLEntries );

      SetStatusHLInitem( SM_AVAILABLE );
      SetRequestHostList( FALSE );
    }
}

int SendRequestHostList( void )
{
  WORD wSeg, wOff, wReturn;

  wSeg = SEG( BroadcastHLEntries.aHostListBuff );
  wOff = OFF( BroadcastHLEntries.aHostListBuff );

  _asm
  {
    push ds
    push di
    push bx

    mov ax, SCS_REQUESTHOSTLIST
    mov ds, wSeg
    mov di, wOff
    mov bx, HLD_MAXNUMHOSTENTRIES

    int SCS_INTNUM

    pop bx
    pop di
    pop ds

    mov wReturn, ax
  }

  if ( wReturn == SCS_ACCEPTED )
    return ( ERR_SUCCESS );
  else
    return ( ERR_INTERNAL );
}

int CancelRequestHostList( void )
{
  _asm
  {
    mov ax, SCS_CANCELREQHOSTLIST
    int SCS_INTNUM
  }

  return ( ERR_SUCCESS );
}

int SaveNewHosts( void )
{
  int iBCHostIdx;

  for ( iBCHostIdx = 0; iBCHostIdx <
BroadcastHLEntries.NumEntries; ++iBCHostIdx )
  {
    if ( FindNodeAddress( &HostListEntries,
          BroadcastHLEntries.aHostListBuff[
iBC`HostIdx
].szNodeAddress ) == FNA_NOTFOUND )
    {
      HostListEntries.aHostListBuff[
HostListEntries.NumEntries++ ] =
          BroadcastHLEntries.aHostListBuff[ iBCHostIdx
];
    }
  }

  return ( ERR_SUCCESS );
}

int FindNodeAddress( HOSTLISTENTRIES
*pHostListEntries, char
*szKeyNodeAddress )
{
  int iHostIdx;
  int iMaxHostIdx = pHostListEntries->NumEntries;

  for ( iHostIdx = 0; iHostIdx < iMaxHostIdx;
++iHostIdx )
  {
    if ( strcmp( pHostListEntries->aHostListBuff[
iHostIdx
].szNodeAddress,
            szKeyNodeAddress ) == 0 )
      return ( iHostIdx );
  }

  return ( FNA_NOTFOUND );
}

LONG FindFirstAvailHost( HOSTLISTENTRIES
*pHostListEntries )
{
  int iHostIdx;
  int iGroupNum, iHostNum;
  int iMaxHostIdx = pHostListEntries->NumEntries;

  for ( iHostIdx = 0; iHostIdx < iMaxHostIdx;
++iHostIdx )
  {
    if ( pHostListEntries->aHostListBuff[ iHostIdx
].HostDataBuff.aHostStatus ==
        SCS_HOSTAVAILABLE )
    {
      iGroupNum = GetGroupNum( iHostIdx );
      iHostNum = ( iHostIdx - GetGroupIdx(
iGroupNum ) ) + 1;
      return ( MAKELONG( iHostNum, iGroupNum ) );

    }
  }

  return ( ( LONG )HLD_NOHOSTAVAIL );
}

int AllocHLMem( HOSTLISTENTRIES
*pHostListEntries, int
iNumEntries )
{

  if ( pHostListEntries->aHostListBuff == NULL )
  {
    if ( ( pHostListEntries->aHostListBuff = (
HOSTLISTBUFF *
)malloc(
          iNumEntries * sizeof ( HOSTLISTBUFF ) +
sizeof ( int )
) ) == NULL )
    {
      TRACE( "ERROR: malloc failed in
AllocHLMem()\n" );
      return ( ERR_INTERNAL );
    }
    else
      fill_str( ( PVOID
)pHostListEntries->aHostListBuff, 0,
iNumEntries *
          sizeof ( HOSTDATABUFF ) + sizeof ( int
) );
  }
  else
  {
  }

  pHostListEntries->NumEntries = iNumEntries;

  return ( ERR_SUCCESS );
}

int GetStatusHLInitem( void )
{
  if ( GetCurrLaunchCode() ==
SUI_LASTCONNECTION )
    return ( SM_AVAILABLE );
  else
    return ( iHLStatus );
}

void SetStatusHLInitem( int iNewHostListStatus )
{
  if ( ( iHLStatus = iNewHostListStatus ) ==
SM_INPROGRESS )
    SetWaitingIcon( SSS_WAITINGICONON, TRUE
);
  else
    SetWaitingIcon( SSS_WAITINGICONOFF, TRUE
);
}

void FreeHLMem( HOSTLISTENTRIES
*pHostListEntries )
{
  if ( pHostListEntries->aHostListBuff != NULL )
  {
    free( pHostListEntries->aHostListBuff );
    pHostListEntries->aHostListBuff = NULL;
  }
}

void FreeAllHLMem( void )
{
  FreeHLMem( &HostListEntries );
  FreeHLMem( &BroadcastHLEntries );
}

BOOL IsZeroString( char szString[] )
{
  int iStrIdx;
  int iStrLen;

  for ( iStrIdx = 0, iStrLen = strlen( szString );
        iStrIdx < iStrLen; ++iStrIdx )
    if ( szString[ iStrIdx ] != '0' )
      return ( FALSE );

  return ( TRUE );
}

#if defined( _MSC_VER )
#pragma warning( default : 4704 )
#endif
Copr. 1995 Zenith Data Systems Corp.

#include "sr.h"
#include "sysnum.h"
#include "k2.h"
#include "sio.h"
#include "sm.h"

#if defined( _MSC_VER )
#pragma warning( disable : 4704 )
#endif

#define STK_SZ (3000)

word ler_stk[STK_SZ+1];

extern char sms[];
extern char strs[],stms[];
extern char already[];
extern char unloaddone[];
extern char unloadnot[];
extern word init_data_end;

extern BOOL fInstaws;

main()
{
  int i;

  sbh_video();
  get_crs();
  crs_x = bars_x;
  crs_y = bars_y;
  mv_crs();

  if ( second_load() )
  {
    i = str_pos( '-', cmd_line );
    if ( i && ( ( cmd_line[i] | 0x20 ) == 'u' ) )
    {
      if( remove_tsr() )
      {
        ShutDownDispatcher();
        dsp( unloaddone );
      }
      else
        dsp( unloadnot );
    }
    else
      dsp( already );

    mv_crs();

    return( 1 );
  }

  sprintf( szTempStr, sms, szSWVersionName );
  dsp( szTempStr );

  get_crs();
  crs_x = bars_x;
  crs_y = bars_y + 3;
  mv_crs();



  DEBUG_BREAK;

  InitUIConfigData();
  InitSavings( SSS_DRIVERSLOADING );
  InitDispatcher();

  malloc_on( SHC_MAXLENHEAP );
  idata_end=&init_data_end;
  icode_beg=main;
  stay_resident(ler_stk,STK_SZ*2);


  install_isr( ( fp )ClockTick, 3500,
          SMD_SCHEDULERS | SMD_HOTKEYS |

          SMD_FARCALLS |
SMD_GENERALTRAPS | SMD_COMMSVCS |
SMD_INTSEVCS | SMD_MOUSEINWATCH );

  install_trap( ( fp )TrapService, 3500,
SMD_FULLREENTER );
  install_fcall( ( fp )FCallService, 4000,
SMD_FULLREENTER, 0,
szHotStr, 0 );

  add_isr_event( SMD_DISPATFREQ );

  return ( 0 );
}

#if defined( _MSC_VER )
#pragma warning( default : 4704 )
#endif


Copr. 1995 Zenith Data Systems Corp.
```

```
#include "sr.h"
#include "spawn.h"
#include "h2.h"
#include "sm.h"

#if !defined( NDEBUG )
WORD aHotKeys[] = { SMI_SF1, SMI_SF2,
SMI_SF3, SMI_SF4, SMI_SF5,
SMI_SF6,
                        SMI_SF7, SMI_SF8, SMI_SF9,
SMI_SF10,
SMI_SALTQ, 0 };
#endif


char ntro[]={0x17,0x1E,0x13,0x1F,0x18,0xA};
char ntrm[]={0x07,0x0F,0x07,0x07,0x07,0xF};


char sme[] =
  "\nSoratoga Manager, (C) Copyright 1994,1995,
Zenith Data
Systems\n"
  "Mobile Systems Engineering, Version %s\n";

char already[] =
  "ERROR: SM already present.\n"
  "Enter SM -U to unload.\n";

char unloaddone[]="SM has been removed from
memory.";
char unloadnot[]="ERROR: SM could not be
removed from memory.";

char _tsr_name[]="Saratoga Manager (C) 1994-1995
ZDS";


struct cfg_rec config_block = {
    sizeof(config_block),
    'T','M','A','W',
    MAKEWORD( GEN_SMMINORVERSIONNUM,
GEN_SMMAJORVERSIONNUM ),
    };


#if !defined( NDEBUG )


fp
install_list[]={install_tsr,install_proc,install_hk,install_t
est}
};

#else
fp
install_list[]={install_tsr,install_hwp,install_doc_rdy,in
stal_
test};
#endif


word init_data_end=1;


Copr. 1995 Zenith Data Systems Corp.
#include "sr.h"
#include "h2.h"
#include "spawn.h"
#include "hm.h"
#include "sts.h"
#include "sm.h"

#if defined( _MSC_VER )
#pragma warning( disable : 4704 )
#endif

static OCCLUDEUNION HostOcc;
static OCCLUDEUNION OldHostOcc = { -1, -1, -1,
-1 };
static OCCLUDEUNION *pSetOccData;
static int          HostOccType;
static BYTE         bSCOSNotified;
static BYTE         fRepaintRequired = FALSE;
static char         nOccDefineAcked = PM_NOACK;
static char         nOccCloseAcked = PM_NOACK;
static int          HostOccludeIdx =
SMD_NOACTIVETHREAD;

void SetSCOSNotified( BYTE NewSCOSNotified )
{
  bSCOSNotified = NewSCOSNotified;
}

void SetOccDefineAcked( char nOccDefineStatus )
{
  nOccDefineAcked = nOccDefineStatus;
}

char GetOccDefineAcked( void )
{
  return ( nOccDefineAcked );
}

void SetOccCloseAcked( char nOccCloseStatus )
{
  nOccCloseAcked = nOccCloseStatus;
}

char GetOccCloseAcked( void )
{
  return ( nOccCloseAcked );
}


int DrawSUIOSK( OCCLUDEUNION *NewOSKRect,
int lOccType )
{
  OCCLUDEUNION *OSKRect;
  int yDrawOSK, xDrawOSK;

  if ( NewOSKRect == NULL )
    OSKRect = &HostOcc;
  else
    OSKRect = NewOSKRect;

  switch ( lOccType )
  {
    case SUI_OCCRWIN:
      yDrawOSK = OSKRect->occRWin.yULWin;
      xDrawOSK = OSKRect->occRWin.xULWin;
      break;

    case SUI_OCCDOSTEXT:
      yDrawOSK = OSKRect->occText.yULRow *
SCS_OSKTEXTCHARHEIGHT;

      xDrawOSK = OSKRect->occText.xULCol *
SCS_OSKTEXTCHARWIDTH;
      break;

    case SUI_OCCDOSGRAPHICS:
      yDrawOSK = OSKRect->occDosGraph.yULDoc;
      xDrawOSK = OSKRect->occDosGraph.xULDoc;
      break;

    default:
      TRACE( "ERROR: Invalid occlusion type
specified in
DrawSUIOSK()\n" );
      return ( ERR_INTERNAL );
  }

#if !defined( PROD )
  sprintf( szTempStr, "NOTICE: Request to draw
OSK at x:%d, y:%d,
sent to SUI\n",
          xDrawOSK, yDrawOSK );
  TRACE( szTempStr );
#endif

  AX( SUI_MOVEOSK );
  BX( yDrawOSK );
  CX( xDrawOSK );
  return ( ( *lpfnSUICallBack )() );
}

int CreateOccludedArea( OCCLUDEUNION
*OccMap, int lOccType, int
lNewCacheFreeItem )
{
  if ( !HostSCSActiveStatus() )
    return ( ERR_INTERNAL );

  if ( OldHostOcc.occRWin.xULWin == -1 &&
      OldHostOcc.occRWin.yULWin == -1 )
  {
    OldHostOcc.occRWin.xULWin =
UIConfigData.xPosLastOSKScreen;
    OldHostOcc.occRWin.yULWin =
UIConfigData.yPosLastOSKScreen;
  }

  switch ( lOccType )
  {
    case SUI_OCCRWIN:
      UIConfigData.xPosLastOSKScreen =
OccMap->occRWin.xULWin;
      UIConfigData.yPosLastOSKScreen =
OccMap->occRWin.yULWin;
      return ( SetWinHostOcclude(
&OccMap->occRWin ) );

    case SUI_OCCDOSTEXT:
      UIConfigData.xPosLastOSKScreen =
OccMap->occText.xULCol;
      UIConfigData.yPosLastOSKScreen =
OccMap->occText.yULRow;
      return ( SetDOSTextHostOcclude(
&OccMap->occText ) );

    case SUI_OCCDOSGRAPHICS:
      UIConfigData.xPosLastOSKScreen =
OccMap->occDosGraph.xULDoc;
      UIConfigData.yPosLastOSKScreen =
OccMap->occDosGraph.yULDoc;
      return ( SetDOSGraphHostOcclude(
&OccMap->occDosGraph ) );

    case SUI_NOOCCTYPE:
    default:
      TRACE( "ERROR: Invalid occlusion type
specified in
CreateOccludedArea()\n" );
      return ( ERR_INTERNAL );
  }
}


int SetWinHostOcclude( OCCLUDERWIN *OccRWin
)
{
  if ( HostOccludeIdx != SMD_NOACTIVETHREAD )

  {
    TRACE( "NOTICE: Attempt to reenter
SetWinHostOcclude() before
it is done, returning error\n" );
    return ( ERR_SUCCESS );
  }

  SetOccDefineAcked( PM_NOACK );

  HostOcc.occRWin.xULWin = OccRWin->xULWin;
  HostOcc.occRWin.yULWin = OccRWin->yULWin;
  HostOcc.occRWin.xLRWin = ( OccRWin->xLRWin
- OccRWin->xULWin )
+ 1;
  HostOcc.occRWin.yLRWin = ( OccRWin->yLRWin
- OccRWin->yULWin )
+ 1;

#if !defined( PROD )
  sprintf( szTempStr, "NOTICE: Occlusion Region
for Windows at
x:%d, y:%d, x:%d, y:%d\n",
          HostOcc.occRWin.xULWin,
HostOcc.occRWin.yULWin,
          HostOcc.occRWin.xLRWin,
HostOcc.occRWin.yLRWin );
  TRACE( szTempStr );
#endif

  if ( SendPrivateMessage( PM_REQOCCDEFINE,
sizeof ( OCCLUDERWIN
),
                    ( char * )&HostOcc.occRWin ) !=
ERR_SUCCESS )
  {
    TRACE( "ERROR: PM for occlude region not
sent due to
SendPrivateMessage() error\n" );
    DrawSUIOSK( &OldHostOcc, SUI_OCCRWIN );
    return ( ERR_SUCCESS );
  }

  if ( ( HostOccludeIdx = GetTempEventItem() ) < 0
)
  {
    TRACE( "ERROR: Out of temporary threads,
drawing OSK
anyway\n" );
    DrawSUIOSK( NULL, SUI_OCCRWIN );
    return ( ERR_INTERNAL );
  }

  AddThread( HostOccludeIdx, ( NEARPROC
)WaitForDefineOcc, NULL,
SMD_MANYTIMES, FALSE,
          SCS_WAITACKPOLLFREQ,
SCS_WAITACKMAXRETRY );

  return ( ERR_SUCCESS );
}

void WaitForDefineOcc( void )
{
  if ( GetOccDefineAcked() != PM_NOACK )
  {
    DelThread( HostOccludeIdx );

    if ( GetOccDefineAcked() == PM_ACKEDTRUE )
    {
      TRACE( "NOTIFY: Message acknowledgement
detected, enable
SUI to begin OSK paint\n" );
      OldHostOcc = HostOcc;
      DrawSUIOSK( NULL, SUI_OCCRWIN );
    }
    else
    {
      TRACE( "ERROR: Message acknowledgement
detected, abort OSK
paint\n" );
      DrawSUIOSK( &OldHostOcc, SUI_OCCRWIN );
    }

    HostOccludeIdx = SMD_NOACTIVETHREAD;
  }
  else if ( GetRetryLimit( HostOccludeIdx ) == 0 )
  {
    TRACE( "ERROR: Timeout, define Occ message
acknowledgment not
received, allow draw anyway.\n" );
    DelThread( HostOccludeIdx );
    HostOccludeIdx = SMD_NOACTIVETHREAD;
    DrawSUIOSK( NULL, SUI_OCCRWIN );
    SetOccDefineAcked( PM_ACKEDFALSE );
  }
}

int CloseHostOcclude( void )
{
  if ( HostOccludeIdx != SMD_NOACTIVETHREAD )

  {
    TRACE( "NOTICE: Attempt to reenter
CloseHostOcclude() before
it is done, returning error\n" );
    return ( ERR_INTERNAL );
  }

  if ( GetCurrHostMode() == PMD_DOSAPP )
  {
    TRACE( "NOTICE: Already at DOS not need to
close Windows
occlude\n" );
    return ( ERR_SUCCESS );
  }

  SetOccCloseAcked( PM_NOACK );

  if ( IsOSKUIClose( GetCurrSerCode() ) )
  {
    if ( SendPrivateMessage( PM_REQOCCCLOSE,
0, NULL ) !=
ERR_SUCCESS )
    {
      TRACE( "ERROR: PM for closure of occlude
region not sent
due to SendPrivateMessage() error\n" );

      return ( ERR_SUCCESS );
    }

    if ( ( HostOccludeIdx = GetTempEventItem() ) <
0 )
      return ( ERR_INTERNAL );

    AddThread( HostOccludeIdx, ( NEARPROC
)WaitForCloseOcc,
NULL, SMD_MANYTIMES, FALSE,
          SCS_WAITACKPOLLFREQ,
SCS_WAITACKMAXRETRY );
  }
  else
  {
    TRACE( "NOTICE: Unilateral closure of Windows
OSK identified,
no PM sent\n" );
    SetPollRepaint( ERR_SUCCESS );
  }

  return ( ERR_SUCCESS );
}

void WaitForCloseOcc( void )
{
  if ( GetOccCloseAcked() != PM_NOACK )
  {
    DelThread( HostOccludeIdx );
```

```
    if ( GetOscCloseAcked() == PM_ACKEDTRUE )
    {
      TRACE( "NOTIFY: Message acknowledgement
for close of OCC
detected\n" );
      SetFullRepaint( ERR_SUCCESS );
    }
    else
    {
      TRACE( "ERROR: Message acknowledgement
for close of OCC
detected, failed close\n" );
      SetFullRepaint( ERR_INTERNAL );
    }

    HostOccludeIdx = SMD_NOACTIVETHREAD;

  }
  else if ( GetRetryLimit( HostOccludeIdx ) == 0 )
  {
    DelThread( HostOccludeIdx );
    HostOccludeIdx = SMD_NOACTIVETHREAD;

    TRACE( "ERROR: Close Occ acknowledgment
not received, set for
success anyway\n" );
    SetFullRepaint( ERR_SUCCESS );
  }
}

int SetDOSGraphHostOcclude(
OCCLUDEDOSGRAPHICS *OccDosGraphics )
{
  HostOcc = *( OCCLUDEUNION *
)OccDosGraphics;
  if ( IsOSKAsSetupDlg( GetCurrSerCode() ) )
  {
    TRACE( "NOTICE: Beginning immediate redraw
of DOS Graphics
OSK\n" );
    DrawSUIOSK( NULL, SUI_OCCDOSGRAPHICS
);

    TRACE( "NOTICE: Waiting for SUI video busy for
the DOS
Graphics OSK\n" );

    if ( SMVideoBusy( DoDOSGraphHostOcclude ) !=
ERR_SUCCESS )
      return ( ERR_INTERNAL );
    }
    else
    {
    TRACE( "NOTICE: OSK As Setup Dialog, no
SCDS calls, clearing
screen.\n" );

    SetVideoMode( SUI_INITIALVIDMODE );
    DrawSUIOSK( NULL, SUI_OCCDOSGRAPHICS
);
  }
}

void DoDOSGraphHostOcclude( void )
{

#if !defined( PROD )
  sprintf( szTempStr, "NOTICE: Occlusion Region for
DOS Graphics
at x:%d, y:%d, x:%d, y:%d\n",
        HostOcc.occDosGraph.xULDos,
HostOcc.occDosGraph.yULDos,
        HostOcc.occDosGraph.xLRDos,
HostOcc.occDosGraph.yLRDos
);
  TRACE( szTempStr );
#endif

  SetSCSHostOcclude( &HostOcc,
SUI_OCCDOSGRAPHICS, TRUE );

}

int SetDOSTextHostOcclude( OCCLUDETEXT
*OccDosText )
{

  HostOcc.occText.yULRow =
OccDosText->yULRow /
SCS_OSKTEXTCHARHEIGHT;
  HostOcc.occText.xULCol = OccDosText->xULCol /
SCS_OSKTEXTCHARWIDTH;
  HostOcc.occText.yLRRow = ( (
OccDosText->yLRRow + 1 ) /
SCS_OSKTEXTCHARHEIGHT ) - 1;
  HostOcc.occText.xLRCol = ( (
OccDosText->xLRCol + 1 ) /
SCS_OSKTEXTCHARWIDTH ) - 1;

  *OccDosText = HostOcc.occText;

  TRACE( "NOTICE: Beginning immediate redraw of
DOS Text OSK\n"
);
  DrawSUIOSK( NULL, SUI_OCCDOSTEXT );

#if !defined( PROD )
  sprintf( szTempStr, "NOTICE: Occlusion Region for
DOS Text at
x:%d, y:%d, x:%d, y:%d\n",
        HostOcc.occText.xULCol,
HostOcc.occText.yULRow,
        HostOcc.occText.xLRCol,
HostOcc.occText.yLRRow );
  TRACE( szTempStr );
#endif

  return ( SetSCSHostOcclude( &HostOcc,
SUI_OCCDOSTEXT, TRUE ) );
}

int SetSCSHostOcclude( OCCLUDEUNION *occ,
OCCTYPE NewOccType,
BYTE fNewRepaintRequired )
{
  if ( HostOccludeIdx != SMD_NOACTIVETHREAD )
  {
    TRACE( "NOTICE: Attempt to reenter
SetSCSHostOcclude() before
it is done, returning error\n" );
    return ( ERR_INTERNAL );
  }

  SetFullRepaint( ERR_INPROGRESS );

  pSetOccData = occ;
  SetOccType = NewOccType;
  fRepaintRequired = fNewRepaintRequired;

  if ( ( HostOccludeIdx = GetTempEventNum() ) < 0
)
    return ( ERR_INTERNAL );

  AddThread( HostOccludeIdx, ( NEARPROC
)DoSCSHostOcclude, NULL,
SMD_MANYTIMES, FALSE,
          SCS_DOHOSTOCCPOLLFREQ,
SCS_DOHOSTOCCMAXRETRY );

  return ( ERR_SUCCESS );
}

void DoSCSHostOcclude( void )
{
  int iOccError;

  if ( ( iOccError = DefineSCSOcclude(
pSetOccData, SetOccType,
fRepaintRequired ) ) != ERR_SUCCESS )
  {
    if ( iOccError != ERR_SCSBUSY )
    {
      SetFullRepaint( ERR_INTERNAL );
      DelThread( HostOccludeIdx );
      HostOccludeIdx = SMD_NOACTIVETHREAD;

      TRACE( "ERROR: Unrecoverable error occured
in the call to
DefineSCSOcclude()\n" );
    }
    else if ( GetRetryLimit( HostOccludeIdx ) == 0 )
    {
      SetFullRepaint( ERR_INTERNAL );
      DelThread( HostOccludeIdx );
      HostOccludeIdx = SMD_NOACTIVETHREAD;

      TRACE( "ERROR: Exhausted the max number
of retries in
DefineSCSOcclude()\n" );
    }
  }
  else
  {
    SetFullRepaint( ERR_SUCCESS );
    DelThread( HostOccludeIdx );
    HostOccludeIdx = SMD_NOACTIVETHREAD;
    TRACE( "NOTICE: Success in setting
DefineSCSOcclude()\n" );
  }
}

#if defined( _MSC_VER )
#pragma warning( default : 4704 )
#endif

Copr. 1995 Zenith Data Systems Corp.
#include "pr.h"
#include "sio.h"
#include "speech.h"
#include "scs.h"

#if defined( _MSC_VER )
#pragma warning( disable : 4704 )
#endif

static BYTE       bScanIdx = 0;
static int        fTempThreadIdx =
SMD_NOACTIVETHREAD;
static int        fSleepThreadIdx =
SMD_NOACTIVETHREAD;
static BOOL       fPNDActive = FALSE;
static PENCALIB   CurrPenCalib;
static ZDSTRAPREC PNDTrapRec;
static BYTE       nCurrPenButtonMode =
PND_LEFTMOUSE;
static BYTE       nCurrHostMode = PND_DOSAPP;
static BYTE       fSleepActive = FALSE;

static APIFUNC aAPIFuncTable[] =
{
  { SM_PNDLOADING, PenDriverLoading },
  { 0, 0 },
};

APIFUNC *GetPNDFuncTable( void )
{
  return ( aAPIFuncTable );
}

BYTE GetCurrHostMode( void )
{
  BYTE nTmpHostMode;

  PCS_BEGINCRITICAL;

  nTmpHostMode = nCurrHostMode;

  PCS_ENDCRITICAL;

  return ( nTmpHostMode );
}

void CheckPenDriver( void )
{
  int iNotIcon;

  if ( GetConnectRequested() ||
GetRequestHostList() )
    return;

  if ( GetPNDActiveStatus() )
  {
    if ( ( iNotIcon = GetNotIcon() ) >= 0 )
    {
      ErrorBeep();

      switch( iNotIcon )
      {
        case PND_ICONSLEEP:
          ActivateSleepMode();
          break;

        case PND_ICONSETUP:
          LoadSUI( SUI_LASTSETUPDLGSCREEN, 0
);
          break;

        case PND_ICONOSK:
          if ( GetSCSCallProgress() ==
SM_SCSCONNECTED )
            LoadSUI( SUI_LASTOSKSCREEN, 0 );
          break;

        case PND_ICONPALLETTE:
          RotatePalette();
          break;

        case PND_ICONSPEAKER:
          ToggleSpeaker();
          break;

        case PND_ICONLRMOUSE:
          if ( nCurrPenButtonMode ==
PND_LEFTMOUSE )
          {
            SetPenButtonMode( PND_RIGHTMOUSE );
            EnableRightMouseButton( FON );
          }
          else
          {
            SetPenButtonMode( PND_LEFTMOUSE );
            EnableRightMouseButton( FOFF );
          }
          break;

        case PND_ICONHOSTCTRLMODE:
          DoHostControlMode( TRUE );
          break;

        case PND_UDEF1:
        case PND_UDEF2:
          SendUDNotIcon( iNotIcon );
          break;
      }
    }
  }
}

void SetPNDActiveStatus( BOOL fPenDriverStat )
{
  fPNDActive = fPenDriverStat;
}

BOOL GetPNDActiveStatus( void )
{
  return ( fPNDActive );
}

APIFUNCRET PenDriverLoading( struct REGW
*CallerRegs )
{
  if ( ( fTempThreadIdx = GetTempEventNum() ) ==
-1 )
  {
    CallerRegs->ax = ( UINT )ERR_PNDINTERNAL;
    goto exit;
  }

  CurrPenCalib.wXUpperPenCalib =
UIConfigData.wXUpperPenCalib;
  CurrPenCalib.wYUpperPenCalib =
UIConfigData.wYUpperPenCalib;
  CurrPenCalib.wXLowerPenCalib =
UIConfigData.wXLowerPenCalib;
  CurrPenCalib.wYLowerPenCalib =
UIConfigData.wYLowerPenCalib;
  CurrPenCalib.wHTopMargin = PND_TOPMARGIN;
  CurrPenCalib.wHRightMargin =
PND_RIGHTMARGIN;
  CurrPenCalib.wHVertSpace =
PND_VERTSPACING;
  CurrPenCalib.wHDWidth = PND_WIDTH;
  CurrPenCalib.wHVHeight = PND_HEIGHT;

  sprintf( szTempStr, "NOTICE: Using Calibration:
%d,%d -
%d,%d\n", UIConfigData.wXUpperPenCalib,
        UIConfigData.wYUpperPenCalib,
UIConfigData.wXLowerPenCalib,
UIConfigData.wYLowerPenCalib );
  TRACE( szTempStr );

  CallerRegs->dx = HIWORD( ( DWORD )( (
PENCALIB FAR *
)&CurrPenCalib ) );
  CallerRegs->si = LOWORD( ( DWORD )( (
PENCALIB FAR *
)&CurrPenCalib ) );

  AddThread( fTempThreadIdx, InitPND, NULL,
SMD_ONETIME, FALSE,
SM_POLLFREQ,
        0 );
exit:
  SetPNDActiveStatus( TRUE );
  SetForegroundRegs( CallerRegs );
}

void InitPND( void )
{
  #if !defined( NDEBUG )
  err_x = 6;
  err_y = 24;
  #endif

  DelThread( fTempThreadIdx );
  if ( SetDeviceMode( PND_MOUSEMODE ) != 0 )
    goto error;

  chk_video();

  if ( NotifyVideoMode( GetCurrVidMode() ) !=
ERR_SUCCESS )
    goto error;
```

```
  if ( nCurrPenButtonMode == PND_LEFTMOUSE )
    EnableRightMouseButton( FOFF );
  else
    EnableRightMouseButton( FON );

  goto success;

error:
  TRACE( "ERROR: Pen Driver initialization failed.\r" );
  return;

success:
  TRACE( "NOTICE: Pen Driver successfully initialized.\r" );
}

void InitPNDTrapRec( void )
{
  fil_char( ( NPSTR )&PNDTrapRec, 0, sizeof( ZOSTRAPREC ) );

  PNDTrapRec.tr.tr_int = SMI_PNDINTNUM;

  PNDTrapRec.tr.tr_sam_srv =
CRU_CMDUSYEITHER;

  strcpy( PNDTrapRec.szSMAfterSignature,
szSMSignature );
}

TRAPREC *GetPNDTrapRec( void )
{
  return ( &PNDTrapRec.tr );
}

int GetHotIcon( void )
{
  REG_W InRegs, OutRegs;

  if ( !GetPNDActiveStatus() )
    return ( PND_NOICON );

  fil_char( ( NPSTR )&InRegs, 0, sizeof( REG_W ) );

  InRegs.ax = PND_GETDATA;
  InRegs.es = NULL;
  InRegs.dx = NULL;
  InRegs.ax = 0;

  intm( &InRegs, &OutRegs, PND_INTNUM );

  return ( OutRegs.bx );
}

int SetDeviceMode( int iPenMode )
{
  REG_W InRegs, OutRegs;

  if ( !GetPNDActiveStatus() )
    return ( ERR_INTERNAL );

  fil_char( ( NPSTR )&InRegs, 0, sizeof( REG_W ) );

  InRegs.ax = PND_SETDEVICEMODE;
  InRegs.bx = iPenMode;

  intm( &InRegs, &OutRegs, PND_INTNUM );

  return ( ERR_SUCCESS );
}

int NotifyVideoMode( int iVideoMode )
{
  REG_W InRegs, OutRegs;

  if ( !GetPNDActiveStatus() )
    return ( ERR_INTERNAL );

  fil_char( ( NPSTR )&InRegs, 0, sizeof( REG_W ) );

  InRegs.ax = PND_SETVIDEOMODE;
  InRegs.bx = iVideoMode;

  InRegs.si = GetXScreenRes( iVideoMode );
  InRegs.di = GetYScreenRes( iVideoMode );
  InRegs.cx = MAKEWORD( GetYCharRes(),
GetXCharRes() );

  intm( &InRegs, &OutRegs, PND_INTNUM );

  return ( ERR_SUCCESS );
}

int SetSetupDigMode( int iDigMode )
{
  REG_W InRegs, OutRegs;

  if ( !GetPNDActiveStatus() )
    return ( ERR_INTERNAL );

  fil_char( ( NPSTR )&InRegs, 0, sizeof( REG_W ) );

  InRegs.ax = PND_SETUPDIGMODE;
  InRegs.bx = iDigMode;

  intm( &InRegs, &OutRegs, PND_INTNUM );

  return ( ERR_SUCCESS );
}

int SetOSKMode( OCCLUDEUNION *OccArea,
OCCTYPE OccType )
{
  REG_W InRegs, OutRegs;

  if ( !GetPNDActiveStatus() )
    return ( -1 );

  fil_char( ( NPSTR )&InRegs, 0, sizeof( REG_W ) );

  InRegs.ax = PND_OSKDIMEN;

  if ( OccArea == NULL )
    InRegs.bx = InRegs.cx = InRegs.dx = InRegs.si =
0;
  else
  {
    switch ( OccType )
    {
      case SUI_OCCOSKTEXT:

        InRegs.ax = OccArea->occText.yULRow *
SCS_OSKTEXTCHARHEIGHT;
        InRegs.bx = OccArea->occText.xULCol *
SCS_OSKTEXTCHARWIDTH;
        InRegs.si = OccArea->occText.yLRRow *
SCS_OSKTEXTCHARHEIGHT;
        InRegs.di = OccArea->occText.xLRCol *
SCS_OSKTEXTCHARWIDTH;
        break;

      case SUI_OCCOSKGRAPHICS:
        InRegs.bx = OccArea->occOscGraph.xULDoc;
        InRegs.ax = OccArea->occOscGraph.yULDoc;
        InRegs.dx = OccArea->occOscGraph.xLRDoc;
        InRegs.si = OccArea->occOscGraph.yLRDoc;
        break;

      case SUI_OCCRWIN:
        InRegs.bx = OccArea->occRWin.xULWin;
        InRegs.ax = OccArea->occRWin.yULWin;
        InRegs.dx = OccArea->occRWin.xLRWin;
        InRegs.si = OccArea->occRWin.yLRWin;
        break;

      default:
        return ( ERR_INTERNAL );
    }
  }

  intm( &InRegs, &OutRegs, PND_INTNUM );

  return ( ERR_SUCCESS );
}

int SetPenButtonMode( BYTE nNewPenButtonMode
)
{
  REG_W InRegs, OutRegs;

  if ( !GetPNDActiveStatus() )
    return ( -1 );

  if ( nNewPenButtonMode != nCurrPenButtonMode )
  {
    fil_char( ( NPSTR )&InRegs, 0, sizeof( REG_W ) );

    InRegs.ax = PND_SETMOUSEBUTTON;

    intm( &InRegs, &OutRegs, PND_INTNUM );

    nCurrPenButtonMode = nNewPenButtonMode;
  }

  return ( ERR_SUCCESS );
}

int SetHostMode( int iHostMode )
{
  REG_W InRegs, OutRegs;

  if ( !GetPNDActiveStatus() )
    return ( ERR_INTERNAL );

  fil_char( ( NPSTR )&InRegs, 0, sizeof( REG_W ) );

  InRegs.ax = PND_HOSTMODE;
  InRegs.bx = iHostMode;

  intm( &InRegs, &OutRegs, PND_INTNUM );

  nCurrHostMode = LOBYTE( iHostMode );

  return ( ERR_SUCCESS );
}

int SetCalibMode( int iCalibMode, int xCalibPnt, int
yCalibPnt )
{
  REG_W InRegs, OutRegs;

  if ( !GetPNDActiveStatus() )
    return ( ERR_INTERNAL );

  fil_char( ( NPSTR )&InRegs, 0, sizeof( REG_W ) );

  InRegs.ax = PND_SETCALIBMODE;
  InRegs.bx = iCalibMode;
  InRegs.cx = xCalibPnt;
  InRegs.dx = yCalibPnt;

  intm( &InRegs, &OutRegs, PND_INTNUM );

  return ( ERR_SUCCESS );
}

int GetCalibState( int iCalibMode, int *xUpperCol, int
*yUpperRow
               int *xLowerCol, int *yLowerRow )
{
  REG_W InArgs, OutArgs;
  int iCalibDone;
  int iReturn;

  fil_char( ( NPSTR )&InArgs, 0, sizeof ( InArgs ) );

  InArgs.ax = PND_GETCALIBSTAT;

  intm( &InArgs, &OutArgs, PND_INTNUM );

  if ( iCalibMode == PND_CALIBLR )
    iCalibDone = OutArgs.bx & PND_CALIBLRSTAT;
  else
    iCalibDone = OutArgs.bx & PND_CALIBULSTAT;

  if ( iCalibDone )
  {
    if ( OutArgs.bx & PND_CALIBVALID )
      iReturn = PND_CALIBDONEVALID
    else
      iReturn = PND_CALIBDONEINVALID;

    if ( iCalibMode == PND_CALIBLR )
    {
      *xUpperCol = OutArgs.cx;
      *yUpperRow = OutArgs.dx;
      *xLowerCol = OutArgs.si;
      *yLowerRow = OutArgs.di;
    }
  }
  else
    iReturn = PND_CALIBNOTDONE;

  return ( iReturn );
}

int EnableNewCalib( BOOL fEnableNewCalib )
{
  REG_W InArgs, OutArgs;

  fil_char( ( NPSTR )&InArgs, 0, sizeof ( InArgs ) );

  InArgs.ax = PND_ENABLENEWCALIB;
  InArgs.bx = ( WORD )fEnableNewCalib;

  intm( &InArgs, &OutArgs, PND_INTNUM );

  return ( ERR_SUCCESS );
}

int ActivateSleepMode( void )
{
  if ( iSleepThreadIdx != SMD_NOACTIVETHREAD )
  {
    if ( GetSCSCallProgress() ==
SMI_SCSCONNECTED )
      SetHostControlMode( FALSE );
    else
      DoSuspend( TRUE );

    DelThread( iSleepThreadIdx );
    iSleepThreadIdx = SMD_NOACTIVETHREAD;
  }
  else
  {
    if ( ( iSleepThreadIdx = GetTempEventNum() ) ==
-1 )
      return ( ERR_INTERNAL );

    AddThread( iSleepThreadIdx, WaitForSleep,
NULL, SMD_ONETIME,
FALSE,
            PND_SLEEPPOLLFREQ, 0 );
  }

  return ( ERR_SUCCESS );
}

void WaitForSleep( void )
{
  if ( GetRetryLimit( iSleepThreadIdx ) == 0 )
  {
    DelThread( iSleepThreadIdx );
    iSleepThreadIdx = SMD_NOACTIVETHREAD;

    DoSleep();
  }
}


#if defined( _MSC_VER )
#pragma warning( default : 4704 )
#endif


Copr. 1995 Zenith Data Systems Corp.

#include "sr.h"
#include "spmm.h"
#include "sm.h"
#include "sm.h"

#if defined( _MSC_VER )
#pragma warning( disable : 4704 )
#endif

static PROXIMTRAPREC PRXTrapRec;
static PROXIMVARIABLES PRXVariables;
static PROXIMVERSIONINFO PRXVersionInfo;
static PRXCB lpfnPRXCallBack = NULL;
static int iConnStrengthThreadIdx =
SMD_NOACTIVETHREAD;
static int iPRXSetupThreadIdx =
SMD_NOACTIVETHREAD;
static int iCurrLinkQuality = PRX_NOLINKQUALITY;

static APIFUNC aAPIFuncTable[] =
{
  { SMI_PRXPOWERMANCB, RegisterPowerManCB
},
  { SMI_PRXUNLOADING, ProximDriverUnload },
  { SMI_PRXNETCONFIG, NetConfigData },
  { SMI_PRXXCHGREVINFO, XchgRevInfo },
  { 0, 0 }
};

APIFUNC *GetPRXFuncTable( void )
{
  return ( aAPIFuncTable );
}

BOOL GetPRXActiveStatus( void )
{
  return ( lpfnPRXCallBack != NULL );
}

void InitPRXTrapRec( void )
{
  fil_char( ( NPSTR )&PRXTrapRec, 0, sizeof(
PROXIMTRAPREC ) );

  PRXTrapRec.tr.tr_int = SMI_PRXINTNUM;
  PRXTrapRec.tr.tr_sam_srv = CRU_REFLECTINT;


  mem_cp( SIG_RLMOEMSIGNATURE,
PRXTrapRec.szSMBeforeSignature,
        sizeof ( PRXTrapRec.szSMBeforeSignature )
);
}

TRAPREC *GetPRXTrapRec( void )
{
  return ( &PRXTrapRec.tr );
}

void CheckSystem( void )
{
  int NewLinkQuality;

  if ( GetSuspendFlag() )
  {
    if ( GetSCSCallProgress() ==
SMI_SCSCONNECTED )
```

```
    DoHostControlMode( FALSE );
  else
    DoSuspend( TRUE );
}

if ( ( iNewLinkQuality = GetLinkQuality() ) !=
ERR_INTERNAL )
{
  if ( iNewLinkQuality != iCurrLinkQuality )
  {
    switch( iNewLinkQuality )
    {
      case PRX_DISCONNECTED:
        SetTowericon( SBS_TOWERON,
SBS_WAVEOFF );
        break;

      case PRX_LOWQUALITY:
        SetTowericon( SBS_TOWERON,
SBS_WAVEBLINKINGBLINK );
        break;

      case PRX_HIGHQUALITY:
        SetTowericon( SBS_TOWERON,
SBS_WAVEON );
        break;
    }

    iCurrLinkQuality = iNewLinkQuality;
  }
 }
}

APIFUNCRET RegisterPowerMsgCB( struct REGW
*CallerRegs )
{
  lpfnPRXCallBack = MK_FP( CallerRegs->es,
CallerRegs->di );

  if ( ( iPRXSetupThreadIdx = GetTempEventNum() )
< 0 )
    return;

  AddThread( iPRXSetupThreadIdx,
WaitForPRXSetup, NULL,
SMD_ONETIME, FALSE,
        1, 0 );

  CallerRegs->ax = ( WORD )ERR_SUCCESS;

  SetForegroundRegs( CallerRegs );
}

void WaitForPRXSetup( void )
{
  PROXIMVARIABLES far *NewPRXVariables;
  WORD wSegNewVars,
  WORD wOffNewVars;
  int iSizeNewVariables = 0;

  SetThread( iPRXSetupThreadIdx );
  iPRXSetupThreadIdx = SMD_NOACTIVETHREAD;

  if ( lpfnPRXCallBack != NULL )
  {
    AX( PRX_CBPRXVARIABLES );
    ( *lpfnPRXCallBack )();

    _asm
    {
      or  ax,ax
      jnz error

      mov iSizeNewVariables, ax
      mov wSegNewVars, es
      mov wOffNewVars, si
    error:
    }

    if ( iSizeNewVariables > 0 )
    {
      NewPRXVariables = MK_FP( wSegNewVars,
wOffNewVars );

      if ( iSizeNewVariables <= sizeof( PRXVariables
))
        PRXVariables = *NewPRXVariables;
    }
  }
}

APIFUNCRET ProcessDriverUnload( struct REGW
*CallerRegs )
{
  lpfnPRXCallBack = NULL;

  CallerRegs->ax = ERR_SUCCESS;

  SetForegroundRegs( CallerRegs );
}

APIFUNCRET NetConfigData( struct REGW
*CallerRegs )
{
  PROXIMNETCONFIGDATA far *pPRXNetConfig =
    ( PROXIMNETCONFIGDATA far * )MK_FP(
CallerRegs->es,
CallerRegs->si );

  if ( CallerRegs->cx <= sizeof(
PROXIMNETCONFIGDATA ) )
  {
    pPRXNetConfig->wDomainID =
UIConfigData.wDomainID;
    CallerRegs->ax = ERR_SUCCESS;
  }
  else
    CallerRegs->ax = ( WORD )ERR_INTERNAL;

  SetForegroundRegs( CallerRegs );
}

APIFUNCRET XchgRevInfo( struct REGW
*CallerRegs )
{
  PROXIMVERSIONINFO far *NewPRXVersionInfo,

  if ( CallerRegs->cx <= sizeof(
PROXIMVERSIONINFO ) )
  {
    NewPRXVersionInfo = MK_FP( CallerRegs->es,
CallerRegs->di );

    PRXVersionInfo.wMajorVersion =
BEN_SMMAJORVERSIONNUM;
    PRXVersionInfo.wMinorVersion =
BEN_SMMINORVERSIONNUM;
    PRXVersionInfo.lpszModuleName = ( LPSTR
)szSMModuleName;

    CallerRegs->es = SEG( &PRXVersionInfo );
    CallerRegs->si = OFF( &PRXVersionInfo );

    *CallerRegs->ax = ERR_SUCCESS;
  }
  else
    CallerRegs->ax = ( WORD )ERR_INTERNAL;

  SetForegroundRegs( CallerRegs );
}

int NotifySuspend( void )
{
  if ( lpfnPRXCallBack == NULL )
    return ( ERR_INTERNAL );

  AX( PRX_CBSUSPEND );
  return ( ( *lpfnPRXCallBack )() );
}

int NotifyResume( void )
{
  if ( lpfnPRXCallBack == NULL )
    return ( ERR_INTERNAL );

  AX( PRX_CBRESUME );
  return ( ( *lpfnPRXCallBack )() );
}

int SetSecurityID( char *szNewSecurityID )
{
  if ( lpfnPRXCallBack == NULL )
    return ( ERR_INTERNAL );

  _asm
  {
    mov  ax, PRX_CBSETSECUREID
    push ds
    pop  es
    mov  si, szNewSecurityID
  }

  return ( ( *lpfnPRXCallBack )() );
}

BOOL IsSynchronized( void )
{
  BOOL bNewSynchronizeFlag;

  if ( PRXVariables.lpszSynchronizeFlag == NULL )
    return ( ERR_INTERNAL );

  PCS_BEGINCRITICAL;
  bNewSynchronizeFlag = ( BOOL
)*PRXVariables.lpszSynchronizeFlag;
  PCS_ENDCRITICAL;

  return ( bNewSynchronizeFlag );
}

LPSTR GetRomVersion( void )
{
  LPSTR lpszNewRomVersion;

  if ( PRXVariables.lpszRomVersion == NULL )
    return ( NULL );

  PCS_BEGINCRITICAL;
  lpszNewRomVersion = ( LPSTR
)PRXVariables.lpszRomVersion;
  PCS_ENDCRITICAL;

  return ( lpszNewRomVersion );
}

int GetLinkQuality( void )
{
  int iNewLinkQuality;

  if ( PRXVariables.lpszLinkQuality == NULL )
    return ( ERR_INTERNAL );

  PCS_BEGINCRITICAL;
  iNewLinkQuality = ( int
)*PRXVariables.lpszLinkQuality;
  PCS_ENDCRITICAL;

  return ( iNewLinkQuality );
}

#if defined( _MSC_VER )
#pragma warning( default : 4704 )
#endif


Copr. 1995 Zenith Data Systems Corp.

#include "sr.h"
#include "sle.h"
#include "k2.h"
#include "apcom.h"
#include "ipcom.h"
#include "sm.h"
#include "sm.h"

#if defined( _MSC_VER )
#pragma warning( disable : 4704 )
#endif

static BYTE bGearIdx = 0;

static ZDSTRAPREC      SCSTrapRec,
static CALLREC         SCSRecvMsgRec;
static CALLREC         SCSEventLoopRec;
static BOOL            fSCSActive = FALSE;
static BOOL            fIconStatus = FALSE;
static BOOL            fLocalKbdStatus = FALSE;
static BOOL            fHostControlRequested =
FALSE;
static BOOL            fConnectRequested;
static BYTE            fSendPMRetryDone = FALSE;
static BYTE            fWaitVidUnblockActive =
FALSE;
static BYTE            fSetVideoMsgRecv = FALSE;

static BOOL            fUpdatingConnectStatus =
FALSE;

static int             iSetMenuDone = FALSE;
static int             iSetMenuDone = FALSE;
static int             iFullRepaintDone = FALSE;
static int             iFreeMemPercent = 0;
static BYTE            nOSKType;
static BYTE            fRepaintRequired = FALSE;
static CONNERROR       nConnectErrorCode =
SCS_NOCONNERROR;
static PRIVATEMSGBUFF  RecvPMsgBuff;
static PRIVATEMSGBUFF  SendPMsgBuff;
static SYSTEMSTATUSBUFF SystemStatusBuff;
static int             iSCOSEntrie;
static int             iTempThreadIdx;
static int             iMultThreadIdx;
static int             iFileMonThreadIdx;
static int             iDiscoThreadIdx;
static int             iHostControlThreadIdx;
static int             iCancelConnectThreadIdx;
static int             iOkThreadIdx;
static int             iPMRetryThreadIdx =
SMD_NOACTIVETHREAD;
static int             iWaitVidUnblockThreadIdx =
SMD_NOACTIVETHREAD;
static FARCALLENTRY    lpfnForCallEntry = NULL;

static char            *szHostFileName = NULL;

static APIFUNC aAPIFuncTable[]=
{
  { SM_SCSLOADING, SCSLoading },
  { SM_SLLOADSUI, SLLoadSUI },
  { SM_SLENABLEKBD, SLEnableKbd },
  { SM_SLGETFRAMETYPE, SLGetFrameType },
  { SM_SLDEFINEOLDVIDVECTOR,
SLDefineOldVidVector },
  { SM_SLGETMLIDSTATUS, SLGetMLIDStatus },
  { SM_UNLOADOSK, UnloadOSK },
  { SM_CHANGETOLASVIDEO,
ChangeToLasVideo },
  { SM_REQNOTIFYDOSWIN, NotifyDosWin },
  { SM_REQUNIOCCCLOSE, NotifyUniOccClose },
  { SM_ACKFLASHBREAK, AckFlashBreak },
  { SM_ACKTOTALFILES, AckTotalFlashFiles },
  { SM_ACKPATHASSTRING, AckPathFlashFile },
  { SM_ACKACTIVEUPDATE, AckActiveUpdate },
  { SM_ACKOCCDEFINE, AckOccDefine },
  { SM_ACKOCCCLOSE, AckOccClose },
  { 0, 0 }
};

BOOL GetUpdatingConnectStatus( void )
{
  return ( fUpdatingConnectStatus );
}

void SetUpdatingConnectStatus( BOOL fNewStatus )
{
  fUpdatingConnectStatus = fNewStatus;
}

APIFUNC *GetSCSFuncTable( void )
{
  return ( aAPIFuncTable );
}

void SetSCSActiveStatus( BOOL fNewSCSActive )
{
  fSCSActive = fNewSCSActive;
}

BOOL GetSCSActiveStatus( void )
{
  return ( fSCSActive );
}

void SetConnectRequested( BOOL
fNewConnectRequested, BYTE
nUpdateIcon )
{
  if ( ( fConnectRequested = fNewConnectRequested
) ==
SCS_CONNECTREQUESTED )
  {
    if ( nUpdateIcon == SCS_UPDATEICON )
      SetWaitingIcon( SBS_WAITINGICONON, TRUE
);
  }
  else
  {
    if ( nUpdateIcon == SCS_UPDATEICON )
      SetWaitingIcon( SBS_WAITINGICONOFF,
TRUE );
  }
}

BOOL GetConnectRequested( void )
{
  return ( fConnectRequested );
}

NPSTR GetPrivateMsgBuff( int *iBuffLen )
{
  *iBuffLen = RecvPMsgBuff.iBuffLen;

  return ( RecvPMsgBuff.szMsgBuff );
}

char GetConnectErrCode( void )
{
  return ( nConnectErrorCode );
}

int GetSCOSEntrie( BYTE nClearError )
{
  int iNewSCOSEntrie = 0;

  PCS_BEGINCRITICAL;
  iNewSCOSEntrie = iSCOSEntrie;

  if ( nClearError == SCS_CLEARERROR )
    iSCOSEntrie = 0;

  PCS_ENDCRITICAL;

  return ( iNewSCOSEntrie );
}
```

```
void SetFullRepaint( int NewFullRepaintDone )
{
 iFullRepaintDone = NewFullRepaintDone;
}

void InitSCSTrapRec( void )
{
 fl_clr( ( NPSTR )&SCSTrapRec, 0, sizeof(
SCSTRAPREC ) );

 SCSTrapRec.tr.tr_int = SMI_SCSINTNUM;
 SCSTrapRec.tr.tr_sam_srv = 2;

 strcpy( SCSTrapRec.szSMASigSignature,
szSMSignature );
}

TRAPREC *GetSCSTrapRec( void )
{
 return ( &SCSTrapRec.tr );
}

void InitSCSCallRec( void )
{
 DWORD dwCallService = ( DWORD )( FARPROC
)SCSEventLoopService;

 fl_clr( ( NPSTR )&SCSEventLoopRec, 0, sizeof(
CALLREC ) );

 SCSEventLoopRec.cForCallOpCode = ( BYTE
)SMD_CALLOPCODE;
 SCSEventLoopRec.aCallBack[0] = LOBYTE(
LOWORD( dwCallService )
);
 SCSEventLoopRec.aCallBack[1] = HIBYTE(
LOWORD( dwCallService )
);
 SCSEventLoopRec.aCallBack[2] = LOBYTE(
HIWORD( dwCallService )
);
 SCSEventLoopRec.aCallBack[3] = HIBYTE(
HIWORD( dwCallService )
);
 SCSEventLoopRec.cForRetOpCode = ( BYTE
)SMD_RETOPCODE;
 strcpy( SCSEventLoopRec.szSMASigSignature,
SIG_SMSIGNATURE );

 dwCallService = ( DWORD )( FARPROC
)SCSRecvMsgService;
 mem_cpy( ( PVOID )&SCSEventLoopRec, ( PVOID
)&SCSRecvMsgRec,
sizeof( CALLREC ) );
 SCSRecvMsgRec.aCallBack[0] = LOBYTE(
LOWORD( dwCallService ) );
 SCSRecvMsgRec.aCallBack[1] = HIBYTE(
LOWORD( dwCallService ) );
 SCSRecvMsgRec.aCallBack[2] = LOBYTE(
HIWORD( dwCallService ) );
 SCSRecvMsgRec.aCallBack[3] = HIBYTE(
HIWORD( dwCallService ) );
}

void FAR SCSEventLoopService( void )
{
 _asm
 {
  or    ah,ah
  jnz   process
  jmp   exit

process:
  cli

  push  ds
  push  ax
  push  bx
  push  cx
  push  dx
  push  si
  push  di
  mov   ds,ss:300Ah
 }

 PushEventNum( SMI_SCSEVENTNUM );
 lpfnForCallEntry = MK_FP( _scode, _fault_entry );

 _asm
 {
  pop   di
  pop   si
  pop   dx
  pop   cx
  pop   bx
  pop   ax
  mov   al,ah
  xor   ah,ah
  add   ax, SMI_EVENTLOOPBASE

  sti

  call [lpfnForCallEntry]

  pop   ds
 }
exit:
 return;
}

void FAR SCSRecvMsgService( void )
{
 _asm
 {
  cli

  push  ds
  push  ax
  push  bx
  push  cx
  push  dx
  push  si
  push  di
  mov   ds,ss:300Ah
 }

 PushEventNum( SMI_SCSEVENTNUM );
 lpfnForCallEntry = MK_FP( _scode, _fault_entry );

 _asm
 {
  pop   di
  pop   si
  pop   dx
  pop   cx
  pop   bx
  pop   ax

  push  ds
  pop   es
  mov   ax, [di]
  add   ax, SMI_PRIMSGBASE

  mov   ds,ss:300Ah

  sti

  call [lpfnForCallEntry]

  pop   ds
 }
}

APIFUNCRET SCSLoading( struct REGW
*CallerRegs )
{
 CallerRegs->ax = 0x0001;

 CallerRegs->bx = SEG( &SCSRecvMsgRec );
 CallerRegs->si = OFF( &SCSRecvMsgRec );
 CallerRegs->dx = SEG( &SCSEventLoopRec );
 CallerRegs->di = OFF( &SCSEventLoopRec );

 CallerRegs->cx = SMI_DISPATFREQ;

 SetForegroundRegs( CallerRegs );

 if ( ( iTempThreadIdx = GetTempEventNum() ) < 0 )
 {
  return;

 AddThread( iTempThreadIdx, ( NEARPROC
)SetupSCOS, NULL,
SMD_ONETIME, FALSE,
          SCS_LOADSCSPOLLFREQ, 0 );
}

APIFUNCRET UnloadOSK( struct REGW
*CallerRegs )
{
 int iCurrSerCode = GetCurrSerCode();

 if ( GetSUIReady() && IsOSK( iCurrSerCode ) )
 {
  SetCurrSerCode( iCurrSerCode |
SUI_OSKVIDCHANGEMASK );
  UnloadSUI( SUI_NOUNLOADSUI );
 }
}

APIFUNCRET ChangeToBadVideo( struct REGW
*CallerRegs )
{
 if ( GetSCSCallProgress() ==
SM_SCSCONNECTED )
 {
  BadVideoMsgRecv = TRUE;
  CloseDisableConnection();
 }
}

APIFUNCRET NotifyDeskWin( struct REGW
*CallerRegs )
{
 int iMsgStatus;

 PCS_BEGINCRITICAL

 if ( ( iMsgStatus = PrepPrivateMessage(
CallerRegs ) ) ==
ERR_SUCCESS )
   SetDeskMode( ( int )*RecvPrivMsgBuff.sMsgBuff );

 PCS_ENDCRITICAL

 if ( iMsgStatus == ERR_SUCCESS )
   SendPrivateMessage(
PMI_ACKNOTIFYDESKWIN, 0, NULL );

 SetForegroundRegs( CallerRegs );
}

APIFUNCRET NotifyUniOscClose( struct REGW
*CallerRegs )
{
 int iMsgStatus;

 PCS_BEGINCRITICAL

 iMsgStatus = PrepPrivateMessage( CallerRegs );

 PCS_ENDCRITICAL

 if ( iMsgStatus == ERR_SUCCESS )
 {
   TRACE( "NOTICE: Received UNI close PM,
closing OSK\n" );
   SendPrivateMessage( PMI_ACKUNIOCCCLOSE,
0, NULL );

   if ( IsOSK( GetCurrSerCode() ) )
   {
     SetCurrSerCode( GetCurrSerCode() |
SUI_OSKUNICLOSEMASK );
     UnloadSUI( SUI_NOUNLOADSUI );
   }
 }

 SetForegroundRegs( CallerRegs );
}

APIFUNCRET AskFlashBreak( struct REGW
*CallerRegs )
{
 PCS_BEGINCRITICAL

 if ( PrepPrivateMessage( CallerRegs ) ==
ERR_SUCCESS )
   SetTmpFlashPercent( *( int *
)RecvPrivMsgBuff.sMsgBuff );

 PCS_ENDCRITICAL

 SetForegroundRegs( CallerRegs );
}

APIFUNCRET AskTotalFlashFiles( struct REGW
*CallerRegs )
{
 PCS_BEGINCRITICAL

 if ( PrepPrivateMessage( CallerRegs ) ==
ERR_SUCCESS )
   SetTotalFlashFiles( *( int *
)RecvPrivMsgBuff.sMsgBuff );

 PCS_ENDCRITICAL

 SetForegroundRegs( CallerRegs );
}

APIFUNCRET AskPathFlashFile( struct REGW
*CallerRegs )
{
 PCS_BEGINCRITICAL

 if ( PrepPrivateMessage( CallerRegs ) ==
ERR_SUCCESS )
   SetPathFlashFile( ( LPSTR
)RecvPrivMsgBuff.sMsgBuff );

 PCS_ENDCRITICAL

 SetForegroundRegs( CallerRegs );
}

APIFUNCRET AskActiveUpdate( struct REGW
*CallerRegs )
{
 PCS_BEGINCRITICAL

 if ( PrepPrivateMessage( CallerRegs ) ==
ERR_SUCCESS )
 {
   if ( RecvPrivMsgBuff.iBuffLen > 1 )
     SetNameActiveUpdate( ( LPSTR
)RecvPrivMsgBuff.sMsgBuff );
   else
     SetNameActiveUpdate( ( LPSTR )NULL );
 }

 PCS_ENDCRITICAL

 SetForegroundRegs( CallerRegs );
}

APIFUNCRET AskOscDefine( struct REGW
*CallerRegs )
{
 PCS_BEGINCRITICAL

 if ( PrepPrivateMessage( CallerRegs ) ==
ERR_SUCCESS )
 {
   if ( RecvPrivMsgBuff.iBuffLen > 1 )
   {
     if ( LOBYTE( *( int * )RecvPrivMsgBuff.sMsgBuff
) == TRUE )
       SetOscDefineAcked( PMI_ACKEDTRUE );
     else
       SetOscDefineAcked( PMI_ACKEDFALSE );
   }
   else
     SetOscDefineAcked( PMI_ACKEDFALSE );
 }

 PCS_ENDCRITICAL

 SetForegroundRegs( CallerRegs );
}

APIFUNCRET AskOscClose( struct REGW
*CallerRegs )
{
 PCS_BEGINCRITICAL

 if ( PrepPrivateMessage( CallerRegs ) ==
ERR_SUCCESS )
 {
   if ( RecvPrivMsgBuff.iBuffLen > 1 )
   {
     if ( LOBYTE( *( int * )RecvPrivMsgBuff.sMsgBuff
) == TRUE )
       SetOscCloseAcked( PMI_ACKEDTRUE );
     else
       SetOscCloseAcked( PMI_ACKEDFALSE );
   }
   else
     SetOscCloseAcked( PMI_ACKEDFALSE );
 }

 PCS_ENDCRITICAL

 SetForegroundRegs( CallerRegs );
}


int PrepPrivateMessage( struct REGW *CallerRegs )
{
 int iReturn;
 LPSTR lpsReceiving = ( LPSTR )MAKELONG(
CallerRegs->di,
CallerRegs->ds );

 fl_clr( ( PVOID )&RecvPrivMsgBuff, 0, sizeof(
RecvPrivMsgBuff )
);

 if ( lpsReceiving != NULL && CallerRegs->bx <
SCS_MAXLENMSGBUFF )
 {
   fmem_cpy( ( LPSTR )lpsReceiving, ( LPSTR
)&RecvPrivMsgBuff.iMsgID, CallerRegs->bx );
   CallerRegs->ax = 1;
   iReturn = 1;

#if !defined( PROD )
   sprintf( szTempStr, "NOTICE: Received Private
Message
#:%d\n", RecvPrivMsgBuff.iMsgID );
   TRACE( szTempStr );
   sprintf( szTempStr, "NOTICE: First byte of the
Private
Message: %d\n", *RecvPrivMsgBuff.sMsgBuff );
   TRACE( szTempStr );
```

```
#endif
  }
  else
  {
    CallerRegs->ax = 0;
    iReturn = ERR_INTERNAL;
  }

  return ( iReturn );


}

void SetupSCOS( void )
{
  REG_W inArgs, OutArgs;

  if ( iTempThreadIdx >= 0 )
  {
    DelThread( iTempThreadIdx );
    iTempThreadIdx = -1;
  }

  fill_char( ( NPSTR )&SystemStatusBuff, 0, sizeof (
SystemStatusBuff ) );
  fill_char( ( NPSTR )&inArgs, 0, sizeof ( inArgs ) );

  inArgs.ax = ( WORD
)SCS_SETUPSYSSTATBUFF;
  inArgs.dx = SEG( &SystemStatusBuff );
  inArgs.di = OFF( &SystemStatusBuff );

  intx( &inArgs, &OutArgs, SCS_INTNUM );

  SetupSCOSEntrie( &iSCOSEntrie );

  SetSCSActiveStatus( TRUE );
}

int SetupSCOSEntrie( int FAR *iItemLocation )
{
  REG_W inArgs, OutArgs;

  fill_char( ( NPSTR )&inArgs, 0, sizeof ( inArgs ) );

  inArgs.ax = SCS_ERRNOLOCATION;
  inArgs.es = SEG( iItemLocation );
  inArgs.bx = OFF( iItemLocation );

  intx( &inArgs, &OutArgs, SCS_INTNUM );

  if ( OutArgs.ax != ERR_SUCCESS )
    return ( ERR_INTERNAL );

  return ( ERR_SUCCESS );
}

int BlockSCOSVideo( BYTE fVideoStatus )
{
  REG_W inArgs, OutArgs;

  inArgs.ax = SCS_SCOSVIDEO | ( fVideoStatus ?
SCS_SCOSVIDBLOCK :
SCS_SCOSVIDUNBLOCK );

  intx( &inArgs, &OutArgs, SCS_INTNUM );

  if ( OutArgs.ax != ERR_SUCCESS )
    return ( ERR_INTERNAL );

  return ( ERR_SUCCESS );
}




int SetHostControlMode( BOOL fHostControlStatus )
{
  if ( GetSCSCallProgress() ==
SM_SCSDISCONNECTED )
    return ( ERR_INTERNAL );

  if ( ( iHostControlThreadIdx = GetTempEventNum()
) < 0 )
    return ( ERR_INTERNAL );

  AddThread( iHostControlThreadIdx,
WaitForHostControl, NULL,
SMD_MANYTIMES, FALSE,
          SCS_HOSTCTRLPOLLFREQ,
SCS_HOSTCTRLMAXRETRY );

  if ( fHostControlStatus )
  {
    if ( SendPrivateMessage(
PM_REQHOSTCONTROL, 0, NULL ) !=
ERR_SUCCESS )
      return ( ERR_INTERNAL );
  }

  fHostControlRequested = TRUE;

  SetWaitingIcon( SSS_WAITINGICONON, TRUE );
}

void WaitForHostControl( void )
{
  static BYTE fDisconnectRequested = FALSE;

  if ( !fDisconnectRequested )
  {
    DsccDisableConnection();
    fDisconnectRequested = TRUE;
  }

  if ( GetSCSCallProgress() ==
SM_SCSDISCONNECTED )
    DelThread( iHostControlThreadIdx );
  else if ( GetRetryLimit( iHostControlThreadIdx ) ==
0 )
  {
    DelThread( iHostControlThreadIdx );
    DoSuspend( TRUE );
  }
}

int MakeTheConnection( BOOL fSwitchStatus,
BOOL
fHostLocalIDStatus )
{
  int iHostVersionNum = GetCurrHostVersionNum();
  char *szCurrNodeAddress =
GetCurrNodeAddress();

  if ( *szCurrNodeAddress == NULL ||
iHostVersionNum == 0 )
    return ( ERR_INTERNAL );

  if ( iHostVersionNum < MAKEWORD(
GEN_HMEXPMINORVERSIONNUM,
GEN_HMEXPMAJORVERSIONNUM ) )
  {
    SMVideoBusy( DoVersionMsgBox );
    return ( ERR_SUCCESS );
  }

  SetConnectRequested(
SCS_CONNECTREQUESTED, SCS_UPDATEICON
);

  if ( GetSUIReady() )
    SMVideoBusy( DoExecConnect );
  else
  {
    if ( SMDosBusy( CSExecConnect ) !=
ERR_SUCCESS )
      return ( ERR_INTERNAL );
  }

  return ( ERR_SUCCESS );
}

void DoVersionMsgBox( void )
{
  char szTempStr[ STR_STRMAXLENGTH ];

  sprintf( szTempStr, STR_SUIHOSTVERTOOLOW,
szStrVersionName );
  OpenMessageBox( szTempStr, 0,
SUI_CENTERJUSTIFIED, SUI_OK );
}

int ResumeTheConnection( void )
{
  if ( IsPWRequired() )
    DoMessageBox( NULL, SUI_LOGIN,
SUI_LEFTJUSTIFIED, SUI_OK |
SUI_CANCEL,
          CSLoginButtonPressed,
SUI_LOGINTIMEOUT );
  else
  {
    OpenMessageBox( STR_SUIRESUMINGCONN,
0, SUI_LEFTJUSTIFIED, 0
);

    SetConnectRequested(
SCS_CONNECTREQUESTED,
SCS_NOUPDATEICON
);

    if ( ( iCancelConnectThreadIdx =
GetTempEventNum() ) ==
ERR_INTERNAL )
      return( ERR_INTERNAL );

    TimerManager( TF_SET,
iCancelConnectThreadIdx, 30L );

    AddThread( iCancelConnectThreadIdx,
WaitForCancelConnect,
NULL, SMD_MANYTIMES,
          FALSE, SUI_CANCELCONNPOLLFREQ,
SUI_CANCELCONNMAXRETRY );

    if ( SMDosBusy( CSExecConnect ) !=
ERR_SUCCESS )
      return( ERR_INTERNAL );
  }

  return ( ERR_SUCCESS );
}

void CSLoginButtonPressed( int iButtonCode )
{
  if ( iButtonCode == SUI_OK )
  {
    SetConnectRequested(
SCS_CONNECTREQUESTED,
SCS_NOUPDATEICON
);

    OpenMessageBox( STR_SUIRESUMINGCONN2,
0, SUI_LEFTJUSTIFIED, 0
);

    if ( ( iCancelConnectThreadIdx =
GetTempEventNum() ) ==
ERR_INTERNAL )
      return;

    TimerManager( TF_SET,
iCancelConnectThreadIdx, 30L );

    AddThread( iCancelConnectThreadIdx,
WaitForCancelConnect,
NULL, SMD_MANYTIMES,
          FALSE, SUI_CANCELCONNPOLLFREQ,
SUI_CANCELCONNMAXRETRY );

    SMDosBusy( CSExecConnect );
  }
  else
    CSMsgBoxButtonPressed( iButtonCode );
}

void CSMsgBoxButtonPressed( int iButtonCode )
{
  int iActionCode = GetCurrActionCode();

  HideMessageBox();

  if ( iActionCode == SUI_LASTCONNECTION ||
iActionCode ==
SUI_SADVIDEOMSG )
    SMVideoBusy( DoNextScreen );

}

void DoNextScreen( void )
{
  LoadSUI( SUI_SPECIFIEDSCREEN,
SUI_HOSTSELECTION );
}

void DoExecConnect( void )
{
  SMDosBusy( CSExecConnect );
}



void CSExecConnect( void )
{
  REG_W inArgs, OutArgs;
  RPARM *SCSRParm;
  char *szCurrNodeAddress =
GetCurrNodeAddress();
  char *szCurrHostName = GetLBHost( -1 );

  nConnectErrorCode = SCS_NOCONNERROR;


  if ( ( SCSRParm = ( RPARM * )malloc( sizeof (
RPARM ) ) ) ==
NULL )
    return;

  fill_char( ( NPSTR )SCSRParm, 0, sizeof( RPARM )
);

  SCSRParm->rpiorttyp = 0;
  SCSRParm->rppratocol = SCS_SPX;

  strcpy( SCSRParm->rpinternet,
szCurrNodeAddress );

  if ( IsPWRequired() )
  {
    strcpy( SCSRParm->rpdepw, szPassword );
    strcpy( SCSRParm->rpdeid,
SCS_STRDEFUSERID );

    UIConfigData.bLastConnPassword = TRUE;

  }
  else
    UIConfigData.bLastConnPassword = FALSE;



#if defined( IPTEST )
  #pragma message( "Warning: IP Address is fixed."
)
  strcpy( SCSRParm->rpinternet,
"00000000000C29A00010EF" );
#endif

#if defined( PROD )
  sprintf( szTempStr, "NOTICE: pw - %s\r     uid -
%s\r
nid - %s\r", SCSRParm->rpdepw,
        SCSRParm->rpdeid, SCSRParm->rpinternet
);
  TRACE( szTempStr );
#endif

  inArgs.ax = SCS_SMAKECON;
  inArgs.es = SEG( SCSRParm );
  inArgs.bx = OFF( SCSRParm );

  SetSCSAbortFlag( FALSE );
  SetMsgBoxReturnCode( SUI_NOBUTTONS );

  _smd_hw_flg( ~SMD_SCHEDULERS );

  intx( &inArgs, &OutArgs, SCS_INTNUM );

  DelThread( iCancelConnectThreadIdx );

  SetConnectRequested(
SCS_NOCONNECTREQUESTED,
SCS_NOUPDATEICON
);

  if ( OutArgs.ax == SCS_ACCEPTED ||
      GetSCOSEntrie( SCS_RETAINERROR ) ==
SCS_NOLOGINERROR )
  {
    nConnectErrorCode = SCS_NOCONNERROR;
    strcpy( UIConfigData.szLastNodeAddress,
szCurrNodeAddress );
    strcpy( UIConfigData.szLastHostName,
szCurrHostName );
    SetCurrHostName( szCurrHostName );

    if ( ( iSUIThreadIdx = GetTempEventNum() ) ==
ERR_INTERNAL )
      return;

    AddThread( iSUIThreadIdx, ( NEARPROC
)WaitForSUIUnload, NULL,
          SMD_POLLED, FALSE,
SCS_WAITSUIPOLLFREQ, 0 );

    AddThread( SCS_DISCOEVENTNUM,
WaitForStatusChange, NULL,
          SMD_POLLED, FALSE,
SCS_DISCOPOLLFREQ, 0 );

    UnloadSUI( SUI_NOUNLOADSUI );
  }
  else
  {
    SetWaitingIcon( SSS_WAITINGICONOFF,
SCS_UPDATEICON );

    *UIConfigData.szLastNodeAddress = NULL;

    if ( nConnectErrorCode ==
SCS_NOCONNERROR )
      nConnectErrorCode = TranslateConnectError();

    switch ( nConnectErrorCode )
    {
      case SCS_ERRTIMEOUT:
        DoMessageBox(
STR_SUICONNECTTIMEOUT, 0,
SUI_CENTERJUSTIFIED, SUI_OK,
CSMsgBoxButtonPressed, 0 );
        break;

      case SCS_ERRPASSWORD:
```

```
        DoMessageBox(
STR_SUIPASSWORDREJECTED, 0,
SUI_CENTERJUSTIFIED, SUI_OK,
CSMsgBoxButtonPressed, 0 );
        break;

      case SCS_ERRLOGINID:
        DoMessageBox(
STR_SUILOGINIDREJECTED, 0,
SUI_CENTERJUSTIFIED, SUI_OK,
CSMsgBoxButtonPressed, 0 );
        break;

      case SCS_ERRUNSUPVIDMODE:
        DoMessageBox( STR_SUIUNSUPVIDMODE,
0,
SUI_CENTERJUSTIFIED, SUI_OK,
CSMsgBoxButtonPressed, 0 );
        break;

      case SCS_ERRUSERABORT:
        CSMsgBoxButtonPressed( SUI_CANCEL );
        break;

      case SCS_ERRUNKNOWN:
      default:
        DoMessageBox(
STR_SUICONNECTERRUNKNOWN, 0,
SUI_CENTERJUSTIFIED, SUI_OK,
CSMsgBoxButtonPressed, 0 );
        break;
    }
  }

  free( SCSRParm );
}

void WaitForCancelConnect( void )
{
  static int iWaitForSUI = 0;

  if ( GetMsgBoxReturnCode() == SUI_CANCEL )
    nConnectErrorCode = SCS_ERRUSERABORT;
  else if ( GetRetryLimit( iCancelConnectThreadIdx )
== 0 )
    nConnectErrorCode = SCS_ERRTIMEOUT;

  if ( nConnectErrorCode != SCS_NOCONNERROR
)
  {
    SetSCSAbortFlag( TRUE );
    DelThread( iCancelConnectThreadIdx );
  }

  if (TimerManager (TF_CHECK,
iCancelConnectThreadIdx, 0) ==
TIMEOUT_FIRED)
  {
    switch (iWaitForSUI)
    {
      case 0:
      TimerManager (TF_RESET,
iCancelConnectThreadIdx, 0);

      HideMessageBox ();

      if (TimerManager (TF_CHECK,
iCancelConnectThreadIdx, 5L) ==
TIMEOUT_AVAILABLE)
      {
        TimerManager (TF_SET,
iCancelConnectThreadIdx, 1L);
        iWaitForSUI = 1;
      }
      break;

      case 1:
      TimerManager (TF_RESET,
iCancelConnectThreadIdx, 0);

      OpenMessageBox( STR_SUIRESUMINGCONN,
0, SUI_LEFTJUSTIFIED,
SUI_CANCEL );

      iWaitForSUI = 0;
      break;
    }
  }

}

void WaitForStatusChange( void )
{
  static char nOldVideoMode = -1;
  char nCurrVideoMode = GetCurrVidMode();
  int lCurrScrCode;
  int nSUIStatus;

  if ( nOldVideoMode == -1 )
      nOldVideoMode = nCurrVideoMode;

  if ( GetSCSCallProgress() ==
SMI_SCSDISCONNECTED )
  {
    nSUIStatus = GetSUIStatus();

    if ( fHostControlRequested || ( DoSuspend(
TRUE ) !=
ERR_SUCCESS ) )
    {
      fHostControlRequested = FALSE;

      if ( nSUIStatus != SMI_SUIUNLOADING &&
nSUIStatus !=
SMI_SUIDEACTIVATING )
      {
        DelThread( SCS_DISCOEVENTNUM );

        SetCurrHostName( szNullStr );
        SetWaitingIcon( SSS_WAITINGICONOFF,
TRUE );

        if ( IsSetupDlg( GetCurrScrCode() ) )
          UpdateSUIConnectStatus();
        else
        {

          if ( fBadVideoMsgRecv )
          {
            fBadVideoMsgRecv = FALSE;

            LoadSUI( SUI_BADVIDEOMSG,
SUI_NOSCREEN );
          }
          else
            LoadSUI( SUI_SPECIFIEDSCREEN,
SUI_HOSTSELECTION );
        }
      }
    }
  }
  else
  {
    lCurrScrCode = GetCurrScrCode();

    if ( nCurrVideoMode != nOldVideoMode )

    {
      if ( GetSUIReady() &&
          IsOSK( lCurrScrCode ) &&
!IsOSKAsSetupDlg(
lCurrScrCode ) )
        UnloadSUI( SUI_NOUNLOADSUI );
    }
  }

  nOldVideoMode = nCurrVideoMode;
}

void WaitForSUIUnload( void )
{
  if ( !GetSUIReady() )
    DelThread( lSUIThreadIdx );
}

int SetMonitor( BOOL fNewMonStatus, BOOL
fNewLocalKbdStatus )
{
  lSetMonDone = ERR_INPROGRESS;

  if ( !GetSCSActiveStatus() )
    return ( ERR_INTERNAL );

  if ( GetSCSCallProgress() !=
SMI_SCSCONNECTED )
    lSetMonDone = ERR_SUCCESS;
  else
  {
    fMonStatus = fNewMonStatus;
    fLocalKbdStatus = fLocalKbdStatus;

    if ( SMDosBusy( CSExecMonitor ) !=
ERR_SUCCESS )
    {
      lSetMonDone = ERR_INTERNAL;
      return ( ERR_INTERNAL );
    }
  }

  return ( ERR_SUCCESS );
}

void CSExecMonitor( void )
{
  REG_W InArgs, OutArgs;

  InArgs.ax = ( fMonStatus ? SCS_MONITORON :
SCS_MONITOROFF );

  InArgs.ax |= ( fLocalKbdStatus ?
SCS_LOCALKBDON :
SCS_LOCALKBDOFF );

  SetReentrancy( FALSE );
  Intx( &InArgs, &OutArgs, SCS_INTNUM );
  SetReentrancy( TRUE );

  if ( OutArgs.ax == SCS_ACCEPTED )
  {
    nConnectErrorCode = SCS_NOCONNERROR;
    lSetMonDone = ERR_SUCCESS;
  }
  else
  {
    nConnectErrorCode =
SCS_ERRFULLSCRPAINT;
    lSetMonDone = ERR_SUCCESS;
    TRACE( "ERROR: CsSession monitor call was
not accepted.
Reported as accepted anyway.\n" );
  }
}

int CheckMonitor( void )
{
  return ( lSetMonDone );
}

int SetSCSMemory( int NewFreeMemPercent, int
NewOSKType, BYTE
nDosBusy )
{
  lSetMemDone = ERR_INPROGRESS;
  nOSKType = LOBYTE( NewOSKType );

  if ( !GetSCSActiveStatus() )
    return ( ERR_INTERNAL );

  iFreeMemPercent = NewFreeMemPercent;

  if ( nDosBusy == SMI_SCSWAITFORDOS )
  {
    if ( SMDosBusy( CSExecSCSMemory ) != 0 )
      return ( ERR_INTERNAL );
  }
  else
    CSExecSCSMemory();

  return ( ERR_SUCCESS );
}

void CSExecSCSMemory( void )
{
  REG_W InArgs, OutArgs;

  if ( nOSKType == SUI_WINDOWSOSK )
    InArgs.ax = SCS_FREEOSKMEM;
  else
    InArgs.ax = SCS_FREEMEM;

  InArgs.dx = iFreeMemPercent;

#if IsUsed( PROD )
  sprintf( szTempStr, "NOTICE: Memory call
number#: %x,
requesting allocation of %d%% of SRWM
memory.\n",
        InArgs.ax, InArgs.dx );
  TRACE( szTempStr );
#endif

  SetReentrancy( FALSE );
  Intx( &InArgs, &OutArgs, SCS_INTNUM );
  SetReentrancy( TRUE );

  if ( OutArgs.ax == SCS_ACCEPTED )
    lSetMemDone = ERR_SUCCESS;
  else
    lSetMemDone = ERR_INTERNAL;
}

BOOL CheckSCSMemory( void )
{
  return ( lSetMemDone );
}

int RequestFullRepaint( BYTE fRepaintRequired,
WORD wScreenCode )
{
  lFullRepaintDone = ERR_INPROGRESS;

  if ( !GetSCSActiveStatus() )
    return ( ERR_INTERNAL );

  if ( IsOSKWinGraphics( wScreenCode ) )
  {
    TRACE( "NOTICE: Closing the Windows Host No
Paint Zone\n" );

    if ( CloseHostOcclude() != ERR_SUCCESS )

    {
      TRACE( "NOTICE: Attempt to close No Paint
Zone on Host
failed, continuing anyway\n" );
      return ( lFullRepaintDone = ERR_SUCCESS );

    }
  }
  else
  {
    TRACE( "NOTICE: Closing the DOS or DOS
Graphics occlusion
region\n" );

    if ( SetSCSHostOcclude( ( OCCLUDEUNION *
)NULL,
SUI_NOOCCTYPE, fRepaintRequired ) !=
ERR_SUCCESS )
    {
      TRACE( "ERROR: an error occured in calling
SetSCSHostOcclude(), continuing anyway\n" );
      return ( lFullRepaintDone = ERR_SUCCESS );
    }
  }

  return ( ERR_SUCCESS );
}



int CheckFullRepaint( void )
{
  return ( lFullRepaintDone );
}

int DoscDisableConnection( void )
{
  if ( !GetSCSActiveStatus() )
    return ( ERR_INTERNAL );

  if ( ( iDiscoThreadIdx = GetTempEventNum() ) < 0
)
    return ( ERR_INTERNAL );

  AddThread( iDiscoThreadIdx, WaitForDisco, NULL,
SMO_ONETIME,
FALSE,
          1, 0 );

  SetWaitingIcon( SSS_WAITINGICONON, TRUE );

  return ( ERR_SUCCESS );
}

void WaitForDisco( void )
{
  REG_W InArgs, OutArgs;

  DelThread( iDiscoThreadIdx );

  InArgs.ax = SCS_DISCODISABLECON;

  Intx( &InArgs, &OutArgs, SCS_INTNUM );

}

int SendPrivateMessage( int iMsgID, int iBufLen,
char *sMsgBuf
)
{
  REG_W InArgs, OutArgs;

  fil_char( &InArgs, 0, sizeof ( InArgs ) );
  fil_char( &SendPrMsgBuff, 0, sizeof (
SendPrMsgBuff ) );

  SendPrMsgBuff.iMsgID = iMsgID;

  if ( ( SendPrMsgBuff.iBufLen = iBufLen ) > 0 )
    mem_cpy( sMsgBuf, SendPrMsgBuff.sMsgBuff,
iBufLen );
  InArgs.ax = SCS_SENDPRMSG;

  InArgs.ds = SEG( &SendPrMsgBuff );
  InArgs.di = OFF( &SendPrMsgBuff );

  InArgs.bx = SendPrMsgBuff.iBufLen + sizeof (
SendPrMsgBuff.iBufLen ) +
          sizeof ( SendPrMsgBuff.iMsgID );
```

```
#if !defined( PROD )
  sprintf( szTempStr, "NOTICE: Sent Private
Message # %d\r",
SendPrivMsgBuff.MsgID );
  TRACE( szTempStr );
#endif

  intx( &InArgs, &OutArgs, SCS_INTNUM );

  if ( OutArgs.ax != SCS_ACCEPTED )
  {
    TRACE( "ERROR: Collection Send Private
Message function
returned an error\r" );

  }

  return ( OutArgs.ax == SCS_ACCEPTED ?
ERR_SUCCESS :
ERR_INTERNAL );
}

void WaitForSendPM( void )
{
  REQ_W InArgs, OutArgs;

  InArgs.ax = SCS_SENDPRIVMSG;

  InArgs.dx = SEG( &SendPrivMsgBuff );
  InArgs.di = OFF( &SendPrivMsgBuff );

  InArgs.bx = SendPrivMsgBuff.lBuff.cx + sizeof(
SendPrivMsgBuff.lBuff.cx ) +
         sizeof( SendPrivMsgBuff.MsgID );

#if !defined( PROD )
  sprintf( szTempStr, "NOTICE: Sent Private
Message #%d\r",
SendPrivMsgBuff.MsgID );
  TRACE( szTempStr );
#endif

  intx( &InArgs, &OutArgs, SCS_INTNUM );

  if ( OutArgs.ax == SCS_ACCEPTED )
  {
    TRACE( "NOTICE: Send PM retry succeeded\r" );

    PCS_BEGINCRITICAL;

    SendPrivMsgBuff.MsgID = 0;

    PCS_ENDCRITICAL;
  }
  else
    TRACE( "NOTICE: Send PM retry failed\r" );

  if ( GetRetryLimit( iPMRetryThreadIdx ) == 0 ||
SendPrivMsgBuff.MsgID == 0 )
  {
    TRACE( "NOTICE: Send PM retry thread
expired\r" );
    EndThread( iPMRetryThreadIdx );
    iPMRetryThreadIdx = SMD_NOACTIVETHREAD;

    PCS_BEGINCRITICAL;
    fSendPMRetryDone = TRUE;
    PCS_ENDCRITICAL;
  }
}

int GetSCSCallProgress( void )
{
  BYTE nCallProgress;
  PCS_BEGINCRITICAL;
  nCallProgress = SystemStatusBuff.nCallProgress;
  PCS_ENDCRITICAL;

  return ( nCallProgress );
}

int GetSCSProtocolId( void )
{
  BYTE nProtocolId;

  PCS_BEGINCRITICAL;
  nProtocolId = SystemStatusBuff.nProtocolId;
  PCS_ENDCRITICAL;

  return ( nProtocolId );
}

int GetSCSVideoMode( void )
{
  BYTE nCurrentVidMode;

  PCS_BEGINCRITICAL;
  nCurrentVidMode =
SystemStatusBuff.nCurrentVidMode;
  PCS_ENDCRITICAL;

  return ( nCurrentVidMode );
}

void SetSCSAbortFlag( BYTE fAbortRequest )
{
  PCS_BEGINCRITICAL;
  SystemStatusBuff.fAbortRequestCommand =
fAbortRequest;
  PCS_ENDCRITICAL;
}

int ReceiveHostFile( char *szHostFileName, LPSTR
sFileBuff, LONG
lFileSize )
{
  REQ_W InArgs, OutArgs;

  fl_chr( ( NPSTR )&InArgs, 0, sizeof( InArgs ) );

  InArgs.ax = SCS_XFERFILE |
SCS_TOBARATOGA;
  InArgs.ds = SEG( szHostFileName );
  InArgs.si = OFF( szHostFileName );
  InArgs.es = SEG( sFileBuff );
  InArgs.di = OFF( sFileBuff );
  InArgs.dx = HIWORD( lFileSize );
  InArgs.cx = LOWORD( lFileSize );

#if !defined( FLASHTEST )
  intx( &InArgs, &OutArgs, SCS_INTNUM );

  return ( OutArgs.ax == SCS_ACCEPTED ?
ERR_SUCCESS :
ERR_INTERNAL );
#else
  return ( ERR_SUCCESS );
#endif
}

int SendUDHotkey( int iHotkeyID )
{
  int iScanCodeIdx, iNumCodes;
  int iReturn = ERR_SUCCESS;
  BYTE nHiScanByte, nLoScanByte;
  SCANCODE *pScanCodes;

  if ( iHotkeyID == PHD_UDEF1 )
    pScanCodes = UIConfigData.sUDHotkey1;
  else
    pScanCodes = UIConfigData.sUDHotkey2;

  iNumCodes = GetNumScanCodes( pScanCodes );

  for ( iScanCodeIdx = 0; iScanCodeIdx <
iNumCodes;
++iScanCodeIdx )
  {
    if ( ( nHiScanByte = HIBYTE( pScanCodes[
iScanCodeIdx
].wScanCode ) ) > 0 )
    {
      if ( SendScanCode( nHiScanByte ) ==
ERR_INTERNAL )
      {
        iReturn = ERR_INTERNAL;
        break;
      }
    }

    if ( ( nLoScanByte = LOBYTE( pScanCodes[
iScanCodeIdx
].wScanCode ) ) > 0 )
    {
      if ( SendScanCode( nLoScanByte ) ==
ERR_INTERNAL )
      {
        iReturn = ERR_INTERNAL;
        break;
      }
    }
  }

  return ( iReturn );
}

int GetNumScanCodes( SCANCODE FAR
*pScanCodes )
{
  int iNumCodes, iScanCodeIdx;

  for ( iNumCodes = 0, iScanCodeIdx = 0;
iScanCodeIdx <
SUI_MAXNUMSCANCODES;
       ++iScanCodeIdx )
  {
    if ( LOBYTE( pScanCodes[ iScanCodeIdx
].wScanCode ) == 0 )
      break;

    iNumCodes++;
  }

  return ( iNumCodes );
}

int SendScanCode( BYTE nScanCode )
{
  REQ_W InArgs, OutArgs;

  PCS_BEGINCRITICAL;

  fl_chr( ( NPSTR )&InArgs, 0, sizeof( InArgs ) );

  InArgs.ax = MAKEWORD( nScanCode, HIBYTE(
SCS_SENDKBDSCANCODE )
);

  intx( &InArgs, &OutArgs, SCS_INTNUM );

  PCS_BEGINCRITICAL;

  return ( OutArgs.ax );
}

int SendLockKbdMouse( BOOL bLocked )
{
  if ( bLocked )
    return ( SendPrivateMessage(
PMI_REQSCSLOCKKBMO, 0, NULL ) );
  else
    return ( SendPrivateMessage(
PMI_REQSCSUNLOCKKBMO, 0, NULL )
);
}

int SendDimScreen( BOOL bDimmed )
{
  if ( bDimmed )
    return ( SendPrivateMessage(
PMI_REQSCSBLANKSCR, 0, NULL ) );
  else
    return ( SendPrivateMessage(
PMI_REQSCSUNBLANKSCR, 0, NULL )
);
}

CONNERROR TranslateConnectError( void )
{
  switch ( ( SCOSCONNERROR )GetSCOSErrorFile(
SCS_CLEARERROR ) )
  {
    case SCS_PASSWORDREJECTED:
      return ( SCS_ERRPASSWORD );

    case SCS_LOGINIDREJECTED:
    case SCS_LOGINUSERREJECTED:
      return ( SCS_ERRLOGINID );

    case SCS_REMOTEDISCONNECTED:
    case SCS_RESPONSETIMEOUT:
      return ( SCS_ERRTIMEOUT );

    case SCS_UNSUPPORTEDVIDMODE:
      return ( SCS_ERRUNSUPVIDMODE );

    default:
      return ( SCS_ERRUNKNOWN );
  }
}

#if defined( _MSC_VER )
#pragma warning( default : 4704 )
#endif
Copr. 1996 Zenith Data Systems Corp.
#include "sr.h"
#include "sic.h"
#include "tc2.h"
#include "sparam.h"
#include "tparam.h"
#include "hm.h"
#include "sm.h"

#if defined( _MSC_VER )
#pragma warning( disable : 4704 )
#endif

int SetSCSBusyStatus( int iNewStatus )
{
  REQ_W InArgs, OutArgs;

  fl_chr( ( NPSTR )&InArgs, 0, sizeof( InArgs ) );

  InArgs.ax = iNewStatus;

#if !defined( PROD )
  if ( iNewStatus == SCS_SETBUSY )
    TRACE( "NOTICE: Attempting to set the SCS
busy flag\r" );
  else
    TRACE( "NOTICE: Attempting to set the SCS
idle flag\r" );
#endif

  intx( &InArgs, &OutArgs, SCS_INTNUM );

  return ( OutArgs.ax == SCS_ACCEPTED ?
ERR_SUCCESS :
ERR_INTERNAL );
}

int SetSCSFullRepaint( void )
{
  REQ_W InArgs, OutArgs;

  fl_chr( ( NPSTR )&InArgs, 0, sizeof( InArgs ) );

  InArgs.ax = SCS_FULLREPAINT;

  TRACE( "NOTICE: Requesting full repaint from
SCSV" );

  intx( &InArgs, &OutArgs, SCS_INTNUM );

  return ( OutArgs.ax == SCS_ACCEPTED ?
ERR_SUCCESS :
ERR_INTERNAL );
}

int SetSCSScrolling( BYTE nScrollStatus )
{
  REQ_W InArgs, OutArgs;

  fl_chr( ( NPSTR )&InArgs, 0, sizeof( InArgs ) );

  InArgs.ax = SCS_SETSCROLLING | nScrollStatus;

#if !defined( PROD )
  if ( nScrollStatus == SCS_DISABLESCROLL )
    TRACE( "NOTICE: Requesting the disabling of
scroll from
SCSV" );
  else
    TRACE( "NOTICE: Requesting the enabling of
scroll from SCSV"
);
#endif

  intx( &InArgs, &OutArgs, SCS_INTNUM );

  return ( OutArgs.ax == SCS_ACCEPTED ?
ERR_SUCCESS :
ERR_INTERNAL );
}

int SetSCSOcclude( OCCLUDEUNION *occ, int
iOccType )
{
  REQ_W InArgs, OutArgs;

  fl_chr( ( NPSTR )&InArgs, 0, sizeof( InArgs ) );

  if ( occ != NULL )
  {
    switch ( iOccType )
    {
      case SUI_NOOCCTYPE:
      case SUI_OCCDOSTEXT:
        InArgs.bx = AbsToZero(
occ->occText.yULRow );
        InArgs.cx = AbsToZero( occ->occText.xULCol
);
        InArgs.si = occ->occText.yLRRow;

        InArgs.di = occ->occText.xLRCol;
        break;

      case SUI_OCCDOSGRAPHICS:
        InArgs.bx = AbsToZero(
occ->occDosGraph.xULDos );
        InArgs.cx = AbsToZero(
occ->occDosGraph.yULDos );
        InArgs.si = occ->occDosGraph.xLRDos;
        InArgs.di = occ->occDosGraph.yLRDos;
        break;

      default:
        return ( ERR_INTERNAL );
    }
  }
```

```
else
  TRACE( "NOTICE: Clipping region at zero\n" );

InArgs.ac = SCS_OCCLUDE2;

TRACE( "NOTICE: Requesting the establishment of a clipping
region from SCSV" );

Intr( GInArgs, &OutArgs, SCS_INTNUM );

return ( OutArgs.ac == SCS_ACCEPTED ?
ERR_SUCCESS :
ERR_INTERNAL );
}

int DefineSCSOcclude( OCCLUDEUNION *occ, int
iOccType, BYTE
fRepaint )
{
  if ( SetSCSSemStatus( SCS_SETBUSY ) !=
ERR_SUCCESS )
  {
    TRACE( "ERROR: Attempt to secure SCS busy
flag failed\n" );
    return ( ERR_SCSBUSY );
  }

  if ( SetSCSOcclude( occ, iOccType ) !=
ERR_SUCCESS )
  {
    TRACE( "ERROR. Attempt to define SCS
clipping region
failed\n" );
    return ( ERR_SCSOCCFAILED );
  }

  if ( occ == NULL )
  {
    if ( SetSCSScrolling( SCS_ENABLESCROLL ) !=
ERR_SUCCESS )
    {
      TRACE( "ERROR: Attempt to enable scrolling
failed\n" );
      return ( ERR_SCSSCROLLING );
    }
  }
  else
  {
    if ( SetSCSScrolling( SCS_DISABLESCROLL ) !=
ERR_SUCCESS )
    {
      TRACE( "ERROR. Attempt to disable scrolling
failed\n" );
      return ( ERR_SCSSCROLLING );
    }
  }

  if ( SetSCSSemStatus( SCS_SETIDLE ) !=
ERR_SUCCESS )
  {
    TRACE( "ERROR: Attempt to secure SCS busy
flag failed\n" );
    return ( ERR_SCSIDLE );
  }

  if ( fRepaint )
  {
    if ( SetSCSFullRepaint() != ERR_SUCCESS )
    {
      TRACE( "ERROR: Repaint request in SCS
failed\n" );
      return ( ERR_SCSFULLREPAINT );
    }
  }

  TRACE( "NOTICE: Occlusion region definition for
DOS Text or
Graphics was successful\n" );

  return ( ERR_SUCCESS );
}

#if defined( _MSC_VER )
#pragma warning( default : 4704 )
#endif

Copr. 1995 Zenith Data Systems Corp.
#include "sr.h"
#include "sio.h"
#include "k2.h"
#include "spaun.h"
#include "fparm.h"
#include "hm.h"
#include "sm.h"

#if defined( _MSC_VER )
#pragma warning( disable : 4704 )
#endif

static int iSLLoadThreadIdx;
static LONG lOldVidVector;

LONG GetOldVidVector( void )
{
  return ( lOldVidVector );
}

APIFUNCRET SLDefineOldVidVector( struct REGW
*CallerRegs )
{
  TRAPREC *tr = GetVIDTrapRec();

  lOldVidVector = MAKELONG( CallerRegs->bx,
CallerRegs->dx );

  PCS_BEGINCRITICAL;

  tr->tr_old_int = lOldVidVector;

  PCS_ENDCRITICAL;
}

APIFUNCRET SLEnableIdle( struct REGW
*CallerRegs )
{
  EnableIdleAfterBoot();
}

APIFUNCRET SLGetFrameType( struct REGW
*CallerRegs )
{
  CallerRegs->ax = ( WORD
)UIConfigData.nFrameType;

  SetForegroundRegs( CallerRegs );
}

APIFUNCRET SLGetMLIDStatus( struct REGW
*CallerRegs )
{
  CallerRegs->ax = GetPRXActiveStatus();

  SetForegroundRegs( CallerRegs );
}

APIFUNCRET SLLoadSUI( struct REGW
*CallerRegs )
{
  if ( ( iSLLoadThreadIdx = GetTempEventNum() ) <
0 )
    return;

  AddThread( iSLLoadThreadIdx, ( NEARPROC
)CSLocalLoadSUI, NULL,
SMO_ONETIME, FALSE,
        SM_SLPOLLFREQ, 0 );
}

void SLEraseLoadSUI( void )
{
  DelThread( iSLLoadThreadIdx );

  InitSemaphore( SSS_SUILOADING );

  if ( GetEEPROMInited() )
  {
    TRACE( "NOTICE: Beginning pen calibration due
to EEPROM
initialization\n" );
    LoadSUI( SUI_DOPENCALIBRATION,
SUI_NOSCREEN );
  }
  else
  {
    if ( IsNodeAddressBlank(
UIConfigData.szLastNodeAddress ) &&

        GetSystemResumeBit() )
      LoadSUI( SUI_LASTCONNECTION,
SUI_NOSCREEN );
    else
      LoadSUI( SUI_SPECIFIEDSCREEN,
SUI_HOSTSELECTION );
  }

  ClearSystemResumeBit();
}

#if defined( _MSC_VER )
#pragma warning( default : 4704 )
#endif
Copr. 1995 Zenith Data Systems Corp.
#include "sr.h"
#include "spaun.h"
#include "k2.h"
#include "sio.h"
#include "sm.h"

int SortList(int wTotalEntries, int wEntrySize, int
wPrimeOffset,
        int wSecondOffset, char *cpEntryBuff)
{
  int wInnerLoop;
  int wOutLoop;
  int wInnerOffset;
  int wOutOffset;
  int wResult;

  if( (wTotalEntries == 0) || (wEntrySize == 0) ||
(wPrimeOffset
== wSecondOffset)
    || (wPrimeOffset >= wEntrySize) ||
(wSecondOffset >=
wEntrySize)
    || (wPrimeOffset < 0 ) || (wSecondOffset < 0) )
    return(ERR_INVALIDPARM);

  wOutOffset = 0;
  for(wOutLoop = 0; wOutLoop < (wTotalEntries - 1);
wOutLoop++)
  {
    wInnerOffset = wOutOffset + wEntrySize;
    for(wInnerLoop = (wOutLoop + 1); wInnerLoop <
wTotalEntries;
wInnerLoop++)
    {

wResult=strcmp(cpEntryBuff+wOutOffset+wPrimeOff
set,
cpEntryBuff+wInnerOffset+wPrimeOffset);
      if(wResult > 0)
        SwapEntries(cpEntryBuff+wOutOffset,
cpEntryBuff+wInnerOffset, wEntrySize);
      if(wResult == 0)
      {

wResult=strcmp(cpEntryBuff+wOutOffset+wSecond
Offset,
cpEntryBuff+wInnerOffset+wSecondOffset);
        if(wResult > 0)
          SwapEntries(cpEntryBuff+wOutOffset,
cpEntryBuff+wInnerOffset, wEntrySize);
      }
      wInnerOffset = wInnerOffset + wEntrySize;
    }
    wOutOffset = wOutOffset + wEntrySize;
  }
  return(ERR_SUCCESS);
}

int SwapEntries(char *cpEntry1, char *cpEntry2, int
wEntrySize)
{
  char cSwapBuf[SRT_MAXLENSWAPBUFF];
  int wRestSize;
  int wCopyUnit;

  if( wEntrySize == 0 )
    return(ERR_INVALIDPARM);

  wRestSize = wEntrySize;
  do
  {
    if(wRestSize >= SRT_MAXLENSWAPBUFF)
      wCopyUnit = SRT_MAXLENSWAPBUFF;
    else
      wCopyUnit = wRestSize;
    mem_cpy(cpEntry1+(wEntrySize-wRestSize),
cSwapBuf,
wCopyUnit);
    mem_cpy(cpEntry2+(wEntrySize-wRestSize),
cpEntry1+(wEntrySize-wRestSize), wCopyUnit);
    mem_cpy(cSwapBuf,
cpEntry2+(wEntrySize-wRestSize),
wCopyUnit);
    wRestSize -= SRT_MAXLENSWAPBUFF;
  } while (wRestSize > 0);

  return(ERR_SUCCESS);
}

long GetEntryOffset(int wTotalEntries, int
wEntrySize, int
wKeyOffset,
        int wKeyNumber, char *cpEntryBuff)
{
  int wLoop;
  int wKeyCount;
  int wOffset;

  if( (wTotalEntries == 0) || (wEntrySize == 0) ||
(wKeyNumber
== 0)
    || (wKeyOffset >= wEntrySize) || (wKeyOffset < 0)
    || (wKeyNumber > wTotalEntries) )
    return((long)ERR_INVALIDPARM);

  wKeyCount=1;
  wOffset=0;

  if(wKeyCount == wKeyNumber)
    return(0L);

  for(wLoop = 1; wLoop < wTotalEntries; wLoop++)
  {
    if( (strcmp(cpEntryBuff+wOffset+wKeyOffset,
cpEntryBuff+wOffset+wEntrySize+wKeyOffset)) != 0)
      wKeyCount++;
    wOffset = wOffset + wEntrySize;
    if(wKeyCount == wKeyNumber)
      return((long)wOffset);
  }

  return((long)ERR_INVALIDPARM);
}
Copr. 1995 Zenith Data Systems Corp.

#include "sr.h"
#include "sio.h"
#include "spaun.h"
#include "k2.h"
#include "sm.h"

#if defined( _MSC_VER )
#pragma warning( disable : 4704 )
#endif

static TRAPREC        SUIMouseTrapRec;
static CALLREC        SUICallRec;
static SUICB          lpfnTempFunc;
static SUIACTIONCODE  ActionCode = 0;
static DWORD          dwOldSUIIntVec;
static int            iTempThreadIdx;
static int            iPrepSUIThreadIdx;
static int            iUnloadSUIThreadIdx;
static int            iCleanupSUIThreadIdx;
static WORD           pJmpBuf[ 9 ];
static BOOL           fVideoBlocked = FALSE;
static char           cSUIStatus =
SM_SUINOTLOADED;
static BYTE           cResidentStatus;
static WORD           wSUIPSP;
static WORD           wSavedSP;
static WORD           wSavedBP;
static CURRHOSTNAME   CurrHostName;

static APIFUNC aAPIFuncTable[] =
{
  { SM_SETCONTRAST, GetSetContrast },
  { SM_SETBRIGHTNESS, GetSetBrightness },
  { SM_CALIBUPLEFT, CalibratePen },
  { SM_CALIBCANCEL, CalibrateCancel },
  { SM_SETAUTOSHUTOFF, GetSetAutoShutOff },
  { SM_SETSLEEPTIME, GetSetSleepTime },
  { SM_REBOOTHOST, RebootHost },
  { SM_ACTIVEUPDATE, RequestActiveUpdate },

  { SM_DOUPDATE, DoUpdate },
  { SM_UPDATEHOSTLIST, UpdateHostList },
  { SM_GETHOSTLISTSTAT, GetHostListStatus },
  { SM_GETCONNECTSTAT, GetConnectStatus },
  { SM_REQUESTCONNECT, RequestConnClose },
  { SM_GETPASSWORDSTAT, GetPasswordStatus
},
  { SM_LSSETNETGROUP, LSGetSetNetGroup },
  { SM_LSSETNETHOST, LSGetSetNetHost },
  { SM_LSSETNETFRAMETYPE,
LSGetSetNetFrameType },
  { SM_SETCONNECTTYPE, GetSetConnectType
},
  { SM_SETPASSWORD, GetSetPassword },
  { SM_UPDATEDIMLOC, UpdateDimenLoc },
  { SM_REQUESTUNLOAD, RequestUnload },
  { SM_SETMSGBOXRETCODE,
SetSUIMSGRetCode },
  { SM_SETUILANGUAGE, GetSetUILanguage },
  { SM_SETACTIVESTAT, SetActiveStatus },
  { SM_SETKEYSTROKE, SetKeyStroke },
  { SM_GETKEYBOARDSTAT, GetKeyboardStatus
},
  { SM_GETABOUTDIALOG, GetAboutDialog },
  { SM_SETUSHOTICON, GetSetUSHotIcon },
  { SM_SETSECURITYID, GetSetSecurityID },
  { SM_SETDOMAINID, GetSetDomainID },
  { SM_SETLOCKKBDMOUSE,
GetSetLockKbdMouse },
  { SM_SETDIMSCREEN, GetSetDimScreen },
  { SM_SETVIDEOBLOCK, BlockUnblockVideo },
  { SM_NOTIFYSCRCODE, NotifyScreenCode },
  { 0, 0 }
};
```

```
APIFUNC *GetSUIFuncTable( void )
{
  return ( aAPIFuncTable );
}

CALLREC FAR *GetSUICallRec( void )
{
  return ( ( CALLREC FAR *)&SUICallRec );
}

TRAPREC *GetSUIMouseTrapRec( void )
{
  SUIMouseTrapRec.tr_int = PNG_INTNUM;
  SUIMouseTrapRec.tr_sem_srv =
CRU_REFLECTINT;

  return ( &SUIMouseTrapRec );
}

int GetCurrActionCode( void )
{
  return ( ActionCode );
}

WORD GetCurrScrCode( void )
{
  return ( wScreenCode );
}

void SetCurrScrCode( WORD wNewScreenCode )
{
  wScreenCode = wNewScreenCode;
}

char GetSUIStatus( void )
{
  return ( nSUIStatus );
}

void InitSUICallRec( void )
{
  DWORD dwCallService = ( DWORD )( FARPROC
)SUICallService;
  fl_clr( ( NPSTR )&SUICallRec, 0, sizeof(
CALLREC ) );

  SUICallRec.cForCallOpCode =
SMD_CALLOPCODE;
  SUICallRec.aCallBack[0] = LOBYTE( LOWORD(
dwCallService ) );
  SUICallRec.aCallBack[1] = HIBYTE( LOWORD(
dwCallService ) );
  SUICallRec.aCallBack[2] = LOBYTE( HIWORD(
dwCallService ) );
  SUICallRec.aCallBack[3] = HIBYTE( HIWORD(
dwCallService ) );
  SUICallRec.cForRetOpCode =
SMD_RETOPCODE;
  strcpy( SUICallRec.szSMASerSignature,
SIG_SMSIGNATURE );

  dwOldSUIIntVec = set_int_vec( SMI_SUIINTNUM,
( DWORD )( (
FARPROC )&SUICallRec ) );
}

void RestoreOldSUIIntVec( void )
{
  set_int_vec( SMI_SUIINTNUM, dwOldSUIIntVec );
}

BOOL GetSUIReady( void )
{
  return ( lpfnSUICallBack != ( SUICB )NULL &&
nSUIStatus ==
SMI_SUILOADED );
}

APIFUNCRET SetActiveStatus( struct REGW
*CallerRegs )
{
  PCS_BEGINCRITICAL;
  lpfnSUICallBack = ( SUICB )MK_FP(
CallerRegs->ds,
CallerRegs->si );
  PCS_ENDCRITICAL;

  wSUIPSP = get_cur_psp();

  CallerRegs->ax = SLH_PARTIALDIALOGSET;
  SetForegroundRegs( CallerRegs );

  nSUIStatus = SMI_SUILOADED;
}

APIFUNCRET RequestUnload( struct REGW
*CallerRegs )
{
  if ( !GetRequestHostList() &&
    GetConnectRequested() ==
SCS_NOCONNECTREQUESTED &&
    GetSCSCallProgress() ==
SMI_SCSCONNECTED )
  {
    CallerRegs->ax = SMI_UNLOADACCEPTED;
    UnloadSUI( SUI_NOUNLOADSUI );
  }
  else
    CallerRegs->ax = SMI_UNLOADDENIED;

  SetForegroundRegs( CallerRegs );
}

APIFUNCRET RequestConnClose( struct REGW
*CallerRegs )
{
  if ( GetConnectRequested() )
    CallerRegs->ax = ERR_SUCCESS;
  else
  {
    if ( IsSetFunction( CallerRegs ) )
    {
      if ( GetSCSCallProgress() ==
SMI_SCSCONNECTED )
        CallerRegs->ax = StartDisableConnection();
      else
        CallerRegs->ax = ( WORD )ERR_INTERNAL;
    }
    else
    {
      if ( GetLBCurrHost() ==
NLG_NOHOSTSELECTED )
      {
        OpenMessageBox(
STR_SUINOHOSTSELECTED, 0,
SUI_CENTERJUSTIFIED, SUI_OK );
        CallerRegs->ax = ( WORD )ERR_INTERNAL;
      }
      else
        CallerRegs->ax = MakeTheConnection( TRUE,
FALSE );
    }
  }

  SetForegroundRegs( CallerRegs );
}

APIFUNCRET GetConnectStatus( struct REGW
*CallerRegs )
{
  char *szHostName;
  int iCallProgress,
  int iProtocolId;
  int iReturn;

  if ( !GetSCSActiveStatus() )
  {
    iReturn = ERR_NOTSUPPORTED;
    goto exit;
  }

  iProtocolId = GetSCSProtocolId();
  iCallProgress = GetSCSCallProgress();

  fl_clr( &CurrHostName, 0, sizeof (
CURRHOSTNAME ) );
  CurrHostName.lpszHostName = szHostName;

  brBlood.lBrolLen = sizeof ( CURRHOSTNAME
);
  brBlood.lBufLen = sizeof ( CURRHOSTNAME );
  brBlood.buf = ( LPVOID )&CurrHostName;

  CallerRegs->ds = SEG( &BufBlood );
  CallerRegs->si = OFF( &BufBlood );

  switch ( iCallProgress )
  {
    case SMI_SCSCONNECTED:
      iReturn = SMI_CONNECTED;

      if ( ( szHostName = GetCurrHostName() ) !=
NULL )
        CurrHostName.lpszHostName = ( LPSTR
)szHostName;
      break;

    case SMI_SCSWAITINGFORCONNECT:
      iReturn = SMI_CONNECTED;
      break;

    case SMI_SCSDIALING:
      iReturn = SMI_CONNECTED;
      break;

    case SMI_SCSLOGGINGIN:
      iReturn = SMI_LOGGINGIN;
      break;

    case SMI_SCSDISCONNECTED:
      iReturn = SMI_DISCONNECTED;
      break;

    default:
      iReturn = ERR_INTERNAL;
      break;
  }

  CallerRegs->ax = iReturn;

  switch ( iProtocolId )
  {
    case SMI_SCSNETWARESPX:
      iReturn = SMI_NETWARESPX;
      break;

    case SMI_SCSASYNC:
      iReturn = SMI_MODEM;
      break;

    default:
      iReturn = ERR_INTERNAL;
      break;
  }

exit:
  CallerRegs->bx = iReturn;
  SetForegroundRegs( CallerRegs );
}

APIFUNCRET BlockUnblockVideo( struct REGW
*CallerRegs )
{
  PCS_BEGINCRITICAL;
  fVideoBlocked = IsSetFunction( CallerRegs );
  PCS_ENDCRITICAL;

  CallerRegs->ax = BlockSCOSVideo( ( BYTE
)fVideoBlocked );

  SetForegroundRegs( CallerRegs );
}

BOOL GetVideoBlocked( void )
{
  return ( fVideoBlocked );
}

int LoadSUI( SUIACTIONCODE NewActionCode,
WORD wNewScreenCode )
{
  WORD wCurrVidMode;
  BYTE nCurrHostMode;

  if ( NewActionCode == SUI_LASTOSKSCREEN )
  {
    if ( IsNoScreen( UIConfigData.nLastOSKScreen )
)
      wNewScreenCode = SUI_DIGALPHA;
    else
      wNewScreenCode =
UIConfigData.nLastOSKScreen;
  }
  else if ( NewActionCode ==
SUI_LASTSETUPDLGSCREEN )
  {
    if ( IsNoScreen(
UIConfigData.nLastSetupDlgScreen ) )
      wNewScreenCode = SUI_HOSTSELECTION;
    else
      wNewScreenCode =
UIConfigData.nLastSetupDlgScreen;
  }

  if ( ( IsSetupDlg( wScreenCode ) && IsSetupDlg(
wNewScreenCode
) ) ||
      ( IsOSK( wScreenCode ) && IsOSK(
wNewScreenCode ) ) )
    return ( ERR_INTERNAL );
  else if ( IsSetupDlg( wScreenCode ) && IsOSK(
wNewScreenCode )
)
    return ( ERR_INTERNAL );

  ActionCode = NewActionCode;

  if ( nSUIStatus == SMI_SUINOTLOADED )
    nSUIStatus = SMI_SUILOADING;

  if ( GetSUIReady() )
    wOldScreenCode = wScreenCode;

  if ( ( iPrepSUIThreadId = GetTempEventNum() )
== ERR_INTERNAL
)
    return ( ERR_INTERNAL );

  AddThread( iPrepSUIThreadId, WaitForPrepSUI,
NULL, SMD_POLLED,
FALSE,
          SUI_LOADSUIPOLLFREQ, 0 );

  wScreenCode = wNewScreenCode;

  if ( IsOSK( wScreenCode ) )
  {
    wCurrVidMode = GetCurrVidMode();
    nCurrHostMode = GetCurrHostMode();

    if ( IsOSKVideoSupported( wCurrVidMode ) &&
nCurrHostMode ==
PNG_DOSAPP )
      wScreenCode |=
SUI_OSKASSETUPDIALOGMASK;

    if ( wCurrVidMode != SUI_TEXTVIDMODE &&
nCurrHostMode !=
PNG_DOSAPP )
      wScreenCode |=
SUI_OSKINWINGRAPHICSMASK;
  }

  return ( ERR_SUCCESS );
}

void WaitForPrepSUI( void )
{
  static PREPSUISTATES iStatePrepSUI =
SUI_NOPREPSTATE;
  int iCheck;

  switch ( iStatePrepSUI )
  {
    case SUI_NOPREPSTATE:
      if ( IsSetupDlg( wScreenCode ) || IsNoScreen(
wScreenCode )
)
      {

        TRACE( "NOTICE: Setup Dialogs or No
Screen"
requested.\n" );

        SetMonitor( FALSE, TRUE );
        iStatePrepSUI = SUI_CHECKMONITOROFF;


      }
      else if ( IsOSKAsSetupDlg( wScreenCode ) )
      {
        TRACE( "NOTICE: OSK as Setup Dialog
requested.\n" );
        SetMonitor( FALSE, FALSE );
        iStatePrepSUI = SUI_CHECKMONITOROFF;


      }
      else
      {
        TRACE( "NOTICE: DOS or Windows OSK
requested, nothing
else to do\n" );
        iStatePrepSUI = SUI_PREPSUCCESS;
      }
      break;

    case SUI_CHECKMONITOROFF:
      iCheck = CheckMonitor();

      if ( iCheck == ERR_SUCCESS )
      {
        if ( IsOSKAsSetupDlg( wOldScreenCode ) )
        {
          TRACE( "NOTICE: Monitor off complete, old
screen - OSK
as setup dialog\n" );
          iStatePrepSUI = SUI_PREPSUCCESS;
        }
        else if ( IsOSK( wOldScreenCode ) )
        {
          TRACE( "NOTICE: Monitor off complete, old
screen -
OSK\n" );
          RequestFullRepaint( FALSE,
wOldScreenCode );
          iStatePrepSUI = SUI_CHECKFULLREPAINT;
        }
        else
        {
          TRACE( "NOTICE: Monitor off complete, no
old screen\n"
```

```
}:
    iStatePropSUI = SUI_PREPSUCCESS;
  }
  }
  else if ( iCheck == ERR_INTERNAL )
    iStatePropSUI = SUI_PREPERROR;
  break;

  case SUI_CHECKFULLREPAINT:
    iCheck = CheckFullRepaint();

    if ( iCheck == ERR_SUCCESS )
    {
      TRACE( "NOTICE: Exclusion region in SCOS
closed through
Full Repaint\n" );
      iStatePropSUI = SUI_PREPSUCCESS;
    }
    else if ( iCheck == ERR_INTERNAL )
    {
      TRACE( "ERROR: Closure of exclusion region
failed in SCOS
through Full Repaint\n" );
      iStatePropSUI = SUI_PREPERROR;
    }
    break;

  case SUI_PREPSUCCESS:
    TRACE( "NOTICE: We're here, we're here!\n" );

    InitSUI();
    SMDoeBusy( CBExecSUI );
    goto end;

  case SUI_PREPERROR:
    TRACE( "ERROR: SUI Load Prep failed\n" );

    if ( nSUIStatus == SMI_SUILOADING )
      nSUIStatus = SMI_SUINOTLOADED;
    else
      nSUIStatus = SMI_SUIINACTIVE;

  default:
end:
    iStatePropSUI = SUI_NOPREPSTATE;
    DelThread( iPropSUIThreadIdx );
    break;
  }
}

void CBExecSUI( void )
{
  int iVideoMode = GetCurrVidMode();

  if ( GetSCSCallProgress() ==
SMI_SCSCONNECTED )
  {
    if ( IsSetupDlg( wScreenCode ) || IsHelpScreen(
wScreenCode ) )
    {
      if ( iVideoMode != SUI_INITIALVIDMODE )
        SetVideoMode( SUI_INITIALVIDMODE );
    }
    else
    {
      if ( IsOSKVideoSupported( iVideoMode ) &&
GetCurrHostMode() == PHD_DOSAPP )
      {
        SetVideoMode( SUI_INITIALVIDMODE );
      }
    }
  }
  else
    SetVideoMode( SUI_INITIALVIDMODE );

  if ( nSUIStatus == SMI_SUILOADING )
  {
    if ( int_doe_prompt() )
    {
      _and_int_flg( ~SMD_SCHEDULERS );

      if ( JimExec( szSUIExecName, NULL ) !=
ERR_SUCCESS )
      {
        SetVideoMode( SUI_TEXTVIDMODE );
        dspf( STR_SUILOADERROR1 );
      }
      else
      {
        if ( (iTempThreadIdx = GetTempEventNum() )
< 0 )
          return;

        AddThread( iTempThreadIdx,
WaitForSUILoad, NULL,
SMD_POLLED, FALSE,
             SUI_LOADSUIPOLLFREQ,
SUI_LOADSUIMAXRETRY );
      }
    }
    else
    {
      SetVideoMode( SUI_TEXTVIDMODE );
      dspf( STR_SUILOADERROR2 );
    }
  }
  else
  {
    nSUIStatus = SMI_SUILOADED;
    SMDoeBusy( CBExecLoadScreen );
  }
}

void WaitForSUILoad( void )
{
  if ( GetSUIReady() )
  {
    DelThread( iTempThreadIdx );
    iTempThreadIdx = SMD_NOACTIVETHREAD;

    SMDoeBusy( CBExecLoadScreen );
  }
}

void CBExecLoadScreen( void )
{
  if ( !GetSUIReady() )
    return;

  switch ( ActionCode )
  {
    case SUI_DOPENCALIBRATION:
      SetSetupDlgMode( PHD_SETUPDLGON );
      DoMessageBox( NULL,
SUI_PENCALIBRATION, SUI_LEFTJUSTIFIED,
SUI_CANCEL,
              CBMsgBoxButtonPressed, 0 );
      break;

    case SUI_LASTCONNECTION:
      SetSetupDlgMode( PHD_SETUPDLGON )
      ResumeTheConnection();
      break;

    case SUI_BADVIDEOMODE:
      SetSetupDlgMode( PHD_SETUPDLGON );
      DoMessageBox( STR_SUIBADVIDEOMSG, 0,
SUI_CENTERJUSTIFIED,
SUI_OK,
              CBMsgBoxButtonPressed, 0 );
      break;

    default:
      if ( IsSetupDlg( wOldScreenCode ) )
        SetSetupDlgMode( PHD_SETUPDLGOFF );
      else if ( IsOSK( wOldScreenCode ) &&
IsOSKAsSetupDlg(
wOldScreenCode ) )
        SetOSKMode( NULL, SUI_NOOCCTYPE );

      if ( IsSetupDlg( wScreenCode ) ||
IsOSKAsSetupDlg(
wScreenCode ) )
        SetSetupDlgMode( PHD_SETUPDLGON );
      DoLoadScreen();
      break;
  }
}

void DoLoadScreen( void )
{
  int iNewScreenCode = LOBYTE( wScreenCode );
  int iOSKConfig;
  int xPosOSK, yPosOSK;

  if ( IsSetupDlg( wScreenCode ) || IsHelpScreen(
wScreenCode ) )
  {
    iOSKConfig = UIConfigData.nLastOSKDlgScreen;
    xPosOSK = 0;
    yPosOSK = 0;
  }
  else
  {
    iOSKConfig = 0;
    xPosOSK = UIConfigData.xPosLastOSKScreen;
    yPosOSK = UIConfigData.yPosLastOSKScreen;
  }

  if ( IsHelpScreen( wScreenCode ) )
  {
    EnableBusyCursor( SUI_BUSYCURSOROFF );

    PCS_BEGINCRITICAL
    AX( SUI_DISPLAYDIALOG );
    BX( iNewScreenCode );
    CX( iOSKConfig );
    SI( yPosOSK );
    DI( xPosOSK );

    ( *lpfnSUICallBack )();
    PCS_ENDCRITICAL
  }
}

int UnloadSUI( BYTE nNewResidentStatus )
{
  if ( !GetSUIReady() )
    return ( ERR_INTERNAL );

  SetWaitRegion( SBS_WAITINGICONON, TRUE );

  if ( nNewResidentStatus == SUI_UNLOADSUI )
    nSUIStatus = SMI_SUIUNLOADING;
  else
    nSUIStatus = SMI_SUIDEACTIVATING;

  nResidentStatus = nNewResidentStatus;

  if ( IsHelpScreen( wScreenCode ) )
    HideMessageBox();

  if ( ( iUnloadSUIThreadIdx = GetTempEventNum()
) < 0 )
    return ( ERR_INTERNAL );

  AddThread( iUnloadSUIThreadIdx,
WaitForUnloadSUI, NULL,
SMD_POLLED, FALSE,
           SUI_UNLOADSUIPOLLFREQ, 0 );

  if ( GetThreadAddress( SCS_DISCOEVENTNUM )
== NULL )
    AddThread( SCS_DISCOEVENTNUM,
WaitForStatusChange, NULL,
           SMD_POLLED, FALSE,
SCS_DISCOPOLLFREQ, 0 );

  return ( ERR_SUCCESS );
}

void WaitForUnloadSUI( void )
{
  static UNLOADSUISTATES iStateUnloadSUI =
SUI_NOUNLOADSUISTATE;

  switch ( iStateUnloadSUI )
  {
    case SUI_NOUNLOADSUISTATE:
      if ( IsOSK( wScreenCode ) )
      {
        GetSUIData();
        iStateUnloadSUI = SUI_GETACTIVEUPDATE;
      }
      else
        iStateUnloadSUI =
SUI_UNLOADSUISUCCESS;
      break;

    case SUI_GETACTIVEUPDATE:
      GetActiveUpdate();
      SetTimeLimit( iUnloadSUIThreadIdx,
SUI_PRIMSGPOLLFREQ );
      iStateUnloadSUI = SUI_DIMSCREEN;
      break;

    case SUI_DIMSCREEN:
      TRACE( "NOTICE: In the SUI_DIMSCREEN
state.\n" );
      SendDimScreen( UIConfigData.bDimScreen );
      SetTimeLimit( iUnloadSUIThreadIdx,
SUI_PRIMSGPOLLFREQ );
      iStateUnloadSUI = SUI_LOCKKBDMOUSE;

      break;

    case SUI_LOCKKBDMOUSE:
      TRACE( "NOTICE: In the
SUI_LOCKKBDMOUSE state.\n" );
      SendLockKbdMouse(
UIConfigData.bLockKbdMouse );
      SetTimeLimit( iUnloadSUIThreadIdx,
SUI_LOADSUIPOLLFREQ );
      iStateUnloadSUI =
SUI_UNLOADSUISUCCESS;
      break;

    case SUI_UNLOADSUISUCCESS:
    default:
      DelThread( iUnloadSUIThreadIdx );
      SMDoeBusy( CBExecUnloadSUI );
      iStateUnloadSUI = SUI_NOCLEANUPSTATE;
      break;
  }
}

void CBExecUnloadSUI( void )
{
  lpfnTempProc = lpfnSUICallBack;

  if ( IsSetupDlg( wScreenCode ) || IsHelpScreen(
wScreenCode ) ||
      IsOSKAsSetupDlg( wScreenCode ) )
    SetSetupDlgMode( PHD_SETUPDLGOFF );
  else if ( IsOSK( wScreenCode ) )
    SetOSKMode( NULL, SUI_NOOCCTYPE );

  if ( nResidentStatus == SUI_UNLOADSUI )
    lpfnSUICallBack = NULL;

  PSP_TERMINATE( wSUIPSP ) = ( LONG )(
FARPROC
)SUITerminateAddress;

  _asm
  {
    cli

    mov wSavedSP, sp
    mov wSavedBP, bp
    mov ax, SUI_CLOSEDIALOG
    xor bx,bx
    mov bl, nResidentStatus

    sti
  };

  ( *lpfnTempProc )( );

  if ( nResidentStatus == SUI_NOUNLOADSUI )
    CleanupUnloadSUI();

}

void SUITerminateAddress( void )
{
  _asm
  {
    mov ds, cs:[0]0Ah
    mov ss, cs:[0]0Ah
    mov sp, wSavedSP
    mov bp, wSavedBP
  };

  CleanupUnloadSUI();
}

void CleanupUnloadSUI( void )
{
  SMREG MinArgs;

  if ( nResidentStatus == SUI_UNLOADSUI )
  {
    if ( !GetPHSActiveStatus() )
    {
      MinArgs = SMEventOutArgs;
      MinArgs.ax = 0x000C;
      mouse( &MinArgs, &SMEventOutArgs );
    }
  }

  AddThread( SUI_CLEANUPEVENTNUM,
WaitForCleanupSUI, NULL,
SMD_POLLED, FALSE,
           SUI_LOADSUIPOLLFREQ, 0 );
}

void WaitForCleanupSUI( void )
{
  static CLEANUPSUISTATES iStateCleanupSUI =
SUI_NOCLEANUPSTATE;
  int iCheck;

  switch ( iStateCleanupSUI )
  {
    case SUI_NOCLEANUPSTATE:
      if ( IsSetupDlg( wScreenCode ) || IsHelpScreen(
wScreenCode )
||
          IsOSKAsSetupDlg( wScreenCode ) )
      {
        TRACE( "NOTICE: Unload of Setup Dialogs or
OSK-As-Setup-Dialog identified.\n" );
        SetMonitor( TRUE, FALSE );
        iStateCleanupSUI =
SUI_CHECKMONITORON;
      }
      else if ( IsOSKVidChange( wScreenCode ) )

      {
        TRACE( "NOTICE: Unload of OSK due to vid
change from DOS
or Windows identified.\n" );
```

```
    RequestFullRepaint( FALSE, wScreenCode );

    iStateCleanupSUI =
SUI_CHECKFULLPAINTCLEANUP;
  }
  else
  {
    TRACE( "NOTICE: Manual reboot of OSK
from DOS or Windows
identified.\n" );
    RequestFullRepaint( TRUE, wScreenCode );

    iStateCleanupSUI =
SUI_CHECKFULLPAINTCLEANUP;
  }
  break;

 case SUI_CHECKMONITORON:
  iCheck = CheckMonitor();

  if ( iCheck == ERR_SUCCESS )
  {
    TRACE( "NOTICE: Collection monitor on
mode successful.\n"
);
    iStateCleanupSUI =
SUI_CLEANUPSUCCESS;
  }
  else if ( iCheck == ERR_INTERNAL )
  {
    TRACE( "NOTICE: Collection monitor on
mode failed.\n" );
    iStateCleanupSUI = SUI_CLEANUPERROR;
  }
  break;

 case SUI_CHECKFULLPAINTCLEANUP:
  iCheck = CheckFullRepaint();

  if ( iCheck == ERR_SUCCESS )
  {
   if ( IsOSKVidChange( wScreenCode ) )

   {
    if ( IsOSKInGraphics( wScreenCode ) )

    {
     TRACE( "NOTICE: Full Repaint successful
for vid
change in SVWIN for Windows OSK.\n" );
     iStateCleanupSUI =
SUI_CLEANUPSUCCESS;
    }
    else
    {
     TRACE( "NOTICE: Full Repaint successful
for vid
change in DOS or DOS Graphics OSK\n" );
     SetMonitor( TRUE, FALSE );
     iStateCleanupSUI =
SUI_CHECKMONITORON;
    }
   }
   else
   {
#if !defined( PROD )
    if ( IsOSKInGraphics( wScreenCode ) )

    {
     TRACE( "NOTICE: Full Repaint successful
for Windows
OSK\n" );
    }
    else
    {
     TRACE( "NOTICE: Repaint successful for
DOS or DOS
Graphics OSK\n" );
    }
#endif
    iStateCleanupSUI =
SUI_CLEANUPSUCCESS;
   }
  }
  else if ( iCheck == ERR_INTERNAL )
  {
   TRACE( "NOTICE: Full Repaint failed for OSK
of unknown
type\n" );
   iStateCleanupSUI = SUI_CLEANUPERROR;
  }
  break;

 case SUI_CLEANUPSUCCESS:
  TRACE( "NOTICE: SUI cleanup successful\n" );

 case SUI_CLEANUPERROR:
 default:
  if ( nResidentStatus == SUI_UNLOADSUI )
     nSUIStatus = SM_SUINOTLOADED;
   else
     nSUIStatus = SM_SUINACTIVE;

   fill_char( szPassword, 0, sizeof ( szPassword ) );

   wScreenCode = wOldScreenCode =
SUI_NOSCREEN;
   iStateCleanupSUI = SUI_NOCLEANUPSTATE;
   DelThread( SUI_CLEANUPEVENTNUM );
   SetWaitingIcon( SSS_WAITINGDONOFF,
TRUE );
   break;
  }
}

#if defined( _MSC_VER )
#pragma warning( default : 4704 )
#endif
Copr. 1995 Zenith Data Systems Corp.
#include "sr.h"
#include "sio.h"
#include "spsum.h"
#include "k2.h"
#include "tm.h"
#include "sm.h"

#if defined( _MSC_VER )
#pragma warning( disable : 4704 )
#endif

static BYTE fSecurityWarning = FALSE;
static BYTE fDomainWarning = FALSE;
static BYTE nMsgBoxReturnCode = 0;
static int iPrevMsgBoxThreadId = -1;

void SetDomainWarning( BYTE
fNewDomainWarning )
{
  fDomainWarning = fNewDomainWarning;
}

void SetSecurityWarning( BYTE
fNewSecurityWarning )
{
  fSecurityWarning = fNewSecurityWarning;
}

void SetMsgBoxReturnCode( BYTE
nNewReturnCode )
{
  PCS_BEGINCRITICAL;
  nMsgBoxReturnCode = nNewReturnCode;
  PCS_ENDCRITICAL;
}

BYTE GetMsgBoxReturnCode( void )
{
  BYTE nReturnCode = nMsgBoxReturnCode;

  nMsgBoxReturnCode = 0;

  return ( nReturnCode );
}

APIFUNCRET SetSUIMBRetCode( struct REGW
*CallerRegs )
{
  SetMsgBoxReturnCode( LOBYTE( CallerRegs->bx
) );

  CallerRegs->ax = ERR_SUCCESS;

  SetForegroundRegs( CallerRegs );
}

APIFUNCRET SetKeyStroke( struct REGW
*CallerRegs )
{
  BYTE nHiScanByte;

  if ( ( nHiScanByte = HIBYTE( CallerRegs->bx ) ) >
0 )
    SendScanCode( nHiScanByte );

  SendScanCode( LOBYTE( CallerRegs->bx ) );

  CallerRegs->ax = ERR_SUCCESS;

  SetForegroundRegs( CallerRegs );
}

APIFUNCRET GetSetLockKbdMouse( struct REGW
*CallerRegs )
{
  BOOL bLockKbdMouse;

  if ( IsGetFunction( CallerRegs ) )
    CallerRegs->ax = UIConfigData.bLockKbdMouse
?
SM_ENABLEDLOCKKBDMOUSE :
             SM_DISABLEDLOCKKBDMOUSE;
  else
  {
    bLockKbdMouse = ( CallerRegs->bx == ( WORD
)SM_ENABLEDLOCKKBDMOUSE );
    CallerRegs->ax = ERR_SUCCESS;

    if ( GetSCSCallProgress() ==
SM_SCSCONNECTED )
    {
      if ( SendLockKbdMouse( bLockKbdMouse ) ==
ERR_SUCCESS )
        UIConfigData.bLockKbdMouse =
bLockKbdMouse;
      else
        CallerRegs->ax = ( WORD )ERR_INTERNAL;
    }
    else
      UIConfigData.bLockKbdMouse =
bLockKbdMouse;
  }

  SetForegroundRegs( CallerRegs );
}

APIFUNCRET GetSetDimScreen( struct REGW
*CallerRegs )
{

  BOOL bDimScreen;

  if ( IsGetFunction( CallerRegs ) )
    CallerRegs->ax = UIConfigData.bDimScreen ?
SM_ENABLEDDIMSCREEN :
             SM_DISABLEDDIMSCREEN;
  else
  {
    bDimScreen = ( CallerRegs->bx == ( WORD
)SM_ENABLEDDIMSCREEN
);
    CallerRegs->ax = ERR_SUCCESS;

    if ( GetSCSCallProgress() ==
SM_SCSCONNECTED )
    {
      if ( SendDimScreen( bDimScreen ) ==
ERR_SUCCESS )
        UIConfigData.bDimScreen = bDimScreen;
      else
        CallerRegs->ax = ( WORD )ERR_INTERNAL;
    }
    else
      UIConfigData.bDimScreen = bDimScreen;
  }

  SetForegroundRegs( CallerRegs );
}

APIFUNCRET GetSetConnectType( struct REGW
*CallerRegs )
{
  if ( CallerRegs->ax & 0x8000 )
    CallerRegs->ax = UIConfigData.bConnectType;
  else
    UIConfigData.bConnectType = CallerRegs->ax;

  SetForegroundRegs( CallerRegs );
}

APIFUNCRET GetKeyBoardStatus( struct REGW
*CallerRegs )
{
  CallerRegs->ax = SM_KBDNOTPRESENT;
  SetForegroundRegs( CallerRegs );
}

APIFUNCRET GetAboutDialog( struct REGW
*CallerRegs )
{
  char szTempStr[ STR_STRMAXLENGTH ];
  int iBIOSVersionNum = GetBIOSVersion();
  int iMsgBoxTotalLines;

  sprintf( szTempStr, STR_SMABOUTBOX,
szUIVersionName, HIBYTE(
iBIOSVersionNum ),
         LOBYTE( iBIOSVersionNum ) );

  iMsgBoxTotalLines = FillMsgBoxBuff( MsgBoxBuff,
szTempStr,
SUI_CENTERJUSTIFIED );

  BuffHead.iStructLen = sizeof ( MSGBOXBUFF );
  BuffHead.iBuffLen = sizeof ( MSGBOXBUFF ) *
iMsgBoxTotalLines;
  BuffHead.Buff = ( LPVOID )MsgBoxBuff;

  CallerRegs->ax = ( WORD )ERR_SUCCESS;
  CallerRegs->dx = SEG( &BuffHead );
  CallerRegs->si = OFF( &BuffHead );

  SetForegroundRegs( CallerRegs );
}

APIFUNCRET GetSetUDHotkeys( struct REGW
*CallerRegs )
{
  BUFFHEADER FAR *pBuffHeader;
  SCANCODE FAR *pScanCodes;
  int iBuffLen;


  if ( IsGetFunction( CallerRegs ) )
  {
    if ( CallerRegs->bx == SUI_UDHOTICON1 )
      pScanCodes = UIConfigData.aUDHotkeys1;
    else
      pScanCodes = UIConfigData.aUDHotkeys2;

    BuffHead.Buff = ( LPVOID )pScanCodes;
    BuffHead.iBuffLen = GetNumScanCodes(
pScanCodes ) * sizeof (
SCANCODE );
    BuffHead.iStructLen = sizeof ( SCANCODE );

    CallerRegs->dx = SEG( &BuffHead );
    CallerRegs->si = OFF( &BuffHead );
    CallerRegs->ax = ERR_SUCCESS;
  }
  else
  {
    pBuffHeader = MK_FP( CallerRegs->dx,
CallerRegs->si );
    pScanCodes = ( SCANCODE FAR *
)pBuffHeader->Buff;

    if ( pBuffHeader == NULL || pScanCodes ==
NULL )
      CallerRegs->ax = ( WORD )ERR_INTERNAL;
    else if ( pBuffHeader->iStructLen == 0 ||
pBuffHeader->iBuffLen == 0 )
      CallerRegs->ax = ( WORD )ERR_INTERNAL;
    else
    {
      iBuffLen = pBuffHeader->iBuffLen >
SUI_MAXNUMSCANCODES *
sizeof ( SCANCODE ) ?
             SUI_MAXNUMSCANCODES * sizeof (
SCANCODE ) :
pBuffHeader->iBuffLen;

      if ( CallerRegs->bx == SUI_UDHOTICON1 )
      {
        fill_char( UIConfigData.aUDHotkeys1, 0,
             SUI_MAXNUMSCANCODES * sizeof (
SCANCODE ) );
        fmem_cpy( ( LPVOID )pScanCodes, ( LPVOID
)UIConfigData.aUDHotkeys1,
             iBuffLen );
      }
      else
      {
        fill_char( UIConfigData.aUDHotkeys2, 0,
             SUI_MAXNUMSCANCODES * sizeof (
SCANCODE ) );
        fmem_cpy( ( LPVOID )pScanCodes, ( LPVOID
)UIConfigData.aUDHotkeys2,
             iBuffLen );
      }

      CallerRegs->ax = ERR_SUCCESS;
    }
  }

  SetForegroundRegs( CallerRegs );
}

APIFUNCRET GetSetSecurityID( struct REGW
*CallerRegs )
{
  LPSTR lpszNewSecurityID;
  int iLenSecurityID;

  if ( IsGetFunction( CallerRegs ) )
  {
```

```
    CallerRegs->ds = SEG(
UIConfigData.szSecurityID );
    CallerRegs->si = OFF( UIConfigData.szSecurityID
);
    CallerRegs->ax = ERR_SUCCESS;
  }
  else
  {
    if ( GetSCSCallProgress() ==
SUI_SCSDISCONNECTED )
    {
      lpszNewSecurityID = MK_FP( CallerRegs->ds,
CallerRegs->si
);
      iLenSecurityID = lstr_len( lpszNewSecurityID );

      if ( lpszNewSecurityID != NULL &&
          iLenSecurityID <=
SUI_MAXLENSECURITYSUI )
      {
        fmem_cp( ( LPVOID )lpszNewSecurityID, (
LPVOID
)UIConfigData.szSecurityID,
                iLenSecurityID + 1 );

        CallerRegs->ax = SetSecurityID(
UIConfigData.szSecurityID
);
      }
      else
        CallerRegs->ax = ( WORD )ERR_INTERNAL;
    }
    else
    {
      if ( !fSecurityWarning )
      {
        OpenMessageBox( STR_SUISECURITYID, 0,
SUI_LEFTJUSTIFIED,
SUI_OK );
        fSecurityWarning = TRUE;
      }

      CallerRegs->ax = ( WORD )ERR_INTERNAL;
    }
  }

  SetForegroundRegs( CallerRegs );
}

APIFUNCRET GetSetDomainID( struct REGW
*CallerRegs )
{
  char nNewDomainID;

  if ( IsGetFunction( CallerRegs ) )
  {
    CallerRegs->ax = ( WORD
)UIConfigData.nDomainID;
  }
  else
  {
    nNewDomainID = LOBYTE( CallerRegs->bx );

    if ( nNewDomainID >= PRX_MINDOMAINID &&
nNewDomainID <=
PRX_MAXDOMAINID )
    {
      UIConfigData.nDomainID = nNewDomainID;

      if ( !fDomainWarning )
      {
        OpenMessageBox( STR_SUIDOMAINID, 0,
SUI_LEFTJUSTIFIED,
SUI_OK );
        fDomainWarning = TRUE;
      }

      CallerRegs->ax = ERR_SUCCESS;
    }
    else
      CallerRegs->ax = ( WORD )ERR_INTERNAL;
  }

  SetForegroundRegs( CallerRegs );
}

APIFUNCRET GetSetUILanguage( struct REGW
*CallerRegs )
{
  CallerRegs->ax = ( WORD )SUI_UIUSENGLISH;

  SetForegroundRegs( CallerRegs );
}

APIFUNCRET RebootHost( struct REGW
*CallerRegs )
{
  REG_W InArgs, OutArgs;

  fl_chr( ( NPSTR )&InArgs, 0, sizeof( InArgs ) );

  InArgs.ax = SCS_REBOOTHOST;

  Isnt( &InArgs, &OutArgs, SCS_INTNUM );

  if ( OutArgs.ax == SCS_ACCEPTED )
    CallerRegs->ax = ERR_SUCCESS;
  else
    CallerRegs->ax = ( WORD )ERR_INTERNAL;

  SetForegroundRegs( CallerRegs );
}

APIFUNCRET GetPasswordStatus( struct REGW
*CallerRegs )
{
  CallerRegs->ax = ( WORD )fPWRequired();

  SetForegroundRegs( CallerRegs );
}

APIFUNCRET GetSetPassword( struct REGW
*CallerRegs )
{
  LPSTR szNewPassword;

  if ( IsGetFunction( CallerRegs ) )
  {
    CallerRegs->ds = SEG( szPassword );
    CallerRegs->si = OFF( szPassword );
  }
  else
  {
    szNewPassword = ( LPSTR )MAKELP(
CallerRegs->ds,
CallerRegs->si );
    fmem_cp( ( LPVOID )szNewPassword, ( LPVOID
)szPassword,
            SUI_MAXLENPASSWORD );
  }

  CallerRegs->ax = ERR_SUCCESS;

  SetForegroundRegs( CallerRegs );
}

APIFUNCRET UpdateHostList( struct REGW
*CallerRegs )
{
  CallerRegs->ax = ( WORD )RequestHostList();

  SetForegroundRegs( CallerRegs );
}

APIFUNCRET GetHostListStatus( struct REGW
*CallerRegs )
{


  if ( !GetSCSActiveStatus() )
    CallerRegs->ax = ( WORD
)ERR_NOTSUPPORTED;


  CallerRegs->ax = GetStatusHLInItem();

  SetForegroundRegs( CallerRegs );
}

APIFUNCRET LBGetSetHostGroup( struct REGW
*CallerRegs )
{
  if ( IsGetFunction( CallerRegs ) )
  {
    if ( GetStatusHLInItem() == SIR_BLANK )
    {
      CallerRegs->ax = ( WORD
)ERR_NOTSUPPORTED;
      goto exit;
    }

    if ( ( int )CallerRegs->bx > 0 )
    {
      ListBoxEntry.lpszEntry = ( LPSTR
)GetLBGroup(
CallerRegs->bx );
      ListBoxEntry.nAttribute =
SUI_LBENTRYENABLED;
      CallerRegs->ds = SEG( &ListBoxEntry );
      CallerRegs->si = OFF( &ListBoxEntry );
      CallerRegs->ax = ERR_SUCCESS;

    }
    else if ( ( int )CallerRegs->bx == 0 )
    {
      ListBoxEntry.lpszEntry = ( LPSTR
)GetLBGroup( -1 );
      ListBoxEntry.nAttribute =
SUI_LBENTRYENABLED;
      CallerRegs->ds = SEG( &ListBoxEntry );
      CallerRegs->si = OFF( &ListBoxEntry );
      CallerRegs->ax = GetLBCurrGroup();
    }
    else
      CallerRegs->ax = GetNumGroupEntries();
  }
  else
  {
    SetLBCurrGroup( CallerRegs->bx );
    CallerRegs->ax = ERR_SUCCESS;
  }

exit:
  SetForegroundRegs( CallerRegs );
}

APIFUNCRET LBGetSetHostHost( struct REGW
*CallerRegs )
{
  if ( IsGetFunction( CallerRegs ) )
  {
    if ( GetStatusHLInItem() == SIR_BLANK )
    {
      CallerRegs->ax = ( WORD
)ERR_NOTSUPPORTED;
      goto exit;
    }

    if ( ( int )CallerRegs->bx > 0 )
    {
      ListBoxEntry.lpszEntry = ( LPSTR )GetLBHost(
CallerRegs->bx
);
      ListBoxEntry.nAttribute = GetLBHostStatus(
CallerRegs->bx
);
      CallerRegs->ds = SEG( &ListBoxEntry );
      CallerRegs->si = OFF( &ListBoxEntry );
      CallerRegs->ax = 0;
    }
    else if ( ( int )CallerRegs->bx == 0 )
    {
      ListBoxEntry.lpszEntry = ( LPSTR )GetLBHost(
SUI_LBCURRENTRY );
      ListBoxEntry.nAttribute = GetLBHostStatus(
SUI_LBCURRENTRY
);
      CallerRegs->ds = SEG( &ListBoxEntry );
      CallerRegs->si = OFF( &ListBoxEntry );
      CallerRegs->ax = ( WORD )GetLBCurrHost();
    }
    else
      CallerRegs->ax = GetNumHostEntries();
  }
  else
  {
    SetLBCurrHost( CallerRegs->bx );
    CallerRegs->ax = 0;
  }

exit
  SetForegroundRegs( CallerRegs );
}

APIFUNCRET UpdateDimenLoc( struct REGW
*CallerRegs )
{
  OCCLUDEUNION OccUnion;
  int ActualVidMode;

  CallerRegs->ax = ( WORD )ERR_SUCCESS;
  ActualVidMode = GetCurrVidMode();

  if ( !GetSCSActiveStatus() || IsSetupDlg(
wScreenCode ) ||
IsNoScreen( wScreenCode ) )
  {
    CallerRegs->ax = ( WORD
)ERR_NOTSUPPORTED;
    goto exit;
  }

  if ( CallerRegs->bx == 0xFFFF && CallerRegs->cx
== 0xFFFF &&
      CallerRegs->si == 0xFFFF && CallerRegs->di
== 0xFFFF )
  {
    UnloadSUI( SUI_HOUNLOADSUI );
  }
  else
  {
    if ( ActualVidMode > SUI_TEXTVIDMODE )
    {
      if ( IsOSKWinGraphics( wScreenCode ) )
      {
        OccUnion.occRWin.yULWin = CallerRegs->bx;
        OccUnion.occRWin.xULWin = CallerRegs->cx;
        OccUnion.occRWin.yLRWin = CallerRegs->si;
        OccUnion.occRWin.xLRWin = CallerRegs->di;

        CallerRegs->ax = CreateOccludedArea(
&OccUnion,
SUI_OCCRWIN, SCS_OSKFREEMEMPERCENT );
        SetOSKMode( &OccUnion, SUI_OCCRWIN );
      }
      else
      {
        OccUnion.occOsGraph.yULDos =
CallerRegs->bx;
        OccUnion.occOsGraph.xULDos =
CallerRegs->cx;
        OccUnion.occOsGraph.yLRDos =
CallerRegs->si;
        OccUnion.occOsGraph.xLRDos =
CallerRegs->di;

        CallerRegs->ax = CreateOccludedArea(
&OccUnion,
SUI_OCCDOSGRAPHICS,
SCS_OSKFREEMEMPERCENT );

        if ( IsOSKAsSetupDlg( wScreenCode ) )

          SetOSKMode( &OccUnion,
SUI_OCCDOSGRAPHICS );
      }
    }
    else
    {
      OccUnion.occText.yULRow = CallerRegs->bx;
      OccUnion.occText.xULCol = CallerRegs->cx;
      OccUnion.occText.yLRRow = CallerRegs->si;
      OccUnion.occText.xLRCol = CallerRegs->di;

      CallerRegs->ax = CreateOccludedArea(
&OccUnion,
SUI_OCCDOSTEXT,
SCS_OSKFREEMEMPERCENT );
      SetOSKMode( &OccUnion, SUI_OCCDOSTEXT
);
    }
  }

exit:
  SetForegroundRegs( CallerRegs );
}

APIFUNCRET GetSetContrast( struct REGW
*CallerRegs )
{
  BYTE nContrastIdx;

  if ( IsGetFunction( CallerRegs ) )
    CallerRegs->ax = ( WORD
)UIConfigData.nContrastIdx;
  else
  {
    nContrastIdx = LOBYTE( CallerRegs->bx );

    if ( ( CallerRegs->ax = ( WORD )SetContrast(
nContrastIdx ) )
          == ERR_SUCCESS )
      UIConfigData.nContrastIdx = nContrastIdx;
  }

  SetForegroundRegs( CallerRegs );
}

APIFUNCRET GetSetBrightness( struct REGW
*CallerRegs )
{
  BYTE nBrightnessIdx;

  if ( IsGetFunction( CallerRegs ) )
    CallerRegs->ax = ( WORD
)UIConfigData.nBrightnessIdx;
  else
  {
    nBrightnessIdx = LOBYTE( CallerRegs->bx );

    if ( ( CallerRegs->ax = ( WORD )SetBrightness(
nBrightnessIdx
))
          == ERR_SUCCESS )
      UIConfigData.nBrightnessIdx = nBrightnessIdx;
  }

  SetForegroundRegs( CallerRegs );
}

APIFUNCRET GetSetAutoShutOff( struct REGW
*CallerRegs )
```

```
{
  if ( IsGetFunction( CallerRegs ) )
    CallerRegs->cx = ( WORD
)UIConfigData.bAutoShutoff;
  else
  {
    if ( LOBYTE( CallerRegs->bx ) == TRUE )
    {
      CallerRegs->ax = SetSuspendTimeout(
SSS_SUSPENDENABLED );
      UIConfigData.bAutoShutoff = TRUE;
    }
    else
    {
      CallerRegs->ax = SetSuspendTimeout(
SSS_SUSPENDDISABLED );

      UIConfigData.bAutoShutoff = FALSE;
    }
  }

  SetForegroundRegs( CallerRegs );
}

APIFUNCRET GetSetSleepTime( struct REGW
*CallerRegs )
{
  BYTE nSleepTimeIdx;

  if ( IsGetFunction( CallerRegs ) )
  {
    if ( UIConfigData.nSleepTimeIdx ==
SSS_SLEEPDISABLED )
      CallerRegs->cx = ( WORD
)SUI_NOSLEEPSLIDERIDX - 1;
    else
      CallerRegs->cx = ( WORD
)UIConfigData.nSleepTimeIdx - 1;
  }
  else
  {
    nSleepTimeIdx = LOBYTE( CallerRegs->bx ) + 1;

    if ( nSleepTimeIdx == SUI_NOSLEEPSLIDERIDX
)
      nSleepTimeIdx = ( BYTE
)SSS_SLEEPDISABLED;

    if ( ( CallerRegs->ax = SetSleepTimeout(
nSleepTimeIdx ) )
         == ERR_SUCCESS )
    {
      if ( nSleepTimeIdx == SSS_SLEEPDISABLED )
      {
        if ( ( CallerRegs->ax = SetPowerEnable(
SSS_POWERMANDISABLED ) )
           == ERR_SUCCESS )
        {
          if ( ( CallerRegs->ax = SetDozeTimeout(
SSS_DOZEDISABLED ) )
              == ERR_SUCCESS )
              UIConfigData.nSleepTimeIdx =
nSleepTimeIdx;
        }
      }
      else
      {
        if ( ( CallerRegs->ax = SetPowerEnable(
SSS_POWERMANENABLED ) )
           == ERR_SUCCESS )
        {
          if ( ( CallerRegs->ax = SetDozeTimeout(
SSS_DOZEDISABLED ) )
              == ERR_SUCCESS )
              UIConfigData.nSleepTimeIdx =
nSleepTimeIdx;
        }
      }
    }
  }

  SetForegroundRegs( CallerRegs );
}

int EnableBusyCursor( int iStatus )
{
  int iReturn;

  AX( SUI_SHOWHIDEBUSYCURSOR );
  BX( iStatus );

  iReturn = ( *lpfnSUICallBack )();

  return ( iReturn );
}

int DoMessageBox( NPSTR szMsgText, int
iSerNumber, char
nAlignment, int iButtons,
                    MODALMSGBOXCB lpCallBack, int
iMsgBoxTimeOut )
{
  if ( !GetSUIReady() )
    return ( ERR_INTERNAL );

  if ( iMsgBoxTimeOut > 0 )
    iMsgBoxTimeOut *= 2;

  if ( ( iProcMsgBoxThreadIdx =
GetTempEventNum() ) < ERR_SUCCESS
)
    return ( ERR_INTERNAL );

  AddThread( iProcMsgBoxThreadIdx, ( NEARPROC
)ProcessMessageBox,
NULL, SMD_POLLED,
          FALSE, SUI_PROCMSGBOXPOLLFREQ,
0 );

  if ( lpCallBack != NULL )
    DoModalMsgBox( lpCallBack, iMsgBoxTimeOut );

  ProcessMessageBox( szMsgText, iSerNumber,
nAlignment, iButtons
);

  return ( ERR_SUCCESS );
}

void ProcessMessageBox( NPSTR szNewMsgText,
int iNewSerNumber,
char nNewAlignment, int iNewButtons )
{
  static NPSTR szMsgText;
  static char nAlignment;
  static int iButtons;
  static int iSerNumber;
  static int iProcMsgBoxState =
SUI_NOPROCMSGBOXSTATE;

  switch ( iProcMsgBoxState )
  {
    case SUI_NOPROCMSGBOXSTATE:
      szMsgText = szNewMsgText;
      iSerNumber = iNewSerNumber;
      nAlignment = nNewAlignment;
      iButtons = iNewButtons;
      iProcMsgBoxState = SUI_HIDEMSGBOX;
      break;

    case SUI_HIDEMSGBOX:
      HideMessageBox();
      iProcMsgBoxState = SUI_SHOWMSGBOX;
      break;

    case SUI_SHOWMSGBOX:
      OpenMessageBox( szMsgText, iSerNumber,
nAlignment, iButtons
);
      iProcMsgBoxState =
SUI_NOPROCMSGBOXSTATE;
      DelThread( iProcMsgBoxThreadIdx );
      break;
  }
}

int OpenMessageBox( NPSTR szMsgText, int
iSerNumber, char
nAlignment, int iButtons )
{
  int iSeg = 0, iOff = 0;
  int iMsgBoxTotalLines;

  if ( !GetSUIReady() )
    return ( ERR_INTERNAL );

  if ( szMsgText != NULL )
    iSerNumber = 0;
  else
    goto exit;

  if ( strlen( szMsgText ) > STR_STRMAXLENERR -
1 )
    return ( ERR_INTERNAL );

  iMsgBoxTotalLines = FillMsgBoxBuff( MsgBoxBuff,
szMsgText,
nAlignment );

  if ( *MsgBoxBuff[ 0 ].lpszText == NULL )
    return ( ERR_INTERNAL );

  BuffHead.iStructLen = sizeof ( MSGBOXBUFF );
  BuffHead.iBuffLen = sizeof ( MSGBOXBUFF ) *
iMsgBoxTotalLines;
  BuffHead.Buff = ( LPVOID )MsgBoxBuff;

  iSeg = SEG( &BuffHead );
  iOff = OFF( &BuffHead );

exit:

  AX( SUI_SHOWMSGBOX );
  BX( iButtons );
  CX( iSerNumber );
  DX( iSeg );
  SI( iOff );

  return ( ( *lpfnSUICallBack )() );
}

int FillMsgBoxBuff( MSGBOXBUFF MsgBoxBuff[],
char *szMsgText,
char nAlignment )
{
  int iTerminator, iMsgBoxLineIdx,
iMsgBoxTotalLines;
  char *szPtrTempStr = szTempMsgStr;

  strcpy( szTempMsgStr, szMsgText );

  fl_char( MsgBoxBuff, 0, sizeof ( MSGBOXBUFF ) *
SUI_SUIMAXMSGBOXLINES );

  for ( iMsgBoxLineIdx = 0, iMsgBoxTotalLines = 0;
        iMsgBoxLineIdx <
SUI_SUIMAXMSGBOXLINES; ++iMsgBoxLineIdx
)
  {
    if ( ( iTerminator = str_pos( STR_SEPARATOR,
szPtrTempStr ) )
> 0 )
    {
      *( szPtrTempStr + ( iTerminator - 1 ) ) = NULL;
      MsgBoxBuff[ iMsgBoxLineIdx ].lpszText = (
LPSTR
)szPtrTempStr;
      MsgBoxBuff[ iMsgBoxLineIdx ].nAlignment =
nAlignment;
      szPtrTempStr += iTerminator;
      iMsgBoxTotalLines++;
    }
    else
      MsgBoxBuff[ iMsgBoxLineIdx ].lpszText =
szNullStr;
  }

  return ( iMsgBoxTotalLines );
}

int HideMessageBox( void )
{
  if ( !GetSUIReady() )
    return ( ERR_INTERNAL );

  AX( SUI_HIDEMSGBOX );

  return ( ( *lpfnSUICallBack )() );
}

int UpdateSUIConnectStatus( void )
{
  if ( !GetSUIReady() )
    return ( ERR_INTERNAL );

  SetUpdatingConnectStatus( TRUE );

  AX( SUI_UPDATECONNECTSTATUS );

  return ( ( *lpfnSUICallBack )() );
}

#if defined( _MSC_VER )
#pragma warning( default : 4704 )
#endif
Copr. 1995 Zenith Data Systems Corp.
#include "sr.h"
#include "ble.h"
#include "sysm.h"
#include "sm.h"

static BYTE fFrameWarning = FALSE;

static char aFrameTypes[][6]=
{
  "802.2",
  "802.3",
  "II",
  "SNAP",
};

APIFUNCRET LSGetSetNetFrameType( struct
REGW *CallerRegs )
{
  if ( IsGetFunction( CallerRegs ) )
  {
    int iCurrFrameIdx = UIConfigData.nFrameType -
PRX_FRAMEBASE;
    CallerRegs->dx = SEG( &ListBoxEntry );
    CallerRegs->si = OFF( &ListBoxEntry );

    if ( ( int )CallerRegs->bx > 0 )
    {
      ListBoxEntry.lpszEntry = ( LPSTR
)aFrameTypes[
CallerRegs->bx - 1 ];
      ListBoxEntry.nAttribute =
SUI_LBENTRYENABLED;
      CallerRegs->ax = ERR_SUCCESS;

    }
    else if ( ( int )CallerRegs->bx == 0 )
    {
      ListBoxEntry.lpszEntry =
        ( LPSTR )aFrameTypes[ iCurrFrameIdx ];
      ListBoxEntry.nAttribute =
SUI_LBENTRYENABLED;
      CallerRegs->ax = iCurrFrameIdx + 1;
    }
    else
      CallerRegs->ax =
PRX_NUMOFAVAILFRAMES;
  }
  else
  {
    if ( !fFrameWarning )
    {
      OpenMessageBox( STR_SUIFRAMETYPE, 0,
SUI_LEFTJUSTIFIED,
SUI_OK );
      fFrameWarning = TRUE;
    }

    UIConfigData.nFrameType = PRX_FRAMEBASE
+ ( CallerRegs->bx -
1 );
    CallerRegs->ax = ERR_SUCCESS;
  }

  SetForegroundRegs( CallerRegs );
}

APIFUNCRET NotifyScreenCode( struct REGW
*CallerRegs )
{
  BYTE nLastOSKScreen,
  BYTE nLastSetupDlgScreen;

  if ( ( nLastOSKScreen = LOBYTE( CallerRegs->bx
) & SUI_OSKMASK
) > 0 )
  {
    if ( IsSetupDlg( GetCurrScrCode() ) )

      UIConfigData.nLastOSKDlgScreen =
nLastOSKScreen;
    else
      UIConfigData.nLastOSKScreen =
nLastOSKScreen;
  }

  if ( ( nLastSetupDlgScreen = LOBYTE(
CallerRegs->bx ) &
SUI_SETUPDLGMASK ) > 0 )
    UIConfigData.nLastSetupDlgScreen =
nLastSetupDlgScreen;

  CallerRegs->ax = ERR_SUCCESS;

  SetForegroundRegs( CallerRegs );
}
Copr. 1995 Zenith Data Systems Corp.
#include "sr.h"
#include "ble.h"
#include "sysm.h"
#include "h2.h"
#include "sm.h"

#if defined( _MSC_VER )
#pragma warning( disable : 4704 )
#endif

static int iCalibMode = -1;
static int iCalibThreadIdx = 0,
static int xCalibCol, yCalibRow;
static BOOL fCalibLowRight;

static CALIBPENSTATES PenCalibStates;

APIFUNCRET CalibratePen( struct REGW
*CallerRegs )
{
  if ( fCalibLowRight )
  {
    CallerRegs->ax = SUI_CALIBLOWRIGHT;
```

```
    CallerRegs->cx = SHC_XVGARES -
SUI_XCALIBPOINT;
    CallerRegs->bx = SHC_YVGARES -
SUI_YCALIBPOINT;
    iCalibLowRight = FALSE;
  }

  if ( IsGetFunction( CallerRegs ) )
    iCalibMode = PHD_CALIBLR;
  else
  {
    iCalibLowRight = TRUE;
    iCalibMode = PHD_CALIBUL;
  }

  if ( ( iCalibThreadIdx = GetTempEventNum() ) < 0 )
  {
    CallerRegs->ax = ( WORD )ERR_INTERNAL;
  }
  else
  {
    PenCalibStates = SUI_INITIALCALIBSTATE;
    xCalibCol = CallerRegs->cx;
    yCalibRow = CallerRegs->bx;
    CallerRegs->ax = ERR_SUCCESS;

    AddThread( iCalibThreadIdx, WaitForPenCalib,
NULL,
SMD_POLLED, FALSE,
            SM_CALIBPOLLFREQ, 0 );
  }

  SetForegroundRegs( CallerRegs );
}

APIFUNCRET CalibrateCancel( struct REGW
*CallerRegs )
{
  DelThread( iCalibThreadIdx );
  EnableNewCalib( FALSE );

  CallerRegs->ax = ERR_SUCCESS;

  SetForegroundRegs( CallerRegs );

  if ( GetCurrActionCode() ==
SUI_LASTCONNECTION )
    LoadSUI( SUI_SPECIFIEDSCREEN,
SUI_HOSTSELECTION );
}

void WaitForPenCalib( void )
{
  int xUpperCol, yUpperRow, xLowerCol,
yLowerRow;
  int iCalibState;
  PENCALIB CurrPenCalib;

  switch( PenCalibStates )
  {
    case SUI_INITIALCALIBSTATE:
      if ( SetCalibMode( iCalibMode, xCalibCol,
yCalibRow ) == 0
)
        PenCalibStates = SUI_CHECKCALIB;
      else
        PenCalibStates = SUI_CALIBERROR;
      break;

    case SUI_CHECKCALIB:
      iCalibState = GetCalibState( iCalibMode,
&xUpperCol,
&yUpperRow,
                    &xLowerCol, &yLowerRow
);

      if ( iCalibState != PHD_CALIBNOTDONE )
      {
        if ( iCalibMode == PHD_CALIBLR )
        {
          if ( iCalibState == PHD_CALIBDONEVALID )
          {
            CurrPenCalib.nXUpperPenCalib =
xUpperCol;
            CurrPenCalib.nYUpperPenCalib =
yUpperRow;
            CurrPenCalib.nXLowerPenCalib =
xLowerCol;
            CurrPenCalib.nYLowerPenCalib =
yLowerRow;

            SetEEMouseConfig( &CurrPenCalib );
            EnableNewCalib( TRUE );

            PenCalibStates = SUI_CALIBSUCCESS;
          }
          else
            PenCalibStates = SUI_CALIBERROR;
        }
        else
          PenCalibStates = SUI_CALIBSUCCESS;
      }
      break;

    case SUI_CALIBERROR:
    case SUI_CALIBSUCCESS:
      AX( SUI_CALIBPOINTDONE );
      ( *pfnSUICallBack )();
      DelThread( iCalibThreadIdx );

      if ( iCalibMode == PHD_CALIBLR &&
GetCurrActionCode() ==
SUI_DOPENCALIBRATION )
        LoadSUI( SUI_SPECIFIEDSCREEN,
SUI_HOSTSELECTION );
      break;
  }
}

#if defined( _MSC_VER )
#pragma warning( default : 4704 )
#endif


Copr. 1996 Zenith Data Systems Corp.


#include "sr.h"
#include "ne.h"
#include "spown.h"
#include "k2.h"
#include "sm.h"
#include "bn.h"
#include "sm.h"

#if defined( _MSC_VER )
#pragma warning( disable : 4704 )
#endif

static FLASHUPDATESTATES FlashUpdateState,
FlashStateOnError;
static MEM_REC MemRec;
static char far *sFlashImageBuff = NULL;
static char *szPathFlashFile = NULL;
static char *szHomeActiveUpdate = NULL;
static int iDoUpdateThreadIdx,
iActiveUpdateThreadIdx;
static int iFlashUpdateState;
static int iTmpFilePercent, iOldTmpFilePercent,
iOldTmpDispPercent;

static int iTotalFlashFiles;
static int iCurrFlashFile;
static LONG lLenCurrFlashFile;
static int iSectorFlashStatus;

APIFUNCRET DoUpdate( struct REGW *CallerRegs
)
{
  if ( GetSCSCallProgress() !=
SM_SCSCONNECTED )
    CallerRegs->ax = ( WORD )ERR_INTERNAL;
  else
  {
    if ( ( iDoUpdateThreadIdx = GetTempEventNum()
) ==
ERR_INTERNAL )
    {
      CallerRegs->ax = ( WORD )ERR_INTERNAL;
    }
    else
    {
      if ( IsFlashSupported() )
      {
        FlashUpdateState = FLU_SAFETYCHECK;
        AddThread( iDoUpdateThreadIdx,
WaitForFlashUpdate, NULL,
SMU_MANYTIMES, FALSE,
                FLU_POLLFREQ, FLU_MAXRETRY );

        CallerRegs->ax = ( WORD )ERR_SUCCESS;
      }
      else
        CallerRegs->ax = ( WORD )ERR_INTERNAL;

    }
  }

  SetForegroundRegs( CallerRegs );
}

APIFUNCRET RequestActiveUpdate( struct REGW
*CallerRegs )
{
  char *szCurrentUpdate = GetHomeActiveUpdate();
  int MsgBoxTotalLines;
  WORD wReturn;
  FLASHUPDATESTATES PowerState;

  if ( *szCurrentUpdate != ' ' && *szCurrentUpdate !=
NULL )
  {
    if ( ( PowerState = CheckFlashPowerState() ) !=
FLU_NOFLUSTATE )
    {
      switch( PowerState )
      {
        case FLU_GETBATTERYINFOERROR:
          MsgBoxTotalLines = FillMsgBoxBuff(
MsgBoxBuff,
STR_FLUGETBATINFOERROR,

SUI_CENTERJUSTIFIED
);
          break;

        case FLU_NOTONACERROR
          MsgBoxTotalLines = FillMsgBoxBuff(
MsgBoxBuff,
STR_FLUNOAC, SUI_CENTERJUSTIFIED );
          break;

        case FLU_BATNOTATTACHEDERROR
          MsgBoxTotalLines = FillMsgBoxBuff(
MsgBoxBuff,
STR_FLUNOBATERROR, SUI_CENTERJUSTIFIED
);
          break;

        case FLU_BATCAPTOOLOWERROR:
          MsgBoxTotalLines = FillMsgBoxBuff(
MsgBoxBuff,
STR_FLUBATTOOLOWERROR,
SUI_CENTERJUSTIFIED );
          break;

        default:
          MsgBoxTotalLines = FillMsgBoxBuff(
MsgBoxBuff,
STR_FLUUNKNOWNBATERROR,
SUI_CENTERJUSTIFIED );
      }

      wReturn = ( WORD
)ERR_UPGRADENOTAVAIL;
    }
    else if ( GetSCSCallProgress() !=
SM_SCSCONNECTED )
    {
      MsgBoxTotalLines = FillMsgBoxBuff(
MsgBoxBuff,
STR_FLUNOCONNECTERROR,
SUI_CENTERJUSTIFIED );
      wReturn = ( WORD
)ERR_UPGRADENOTAVAIL;
    }
    else if ( GetLinkQuality() != PSX_HIGHQUALITY
)
    {
      MsgBoxTotalLines = FillMsgBoxBuff(
MsgBoxBuff,
STR_FLULINKTOOLOWERROR,
SUI_CENTERJUSTIFIED );
      wReturn = ( WORD
)ERR_UPGRADENOTAVAIL;
    }
    else if ( GetCurrHostMode() != PHD_DOSAPP )
    {
      MsgBoxTotalLines = FillMsgBoxBuff(
MsgBoxBuff,
STR_FLUNOTINDOSAPP, SUI_CENTERJUSTIFIED
);
      wReturn = ( WORD
)ERR_UPGRADENOTAVAIL;
    }
    else
    {
      MsgBoxBuff[0].lpszText = ( LPSTR
)szCurrentUpdate;
      MsgBoxBuff[0].wAlignment =
SUI_CENTERJUSTIFIED;
      MsgBoxTotalLines = 1;
      wReturn = ERR_SUCCESS;
      TRACE( "NOTICE: Flash upgrade safety checks
passed.\n" );
    }
  }
  else
  {
    MsgBoxTotalLines = FillMsgBoxBuff(
MsgBoxBuff,
STR_FLUNOFLASHFILES,
SUI_CENTERJUSTIFIED );
    wReturn = ( WORD )ERR_UPGRADENOTAVAIL;

  }

  BuffHead.iBuffLen = sizeof ( MSGBOXBUFF );
  BuffHead.iBuffLen = sizeof ( MSGBOXBUFF ) *
MsgBoxTotalLines;
  BuffHead.Buff = ( LPVOID )MsgBoxBuff;

  CallerRegs->dx = SEG( &BuffHead );
  CallerRegs->si = OFF( &BuffHead );
  CallerRegs->ax = wReturn;

  SetForegroundRegs( CallerRegs );
}


void WaitForFlashUpdate( void )
{
  int iSizeFlashSector,
  int iNumberOfFlash,
  int iNewTmpFilePercent, iNewTmpDispPercent;
  int iRetryLimit = GetRetryLimit(
iDoUpdateThreadIdx );
  FlashStateOnError = FlashUpdateState,

  switch ( FlashUpdateState )
  {
    case FLU_NOFLUSTATE

    case FLU_SAFETYCHECK:
      FlashUpdateState = FLU_INITMEM;

      SetWaitingIcon( SSS_WAITINGICONON, TRUE
);

      if ( UIConfigData.nSleepTimeIdx !=
SSS_SLEEPDISABLED )
      {
        SetPowerEnable(
SSS_POWERMANDISABLED );
        TRACE( "NOTICE: Disabled powerman for
flash update\n" );
      }
      break;


    case FLU_INITMEM:
      TRACE( "NOTICE: Initializing and allocating
memory\n" );

      if ( ( szPathFlashFile = ( NPSTR )malloc(
SCS_MAXLENFILENAME + 1 ) ) == NULL )
        FlashUpdateState = FLU_MEMERROR;
      else
      {
        if ( SMDosAlloc( GetFlashImageBuff ) !=
ERR_SUCCESS )
          FlashUpdateState = FLU_MEMERROR;
        else
        {
          FlashUpdateState = FLU_ALLOCDOSMEM;
          ResetRetryLimit( iDoUpdateThreadIdx );
        }
      }
      break;

    case FLU_ALLOCDOSMEM:
      if ( sFlashImageBuff == NULL )
      {
        if ( iRetryLimit == FLU_MAXDOSBUSY )
        {
          TRACE( "ERROR: Failed to allocate required
buffers\n" );
          FlashUpdateState = FLU_MEMERROR;
        }
      }
      else
      {
        TRACE( "NOTICE: Successfully acquired
memory\n" );

        iTotalFlashFiles = FLU_NUMBERUNKNOWN;
        iCurrFlashFile = 0;

        _fmemset( szPathFlashFile, 0,
SCS_MAXLENFILENAME );

        FlashUpdateState =
FLU_SENDREQFLASHUPD;
        ResetRetryLimit( iDoUpdateThreadIdx );

      }
      break;
```

```
    case FLU_SENDREQFLASHUPD:
      TRACE( "NOTICE: Requesting the flash
upgrade from the
Host\n" );
      dSizeFlashSector = FLU_SIZEFLASHSECTOR /
1024;

      if ( SendPrivateMessage(
PMI_REQFLASHUPD, sizeof( int ),
          ( NPSTR )&dSizeFlashSector ) !=
ERR_SUCCESS )
        FlashUpdateState =
FLU_SENDPRIMSGERROR;
      else
      {
        if ( iRetryLimit == 0 )
          SetRetryLimit( iDoUpdateThreadIdx, 1 );

        SetTmpFilePercent( 0 );
        SetTimeLimit( iDoUpdateThreadIdx,
FLU_PRIMSGPOLLFREQ );
        FlashUpdateState =
FLU_WAITFORTMPFLASHFILES;
      }
      break;

    case FLU_WAITFORTMPFLASHFILES:
      iNewTmpFilePercent = GetTmpFilePercent();

      if ( iNewTmpFilePercent == 0 )
      {
        if ( iRetryLimit == FLU_MAXPCNTTMPFILE )

        {
          TRACE( "ERROR: Timeout waiting for first
percent of
temp files.\n" );
          FlashUpdateState =
FLU_NOACKTEMPFILESERROR;
        }
        else if ( iRetryLimit %
FLU_MODPCNTTMPFILE == 0 )
        {
          TRACE( "ERROR: Requesting flash update
from host once
again\n" );
          FlashUpdateState =
FLU_SENDREQFLASHUPD;
        }
      }
      else
      {
        UpdateTmpFilePercentage(
iNewTmpFilePercent );
        iOldTmpFilePercent = iNewTmpFilePercent;
        iOldTmpDispPercent = iNewTmpDispPercent =
(
iNewTmpFilePercent * 2 ) / 100
        FlashUpdateState =
FLU_UPDATETMPFILEPERCENT;
        ResetRetryLimit( iDoUpdateThreadIdx );
      }
      break;

    case FLU_UPDATETMPFILEPERCENT:
      iNewTmpFilePercent = GetTmpFilePercent();

      iNewTmpDispPercent = ( iNewTmpFilePercent *
2 ) / 100;
      if ( iNewTmpFilePercent == iOldTmpFilePercent
)
      {
        if ( iRetryLimit == FLU_MAXPCNTTMPFILE ||
            iNewTmpFilePercent == 100 )
        {
          ResetRetryLimit( iDoUpdateThreadIdx );
          FlashUpdateState =
FLU_WAITFORNUMFILES;
          TRACE( "NOTICE: Done waiting for number
of files,
onwards\n" );

#if !defined( PROD )
          if ( iNewTmpFilePercent != 100 )
            TRACE( "ERROR: Timeout waiting for next
percent of
temp files.\n" );
#endif
        }
      }
      else
      {
        ResetRetryLimit( iDoUpdateThreadIdx );
        iOldTmpFilePercent = iNewTmpFilePercent;

        if ( iNewTmpDispPercent !=
iOldTmpDispPercent )
        {
          TRACE( "NOTICE: Updating percentage of
tmp file
processing\n" );
          UpdateTmpFilePercentage(
iNewTmpFilePercent );
          iOldTmpDispPercent =
iNewTmpDispPercent;
        }
      }
      break;

    case FLU_WAITFORNUMFILES:
      TRACE( "NOTICE: Waiting for total number of
flash files\n"
);

      iNumberOfFlash = GetTotalFlashFiles();

      if ( iNumberOfFlash ==
FLU_NUMBERUNKNOWN )
      {
        if ( iRetryLimit == FLU_MAXUPDREQ )

        {
          TRACE( "ERROR: Timeout waiting for
number of flash
files.\n" );
          FlashUpdateState =
FLU_NOACKNUMFILESERROR;
        }
      }
      else if ( iNumberOfFlash <=
FLU_ERRHOSTBASE )
      {
#if !defined( PROD )
        sprintf( szTempStr, "NOTICE: Number of flash
files
returned as an error code - %d\n", iNumberOfFlash );

        TRACE( szTempStr );
#endif
        switch ( iNumberOfFlash )
        {
          case FLU_ERRREADHOSTDAT:
            FlashUpdateState = FLU_READHOSTDAT;
            break;

          case FLU_ERRMISSINGFILE:
            FlashUpdateState = FLU_MISSINGFILE;
            break;

          case FLU_ERRNOFLASHFILES:
            FlashUpdateState = FLU_NOFLASHFILES;
            break;

          case FLU_ERROUTOFDISKSPACE:
            FlashUpdateState =
FLU_OUTOFDISKSPACE;
            break;

          case FLU_ERRFILECORRUPTED:
            FlashUpdateState =
FLU_FILECORRUPTED;
            break;

          case FLU_ERRNOCHECKSUM:
            FlashUpdateState = FLU_NOCHECKSUM;

            break;

          default:
            FlashUpdateState =
FLU_HOSTUNKNOWNERR;
            break;
        }
      }
      else
      {
        WORD wExtendedMem =
GetSizeOfExtendedMem();

#if !defined( PROD )
        sprintf( szTempStr, "NOTICE: Number of flash
files - %d
\n", iNumberOfFlash );
        TRACE( szTempStr );
#endif
        if ( iNumberOfFlash >
FLU_2MEGTHREASHHOLD &&
            wExtendedMem <
FLU_1MEGEXTENDEDRAM )
        {
          FlashUpdateState =
FLU_1MEGSYSTEMERROR;
        }
        else if ( iNumberOfFlash ==
FLU_2MEGTHREASHHOLD &&
            wExtendedMem ==
FLU_1MEGEXTENDEDRAM )
        {
          FlashUpdateState =
FLU_2MEGSYSTEMERROR;

        }
        else
        {
          iCurrFlashFile = 1;

          FlashUpdateState = FLU_SENDREQPATH;
          SetDlogFlash( ( iNumberOfFlash >
FLU_2MEGTHREASHHOLD )
);
          SetTimeLimit( iDoUpdateThreadIdx,
FLU_POLLFREQ );
          ResetRetryLimit( iDoUpdateThreadIdx );
        }
      }
      break;

    case FLU_SENDREQPATH:
      *szPathFlashFile = NULL;

      if ( SendPrivateMessage(
PMI_REQPATHFROMIDX, sizeof( int
),
                    ( NPSTR )&iCurrFlashFile )
!=
ERR_SUCCESS )
        FlashUpdateState =
FLU_SENDPRIMSGERROR;
      else
      {
        if ( iRetryLimit == 0 )
          SetRetryLimit( iDoUpdateThreadIdx, 1 );

        FlashUpdateState =
FLU_WAITFORPATHFLASHFILE;
        SetTimeLimit( iDoUpdateThreadIdx,
FLU_PRIMSGPOLLFREQ );
      }
      break;

    case FLU_WAITFORPATHFLASHFILE:
      if ( *GetPathFlashFile() == NULL )
      {
        if ( iRetryLimit < FLU_MAXPATHREQ )
        {
          TRACE( "ERROR: Timeout waiting for
response to path
request\n" );
          FlashUpdateState =
FLU_NOACEPATHERROR;
        }
        else if ( iRetryLimit % FLU_MODPATHREQ
== 0 )
        {
          TRACE( "NOTICE: Trying again to receive
the next path
name\n" );
          FlashUpdateState = FLU_SENDREQPATH;
        }
      }
      else
      {
        if ( *ParseForFileName( GetPathFlashFile() )
==
FLU_FLASHFILEID )
        {
          FlashUpdateState =
FLU_RECEIVEHOSTFILE;
          ResetRetryLimit( iDoUpdateThreadIdx );
          SetTimeLimit( iDoUpdateThreadIdx,
FLU_POLLFREQ );
        }
        else
        {
          TRACE( "NOTICE: Protected file
encountered, skipping to
the next file\n" );
          goto after_flash;
        }
      }
      break;

    case FLU_RECEIVEHOSTFILE:
#if !defined( PROD )
      sprintf( szTempStr, "NOTICE: File name
received - %s \n",
          GetPathFlashFile() );
      TRACE( szTempStr );
#endif
      if ( ReceiveHostFile( GetPathFlashFile(),
sFlashImageBuff,
FLU_SIZEFLASHSECTOR )
          != ERR_SUCCESS )
      {
        if ( iRetryLimit == FLU_MAXRECVFILEREQ )
        {
          if ( iCurrFlashFile > 1 )
          {
            TRACE( "ERROR: Timeout waiting for
successful
ReceiveHostFile() request, from sector\n" );
            FlashUpdateState =
FLU_NOACKRECEIVEFATALERROR;
          }
          else
          {
            TRACE( "ERROR: Timeout waiting for
successful
ReceiveHostFile() request\n" );
            FlashUpdateState =
FLU_NOACKRECEIVEFILEERROR;
          }
        }
      }
      else
      {
        TRACE( "NOTICE: Finally beginning reflash of
the
specified sector\n" );
        FlashUpdateState = FLU_FLASHIT;
        ResetRetryLimit( iDoUpdateThreadIdx );
      }
      break;

    case FLU_FLASHIT:
      if ( ( iSectorFlashStatus = FlashSector(
sFlashImageBuff,
            iCurrFlashFile ) ) !=
SBS_FLASHSUCCESS )
      {
        if ( iSectorFlashStatus ==
SBS_FLASHNOTATTACHED ||
            iRetryLimit == FLU_MAXFLASHIT )

          FlashUpdateState =
FLU_FLASHFATALERROR;
      }
      else
      {
after_flash:
        UpdateFlashPercentage( iCurrFlashFile );
        ResetRetryLimit( iDoUpdateThreadIdx );

        if ( ++iCurrFlashFile > iTotalFlashFiles )
          FlashUpdateState = FLU_CLEAREEROM;
        else
          FlashUpdateState = FLU_SENDREQPATH;

      }
      break;

    case FLU_CLEAREEROM:
      TRACE( "NOTICE: Clearing EEPROM\n" );

      if ( ClearEEPROM() != ERR_SUCCESS )
      {
        if ( iRetryLimit == FLU_MAXCLEAREEROM )

          FlashUpdateState =
FLU_EEROMNOCLRERROR;
      }
      else
      {
        ResetRetryLimit( iDoUpdateThreadIdx );
        FlashUpdateState =
FLU_FLASHUPDATECOMPLETE;
        SendPrivateMessage( PMI_REQFLASHDONE,
0, NULL );
      }
      break;

    case FLU_FLASHUPDATECOMPLETE:
      SendPrivateMessage( PMI_REQFLASHDONE,
0, NULL );
      FlashUpdateState = FLU_REBOOT;
      SetTimeLimit( iDoUpdateThreadIdx,
FLU_PRIMSGPOLLFREQ );
      break;

    case FLU_REBOOT:
      reboot( CRU_COLDBOOT );
      break;

    default:
      WaitForFlashError();
  }

  if ( FlashUpdateState >
FLU_BEGINERRORSTATES )
    WaitForFlashError();
}

void WaitForFlashError( void )
{
```

```
  SendPrivateMessage( PM_REQFLASHDONE, 0,
NULL );

  if ( sFlashImageBuff == NULL )
  {
    DelThread( iDoUpdateThreadIdx );
    SetWaitingIcon( SSS_WAITINGICONOFF, TRUE
);
  }
  else
  {
    SetRetryLimit( iDoUpdateThreadIdx, 1 );
    HideMessageBox();
    SMDoeSoon( ReleaseFlashMem );
    return;
  }

  switch ( FlashUpdateState )
  {
    case FLU_NOFLASHFILES:
      OpenMessageBox( STR_FLUNOFLASHFILES,
0, SUI_LEFTJUSTIFIED,
SUI_OK );
      break;

    case FLU_READHOSTDAT:
      OpenMessageBox( STR_FLUREADHOSTDAT,
0, SUI_LEFTJUSTIFIED
SUI_OK );
      break;

    case FLU_MISSINGFILE:
      OpenMessageBox( STR_FLUMISSINGFLASH,
0, SUI_LEFTJUSTIFIED,
SUI_OK );
      break;

    case FLU_OUTOFDISKSPACE:
      OpenMessageBox(
STR_FLUOUTOFDISKSPACE, 0,
SUI_LEFTJUSTIFIED, SUI_OK );
      break;

    case FLU_FILECORRUPTED
      OpenMessageBox(
STR_FLUFILECORRUPTED, 0,
SUI_LEFTJUSTIFIED,
SUI_OK );
      break;

    case FLU_NOCHECKSUM
      OpenMessageBox( STR_FLUNOCHECKSUM,
0, SUI_LEFTJUSTIFIED,
SUI_OK );
      break;

    case FLU_NOACKTEMPFILESERROR:
      OpenMessageBox(
STR_FLUNOACKTMPERROR, 0,
SUI_LEFTJUSTIFIED,
SUI_OK );
      break;

    case FLU_NOACKNUMFILESERROR
      OpenMessageBox(
STR_FLUNOACKNUMFILEERR, 0,
SUI_LEFTJUSTIFIED, SUI_OK );
      break;

    case FLU_NOACKPATHERROR:
      OpenMessageBox(
STR_FLUNOACKPATHERROR, 0,
SUI_LEFTJUSTIFIED, SUI_OK );
      break;

    case FLU_NOACKRECEIVEFILEERROR
      OpenMessageBox(
STR_FLUNOACKRECVFILEERR, 0,
SUI_LEFTJUSTIFIED, SUI_OK );
      break;

    case FLU_NOACKRECEIVEFATALERROR:
      OpenMessageBox(
STR_FLUNOACKRECVFATAL, 0,
SUI_LEFTJUSTIFIED, SUI_OK );
      break;

    case FLU_SENDPRIMSGERROR:
      OpenMessageBox( STR_FLUSENDPRIMSG, 0,
SUI_LEFTJUSTIFIED,
SUI_OK );
      break;

    case FLU_1MEGSYSTEMERROR:
      OpenMessageBox(
STR_FLU1MEGSYSERROR, 0,
SUI_LEFTJUSTIFIED,
SUI_OK );
      break;

    case FLU_2MEGSYSTEMERROR:
      OpenMessageBox(
STR_FLU2MEGSYSERROR, 0,
SUI_LEFTJUSTIFIED,
SUI_OK );
      break;

    case FLU_FLASHFATALERROR:
      switch ( iModemFlashState )
      {
        case SSS_FLASHACNOTATTACHED:
          OpenMessageBox( STR_FLUNOAC, 0,
SUI_LEFTJUSTIFIED,
SUI_OK );
          break;

        case SSS_FLASHERASEERROR:
          OpenMessageBox( STR_FLUFLASHERASE,
0,
SUI_LEFTJUSTIFIED, SUI_OK );
          break;

        case SSS_FLASHPROGERROR:
          OpenMessageBox( STR_FLUFLASHPROG,
0, SUI_LEFTJUSTIFIED,
SUI_OK );
          break;

        default:
          OpenMessageBox(
STR_FLUFLASHUNKNOWN, 0,
SUI_LEFTJUSTIFIED, SUI_OK );
          break;
      }
      break;

    case FLU_SERONNOCLRERROR:
      OpenMessageBox( STR_FLUSERONNOCLR,
0, SUI_LEFTJUSTIFIED,
SUI_OK );
      break;

    case FLU_HOSTUNKNOWNERR
      OpenMessageBox(
STR_FLUUNKNOWNHOSTERR, 0,
SUI_LEFTJUSTIFIED, SUI_OK );
      break;

    case FLU_MEMERROR:
      OpenMessageBox(
STR_FLURAMALLOCATION, 0,
SUI_LEFTJUSTIFIED,
SUI_OK );
      break;

    default:
      OpenMessageBox(
STR_FLUUNKNOWNERROR, 0,
SUI_LEFTJUSTIFIED,
SUI_OK );
  }
}

void GetFlashImageBuff( void )
{
  WORD wSector;

  TRACE( "NOTICE: Allocating memory from
CoSession for the
reflash buffer\n" );

  SetSCSMemory( SCS_DLGFREEMEMPERCENT,
SCS_FREEMEM, ( BYTE
)SM_SCSNOWAITFORDOS );

  if ( ( wSector = GetFreeMCB( ( WORD )(
FLU_SIZEFLASHSECTOR / 16
) ) ) != 0 )
    sFlashImageBuff = MK_FP( wSector, 0 );
}

void ReleaseFlashMem( void )
{
  if ( szPathFlashFile != NULL )
  {
    free( szPathFlashFile );
    szPathFlashFile = NULL;
  }

  if ( sFlashImageBuff != NULL )
  {
    SetFreeMCB( SEG( sFlashImageBuff ) );
    sFlashImageBuff = NULL;
  }

  TRACE( "NOTICE: Returning memory to
CoSession, used by the
reflash buffer\n" );

  SetSCSMemory( 0, SCS_FREEMEM, ( BYTE
)SM_SCSNOWAITFORDOS );


  if ( UIConfigData.iSleepTimeIdx !=
SSS_SLEEPDISABLED )
    SetPowerEnable( SSS_POWERMANENABLED );

}

int UpdateTmpFilePercentage( int
iNewTmpFilePercent )
{
  int iPercentage;

  iPercentage = ( iNewTmpFilePercent * 2 ) / 100;

  AX( SUI_UPDATEFLASHPRCNT );
  BX( iPercentage );

  ( *pfnSUICallBack )();

  return ( ERR_SUCCESS );
}

int UpdateFlashPercentage( int iFlashFileNum )
{
  int iPercentage;

  if ( iTotalFlashFiles == 0 )
    return ( ERR_INTERNAL );

  iPercentage = ( iFlashFileNum * 100 ) /
iTotalFlashFiles;

  AX( SUI_UPDATEFLASHPRCNT );
  BX( iPercentage );

  ( *pfnSUICallBack )();

  return ( ERR_SUCCESS );
}

int GetActiveUpdate( void )
{
  if ( GetSCSCallProgress() !=
SM_SCSCONNECTED )
    TRACE( "NOTICE: Not currently connected for
GetActiveUpdate(), sending PM anyway\n" );

  if ( isFlashSupported() )
  {
    if ( szNameActiveUpdate == NULL )
      if ( ( szNameActiveUpdate = ( NPSTR )malloc(
SUI_MAXLENACTIVEUPD + 1 ) ) == NULL )
        return ( ERR_INTERNAL );

    fl_str( szNameActiveUpdate, 0,
SUI_MAXLENACTIVEUPD + 1 );

    if ( SendPrivateMessage(
PM_REQACTIVEUPGRADE, 0, NULL ) !=
ERR_SUCCESS )
      return ( ERR_INTERNAL );

    TRACE( "NOTICE: Sent Private Message to
determine the name of
the active upgrade on the Host.\n" );

    if ( ( iActiveUpdateThreadIdx =
GetTempEventIndex() ) ==
ERR_INTERNAL )
      return ( ERR_INTERNAL );

    AddThread( iActiveUpdateThreadIdx,
WaitForActiveUpdate, NULL,
SMD_MANYTIMES,
              FALSE, FLU_PRIMSGPOLLFREQ,
FLU_MAXRETRY );


  }
  else
  {
    TRACE( "ERROR: Flash not supported\n" );
    return ( ERR_INTERNAL );
  }

  return ( ERR_SUCCESS );
}

void WaitForActiveUpdate( void )
{
  int iRetryLimit = GetRetryLimit(
iActiveUpdateThreadIdx );

  if ( *GetNameActiveUpdate() == NULL )
  {
    if ( iRetryLimit < FLU_MAXACTUPDREQ )

      DelThread( iActiveUpdateThreadIdx );
    else if ( iRetryLimit % FLU_MODACTUPDREQ
== 0 )
    {
      if ( SendPrivateMessage(
PM_REQACTIVEUPGRADE, 0, NULL ) !=
ERR_SUCCESS )
        DelThread( iActiveUpdateThreadIdx );
    }
  }
  else
    DelThread( iActiveUpdateThreadIdx );
}

int SetPathFlashFile( LPSTR szNewPathFlashFile )
{
  if ( szPathFlashFile == NULL )
    return ( ERR_INTERNAL );
  PCS_BEGINCRITICAL;
  fmem_cp( ( LPVOID )szNewPathFlashFile, (
LPVOID
)szPathFlashFile,
          fstr_len( szNewPathFlashFile ) + 1 );
  PCS_ENDCRITICAL;

  return ( ERR_SUCCESS );
}

char *GetPathFlashFile( void )
{
  return ( szPathFlashFile );
}

int SetTotalFlashFiles( int iNewTotalFlashFiles )
{
  iTotalFlashFiles = iNewTotalFlashFiles;

  return ( ERR_SUCCESS );
}

int GetTotalFlashFiles( void )
{
  int iReturn,

  PCS_BEGINCRITICAL;
  iReturn = iTotalFlashFiles
  PCS_ENDCRITICAL;

  return ( iReturn );
}

int SetNameActiveUpdate( LPSTR
szNewActiveUpdate )
{
  if ( szNameActiveUpdate == NULL )
    return ( ERR_INTERNAL );

  PCS_BEGINCRITICAL;
  if ( szNewActiveUpdate == NULL )
    *szNameActiveUpdate = ' ';
  else
    fmem_cp( ( LPVOID )szNewActiveUpdate, (
LPVOID
)szNameActiveUpdate,
            SUI_MAXLENACTIVEUPD );
  PCS_ENDCRITICAL;

  return ( ERR_SUCCESS );
}

char *GetNameActiveUpdate( void )
{
  if ( szNameActiveUpdate == NULL )
    return ( szNullStr );
  else
    return ( szNameActiveUpdate );
}

int SetTmpFilePercent( int iNewPercent )
{
  iTmpFilePercent = iNewPercent;

  return ( ERR_SUCCESS );
}

int GetTmpFilePercent( void )
{
  int iReturn;

  PCS_BEGINCRITICAL;
  iReturn = iTmpFilePercent;
  PCS_ENDCRITICAL;

  return ( iReturn );
}
```

```
FLASHUPDATESTATES CheckFlashPowerState(
void )
{
  LONG lBatteryInfo = GetBatteryInfo();

  if ( lBatteryInfo ==
SSS_GETBATTERYINFOERROR )
    return ( FLU_GETBATTERYINFOERROR );

  if ( ( lBatteryInfo & SSS_ACDCSTATEMASK ) !=
SSS_ACDCSTATEMASK )
    return ( FLU_NOTONACERROR );

  if ( ( lBatteryInfo &
SSS_BATTERYATTACHEDMASK ) !=
SSS_BATTERYATTACHED )
    return ( FLU_BATNOTATTACHEDERROR );

  if ( HIBYTE( LOWORD( ( lBatteryInfo &
SSS_BATTERYCAPACITYMASK )
) ) < SSS_BATTERYFLASHMINCAP )
    return ( FLU_BATCAPTOOLOWERROR );

  return ( FLU_NOFLUSTATE );
}

#if defined( _MSC_VER )
#pragma warning( default : 4704 )
#endif
Copr. 1995 Zenith Data Systems Corp
#include "sr.h"
#include "sis.h"
#include "sgeum.h"
#include "sm.h"

#if defined( _MSC_VER )
#pragma warning( disable : 4704 )
#endif

TIMEOUT timeoutState = TIMEOUT_AVAILABLE;

static void TimeoutFire ( void );

static DOSBUSYCB fnDosBusyCallBack = NULL;
static VIDBUSYCB fnVidBusyCallBack1 = NULL;
static VIDBUSYCB fnVidBusyCallBack2 = NULL;
static MODALMSGBOXCB fnMsgBoxCallBack =
NULL;
static int nTempThreadIdx =
SMD_NOACTIVETHREAD;
static int iClkThreadIdx;
static int iVideoBusyThreadIdx =
SMD_NOACTIVETHREAD;
static int iSpkrThreadIdx =
SMD_NOACTIVETHREAD;
BYTE aDummyPCB1[] = "0";
BYTE aDummyPCB2[] = "0";

static char *sVideoStateBuff;

void GetForegroundRegs( struct REGW *inRegs )
{
  register struct sreg *s;
  register struct REGW *r;
  struct glob_stk far *g;

  r = inRegs;
  s = _int_frame;

  r->ax = s->ax;
  r->bp = s->bp;
  r->di = s->di;
  r->si = s->si;
  r->ss = s->ss;

  *(word*)&p = s->saved_sp;
  *((word*)&p+1) = s->saved_ss;

  r->ds = g->ds;
  r->es = g->es;
  r->bx = g->bx;
  r->cx = g->cx;
}

void SetForegroundRegs( struct REGW *OutRegs )
{
  struct sreg *s;
  struct REGW *r;
  struct glob_stk far *g;

  r = OutRegs;
  s = _int_frame;

  s->ax = r->ax;
  s->bp = r->bp;
  s->di = r->di;
  s->si = r->si;
  s->ss = r->ss;

  g = ( struct glob_stk far * )MK_FP( s->saved_ss,
s->saved_sp );

  g->ds = r->ds;
  g->es = r->es;
  g->bx = r->bx;
  g->cx = r->cx;
}

#if defined( PROD )
void Trace( char *szOutStr )
{
  REG_W inRegs, OutRegs;

  _fmemset( (NPSTR )&inRegs, 0, sizeof( REG_W ) );

  inRegs.ax = SID_FUNCNUM | SID_OUTSTRING;
  inRegs.si = SID_SIG;
  inRegs.di = SID_DISIG;
  inRegs.ds = SEG( szOutStr );
  inRegs.dx = OFF( szOutStr );

  intx( &inRegs, &OutRegs, SID_INTNUM );
}
#endif

void CallAPIFunction( APIFUNC aAPIFuncTable[] )
{
  APIFUNCPTR lpAPIFunction;
  struct REGW CallerRegs;

  PCS_BEGINCRITICAL
  GetForegroundRegs( &CallerRegs );
  PCS_ENDCRITICAL

  lpAPIFunction = ( APIFUNCPTR )GetAPIFunction(
aAPIFuncTable,
&CallerRegs );

  if ( lpAPIFunction != NULL )
    ( *lpAPIFunction )( &CallerRegs );
  else
  {
    CallerRegs.ax = ( WORD
)ERR_NOTSUPPORTED;
    SetForegroundRegs( &CallerRegs );
  }
}

NEARPROC GetAPIFunction( APIFUNC
aAPIFuncTable[], struct REGW
*pCallerRegs )
{
  WORD wFuncCode = pCallerRegs->ax & 0x7FFF;
  int iFuncIdx = 0;

  if ( aAPIFuncTable == NULL )
    return ( NULL );

  while ( TRUE )
  {
    if ( wFuncCode == aAPIFuncTable[ iFuncIdx
].wFuncCode )
      return( aAPIFuncTable[ iFuncIdx ].lpAPIFunc );

    if ( aAPIFuncTable[ ++iFuncIdx ].wFuncCode ==
0 &&
        aAPIFuncTable[ iFuncIdx ].lpAPIFunc ==
NULL )
      return ( NULL );
  }
}

int ErrorBeep( void )
{
  sound( SMU_ERRORFREQ, SMU_ERRORDUR );

  if ( iSpkrThreadIdx >= 0 )
  {
    TRACE( "NOTICE: ErrorBeep() reentered\n" );
    return ( ERR_SUCCESS );
  }

  if ( ( iSpkrThreadIdx = GetTempEventNum() ) < 0 )
    return ( ERR_INTERNAL );

  AddThread( iSpkrThreadIdx, SetSpkrRestore,
NULL, SMD_ONETIME,
FALSE, SMC_SPKRPOLLFREQ,
           0 );

  return ( ERR_SUCCESS );
}

void OnSpkrRestore( void )
{
  DelThread( iSpkrThreadIdx );

  iSpkrThreadIdx = SMD_NOACTIVETHREAD;

  TRACE( "NOTICE: Speaker frequency restored for
PDV" );

  SetPenSpkrFreq();
}

int SMDosBusy( DOSBUSYCB fnCallBack )
{
  if ( iTempThreadIdx >= 0 )
  {
    TRACE( "ERROR: SMDosBusy was reentered\n"
);
    DEBUG_BREAK;
    return ( 0 );
  }

  if ( ( iTempThreadIdx = GetTempEventNum() ) < 0
)
    return ( ERR_INTERNAL );

  fnDosBusyCallBack = fnCallBack;

  AddThread( iTempThreadIdx, SMCheckDosBusy,
NULL, SMD_MANYTIMES,
FALSE, DBT_POLLFREQ,
           DBT_MAXRETRY );

  return ( ERR_SUCCESS );
}

void SMCheckDosBusy( void )
{
  BOOL fModeDosBusy = FALSE;

  if ( *_inr_flg_ptr & ~SMD_SCHEDULERS )
    return;

  if ( dos_busy( 0 ) )
  {
    if ( GetRetryLimit( iTempThreadIdx ) == 0 )
    {
      TRACE( "ERROR: Timed out waiting for DOS
busy\n" );
      DEBUG_BREAK;
    }
    else
      return;
  }

  DelThread( iTempThreadIdx );
  iTempThreadIdx = SMD_NOACTIVETHREAD;

  ( *fnDosBusyCallBack )();
}

int SMVideoBusy( VIDBUSYCB fnCallBack )
{
  if ( fnVidBusyCallBack1 != NULL )
  {
    if ( fnVidBusyCallBack2 != NULL )
    {
      TRACE( "NOTICE: SMVideoBusy() reentered
more than twice,
waiting for SUI video busy\n" );
      DEBUG_BREAK;
      return ( ERR_INTERNAL );
    }
    else
    {
      TRACE( "NOTICE: SMVideoBusy() reentered
waiting for SUI
video busy\n" );
      fnVidBusyCallBack2 = fnCallBack;
    }
  }
  else
    fnVidBusyCallBack1 = fnCallBack;

  if ( iVideoBusyThreadIdx ==
SMD_NOACTIVETHREAD )
  {
    if ( ( iVideoBusyThreadIdx =
GetTempEventNum() ) < 0 )
      return ( ERR_INTERNAL );

    AddThread( iVideoBusyThreadIdx,
SMCheckVideoBusy, NULL,
SMD_POLLED, FALSE,
           SCS_VIDBLOCKPOLLFREQ, 0 );
  }

  return ( ERR_SUCCESS );
}

void SMCheckVideoBusy( void )
{
  static BYTE nCntVideoBlocked = 0;

  if ( IsGetVideoBlocked() )
  {
    if ( ++nCntVideoBlocked >= 3 )
    {
      nCntVideoBlocked = 0;
      DelThread( iVideoBusyThreadIdx );
      iVideoBusyThreadIdx =
SMD_NOACTIVETHREAD;
      TRACE( "NOTICE: SUI video not busy, notify
the threads\n"
);

      if ( fnVidBusyCallBack1 != NULL )
      {
        ( *fnVidBusyCallBack1 )();
        fnVidBusyCallBack1 = NULL;
      }

      if ( fnVidBusyCallBack2 != NULL )
      {
        ( *fnVidBusyCallBack2 )();
        fnVidBusyCallBack2 = NULL;
      }
    }
  }
  else
    nCntVideoBlocked = 0;
}

void SetReentrancy( BOOL fEnable )
{
  static BYTE bOldInrFlg;

  if ( fEnable )
  {
    PCS_BEGINCRITICAL;
    bOldInrFlg = *_inr_flg_ptr;
    *_inr_flg_ptr = SMD_NOREENTRANCE;
    PCS_ENDCRITICAL;
  }
  else
  {
    PCS_BEGINCRITICAL;
    *_inr_flg_ptr = bOldInrFlg;
    PCS_ENDCRITICAL;
  }
}

int RestoreVideoMode( void )
{

  if ( sVideoStateBuff == NULL )
    return ( ERR_INTERNAL );


  VideoState( sVideoStateBuff,
SHC_VIDEOHARDWARE |
SHC_VIDEODATAAREA | SHC_COLORPALREGS,
           SHC_RESTOREVIDEO );

  free( sVideoStateBuff );

  sVideoStateBuff = NULL;

  return ( ERR_SUCCESS );
}

WORD SetVideoMode( BYTE nRequestedMode )
{
  int AX;

  AX = MAKEWORD( nRequestedMode, 0 );
  int10( AX );

  return ( ERR_SUCCESS );
}
```

```
int VideoState( char *sVidBuff, char nDataType, char
nOperation )
{
  REG_W InRegs, OutRegs;

  fl_chr( ( NPSTR )&InRegs, 0, sizeof( REG_W ) );

  if ( nOperation != SHC_SIZEOFBUFF )
  {
    if ( sVidBuff != NULL )
    {
      InRegs.es = SEG( sVidBuff );
      InRegs.bx = OFF( sVidBuff );
    }
    else
      return ( ERR_INTERNAL );
  }

  InRegs.ax = ( int )nDataType;
  InRegs.bx = MAKEWORD( nOperation,
SHC_VIDSTATEFUNC );

  intm( &InRegs, &OutRegs, 0x10 );

  if ( nOperation == SHC_SIZEOFBUFF )
    return ( OutRegs.bx );
  else
    return ( ERR_SUCCESS );
}

int JmExec( char szProgName[], char
sCmdLineParm[] )
{
  int iReturn = 0;
  EXECPARMS ep;
  BYTE sCmdLineTail[] = "\0\r";
  WORD wSegEP, wOffEP, wSegPN, wOffPN;
  WORD wOldPSP;

  ep.wSegEnv = 0;

  if ( sCmdLineParm == NULL )
  {
    ep.wOffCmdLineTail = OFF( sCmdLineTail );
    ep.wSegCmdLineTail = SEG( sCmdLineTail );
  }
  else
  {
    ep.wOffCmdLineTail = OFF( sCmdLineParm );
    ep.wSegCmdLineTail = SEG( sCmdLineParm );
  }

  ep.wOffFCB1 = OFF( sDummyFCB1 );
  ep.wSegFCB1 = SEG( sDummyFCB1 );
  ep.wOffFCB2 = OFF( sDummyFCB2 );
  ep.wSegFCB2 = SEG( sDummyFCB2 );

  wSegEP = SEG( &ep );
  wOffEP = OFF( &ep );
  wSegPN = SEG( szProgName );
  wOffPN = OFF( szProgName );

  wOldPSP = set_my_psp();

  AX( SMD_DOSEXEC );
  ES( wSegEP );
  BX( wOffEP );
  DS( wSegPN );
  DX( wOffPN );

  _asm
  {
    int 21h
    jnc success
    mov iReturn,ax
  };

success:
  restore_psp( wOldPSP );
  return ( iReturn );
}

WORD GetFreeMCB( WORD wNumPara )
{
  REG_W InRegs, OutRegs;
  WORD wReturn = 0, wFlags;

  fl_chr( ( NPSTR )&InRegs, 0, sizeof( REG_W ) );

  InRegs.ax = SMD_DOSALLOCMEM;
  InRegs.bx = wNumPara;

  PCB_BEGINCRITICAL;

  wFlags = intm( &InRegs, &OutRegs, SMD_DOSINT
);

  PCB_ENDCRITICAL;

  if ( !( wFlags & GEN_CARRYFLAG ) )
    return ( OutRegs.ax );
  else
    return ( 0 );
}

int SetFreeMCB( WORD wSegment )
{
  REG_W InRegs, OutRegs;
  WORD wFlags;

  fl_chr( ( NPSTR )&InRegs, 0, sizeof( REG_W ) );

  InRegs.ax = SMD_DOSFREEMEM;
  InRegs.es = wSegment;

  PCB_BEGINCRITICAL;

  wFlags = intm( &InRegs, &OutRegs, SMD_DOSINT
);

  PCB_ENDCRITICAL;

  if ( !( wFlags & GEN_CARRYFLAG ) )
    return ( ERR_SUCCESS );
  else
    return ( OutRegs.ax );
}

int StuffKeyStr( char *szStr )
{
  char *sKey = szStr;

  if ( strlen( szStr ) > SHC_MAXLENKBBUFF )
    return ( ERR_INTERNAL );

  while ( TRUE )
  {
    if ( *sKey )
      stuff_key( MAKEWORD( *sKey++, 0 ) );
    else
      return ( ERR_SUCCESS );
  }
}


BOOL IsOurFunction( struct REGW *CallerRegs )
{
  return ( CallerRegs->ax & 0x0000 );
}

char *ParseForFileName( char *szPathName )
{
  int iChar;

  for ( iChar = strlen( szPathName ) - 1; iChar >= 0;
--iChar )
  {
    if ( szPathName[ iChar ] == '\\' )
      return ( szPathName + iChar + 1 );
  }

  return ( NULL );
}

BOOL IsNodeAddressBlank( char *szNodeAddress )
{

  return ( strlen( szNodeAddress ) == 0 );


}

int DoModalMsgBox( MODALMSGBOXCB
fnCallBack, int iMsgBoxTimeOut )
{
  if ( ( fnMsgBoxCallBack = fnCallBack ) == NULL )
    return ( ERR_INTERNAL );

  if ( ( iOkThreadIdx = GetTempEventNum() ) <
ERR_SUCCESS )
    return ( ERR_INTERNAL );

  SetMsgBoxReturnCode( SUI_NOBUTTONS );

  if ( iMsgBoxTimeOut > 0 )
    AddThread( iOkThreadIdx, WaitForOK, NULL,
SMD_MANYTIMES,
FALSE, SUI_MSGBOXPOLLFREQ,
            iMsgBoxTimeOut );
  else
    AddThread( iOkThreadIdx, WaitForOK, NULL,
SMD_POLLED, FALSE,
SUI_MSGBOXPOLLFREQ,
            0 );

  return ( ERR_SUCCESS );
}

void WaitForOK( void )
{
  int iButtonCode;

  if ( ( iButtonCode = GetMsgBoxReturnCode() ) !=
SUI_NOBUTTONS )
  {
    DelThread( iOkThreadIdx );
    ( *fnMsgBoxCallBack )( iButtonCode );
  }
  else if ( GetThreadType( iOkThreadIdx ) ==
SMD_MANYTIMES )
  {
    if ( GetRetryLimit( iOkThreadIdx ) == 0 )
    {
      DelThread( iOkThreadIdx );
      ( *fnMsgBoxCallBack )( SUI_NOBUTTONS );
    }
  }
}

int AbsToZero( int iValue )
{
  return ( iValue < 0 ? 0 : iValue );
}

TIMEOUT TimerManager (TIMEOUT_FLAG
fTimeout, int iThreadIdx, long
lTicks)
{
  static int iTimeoutThreadIdx;
  static int iThreadInUseIdx = -1;
  TIMEOUT timeoutReply;

  switch (fTimeout)
  {
    case TF_SET:
    if (timeoutStatus == TIMEOUT_AVAILABLE)
    {
      if ( ( iTimeoutThreadIdx =
GetTempEventNum() ) !=
ERR_INTERNAL )
      {
        AddThread( iTimeoutThreadIdx,
TimeoutFire, NULL,
SMD_ONETIME, FALSE,
                lTicks, 0 );
        timeoutStatus = TIMEOUT_RUNNING;
        iThreadInUseIdx = iThreadIdx;

        timeoutReply = timeoutStatus;
      }
      else
        timeoutReply = TIMEOUT_ERROR;
    }
    break;

    case TF_RESET:
    if (iThreadInUseIdx == iThreadIdx)
    {
      timeoutStatus = TIMEOUT_AVAILABLE;
      timeoutReply = timeoutStatus;
      iThreadInUseIdx = -1;
    }
    else
      timeoutReply = TIMEOUT_NOTAVAILABLE;
    break;

    case TF_CHECK:
    if (iThreadInUseIdx == iThreadIdx ||
timeoutStatus ==
TIMEOUT_AVAILABLE)
      timeoutReply = timeoutStatus;
    else
      timeoutReply = TIMEOUT_NOTAVAILABLE;
    break;
  }

  return timeoutReply;
}

static void TimeoutFire ( void )
{
  timeoutStatus = TIMEOUT_FIRED;
}

#if defined( _MSC_VER )
#pragma warning( default : 4704 )
#endif



Copr. 1995 Zenith Data Systems Corp.
#include "zr.h"
#include "sio.h"
#include "spawn.h"
#include "sm.h"

#if defined( _MSC_VER )
#pragma warning( disable : 4704 )
#endif

static ZDSTRAPREC VIDTrapRec;
static char nXCharRes = -1;
static char nYCharRes = -1;
static int iYScreenRes = -1;
static iCurrVidMode = 0;

static iPostNotifyThreadIdx = -1;

void InitVIDTrapRec( void )
{
  fl_chr( ( NPSTR )&VIDTrapRec, 0, sizeof(
ZDSTRAPREC ) );

  VIDTrapRec.tr.tr_int = BSS_VIDEOINTNUM;

  VIDTrapRec.tr.tr_sem_crv =
CRU_ONBUSYCLIENT;

  strcpy( VIDTrapRec.szSHAfterSignature,
szSHASignature );
}

TRAPREC *GetVIDTrapRec( void )
{
  return ( &VIDTrapRec.tr );
}

char GetYCharRes( void )
{
  if ( nYCharRes > 0 )
    return ( nYCharRes );
  else
    return ( SCS_HEIGHTOFTEXTCHAR );
}

char GetXCharRes( void )
{
  if ( nXCharRes > 0 )
    return ( nXCharRes );
  else
    return ( SCS_WIDTHOFTEXTCHAR );
}

int GetXScreenRes( int iVideoMode )
{
  switch ( iVideoMode )
  {
    case 0x00:
    case 0x01:
      return ( 320 );

    case 0x02:
    case 0x03:
      return ( 640 );

    case 0x04:
    case 0x05:
      return ( 320 );

    case 0x06:
      return ( 640 );

    case 0x07:
      return ( 720 );

    case 0x08:
    case 0x09:
    case 0x0A:
    case 0x0B:
    case 0x0C:
      return ( ERR_INTERNAL );

    case 0x0D:
      return ( 320 );

    case 0x0E:
    case 0x0F:
    case 0x10:
    case 0x11:
    case 0x12:
      return ( 640 );

    default:
      return ( ERR_INTERNAL );
  }
}

int GetYScreenRes( int iVideoMode )
{
  if ( iVideoMode == SBS_HIGHTEXTVIDMODE &&
iYScreenRes > 0 )
    return ( iYScreenRes );
  else
  {
    switch ( iVideoMode )
```

```
  {
    case 0x30
    case 0x31
    case 0x32
    case 0x33
    case 0x34
    case 0x35
    case 0x36:
      return ( 400 );

    case 0x37:
      return ( 350 );

    case 0x08:
    case 0x38
    case 0x3A:
    case 0x35
    case 0x0C:
      return ( ERR_INTERNAL );

    case 0x80:
    case 0x3E:
      return ( 200 );

    case 0x3F:
    case 0x11
      return ( 350 );

    case 0x11:
    case 0x12:
      return ( 400 );

    default
      return ( ERR_INTERNAL );
   }
  }
}

int GetCurVidMode( void )
{
  return ( iCurrVidMode );
}

BOOL VIDTrapService( void )
{
  struct REGW Regs;
  BOOL fReturn = TRUE;

  GetForegroundRegs( &Regs )

  switch ( HIBYTE( Regs.ax ) )
  {
   case SSS_SETVIDEOMODEFUNCS
     TRACE( "NOTICE: Set video mode
intercepted\n" );

     iCurrVidMode = LOBYTE( Regs.ax ) &
~SSS_VIDMODEMASK;

     AfterModePenNotify();
     break;

   case SSS_CHARACTERGENFUNCS
     TRACE( "NOTICE: Set text font after mode set
intercepted\n"
);

     if ( iCurrVidMode ==
SSS_HIGHTEXTVIDMODE )
       AfterModePenNotify();
     break;

   default
     return ( FALSE );
  }

  return ( TRUE );
}

void AfterModePenNotify( void )
{
  if ( iPenNotifyThreadId >= 0 )
    return;

  if ( ( iPenNotifyThreadId = GetTempEventNum() )
< 0 )
    return;

  AddThread( iPenNotifyThreadId,
WaitForPenNotify, NULL,
SMD_ONETIME, FALSE,
         SSS_PENNOTIFYPOLLFREQ, 0 );
}

void WaitForPenNotify( void )
{
  char FAR *pNumScreenRows = ( char FAR *
)BHC_ADDSCREENROWS;
  char FAR *pNumCharScans = ( char FAR *
)BHC_ADDCHARSCANLINES;

  DelThread( iPenNotifyThreadId );
  iPenNotifyThreadId = -1;

  if ( iCurrVidMode == SSS_HIGHTEXTVIDMODE )
  {
    nYCharRes = *pNumCharScans;
    iYScreenRes = nYCharRes * (
*pNumScreenRows + 1 );
  }
  else
    iYScreenRes = -1;

  NotifyVideoMode( iCurrVidMode );
}

#if defined( _MSC_VER )
#pragma warning( default : 4704 )
#endif
```

```
Copr. 1995 Zenith Data Systems Corp.

MAX_STK_TOP    =    01700h

CMD_LINE_SZ    =    80h
MIN_STK_SZ     =    100h

_TEXT    segment   byte public 'CODE'
_TEXT    ends
_VTX segment byte public 'CODE'
_VTX ends
_ITEXT    segment   byte public 'CODE'
_ITEXT    ends
_ZTEXT    segment   byte public 'CODE'
_ZTEXT    ends
_PITEXT SEGMENT PARA PUBLIC 'CODE'
_PITEXT ENDS
_FXDATA   segment word public 'DATA'
_FXDATA   ends
_FDATA    segment word public 'DATA'
_FDATA    ends
_VDATA    segment word public 'DATA'
_VDATA    ends
_RDATA    segment word public 'DATA'
_RDATA    ends
_IDATA    segment word public 'DATA'
_IDATA    ends
_DATA     segment word public 'DATA'
_DATA     ends
_BSS segment word public 'BSS'
_BSS ends
_BSSEND segment byte public 'BSSEND'
_BSSEND ends


CGROUP    group _TEXT,_VTX,_ITEXT,_ZTEXT
DGROUP    group
_FDATA,_FXDATA,_VDATA,_RDATA,_IDATA,_DAT
A,_BSS,_BSSEND
    assume
cs:CGROUP,ds:DGROUP,ss:DGROUP

_STACK  SEGMENT WORD STACK 'STACK'
_STACK  ENDS

__setseed    =    0017Eh
public __setseed


dly      MACRO    n
    REPT n
      jmp short $+2
    ENDM
       ENDM

inc2     MACRO    reg
       inc reg
       inc reg
       ENDM

dec2     MACRO    reg
       dec reg
       dec reg
       ENDM

OP_RET    =    0C3h
OP_CALN   =    0E8h

pel MACRO    seg_reg
    push ss
    pop seg_reg
    ENDM


_DATA    segment word public 'DATA'
```

```
extrn
data_beg:byte,_sel_ptr:byte,idata_beg:byte,fxdata_b
eg:byte
extrn vdata_beg:byte,rdata_beg:byte,bss_lop:byte

public __sdata,__scode
public __dummy_ret,exit_rdy,pel_ret,__ler_fg_ptr
__ler_fg_ptr  dw  offset CGROUP:__ler_fg
__scode       dw  CGROUP
__sdata       dw  DGROUP


pel_ret  dw  offset CGROUP:__dummy_ret
_DATA    ends

_IDATA    segment word public 'DATA'
__heap         dw  offset DGROUP:bss_top
__env          dw  0
_cmd_line dw  0
_icode_beg    dw  0
_idata_end    dw  0
vtx_size  dw  0
vtx_target    dw  0
vtx_ovl       dw  offset CGROUP:__dummy_ret
exit_vec  dw  offset CGROUP:__dummy_ret
target_data   dw  0
source_data   dw  0
data_gap  dw  0
rec_size  dw  0
exit_rdy  dw  offset CGROUP:__dummy_ret
rec_enabled    db  0
extrn _config_block:byte
extrn __ler_name:byte
extrn idata_beg:byte
extrn __max_stack:word
public rec_enabled,exit_rdy,__heap,__env
public
target_data,source_data,data_gap,rec_size,exit_vec
public
_cmd_line,_icode_beg,_idata_end,vtx_size,vtx_target
,vtx_ovl

_IDATA ends

_BSS segment word public 'BSS'
extrn bss_beg:byte
_resident db  3 dup(?)
__my_psp  dw  1 dup(?)
psp_tbl       dw  1 dup(?)

__slot_list   dw  1 dup(?)
_rec_stack_beg dw  1 dup(?)
_rec_free_stack    dw  1 dup(?)
public _rec_stack_beg,_rec_free_stack,__slot_list

public __my_psp,_cmd_line,_resident,psp_tbl
_BSS ends


_ITEXT   segment   byte public 'CODE'
    ASSUME
CS:CGROUP,DS:DGROUP,SS:DGROUP

extrn ler_psp:word,ler_split:byte
extrn vtx_beg:byte
extrn itext_beg:byte
extrn ptx_beg:byte
extrn code_top:byte

public set_stack
set_stack  proc near
        cld
        pop si
        mov dx,ds
        mov ax,word ptr ds:[2ch]
        mov bp,DGROUP
        mov ds,bp
        mov es,bp
        mov [__env],ax
        mov cx,offset DGROUP:bss_top
        mov di,offset DGROUP:bss_beg
        sub cx,di
        xor ax,ax
        mov es:[__bss_off],ax
        shr cx,1
        rep stosw
        mov [__my_psp],dx


        mov es,dx
        mov bx,MAX_STK_TOP
        mov ax,[__max_stack]
        add ax,di
        jnc ssmd0
ssmd_1:      mov ax,bx
ssmd0:       cmp ax,bx
        ja  ssmd_1
        mov cl,4
        shr ax,cl
```

```
        add ax,CMD_LINE_SZ/16
        xchg ax,bx
        add bx,bp
        sub bx,dx
        mov ah,4Ah
        int 21h
        jnc ssm1
        mov ah,4Ah
        int 21h
        jc  ssm_err

ssm1:        mov ax,bp
        add bx,dx
        sub bx,bp
        shl bx,cl
        sub bx,CMD_LINE_SZ
        mov [_cmd_line],bx
        cli
        mov ss,bp
        mov sp,bx
        sti
        cmp sp,offset
DGROUP:bss_top+MIN_STK_SZ
        jb  ssm_err
        add dx,8
        mov es:[ler_psp],dx
        mov [psp_tbl],dx
        mov ax,offset CGROUP:ptx_beg
        sub ax,offset CGROUP:vtx_beg
        mov [vtx_size],ax
        jmp si

ssm_err: mov ax,4c01h
        int 21h

set_stack endp

_PITEXT  segment
assume cs:_PITEXT

public get_cmd_arg
get_cmd_arg    proc far
        cld


        mov di,[_cmd_line]
        mov ds,[__my_psp]
        pel es
        mov si,80h
        mov cx,7fh
        and cl,[si]
        inc si
        rep movsb
        xor ax,ax
        stosb


        push ds
        pop es
        pel ds
        mov di,102h
        mov si,offset DGROUP:_config_block+2
        movsw
        movsw
        movsw


        mov cl,32
        mov di,5ch
        mov si,offset DGROUP:__ler_name
        rep movsb

        ret
get_cmd_arg    endp
_PITEXT  ends

assume cs:CGROUP

init_fdata:   cld


        mov si,offset DGROUP:fxdata_beg
        mov di,offset DGROUP:vdata_beg
ifd_lp:      cmp si,offset DGROUP:fdata_beg
        jae ifd1
        lodsw
        xchg ax,bx
        lodsw
        sub ax,bx
        mov ss:[bx-2],ax
        mov byte ptr ss:[bx-3],OP_CALN
        jmp ifd_lp

public init_rdata
init_rdata:  mov si,offset DGROUP:rdata_beg
        mov di,offset DGROUP:vdata_beg

ifd1:        sti
        cld
```

```
        cmp  si,di
        jae  lld_ex
        lodsw
        mov  word ptr [si-2],offset
 DGROUP:__dummy_ret
        push si
        push di
        call ax
        pop  di
        pop  si
        pop  ds
        jmp  lld1

lld_ex:         ret

_TEXT   SEGMENT
public start
start           jmp  start1

public go_res
go_res:         rep  movsb
        int  21h
__dummy_ret:  ret
__dummy_iret: iret
public __dummy_ret,__dummy_iret
extrn __int_flg:byte,__lim_off:word
_TEXT   ENDS

extrn ser_data:word
extrn _main:near
start1          call set_smem
        call get_cmd_arg
        call init_fdata
        call _main
        push ax
        mov  byte ptr cs:[__ter_flg],07h
        mov  es,[__env]
        mov  ah,49h
env_patch label word
public env_patch
        int  21h
        cmp  [res_enabled],1
        jz   tsr2

tsr1            xor  bx,bx
        mov  es:[bx],bx
        call word ptr [sed_rdy]
        pop  ax
        mov  ah,4ch
        int  21h
public _exit
_exit:          pop  ax
        jmp  short tsr1

tsr2:           mov  ax,[__heap]
        add  ax,0fh
        mov  cl,4
        shr  ax,cl
        add  ax,DGROUP
        sub  ax,[__my_psp]
        xchg ax,dx

        mov  si,offset DGROUP:data_beg
        mov  ax,_DATA
        mov  bp,[_idata_end]
        inc2 bp
        sub  bp,offset DGROUP:data_beg
        jbe  tsr3
        shr  bp,cl
        add  ax,bp
        shl  bp,cl
        add  si,bp

tsr3.           mov  bx,offset DGROUP:vis_beg
        mov  bp,[vis_size]
        mov  di,[_mode_beg]
        or   di,di
        jnz  tsr3_1
        mov  di,bx
tsr3_1:         cmp  di,bx
        jbe  tsr3_2
        mov  di,bx
tsr3_2:         mov  [vis_target],di
        add  di,bp
        add  di,0fh
        shr  di,cl
        mov  bx,ax
        add  bx,di

tsr4;           mov  [target_data],bx
        mov  [source_data],si
        sub  ax,bx
        mov  [data_gap],ax
        sub  dx,ax
        mov  [res_size],dx
        sub  [__edata],ax
```

```
        mov  byte ptr [_resident],0ffh
        call init_state

        cli
        call word ptr [vis_svd]
        sti

        nop
        xchg bx,bx
fr_graph  label    word

        nop
        xchg bx,bx
fr_lmem_mv    label    word

        nop
        xchg bx,bx
fr_ega_gr label word

        nop
        xchg bx,bx
fr_setvga     label word

        nop
        xchg bx,bx
fr_ cw_app    label    word

        nop
        xchg bx,bx
fr_vapth label word

        nop
        xchg bx,bx
fr_apw_fx     label    word

        mov  ax,[__edata]
        mov  es:[fer_data],ax
        mov  es,[target_data]
        mov  si,[source_data]
        mov  dx,[res_size]
        xor  di,di
        mov  ax,[__heap]
        add  ax,0fh
        and  al,0f0h
        mov  [__heap],ax
        xchg ax,ax
        sub  ax,si
        cld
        cli
        mov  es:[__ter_flg],0
        pop  ax
        mov  ah,31h
        nop
        xchg bx,bx
fr_lim_res    label word
        call go_res
fr_go_res label word

public
fr_go_res,fr_lim_res,fr_apw_fx,fr_cw_app,fr_apps
pe i_grape
public fr_lmem_mv,fr_ega_gr,fr_vapth

_ITEXT   ends

end start
Copr. 1996 Zenith Data Systems Corp.
tLISTBOXENTRY struc
lpszEntry dd 0
cAttribute db 0
ends

MS_LEFTJUSTIFIED equ 0
MS_CENTERED equ 1
MS_RIGHTJUSTIFIED equ 2

PENDRIVER_INTERRUPT equ 07h
SM_FUNCTION_INTERRUPT equ 60h

SM_GET_KEYBOARD_STATUS equ 062h
SM_GET_USER_INTERFACE_LANGUAGE equ
066h
SM_SET_ACTIVE_STATUS equ 064h
SM_GET_INITIAL_SCREEN equ 0006h
SM_GET_ABOUT_DIALOG equ 063h
SM_GET_NEXT_CREDITS_DIALOG equ 64h
SM_UPDATE_DIMENSIONS equ 063h
SM_REQUEST_UNLOAD equ 0006h
SM_REPORT_BUTTON_CLICKED equ 0009H
SM_CALIBRATE_UPPERLEFT equ 3ch
```

```
SM_CALIBRATE_LOWERRIGHT equ 000Ch
SM_CANCEL_CALIBRATION equ 00ch
SM_REBOOT_HOST equ 011h
SM_SET_KEYSTROKE equ 00h
SM_REQUEST_ACTIVE_FLASH_UPGRADE equ
12h
SM_PERFORM_FLASH_UPDATE equ 13h
SM_GET_CONNECTION_STATUS equ 22h
SM_GET_HOST_LIST_STATUS equ 21h
SM_UPDATE_HOST_LIST equ 20h
SM_GET_PASSWORD_STATUS equ 20h
SM_REQUEST_CONNECTION equ 23h
SM_REQUEST_DISCONNECTION equ 0023h
SM_ABORT_REQUEST_CONNECTION equ 24h

SM_TEST_FUNCTION equ 0FFFFh

UI_REQUEST_CLOSURE equ 083h
UI_REQUEST_DISPLAY equ 081h
UI_SHOW_MESSAGE_BOX equ 089h
UI_HIDE_MESSAGE_BOX equ 08Ah
UI_CALIBRATION_COMPLETE equ 0Ch
UI_FLASH_UPDATE_PERCENTAGE equ 14h
UI_GET_SUI_VERSION_NUMBER equ 0Dh
GET_HOST_LIST_STATUS      equ 021h

RES_NO_SCREEN        EQU 0
RES_OSK_ALPHA        EQU 1
RES_OSK_NUM          EQU 2
RES_OSK_FULL         EQU 3
RES_OSK_BIG          EQU 4
RES_OSK_BIG_ALPHA    EQU 5
RES_OSK_BIG_NUM      EQU 6
RES_OSK_BIG_FULL     EQU 7
RES_SETUPS_HOST      EQU 8h
RES_SETUPS_HOTKEYS   EQU 10h
RES_SETUPS_MAINTENANCE EQU 24h
RES_SETUPS_MODEM     EQU 22h
RES_SETUPS_POWER     EQU 40h
RES_SETUPS_SCREEN    EQU 48h

GETSET_AUTOMATIC_SHUTOFF       equ 0Ch
GETSET_BRIGHTNESS              equ 0Ah
GETSET_CONTRAST                equ 0Bh
GETSET_CUSTOM_AUTOANSWER_STRING equ
36h
GETSET_CUSTOM_CONNECT_STRING   equ 38h
GETSET_CUSTOM_DISCONNECT_STRING equ
37h
GETSET_CUSTOM_INIT_STRING      equ 036h
GETSET_HOST_CONNECTION_TYPE    equ 12ch
GETSET_MODEM_ANSWER_ON_RING    equ
033h
GETSET_MODEM_BAUD_RATE_ENTRY   equ
38h
GETSET_MODEM_HOST_DESC_ENTRY   equ
30h
GETSET_MODEM_HOST_PHONE_ENTRY  equ
27h
GETSET_MODEM_MANUFACTURER_ENTRY equ
30h
GETSET_MODEM_PREFIX            equ 030h
GETSET_MODEM_RETRY_DELAY       equ 034h
GETSET_MODEM_RETRY_LIMIT       equ 033h
GETSET_MODEM_SUFFIX            equ 031h
GETSET_MODEM_TONE_OR_PULSE     equ 03h
GETSET_NETWORK_GROUP_ENTRY     equ 2ah
GETSET_NETWORK_HOST_ENTRY      equ 2bh
GETSET_PASSWORD                equ 02eh
GETSET_SLEEPMODE_PERIOD        equ 1Bh
GETSET_SECURITY_ID             equ 06h
GETSET_DOMAIN_ID               equ 07h
GETSET_LOCK_HOST_KEYBOARD      equ 08h
GETSET_ON_HOST_SCREEN          equ 0Ah
GETSET_USER_DEFINED_HOT_ICON   equ 09h
GETSET_USER_ID                 equ 03ch

Copr. 1996 Zenith Data Systems Corp.
        .MODEL  small

SM_SUIEVENTNUM EQU 0

extrn _PushEventNum:near
extrn _lpfnForCallEntry:near

_TEXT SEGMENT WORD PUBLIC 'CODE'
ASSUME DS: DGROUP, SS: DGROUP

ASSUME CS: _TEXT

public _SUICallService
_SUICallService PROC far

        push   bp
```

```
        mov    bp,sp

        cli

        push   ds
        push   ax
        push   bx
      push cx
        push   dx
        mov    ds, cs:000Ah

        mov    ax, SM_SUIEVENTNUM
      push ax
        call   _PushEventNum
      add sp,2

        pop    dx
        pop    cx
        pop    bx
        pop    ax

        sti

        call   DWORD PTR _lpfnForCallEntry

        pop    ds
        mov    sp,bp
        pop    bp
        ret

_SUICallService    ENDP

public _GetPendingEvent
_GetPendingEvent PROC near

        push   bp
        mov    bp,sp

        mov    ax, cs:0010h

        mov    sp,bp
        pop    bp
        ret

_GetPendingEvent ENDP

_TEXT ENDS

END
Copr. 1996 Zenith Data Systems Corp.
include pd.inc

        .MODEL  small

_TEXT SEGMENT WORD PUBLIC 'CODE'
ASSUME DS: DGROUP, SS: DGROUP

ASSUME CS: _TEXT

public _SetPenSplFreq
_SetPenSplFreq proc near
        push   bp
        mov    bp,sp

        mov    al, PD_TIMER2_16BIT_MODE
        cli
        out    43h, al
        jmp    short $+2
        mov    ax, PD_PSEO_FREQUENCY
        out    42h, al
        jmp    short $+2
        mov    al, ah
        out    42h, al
        sti

        mov    sp,bp
        pop    bp
        ret
_SetPenSplFreq endp

_TEXT ENDS

END

Copr. 1996 Zenith Data Systems Corp.
#include "sr.h"
#include "sio.h"
#include "sysnum.h"
#include "frame.h"
#include "sm.h"
#include "ui.h"

#if defined( _MSC_VER )
#pragma warning( disable : 4704 )
#endif

static char szPrompt[] = STR_PROMPT;
static char szLSLProg[] = STR_LSL;
```

```
static char szLSLProgParm[
SL_LSL_CMD_LENGTH ];
static char szIPXODIProg[] = STR_IPXODI;
static char szProximProg[] = STR_PROXIM;
static char szSMANProg[] =
STR_SMANPROGNAME;
static char szSViewProg[] =
STR_SVIEWPROGNAME;
static char szSViewParm[] =
STR_WELCOMESCREEN;
static char szPenDrvProg[] =
STR_PDRVPROGNAME;
static char szSDrvNetProg[] =
STR_SDRVNETPROGNAME;
static char szRWinProg[] = STR_RWINPROGNAME;
static char szCommandProg[] =
STR_COMMANDPROGNAME;
static char szCommandParm[] =
STR_COMMANDPARM;
static char szCommandDir[] = STR_COMMANDDIR;
static char szFormatPrompt[ 10 ];
static char szCommandLine[ 80 ];
static char szNullStr[] = "\0";
static char szOutStr[ 80 ];
static char szProgParmsStr[ 80 ];

static BOOL fExit, fNextCommand, fAutoStart =
FALSE, fError =
FALSE;
static BYTE fVIDRedir = FALSE, fTitleScreen =
FALSE, fLoadSMLow =
FALSE,
        fAllowAbort = FALSE;
static char *sToken, *szProgName, *szProgParms;

static int iErrorCode = ERR_SUCCESS;
static int iCol;
static WORD wParms;
static word alerStack[ MAX_STACKSIZE + 1 ];

static GENERALSTATEIDXS lGeneralState;
static COMMANDSTATEIDXS lCommandState;
static TRAPREC VIDTrapRec;
static TRAPREC SMTrapRec;

void main()
{
 int iCmdLineIdx;
 BYTE nLenCmdLine;

 sprintf( szFormatPrompt, "\n%s", szPrompt );

 init_video();
 get_cro();
 oro_x = boro_x;
 oro_y = boro_y;
 clr_oro();

 fExit = FALSE;

 iCmdLineIdx = str_posi( '-', cmd_line );
 nLenCmdLine = str_len( cmd_line );

 while ( iCmdLineIdx > 0 && iCmdLineIdx <
nLenCmdLine )
 {
  switch ( cmd_line[ iCmdLineIdx ] | 0x20 )
  {
   case 'a':
    fAutoStart = TRUE;

    if ( ( ( cmd_line[ iCmdLineIdx + 1 ] ) | 0x20 ) ==
'v' ) )
    {
     fTitleScreen = TRUE;
     fVIDRedir = TRUE;
    }
    break;

   case 'l':
    fLoadSMLow = TRUE;
    break;

   case 'c':
    fAllowAbort = TRUE;
    break;

   default:
    printf( "\nERROR: invalid parameter\n" );
    break;
  }

  *( cmd_line + iCmdLineIdx - 1 ) = ' ';

  iCmdLineIdx = str_posi( '-', cmd_line );
 }

 if ( fVIDRedir )
 {
   printf( "Saratoga Loader, Copyright (c) 1994-1995
Zenith Data
Sys-tems\n" );
   printf( "Mobile Systems Engineering Version
1.1\n" );
 }

 if ( fAutoStart )
 {
  clr_scr();

  oro_x = 0;
  oro_y = 0;
  mv_oro();

  if ( fTitleScreen )
  {
   RunProgram( szSViewProg, szSViewParm );
  }

  if ( KeyPressed( 2 ) )
  {
   switch( GetActionKey() )
   {
    case KBD_DIAG:
     change_dir( szCommandDir );
     RunProgram( szCommandProg,
szCommandParm );
     DoExit( 1 );
     break;

    case KBD_ABORTLOAD:
     if ( fAllowAbort )
      DoExit( 1 );
     break;
   }
  }
 }

 do
 {
  *_sl = 0;

  if ( fError )
   fil_chr( szCommandLine, 0, sizeof(
szCommandLine ) );
  else
   fError = FALSE;

  if ( fAutoStart )
  {
   printf( szFormatPrompt );
   edit_str( szCommandLine,
MAX_WIDTHOFSCREEN - sizeof(
szPrompt ), &iCol, pokey );
   up_case( szCommandLine );
  }
  else
  {
   szCommandLine[0] = 'C';
   szCommandLine[1] = 'W';
   fAutoStart = FALSE;
  }

  sToken = szCommandLine;
  lGeneralState = STM_COMMAND;
  lCommandState = COM_UNKNOWN;
  fNextCommand = FALSE;

  while ( *sToken != NULL && !fNextCommand &&
!fExit )
  {
   if ( lGeneralState > STM_UNKNOWN )
    lGeneralState = STM_UNKNOWN;

   if ( ( iErrorCode = ( *fnStateTableProcs[
lGeneralState ]
)() ) == ERR_INTERNAL )
    fExit = TRUE;
  }
 }while ( !fExit );

 DoExit( 0 );
}

void DoExit( int iStatus )
{
 RemoveVidTrap();
 SetVideoMode( SUI_TEXTVIDMODE | 0x80 );

 exit( iStatus );
}

int ProcessIdle( void )
{
 return ( ERR_SUCCESS );
}

int ParseCommand( void )
{
 switch ( *sToken )
 {
  case 'R':
   if ( *( sToken + 1 ) == VAL_SPACE )
   {
    lGeneralState = STM_PARM;
    lCommandState = COM_RUNPROG;
    sToken += 2;
   }
   else if ( *( sToken + 1 ) == NULL )
   {
    lGeneralState = STM_EXECUTE;
    lCommandState = COM_RUNSM;
   }
   else
    goto com_unknown;
   break;

  case 'C':
   if ( *( sToken + 2 ) == NULL )
   {
    lGeneralState = STM_EXECUTE;

    if ( *( sToken + 1 ) == 'D' )
     lCommandState = COM_RUNDOSCOS;
    else if ( *( sToken + 1 ) == 'W' )
     lCommandState = COM_RUNWINCOS;
    else
     goto com_unknown;
   }
   else
    goto com_unknown;
   break;

  case 'X':
   if ( *( sToken + 1 ) == 'X' )
    lGeneralState = STM_EXIT;
   else
    goto com_unknown;
   break;

  default:
com_unknown:
   printf( "\nERROR: command unknown" );
   fError = fNextCommand = TRUE;
 }

 return ( ERR_SUCCESS );
}

int ParseParameters( void )
{
 switch ( lCommandState )
 {
  case COM_RUNPROG:
   if ( ( wParms = str_posi( VAL_SPACE, sToken )
) > 0 )
   {
    *( sToken + ( wParms - 1 ) ) = NULL;
    szProgName = sToken;
    sToken += wParms;
    sprintf( szProgParmsStr, " %s%s", sToken );
    szProgParms = szProgParmsStr;
   }
   else
   {
    szProgName = sToken;
    szProgParms = szNullStr;
   }

   lGeneralState = STM_EXECUTE;
   break;

  default:
   fError = TRUE;
   printf( "\nERROR: unknown command in the
parse parameter
state" );
   break;
 }

 return ( ERR_SUCCESS );
}

int ExecuteCommand( void )
{
 if ( fVIDRedir )
  printf( "\n" );

 switch ( lCommandState )
 {
  case COM_RUNSM:
   fNextCommand = TRUE;
   RunProgram( szSMANProg, szNullStr );
   break;

  case COM_RUNDOSCOS:
  case COM_RUNWINCOS:
   fNextCommand = TRUE;

   if ( fVIDRedir )
    InitTraps( ITR_SETVIDTRAP );
   else
    InitTraps( ITR_NOSETVIDTRAP );

   if ( LoadSM( fLoadSMLow ?
SMD_ALLOCFIRSTFIT :
SMD_ALLOCBESTFIT ) != ERR_SUCCESS )
    break;

   strcpy( szLSLProgParm, " " );

   switch ( GetFrameType() )
   {
    case SL_FT_E802_2:
     strcat( szLSLProgParm,
SL_LSL_CMD_E802_2 );
     break;

    case SL_FT_EII:
     strcat( szLSLProgParm, SL_LSL_CMD_EII );
     break;

    case SL_FT_ESNAP:
     strcat( szLSLProgParm,
SL_LSL_CMD_ESNAP );
     break;

    case SL_FT_E802_3:
     strcat( szLSLProgParm,
SL_LSL_CMD_E802_3 );
     break;

    default:
     if ( fVIDRedir )
      printf( "ERROR: Invalid Frame Type
detected.  The
default Frame Type 802.3 will be used.\n" );
     strcat( szLSLProgParm,
SL_LSL_CMD_E802_3 );
     break;
   }

   if (
#if defined( MOUSE )
     RunProgram( "mouse.com", szNullStr ) !=
ERR_SUCCESS
||
#else
     RunProgram( szPenDrvProg, szNullStr ) !=
ERR_SUCCESS
||
#endif
     LoadNetwork() != ERR_SUCCESS ||
     RunProgram( szSDrvNetProg, " -N1
-C0040 -WT20V" ) !=
ERR_SUCCESS )
    break;

   if ( lCommandState == COM_RUNWINCOS )
    RunProgram( szRWinProg, szNullStr );

   KickSM();
   break;

  case COM_RUNPROG:
   fNextCommand = TRUE;
   RunProgram( szProgName, szProgParms );
   break;

  default:
   fError = TRUE;
   printf( "\nERROR: unknown command in the
execution state"
);
   break;
 }

 return ( ERR_SUCCESS );
}

int ProcessSLExit( void )
{
 fExit = TRUE;

 return ( ERR_SUCCESS );
}

int ProcessStateUnknown( void )
{
 printf( "\nERROR: unknown state" );

 return ( ERR_INTERNAL );
}

int RunProgram( char *szProgName, char
*szProgParms )
```

```
{
  int iSpawnReturn;

  if ( ( iSpawnReturn = spawn_ar( szProgName,
szProgParms ) ) >=
0 )
    iSpawnReturn = ERR_SUCCESS;
  else
  {
    if ( fVIDRedir )
      printf( "\nERROR: %s, spawn error %d",
szProgName,
        iSpawnReturn );
    fError = TRUE;
  }

  return ( iSpawnReturn );
}

int LoadMLID( char *szProgName )
{
  int iLoadIdx;

  for ( iLoadIdx = 0; iLoadIdx <
MAX_MLIDLOADRETRY; ++iLoadIdx )
  {
    if ( RunProgram( szProgName, szNullStr ) !=
ERR_SUCCESS )
      return ( ERR_INTERNAL );

    if ( GetMLIDStatus() == TRUE )
      return ( ERR_SUCCESS );
  }

  sprintf( szOutStr,
    "\nERROR: The load sequence was aborted
due to a
failure in the loading of %s.\n",
      szProgramProg );

  DisplayError( szOutStr );

  return ( ERR_INTERNAL );
}

int EnableKbd( void )
{
  REG_W InArgs, OutArgs;

  fill_chr( &InArgs, 0, sizeof ( InArgs ) );

  InArgs.ax = SMI_SLENABLEKBD;

  intm( &InArgs, &OutArgs, SMI_SCSINTNUM );

  return ( 0 );
}

int GetFrameType( void )
{
  REG_W InArgs, OutArgs;

  fill_chr( &InArgs, 0, sizeof ( InArgs ) );

  InArgs.ax = SMI_SLGETFRAMETYPE;

  intm( &InArgs, &OutArgs, SMI_SCSINTNUM );

  return ( OutArgs.ax );
}

int GetMLIDStatus( void )
{
  REG_W InArgs, OutArgs;

  fill_chr( &InArgs, 0, sizeof ( InArgs ) );

  InArgs.ax = SMI_SLGETMLIDSTATUS;

  intm( &InArgs, &OutArgs, SMI_SCSINTNUM );

  return ( OutArgs.ax );
}

void SetOldVidVector( LONG lOldVidVector )
{
  REG_W InArgs, OutArgs;

  fill_chr( &InArgs, 0, sizeof ( InArgs ) );

  InArgs.ax = SMI_SLDEFINEOLDVIDVECTOR;
  InArgs.bx = OFF( lOldVidVector );
  InArgs.dx = SEG( lOldVidVector );
  intm( &InArgs, &OutArgs, SMI_SCSINTNUM );
}

int KickSUI( void )
{
  REG_W InArgs, OutArgs;

  RemoveVidTrap();

  fill_chr( &InArgs, 0, sizeof ( InArgs ) );

  InArgs.ax = SMI_SLLOADSUI;

  intm( &InArgs, &OutArgs, SMI_SCSINTNUM );

  EnableKbd();

  return ( 0 );
}

int LoadPM( int iMemStrategy )
{
  int iRunStatus;

  if ( iMemStrategy != SMD_ALLOCFIRSTFIT )
  {
    PatchMCB();
    SetMemStrategy( iMemStrategy );
  }

  iRunStatus = RunProgram( szPMAINProg,
szNullStr );

  SetMemStrategy( SMD_ALLOCFIRSTFIT );

  return ( iRunStatus );
}

int LoadNetwork( void )
{
  if ( RunProgram( szLSLProg, szLSLProgParm ) !=
ERR_SUCCESS ||
      LoadMLID( szProtomProg )          !=
ERR_SUCCESS ||
      RunProgram( szIPXODIProg, szNullStr ) !=
ERR_SUCCESS )
    return ( ERR_INTERNAL );

  return ( ERR_SUCCESS );
}

int KeyPressed( int iDelay )
{
  int iTickCount;
  long lSyncCount;

  kbflag = 0;

  if ( !fVIDRedir )
  {
    if ( fAllowAbort )
      printf( "\n[CTRL]+[ALT]+A to abort load
sequence or
[CTRL]+[ALT]+D to load diagnostic...\n" );
    else
      printf( "\n[CTRL]+[ALT]+D to load
diagnostic...\n" );
  }

  for ( iTickCount = 0; iTickCount < iDelay;
++iTickCount )
  {
    lSyncCount = sync_timer();

    while ( TRUE )
    {
      if ( sync_timer() - lSyncCount >= 20 )
        break;

      if ( anykey() )
        return ( TRUE );
    }
  }

  return ( FALSE );
}

ACTIONKEYS GetActionKey( void )
{
  WORD wKey;

  if ( anykey() )
  {
    wKey = getkey();

    if ( kbflag & KBD_CTRLMASK &&
        kbflag & KBD_ALTMASK )
    {
      switch( wKey )
      {
        case KBD_DSCAN:
          return ( KBD_DIAG );

        case KBD_ASCAN:
          return ( KBD_ABORTLOAD );
      }
    }
  }

  return ( KBD_NOACTIONKEY );
}

void InitTraps( BYTE eVidTrapStatus )
{
  install_trap( ( fp )TrapService, MAX_STACKSIZE *
sizeof ( int
), SMD_FULLREENTER );
  enable_int( siotStack, MAX_STACKSIZE * sizeof (
int ) );

  if ( eVidTrapStatus == ITR_SETVIDTRAP )
  {
    VIDTrapRec.tr_int = SSS_VIDINTNUM;
    VIDTrapRec.tr_sem_arr =
CRU_ONBUSYOLDINT;

    add_trap( &VIDTrapRec );

    fVIDRedir = TRUE;
  }

  SMITrapRec.tr_int = SSS_SLINTNUM;
  SMITrapRec.tr_sem_arr = CRU_ONBUSYOLDINT;

  add_trap( &SMITrapRec );
}

BOOL RemoveVidTrap( void )
{
  BOOL fReturn = FALSE;
  DWORD dwCurrVidTrap;
  DWORD dwOldVidTrap = VIDTrapRec.tr_old_int;

  PCS_BEGINCRITICAL;

  if ( VIDTrapRec.tr_int > 0 )
  {
    SetOldVidVector( dwOldVidTrap );
    if ( ( dwCurrVidTrap = clr_trap( &VIDTrapRec ) )
!=
dwOldVidTrap )
      set_int_vec( SSS_VIDINTNUM, dwCurrVidTrap
);

    VIDTrapRec.tr_int = 0;

    fReturn = TRUE;
    fVIDRedir = FALSE;
  }

  PCS_ENDCRITICAL;

  return ( fReturn );
}

void DisplayError( char *szErrStr )
{
  RemoveVidTrap();
  SetVideoMode( SUI_TEXTVIDMODE | 0x80 );

  printf( szErrStr );
}

WORD TrapService( struct trap_rec *CurrTrapRec )
{
  struct REGW InRegs, OutRegs;
  WORD wFlags;

  GetForegroundRegs( &InRegs );

  switch ( CurrTrapRec->tr_int )
  {
    case SSS_VIDINTNUM:
      switch ( HIBYTE( InRegs.ax ) )
      {
        case SSS_TELETYPE:
          break;

        case SSS_RELOCATEDSCRADDR:

          wFlags = intm( &InRegs, &OutRegs,
SSS_VIDINTNUM );
          SetForegroundRegsFlags( &OutRegs,
SFR_SETFLAGS, wFlags
);
          SetVideoMode( SUI_INITIALVIDMODE );

          break;

        default:
          return ( ( WORD )CurrTrapRec );
      }
      break;

    case SSS_SLINTNUM:
      wFlags = intm( &InRegs, &OutRegs,
SSS_INTNUM );
      SetForegroundRegsFlags( &OutRegs,
SFR_SETFLAGS, wFlags );
      break;

    default:
      return ( ( WORD )CurrTrapRec );
  }

  return ( 0 );
}

void GetForegroundRegs( struct REGW *InRegs )
{
  register struct sreg *s;
  register struct REGW *r;
  struct glob_stk far *p;

  r = InRegs;
  s = _int_frame;

  r->es = s->es;
  r->bp = s->bp;
  r->di = s->di;
  r->si = s->si;
  r->cx = s->cx;

  *(word*)&p = s->saved_sp;
  *((word*)&p)+1) = s->saved_ss;

  r->ds = p->ds;
  r->dx = p->dx;
  r->bx = p->bx;
  r->ax = p->ax;
}

void SetForegroundRegsFlags( struct REGW
*OutRegs, BYTE
fSetFlags, WORD wFlags )
{
  struct sreg *s;
  struct REGW *r;
  struct glob_stk far *p;

  r = OutRegs;
  s = _int_frame;

  s->es = r->es;
  s->bp = r->bp;
  s->di = r->di;
  s->si = r->si;
  s->cx = r->cx;

  p = ( struct glob_stk far * )MK_FP( s->saved_ss,
s->saved_sp );

  p->ds = r->ds;
  p->dx = r->dx;
  p->bx = r->bx;
  p->ax = r->ax;

  if ( fSetFlags == SFR_SETFLAGS )
    p->Flags = wFlags;
}

WORD SetVideoMode( BYTE nRequestedMode )
{
  int AX;

  AX = MAKEWORD( nRequestedMode, 0 );
  int10( AX );

  return ( 0 );
}


#if defined( _MSC_VER )
#pragma warning( default : 4704 )
#endif
Copr. 1995 Zenith Data Systems Corp.

#include "sr.h"
#include "sio.h"
#include "spawn.h"
#include "frame.h"
#include "sm.h"

#define MCB_TARGETSEGMENT 0xC000
#define MCB_TARGETSEGSIZE 0x1000
#define MCB_OWNERDOS 0x0000

MCB far *GetFirstMCB( void );
MCB far *GetNextMCB( MCB far *pCurrMCB );
MCB far *GetLastMCB( void );
```

```
int PatchMCB( void )
{
 MCB far *lpLastMCB,
 MCB far *lpBeyondLastMCB,
 MCB far *lpTargetMCB,

 PCS_BEGINCRITICAL

 if ( ( lpLastMCB = GetLastMCB() ) == NULL )
  return ( ERR_INTERNAL );

 lpLastMCB->cType = 'M';
 lpLastMCB->wSize -= 1;

 if ( ( lpBeyondLastMCB = GetNextMCB(
lpLastMCB ) ) == NULL )
  return ( ERR_INTERNAL );

 lpBeyondLastMCB->cType = 'M';
 lpBeyondLastMCB->wSize =
MCB_TARGETSEGMENT - SEG(
lpBeyondLastMCB ) - 1;
 lpBeyondLastMCB->wOwner =
MCB_OWNERDOS;

 lpTargetMCB = ( MCB far * )MK_FP(
MCB_TARGETSEGMENT, 0 );
 lpTargetMCB->cType = 'Z';
 lpTargetMCB->wOwner = 0,
 lpTargetMCB->wSize = ( WORD
)MCB_TARGETSEGSIZE - 1,

 return ( ERR_SUCCESS );
}

int SetMemStrategy( int iStatCode )
{
 REG_W InRegs, OutRegs,
 WORD wFlags,

 _fmemset( (NPSTR )&InRegs, 0, sizeof( REG_W ) );

 InRegs.ax = SMD_GETSETALLOCSTRAT |
SMD_SETALLOCSTRAT,
 InRegs.bx = iStatCode,

 wFlags = Intn( &InRegs, &OutRegs, SMD_DOSINT
);

 if ( !( wFlags & GEN_CARRYFLAG ) )
  return ( ERR_SUCCESS );
 else
  return ( ERR_INTERNAL );
}

MCB far *GetFirstMCB( void )
{
 REG_W InRegs, OutRegs;
 WORD wFlags,
 unsigned far *lpListOfLists,

 _fmemset( (NPSTR )&InRegs, 0, sizeof( REG_W ) );

 InRegs.ax = SMD_GETLISTOFLISTS;

 wFlags = Intn( &InRegs, &OutRegs, SMD_DOSINT
);

 if ( !( wFlags & GEN_CARRYFLAG ) )
 {
  lpListOfLists = ( unsigned far * ) MK_FP(
OutRegs.es,
OutRegs.bx - 2 );

  return ( ( MCB far * ) MK_FP( *lpListOfLists, 0 ) );
 }
 else
  return ( NULL );
}

MCB far *GetNextMCB( MCB far *lpCurrMCB )
{
 return ( MK_FP( SEG( lpCurrMCB ) +
lpCurrMCB->wSize + 1, 0 ) );

}

MCB far *GetLastMCB( void )
{
 MCB far *lpLastMCB = GetFirstMCB();

 while ( TRUE )
 {
  if ( lpLastMCB == NULL )
   return ( NULL );

  lpLastMCB = GetNextMCB( lpLastMCB );

  if ( lpLastMCB->cType == 'Z' )
   return ( lpLastMCB );
 }
}


Copr. 1995 Zenith Data Systems Corp.

#include "cs.h"
#include "spawn.h"
#include "sm.h"
#include "tm.h"

BOOL f2MegFlash = FALSE;
static BYTE nCurrVidPalette = 0,
static BYTE nCurrSpeakerState = PON;
static BYTE nCurrRightMouseButton = POFF;
static BYTE fSuspendInProgress = POFF;

BYTE aBrightValues[] =
{
0,
3,
6,
8,
10,
21,
26,
27,
29,
31,
33,
36,
37,
39,
41,
43,
45,
47,
49,
51,
53,
55,
57,
59,
};

BYTE aContrastValues[] =
{
26,
27
28,
29,
30,
31,
32
34,
36,
38,
39,
40,
41,
42,
43
44,
45,
46,
47,
48,
49,
50,
51,
53,
};

int SetContrast( BYTE nContrastIdx )
{
 REG_W InRegs, OutRegs;
 WORD wFlags;

 _fmemset( (NPSTR )&InRegs, 0, sizeof( REG_W ) );

 InRegs.ax = SSS_SARATOGAFUNC;
 InRegs.bx = SSS_ADJUSTCONTRAST;
 InRegs.cx |= aContrastValues[ nContrastIdx ];

#if idefined( NOINT15 )
 wFlags = Intn( &InRegs, &OutRegs,
SSS_SLINTNUM );
#else
 wFlags = 0;
#endif

 if ( !( wFlags & GEN_CARRYFLAG ) )
  return ( ERR_SUCCESS );
 else
  return ( ERR_INTERNAL );
}

int SetBrightness( BYTE nBrightnessIdx )
{
 REG_W InRegs, OutRegs,
 WORD wFlags.

 _fmemset( (NPSTR )&InRegs, 0, sizeof( REG_W ) );

 InRegs.ax = SSS_SARATOGAFUNC;
 InRegs.bx = SSS_ADJUSTBRIGHTNESS;
 InRegs.cx |= aBrightValues[ nBrightnessIdx ];

#if idefined( NOINT15 )
 wFlags = Intn( &InRegs, &OutRegs,
SSS_SLINTNUM );
#else
 wFlags = 0;
#endif

 if ( !( wFlags & GEN_CARRYFLAG ) )
  return ( ERR_SUCCESS );
 else
  return ( ERR_INTERNAL );
}

int SetPowerEnable( BYTE nPowerEnable )
{
 REG_W InRegs, OutRegs.
 WORD wFlags.

 _fmemset( (NPSTR )&InRegs, 0, sizeof( REG_W ) );

 InRegs.ax = SSS_SARATOGAFUNC;
 InRegs.bx = SSS_SETPOWERENABLE;
 InRegs.cx |= ( WORD )nPowerEnable;


#if idefined( NOINT15 )
 wFlags = Intn( &InRegs, &OutRegs,
SSS_SLINTNUM );
#else
 wFlags = 0;
#endif

 if ( !( wFlags & GEN_CARRYFLAG ) )
  return ( ERR_SUCCESS );
 else
  return ( ERR_INTERNAL );
}

int SetDozeTimeout( BYTE nDozeIdx )
{
 REG_W InRegs, OutRegs.
 WORD wFlags.

 _fmemset( (NPSTR )&InRegs, 0, sizeof( REG_W ) );

 InRegs.ax = SSS_SARATOGAFUNC;
 InRegs.bx = SSS_SETDOZETIMEOUT,
 InRegs.cx |= ( WORD )nDozeIdx;

#if idefined( NOINT15 )
 wFlags = Intn( &InRegs, &OutRegs,
SSS_SLINTNUM );
#else
 wFlags = 0;
#endif

 if ( !( wFlags & GEN_CARRYFLAG ) )
  return ( ERR_SUCCESS );
 else
  return ( ERR_INTERNAL );
}

int SetSleepTimeout( BYTE nSleepIdx )
{
 REG_W InRegs, OutRegs;
 WORD wFlags;

 _fmemset( (NPSTR )&InRegs, 0, sizeof( REG_W ) );

 InRegs.ax = SSS_SARATOGAFUNC;
 InRegs.bx = SSS_SETSLEEPTIMEOUT;
 InRegs.cx |= nSleepIdx;

#if idefined( NOINT15 )
 wFlags = Intn( &InRegs, &OutRegs,
SSS_SLINTNUM );
#else
 wFlags = 0;
#endif

 if ( !( wFlags & GEN_CARRYFLAG ) )
  return ( ERR_SUCCESS );
 else
  return ( ERR_INTERNAL );
}

int SetSuspendTimeout( BYTE nSuspendIdx )
{
 REG_W InRegs, OutRegs,
 WORD wFlags.

 _fmemset( (NPSTR )&InRegs, 0, sizeof( REG_W ) );

 InRegs.ax = SSS_SARATOGAFUNC;
 InRegs.bx = SSS_SETSUSPENDTIMEOUT,
 InRegs.cx |= nSuspendIdx;

#if idefined( NOINT15 )
 wFlags = Intn( &InRegs, &OutRegs,
SSS_SLINTNUM );
#else
 wFlags = 0;
#endif

 if ( !( wFlags & GEN_CARRYFLAG ) )
  return ( ERR_SUCCESS );
 else
  return ( ERR_INTERNAL );
}

void Set2MegFlash( BOOL bNew2MegFlash )
{
 f2MegFlash = bNew2MegFlash;
}

BOOL IsFlashSupported( void )
{
 REG_W InRegs, OutRegs.

 _fmemset( (NPSTR )&InRegs, 0, sizeof( InRegs ) );

 InRegs.ax = SSS_SARATOGAFLASH;
 InRegs.ax |= SSS_FLASHAVAILABLE;

#if idefined( FLASHTEST )
 Intn( &InRegs, &OutRegs, SSS_SLINTNUM );
#else
 return ( TRUE );
#endif

 return ( OutRegs.ax ==
SSS_FLASHAVAILRETCODE );
}

int FlashSector( LPSTR aFlashImageBuff, int
lCurrFlashFile )
{
 REG_W InRegs, OutRegs,
 int iFlashSector, iReturn;
 WORD wFlags;
 LONG l20bitEEAdd

 if ( lCurrFlashFile == 0 || aFlashImageBuff ==
NULL )
  return ( ERR_INVALIDPARAM );

 if ( EnableFlashWrite( TRUE ) != ERR_SUCCESS
)
  return ( ERR_INTERNAL );

 _fmemset( &InRegs, 0, sizeof( InRegs ) );

 if ( f2MegFlash )
  iFlashSector = SSS_2MEGBASESECTOR + (
lCurrFlashFile - 1 );
 else
  iFlashSector = SSS_1MEGBASESECTOR + (
lCurrFlashFile - 1 );

 l20bitEEAdd = ( ( LONG )SEG( aFlashImageBuff )
* 16 ) + OFF(
aFlashImageBuff );

 InRegs.ax = MAKEWORD( SSS_FLASHWROTEXT,
HIBYTE(
SSS_SARATOGAFLASH ) );
 InRegs.bx = MAKEWORD( LOBYTE( HIWORD(
l20bitEEAdd ) ),
          LOBYTE( iFlashSector ) );
 InRegs.di = LOWORD( l20bitEEAdd );

#if idefined( FLASHTEST )
 wFlags = Intn( &InRegs, &OutRegs,
SSS_SLINTNUM );
#else
 wFlags = 0;
#endif

 if ( !( wFlags & GEN_CARRYFLAG ) )
  iReturn = SSS_FLASHSUCCESS;
 else
  iReturn = HIBYTE( OutRegs.ax );

 EnableFlashWrite( FALSE );

 return ( iReturn );
}
```

```
int EnableFlashWrite( BOOL fEnable )
{
  REG_W InRegs, OutRegs,
  WORD wFlags;

  fl_chr( &InRegs, 0, sizeof( InRegs ) );

  InRegs.ax = MAKEWORD( LOBYTE( ( fEnable ?
SSS_ENABLEWRITE :
SSS_DISABLEWRITE ) ),
              HIBYTE( SSS_SARATOGAFUNC
) );
  InRegs.bx = SSS_ENABLEDISABLEWRITE;

#if defined( FLASHTEST )
  wFlags = Intx( &InRegs, &OutRegs,
SSS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

int RotatePalette( void )
{
  REG_W InRegs, OutRegs,
  int iCurrVideoMode = GetCurrVidMode(),
  BYTE nNewVidPalette,

  fl_chr( ( NPSTR )&InRegs, 0, sizeof( REG_W ) );

  if ( iCurrVideoMode == SUI_INITIALVIDMODE )
  {
    if ( nCurrVidPalette != SSS_INVVIDPALLETTE )
      nNewVidPalette = SSS_INVVIDPALLETTE;
    else
      nNewVidPalette = SSS_DEFVIDPALLETTE;
  }
  else
  {
    if ( ( nNewVidPalette = nCurrVidPalette + 1 ) >
        SSS_MAXNUMVIDPAL )
      nNewVidPalette = SSS_DEFVIDPALLETTE.
  }

  InRegs.ax = ( WORD )( SSS_VIDEO |
nNewVidPalette );
  InRegs.bx = ( WORD )( SSS_VIDEOPALLETTE );

#if defined( NOINT15 )
  Intx( &InRegs, &OutRegs, SSS_VIDINTNUM );
#else
#endif

  nCurrVidPalette = nNewVidPalette.

  return ( ERR_SUCCESS );
}

int ToggleSpeaker( void )
{
  REG_W InRegs, OutRegs;
  WORD wFlags;
  BYTE nNewSpeakerState;

  fl_chr ( NPSTR )&InRegs, 0, sizeof( REG_W ) );

  if ( nCurrSpeakerState == FON )
    nNewSpeakerState = FOFF.
  else
    nNewSpeakerState = FON;

  InRegs.ax = SSS_SARATOGAFUNC |
nNewSpeakerState;
  InRegs.bx = SSS_ENABLESPEAKER;

#if defined( NOINT15 )
  wFlags = Intx( &InRegs, &OutRegs,
SSS_SLINTNUM );
#else
  wFlags = 0.
#endif

  if ( !( wFlags & GEN_CARRYFLAG ) )
  {
    nCurrSpeakerState = nNewSpeakerState;
    return ( ERR_SUCCESS );
  }
  else
    return ( ERR_INTERNAL );
}

BYTE GetRightMouseStatus( void )
{
  return ( nCurrRightMouseButton );
}

int EnableRightMouseButton( BYTE
nNewRightMouseButton )
{
  REG_W InRegs, OutRegs;
  WORD wFlags;

  fl_chr( ( NPSTR )&InRegs, 0, sizeof( REG_W ) );

  InRegs.ax = SSS_SARATOGAFUNC |
nNewRightMouseButton;
  InRegs.bx = SSS_ENABLERIGHTMOUSE;

#if defined( NOINT15 )
  wFlags = Intx( &InRegs, &OutRegs,
SSS_SLINTNUM );
#else
  wFlags = 0;
#endif

  if ( !( wFlags & GEN_CARRYFLAG ) )
  {
    nCurrRightMouseButton =
nNewRightMouseButton;
    return ( ERR_SUCCESS );
  }
  else
    return ( ERR_INTERNAL );
}

int SetTowerIcon( BYTE nTowerStatus, BYTE
nWavesStatus )
{
  REG_W InRegs, OutRegs,
  WORD wFlags;

  fl_chr( ( NPSTR )&InRegs, 0, sizeof( REG_W ) );

  InRegs.ax = SSS_SARATOGAFUNC |
nTowerStatus;
  InRegs.bx = SSS_TOWERWAVEICON;
  InRegs.cx = ( WORD )nWavesStatus.

#if defined( NOINT15 )
  wFlags = Intx( &InRegs, &OutRegs,
SSS_SLINTNUM );
#else
  wFlags = 0,
#endif

  if ( !( wFlags & GEN_CARRYFLAG ) )
    return ( ERR_SUCCESS );
  else
    return ( ERR_INTERNAL );
}

int GoSleep( void )
{
  REG_W InRegs, OutRegs;
  WORD wFlags;

  fl_chr( ( NPSTR )&InRegs, 0, sizeof( REG_W ) );

  InRegs.ax = SSS_SARATOGAFUNC;
  InRegs.bx = SSS_GOTOSLEEP;

#if defined( NOINT15 )
  wFlags = Intx( &InRegs, &OutRegs,
SSS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

int DoSuspend( BOOL fSaveEEROMData )
{
  REG_W InRegs, OutRegs;

  fl_chr( ( NPSTR )&InRegs, 0, sizeof( REG_W ) );

  if ( fSaveEEROMData )
    SetEEUIData();

  InRegs.ax = SSS_SARATOGAFUNC;
  InRegs.bx = SSS_GOTOSUSPEND;

#if defined( NOINT15 )
  Intx( &InRegs, &OutRegs, SSS_SLINTNUM );
#else
#endif

  return ( ERR_INTERNAL );
}

int SetSuspendFlagPointer( void )
{
  REG_W InRegs, OutRegs;
  WORD wFlags;

  fl_chr( ( NPSTR )&InRegs, 0, sizeof( REG_W ) );

  InRegs.ax = SSS_SARATOGAFUNC;
  InRegs.bx = SSS_SUSPENDFLAGPTR;
  InRegs.cx = SEG( &fSuspendInProgress );
  InRegs.dx = OFF( &fSuspendInProgress );

#if defined( NOINT15 )
  wFlags = Intx( &InRegs, &OutRegs,
SSS_SLINTNUM );
#else
  wFlags = 0;
#endif

  if ( !( wFlags & GEN_CARRYFLAG ) )
  {
    SetSuspendFlag( FOFF );
    return ( ERR_SUCCESS );
  }
  else
    return ( ERR_INTERNAL );
}

void SetSuspendFlag( BOOL fStatus )
{
  PCS_BEGINCRITICAL;
  fSuspendInProgress = LOBYTE( fStatus );
  PCS_ENDCRITICAL;
}

BOOL GetSuspendFlag( void )
{
  BOOL fReturn;

  PCS_BEGINCRITICAL;
  fReturn = fSuspendInProgress;
  PCS_ENDCRITICAL;

  return ( fReturn );
}

int GetSystemResumeBit( void )
{
  REG_W InRegs, OutRegs;
  WORD wFlags;

  fl_chr( ( NPSTR )&InRegs, 0, sizeof( REG_W ) );

  InRegs.ax = SSS_SARATOGAFUNC;
  InRegs.bx = SSS_GETSYSRESUMEBIT;

#if defined( NOINT15 )
  wFlags = Intx( &InRegs, &OutRegs,
SSS_SLINTNUM );
#else
  wFlags = 0;
#endif

  if ( !( wFlags & GEN_CARRYFLAG ) )
    return ( OutRegs.ax & 0x00FF );
  else
    return ( ERR_INTERNAL );
}

int ClearSystemResumeBit( void )
{
  REG_W InRegs, OutRegs;
  WORD wFlags;

  fl_chr( ( NPSTR )&InRegs, 0, sizeof( REG_W ) );

  InRegs.ax = SSS_SARATOGAFUNC;
  InRegs.bx = SSS_CLEARSYSRESUMEBIT;

#if defined( NOINT15 )
  wFlags = Intx( &InRegs, &OutRegs,
SSS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

int SetWaitingIcon( BYTE nWaitingIconStatus, BYTE
fBusyCursor )
{
  REG_W InRegs, OutRegs;
  WORD wFlags;

  fl_chr( ( NPSTR )&InRegs, 0, sizeof( REG_W ) );

  InRegs.ax = SSS_SARATOGAFUNC;
  InRegs.bx = SSS_WAITINGICON;
  InRegs.ax |= nWaitingIconStatus.

#if defined( NOINT15 )
  wFlags = Intx( &InRegs, &OutRegs,
SSS_SLINTNUM );
#else
  wFlags = 0,
#endif

  if ( nWaitingIconStatus ==
SSS_WAITINGICONOFF )
  {
    if ( fBusyCursor )
      EnableBusyCursor( SUI_BUSYCURSOROFF );

    GetHotIcon();
  }
  else
  {
    if ( fBusyCursor )
      EnableBusyCursor( SUI_BUSYCURSORON );

  }

  if ( !( wFlags & GEN_CARRYFLAG ) )
    return ( ERR_SUCCESS );
  else
    return ( ERR_INTERNAL );
}

int EnableKbdAfterBoot( void )
{
  REG_W InRegs, OutRegs,
  WORD wFlags,

  fl_chr( ( NPSTR )&InRegs, 0, sizeof( REG_W ) );

  InRegs.ax = SSS_SARATOGAFUNC;
  InRegs.bx = SSS_ENABLEKBD;

#if defined( NOINT15 )
  wFlags = Intx( &InRegs, &OutRegs,
SSS_SLINTNUM ),
#else
  wFlags = 0;
#endif

  if ( !( wFlags & GEN_CARRYFLAG ) )
    return ( ERR_SUCCESS );
  else
    return ( ERR_INTERNAL );
}

LONG GetBatteryInfo( void )
{
  REG_W InRegs, OutRegs,
  WORD wFlags;

  fl_chr( ( NPSTR )&InRegs, 0, sizeof( REG_W ) );

  InRegs.ax = SSS_SARATOGAFUNC;
  InRegs.bx = SSS_GETBATTERYINFO;

#if defined( NOINT15 )
  wFlags = Intx( &InRegs, &OutRegs,
SSS_SLINTNUM );
#else
  wFlags = 0,
#endif

  if ( !( wFlags & GEN_CARRYFLAG ) )
#if defined( NOINT15 )
    return ( MAKELONG( OutRegs.ax, OutRegs.bx )
);
#else
    return ( SSS_NOINT15BATTERYINFO );
#endif
  else
    return ( SSS_GETBATTERYINFOERROR );

}

WORD GetSizeOfExtendedMem( void )
{
  BYTE nExtMemHigh, nExtMemLow,

  PCS_BEGINCRITICAL
```

```
  outp( SSS_CMOSPORT,
SSS_CMOSREADHIGHBYTE );
  nExtMemHigh = inportb(
SSS_CMOSEXTENDEDMEM );
  outp( SSS_CMOSPORT,
SSS_CMOSREADLOWBYTE )
  nExtMemLow = inportb(
SSS_CMOSEXTENDEDMEM );

  PCS_ENDCRITICAL

  return ( MAKEWORD( nExtMemLow,
nExtMemHigh ) );
}

int GetBIOSVersion( void )
{
  REG_W InRegs, OutRegs;
  WORD wFlags;

  fil_char( ( NPSTR )&InRegs, 0, sizeof( REG_W ) );

  InRegs.ax = SSS_SARATOGAFUNC;
  InRegs.bx = SSS_GETBIOSVERSION;

#if !defined( NOINT15 )
  wFlags = intm( &InRegs, &OutRegs,
SSS_SLINTNUM );
#else
  wFlags = 0;
#endif

  if ( !( wFlags & GEN_CARRYFLAG ) )
#if !defined( NOINT15 )
    return ( OutRegs.ax );
#else
    return ( 0 );
#endif
  else
    return ( 0 );
}
Copr 1995 Zenith Data Systems Corp.


#include "sr.h"
#include "sw.h"
#include "spsum.h"
#include "sm.h"

#define SMD_MAXGEARIMAGES 6

#if defined( _MSC_VER )
#pragma warning( disable : 4756 )
#endif

static char sGearImages[] = { "|/-\\" };

static BYTE nClockReenterCount = 0;
static WORD wLastKey;
static BOOL fDispatchActive = FALSE;
static BOOL fReentrInstalled = FALSE;
static int aEventStack[ SMD_EVENTSTACKLIMIT ];
static int iEventStackPtr =
SMD_EVENTSTACKLIMIT - 1;
static int iTempThreadIdx = -1;


EVENT EventQueue[ SMD_MAXTHREADS ];

int AddThread( int Idx, NEARPROC lpThread,
APIFUNC
aAPIFuncTable[],
        THREADTYPEID ThreadTypeId, BOOL
fReentrant, LONG
lTimeLimit,
        int iRetryLimit )
{
  if ( Idx >= SMD_MAXTHREADS )
    return ( ERR_INTERNAL );

  PCS_BEGINCRITICAL
  EventQueue[ Idx ].lpThread = lpThread;
  EventQueue[ Idx ].aAPIFuncTable =
aAPIFuncTable;
  EventQueue[ Idx ].ThreadTypeId = ThreadTypeId;
  EventQueue[ Idx ].lTimeLimit = lTimeLimit;
  EventQueue[ Idx ].lTimeCurrent = 0L;
  EventQueue[ Idx ].iRetryLimit = iRetryLimit;
  EventQueue[ Idx ].iInitRetryLimit = iRetryLimit;
  EventQueue[ Idx ].nReenterCount = 0;
  EventQueue[ Idx ].bReentrant = fReentrant;
  PCS_ENDCRITICAL

  return ( ERR_SUCCESS );
}

BYTE IsThreadActive( int Idx )
{
  BYTE fThreadStatus;
  NEARPROC lpThread;

  if ( Idx >= SMD_MAXTHREADS )
    return ( FALSE );

  lpThread = EventQueue[ Idx ].lpThread;

  PCS_BEGINCRITICAL

  fThreadStatus = ( lpThread != NULL && lpThread
!= ( NEARPROC
)SMD_THREADACTIVE );

  PCS_ENDCRITICAL

  return ( fThreadStatus );
}

void ResetTime( int Idx )
{
  if ( Idx >= SMD_MAXTHREADS )
    return;

  EventQueue[ Idx ].lTimeCurrent = 0;
}

int SetRetryLimit( int Idx, int iNewRetryLimit )
{
  if ( Idx >= SMD_MAXTHREADS )
    return ( ERR_INTERNAL );

  PCS_BEGINCRITICAL
  EventQueue[ Idx ].iRetryLimit = iNewRetryLimit;
  EventQueue[ Idx ].lTimeCurrent = 0;
  PCS_ENDCRITICAL

  return ( ERR_SUCCESS );
}

BYTE GetRetryLimit( int Idx )
{
  int iReturn;

  if ( Idx >= SMD_MAXTHREADS )
    return ( 0 );

  if ( ( iReturn = EventQueue[ Idx ].iRetryLimit ) < 0
)
    iReturn = 0;

  return ( iReturn );
}

BYTE GetInitRetryLimit( int Idx )
{
  int iReturn;

  if ( Idx >= SMD_MAXTHREADS )
    return ( 0 );

  if ( ( iReturn = EventQueue[ Idx ].iInitRetryLimit ) <
0 )
    iReturn = 0;

  return ( iReturn );
}

int ResetRetryLimit( int Idx )
{
  if ( Idx >= SMD_MAXTHREADS )
    return ( ERR_INTERNAL );

  PCS_BEGINCRITICAL
  EventQueue[ Idx ].iRetryLimit = EventQueue[ Idx
].iInitRetryLimit;
  EventQueue[ Idx ].lTimeCurrent = 0;
  PCS_ENDCRITICAL

  return ( ERR_SUCCESS );
}

int SetTimeLimit( int Idx, LONG lNewTimeLimit )
{
  if ( Idx >= SMD_MAXTHREADS )
    return ( ERR_INTERNAL );


  PCS_BEGINCRITICAL
  EventQueue[ Idx ].lTimeLimit = lNewTimeLimit;
  PCS_ENDCRITICAL

  return ( ERR_SUCCESS );
}

THREADTYPEID GetThreadType( int Idx )
{
  if ( Idx >= SMD_MAXTHREADS )
    return ( ERR_INTERNAL );

  return ( EventQueue[ Idx ].ThreadTypeId );
}

NEARPROC GetThreadAddress( int Idx )
{
  if ( Idx >= SMD_MAXTHREADS )
    return ( ( NEARPROC )NULL );

  return ( EventQueue[ Idx ].lpThread );
}

int DelThread( int Idx )
{
  int iReturn = 0;

  if ( Idx >= SMD_MAXTHREADS || Idx < 0 )
  {
    TRACE( "ERROR: Invalid thread ID passed to
DelThread()" );
    return ( ERR_INTERNAL );
  }

  PCS_BEGINCRITICAL
  EventQueue[ Idx ].lpThread = NULL;
  PCS_ENDCRITICAL

#if !defined( PROD )
  sprintf( szTempStr, "NOTICE: Temp thread
deallocated - %d\r",
Idx );
  TRACE( szTempStr );
#endif

  return ( iReturn );
}

int InitDispatcher( void )
{
  iTempThreadIdx = GetTempEventNum();

  if ( iTempThreadIdx < 0 )
    return ( ERR_INTERNAL );

  fil_char( ( NPSTR )EventQueue, 0, sizeof(
EventQueue ) );

  AddThread( iTempThreadIdx, InstallRecv, NULL,
SMD_ONETIME,
FALSE, 0L, POLLFREQ,
        0 );

  InitVIDTrapRec();
  add_trap( GetVIDTrapRec() );

  InitPNDTrapRec();
  add_trap( GetPNDTrapRec() );

  InitSCSTrapRec();
  add_trap( GetSCSTrapRec() );

  InitPRXTrapRec();
  add_trap( GetPRXTrapRec() );

  AddThread( SM_PNDEVENTNUM, NULL,
GetPNDFuncTable(),
SMD_ONDEMAND, FALSE,
        SM_PNDPOLLFREQ, 0 );
  AddThread( SM_SUBEVENTNUM, NULL,
GetSUBFuncTable(),
SMD_ONDEMAND, FALSE,
        SM_SUBPOLLFREQ, 0 );
  AddThread( SM_SCSEVENTNUM, NULL,
GetSCSFuncTable(),
SMD_ONDEMAND, TRUE,
        SM_SCSPOLLFREQ, 0 );
  AddThread( SM_PRXEVENTNUM, NULL,
GetPRXFuncTable(),
SMD_ONDEMAND, FALSE,
        SM_PRXPOLLFREQ, 0 );
}

int ShutDownDispatcher( void )
{
  RestoreOldKbdVec();
  return ( 0 );
}

void InstallRecv( void )
{
  DelThread( iTempThreadIdx );

  AddThread( PND_EVENTNUM, CheckPenDriver,
NULL, SMD_POLLED,
FALSE,
        PND_POLLFREQ, 0 );
  AddThread( PRX_EVENTNUM, CheckSystem,
NULL, SMD_POLLED,
        FALSE, PRX_POLLFREQ, 0 );

  InitSUICallRec();
  InitSCSCallRec();

  SetSuspendFlagPointer();
  add_trap( GetSUIMouseTrapRec() );

  fReentInstalled = TRUE;
}


void Dispatch( THREADTYPEID ActiveThreadId, int
iEventThreadIdx )
{
  int iThreadIdx;
  BOOL fInstEntry = FALSE;
  EVENT *ev;
  NEARPROC lpOriginalThread = NULL;

  struct REGW Regs;

  if ( iEventThreadIdx >= SMD_MAXTHREADS )
    goto Exit;

  SetDispatchActive( TRUE );

  ev = &EventQueue[ iEventThreadIdx ];

  if ( ActiveThreadId == SMD_ONDEMAND )
  {
    if ( ev->bReentrant || ev->nReenterCount == 0 )
    {
      PCS_BEGINCRITICAL
      ++ev->nReenterCount;
      PCS_ENDCRITICAL

      if ( ev->aAPIFuncTable != NULL )
        CallAPIFunction( ev->aAPIFuncTable );
      else
        TRACE( "ERROR: Function table is NULL in
dispatcher" );

      PCS_BEGINCRITICAL
      --ev->nReenterCount;
      PCS_ENDCRITICAL
    }
    else
    {
      GetForegroundRegs( &Regs );
      Regs.ax = ( WORD )ERR_INTERNAL;
      SetForegroundRegs( &Regs );
    }

    goto Exit;
  }


  for ( iThreadIdx = 0; iThreadIdx <
SMD_MAXTHREADS; ++iThreadIdx
)
  {
    ev = &EventQueue[ iThreadIdx ];

    if ( ev->lpThread != NULL )
    {
      if ( ev->ThreadTypeId == ActiveThreadId ||
          ActiveThreadId ==
SMD_ALLTHREADTYPES )
      {

        if ( ev->bReentrant || ev->nReenterCount == 0
)
        {
          PCS_BEGINCRITICAL
          ++ev->nReenterCount;
          PCS_ENDCRITICAL
        }
        else
        {
#if !defined( PROD )
          sprintf( szTempStr, "NOTICE: Thread #%d
reentered, but
returned\r", iThreadIdx );
          TRACE( szTempStr );
#endif
          goto Exit;
        }

        switch ( ev->ThreadTypeId )
        {
          case SMD_ONETIME:
            if ( ev->lTimeCurrent >= 0 )
            {
              if ( ++ev->lTimeCurrent >= ev->lTimeLimit
}
```

```
        {
          ov->lTimeCurrent = -1;
          TRACE( "NOTICE: ONETIME thread
expired" );
        }
        else
          fNextEntry = TRUE;
      }
      else
        fNextEntry = TRUE;
      break;

    case SMD_MANYTIMES:
      if ( ov->lTimeCurrent >= 0 )
      {
        if ( ++ov->lTimeCurrent >= ov->lTimeLimit
)
        {
          if ( --ov->lRetryLimit == 0 )
          {
            ov->lTimeCurrent = -1;
            TRACE( "NOTICE: MANYTIMES
thread expired" );
          }
          else
            ov->lTimeCurrent = 0;
        }
        else
          fNextEntry = TRUE;
      }
      else
        fNextEntry = TRUE;
      break;

    case SMD_POLLED:
      if ( ++ov->lTimeCurrent >= ov->lTimeLimit )
        ov->lTimeCurrent = 0;
      else
        fNextEntry = TRUE;
      break;

    default:
      fNextEntry = TRUE;
      break;
    }
  }
  else
    fNextEntry = TRUE;

  if ( fNextEntry )
  {
    fNextEntry = FALSE;
    PCS_BEGINCRITICAL
    --ov->nReenterCount;
    PCS_ENDCRITICAL
  }
  else
  {
    if ( ov->lpThread != NULL && ov->lpThread != ( NEARPROC
)SMD_THREADACTIVE )
    {
      lpOriginalThread = ov->lpThread;
      ( *ov->lpThread )();

      PCS_BEGINCRITICAL
      if ( lpOriginalThread == ov->lpThread &&
        ( WORD )( ov->nReenterCount - 1 ) <
        ( WORD )ov->nReenterCount )
        --ov->nReenterCount;
      PCS_ENDCRITICAL
    }
  }
 }

}

Exit:
  SetDispatchActive( FALSE );
}

WORD TrapService( struct trap_rec *CurTrapRec )
{
  REG_W Regs;
  MREG MinArgs;
  WORD wReturn = 0;

  switch ( CurTrapRec->tr_int )
  {
    case SMI_SUIINTNUM:
      Dispatch( SMD_ONDEMAND,
SMI_SUIEVENTNUM );
      break;

    case SMI_SCSINTNUM:
      Dispatch( SMD_ONDEMAND,
SMI_SCSEVENTNUM );
      break;

    case SMI_PNDINTNUM:
      Dispatch( SMD_ONDEMAND,
SMI_PNDEVENTNUM );
      break;

    case SMI_FRXINTNUM:
      Dispatch( SMD_ONDEMAND,
SMI_FRXEVENTNUM );
      break;

    case SSS_VIDINTNUM:
      VIDTrapService();
      return ( ( WORD )CurTrapRec );
      break;

    case PND_INTNUM:
      GetForegroundRegs( &Regs );

      if ( Regs.ax == PND_SETEVENTHANDLER &&
!GetPNDActiveStatus() )
      {
        MinArgs.ax = 0x000C;
        MinArgs.es = Regs.es;
        MinArgs.dx = Regs.dx;
        MinArgs.ss = Regs.ss;

        mouse( &MinArgs, &MEventOutArgs );
      }
      else
        return ( ( WORD )CurTrapRec );

    default:
      return ( ( WORD )CurTrapRec );
  }
  return ( wReturn );
}

void FCallService( WORD wAX )
{
  switch ( PopEventNum() )
  {
    case SMI_SUIEVENTNUM:
      Dispatch( SMD_ONDEMAND,
SMI_SUIEVENTNUM );
      break;

    case SMI_SCSEVENTNUM:
      Dispatch( SMD_ONDEMAND,
SMI_SCSEVENTNUM );
      break;

  }
}

void ClockTick( void )
{

  add_inc_event( SMD_DISPATFREQ );

    Dispatch( SMD_ALLTHREADTYPES, 0 );

}

void DecClockReCount( void )
{
  PCS_BEGINCRITICAL;
  --nClockReenterCount;
  PCS_ENDCRITICAL;
}

#if !defined( NDEBUG )
void KbdService( WORD wHotKey )
{

  wLastKey = wHotKey;

}

WORD GetLastKey( void )
{
  WORD wTempLastKey = wLastKey;
  wLastKey = 0;

  return ( wTempLastKey );
}
#endif

void SetDispatchActive( BOOL bNewDispatchActive
)
{
  PCS_BEGINCRITICAL
  fDispatchActive = bNewDispatchActive;
  PCS_ENDCRITICAL
}

BOOL GetDispatchActive( void )
{
  BOOL fCurrentDisActive;

  PCS_BEGINCRITICAL
  fCurrentDisActive = fDispatchActive;
  PCS_ENDCRITICAL

  return ( fCurrentDisActive );
}

void CrankGear( BYTE *bGearIdx, char *szLabel )
{
  BYTE bNewGearIdx = *bGearIdx;
  if ( ++bNewGearIdx == SMD_MAXGEARIMAGES )
    bNewGearIdx = 0;

  ++ool_x;

  *bGearIdx = bNewGearIdx;
}

void PushEventNum( int iEventNum )
{
  aEventStack[ iEventStackPtr ] = iEventNum;
  iEventStackPtr = iEventStackPtr > 0 ?
iEventStackPtr - 1 :
iEventStackPtr;
}

int PopEventNum( void )
{
  int iReturn;

  PCS_BEGINCRITICAL
  iEventStackPtr = iEventStackPtr <
SMD_EVENTSTACKLIMIT - 1 ?
iEventStackPtr + 1 : iEventStackPtr;
  iReturn = aEventStack[ iEventStackPtr ];
  PCS_ENDCRITICAL

  return ( iReturn );
}

int GetTempEventNum( void )
{
  register int iThreadIdx;
  int iReturn = ERR_INTERNAL;

  PCS_BEGINCRITICAL

  for ( iThreadIdx = SMD_REUSETHREADS - 1;
iThreadIdx <
SMD_MAXTHREADS;
      ++iThreadIdx )
  {
    if ( EventQueue[ iThreadIdx ].lpThread == NULL )

    {
#if !defined( PROD )
      sprintf( szTempStr, "NOTICE: Temp thread
allocated - %d\n",
iThreadIdx );
      TRACE( szTempStr );
#endif
      iReturn = iThreadIdx;
      EventQueue[ iThreadIdx ].lpThread = (
NEARPROC
)SMD_THREADACTIVE;
      break;
    }
  }

  PCS_ENDCRITICAL

#if !defined( PROD )
  if ( iReturn == ERR_INTERNAL )
    TRACE( "ERROR: Out of temporary threads" );
#endif

  return ( iReturn );
}

#if defined( _MSC_VER )
#pragma warning( default : 4704 )
#endif
Copr. 1995 Zenith Data Systems Corp.

#include "sr.h"
#include "ui.h"
#include "sysum.h"
#include "k3.h"
#include "frame.h"
#include "sm.h"

#if defined( _MSC_VER )
#pragma warning( disable : 4704 )
#endif

THREADTYPEID ActiveThreadType =
SMD_NOTHREAD;

char      szSMSignature[] =
SIG_SMSIGNATURE;
char      szSMVersionName[] =
STR_SMVERSIONNAME;
char      szSMVersionNum[] =
STR_SMVERSIONNUM;
char      szSMModuleName[] =
STR_SMMODULENAME;
char      szSUIExecName[] = SUI_EXECNAME;
char      szSCSAbortComm[] =
SMI_SCSABORTCOMM;
char      szTempStr[ GEN_MAXLENTEMPSTR ];
char      szTempMsgStr[
GEN_MAXLENTEMPSTR * 2 ];
char      szNullStr[] = "\0";
SCANCODE    aUIHotkey1Def[] =
SUI_UIHOTKEY1DEF;
char      szPassword[ SUI_MAXLENPASSWORD
+ 1 ];
char      cRLINetNum = 0;
char      fEEPROMInited = FALSE;
WORD       wScreenCode = SUI_NOSCREEN;
WORD       wOldScreenCode =
SUI_NOSCREEN;
MREG       MEventOutArgs;
FARCALLENTRY lpfnFarCallEntry = NULL;
SUICB      lpfnSUICallBack = NULL;
UICONFIGDATA UIConfigData;
LISTBOXENTRY ListBoxEntry;
MSGBOXBUFF   MsgBoxBuff[
SMI_SUMAXMSGBOXLINES ];
SUPPHEADER   SetHead;

BOOL fConnectRequested = FALSE;

char GetEEPROMInited( void )
{
  return ( fEEPROMInited );
}

void InitUIConfigData( void )
{
  if ( GetEEUIData( &UIConfigData ) ==
ERR_SUCCESS )
  {
    if ( UIConfigData.cMajorVersionNum ==
GEN_SUMAJORVERSIONNUM
&&
       UIConfigData.cMinorVersionNum ==
GEN_SUMINORVERSIONNUM )
    {
      if ( ( ( int )UIConfigData.wXLowerPenCalib -
         ( int )UIConfigData.wXUpperPenCalib ) >=
200 )
      {
        if ( UIConfigData.wXUpperPenCalib ==
PND_XUPPERPENCALIB
&&
          UIConfigData.wYUpperPenCalib ==
PND_YUPPERPENCALIB
&&
          UIConfigData.wXLowerPenCalib ==
PND_XLOWERPENCALIB
&&
          UIConfigData.wYLowerPenCalib ==
PND_YLOWERPENCALIB )
          InitEEPROM();
      }
      else
        InitEEPROM();

    }
    else
      InitEEPROM();
  }
  else
    InitEEPROM();

  fill_char( &MEventOutArgs, 0, sizeof ( MREG ) );
  lpfnFarCallEntry = MK_FP( _ocode, _fcall_entry );
}

void InitEEPROM( void )
{
  TRACE( "ERROR: Invalid values or unable to read
from EEPROM\n"
);

  fill_char( &UIConfigData, 0, sizeof ( UICONFIGDATA
) );

  UIConfigData.wBuffLen       = sizeof (
UICONFIGDATA );
```

```
  UIConfigData.nMajorVersionNum =
GEN_SWMAJORVERSIONNUM;
  UIConfigData.nMinorVersionNum =
GEN_SWMINORVERSIONNUM;
  UIConfigData.bConnectType    =
SUI_NETWORKCONNECT;
  UIConfigData.nDomainID       = PRX_DOMAINS;

  UIConfigData.nContrastIdx    =
SHC_DEFCONTRASTIDX;
  UIConfigData.nBrightnessIdx  =
SHC_DEFBRIGHTNESSIDX;

  UIConfigData.nSleepTimeIdx   =
SSS_SLEEPDISABLED;
  UIConfigData.bAutoShutoff    = FALSE;

  UIConfigData.nUILanguage     =
SUI_UIUSENGLISH;
  UIConfigData.nFrameType      =
PRX_FRAME8023;

  UIConfigData.nLastOSKScreen     =
SUI_BIGALPHA;
  UIConfigData.nLastOSKDlgScreen  =
SUI_BIGALPHA;
  UIConfigData.nLastSetupDlgScreen =
SUI_HOSTSELECTION;

  UIConfigData.xPosLastOSKScreen  =
SUI_XULBIGALPHA;
  UIConfigData.yPosLastOSKScreen  =
SUI_YULBIGALPHA;

  mem_set( sUIHotIconIDef,
UIConfigData.szUIHotIcon1,
SUI_MAXLENDEFHOTICON );

  TRACE( "NOTICE: Using pen calibration values
set to zero.\r" );

  UIConfigData.wXUpperPenCalib =
PND_XUPPERPENCALIB;
  UIConfigData.wYUpperPenCalib =
PND_YUPPERPENCALIB;
  UIConfigData.wXLowerPenCalib =
PND_XLOWERPENCALIB;
  UIConfigData.wYLowerPenCalib =
PND_YLOWERPENCALIB;

  fEEPROMdated = TRUE;

  SetEEUIData();

  SetContrast( UIConfigData.nContrastIdx );
  SetBrightness( UIConfigData.nBrightnessIdx );
}

void InitSUI( void )
{
  SetDomainWarning( FALSE );
  SetSecurityWarning( FALSE );
}

void InitServices( BYTE nInitType )
{
  if ( nInitType == SSS_DRIVERSLOADING )
  {
    TRACE( "NOTICE: Power management disabled
for driver load
sequence.\r" );
    SetPowerEnable( SSS_POWERMANDISABLED
);
  }
  else if ( nInitType == SSS_SUILOADING )
  {
    if ( SetSleepTimeout(
UIConfigData.nSleepTimeIdx ) ==
ERR_SUCCESS )
    {
      if ( UIConfigData.nSleepTimeIdx ==
SSS_SLEEPDISABLED )
      {
        TRACE( "NOTICE: Power management now
disabled, DOZE
disabled\r" );
        SetPowerEnable(
SSS_POWERMANDISABLED );
        SetDozeTimeout( SSS_DOZEDISABLED );
      }
      else
      {
        TRACE( "NOTICE: Power management now
enabled, DOZE
disabled\r" );
        SetPowerEnable(
SSS_POWERMANENABLED );
        SetDozeTimeout( SSS_DOZEDISABLED );
```

```
      }

      if ( UIConfigData.bAutoShutoff )
      {
        TRACE( "NOTICE: Suspend after 60 minutes
enabled\r" );
        SetSuspendTimeout( SSS_SUSPEND60MIN
);
      }
      else
      {
        TRACE( "NOTICE: Suspend disabled\r" );
        SetSuspendTimeout(
SSS_SUSPENDDISABLED );
      }
    }
  }
}

int GetEEMouseConfig( void )
{
  REG_W InRegs, OutRegs;
  PENCALIB pc;
  WORD wFlags;

  fl_clr( &InRegs, 0, sizeof ( REG_W ) );
  f_clr( &pc, 0, sizeof ( PENCALIB ) );

  InRegs.ax = SSS_SARATOGAFUNC;
  InRegs.bx = SSS_EEPROMTOMEMORY;
  InRegs.cx = SSS_LENMOUSECFGDATA;
  InRegs.dx = PND_OFFCALIB;

  InRegs.es = SEG( &pc );
  InRegs.di = OFF( &pc );

#if !defined( NOINT15 )
  wFlags = Intx( &InRegs, &OutRegs,
SSS_SLINTNUM );
#else
  wFlags = 0;
#endif

  if ( !( wFlags & GEN_CARRYFLAG ) )
  {
    UIConfigData.wXUpperPenCalib =
pc.wXUpperPenCalib;
    UIConfigData.wYUpperPenCalib =
pc.wYUpperPenCalib;
    UIConfigData.wXLowerPenCalib =
pc.wXLowerPenCalib;
    UIConfigData.wYLowerPenCalib =
pc.wYLowerPenCalib;

    return ( ERR_SUCCESS );
  }
  else
    return ( ERR_INTERNAL );
}

int SetEEMouseConfig( PENCALIB *pc )
{
  UIConfigData.wXUpperPenCalib =
pc->wXUpperPenCalib;
  UIConfigData.wYUpperPenCalib =
pc->wYUpperPenCalib;
  UIConfigData.wXLowerPenCalib =
pc->wXLowerPenCalib;
  UIConfigData.wYLowerPenCalib =
pc->wYLowerPenCalib;

  return ( SetEEUIData() );
}

int SetEEUIData( void )
{
  REG_W InRegs, OutRegs;
  WORD wFlags;
  UICONFIGDATA OldUIConfigData;
  int iReturn = ERR_SUCCESS;

  fl_clr( &OldUIConfigData, 0, sizeof (
UICONFIGDATA ) );

  if ( GetEEUIData( &OldUIConfigData ) ==
ERR_SUCCESS )
  {
    if ( mem_cmp( ( NPSTR )&OldUIConfigData, (
NPSTR
)&UIConfigData,
        sizeof( UICONFIGDATA ) ) != sizeof(
UICONFIGDATA ) )
    {
      fl_clr( &InRegs, 0, sizeof ( REG_W ) );

      InRegs.ax = SSS_SARATOGAFUNC;
      InRegs.bx = SSS_MEMORYTOEEPROM;
```

```
      InRegs.cx = sizeof ( UICONFIGDATA );
      InRegs.dx = SSS_OFFUICFGDATA;
      InRegs.es = SEG( &UIConfigData );
      InRegs.di = OFF( &UIConfigData );

#if !defined( NOINT15 )
      PCS_BEGINCRITICAL
      wFlags = Intx( &InRegs, &OutRegs,
SSS_SLINTNUM );
      PCS_ENDCRITICAL
#else
      wFlags = 0;
#endif
      if ( !( wFlags & GEN_CARRYFLAG ) )
        iReturn = ERR_SUCCESS;
      else
        iReturn = ERR_INTERNAL;
    }
  }
  else
    iReturn = ERR_INTERNAL;

#if !defined( PROD )
  if ( iReturn == ERR_INTERNAL )
    TRACE( "ERROR: SetEEUIData() error returned
from extended
BIOS call to save EEPROM data\r" );
#endif

  return ( iReturn );
}

int GetEEUIData( UICONFIGDATA
*CurrUIConfigData )
{
  REG_W InRegs, OutRegs;
  WORD wFlags;
  UICONFIGDATA TempUIConfigData;

  fl_clr( &InRegs, 0, sizeof ( REG_W ) );

  InRegs.ax = SSS_SARATOGAFUNC;
  InRegs.bx = SSS_EEPROMTOMEMORY;
  InRegs.cx = sizeof ( UICONFIGDATA );
  InRegs.dx = SSS_OFFUICFGDATA;
  InRegs.es = SEG( &TempUIConfigData );
  InRegs.di = OFF( &TempUIConfigData );

#if !defined( NOINT15 )
  PCS_BEGINCRITICAL
  wFlags = Intx( &InRegs, &OutRegs,
SSS_SLINTNUM );
  PCS_ENDCRITICAL
#else
  wFlags = 0;
#endif

  if ( !( wFlags & GEN_CARRYFLAG ) )
  {
    *CurrUIConfigData = TempUIConfigData;

    return ( ERR_SUCCESS );
  }
  else
    return ( ERR_INTERNAL );
}

int ClearEEPROM( void )
{
  REG_W InRegs, OutRegs;
  WORD wFlags;
  UICONFIGDATA UINullData;

  fl_clr( &InRegs, 0, sizeof ( InRegs ) );
  fl_clr( &UINullData, 0, sizeof ( UINullData ) );

  InRegs.ax = SSS_SARATOGAFUNC;
  InRegs.bx = SSS_MEMORYTOEEPROM;
  InRegs.cx = sizeof ( UICONFIGDATA );
  InRegs.dx = SSS_OFFUICFGDATA;
  InRegs.es = SEG( &UINullData );
  InRegs.di = OFF( &UINullData );

#if !defined( FLASHTEST )
  wFlags = Intx( &InRegs, &OutRegs,
SSS_SLINTNUM );
#else
  wFlags = 0;
#endif

  if ( !( wFlags & GEN_CARRYFLAG ) )
    return ( ERR_SUCCESS );
  else
    return ( ERR_INTERNAL );
}

#if defined( _MSC_VER )
#pragma warning( default : 4704 )
#endif
```

```
Copr. 1995 Zenith Data Systems Corp.

#include "sr.h"
#include "spawn.h"
#include "h2.h"
#include "sio.h"
#include "sml.h"

#if defined( _MSC_VER )
#pragma warning( disable : 4704 )
#endif

HOSTLISTENTRIES HostListEntries = { 0, 0 };
static HOSTLISTENTRIES BroadcastHLEntries = {
0, 0 };
static int          iHLStatus = SHR_BLANK;
static int          iHLThreadId = -1;
static int          iHostFetchThreadIdx;
static int          iLBCurrHost = 0;
static int          iLBCurrGroup = 0;
static int          iCurrGroupIdx = 0;
static int          iNumGroups = 0;
static char         szWorkAroundNodeAdd[
SCS_MAXLENNODEADD ];
static char         szSerialBuf[
SCS_MAXLENSERIALNUM ];
static char         szCurrHostName[
SCS_MAXLENHOSTNAME + 1 ];

static char         fRequestHostList = FALSE;

void SetCurrHostName( char *szNewCurrHostName
)
{
  strcpy( szCurrHostName, szNewCurrHostName );
}

char *GetCurrHostName( void )
{
  return ( szCurrHostName );
}

int GetLBCurrHost( void )
{
  return ( iLBCurrHost );
}

void SetLBCurrHost( int iNewLBCurrHost )
{
  iLBCurrHost = iNewLBCurrHost;
}

char GetRequestHostList( void )
{
  return ( fRequestHostList );
}

void SetRequestHostList( int iNewRequestHostList )
{
  PCS_BEGINCRITICAL;
  fRequestHostList = LOBYTE( iNewRequestHostList
);
  PCS_ENDCRITICAL;
}

int GetLBCurrGroup( void )
{
  return ( iLBCurrGroup );
}

void SetLBCurrGroup( int iNewLBCurrGroup )
{
  if ( iLBCurrGroup != iNewLBCurrGroup )
    iCurrGroupIdx = GetGroupIdx( iNewLBCurrGroup
);

  iLBCurrGroup = iNewLBCurrGroup;
}

char *GetLBGroup( int iGroupNum )
{
  int iUseGroup;
  char *szReturn;
  int iLBGroupIdx;

  if ( iHLStatus != SHR_AVAILABLE ||
HostListEntries.iNumEntries
== 0 )
    return ( szNoHdr );

  iUseGroup = ( iGroupNum ==
SUI_LBCURRENTRY ? iLBCurrGroup :
iGroupNum );

  iLBGroupIdx = GetGroupIdx( iUseGroup );

  szReturn = HostListEntries.aHostListBuf[
iLBGroupIdx
].HostDataBuf.szGroupName;
```

```
    return ( szReturn == NULL ? szNullStr : szReturn
);
}

char *GetLBHost( int iHostNum )
{
  char *szReturn;

  if ( GetCurrActionCode() ==
SUI_LASTCONNECTION )
    return ( UiConfigData.szLastHostName );

  if ( HLStatus != SMI_AVAILABLE ||
HostListEntries.iNumEntries
== 0 )
    return ( szNullStr );

  szReturn = HostListEntries.aHostListBuff[
GetHostIdx( iHostNum
) ].HostDataBuff.szHostName;

  return ( szReturn == NULL ? szNullStr : szReturn
);
}

int GetLBHostStatus( int iHostNum )
{
  int iReturn;

  if ( HLStatus != SMI_AVAILABLE ||
HostListEntries.iNumEntries
== 0 )
    return ( SUI_LBENTRYENABLED );

  iReturn = HostListEntries.aHostListBuff[
GetHostIdx( iHostNum )
].HostDataBuff.nHostStatus;

  if ( iReturn == SCS_HOSTAVAILABLE )
    iReturn = SUI_LBENTRYENABLED;
  else
    iReturn = SUI_LBENTRYDISABLED;

  return ( iReturn );
}

int SetLBHostStatus( int iHostNum, BYTE
nNewHostStatus )
{
  if ( HLStatus != SMI_AVAILABLE ||
HostListEntries.iNumEntries
== 0 )
    return ( ERR_INTERNAL );

  HostListEntries.aHostListBuff[ GetHostIdx(
iHostNum ) ]
].HostDataBuff.nHostStatus = nNewHostStatus;

  return ( ERR_SUCCESS );
}

char *GetCurrNodeAddress( void )
{
  int iHostIdx;
  char *szReturn = NULL;

  if ( GetCurrActionCode() ==
SUI_LASTCONNECTION )
    return ( UiConfigData.szLastNodeAddress );

  if ( HLStatus != SMI_AVAILABLE ||
HostListEntries.iNumEntries
== 0 )
    return ( szNullStr );

  if ( iLBCurrHost > 0 )
  {
    iHostIdx = GetGroupIdx( iLBCurrGroup ) + (
iLBCurrHost - 1 );
    szReturn = HostListEntries.aHostListBuff[
iHostIdx
].szNodeAddress;
  }

  return ( szReturn == NULL ? szNullStr : szReturn
);
}

WORD GetCurrHostVersionNum( void )
{
  int iHostIdx;
  BYTE nMinorVersion;
  BYTE nMajorVersion;

  if ( HLStatus != SMI_AVAILABLE ||
HostListEntries.iNumEntries
== 0 )
    return ( 0 );

  if ( iLBCurrHost > 0 )
    iHostIdx = GetHostIdx( SUI_LBCURRENTRY );
  else
    return ( 0 );

  nMinorVersion = HostListEntries.aHostListBuff[
iHostIdx
].HostDataBuff.nMinorVersion;
  nMajorVersion = HostListEntries.aHostListBuff[
iHostIdx
].HostDataBuff.nMajorVersion;

  return ( MAKEWORD( nMinorVersion,
nMajorVersion ) );
}

BOOL IsPWRequired( void )
{
  BOOL iReturn = FALSE;

  if ( GetCurrActionCode() ==
SUI_LASTCONNECTION )
    return ( UiConfigData.bLastConnPassword );

  if ( HLStatus != SMI_AVAILABLE ||
HostListEntries.iNumEntries
== 0 )
    return ( FALSE );

  if ( iLBCurrHost > 0 )
    iReturn = HostListEntries.aHostListBuff[
GetHostIdx(
SUI_LBCURRENTRY ) ].HostDataBuff
              .bPasswordProtect;

  return ( iReturn );
}

int GetNumHostEntries( void )
{
  int iHostGroupIdx;

  if ( HLStatus != SMI_AVAILABLE )
    return ( ERR_INTERNAL );

  if ( ( iHostGroupIdx = GetGroupIdx( iLBCurrGroup
+ 1 ) ) >= 0 )
    return ( iHostGroupIdx - iCurrGroupIdx );
  else
    return ( HostListEntries.iNumEntries -
iCurrGroupIdx );
}

int GetNumGroupEntries( void )
{
  if ( HLStatus != SMI_AVAILABLE )
    return ( ERR_INTERNAL );

  return ( iNumGroups );
}

int GetGroupIdx( int iGroupNum )
{
  LONG lGroupIdx;

  lGroupIdx = GetEntryOffset(
HostListEntries.iNumEntries,
            sizeof ( HOSTLISTBUFF ),
SCS_MAXLENNODEADD,
            iGroupNum, ( NPSTR
)HostListEntries.aHostListBuff );

  if ( lGroupIdx >= 0 )
    return ( ( int )lGroupIdx / sizeof (
HOSTLISTBUFF ) );
  else
    return ( ERR_INTERNAL );
}

int GetGroupNum( int iHostIdx )
{
  LONG lLowGroupIdx = 0L;
  LONG lHighGroupIdx = 0L;
  int iGroupNum;

  for ( iGroupNum = 1; lHighGroupIdx >= 0;
++iGroupNum )
  {
    lLowGroupIdx = lHighGroupIdx;
    lHighGroupIdx = GetEntryOffset(
HostListEntries.iNumEntries,
            sizeof ( HOSTLISTBUFF
),
SCS_MAXLENNODEADD,
            iGroupNum, ( NPSTR
)HostListEntries.aHostListBuff );
    lHighGroupIdx /= sizeof ( HOSTLISTBUFF );

    if ( ( LONG )iHostIdx >= lLowGroupIdx && (
LONG )iHostIdx <
lHighGroupIdx )
      return ( iGroupNum );
  }

  return ( HLD_NOTINGROUP );
}

int GetHostIdx( int iHostNum )
{
  int iUseHost;
  int iHostIdx;

  iUseHost = ( iHostNum == SUI_LBCURRENTRY ?
iLBCurrHost :
iHostNum );
  iHostIdx = iCurrGroupIdx + ( iUseHost - 1 );

  return ( iHostIdx );
}

int SortGroupHost( void )
{
  int iGroupNum;
  int iSortStatus;

  iSortStatus =
    SortList( HostListEntries.iNumEntries, sizeof (
HOSTLISTBUFF
),
            SCS_OFFGROUPKEY,
SCS_OFFHOSTKEY,
            ( NPSTR )HostListEntries.aHostListBuff );

  if ( iSortStatus == ERR_SUCCESS )
  {
    for ( iNumGroups = 0, iGroupNum = 1;
iGroupNum <=
HostListEntries.iNumEntries;
        ++iGroupNum )
    {
      if ( GetGroupIdx( iGroupNum ) >= 0 )
        iNumGroups++;
    }
  }

  return ( iSortStatus );
}

int SortSerialNums( void )
{
  int iEntryIdx;

  if ( HostListEntries.aHostListBuff == NULL ||
HostListEntries.iNumEntries == 0 )
    return ( ERR_INTERNAL );

  for ( iEntryIdx = 0; iEntryIdx <
HostListEntries.iNumEntries;
++iEntryIdx )
    HostListEntries.aHostListBuff[ iEntryIdx ].
      HostDataBuff.szHostSerial[
SCS_MAXLENSERIALNUM - 1 ] = 0;

  return ( SortList( HostListEntries.iNumEntries,
sizeof (
HOSTLISTBUFF ),
          SCS_OFFSERIALNUM, NULL, ( NPSTR
)HostListEntries.aHostListBuff ) );
}

int ValidateSerialNums( void )
{
  int iEntryIdx, iNextEntryIdx;
  int iSerialStatus = HLD_VALIDSERIALS;

  szSerialDup[0] = '\0';

  if ( SortSerialNums() != ERR_SUCCESS )
    return ( FALSE );

  for ( iEntryIdx = 0; iEntryIdx <
HostListEntries.iNumEntries;
++iEntryIdx )
  {
    if ( IsZeroString( HostListEntries.aHostListBuff[
iEntryIdx
].
                HostDataBuff.szHostSerial ) )
      iSerialStatus = HLD_INVALIDSERIALS;
    else
    {
      if ( ( iNextEntryIdx = iEntryIdx + 1 ) <
HostListEntries.iNumEntries )
      {
        if ( !strcmp( HostListEntries.aHostListBuff[
iEntryIdx
].HostDataBuff.szHostSerial,
                HostListEntries.aHostListBuff[
iNextEntryIdx ].
                HostDataBuff.szHostSerial ) )
          iSerialStatus = HLD_DUPLICATESERIALS;
      }
    }

    if ( iSerialStatus != HLD_VALIDSERIALS )

    {
      strcpy( szSerialDup,
HostListEntries.aHostListBuff[
iEntryIdx ].
                HostDataBuff.szHostSerial );
      break;
    }
  }

  return ( iSerialStatus );
}

int RequestHostList( void )
{
  SetRequestHostList( TRUE );

  if ( !GetSCSActiveStatus() )
    return ( ERR_INTERNAL );

  if ( ( AllocHLMem( &HostListEntries,
HLD_MAXNUMHOSTENTRIES ) )
!= ERR_SUCCESS )
    return ( ERR_OUTOFMEM );

  if ( ( AllocHLMem( &BroadcastHLEntries,
HLD_MAXNUMHOSTENTRIES )
) != ERR_SUCCESS )
    return ( ERR_OUTOFMEM );

  HostListEntries.iNumEntries = 0;
  iLBCurrHost = iLBCurrGroup = 0;

  if ( ( SendRequestHostList() == ERR_SUCCESS )
&&
      ( ( iWaitForHLThreadIdx =
GetTempEventItem() ) >= 0 ) )
  {
    AddThread( iWaitForHLThreadIdx, WaitForHLD,
NULL,
SMO_MANYTIMES, FALSE,
            HLD_POLLFREQ, HLD_MAXRETRIES );

    SetStatusHLInMem( SMI_INPROGRESS );
  }
  else
  {
    FreeHLMem( &HostListEntries );
    FreeHLMem( &BroadcastHLEntries );
    SetStatusHLInMem( SMI_AVAILABLE );
    return ( ERR_INTERNAL );
  }

  return ( ERR_SUCCESS );
}

void WaitForHLD( void )
{
  int iNumEntries;
  int iConstStatus;
  LONG lGroupHostNums;
  int iHostConnectIdx;

  CancelRequestHostList();

  if ( ( iNumEntries = *( int *
)BroadcastHLEntries.aHostListBuff
) > 0 )
  {
    BroadcastHLEntries.iNumEntries = iNumEntries;

    mem_mv( ( PVOID )( ( BYTE * )(
BroadcastHLEntries.aHostListBuff ) +
SCS_HOSTLISTNUMOFFSET ),
          ( PVOID )(
BroadcastHLEntries.aHostListBuff ),
iNumEntries *
          sizeof ( HOSTLISTBUFF ) + sizeof ( int ) );

    SaveNewHosts();
  }

  if ( GetRetryLimit( iWaitForHLThreadIdx ) > 0 &&
SendRequestHostList() == ERR_SUCCESS )
  {
    SetStatusHLInMem( SMI_INPROGRESS );
  }
  else
  {
    DelThread( iWaitForHLThreadIdx );
```

```
    if ( HostListEntries.iNumEntries > 0 )
    {
      AllocHLMem( &HostListEntries,
HostListEntries.iNumEntries
);

    if ( ( iSerialStatus = ValidateSerialNums() ) !=
HLD_VALIDSERIALS )
    {
      if ( iSerialStatus == HLD_INVALIDSERIALS )
        OpenMessageBox(
STR_HLDINVSERIALNUMS, 0,
SUI_LEFTJUSTIFIED, SUI_OK );
      else
        OpenMessageBox(
STR_HLDDUPSERIALNUMS, 0,
SUI_LEFTJUSTIFIED, SUI_OK );
    }

    SetGroupHost();

    if ( GetSCSCurrProgress() !=
SMI_SCSDISCONNECTED )
    {
      if ( ( iHostConnectIdx = FindNodeAddress(
&HostListEntries,

UlConfigData.achLastNodeAddress )
) != FNA_NOTFOUND )
        HostListEntries.aHostListBuff[
iHostConnectIdx ].
                    HostDataBuff.aHostStatus =
SCS_HOSTAVAILABLE;
    }

    if ( ( lGroupHostNums = FindFirstAvailHost(
&HostListEntries ) ) != HLD_NOHOSTAVAIL )
    {
      ILSCurrGroup = HIWORD( lGroupHostNums );
      ILSCurrHost = LOWORD( lGroupHostNums );
    }
    else
    {
      ILSCurrGroup = iNumGroups > 0 ? 1 : 0;
      ILSCurrHost = 0
    }
  }
  else
  {
    FreeHLMem( &HostListEntries );
    ILSCurrGroup = 0;
    ILSCurrHost = 0;
  }

  FreeHLMem( &BroadcastHLEntries );

  SetStatusHLInMem( SMI_AVAILABLE );
  SetRequestHostList( FALSE );
 }
}

int SendRequestHostList( void )
{
 WORD wSeg, wOff, wReturn,

 wSeg = SEG( BroadcastHLEntries.aHostListBuff );
 wOff = OFF( BroadcastHLEntries.aHostListBuff );

 _asm
 {
  push ds
  push di
  push bx

  mov ax, SCS_REQUESTHOSTLIST
  mov dx, wSeg
  mov di, wOff
  mov bx, HLD_MAXNUMHOSTENTRIES

  int SCS_INTNUM

  pop bx
  pop di
  pop dx

  mov wReturn, ax
 }

 if ( wReturn == SCS_ACCEPTED )
  return ( ERR_SUCCESS );
 else
  return ( ERR_INTERNAL );
}

int CancelRequestHostList( void )
{
 _asm
 {
  mov ax, SCS_CANCELREQHOSTLIST
  int SCS_INTNUM
 }

 return ( ERR_SUCCESS );
}

int SaveNewHosts( void )
{
 int iBCHostIdx;

 for ( iBCHostIdx = 0; iBCHostIdx <
BroadcastHLEntries.iNumEntries; ++iBCHostIdx )
 {
  if ( FindNodeAddress( &HostListEntries,
      BroadcastHLEntries.aHostListBuff[
iBCHostIdx
].achNodeAddress ) == FNA_NOTFOUND )
  {
    HostListEntries.aHostListBuff[
HostListEntries.iNumEntries++ ] =
      BroadcastHLEntries.aHostListBuff[ iBCHostIdx
];
  }
 }

 return ( ERR_SUCCESS );
}

int FindNodeAddress( HOSTLISTENTRIES
*pHostListEntries, char
*achKeyNodeAddress )
{
 int iHostIdx,
 int iMaxHostIdx = pHostListEntries->iNumEntries;

 for ( iHostIdx = 0; iHostIdx < iMaxHostIdx,
++iHostIdx )
 {
  if ( strcmp( pHostListEntries->aHostListBuff[
iHostIdx
].achNodeAddress,
          achKeyNodeAddress ) == 0 )
   return ( iHostIdx );
 }

 return ( FNA_NOTFOUND );
}

LONG FindFirstAvailHost( HOSTLISTENTRIES
*pHostListEntries )
{
 int iHostIdx,
 int iGroupNum, iHostNum,
 int iMaxHostIdx = pHostListEntries->iNumEntries,

 for ( iHostIdx = 0; iHostIdx < iMaxHostIdx,
++iHostIdx )
 {
  if ( pHostListEntries->aHostListBuff[ iHostIdx
].HostDataBuff.aHostStatus ==
      SCS_HOSTAVAILABLE )
  {
   iGroupNum = GetGroupNum( iHostIdx );
   iHostNum = ( iHostIdx - GetGroupIdx(
iGroupNum ) ) + 1;
   return ( MAKELONG( iHostNum, iGroupNum ) );
  }
 }

 return ( ( LONG )HLD_NOHOSTAVAIL );
}

int AllocHLMem( HOSTLISTENTRIES
*pHostListEntries, int
iNumEntries )
{

 if ( pHostListEntries->aHostListBuff == NULL )
 {
  if ( ( pHostListEntries->aHostListBuff = (
HOSTLISTBUFF *
)malloc(
        iNumEntries * sizeof ( HOSTLISTBUFF ) +
sizeof ( int )
) ) == NULL )
  {
   TRACE( "ERROR: malloc failed in
AllocHLMem()\n" );
   return ( ERR_INTERNAL );
  }
  else
   fil_char( ( PVOID
)pHostListEntries->aHostListBuff, 0,
iNumEntries *
         sizeof ( HOSTDATABUFF ) + sizeof ( int
) );
 }
 else
 {
 }

 pHostListEntries->iNumEntries = iNumEntries;

 return ( ERR_SUCCESS );
}

int GetStatusHLInMem( void )
{
 if ( GetCurrActionCode() ==
SUI_LASTCONNECTION )
  return ( SMI_AVAILABLE );
 else
  return ( iHLStatus );
}

void SetStatusHLInMem( int iNewHostListStatus )
{
 if ( ( iHLStatus = iNewHostListStatus ) ==
SMI_INPROGRESS )
  SetWaitingIcon( SSS_WAITINGICONON, TRUE
);
 else
  SetWaitingIcon( SSS_WAITINGICONOFF, TRUE
);
}

void FreeHLMem( HOSTLISTENTRIES
*pHostListEntries )
{
 if ( pHostListEntries->aHostListBuff != NULL )
 {
  free( pHostListEntries->aHostListBuff );
  pHostListEntries->aHostListBuff = NULL;
 }
}

void FreeAllHLMem( void )
{
 FreeHLMem( &HostListEntries );
 FreeHLMem( &BroadcastHLEntries );
}

BOOL IsZeroString( char achString[] )
{
 int iStrIdx,
 int iStrLen,

 for ( iStrIdx = 0, iStrLen = strlen( achString ),
       iStrIdx < iStrLen; ++iStrIdx )
  if ( achString[ iStrIdx ] != '0' )
   return ( FALSE );

 return ( TRUE );
}

#if defined( _MSC_VER )
#pragma warning( default : 4704 )
#endif
Copr. 1995 Zenith Data Systems Corp.

#include "sr.h"
#include "spawn.h"
#include "t2.h"
#include "sio.h"
#include "sm.h"

#if defined( _MSC_VER )
#pragma warning( disable : 4704 )
#endif

#define STK_SZ (5000)
word isr_stk[STK_SZ+1];



extern char erro[];
extern char alrro[],alrrm[];
extern char already[];
extern char unloaddone[];
extern char unloadnot[];
extern word init_data_end;

extern BOOL Bisture;



main()
{
 int i;

 chk_video();
 get_crs();
 crs_x = bars_x;
 crs_y = bars_y;
 mv_crs();

 if ( second_load() )
 {
  i = str_pos( '/', cmd_line );
  if ( i && ( ( cmd_line[i] | 0x20 ) == 'u' ) )
  {
   if( remove_tsr() )
   {
    ShutDownDispatcher();
    dspl( unloaddone );
   }
   else
    dspl( unloadnot );
  }
  else
   dspl( already );

  mv_crs();

  return( 1 );
 }


 sprintf( szTempStr, umo, szSMVersionName );
 dspl( szTempStr );

 get_crs();
 crs_x = bars_x;
 crs_y = bars_y + 3;
 mv_crs();




 DEBUG_BREAK

 InitAConfigData();
 InitSavetags( SSS_DRIVERSLOADING );
 InitDispatcher();

 malloc_on( SMC_MAXLENHEAP );
 fdata_end=&init_data_end;
 leds_begmain,
 stay_resident(isr_stk,STK_SZ*2);



 install_isr( ( fp )ClockTick, 3000,
          SMD_SCHEDULERS | SMD_HOTKEYS |

          SMD_FARCALLS |
SMD_GENERALTRAPS | SMD_COMMSVCS |
SMD_INTSSVCS | SMD_MOUSEDWATCH );

 install_trap( ( fp )TrapService, 2500,
SMD_FULLREENTER );
 install_fcall( ( fp )FCallService, 4000,
SMD_FULLREENTER, 0,
schbuffer, 0 );

 add_tsr_event( SMD_DISPATFREQ );

 return ( 0 );
}

#if defined( _MSC_VER )
#pragma warning( default . 4704 )
#endif




Copr. 1995 Zenith Data Systems Corp.


#include "sr.h"
#include "spawn.h"
#include "t2.h"
#include "sm.h"

#if !defined( NDEBUG )
WORD aHotKeys[] = { SMI_SF1, SMI_SF2,
SMI_SF3, SMI_SF4, SMI_SF5,
SMI_SF6,
               SMI_SF7, SMI_SF8, SMI_SF9,
SMI_SF10,
SMI_SALTQ, 0 };
#endif



char alrro[]={0x17,0x1E,0x12,0x17,0x18,0xA};
char alrrm[]={0x07,0x07,0x07,0x07,0x07,0x0F};



char erro[] =
```

```
  "\nSystemSoft Manager, (C) Copyright 1994,1995, Zenith Data Systems\n"
  "Mobile Systems Engineering, Version %s\n";

char already[] =
  "ERROR: SM already present.\n"
  "Enter SM -U to unload.\n";

char unloaddone[]="SM has been removed from memory.";
char unloadnot[]="ERROR: SM could not be removed from memory.";

char _tsr_name[]="Sentinel Manager (C) 1994-1995 ZDS";


struct cfg_rec config_block = {
    sizeof(config_block),
    'S','M','A','W',
    MAKEWORD( GEN_SMMINORVERSIONNUM, GEN_SMMAJORVERSIONNUM ),
    };



#if !defined( NDEBUG )


fp install_list[]={install_tsc,install_trap,install_hk,install_fcall
};

#else
fp
install_list[]={install_tsc,install_trap,install_dos_rdy,install_fcall};
#endif



word md_data_end=1;


Copr 1995 Zenith Data Systems Corp.
#include "sr.h"
#include "tc2.h"
#include "apown.h"
#include "hm.h"
#include "sc.h"
#include "sm.h"

#if defined( _MSC_VER )
#pragma warning( disable : 4704 )
#endif

static OCCLUDEUNION HostOcc;
static OCCLUDEUNION OldHostOcc = { -1, -1, -1, -1 };
static OCCLUDEUNION *pSetOccData;
static int      iSetOccType;
static BYTE       fSCOSNotified;
static BYTE       fRepaintRequired = FALSE;
static char      nOccDefineAcked = PM_NOACK;
static char      nOccCloseAcked = PM_NOACK;
static int      iHostOccludeIdx = SMD_NOACTIVETHREAD;


void SetSCOSNotified( BYTE NewSCOSNotified )
{
  fSCOSNotified = NewSCOSNotified;
}

void SetOccDefineAcked( char nOccDefineStatus )
{
  nOccDefineAcked = nOccDefineStatus;
}

char GetOccDefineAcked( void )
{
  return ( nOccDefineAcked );
}

void SetOccCloseAcked( char nOccCloseStatus )
{
  nOccCloseAcked = nOccCloseStatus;
}

char GetOccCloseAcked( void )
{
  return ( nOccCloseAcked );
}


int DrawSUIOSK( OCCLUDEUNION *NewOSKRect, int iOccType )
{
  OCCLUDEUNION *OSKRect;
  int yDrawOSK, xDrawOSK;

  if ( NewOSKRect == NULL )
    OSKRect = &HostOcc;
  else
    OSKRect = NewOSKRect;

  switch ( iOccType )
  {
   case SUI_OCCRWIN:
    yDrawOSK = OSKRect->occRWin.yULWin;
    xDrawOSK = OSKRect->occRWin.xULWin;
    break;

   case SUI_OCCDOSTEXT:
    yDrawOSK = OSKRect->occText.yULRow *
SCS_OSKTEXTCHARHEIGHT;

    xDrawOSK = OSKRect->occText.xULCol *
SCS_OSKTEXTCHARWIDTH;
    break;

   case SUI_OCCDOSGRAPHICS:
    yDrawOSK = OSKRect->occDosGraph.yULDos;
    xDrawOSK = OSKRect->occDosGraph.xULDos;
    break;

   default:
    TRACE( "ERROR: Invalid occlusion type specified in DrawSUIOSK()\r" );
    return ( ERR_INTERNAL );
  }

#if !defined( PROD )
  sprintf( szTempStr, "NOTICE: Request to draw OSK at x:%d, y:%d,
sent to SUI\r",
       xDrawOSK, yDrawOSK );
  TRACE( szTempStr );
#endif

  AX( SUI_MOVEOSK );
  BX( yDrawOSK );
  CX( xDrawOSK );
  return ( ( *lpfnSUICallBack )() );
}

int CreateOccludedArea( OCCLUDEUNION *OccMap, int iOccType, int
Str*, *echoFromItem )
{
  if ( !GetSCSActiveState() )
    return ( ERR_INTERNAL );

  if ( OldHostOcc.occRWin.xULWin == -1 &&
    OldHostOcc.occRWin.yULWin == -1 )
  {
    OldHostOcc.occRWin.xULWin =
UIConfigData.xPosLastOSKScreen;
    OldHostOcc.occRWin.yULWin =
UIConfigData.yPosLastOSKScreen;
  }

  switch ( iOccType )
  {
    case SUI_OCCRWIN:
     UIConfigData.xPosLastOSKScreen =
OccMap->occRWin.xULWin;
     UIConfigData.yPosLastOSKScreen =
OccMap->occRWin.yULWin;
     return ( SetWinHostOcclude(
&OccMap->occRWin ) );

    case SUI_OCCDOSTEXT:
     UIConfigData.xPosLastOSKScreen =
OccMap->occText.xULCol;
     UIConfigData.yPosLastOSKScreen =
OccMap->occText.yULRow;
     return ( SetDOSTextHostOcclude(
&OccMap->occText ) );

    case SUI_OCCDOSGRAPHICS:
     UIConfigData.xPosLastOSKScreen =
OccMap->occDosGraph.xULDos;
     UIConfigData.yPosLastOSKScreen =
OccMap->occDosGraph.yULDos;
     return ( SetDOSGraphHostOcclude(
&OccMap->occDosGraph ) );

    case SUI_NOOCCTYPE:
    default:
     TRACE( "ERROR: Invalid occlusion type
specified in
CreateOccludeArea()\r" );
     return ( ERR_INTERNAL );
  }
}


int SetWinHostOcclude( OCCLUDERWIN *OccRWin
)
{
  if ( iHostOccludeIdx != SMD_NOACTIVETHREAD )

  {
    TRACE( "NOTICE: Attempt to reenter
SetWinHostOcclude() before
it is done, returning error\r" );
    return ( ERR_SUCCESS );
  }

  SetOccDefineAcked( PM_NOACK );

  HostOcc.occRWin.xULWin = OccRWin->xULWin;
  HostOcc.occRWin.yULWin = OccRWin->yULWin;
  HostOcc.occRWin.xLRWin = ( OccRWin->xLRWin
- OccRWin->xULWin )
+ 1;
  HostOcc.occRWin.yLRWin = ( OccRWin->yLRWin
- OccRWin->yULWin )
+ 1;

#if !defined( PROD )
  sprintf( szTempStr, "NOTICE: Occlusion Region
for Windows at
x:%d, y:%d, x:%d, y:%d\r",
         HostOcc.occRWin.xULWin,
HostOcc.occRWin.yULWin,
         HostOcc.occRWin.xLRWin,
HostOcc.occRWin.yLRWin );
  TRACE( szTempStr );
#endif

  if ( SendPrivateMessage( PM_REQOCCDEFINE,
sizeof ( OCCLUDERWIN
),
                ( char * )&HostOcc.occRWin ) !=
ERR_SUCCESS )
  {
    TRACE( "ERROR: PM for occlude region not
sent due to
SendPrivateMessage() error\r" );
    DrawSUIOSK( &OldHostOcc, SUI_OCCRWIN );
    return ( ERR_SUCCESS );
  }

  if ( ( iHostOccludeIdx = GetTempEventNum() ) < 0
)
  {
    TRACE( "ERROR: Out of temporary threads,
drawing OSK
anyway\r" );
    DrawSUIOSK( NULL, SUI_OCCRWIN );
    return ( ERR_INTERNAL );
  }

  AddThread( iHostOccludeIdx, ( NEARPROC
)WaitForDefineOcc, NULL,
SMD_MANYTIMES, FALSE,
          SCS_WAITACKPOLLFREQ,
SCS_WAITACKMAXRETRY );

  return ( ERR_SUCCESS );
}

void WaitForDefineOcc( void )
{
  if ( GetOccDefineAcked() != PM_NOACK )
  {
    DelThread( iHostOccludeIdx );

    if ( GetOccDefineAcked() == PM_ACKEDTRUE )
    {
     TRACE( "NOTIFY: Message acknowledgement
detected, enable
SUI to begin OSK paint\r" );
     OldHostOcc = HostOcc;
     DrawSUIOSK( NULL, SUI_OCCRWIN );
    }
    else
    {
     TRACE( "ERROR: Message acknowledgement
detected, abort OSK
paint\r" );
     DrawSUIOSK( &OldHostOcc, SUI_OCCRWIN );

    }

    iHostOccludeIdx = SMD_NOACTIVETHREAD;

  }
  else if ( GetRetryLimit( iHostOccludeIdx ) == 0 )
  {
    TRACE( "ERROR: Timeout, define Occ message
acknowledgment not
received, allow draw anyway.\r" );
    DelThread( iHostOccludeIdx );
    iHostOccludeIdx = SMD_NOACTIVETHREAD;
    DrawSUIOSK( NULL, SUI_OCCRWIN );
    SetOccDefineAcked( PM_ACKEDFALSE );
  }
}

int CloseHostOcclude( void )
{
  if ( iHostOccludeIdx != SMD_NOACTIVETHREAD )

  {
    TRACE( "NOTICE: Attempt to reenter
CloseHostOcclude() before
it is done, returning error\r" );
    return ( ERR_INTERNAL );
  }

  if ( GetCurrHostMode() == PMD_DOSAPP )
  {
    TRACE( "NOTICE: Already at DOS not need to
close Windows
occlude\r" );
    return ( ERR_SUCCESS );
  }

  SetOccCloseAcked( PM_NOACK );

  if ( IsOSKUnitClose( GetCurrSetCode() ) )
  {
    if ( SendPrivateMessage( PM_REQOCCCLOSE,
0, NULL ) !=
ERR_SUCCESS )
    {
      TRACE( "ERROR: PM for closure of occlude
region not sent
due to SendPrivateMessage() error\r" );

      return ( ERR_SUCCESS );
    }

    if ( ( iHostOccludeIdx = GetTempEventNum() ) <
0 )
      return ( ERR_INTERNAL );

    AddThread( iHostOccludeIdx, ( NEARPROC
)WaitForCloseOcc,
NULL, SMD_MANYTIMES, FALSE,
          SCS_WAITACKPOLLFREQ,
SCS_WAITACKMAXRETRY );
  }
  else
  {
    TRACE( "NOTICE: Unilateral closure of Windows
OSK identified,
no PM sent\r" );
    SetFullRepaint( ERR_SUCCESS );
  }

  return ( ERR_SUCCESS );
}

void WaitForCloseOcc( void )
{
  if ( GetOccCloseAcked() != PM_NOACK )
  {
    DelThread( iHostOccludeIdx );

    if ( GetOccCloseAcked() == PM_ACKEDTRUE )
    {
     TRACE( "NOTIFY: Message acknowledgement
for close of OCC
detected\r" );
     SetFullRepaint( ERR_SUCCESS );
    }
    else
    {
     TRACE( "ERROR: Message acknowledgement
for close of OCC
detected, failed close\r" );
     SetFullRepaint( ERR_INTERNAL );
    }

    iHostOccludeIdx = SMD_NOACTIVETHREAD;

  }
  else if ( GetRetryLimit( iHostOccludeIdx ) == 0 )
  {
    DelThread( iHostOccludeIdx );
    iHostOccludeIdx = SMD_NOACTIVETHREAD;
```

```
    TRACE( "ERROR: Close Occ acknowledgment
not received, set for
success anyway\r" );
    SetFullRepaint( ERR_SUCCESS );
  }
}

int SetDOSGraphHostOcclude(
OCCLUDEDOSGRAPHICS *OccDosGraphics )
{
  HostOcc = ( OCCLUDEUNION *
)OccDosGraphics;
  if ( IsOSKAsSetupDlg( GetCurrScrCode() ) )
  {
    TRACE( "NOTICE: Beginning immediate redraw
of DOS Graphics
OSK\r" );
    DrawSUIOSK( NULL, SUI_OCCDOSGRAPHICS
);

    TRACE( "NOTICE: Waiting for SUI video busy for
the DOS
Graphics OSK\r" );

    if ( SUIVideoBusy( DoDOSGraphHostOcclude ) !=
ERR_SUCCESS )
      return ( ERR_INTERNAL );
  }
  else
  {
    TRACE( "NOTICE: OSK As Setup Dialog, no
SCOS calls, clearing
screen.\r" );

    SetVideoMode( SUI_INITIALVIDMODE );
    DrawSUIOSK( NULL, SUI_OCCDOSGRAPHICS
);
  }
}

void DoDOSGraphHostOcclude( void )
{

#if defined( PROD )
  sprintf( szTempStr, "NOTICE: Occlusion Region for
DOS Graphics
at x:%d, y:%d, x:%d, y:%d\r",
         HostOcc.occDosGraph.xULDos,
HostOcc.occDosGraph.yULDos,
         HostOcc.occDosGraph.xLRDos,
HostOcc.occDosGraph.yLRDos
);
  TRACE( szTempStr );
#endif

  SetSCSHostOcclude( &HostOcc,
SUI_OCCDOSGRAPHICS, TRUE );

}

int SetDOSTextHostOcclude( OCCLUDETEXT
*OccDosText )
{

  HostOcc.occText.yULRow =
OccDosText->yULRow /
SCS_OSKTEXTCHARHEIGHT;
  HostOcc.occText.xULCol = OccDosText->xULCol /
SCS_OSKTEXTCHARWIDTH;
  HostOcc.occText.yLRRow = ( (
OccDosText->yLRRow + 1 ) /
SCS_OSKTEXTCHARHEIGHT ) - 1;
  HostOcc.occText.xLRCol = ( (
OccDosText->xLRCol + 1 ) /
SCS_OSKTEXTCHARWIDTH ) - 1;

  *OccDosText = HostOcc.occText;

  TRACE( "NOTICE: Beginning immediate redraw of
DOS Text OSK\r"
);
  DrawSUIOSK( NULL, SUI_OCCDOSTEXT );

#if defined( PROD )
  sprintf( szTempStr, "NOTICE: Occlusion Region for
DOS Text at
x:%d, y:%d, x:%d, y:%d\r",
         HostOcc.occText.xULCol,
HostOcc.occText.yULRow,
         HostOcc.occText.xLRCol,
HostOcc.occText.yLRRow );
  TRACE( szTempStr );
```

```
#endif

  return ( SetSCSHostOcclude( &HostOcc,
SUI_OCCDOSTEXT, TRUE ) );
}

int SetSCSHostOcclude( OCCLUDEUNION *occ,
OCCTYPE iNewOccType,
BYTE bNewRepaintRequired )
{
  if ( iHostOccludeIds != SMD_NOACTIVETHREAD )

  {
    TRACE( "NOTICE: Attempt to reenter
SetSCSHostOcclude() before
it is done, returning error\r" );
    return ( ERR_INTERNAL );
  }

  SetFullRepaint( ERR_INPROGRESS );

  pSetOccData = occ;
  iSetOccType = iNewOccType;
  bRepaintRequired = bNewRepaintRequired;

  if ( ( iHostOccludeIds = GetTempEventNum() ) < 0
)
    return ( ERR_INTERNAL );

  AddThread( iHostOccludeIds, ( NEARPROC
)DoSCSHostOcclude, NULL,
SMD_MANYTIMES, FALSE,
         SCS_DOHOSTOCCPOLLFREQ,
SCS_DOHOSTOCCMAXRETRY );

  return ( ERR_SUCCESS );
}

void DoSCSHostOcclude( void )
{
  int iOccError;

  if ( ( iOccError = DefineSCSOcclude(
pSetOccData, iSetOccType,
bRepaintRequired ) ) != ERR_SUCCESS )
  {
    if ( iOccError != ERR_SCSBUSY )
    {
      SetFullRepaint( ERR_INTERNAL );
      DelThread( iHostOccludeIds );
      iHostOccludeIds = SMD_NOACTIVETHREAD;

      TRACE( "ERROR: Unrecoverable error occurred
in the call to
DefineSCSOcclude()\r" );
    }
    else if ( GetRetryLimit( iHostOccludeIds ) == 0 )
    {
      SetFullRepaint( ERR_INTERNAL );
      DelThread( iHostOccludeIds );
      iHostOccludeIds = SMD_NOACTIVETHREAD;

      TRACE( "ERROR: Exhausted the max number
of retries in
DefineSCSOcclude()\r" );
    }
  }
  else
  {
    SetFullRepaint( ERR_SUCCESS );
    DelThread( iHostOccludeIds );
    iHostOccludeIds = SMD_NOACTIVETHREAD;
    TRACE( "NOTICE: Success in calling
DefineSCSOcclude()\r" );
  }

}

#if defined( _MSC_VER )
#pragma warning( default : 4704 )
#endif

Copr. 1995 Zenith Data Systems Corp.
#include "sr.h"
#include "sio.h"
#include "spen.h"
#include "sus.h"

#if defined( _MSC_VER )
#pragma warning( disable : 4704 )
#endif

static BYTE      bSearchs = 0;
static int       iTempThreadIds =
SMD_NOACTIVETHREAD;
```

```
static int       iSleepThreadIds =
SMD_NOACTIVETHREAD;
static BOOL      fPNDActive = FALSE;
static PENCALIB  CurrPenCalib;
static ZDSTRAPREC PNDTrapRec;
static BYTE      nCurrPenButtonMode =
PND_LEFTMOUSE;
static BYTE      nCurrHostMode = PND_DOSAPP;
static BYTE      fSleepActive = FALSE;

static APIFUNC aAPIFuncTable[] =
{
  { SMI_PNDLOADING, PenDriverLoading },
  { 0, 0 }
};

APIFUNC *GetPNDFuncTable( void )
{
  return ( aAPIFuncTable );
}

BYTE GetCurrHostMode( void )
{
  BYTE nTempHostMode;

  PCS_BEGINCRITICAL;

  nTempHostMode = nCurrHostMode;

  PCS_ENDCRITICAL;

  return ( nTempHostMode );
}

void CheckPenEvent( void )
{
  int iHotItem;

  if ( GetConnectRequested() ||
GetRequestHostList() )
    return;

  if ( GetPNDActiveStatus() )
  {
    if ( ( iHotItem = GetHotItem() ) >= 0 )
    {
      EnvSleep();

      switch( iHotItem )
      {
        case PND_ICONSLEEP:
          ActivateSleepMode();
          break;

        case PND_ICONSETUP:
          LoadSUI( SUI_LASTSETUPDLGSCREEN, 0
);
          break;

        case PND_ICONOSK:
          if ( GetSCSCallProgress() ==
SMI_SCSCONNECTED )
            LoadSUI( SUI_LASTOSKSCREEN, 0 );
          break;

        case PND_ICONPALLETTE:
          RotatePalette();
          break;

        case PND_ICONSPEAKER:
          ToggleSpeaker();
          break;

        case PND_ICONLRMOUSE:
          if ( nCurrPenButtonMode ==
PND_LEFTMOUSE )
          {
            SetPenButtonMode( PND_RIGHTMOUSE );
            EnableRightMouseButton( FON );
          }
          else
          {
            SetPenButtonMode( PND_LEFTMOUSE );
            EnableRightMouseButton( FOFF );
          }
          break;

        case PND_ICONHOSTCTRLMODE:
          SetHostControlMode( TRUE );
          break;

        case PND_UDEF1:
        case PND_UDEF2:
          SendUDHotItem( iHotItem );
          break;
      }
    }
  }
}
```

```
void SetPNDActiveStatus( BOOL fPenDriverStat )
{
  fPNDActive = fPenDriverStat;
}

BOOL GetPNDActiveStatus( void )
{
  return ( fPNDActive );
}

APIFUNCRET PenDriverLoading( struct REGW
*CallerRegs )
{
  if ( ( iTempThreadIds = GetTempEventNum() ) ==
-1 )
  {
    CallerRegs->ax = ( UINT )ERR_PNDINTERNAL;
    goto exit;
  }

  CurrPenCalib.wXUpperPenCalib =
UIConfigData.wXUpperPenCalib;
  CurrPenCalib.wYUpperPenCalib =
UIConfigData.wYUpperPenCalib;
  CurrPenCalib.wXLowerPenCalib =
UIConfigData.wXLowerPenCalib;
  CurrPenCalib.wYLowerPenCalib =
UIConfigData.wYLowerPenCalib;
  CurrPenCalib.wHTopMargin = PND_TOPMARGIN;
  CurrPenCalib.wHRightMargin =
PND_RIGHTMARGIN;
  CurrPenCalib.wHVertSpace =
PND_VERTSPACING;
  CurrPenCalib.wHDWidth = PND_WIDTH;
  CurrPenCalib.wHVHeight = PND_HEIGHT;

  sprintf( szTempStr, "NOTICE: Using Calibration:
%d,%d -
%d,%d\r", UIConfigData.wXUpperPenCalib,
         UIConfigData.wYUpperPenCalib,
UIConfigData.wXLowerPenCalib,
UIConfigData.wYLowerPenCalib );
  TRACE( szTempStr );

  CallerRegs->dx = HIWORD( ( ( DWORD )( (
PENCALIB FAR *
)&CurrPenCalib ) ) );
  CallerRegs->si = LOWORD( ( ( DWORD )( (
PENCALIB FAR *
)&CurrPenCalib ) ) );

  AddThread( iTempThreadIds, InitPND, NULL,
SMD_ONETIME, FALSE,
SUI_POLLFREQ,
         0 );
exit:
  SetPNDActiveStatus( TRUE );
  SetForegroundRegs( CallerRegs );
}

void InitPND( void )
{
  #if !defined( NDEBUG )
  am_x = 0;
  am_y = 34;
  #endif

  DelThread( iTempThreadIds );
  if ( SetDeviceMode( PND_MOUSEMODE ) != 0 )
    goto error;

  init_video();

  if ( NotifyVideoMode( GetCurrVidMode() ) !=
ERR_SUCCESS )
    goto error;

  if ( nCurrPenButtonMode == PND_LEFTMOUSE )
    EnableRightMouseButton( FOFF );
  else
    EnableRightMouseButton( FON );


  goto success;

error:
  TRACE( "ERROR: Pen Driver initialization failed.\r"
);
  return;

success:
  TRACE( "NOTICE: Pen Driver successfully
initialized.\r" );
}

void InitPNDTrapRec( void )
{
```

```
  fil_char( ( NPSTR )&PNDTrapRec, 0, sizeof(
ZOSTRAPREC ) );

  PNDTrapRec.tr.tr_int = SMI_PNDINTNUM;

  PNDTrapRec.tr.tr_sem_srv =
CRU_ONBUSYEITHER;

  strcpy( PNDTrapRec.szSMAfterSignature,
szSMSignature );
}

TRAPREC *GetPNDTrapRec( void )
{
  return ( &PNDTrapRec.tr );
}

int GetVersion( void )
{
  REG_W InRegs, OutRegs;

  if ( !GetPNDActiveStatus() )
    return ( PND_NOICON );

  fil_char( ( NPSTR )&InRegs, 0, sizeof( REG_W ) );

  InRegs.ax = PND_GETDATA;
  InRegs.es = NULL;
  InRegs.ds = NULL;
  InRegs.cx = 0;

  intx( &InRegs, &OutRegs, PND_INTNUM );

  return ( OutRegs.bx );
}

int SetDeviceMode( int iPenMode )
{
  REG_W InRegs, OutRegs;

  if ( !GetPNDActiveStatus() )
    return ( ERR_INTERNAL );

  fil_char( ( NPSTR )&InRegs, 0, sizeof( REG_W ) );

  InRegs.ax = PND_SETDEVICEMODE;
  InRegs.bx = iPenMode;

  intx( &InRegs, &OutRegs, PND_INTNUM );

  return ( ERR_SUCCESS );
}

int NotifyVideoMode( int iVideoMode )
{
  REG_W InRegs, OutRegs;

  if ( !GetPNDActiveStatus() )
    return ( ERR_INTERNAL );

  fil_char( ( NPSTR )&InRegs, 0, sizeof( REG_W ) );

  InRegs.ax = PND_SETVIDEOMODE;
  InRegs.bx = iVideoMode;

  InRegs.si = GetXScreenRes( iVideoMode );
  InRegs.di = GetYScreenRes( iVideoMode );
  InRegs.cx = MAKEWORD( GetYCharRes(),
GetXCharRes() );

  intx( &InRegs, &OutRegs, PND_INTNUM );

  return ( ERR_SUCCESS );
}

int SetSetupDigMode( int iDigMode )
{
  REG_W InRegs, OutRegs;

  if ( !GetPNDActiveStatus() )
    return ( ERR_INTERNAL );

  fil_char( ( NPSTR )&InRegs, 0, sizeof( REG_W ) );

  InRegs.ax = PND_SETUPDIGMODE;
  InRegs.bx = iDigMode;

  intx( &InRegs, &OutRegs, PND_INTNUM );

  return ( ERR_SUCCESS );
}

int SetOSKMode( OCCLUDEUNION *OccArea
OCCTYPE OccType )
{
  REG_W InRegs, OutRegs;

  if ( !GetPNDActiveStatus() )
    return ( -1 );

  fil_char( ( NPSTR )&InRegs, 0, sizeof( REG_W ) );

  InRegs.ax = PND_OSKDIMEN;

  if ( OccArea == NULL )
    InRegs.bx = InRegs.cx = InRegs.dx = InRegs.si =
0;
  else
  {
    switch ( OccType )
    {
      case SUI_OCCOOSTEXT:

        InRegs.cx = OccArea->oosText.yULRow *
SCS_OSKTEXTCHARHEIGHT;
        InRegs.bx = OccArea->oosText.xULCol *
SCS_OSKTEXTCHARWIDTH;
        InRegs.si = OccArea->oosText.yLRRow *
SCS_OSKTEXTCHARHEIGHT;
        InRegs.dx = OccArea->oosText.xLRCol *
SCS_OSKTEXTCHARWIDTH;
        break;

      case SUI_OCCDOSGRAPHICS:
        InRegs.bx = OccArea->oosDosGraph.xULDos;
        InRegs.cx = OccArea->oosDosGraph.yULDos;
        InRegs.dx = OccArea->oosDosGraph.xLRDos;
        InRegs.si = OccArea->oosDosGraph.yLRDos;
        break;

      case SUI_OCCRWIN:
        InRegs.bx = OccArea->oosRWin.xULWin;
        InRegs.cx = OccArea->oosRWin.yULWin;
        InRegs.dx = OccArea->oosRWin.xLRWin;
        InRegs.si = OccArea->oosRWin.yLRWin;
        break;

      default:
        return ( ERR_INTERNAL );
    }
  }

  intx( &InRegs, &OutRegs, PND_INTNUM );

  return ( ERR_SUCCESS );
}

int SetPenButtonMode( BYTE nNewPenButtonMode
)
{
  REG_W InRegs, OutRegs;

  if ( !GetPNDActiveStatus() )
    return ( -1 );

  if ( nNewPenButtonMode != nCurrPenButtonMode )
  {
    fil_char( ( NPSTR )&InRegs, 0, sizeof( REG_W ) );

    InRegs.ax = PND_SETMOUSEBUTTON;

    intx( &InRegs, &OutRegs, PND_INTNUM );

    nCurrPenButtonMode = nNewPenButtonMode;
  }

  return ( ERR_SUCCESS );
}

int SetHostMode( int iHostMode )
{
  REG_W InRegs, OutRegs;

  if ( !GetPNDActiveStatus() )
    return ( ERR_INTERNAL );

  fil_char( ( NPSTR )&InRegs, 0, sizeof( REG_W ) );

  InRegs.ax = PND_HOSTMODE;
  InRegs.bx = iHostMode;

  intx( &InRegs, &OutRegs, PND_INTNUM );

  nCurrHostMode = LOBYTE( iHostMode );

  return ( ERR_SUCCESS );
}

int SetCalibMode( int iCalibMode, int xCalibPnt, int
yCalibPnt )
{
  REG_W InRegs, OutRegs;

  if ( !GetPNDActiveStatus() )
    return ( ERR_INTERNAL );

  fil_char( ( NPSTR )&InRegs, 0, sizeof( REG_W ) );

  InRegs.ax = PND_SETCALIBMODE;
  InRegs.bx = iCalibMode;
  InRegs.cx = xCalibPnt;
  InRegs.dx = yCalibPnt;

  intx( &InRegs, &OutRegs, PND_INTNUM );

  return ( ERR_SUCCESS );
}

int GetCalibState( int iCalibMode, int *xUpperCol, int
*yUpperRow,
                   int *xLowerCol, int *yLowerRow )
{
  REG_W InArgs, OutArgs;
  int iCalibDone;
  int iReturn;

  fil_char( ( NPSTR )&InArgs, 0, sizeof( InArgs ) );

  InArgs.ax = PND_GETCALIBSTAT;

  intx( &InArgs, &OutArgs, PND_INTNUM );

  if ( iCalibMode == PND_CALIBLR )
    iCalibDone = OutArgs.bx & PND_CALIBLRSTAT;
  else
    iCalibDone = OutArgs.bx & PND_CALIBULSTAT;

  if ( iCalibDone )
  {
    if ( OutArgs.bx & PND_CALIBVALID )
      iReturn = PND_CALIBDONEVALID;
    else
      iReturn = PND_CALIBDONEINVALID;

    if ( iCalibMode == PND_CALIBLR )
    {
      *xUpperCol = OutArgs.cx;
      *yUpperRow = OutArgs.dx;
      *xLowerCol = OutArgs.si;
      *yLowerRow = OutArgs.di;
    }
  }
  else
    iReturn = PND_CALIBNOTDONE;

  return ( iReturn );
}

int EnableNewCalib( BOOL fEnableNewCalib )
{
  REG_W InArgs, OutArgs;

  fil_char( ( NPSTR )&InArgs, 0, sizeof( InArgs ) );

  InArgs.ax = PND_ENABLENEWCALIB;
  InArgs.bx = ( WORD )fEnableNewCalib;

  intx( &InArgs, &OutArgs, PND_INTNUM );

  return ( ERR_SUCCESS );
}

int ActivateSleepMode( void )
{
  if ( iSleepThreadId != SMD_NOACTIVETHREAD )
  {
    if ( GetSCSCallProgress() ==
SMI_SCSCONNECTED )
      DoHostControlMode( FALSE );
    else
      DoSuspend( TRUE );

    DelThread( iSleepThreadId );
    iSleepThreadId = SMD_NOACTIVETHREAD;
  }
  else
  {
    if ( ( iSleepThreadId = GetTempEventNum() ) ==
-1 )
      return ( ERR_INTERNAL );

    AddThread( iSleepThreadId, WaitForSleep,
NULL, SMD_ONETIME,
FALSE,
              PND_SLEEPPOLLFREQ, 0 );
  }

  return ( ERR_SUCCESS );
}

void WaitForSleep( void )
{
  if ( GetRetryLimit( iSleepThreadId ) == 0 )
  {
    DelThread( iSleepThreadId );
    iSleepThreadId = SMD_NOACTIVETHREAD;

    DoSleep();
    }
}

#if defined( _MSC_VER )
#pragma warning( default : 4704 )
#endif

Copr. 1996 Zenith Data Systems Corp.

#include "sr.h"
#include "spown.h"
#include "sio.h"
#include "sm.h"

#if defined( _MSC_VER )
#pragma warning( disable : 4704 )
#endif

static PROXIMTRAPREC PRXTrapRec;
static PROXIMVARIABLES PRXVariables;
static PROXIMVERSIONINFO PRXVersionInfo;
static PRXCB lpfnPRXCallBack = NULL;
static int iConnStrengthThreadId =
SMD_NOACTIVETHREAD;
static int iPRXSetupThreadId =
SMD_NOACTIVETHREAD;
static int iCurrLinkQuality = PRX_NOLINKQUALITY;

static APIFUNC aAPIFuncTable[] =
{
  { SMI_PRXPOWERMANCE, RegisterPowerManCB
},
  { SMI_PRXUNLOADING, PrxmDriverUnload },
  { SMI_PRXNETCONFIG, NetConfigData },
  { SMI_PRXCHGREVINFO, XchgRevInfo },
  { 0, 0 }
};

APIFUNC *GetPRXFuncTable( void )
{
  return ( aAPIFuncTable );
}

BOOL GetPRXActiveStatus( void )
{
  return ( lpfnPRXCallBack != NULL );
}

void InitPRXTrapRec( void )
{
  fil_char( ( NPSTR )&PRXTrapRec, 0, sizeof(
PROXIMTRAPREC ) );

  PRXTrapRec.tr.tr_int = SMI_PRXINTNUM;
  PRXTrapRec.tr.tr_sem_srv = CRU_REFLECTINT;


  mem_cp( SMI_RUNCEIMSIGNATURE,
PRXTrapRec.szSMBeforeSignature,
         sizeof( PRXTrapRec.szSMBeforeSignature )
);
}

TRAPREC *GetPRXTrapRec( void )
{
  return ( &PRXTrapRec.tr );
}

void CheckSystem( void )
{
  int iNewLinkQuality;

  if ( GetSuspendFlag() )
  {
    if ( GetSCSCallProgress() ==
SMI_SCSCONNECTED )
      DoHostControlMode( FALSE );
    else
      DoSuspend( TRUE );
  }

  if ( ( iNewLinkQuality = GetLinkQuality() ) !=
ERR_INTERNAL )
  {
    if ( iNewLinkQuality != iCurrLinkQuality )
    {
      switch( iNewLinkQuality )
      {
        case PRX_DISCONNECTED:
          SetTowerIcon( SBS_TOWERON,
SBS_WAVESOFF );
          break;

        case PRX_LOWQUALITY:
          SetTowerIcon( SBS_TOWERON,
SBS_WAVESHIGHBLINK );
          break;
```

```
      case PRX_HIGHQUALITY
        SetTowerIcon( SBS_TOWERON,
SBS_WAVESON );
        break;
    }

    lCurLinkQuality = lNewLinkQuality;
  }
 }
}

APIFUNCRET RegisterPowerMonCB( struct REGW
*CallerRegs )
{
  lpfnPRXCallBack = MK_FP( CallerRegs->es,
CallerRegs->di );

  if ( ( lPRXSetupThreadId = GetTempEventNum() )
< 0 )
    return;

  AddThread( lPRXSetupThreadId,
WaitForPRXSetup, NULL,
SMO_ONETIME, FALSE,
        1, 0 );

  CallerRegs->ax = ( WORD )ERR_SUCCESS;

  SetForegroundRegs( CallerRegs );
}

void WaitForPRXSetup( void )
{
  PROXIMVARIABLES far *NewPRXVariables;
  WORD wSegNewVars;
  WORD wOffNewVars;
  int iSizeNewVariables = 0;

  SetThread( lPRXSetupThreadId );
  lPRXSetupThreadId = SMO_NOACTIVETHREAD;

  if ( lpfnPRXCallBack != NULL )
  {
    AX( PRX_CSPRXVARIABLES );
    ( *lpfnPRXCallBack )();

    _asm
    {
      or  ax,ax
      jnz error

      mov iSizeNewVariables, cx
      mov wSegNewVars, es
      mov wOffNewVars, di
    error:
    }

    if ( iSizeNewVariables > 0 )
    {
      NewPRXVariables = MK_FP( wSegNewVars,
wOffNewVars );

      if ( iSizeNewVariables == sizeof ( PRXVariables
) )
        PRXVariables = *NewPRXVariables;
    }
  }
}

APIFUNCRET ProximDriverUnload( struct REGW
*CallerRegs )
{
  lpfnPRXCallBack = NULL;

  CallerRegs->ax = ERR_SUCCESS;

  SetForegroundRegs( CallerRegs );
}

APIFUNCRET NetConfigData( struct REGW
*CallerRegs )
{
  PROXIMNETCONFIGDATA far *pPRXNetConfig =
    ( PROXIMNETCONFIGDATA far * )MK_FP(
CallerRegs->es,
CallerRegs->si );

  if ( CallerRegs->cx == sizeof (
PROXIMNETCONFIGDATA ) )
  {
    pPRXNetConfig->DomainID =
UlConfigData.nDomainID;
    CallerRegs->ax = ERR_SUCCESS;
  }
  else
    CallerRegs->ax = ( WORD )ERR_INTERNAL;

  SetForegroundRegs( CallerRegs );
}

APIFUNCRET XchgRevInfo( struct REGW
*CallerRegs )
{
  PROXIMVERSIONINFO far *NewPRXVersionInfo;

  if ( CallerRegs->cx == sizeof (
PROXIMVERSIONINFO ) )
  {
    newPRXVersionInfo = MK_FP( CallerRegs->es,
CallerRegs->di );


    PRXVersionInfo.wMajorVersion =
GEN_SUBMAJORVERSIONNUM;
    PRXVersionInfo.wMinorVersion =
GEN_SUBMINORVERSIONNUM;
    PRXVersionInfo.lpszModuleName = ( LPSTR
)szSubModuleName;

    CallerRegs->es = SEG( &PRXVersionInfo );
    CallerRegs->di = OFF( &PRXVersionInfo );

    CallerRegs->ax = ERR_SUCCESS;
  }
  else
    CallerRegs->ax = ( WORD )ERR_INTERNAL;

  SetForegroundRegs( CallerRegs );
}

int NotifySuspend( void )
{
  if ( lpfnPRXCallBack == NULL )
    return ( ERR_INTERNAL );

  AX( PRX_CSSUSPEND );
  return ( ( *lpfnPRXCallBack )() );
}

int NotifyResume( void )
{
  if ( lpfnPRXCallBack == NULL )
    return ( ERR_INTERNAL );

  AX( PRX_CSRESUME );
  return ( ( *lpfnPRXCallBack )() );
}

int SetSecurityID( char *szNewSecurityID )
{
  if ( lpfnPRXCallBack == NULL )
    return ( ERR_INTERNAL );

  _asm
  {
    mov  ax, PRX_CSSETSECUREID
    push ds
    pop  es
    mov  di, szNewSecurityID
  }

  return ( ( *lpfnPRXCallBack )() );
}

BOOL IsSynchronized( void )
{
  BOOL bNewSynchronizeFlag;

  if ( PRXVariables.lpszSynchronizeFlag == NULL )
    return ( ERR_INTERNAL );

  PCS_BEGINCRITICAL;
  bNewSynchronizeFlag = ( BOOL
)*PRXVariables.lpszSynchronizeFlag;
  PCS_ENDCRITICAL;

  return ( bNewSynchronizeFlag );
}

LPSTR GetRomVersion( void )
{
  LPSTR lpszNewRomVersion;

  if ( PRXVariables.lpszRomVersion == NULL )
    return ( NULL );

  PCS_BEGINCRITICAL;
  lpszNewRomVersion = ( LPSTR
)PRXVariables.lpszRomVersion;
  PCS_ENDCRITICAL;

  return ( lpszNewRomVersion );
}

int GetLinkQuality( void )
{
  int lNewLinkQuality;

  if ( PRXVariables.lpszLinkQuality == NULL )
    return ( ERR_INTERNAL );

  PCS_BEGINCRITICAL;
  lNewLinkQuality = ( int
)*PRXVariables.lpszLinkQuality;
  PCS_ENDCRITICAL;

  return ( lNewLinkQuality );
}

#if defined( _MSC_VER )
#pragma warning( default : 4704 )
#endif


Copr. 1995 Zenith Data Systems Corp.

#include "ui.h"
#include "sis.h"
#include "sl.h"
#include "sparm.h"
#include "sperm.h"
#include "sm.h"
#include "smh.h"

#if defined( _MSC_VER )
#pragma warning( disable : 4704 )
#endif

static BYTE bGearIdx = 0;

static ZDSTRAPREC       SCSTrapRec;
static CALLREC          SCSServiceRec;
static CALLREC          SCSEventLoopRec;
static BOOL             fSCSActive = FALSE;
static BOOL             fMenStatus = FALSE;
static BOOL             fLocalKbdStatus = FALSE;
static BOOL             fHostControlRequested =
FALSE;
static BOOL             fConnectRequested;
static BYTE             fSendPWRetryDone = FALSE;
static BYTE             fWaitVidUnblockActive =
FALSE;
static BYTE             fBadVideoMsgRecv = FALSE;

static BOOL             fUpdatingConnectStatus =
FALSE;

static int              fSetManDone = FALSE;
static int              fSetMemDone = FALSE;
static int              fFullRepaintDone = FALSE;
static int              iFreeMemPercent = 0;
static BYTE               eOSKType;
static BYTE             fRepaintRequired = FALSE;
static CONNERROR        nConnectErrorCode =
SCS_NOCONNERROR;
static PRIVATEMSGBUFF   RecvPrivMsgBuff;
static PRIVATEMSGBUFF   SendPrivMsgBuff;
static SYSTEMSTATUSBUFF SystemStatusBuff;
static int              iSCOSEntrie;
static int              iTempThreadId;
static int              iSUIThreadId;
static int              iPSetMemThreadId;
static int              iDisconThreadId;
static int              iHostControlThreadId;
static int              iCancelConnectThreadId;
static int              iChThreadId;
static int              iPSRetryThreadId =
SMO_NOACTIVETHREAD;
static int              iWaitVidUnblockThreadId =
SMO_NOACTIVETHREAD;
static FARCALLENTRY     lpfnFarCallEntry = NULL;

static char             *szHostFileName = NULL;

static APIFUNC aAPIFuncTable[]=
{
  { SMI_SCSLOADING, SCSLoading },
  { SMI_SLLOADSUI, SLLoadSUI },
  { SMI_SLENABLEKBD, SLEnableKbd },
  { SMI_SLGETFRAMETYPE, SLGetFrameType },
  { SMI_SLDEFINEOLDVIDVECTOR,
SLDefineOldVidVector },
  { SMI_SLGETMLIDSTATUS, SLGetMLIDStatus },
  { SMI_UNLOADOSK, UnloadOSK },
  { SMI_CHANGETOBADVIDEO,
ChangeToBadVideo },
  { SMI_REQNOTIFYDOSWIN, NotifyDosWin },
  { SMI_REQUNIOCCCLOSE, NotifyUniOccClose },
  { SMI_ACKFLASHBREAK, AckFlashBreak },
  { SMI_ACKTOTALFILES, AckTotalFlashFiles },
  { SMI_ACKPATHASSTRING, AckPathFlashFile },
  { SMI_ACKACTIVEUPDATE, AckActiveUpdate },
  { SMI_ACKOCCDEFINE, AckOccDefine },
  { SMI_ACKOCCCLOSE, AckOccClose },
  { 0, 0 }
};

BOOL GetUpdatingConnectStatus( void )
{
  return ( fUpdatingConnectStatus );
}

void SetUpdatingConnectStatus( BOOL fNewStatus )
{
  fUpdatingConnectStatus = fNewStatus;
}

APIFUNC *GetSCSFuncTable( void )
{
  return ( aAPIFuncTable );
}

void SetSCSActiveStatus( BOOL fNewSCSActive )
{
  fSCSActive = fNewSCSActive;
}

BOOL GetSCSActiveStatus( void )
{
  return ( fSCSActive );
}

void SetConnectRequested( BOOL
fNewConnectRequested, BYTE
nUpdateIcon )
{
  if ( ( fConnectRequested = fNewConnectRequested
) ==
SCS_CONNECTREQUESTED )
  {
    if ( nUpdateIcon == SCS_UPDATEICON )
      SetWaitingIcon( SBS_WAITINGICONON, TRUE
);
  }
  else
  {
    if ( nUpdateIcon == SCS_UPDATEICON )
      SetWaitingIcon( SBS_WAITINGICONOFF,
TRUE );
  }
}

BOOL GetConnectRequested( void )
{
  return ( fConnectRequested );
}

NPSTR GetPrivateMsgBuff( int *iBuffLen )
{
  *iBuffLen = RecvPrivMsgBuff.iBuffLen;

  return ( RecvPrivMsgBuff.aMsgBuff );
}

char GetConnectErrCode( void )
{
  return ( nConnectErrorCode );
}

int GetSCOSEntrie( BYTE nClearError )
{
  int iNewSCOSEntrie = 0;

  PCS_BEGINCRITICAL;
  iNewSCOSEntrie = iSCOSEntrie;

  if ( nClearError == SCS_CLEARERROR )
    iSCOSEntrie = 0;

  PCS_ENDCRITICAL;

  return ( iNewSCOSEntrie );
}

void SetFullRepaint( int fNewFullRepaintDone )
{
  fFullRepaintDone = fNewFullRepaintDone;
}

void InitSCSTrapRec( void )
{
  fc_chr( ( NPSTR )&SCSTrapRec, 0, sizeof(
ZDSTRAPREC ) );

  SCSTrapRec.tr.tr_int = SMI_SCSINITNUM;
  SCSTrapRec.tr.tr_com_cnt = 2;

  strcpy( SCSTrapRec.szSMAbortSignature,
szSMSignature );
}

TRAPREC *GetSCSTrapRec( void )
{
```

```
  return ( &SCSTrapRec.ir );
}

void InitSCSCallRec( void )
{
  DWORD dwCallService = ( DWORD )( FARPROC
)SCSEventLoopService;

  fi_str( ( NPSTR )&SCSEventLoopRec, 0, sizeof(
CALLREC ) );

  SCSEventLoopRec.cFarCallOpCode = ( BYTE
)SMD_CALLOPCODE;
  SCSEventLoopRec.aCallSeek[0] = LOBYTE(
LOWORD( dwCallService )
);
  SCSEventLoopRec.aCallSeek[1] = HIBYTE(
LOWORD( dwCallService )
);
  SCSEventLoopRec.aCallSeek[2] = LOBYTE(
HIWORD( dwCallService )
);
  SCSEventLoopRec.aCallSeek[3] = HIBYTE(
HIWORD( dwCallService )
);
  SCSEventLoopRec.cFarRetOpCode = ( BYTE
)SMD_RETOPCODE;
  strcpy( SCSEventLoopRec.szSMAlertSignature,
SMD_SIGNATURE );

  dwCallService = ( DWORD )( FARPROC
)SCSRecvMsgService;
  mem_cp( ( PVOID )&SCSEventLoopRec, ( PVOID
)&SCSRecvMsgRec,
sizeof( CALLREC ) );
  SCSRecvMsgRec.aCallSeek[0] = LOBYTE(
LOWORD( dwCallService ) );
  SCSRecvMsgRec.aCallSeek[1] = HIBYTE(
LOWORD( dwCallService ) );
  SCSRecvMsgRec.aCallSeek[2] = LOBYTE(
HIWORD( dwCallService ) );
  SCSRecvMsgRec.aCallSeek[3] = HIBYTE(
HIWORD( dwCallService ) );
}

void FAR SCSEventLoopService( void )
{
  _asm
  {
    or   ah,ah
    jnz  process
    jmp  exit

process:
    cli

    push ds
    push ax
    push bx
    push cx
    push dx
    push si
    push di
    mov  ds,cs:SMDAh
  }

  PushEventNum( SM_SCSEVENTNUM );
  lpfnFarCallEntry = MK_FP( _ssode, _fcall_entry );

  _asm
  {
    pop  di
    pop  si
    pop  dx
    pop  cx
    pop  bx
    pop  ax
    mov  al,ch
    xor  ah,ah
    add  ax, SM_EVENTLOOPBASE

    sti

    call [lpfnFarCallEntry]

    pop  ds
  }

exit:
  return;
}

void FAR SCSRecvMsgService( void )
{
  _asm
  {
    cli

    push ds
    push ax
    push bx
    push cx
    push dx
    push si
    push di
    mov  ds,cs:SMDAh
  }

  PushEventNum( SM_SCSEVENTNUM );
  lpfnFarCallEntry = MK_FP( _ssode, _fcall_entry );

  _asm
  {
    pop  di
    pop  si
    pop  dx
    pop  cx
    pop  bx
    pop  ax

    push ds
    pop  ds
    mov  ax, [di]
    add  ax, SM_PRIVMSGBASE

    mov  ds,cs:SMDAh

    sti

    call [lpfnFarCallEntry]

    pop  ds
  }
}

APIFUNCRET SCSLoading( struct REGW
*CallerRegs )
{
  CallerRegs->ax = 0x0001;

  CallerRegs->bx = SEG( &SCSRecvMsgRec );
  CallerRegs->si = OFF( &SCSRecvMsgRec );
  CallerRegs->dx = SEG( &SCSEventLoopRec );
  CallerRegs->di = OFF( &SCSEventLoopRec );

  CallerRegs->cx = SMD_DISPATFREQ;

  SetForegroundRegs( CallerRegs );

  if ( ( iTempThreadId = GetTempEventNum() ) < 0
)
    return;

  AddThread( iTempThreadId, ( NEARPROC
)SetupSCOS, NULL,
SMD_ONETIME, FALSE,
           SCS_LOADSCSPOLLFREQ, 0 );
}

APIFUNCRET UnloadOSX( struct REGW
*CallerRegs )
{
  int iCurrSerCode = GetCurrSerCode();

  if ( GetSUIReady() && IsOSX( iCurrSerCode ) )
  {
    SetCurrSerCode( iCurrSerCode |
SUI_OSXVIDCHANGEMASK );
    UnloadSUI( SUI_NOUNLOADSUI );
  }
}

APIFUNCRET ChangeToBadVideo( struct REGW
*CallerRegs )
{
  if ( GetSCSCallProgress() ==
SM_SCSCONNECTED )
  {
    BadVideoMsgRecv = TRUE;
    CloseDisableConnection();
  }
}

APIFUNCRET NotifyOsdWin( struct REGW
*CallerRegs )
{
  int iMsgStatus;

  PCS_BEGINCRITICAL

  if ( ( iMsgStatus = PrepPrivateMessage(
CallerRegs ) ) ==
ERR_SUCCESS )
    SetHostMode( ( int )*RecvPrMsgBuff.aMsgBuff );

  PCS_ENDCRITICAL

  if ( iMsgStatus == ERR_SUCCESS )
    SendPrivateMessage(
PM_ACKNOTIFYDOSWIN, 0, NULL );

  SetForegroundRegs( CallerRegs );
}

APIFUNCRET NotifyUnlOscClose( struct REGW
*CallerRegs )
{
  int iMsgStatus;

  PCS_BEGINCRITICAL

  iMsgStatus = PrepPrivateMessage( CallerRegs );

  PCS_ENDCRITICAL

  if ( iMsgStatus == ERR_SUCCESS )
  {
    TRACE( "NOTICE: Received UNI close PM,
closing OSXV" );
    SendPrivateMessage( PM_ACKUNIOCCCLOSE,
0, NULL );

    if ( IsOSX( GetCurrSerCode() ) )
    {
      SetCurrSerCode( GetCurrSerCode() |
SUI_OSXUNICLOSEMASK );
      UnloadSUI( SUI_NOUNLOADSUI );
    }
  }

  SetForegroundRegs( CallerRegs );
}

APIFUNCRET AskFlashBreak( struct REGW
*CallerRegs )
{
  PCS_BEGINCRITICAL

  if ( PrepPrivateMessage( CallerRegs ) ==
ERR_SUCCESS )
    SetTmpFilePercent( *( int *
)RecvPrMsgBuff.aMsgBuff );

  PCS_ENDCRITICAL

  SetForegroundRegs( CallerRegs );
}

APIFUNCRET AskTotalFlashFiles( struct REGW
*CallerRegs )
{
  PCS_BEGINCRITICAL

  if ( PrepPrivateMessage( CallerRegs ) ==
ERR_SUCCESS )
    SetTotalFlashFiles( *( int *
)RecvPrMsgBuff.aMsgBuff );

  PCS_ENDCRITICAL

  SetForegroundRegs( CallerRegs );
}

APIFUNCRET AskPathFlashFile( struct REGW
*CallerRegs )
{
  PCS_BEGINCRITICAL

  if ( PrepPrivateMessage( CallerRegs ) ==
ERR_SUCCESS )
    SetPathFlashFile( ( LPSTR
)RecvPrMsgBuff.aMsgBuff );

  PCS_ENDCRITICAL

  SetForegroundRegs( CallerRegs );
}

APIFUNCRET AskActiveUpdate( struct REGW
*CallerRegs )
{
  PCS_BEGINCRITICAL

  if ( PrepPrivateMessage( CallerRegs ) ==
ERR_SUCCESS )
  {
    if ( RecvPrMsgBuff.iBuffLen > 1 )
      SetNameActiveUpdate( ( LPSTR
)RecvPrMsgBuff.aMsgBuff );
    else
      SetNameActiveUpdate( ( LPSTR )NULL );
  }

  PCS_ENDCRITICAL

  SetForegroundRegs( CallerRegs );
}

APIFUNCRET AskOscDefine( struct REGW
*CallerRegs )
{
  PCS_BEGINCRITICAL

  if ( PrepPrivateMessage( CallerRegs ) ==
ERR_SUCCESS )
  {
    if ( RecvPrMsgBuff.iBuffLen > 1 )
    {
      if ( LOBYTE( *( int * )RecvPrMsgBuff.aMsgBuff
) == TRUE )
        SetOscDefineAcked( PM_ACKEDTRUE );
      else
        SetOscDefineAcked( PM_ACKEDFALSE );
    }
    else
      SetOscDefineAcked( PM_ACKEDFALSE );
  }

  PCS_ENDCRITICAL

  SetForegroundRegs( CallerRegs );
}

APIFUNCRET AskOscClose( struct REGW
*CallerRegs )
{
  PCS_BEGINCRITICAL

  if ( PrepPrivateMessage( CallerRegs ) ==
ERR_SUCCESS )
  {
    if ( RecvPrMsgBuff.iBuffLen > 1 )
    {
      if ( LOBYTE( *( int * )RecvPrMsgBuff.aMsgBuff
) == TRUE )
        SetOscCloseAcked( PM_ACKEDTRUE );
      else
        SetOscCloseAcked( PM_ACKEDFALSE );
    }
    else
      SetOscCloseAcked( PM_ACKEDFALSE );
  }

  PCS_ENDCRITICAL

  SetForegroundRegs( CallerRegs );
}


int PrepPrivateMessage( struct REGW *CallerRegs )
{
  int iReturn;
  LPSTR lpsRecvMsg = ( LPSTR )MAKELONG(
CallerRegs->di,
CallerRegs->dx );

  fi_str( ( PVOID )&RecvPrMsgBuff, 0, sizeof(
RecvPrMsgBuff )
);

  if ( lpsRecvMsg != NULL && CallerRegs->bx <
SCS_MAXLENMSGBUFF )
  {
    fmem_cp( ( LPSTR )lpsRecvMsg, ( LPSTR
)&RecvPrMsgBuff.iMsgID, CallerRegs->bx );
    CallerRegs->ax = 1;
    iReturn = 0;

#if !defined( PROD )
    sprintf( szTempStr, "NOTICE: Received Private
Message
0:%d", RecvPrMsgBuff.iMsgID );
    TRACE( szTempStr );
    sprintf( szTempStr, "NOTICE: First byte of the
Private
Message: %d", *RecvPrMsgBuff.aMsgBuff );
    TRACE( szTempStr );
#endif
  }
  else
  {
    CallerRegs->ax = 0;
    iReturn = ERR_INTERNAL;
  }

  return ( iReturn );


}

void SetupSCOS( void )
{
  REG_W InArgs, OutArgs;

  if ( iTempThreadId >= 0 )
```

```
{
  DelThread( lTempThreadIdx );
  lTempThreadIdx = -1;
}

fl_chr( ( NPSTR )&SystemStatusBuff, 0, sizeof (
SystemStatusBuff ) );
fl_chr( ( NPSTR )&InArgs, 0, sizeof ( InArgs ) );

InArgs.ax = ( WORD
)SCS_SETUPSYSSTATBUFF;
InArgs.dx = SEG( &SystemStatusBuff );
InArgs.di = OFF( &SystemStatusBuff );

intm( &InArgs, &OutArgs, SCS_INTNUM );

SetupSCOSEntNo( &SCOSEntNo );

SetSCSActiveStatus( TRUE );
}

int SetupSCOSEntNo( int FAR *ItemLocation )
{
  REG_W InArgs, OutArgs;

  fl_chr( ( NPSTR )&InArgs, 0, sizeof ( InArgs ) );

  InArgs.ax = SCS_ERRNOLOCATION;
  InArgs.es = SEG( ItemLocation );
  InArgs.bx = OFF( ItemLocation );

  intm( &InArgs, &OutArgs, SCS_INTNUM );

  if ( OutArgs.ax != ERR_SUCCESS )
    return ( ERR_INTERNAL );

  return ( ERR_SUCCESS );
}

int BlankSCOSVideo( BYTE fVideoStatus )
{
  REG_W InArgs, OutArgs;

  InArgs.ax = SCS_SCOSVIDEO | ( fVideoStatus ?
SCS_SCOSVIDBLOCK :
SCS_SCOSVIDUNBLOCK );

  intm( &InArgs, &OutArgs, SCS_INTNUM );

  if ( OutArgs.ax != ERR_SUCCESS )
    return ( ERR_INTERNAL );

  return ( ERR_SUCCESS );
}


int DoHostControlMode( BOOL fHostControlStatus )
{
  if ( GetSCSCallProgress() ==
SM_SCSDISCONNECTED )
    return ( ERR_INTERNAL );

  if ( ( fHostControlThreadIdx = GetTempEventNum()
) < 0 )
    return ( ERR_INTERNAL );

  AddThread( fHostControlThreadIdx,
WaitForHostControl, NULL,
SMD_MANYTIMES, FALSE,
          SCS_HOSTCTRLPOLLFREQ,
SCS_HOSTCTRLMAXRETRY );

  if ( fHostControlStatus )
  {
    if ( SendPrivateMessage(
PM_REQHOSTCONTROL, 0, NULL ) !=
ERR_SUCCESS )
      return ( ERR_INTERNAL );
  }

  fHostControlRequested = TRUE;

  SetWaitingIcon( SSS_WAITINGICONON, TRUE );
}

void WaitForHostControl( void )
{
  static BYTE fDisconnectRequested = FALSE;

  if ( !fDisconnectRequested )
  {
    DisableConnection();
    fDisconnectRequested = TRUE;
  }

  if ( GetSCSCallProgress() ==
SM_SCSDISCONNECTED )
    DelThread( fHostControlThreadIdx );
  else if ( GetRetryLimit( fHostControlThreadIdx ) ==
0 )
  {
    DelThread( fHostControlThreadIdx );
    DoSuspend( TRUE );
  }
}

int MakeTheConnection( BOOL fNewHostStatus,
BOOL
fNewLocalKbdStatus )
{
  int fHostVersionNum = GetCurrHostVersionNum();
  char *szCurrNodeAddress =
GetCurrNodeAddress();

  if ( *szCurrNodeAddress == NULL ||
fHostVersionNum == 0 )
    return ( ERR_INTERNAL );

  if ( fHostVersionNum < MAKEWORD(
GEN_HMELPMINORVERSIONNUM,
GEN_HMELPMAJORVERSIONNUM ) )
  {
    SMVideoBusy( DoVersionMsgBox );
    return ( ERR_SUCCESS );
  }

  SetConnectRequested(
SCS_CONNECTREQUESTED, SCS_UPDATEICON
);

  if ( GetSUIReady() )
    SMVideoBusy( DoExecConnect );
  else
  {
    if ( SMDosBusy( CSExecConnect ) !=
ERR_SUCCESS )
      return ( ERR_INTERNAL );
  }

  return ( ERR_SUCCESS );
}

void DoVersionMsgBox( void )
{
  char szTempStr[ STR_STRMAXLENERR ];

  sprintf( szTempStr, STR_SUIHOSTVERTOOLOW,
szSMVersionName );
  OpenMessageBox( szTempStr, 0,
SUI_CENTERJUSTIFIED, SUI_OK );
}

int ResumeTheConnection( void )
{
  if ( IsPWRequired() )
    DoMessageBox( NULL, SUI_LOGIN,
SUI_LEFTJUSTIFIED, SUI_OK |
SUI_CANCEL,
          CSLoginButtonPressed,
SUI_LOGINTIMEOUT );
  else
  {
    OpenMessageBox( STR_SUIRESUMINGCONN,
0, SUI_LEFTJUSTIFIED, 0
);

    SetConnectRequested(
SCS_CONNECTREQUESTED,
SCS_NOUPDATEICON
);

    if ( ( lCancelConnectThreadIdx =
GetTempEventNum() ) ==
ERR_INTERNAL )
      return( ERR_INTERNAL );

    TimerManager( TF_SET,
lCancelConnectThreadIdx, 30L );

    AddThread( lCancelConnectThreadIdx,
WaitForCancelConnect,
NULL, SMD_MANYTIMES,
          FALSE, SUI_CANCELCONNPOLLFREQ,
SUI_CANCELCONNMAXRETRY );

    if ( SMDosBusy( CSExecConnect ) !=
ERR_SUCCESS )
      return( ERR_INTERNAL );
  }

  return ( ERR_SUCCESS );
}

void CSLoginButtonPressed( int ButtonCode )
{
  if ( ButtonCode == SUI_OK )
  {
    SetConnectRequested(
SCS_CONNECTREQUESTED,
SCS_NOUPDATEICON
);

    OpenMessageBox( STR_SUIRESUMINGCONN2,
0, SUI_LEFTJUSTIFIED, 0
);

    if ( ( lCancelConnectThreadIdx =
GetTempEventNum() ) ==
ERR_INTERNAL )
      return;

    TimerManager( TF_SET,
lCancelConnectThreadIdx, 30L );

    AddThread( lCancelConnectThreadIdx,
WaitForCancelConnect,
NULL, SMD_MANYTIMES,
          FALSE, SUI_CANCELCONNPOLLFREQ,
SUI_CANCELCONNMAXRETRY );

    SMDosBusy( CSExecConnect );
  }
  else
    CSMsgBoxButtonPressed( ButtonCode );
}

void CSMsgBoxButtonPressed( int ButtonCode )
{
  int ActionCode = GetCurrActionCode();

  HideMessageBox();

  if ( ActionCode == SUI_LASTCONNECTION ||
ActionCode ==
SUI_BADVIDEOMSG )
    SMVideoBusy( DoHostScreen );

}

void DoHostScreen( void )
{
  LoadSUI( SUI_SPECIFIEDSCREEN,
SUI_HOSTSELECTION );
}

void DoExecConnect( void )
{
  SMDosBusy( CSExecConnect );
}


void CSExecConnect( void )
{
  REG_W InArgs, OutArgs;
  RPARM *SCSRParm;
  char *szCurrNodeAddress =
GetCurrNodeAddress();
  char *szCurrHostName = GetLBHost( -1 );

  nConnectErrorCode = SCS_NOCONNERROR;


  if ( ( SCSRParm = ( RPARM * )malloc( sizeof (
RPARM ) ) ) ==
NULL )
    return;

  fl_chr( ( NPSTR )SCSRParm, 0, sizeof( RPARM )
);

  SCSRParm->rpstatmsgp = 0;
  SCSRParm->rpprotocol = SCS_SPX;

  strcpy( SCSRParm->rpinternet,
szCurrNodeAddress );

  if ( IsPWRequired() )
  {
    strcpy( SCSRParm->rpdspw, szPassword );
    strcpy( SCSRParm->rpdsid,
SCS_STRDEFUSERID );

    UIConfigData.bLastConnPassword = TRUE;

  }
  else
    UIConfigData.bLastConnPassword = FALSE;



#if defined( IPTEST )
  #pragma message( "Warning: IP Address is fixed."
)
  strcpy( SCSRParm->rpinternet,
"0000000000020A0001FEF" );
#endif

#if !defined( PROD )
  sprintf( szTempStr, "NOTICE: pw - %s\r       uid -
%s\r
nid - %s\r", SCSRParm->rpdspw,
          SCSRParm->rpdsid, SCSRParm->rpinternet
);
  TRACE( szTempStr );
#endif

  InArgs.ax = SCS_SMAKECON;
  InArgs.es = SEG( SCSRParm );
  InArgs.bx = OFF( SCSRParm );

  SetSCSAbortFlag( FALSE );
  SetMsgBoxReturnCode( SUI_NOBUTTONS );

  _and_tsr_flg( ~SMD_SCHEDULERS );

  intm( &InArgs, &OutArgs, SCS_INTNUM );

  DelThread( lCancelConnectThreadIdx );

  SetConnectRequested(
SCS_NOCONNECTREQUESTED,
SCS_NOUPDATEICON
);

  if ( OutArgs.ax == SCS_ACCEPTED ||
      GetSCOSEntNo( SCS_RETAINERROR ) ==
SCS_NOLOGINERROR )
  {
    nConnectErrorCode = SCS_NOCONNERROR;
    strcpy( UIConfigData.szLastNodeAddress,
szCurrNodeAddress );
    strcpy( UIConfigData.szLastHostName,
szCurrHostName );
    SetCurrHostName( szCurrHostName );

    if ( ( lSUIThreadIdx = GetTempEventNum() ) ==
ERR_INTERNAL )
      return;

    AddThread( lSUIThreadIdx, ( NEARPROC
)WaitForSUIUnload, NULL,
          SMD_POLLED, FALSE,
SCS_WAITSUIPOLLFREQ, 0 );

    AddThread( SCS_DISCOEVENTNUM,
WaitForStatusChange, NULL,
          SMD_POLLED, FALSE,
SCS_DISCOPOLLFREQ, 0 );

    UnloadSUI( SUI_NOUNLOADSUI );
  }
  else
  {
    SetWaitingIcon( SSS_WAITINGICONOFF,
SCS_UPDATEICON );

    *UIConfigData.szLastNodeAddress = NULL;

    if ( nConnectErrorCode ==
SCS_NOCONNERROR )
      nConnectErrorCode = TranslateConnectError();

    switch ( nConnectErrorCode )
    {
      case SCS_ERRTIMEOUT:
        DoMessageBox(
STR_SUICONNECTTIMEOUT, 0,
SUI_CENTERJUSTIFIED, SUI_OK,
CSMsgBoxButtonPressed, 0 );
        break;

      case SCS_ERRPASSWORD:
        DoMessageBox(
STR_SUIPASSWORDREJECTED, 0,
SUI_CENTERJUSTIFIED, SUI_OK,
CSMsgBoxButtonPressed, 0 );
        break;

      case SCS_ERRLOGINID:
        DoMessageBox(
STR_SUILOGINIDREJECTED, 0,
SUI_CENTERJUSTIFIED, SUI_OK,
CSMsgBoxButtonPressed, 0 );
        break;

      case SCS_ERRUNSUPVIDMODE:
        DoMessageBox( STR_SUIUNSUPVIDMODE,
0,
SUI_CENTERJUSTIFIED, SUI_OK,
CSMsgBoxButtonPressed, 0 );
```

```
          break;

        case SCS_ERRUSERABORT
          CSMsgBoxButtonPressed( SUI_CANCEL );
          break;

        case SCS_ERRUNKNOWN
        default:
          DoMessageBox(
STR_SUICONNECTERRUNKNOWN, 0,
SUI_CENTERJUSTIFIED, SUI_OK,
CSMsgBoxButtonPressed, 0 );
          break;
      }
    }

    free( SCSRParm );
}

void WaitForCancelConnect( void )
{
  static int iWaitForSUI = 0;

  if ( GetMsgBoxReturnCode() == SUI_CANCEL )
    nConnectErrorCode = SCS_ERRUSERABORT;
  else if ( GetEntryLimit( iCancelConnectThreadId )
== 0 )
    nConnectErrorCode = SCS_ERRTIMEOUT;

  if ( nConnectErrorCode != SCS_NOCONNERROR
)
  {
    SetSCSAbortFlag( TRUE );
    DelThread( iCancelConnectThreadId );
  }

  if (TimerManager (TF_CHECK,
iCancelConnectThreadId, 0) ==
TIMEOUT_FIRED)
  {
    switch (iWaitForSUI)
    {
      case 0:
      TimerManager (TF_RESET,
iCancelConnectThreadId, 0);

      HideMessageBox ();

      if (TimerManager (TF_CHECK,
iCancelConnectThreadId, 0L) ==
TIMEOUT_AVAILABLE)
      {
        TimerManager (TF_SET,
iCancelConnectThreadId, 1L);
        iWaitForSUI = 1;
      }
      break;

      case 1:
      TimerManager (TF_RESET,
iCancelConnectThreadId, 0);

      OpenMessageBox( STR_SUIRESUMINGCONN,
0, SUI_LEFTJUSTIFIED,
SUI_CANCEL );

      iWaitForSUI = 0;
      break;
    }
  }

}

void WaitForStatusChange( void )
{
  static char nOldVideoMode = -1;
  char nCurrVideoMode = GetCurrVidMode();
  int iCurrScrCode;
  int nSUIStatus;

  if ( nOldVideoMode == -1 )
    nOldVideoMode = nCurrVideoMode;

  if ( GetSCSCallProgress() ==
SMI_SCSDISCONNECTED )
  {
    nSUIStatus = GetSUIStatus();

    if ( !HostControlRequested || ( DoSuspend(
TRUE ) !=
ERR_SUCCESS ) )
    {
      bHostControlRequested = FALSE;

      if ( nSUIStatus != SMI_SUIUNLOADING &&
nSUIStatus !=
SMI_SUIDEACTIVATING )
      {
        DelThread( SCS_DISCOEVENTNUM );
        SetCurrHostName( szHostStr );
        SetWaitingIcon( SSS_WAITINGICONOFF,
TRUE );

        if ( !nSetupDlg( GetCurrScrCode() ) )
          UpdateSUIConnectStatus();
        else
        {

          if ( !BadVideoMsgRecv )
          {
            BadVideoMsgRecv = FALSE;

            LoadSUI( SUI_BADVIDEOMSG,
SUI_NOSCREEN );
          }
          else
            LoadSUI( SUI_SPECIFIEDSCREEN,
SUI_HOSTSELECTION );
        }
      }
    }
  }
  else
  {
    iCurrScrCode = GetCurrScrCode();

    if ( nCurrVideoMode != nOldVideoMode )

    {
      if ( GetSUIReady() &&
          !nOSE( iCurrScrCode ) &&
!nOSEAnSetupDlg(
iCurrScrCode ) )
          UnloadSUI( SUI_NOUNLOADSUI );
    }
  }

  nOldVideoMode = nCurrVideoMode;
}

void WaitForSUIUnload( void )
{
  if ( !GetSUIReady() )
    DelThread( iSUIThreadId );
}

int SetMonitor( BOOL bNewMonStatus, BOOL
bNewLocalKbdStatus )
{
  iSetMonDone = ERR_INPROGRESS;

  if ( !GetSCSActiveStatus() )
    return ( ERR_INTERNAL );

  if ( GetSCSCallProgress() !=
SMI_SCSCONNECTED )
    iSetMonDone = ERR_SUCCESS;
  else
  {
    bMonStatus = bNewMonStatus;
    bLocalKbdStatus = bLocalKbdStatus;

    if ( SMDosBusy( CSExecMonitor ) !=
ERR_SUCCESS )
    {
      iSetMonDone = ERR_INTERNAL;
      return ( ERR_INTERNAL );
    }
  }

  return ( ERR_SUCCESS );
}

void CSExecMonitor( void )
{
  REG_W InArgs, OutArgs;

  InArgs.ax = ( bMonStatus ? SCS_MONITORON :
SCS_MONITOROFF );
  InArgs.ax |= ( bLocalKbdStatus ?
SCS_LOCALKBDON :
SC*_LOCALKBDOFF );

  SetReentrancy( FALSE );
  Intx( &InArgs, &OutArgs, SCS_INTNUM );
  SetReentrancy( TRUE );

  if ( OutArgs.ax == SCS_ACCEPTED )
  {
    nConnectErrorCode = SCS_NOCONNERROR;
    iSetMonDone = ERR_SUCCESS;
  }
  else
  {
    nConnectErrorCode =
SCS_ERRFULLSCRPAINT;
    iSetMonDone = ERR_SUCCESS;
    TRACE( "ERROR: CoSession monitor call was
not accepted.
Reported as accepted anyway.\n" );
  }
}

int CheckMonitor( void )
{
  return ( iSetMonDone );
}

int SetSCSMemory( int iNewFreeMemPercent, int
iNewOSKType, BYTE
nDosBusy )
{
  iSetMemDone = ERR_INPROGRESS;
  nOSKType = LOBYTE( iNewOSKType );

  if ( !GetSCSActiveStatus() )
    return ( ERR_INTERNAL );

  iFreeMemPercent = iNewFreeMemPercent;

  if ( nDosBusy == SMI_SCSWAITFORDOS )
  {
    if ( SMDosBusy( CSExecSCSMemory ) != 0 )
      return ( ERR_INTERNAL );
  }
  else
    CSExecSCSMemory();

  return ( ERR_SUCCESS );
}

void CSExecSCSMemory( void )
{
  REG_W InArgs, OutArgs;

  if ( nOSKType == SUI_WINDOWSOSK )
    InArgs.ax = SCS_FREEOSKMEM;
  else
    InArgs.ax = SCS_FREEMEM;

  InArgs.dx = iFreeMemPercent;

#if !defined( PROD )
  sprintf( szTempStr, "NOTICE: Memory call
number0: %x,
requesting allocation of %d%% of SRAM
memory.\n",
           InArgs.ax, InArgs.dx );
  TRACE( szTempStr );
#endif

  SetReentrancy( FALSE );
  Intx( &InArgs, &OutArgs, SCS_INTNUM );
  SetReentrancy( TRUE );

  if ( OutArgs.ax == SCS_ACCEPTED )
    iSetMemDone = ERR_SUCCESS;
  else
    iSetMemDone = ERR_INTERNAL;
}

BOOL CheckSCSMemory( void )
{
  return ( iSetMemDone );
}

int RequestFullRepaint( BYTE iRepaintRequired,
WORD wScreenCode )
{
  iFullRepaintDone = ERR_INPROGRESS;

  if ( !GetSCSActiveStatus() )
    return ( ERR_INTERNAL );

  if ( !nOSKNoGraphics( wScreenCode ) )
  {
    TRACE( "NOTICE: Closing the Windows Host No
Paint Zone\n" );

    if ( CloseHostOccludes() != ERR_SUCCESS )

    {
      TRACE( "NOTICE: Attempt to close No Paint
Zone on Host
failed, continuing anyway\n" );
      return ( iFullRepaintDone = ERR_SUCCESS );

    }
  }
  else
  {
      TRACE( "NOTICE: Closing the DOS or DOS
Graphics exclusion
region\n" );

      if ( SetSCSHostOccludes( OCCLUDEUNION *
NULL,
SUI_NOOCCTYPE, iRepaintRequired ) !=
ERR_SUCCESS )
      {
        TRACE( "ERROR: an error occured in calling
SetSCSHostOccludes(), continuing anyway\n" );
        return ( iFullRepaintDone = ERR_SUCCESS );
      }
  }

  return ( ERR_SUCCESS );
}

int CheckFullRepaint( void )
{
  return ( iFullRepaintDone );
}

int DiscoDisableConnection( void )
{
  if ( !GetSCSActiveStatus() )
    return ( ERR_INTERNAL );

  if ( ( iDiscoThreadId = GetTempEventNum() ) < 0
)
    return ( ERR_INTERNAL );

  AddThread( iDiscoThreadId, WaitForDisco, NULL,
SMD_ONETIME,
FALSE,
         1, 0 );

  SetWaitingIcon( SSS_WAITINGICONON, TRUE );

  return ( ERR_SUCCESS );
}

void WaitForDisco( void )
{
  REG_W InArgs, OutArgs;

  DelThread( iDiscoThreadId );

  InArgs.ax = SCS_DISCODISABLECON;

  Intx( &InArgs, &OutArgs, SCS_INTNUM );

}

int SendPrivateMessage( int iMsgID, int iBuffLen,
char *sMsgBuff
)
{
  REG_W InArgs, OutArgs;

  fill_chr( &InArgs, 0, sizeof ( InArgs ) );
  fill_chr( &SendPrMsgBuff, 0, sizeof (
SendPrMsgBuff ) );

  SendPrMsgBuff.iMsgID = iMsgID;

  if ( ( SendPrMsgBuff.iBuffLen = iBuffLen ) > 0 )
    mem_cp( sMsgBuff, SendPrMsgBuff.sMsgBuff,
iBuffLen );
  InArgs.ax = SCS_SENDPRMSG;

  InArgs.ds = SEG( &SendPrMsgBuff );
  InArgs.di = OFF( &SendPrMsgBuff );

  InArgs.bx = SendPrMsgBuff.iBuffLen + sizeof (
SendPrMsgBuff.iBuffLen ) +
           sizeof ( SendPrMsgBuff.iMsgID );

#if !defined( PROD )
  sprintf( szTempStr, "NOTICE: Sent Private
Message #%d\n",
SendPrMsgBuff.iMsgID );
  TRACE( szTempStr );
#endif

  Intx( &InArgs, &OutArgs, SCS_INTNUM );

  if ( OutArgs.ax != SCS_ACCEPTED )
  {
    TRACE( "ERROR: CoSession Send Private
Message function
returned an error\n" );
```

```
}

  return ( OutArgs.ax == SCS_ACCEPTED ?
ERR_SUCCESS :
ERR_INTERNAL );
}

void WaitForSendPM( void )
{
  REG_W InArgs, OutArgs;

  InArgs.ax = SCS_SENDPRIVMSG;

  InArgs.ds = SEG( &SendPMMsgBuff );
  InArgs.si = OFF( &SendPMMsgBuff );

  InArgs.bx = SendPMMsgBuff.lBuffLen + sizeof(
SendPMMsgBuff.lBuffLen ) +
            sizeof( SendPMMsgBuff.lMsgID );

#if !defined( PROD )
  sprintf( szTempStr, "NOTICE: Sent Private
Message 0:%d\n",
SendPMMsgBuff.lMsgID );
  TRACE( szTempStr );
#endif

  intx( &InArgs, &OutArgs, SCS_INTNUM );

  if ( OutArgs.ax == SCS_ACCEPTED )
  {
    TRACE( "NOTICE: Send PM retry succeeded" );

    PCS_BEGINCRITICAL;

    SendPMMsgBuff.lMsgID = 0;

    PCS_ENDCRITICAL;
  }
  else
    TRACE( "NOTICE: Send PM retry failed\n" );

  if ( GetRetryLimit( iPMRetryThreadIdx ) == 0 ||
SendPMMsgBuff.lMsgID == 0 )
  {
    TRACE( "NOTICE: Send PM retry thread
expired" );
    DelThread( iPMRetryThreadIdx );
    iPMRetryThreadIdx = SMD_NOACTIVETHREAD;

    PCS_BEGINCRITICAL;
    fSendPMRetryDone = TRUE;
    PCS_ENDCRITICAL;
  }
}

int GetSCSCallProgress( void )
{
  BYTE nCallProgress;
  PCS_BEGINCRITICAL
  nCallProgress = SystemStatusBuff.nCallProgress;
  PCS_ENDCRITICAL

  return ( nCallProgress );
}

int GetSCSProtocolId( void )
{
  BYTE nProtocolId;

  PCS_BEGINCRITICAL
  nProtocolId = SystemStatusBuff.nProtocolId;
  PCS_ENDCRITICAL

  return ( nProtocolId );
}

int GetSCSVideoMode( void )
{
  BYTE nCurrentVidMode;

  PCS_BEGINCRITICAL
  nCurrentVidMode =
SystemStatusBuff.nCurrentVidMode;
  PCS_ENDCRITICAL

  return ( nCurrentVidMode );
}

void SetSCSAbortFlag( BYTE NewAbortRequest )
{
  PCS_BEGINCRITICAL
  SystemStatusBuff.bAbortRequestConnect =
NewAbortRequest;
  PCS_ENDCRITICAL

}

int ReceiveHostFile( char *szHostFileName, LPSTR
sFileBuff, LONG
lFileSize )
{
  REG_W InArgs, OutArgs;

  fill_char( ( NPSTR )&InArgs, 0, sizeof ( InArgs ) );

  InArgs.ax = SCS_XFERFILE |
SCS_TOSARATOGA;
  InArgs.ds = SEG( szHostFileName );
  InArgs.si = OFF( szHostFileName );
  InArgs.es = SEG( sFileBuff );
  InArgs.di = OFF( sFileBuff );
  InArgs.dx = HIWORD( lFileSize );
  InArgs.cx = LOWORD( lFileSize );

#if !defined( FLASHTEST )
  intx( &InArgs, &OutArgs, SCS_INTNUM );

  return ( OutArgs.ax == SCS_ACCEPTED ?
ERR_SUCCESS :
ERR_INTERNAL );
#else
  return ( ERR_SUCCESS );
#endif
}

int SendUDHotkeys( int iHotkeyID )
{
  int iScanCodeIdx, iNumCodes;
  int iReturn = ERR_SUCCESS;
  BYTE nHiScanByte, nLoScanByte;
  SCANCODE *pScanCodes;

  if ( iHotkeyID == PHD_UDEF1 )
    pScanCodes = UIConfigData.aUDHotkey1;
  else
    pScanCodes = UIConfigData.aUDHotkey2;

  iNumCodes = GetNumScanCodes( pScanCodes );

  for ( iScanCodeIdx = 0; iScanCodeIdx <
iNumCodes;
++iScanCodeIdx )
  {
    if ( ( nHiScanByte = HIBYTE( pScanCodes[
iScanCodeIdx
].wScanCode ) ) != 0 )
    {
      if ( SendScanCode( nHiScanByte ) ==
ERR_INTERNAL )
      {
        iReturn = ERR_INTERNAL;
        break;
      }
    }

    if ( ( nLoScanByte = LOBYTE( pScanCodes[
iScanCodeIdx
].wScanCode ) ) != 0 )
    {
      if ( SendScanCode( nLoScanByte ) ==
ERR_INTERNAL )
      {
        iReturn = ERR_INTERNAL;
        break;
      }
    }
  }

  return ( iReturn );
}

int GetNumScanCodes( SCANCODE FAR
*pScanCodes )
{
  int iNumCodes, iScanCodeIdx;

  for ( iNumCodes = 0, iScanCodeIdx = 0;
iScanCodeIdx <
SUI_MAXNUMSCANCODES;
       ++iScanCodeIdx )
  {
    if ( LOBYTE( pScanCodes[ iScanCodeIdx
].wScanCode ) == 0 )
      break;

    iNumCodes++;
  }

  return ( iNumCodes );
}

int SendScanCode( BYTE nScanCode )
{
  REG_W InArgs, OutArgs;

  PCS_BEGINCRITICAL;

  fill_char( ( NPSTR )&InArgs, 0, sizeof ( InArgs ) );

  InArgs.ax = MAKEWORD( nScanCode, HIBYTE(
SCS_SENDHSOSCANCODE )
);

  intx( &InArgs, &OutArgs, SCS_INTNUM );

  PCS_BEGINCRITICAL;

  return ( OutArgs.ax );
}

int SendLockKbdMouse( BOOL bLocked )
{
  if ( bLocked )
    return ( SendPrivateMessage(
PM_REQSCSLOCKKBMO, 0, NULL ) );
  else
    return ( SendPrivateMessage(
PM_REQSCSUNLOCKKBMO, 0, NULL )
);
}

int SendDimScreen( BOOL bDimmed )
{
  if ( bDimmed )
    return ( SendPrivateMessage(
PM_REQSCSBLANKSCR, 0, NULL ) );
  else
    return ( SendPrivateMessage(
PM_REQSCSUNBLANKSCR, 0, NULL )
);
}

CONNERROR TranslateConnectError( void )
{
  switch ( ( SCOSCONNERROR )GetSCOSInfo(
SCS_CLEARERROR ) )
  {
    case SCS_PASSWORDREJECTED:
      return ( SCS_ERRPASSWORD );

    case SCS_LOGINIDREJECTED:
    case SCS_LOGINUSERREJECTED:
      return ( SCS_ERRLOGINID );

    case SCS_REMOTEDISCONNECTED:
    case SCS_RESPONSETIMEOUT:
      return ( SCS_ERRTIMEOUT );

    case SCS_UNSUPPORTEDVIDMODE:
      return ( SCS_ERRUNSUPVIDMODE );

    default:
      return ( SCS_ERRUNKNOWN );
  }
}

#if defined( _MSC_VER )
#pragma warning( default : 4704 )
#endif
Copr. 1995 Zenith Data Systems Corp.
#include "sr.h"
#include "sio.h"
#include "k2.h"
#include "spave.h"
#include "pparm.h"
#include "hm.h"
#include "sm.h"

#if defined( _MSC_VER )
#pragma warning( disable : 4704 )
#endif

int SetSCSBusyStatus( int NewStatus )
{
  REG_W InArgs, OutArgs;

  fill_char( ( NPSTR )&InArgs, 0, sizeof ( InArgs ) );

  InArgs.ax = NewStatus;

#if !defined( PROD )
  if ( NewStatus == SCS_SETBUSY )
    TRACE( "NOTICE: Attempting to set the SCS
busy flag\n" );
  else
    TRACE( "NOTICE: Attempting to set the SCS
idle flag\n" );
#endif

  intx( &InArgs, &OutArgs, SCS_INTNUM );

  return ( OutArgs.ax == SCS_ACCEPTED ?
ERR_SUCCESS :
ERR_INTERNAL );
}

int SetSCSFullRepaint( void )
{
  REG_W InArgs, OutArgs;

  fill_char( ( NPSTR )&InArgs, 0, sizeof ( InArgs ) );

  InArgs.ax = SCS_FULLREPAINT;

  TRACE( "NOTICE: Requesting full repaint from
SCSV" );

  intx( &InArgs, &OutArgs, SCS_INTNUM );

  return ( OutArgs.ax == SCS_ACCEPTED ?
ERR_SUCCESS :
ERR_INTERNAL );
}

int SetSCSScrolling( BYTE nScrollStatus )
{
  REG_W InArgs, OutArgs;

  fill_char( ( NPSTR )&InArgs, 0, sizeof ( InArgs ) );

  InArgs.ax = SCS_SETSCROLLING | nScrollStatus;

#if !defined( PROD )
  if ( nScrollStatus == SCS_DISABLESCROLL )
    TRACE( "NOTICE: Requesting the disabling of
scroll from
SCSV" );
  else
    TRACE( "NOTICE: Requesting the enabling of
scroll from SCSV"
);
#endif

  intx( &InArgs, &OutArgs, SCS_INTNUM );

  return ( OutArgs.ax == SCS_ACCEPTED ?
ERR_SUCCESS :
ERR_INTERNAL );
}

int SetSCSOcclude( OCCLUDEUNION *occ, int
iOccType )
{
  REG_W InArgs, OutArgs;

  fill_char( ( NPSTR )&InArgs, 0, sizeof ( InArgs ) );

  if ( occ != NULL )
  {
    switch ( iOccType )
    {
      case SUI_NOOCCTYPE:
      case SUI_OCCDOSTEXT:
        InArgs.bx = AbsToZero(
occ->occText.yULRow );
        InArgs.cx = AbsToZero( occ->occText.xULCol
);
        InArgs.si = occ->occText.yLRRow;

        InArgs.di = occ->occText.xLRCol;
        break;

      case SUI_OCCDOSGRAPHICS:
        InArgs.bx = AbsToZero(
occ->occDosGraph.xULDos );
        InArgs.cx = AbsToZero(
occ->occDosGraph.yULDos );
        InArgs.si = occ->occDosGraph.xLRDos;
        InArgs.di = occ->occDosGraph.yLRDos;
        break;

      default:
        return ( ERR_INTERNAL );
    }
  }
  else
    TRACE( "NOTICE: Clipping region at zero\n" );

  InArgs.ax = SCS_OCCLUDE2;

  TRACE( "NOTICE: Requesting the establishment
of a clipping
region from SCSV" );

  intx( &InArgs, &OutArgs, SCS_INTNUM );

  return ( OutArgs.ax == SCS_ACCEPTED ?
ERR_SUCCESS :
ERR_INTERNAL );
}

int DefineSCSOcclude( OCCLUDEUNION *occ, int
iOccType, BYTE
```

```
fRepaint )
{
 if ( SetSCSSemStatus( SCS_SETBUSY ) !=
ERR_SUCCESS )
 {
  TRACE( "ERROR: Attempt to secure SCS busy
flag failed\r" );
  return ( ERR_SCSBUSY );
 }

 if ( SetSCSOcclude( ooo, lOccType ) !=
ERR_SUCCESS )
 {
  TRACE( "ERROR: Attempt to define SCS
clipping region
failed\r" );
  return ( ERR_SCSOCCFAILED );
 }

 if ( ooo == NULL )
 {
  if( SetSCSScrolling( SCS_ENABLESCROLL ) !=
ERR_SUCCESS )
  {
   TRACE( "ERROR: Attempt to enable scrolling
failed\r" );
   return ( ERR_SCSSCROLLING );
  }
 }
 else
 {
  if ( SetSCSScrolling( SCS_DISABLESCROLL ) !=
ERR_SUCCESS )
  {
   TRACE( "ERROR: Attempt to disable scrolling
failed\r" );
   return ( ERR_SCSSCROLLING );
  }
 }

 if ( SetSCSSemStatus( SCS_SETIDLE ) !=
ERR_SUCCESS )
 {
  TRACE( "ERROR: Attempt to secure SCS busy
flag failed\r" );
  return ( ERR_SCSIDLE );
 }

 if ( fRepaint )
 {
  if ( SetSCSFullRepaint() != ERR_SUCCESS )
  {
   TRACE( "ERROR: Repaint request in SCS
failed\r" );
   return ( ERR_SCSFULLREPAINT );
  }
 }

 TRACE( "NOTICE: Occlusion region definition for
DOS Text or
Graphics was successful\r" );

 return ( ERR_SUCCESS );
}

#if defined( _MSC_VER   )
#pragma warning( default : 4704 )
#endif

Copr. 1995 Zenith Data Systems Corp.
#include "sr.h"
#include "sio.h"
#include "k2.h"
#include "sprum.h"
#include "lpenm.h"
#include "lsm.h"
#include "sm.h"

#if defined( _MSC_VER   )
#pragma warning( disable : 4704 )
#endif

static int iSLLoadThreadIdx;
static LONG lOldVidVector;


LONG GetOldVidVector( void )
{
 return ( lOldVidVector );
}

APIFUNCRET SLDefineOldVidVector( struct REGW
*CallerRegs )
{
 TRAPREC *tr = GetVIOTrapRec();

 lOldVidVector = MAKELONG( CallerRegs->bx,
CallerRegs->ax );

 PCS_BEGINCRITICAL;

 tr->tr_old_int = lOldVidVector;

 PCS_ENDCRITICAL;
}

APIFUNCRET SLEnableIOrd( struct REGW
*CallerRegs )
{
 EnableIOrdAfterBoot();
}

APIFUNCRET SLGetFrameType( struct REGW
*CallerRegs )
{
 CallerRegs->ax = ( WORD
)UIConfigData.wFrameType;

 SetForegroundRegs( CallerRegs );
}

APIFUNCRET SLGetNLIOStatus( struct REGW
*CallerRegs )
{
 CallerRegs->ax = GetPBXActiveStatus();

 SetForegroundRegs( CallerRegs );
}

APIFUNCRET SLLoadSUI( struct REGW
*CallerRegs )
{
 if ( ( iSLLoadThreadIdx = GetTempEventNum() ) <
0 )
  return;

 AddThread( iSLLoadThreadIdx, ( NEARPROC
)CBExecLoadSUI, NULL,
SMD_ONETIME, FALSE,
         SM_SLPOLLFREQ, 0 );
}

void CBExecLoadSUI( void )
{
 DelThread( iSLLoadThreadIdx );

 InitServicing( SBS_SUILOADING );

 if ( GetEEPROMInited() )
 {
  TRACE( "NOTICE: Beginning pen calibration due
to EEPROM
initialization\r" );
  LoadSUI( SUI_DOPENCALIBRATION,
SUI_NOSCREEN );
 }
 else
 {
  if ( !IsNodeAddressBlank(
UIConfigData.szLastNodeAddress ) &&

      GetSystemResumeBit() )
   LoadSUI( SUI_LASTCONNECTION,
SUI_NOSCREEN );
  else
   LoadSUI( SUI_SPECIFIEDSCREEN,
SUI_HOSTSELECTION );
 }

 ClearSystemResumeBit();
}

#if defined( _MSC_VER   )
#pragma warning( default : 4704 )
#endif
Copr. 1995 Zenith Data Systems Corp.
#include "sr.h"
#include "sprum.h"
#include "k2.h"
#include "sio.h"
#include "sm.h"



int SortList(int wTotalEntries, int wEntrySize, int
wPrimeOffset,
          int wSecondOffset, char *spEntryBuff)
{
 int wInnerLoop;
 int wOutLoop;
 int wInnerOffset;
 int wOutOffset;
 int wResult;

 if( (wTotalEntries == 0) || (wEntrySize == 0) ||
(wPrimeOffset
== wSecondOffset)
   || (wPrimeOffset >= wEntrySize) ||
(wSecondOffset >=
wEntrySize)
   || (wPrimeOffset < 0 ) || (wSecondOffset < 0) )
  return(ERR_INVALIDPARM);

 wOutOffset = 0;
 for(wOutLoop = 0; wOutLoop < (wTotalEntries - 1);
wOutLoop++)
 {
  wInnerOffset = wOutOffset + wEntrySize;
  for(wInnerLoop = (wOutLoop + 1); wInnerLoop <
wTotalEntries;
wInnerLoop++)
  {

wResult=strcmp(spEntryBuff+wOutOffset+wPrimeOff
set,
spEntryBuff+wInnerOffset+wPrimeOffset);
    if(wResult > 0)
     SwapEntries(spEntryBuff+wOutOffset,
spEntryBuff+wInnerOffset, wEntrySize);
    if(wResult == 0)
    {

wResult=strcmp(spEntryBuff+wOutOffset+wSecond
Offset,
spEntryBuff+wInnerOffset+wSecondOffset);
     if(wResult > 0)
      SwapEntries(spEntryBuff+wOutOffset,
spEntryBuff+wInnerOffset, wEntrySize);
    }
    wInnerOffset = wInnerOffset + wEntrySize;
  }
  wOutOffset = wOutOffset + wEntrySize;
 }
 return(ERR_SUCCESS);
}

int SwapEntries(char *spEntry1, char *spEntry2, int
wEntrySize)
{
 char sSwapBuff[SRT_MAXLENSWAPBUFF];
 int  wRestSize;
 int  wCopyUnit;

 if( wEntrySize == 0 )
  return(ERR_INVALIDPARM);

 wRestSize = wEntrySize;
 do
 {
  if(wRestSize >= SRT_MAXLENSWAPBUFF)
   wCopyUnit = SRT_MAXLENSWAPBUFF;
  else
   wCopyUnit = wRestSize;
  mem_cp(spEntry1+(wEntrySize-wRestSize),
sSwapBuff,
wCopyUnit);
  mem_cp(spEntry2+(wEntrySize-wRestSize),
spEntry1+(wEntrySize-wRestSize), wCopyUnit);
  mem_cp(sSwapBuff,
spEntry2+(wEntrySize-wRestSize),
wCopyUnit);
  wRestSize -= SRT_MAXLENSWAPBUFF;
 } while (wRestSize > 0);

 return(ERR_SUCCESS);
}

long GetEntryOffset(int wTotalEntries, int
wEntrySize, int
wKeyOffset,
          int wKeyNumber, char *spEntryBuff)
{
 int wLoop;
 int wKeyCount;
 int wOffset;

 if( (wTotalEntries <= 0) || (wEntrySize <= 0) ||
(wKeyNumber
<= 0)
   || (wKeyOffset >= wEntrySize) || (wKeyOffset < 0
)
   || (wKeyNumber > wTotalEntries) )
  return((long)ERR_INVALIDPARM);

 wKeyCount=1;
 wOffset=0;

 if(wKeyCount == wKeyNumber)
  return(0L);

 for(wLoop = 1; wLoop < wTotalEntries; wLoop++)
 {
  if( (strcmp(spEntryBuff+wOffset+wKeyOffset,
spEntryBuff+wOffset+wEntrySize+wKeyOffset)) != 0)
   wKeyCount++;
  wOffset = wOffset + wEntrySize;

  if(wKeyCount == wKeyNumber)
   return((long)wOffset);
 }

 return((long)ERR_INVALIDPARM);
}
Copr. 1995 Zenith Data Systems Corp.


#include "sr.h"
#include "sio.h"
#include "sprum.h"
#include "k2.h"
#include "sm.h"

#if defined( _MSC_VER )
#pragma warning( disable : 4704 )
#endif

static TRAPREC         SUIMouseTrapRec;
static CALLREC         SUICallRec;
static SUICS           lpfnTempProc;
static SUIACTIONCODE   ActionCode = 0;
static DWORD           dwOldSUIIntVec;
static int             iTempThreadIdx;
static int             iPrepSUIThreadIdx;
static int             iUnloadSUIThreadIdx;
static int             iCleanupSUIThreadIdx;
static WORD            pJmpBuff[ 6 ];
static BOOL            fVideoBlocked = FALSE;
static char            cSUIStatus =
SM_SUINOTLOADED;
static BYTE            cResidentStatus;
static WORD            wSUIPSP;
static WORD            wSavedSP;
static WORD            wSavedBP;
static CURRHOSTNAME    CurrHostName;

static APIFUNC aAPIFuncTable[] =
{
 { SM_SETCONTRAST, GetSetContrast },
 { SM_SETBRIGHTNESS, GetSetBrightness },
 { SM_CALIBUPLEFT, CalibratePen },
 { SM_CALIBCANCEL, CalibrateCancel },
 { SM_SETAUTOSHUTOFF, GetSetAutoShutOff },
 { SM_SETSLEEPTIME, GetSetSleepTime },
 { SM_REBOOTHOST, RebootHost },
 { SM_ACTIVEUPDATE, RequestActiveUpdate },

 { SM_DOUPDATE, SetUpdate },
 { SM_UPDATEHOSTLIST, UpdateHostList },
 { SM_GETHOSTLISTSTAT, GetHostListStatus },
 { SM_GETCONNECTSTAT, GetConnectStatus },
 { SM_REQUESTCONNECT, RequestConnClose },
 { SM_GETPASSWORDSTAT, GetPasswordStatus
},
 { SM_LBSETNETGROUP, LBGetSetNetGroup },
 { SM_LBSETNETHOST, LBGetSetNetHost },
 { SM_LBSETNETFRAMETYPE,
LBGetSetNetFrameType },
 { SM_SETCONNECTTYPE, GetSetConnectType
},
 { SM_SETPASSWORD, GetSetPassword },
 { SM_UPDATESMALOC, UpdateDimenLoc },
 { SM_REQUESTUNLOAD, RequestUnload },
 { SM_SETMSGBOXRETCODE,
SetSUIMBRetCode },
 { SM_SETUILANGUAGE, GetSetUILanguage },
 { SM_SETACTIVESTAT, SetActiveStatus },
 { SM_SETKEYSTROKE, SetKeyStroke },
 { SM_GETKEYBOARDSTAT, GetKeyboardStatus
},
 { SM_GETABOUTDIALOG, GetAboutDialog },
 { SM_SETUSHOTICON, GetSetUIHotIcon },
 { SM_SETSECURITYID, GetSetSecurityID },
 { SM_SETDOMAINID, GetSetDomainID },
 { SM_SETLOCKKBDMOUSE,
GetSetLockKbdMouse },
 { SM_SETDIMSCREEN, GetSetDimScreen },
 { SM_SETVIDEOBLOCK, BlockUnblockVideo },
 { SM_NOTIFYSCRCODE, NotifyScreenCode },
 { 0, 0 }
};

APIFUNC *GetSUIFuncTable( void )
{
 return ( aAPIFuncTable );
}

CALLREC FAR *GetSUICallRec( void )
{
 return ( ( CALLREC FAR * )&SUICallRec );
}

TRAPREC *GetSUIMouseTrapRec( void )
{
 SUIMouseTrapRec.tr_int = PND_INTNUM;
 SUIMouseTrapRec.tr_num_srv =
CRU_REFLECTINT;
```

```
  return ( &SUIMouseTrapRec );
}

int GetCurrActionCode( void )
{
  return ( ActionCode );
}

WORD GetCurrScrCode( void )
{
  return ( wScreenCode );
}

void SetCurrScrCode( WORD wNewScreenCode )
{
  wScreenCode = wNewScreenCode;
}

char GetSUIStatus( void )
{
  return ( nSUIStatus );
}

void InitSUICallRec( void )
{
  DWORD dwCallService = ( DWORD )( FARPROC
)SUICallService,
  fc_smr( NPSTR )&SUICallRec, 0, sizeof(
CALLREC ) );

  SUICallRec.cFarCallOpCode =
SMO_CALLOPCODE;
  SUICallRec.aCallSeam[0] = LOBYTE( LOWORD(
dwCallService ) );
  SUICallRec.aCallBack[1] = HIBYTE( LOWORD(
dwCallService ) );
  SUICallRec.aCallBack[2] = LOBYTE( HIWORD(
dwCallService ) );
  SUICallRec.aCallBack[3] = HIBYTE( HIWORD(
dwCallService ) );
  SUICallRec.cFarRetOpCode =
SMO_RETOPCODE;
  strcpy( SUICallRec.szSMAfterSignature,
SIG_SMSIGNATURE );

  dwOldSUIIntVec = set_int_vec( SMI_SUINITNUM,
( DWORD )( 
FARPROC )&SUICallRec ) );
}

void RestoreOldSUIIntVec( void )
{
  set_int_vec( SMI_SUINITNUM, dwOldSUIIntVec );
}

BOOL GetSUIReady( void )
{
  return ( lpfnSUICallBack != ( SUICB )NULL &&
nSUIStatus ==
SMI_SUILOADED );
}

APIFUNCRET SetActiveStatus( struct REGW
*CallerRegs )
{
  PCS_BEGINCRITICAL
  lpfnSUICallBack = ( SUICB )MK_FP(
CallerRegs->ds,
CallerRegs->si )
  PCS_ENDCRITICAL

  wSUIPSP = get_cur_psp();

  CallerRegs->ax = SUI_PARTIALDIALOGSET;
  SetForegroundRegs( CallerRegs );

  nSUIStatus = SMI_SUILOADED
}

APIFUNCRET RequestUnload( struct REGW
*CallerRegs )
{
  if ( !GetRequestHostList() &&
      GetConnectRequested() ==
SCS_NOCONNECTREQUESTED &&
      GetSCSCallProgress() ==
SMI_SCSCONNECTED )
  {
    CallerRegs->ax = SMI_UNLOADACCEPTED;
    UnloadSUI( SUI_NOUNLOADSUI );
  }
  else
    CallerRegs->ax = SMI_UNLOADDENIED;

  SetForegroundRegs( CallerRegs );
}

APIFUNCRET RequestConnClose( struct REGW
*CallerRegs )
{
  if ( GetConnectRequested() )
    CallerRegs->ax = ERR_SUCCESS;
  else
  {
    if ( IsGetFunction( CallerRegs ) )
    {
      if ( GetSCSCallProgress() ==
SMI_SCSCONNECTED )
        CallerRegs->ax = SlessDisableConnection();
      else
        CallerRegs->ax = ( WORD )ERR_INTERNAL;
    }
    else
    {
      if ( GetLSCurrHost() ==
HLD_NOHOSTSELECTED )
      {
        OpenMessageBox(
STR_SUINOHOSTSELECTED, 0,
SUI_CENTERJUSTIFIED, SUI_OK );
        CallerRegs->ax = ( WORD )ERR_INTERNAL;
      }
      else
        CallerRegs->ax = MakeTheConnection( TRUE,
FALSE );
    }
  }

  SetForegroundRegs( CallerRegs );
}

APIFUNCRET GetConnectStatus( struct REGW
*CallerRegs )
{
  char *szHostName;
  int iCallProgress;
  int iProtocolId;
  int iReturn;

  if ( !GetSCSActiveStatus() )
  {
    iReturn = ERR_NOTSUPPORTED;
    goto exit;
  }

  iProtocolId = GetSCSProtocolId();
  iCallProgress = GetSCSCallProgress();

  fc_ctrl( &CurrHostName, 0, sizeof(
CURRHOSTNAME ) );
  CurrHostName.lpszHostName = szNullStr;

  SuffHead.iBuffLen = sizeof ( CURRHOSTNAME
);
  SuffHead.iBuffLen = sizeof ( CURRHOSTNAME );
  SuffHead.Buff = ( LPVOID )&CurrHostName;

  CallerRegs->dx = SEG( &SuffHead );
  CallerRegs->si = OFF( &SuffHead );

  switch ( iCallProgress )
  {
    case SMI_SCSCONNECTED:
      iReturn = SMI_CONNECTED;

      if ( ( szHostName = GetCurrHostName() ) !=
NULL )
        CurrHostName.lpszHostName = ( LPSTR
)szHostName;
      break;

    case SMI_SCSWAITINGFORCONNECT:
      iReturn = SMI_CONNECTED;
      break;

    case SMI_SCSDIALING:
      iReturn = SMI_CONNECTED;
      break;

    case SMI_SCSLOGGINGIN:
      iReturn = SMI_LOGGINGIN;
      break;

    case SMI_SCSDISCONNECTED:
      iReturn = SMI_DISCONNECTED;
      break;

    default:
      iReturn = ERR_INTERNAL;
      break;
  }

  CallerRegs->ax = iReturn;

  switch ( iProtocolId )
  {
    case SMI_SCSNETWAREIPX:
      iReturn = SMI_NETWAREIPX;
      break;

    case SMI_SCSASYNC:
      iReturn = SMI_MODEM;
      break;

    default:
      iReturn = ERR_INTERNAL;
      break;
  }

exit:
  CallerRegs->bx = iReturn;
  SetForegroundRegs( CallerRegs );
}

APIFUNCRET BlockUnblockVideo( struct REGW
*CallerRegs )
{
  PCS_BEGINCRITICAL;
  bVideoBlocked = IsGetFunction( CallerRegs );
  PCS_ENDCRITICAL;

  CallerRegs->ax = BlockSCSVideo( ( BYTE
)bVideoBlocked );

  SetForegroundRegs( CallerRegs );
}

BOOL GetVideoBlocked( void )
{
  return ( bVideoBlocked );
}

int LoadSUI( SUIACTIONCODE NewActionCode,
WORD wNewScreenCode )
{
  WORD wCurrVidMode,
  BYTE nCurrHostMode;

  if ( NewActionCode == SUI_LASTOSKSCREEN )
  {
    if ( IsNoScreen( UIConfigData.nLastOSKScreen )
)
      wNewScreenCode = SUI_SIGALPHA;
    else
      wNewScreenCode =
UIConfigData.nLastOSKScreen;
  }
  else if ( NewActionCode ==
SUI_LASTSETUPDLGSCREEN )
  {
    if ( IsNoScreen(
UIConfigData.nLastSetupDlgScreen ) )
      wNewScreenCode = SUI_HOSTSELECTION;
    else
      wNewScreenCode =
UIConfigData.nLastSetupDlgScreen;
  }

  if ( ( IsSetupDlg( wScreenCode ) && IsSetupDlg(
wNewScreenCode
) ) ||
    ( IsOSK( wScreenCode ) && IsOSK(
wNewScreenCode ) ) )
    return ( ERR_INTERNAL );
  else if ( IsSetupDlg( wScreenCode ) && IsOSK(
wNewScreenCode )
)
    return ( ERR_INTERNAL );

  ActionCode = NewActionCode;

  if ( nSUIStatus == SMI_SUINOTLOADED )
    nSUIStatus = SMI_SUILOADING;

  if ( GetSUIReady() )
    wOldScreenCode = wScreenCode;

  if ( ( iPrepSUIThreadIdx = GetTempEventNum() )
== ERR_INTERNAL
)
    return ( ERR_INTERNAL );

  AddThread( iPrepSUIThreadIdx, WaitForPrepSUI,
NULL, SMO_POLLED,
FALSE,
        SUI_LOADSUIPOLLFREQ, 0 );

  wScreenCode = wNewScreenCode;

  if ( IsOSK( wScreenCode ) )
  {
    wCurrVidMode = GetCurrVidMode(),
    nCurrHostMode = GetCurrHostMode();

    if ( IsOSKVideoSupported( wCurrVidMode ) &&
nCurrHostMode ==
PHD_DOSAPP )
      wScreenCode |=
SUI_OSKASSETUPDIALOGMASK;

    if ( wCurrVidMode != SUI_TEXTVIDMODE &&
nCurrHostMode !=
PHD_DOSAPP )
      wScreenCode |=
SUI_OSKINWINGRAPHICSMASK;
  }

  return ( ERR_SUCCESS );
}

void WaitForPrepSUI( void )
{
  static PREPSUISTATES iStatePrepSUI =
SUI_NOPREPSTATE;
  int iCheck;

  switch ( iStatePrepSUI )
  {
    case SUI_NOPREPSTATE
      if ( IsSetupDlg( wScreenCode ) || IsNoScreen(
wScreenCode )
)
      {

        TRACE( "NOTICE: Setup Dialogs or No
Screen"
requested.\r" );

        SetMonitor( FALSE, TRUE );
        iStatePrepSUI = SUI_CHECKMONITOROFF;

      }
      else if ( IsOSKAsSetupDlg( wScreenCode ) )
      {
        TRACE( "NOTICE: OSK as Setup Dialog
requested.\r" );
        SetMonitor( FALSE, FALSE );
        iStatePrepSUI = SUI_CHECKMONITOROFF;

      }
      else
      {
        TRACE( "NOTICE: DOS or Windows OSK
requested, nothing
else to do\r" );
        iStatePrepSUI = SUI_PREPSUCCESS;
      }
      break;

    case SUI_CHECKMONITOROFF:
      iCheck = CheckMonitor();

      if ( iCheck == ERR_SUCCESS )
      {
        if ( IsOSKAsSetupDlg( wOldScreenCode ) )
        {
          TRACE( "NOTICE: Monitor off complete, old
screen - OSK
as setup dialog\r" );
          iStatePrepSUI = SUI_PREPSUCCESS;
        }
        else if ( IsOSK( wOldScreenCode ) )
        {
          TRACE( "NOTICE: Monitor off complete, old
screen -
OSK\r" );
          RequestFullRepaint( FALSE,
wOldScreenCode );
          iStatePrepSUI = SUI_CHECKFULLREPAINT;
        }
        else
        {
          TRACE( "NOTICE: Monitor off complete, no
old screen\r"
);
          iStatePrepSUI = SUI_PREPSUCCESS;
        }
      }
      else if ( iCheck == ERR_INTERNAL )
        iStatePrepSUI = SUI_PREPERROR;
      break;

    case SUI_CHECKFULLREPAINT:
      iCheck = CheckFullRepaint();

      if ( iCheck == ERR_SUCCESS )
      {
```

```
      TRACE( "NOTICE: Occlusion region in SCOS
closed through
Full Repaint\n" );
      iStatePrepSUI = SUI_PREPSUCCESS;
    }
    else if ( iCheck == ERR_INTERNAL )
    {
      TRACE( "ERROR: Closure of occlusion region
failed in SCOS
through Full Repaints" );
      iStatePrepSUI = SUI_PREPERROR;
    }
    break;

  case SUI_PREPSUCCESS:
    TRACE( "NOTICE: We're here, we're here!\n" );

    InitSUI();
    SMDoeBusy( CSExecSUI );
    goto end;

  case SUI_PREPERROR:
    TRACE( "ERROR: SUI Load Prep failed\n" );

    if ( nSUIStatus == SM_SUILOADING )
      nSUIStatus = SM_SUINOTLOADED;
    else
      nSUIStatus = SM_SUINACTIVE;

  default:
end:
    iStatePrepSUI = SUI_NOPREPSTATE;
    DelThread( iPrepSUIThreadIdx );
    break;
  }
}

void CSExecSUI( void )
{
  int iVideoMode = GetCurrVidMode();

  if ( GetSCSCallProgress() ==
SM_SCSCONNECTED )
  {
    if ( IsSetupDlg( wScreenCode ) || IsNoScreen(
wScreenCode ) )

    {
      if ( iVideoMode != SUI_INITIALVIDMODE )
        SetVideoMode( SUI_INITIALVIDMODE );
    }
    else
    {
      if ( IsOSKVideoSupported( iVideoMode ) &&
GetCurrHostMode() == PND_DOSAPP )
      {
        SetVideoMode( SUI_INITIALVIDMODE );
      }
    }
  }
  else
    SetVideoMode( SUI_INITIALVIDMODE );

  if ( nSUIStatus == SM_SUILOADING )
  {
    if ( !ini_dos_prompt() )
    {
      _snd_for_0g( ~SMD_SCHEDULERS );

      if ( ImExec( szSUIExecName, NULL ) !=
ERR_SUCCESS )
      {
        SetVideoMode( SUI_TEXTVIDMODE );
        dspE( STR_SUILOADERROR1 );
      }
      else
      {
        if ( ( iTempThreadIdx = GetTempEventNum() )
< 0 )
          return;

        AddThread( iTempThreadIdx,
WaitForSUILoad, NULL,
SMD_POLLED, FALSE,
              SUI_LOADSUIPOLLFREQ,
SUI_LOADSUIMAXRETRY );
      }
    }
    else
    {
      SetVideoMode( SUI_TEXTVIDMODE );
      dspE( STR_SUILOADERROR2 );
    }
  }
  else
  {
    nSUIStatus = SM_SUILOADED;
    SMDoeBusy( CSExecLoadScreen );
  }
}

void WaitForSUILoad( void )
{
  if ( GetSUIReady() )
  {
    DelThread( iTempThreadIdx );
    iTempThreadIdx = SMD_NOACTIVETHREAD;

    SMDoeBusy( CSExecLoadScreen );
  }
}

void CSExecLoadScreen( void )
{
  if ( !GetSUIReady() )
    return;

  switch ( ActionCode )
  {
    case SUI_DOPENCALIBRATION:
      SetSetupDlgMode( PND_SETUPDLGON );
      DoMessageBox( NULL,
SUI_PENCALIBRATION, SUI_LEFTJUSTIFIED,
SUI_CANCEL,
              CSMsgBoxButtonPressed, 0 );
      break;

    case SUI_LASTCONNECTION:
      SetSetupDlgMode( PND_SETUPDLGON );
      ResumeTheConnection();
      break;

    case SUI_BADVIDEOMSG:
      SetSetupDlgMode( PND_SETUPDLGON );
      DoMessageBox( STR_SUIBADVIDEOMSG, 0,
SUI_CENTERJUSTIFIED,
SUI_OK,
              CSMsgBoxButtonPressed, 0 );
      break;

    default:
      if ( IsSetupDlg( wOldScreenCode ) )
        SetSetupDlgMode( PND_SETUPDLGOFF );
      else if ( IsOSK( wOldScreenCode ) &&
!IsOSKAsSetupDlg(
wOldScreenCode ) )
        SetOSKMode( NULL, SUI_NOOCCTYPE );

      if ( IsSetupDlg( wScreenCode ) ||
IsOSKAsSetupDlg(
wScreenCode ) )
        SetSetupDlgMode( PND_SETUPDLGON );
      DoLoadScreen();
      break;
  }
}

void DoLoadScreen( void )
{
  int iNewScreenCode = LOBYTE( wScreenCode );
  int iOSKConfig;
  int xPosOSK, yPosOSK;

  if ( IsSetupDlg( wScreenCode ) || IsNoScreen(
wScreenCode ) )
  {
    iOSKConfig = UIConfigData.iLastOSKDlgScreen;
    xPosOSK = 0;
    yPosOSK = 0;
  }
  else
  {
    iOSKConfig = 0;
    xPosOSK = UIConfigData.xPosLastOSKScreen;
    yPosOSK = UIConfigData.yPosLastOSKScreen;
  }

  if ( !IsNoScreen( wScreenCode ) )
  {
    EnableBusyCursor( SUI_BUSYCURSOROFF );


    PCB_BEGINCRITICAL
    AX( SUI_DISPLAYDIALOG );
    BX( iNewScreenCode );
    CX( iOSKConfig );
    SI( yPosOSK );
    DI( xPosOSK );

    ( *lpfnSUICallBack )();
    PCB_ENDCRITICAL
  }
}

int UnloadSUI( BYTE nNewResidentStatus )
{
  if ( !GetSUIReady() )
    return ( ERR_INTERNAL );

  SetWaitingIcon( SSS_WAITINGICONON, TRUE );


  if ( nNewResidentStatus == SUI_UNLOADSUI )
    nSUIStatus = SM_SUIUNLOADING;
  else
    nSUIStatus = SM_SUIDEACTIVATING;

  nResidentStatus = nNewResidentStatus;

  if ( IsNoScreen( wScreenCode ) )
    HideMessageBox();

  if ( ( iUnloadSUIThreadIdx = GetTempEventNum()
) < 0 )
    return ( ERR_INTERNAL );

  AddThread( iUnloadSUIThreadIdx,
WaitForUnloadSUI, NULL,
SMD_POLLED, FALSE,
          SUI_UNLOADSUIPOLLFREQ, 0 );

  if ( GetThreadAddress( SCS_DISCOEVENTNUM )
== NULL )
    AddThread( SCS_DISCOEVENTNUM,
WaitForStatusChange, NULL,
          SMD_POLLED, FALSE,
SCS_DISCOPOLLFREQ, 0 );

  return ( ERR_SUCCESS );
}

void WaitForUnloadSUI( void )
{
  static UNLOADSUISTATES iStateUnloadSUI =
SUI_NOUNLOADSUISTATE;

  switch ( iStateUnloadSUI )
  {
    case SUI_NOUNLOADSUISTATE:
      if ( IsOSK( wScreenCode ) )
      {
        GetSUIState();
        iStateUnloadSUI = SUI_GETACTIVEUPDATE;
      }
      else
        iStateUnloadSUI =
SUI_UNLOADSUISUCCESS;
      break;

    case SUI_GETACTIVEUPDATE:
      GetActiveUpdate();
      SetTimeLimit( iUnloadSUIThreadIdx,
SUI_PRIMSGPOLLFREQ );
      iStateUnloadSUI = SUI_DIMSCREEN;
      break;

    case SUI_DIMSCREEN:
      TRACE( "NOTICE: In the SUI_DIMSCREEN
state.\n" );
      SendDimScreen( UIConfigData.bDimScreen );
      SetTimeLimit( iUnloadSUIThreadIdx,
SUI_PRIMSGPOLLFREQ );
      iStateUnloadSUI = SUI_LOCKKBDMOUSE;

      break;

    case SUI_LOCKKBDMOUSE:
      TRACE( "NOTICE: In the
SUI_LOCKKBDMOUSE state.\n" );
      SendLockKbdMouse(
UIConfigData.bLockKbdMouse );
      SetTimeLimit( iUnloadSUIThreadIdx,
SUI_LOADSUIPOLLFREQ );
      iStateUnloadSUI =
SUI_UNLOADSUISUCCESS;
      break;

    case SUI_UNLOADSUISUCCESS:
    default:
      DelThread( iUnloadSUIThreadIdx );
      SMDoeBusy( CSExecUnloadSUI );
      iStateUnloadSUI = SUI_NOCLEANUPSTATE;
      break;
  }
}

void CSExecUnloadSUI( void )
{
  lpfnTempProc = lpfnSUICallBack;

  if ( IsSetupDlg( wScreenCode ) || IsNoScreen(
wScreenCode ) ||
      IsOSKAsSetupDlg( wScreenCode ) )
    SetSetupDlgMode( PND_SETUPDLGOFF );
  else if ( IsOSK( wScreenCode ) )
    SetOSKMode( NULL, SUI_NOOCCTYPE );

  if ( nResidentStatus == SUI_UNLOADSUI )
    lpfnSUICallBack = NULL;

  PSP_TERMINATE( wSUIPSP ) = ( LONG )(
FARPROC
)SUITerminateAddress;

  _asm
  {
    cli

    mov wSavedSP, sp
    mov wSavedBP, bp
    mov ax, SUI_CLOSEDIALOG
    xor bx,bx
    mov bl, nResidentStatus

    sti
  };

  ( *lpfnTempProc )( );

  if ( nResidentStatus == SUI_NOUNLOADSUI )
    CleanupUnloadSUI();

}

void SUITerminateAddress( void )
{
  _asm
  {
    mov ds, cs:DGROUP
    mov es, cs:DGROUP
    mov sp, wSavedSP
    mov bp, wSavedBP
  };

  CleanupUnloadSUI();
}

void CleanupUnloadSUI( void )
{
  MREG MinArgs;

  if ( nResidentStatus == SUI_UNLOADSUI )
  {
    if ( !GetPNDActiveStatus() )
    {
      MinArgs = MEventOutArgs;
      MinArgs.ax = 0x000C;
      memcpy( &MinArgs, &MEventOutArgs );
    }
  }

  AddThread( SUI_CLEANUPEVENTNUM,
WaitForCleanupSUI, NULL,
SMD_POLLED, FALSE,
          SUI_LOADSUIPOLLFREQ, 0 );
}

void WaitForCleanupSUI( void )
{
  static CLEANUPSUISTATES iStateCleanupSUI =
SUI_NOCLEANUPSTATE;
  int iCheck;

  switch ( iStateCleanupSUI )
  {
    case SUI_NOCLEANUPSTATE:
      if ( IsSetupDlg( wScreenCode ) || IsNoScreen(
wScreenCode )
||
          IsOSKAsSetupDlg( wScreenCode ) )
      {
        TRACE( "NOTICE: Unload of Setup Dialogs or
OSK-As-Setup-Dialog identified.\n" );
        SetMonitor( TRUE, FALSE );
        iStateCleanupSUI =
SUI_CHECKMONITORON;
      }
      else if ( IsOSKVidChange( wScreenCode ) )

      {
        TRACE( "NOTICE: Unload of OSK due to vid
change from DOS
or Windows identified.\n" );
        RequestFullRepaint( FALSE, wScreenCode );

        iStateCleanupSUI =
SUI_CHECKFULLPAINTCLEANUP;
      }
      else
      {
        TRACE( "NOTICE: Manual unload of OSK
from DOS or Windows
identified.\n" );
        RequestFullRepaint( TRUE, wScreenCode );
```

```
        iStateCleanupSUI =
SUI_CHECKFULLPAINTCLEANUP;
      }
      break;

    case SUI_CHECKMONITORON:
      iCheck = CheckMonitor();

      if ( iCheck == ERR_SUCCESS )
      {
        TRACE( "NOTICE: DoSession monitor on
mode successful.\n"
);
        iStateCleanupSUI =
SUI_CLEANUPSUCCESS;
      }
      else if ( iCheck == ERR_INTERNAL )
      {
        TRACE( "NOTICE: DoSession monitor on
mode failed.\n" );
        iStateCleanupSUI = SUI_CLEANUPERROR;
      }
      break;

    case SUI_CHECKFULLPAINTCLEANUP:
      iCheck = CheckFullRepaint();

      if ( iCheck == ERR_SUCCESS )
      {
        if ( IsOSKVidChange( wScreenCode ) )

        {
          if ( IsOSKInGraphics( wScreenCode ) )

          {
            TRACE( "NOTICE: Full Repaint successful
for vid
change in [illegible] for Windows OSKV" );
            iStateCleanupSUI =
SUI_CLEANUPSUCCESS;
          }
          else
          {
            TRACE( "NOTICE: Full Repaint successful
for vid
change in DOS or DOS Graphics OSKV" );
            SetMonitor( TRUE, FALSE );
            iStateCleanupSUI =
SUI_CHECKMONITORON;
          }
        }
        else
        {
#if !defined( PROD )
          if ( IsOSKInGraphics( wScreenCode ) )

          {
            TRACE( "NOTICE: Full Repaint successful
for Windows
OSKV" );
          }
          else
          {
            TRACE( "NOTICE: Repaint successful for
DOS or DOS
Graphics OSKV" );
          }
#endif
          iStateCleanupSUI =
SUI_CLEANUPSUCCESS
        }
      }
      else if ( iCheck == ERR_INTERNAL )
      {
        TRACE( "NOTICE: Full Repaint failed for OSK
of unknown
type\n" );
        iStateCleanupSUI = SUI_CLEANUPERROR;
      }
      break;

    case SUI_CLEANUPSUCCESS:
      TRACE( "NOTICE: SUI cleanup successful\n" );

    case SUI_CLEANUPERROR:
    default:
      if ( nResidentStatus == SUI_UNLOADSUI )
        nSUIStatus = SMI_SUINOTLOADED;
      else
        nSUIStatus = SMI_SUIINACTIVE;

      fl_chr( szPassword, 0, sizeof( szPassword ) );

      wScreenCode = wOldScreenCode =
SUI_NOSCREEN;
      iStateCleanupSUI = SUI_NOCLEANUPSTATE;
      SetThread( SUI_CLEANUPEVENTNUM );
      SetWaitingIcon( SSS_WAITINGICONOFF,
TRUE );
            break;
    }
}

#if defined( _MSC_VER )
#pragma warning( default : 4704 )
#endif
Copr. 1995 Zenith Data Systems Corp.
#include "sr.h"
#include "sio.h"
#include "spsun.h"
#include "ti2.h"
#include "im.h"
#include "sui.h"

#if defined( _MSC_VER )
#pragma warning( disable : 4704 )
#endif

static BYTE fSecurityWarning = FALSE;
static BYTE fDomainWarning = FALSE;
static BYTE nMsgBoxReturnCode = 0;
static int iPendingBoxThreadId = -1;

void SetDomainWarning( BYTE
fNewDomainWarning )
{
  fDomainWarning = fNewDomainWarning;
}

void SetSecurityWarning( BYTE
fNewSecurityWarning )
{
  fSecurityWarning = fNewSecurityWarning;
}

void SetMsgBoxReturnCode( BYTE
nNewReturnCode )
{
  PCS_BEGINCRITICAL;
  nMsgBoxReturnCode = nNewReturnCode;
  PCS_ENDCRITICAL;
}

BYTE GetMsgBoxReturnCode( void )
{
  BYTE nReturnCode = nMsgBoxReturnCode;

  nMsgBoxReturnCode = 0;

  return ( nReturnCode );
}

APIFUNCRET SetSUIMBRetCode( struct REGW
*CallerRegs )
{
  SetMsgBoxReturnCode( LOBYTE( CallerRegs->bx
) );

  CallerRegs->ax = ERR_SUCCESS;

  SetForegroundRegs( CallerRegs );
}

APIFUNCRET SetKeyStroke( struct REGW
*CallerRegs )
{
  BYTE nHiScanByte;

  if ( ( nHiScanByte = HIBYTE( CallerRegs->bx ) ) >
0 )
    SendScanCode( nHiScanByte );

  SendScanCode( LOBYTE( CallerRegs->bx ) );

  CallerRegs->ax = ERR_SUCCESS;

  SetForegroundRegs( CallerRegs );
}

APIFUNCRET GetSetLockKbdMouse( struct REGW
*CallerRegs )
{
  BOOL bLockKbdMouse;

  if ( IsGetFunction( CallerRegs ) )
    CallerRegs->ax = UIConfigData.bLockKbdMouse
?
SMI_ENABLEDLOCKKBDMOUSE :
                SMI_DISABLEDLOCKKBDMOUSE;
  else
  {
    bLockKbdMouse = ( CallerRegs->bx == ( WORD
)SMI_ENABLEDLOCKKBDMOUSE );
    CallerRegs->ax = ERR_SUCCESS.

    if ( GetSCSCallProgress() ==
SMI_SCSCONNECTED )
    {
      if ( SendLockKbdMouse( bLockKbdMouse ) ==
ERR_SUCCESS )
        UIConfigData.bLockKbdMouse =
bLockKbdMouse;
      else
        CallerRegs->ax = ( WORD )ERR_INTERNAL,
    }
    else
      UIConfigData.bLockKbdMouse =
bLockKbdMouse.
  }

  SetForegroundRegs( CallerRegs );
}

APIFUNCRET GetSetDimScreen( struct REGW
*CallerRegs )
{

  BOOL bDimScreen;

  if ( IsGetFunction( CallerRegs ) )
    CallerRegs->ax = UIConfigData.bDimScreen ?
SMI_ENABLEDDIMSCREEN :
                SMI_DISABLEDDIMSCREEN;
  else
  {
    bDimScreen = ( CallerRegs->bx == ( WORD
)SMI_ENABLEDDIMSCREEN
);
    CallerRegs->ax = ERR_SUCCESS;

    if ( GetSCSCallProgress() ==
SMI_SCSCONNECTED )
    {
      if ( SendDimScreen( bDimScreen ) ==
ERR_SUCCESS )
        UIConfigData.bDimScreen = bDimScreen;
      else
        CallerRegs->ax = ( WORD )ERR_INTERNAL;
    }
    else
      UIConfigData.bDimScreen = bDimScreen;
  }

  SetForegroundRegs( CallerRegs );
}

APIFUNCRET GetSetConnectType( struct REGW
*CallerRegs )
{
  if ( CallerRegs->ax & 0x0000 )
    CallerRegs->ax = UIConfigData.bCnctType;
  else
    UIConfigData.bCnctType = CallerRegs->ax;

  SetForegroundRegs( CallerRegs );
}

APIFUNCRET GetKeyboardStatus( struct REGW
*CallerRegs )
{
  CallerRegs->ax = SMI_KBDNOTPRESENT;
  SetForegroundRegs( CallerRegs );
}

APIFUNCRET GetAboutDialog( struct REGW
*CallerRegs )
{
  char szTempStr[ STR_STRMAXLENGTH ];
  int iBIOSVersionNum = GetBIOSVersion();
  int iMsgBoxTotalLines;

  sprintf( szTempStr, STR_SMIABOUTBOX,
szSWVersionName, HIBYTE(
iBIOSVersionNum ),
          LOBYTE( iBIOSVersionNum ) );

  iMsgBoxTotalLines = FillMsgBoxBuff( MsgBoxBuff,
szTempStr,
SUI_CENTERJUSTIFIED );

  BuffHead.iStructLen = sizeof( MSGBOXBUFF );
  BuffHead.iBuffLen = sizeof( MSGBOXBUFF ) *
iMsgBoxTotalLines;
  BuffHead.Buff = ( LPVOID )MsgBoxBuff;

  CallerRegs->ax = ( WORD )ERR_SUCCESS;
  CallerRegs->dx = SEG( &BuffHead );
  CallerRegs->si = OFF( &BuffHead );

  SetForegroundRegs( CallerRegs );
}

APIFUNCRET GetSetUDHotkeys( struct REGW
*CallerRegs )
{
  BUFFHEADER FAR *pBuffHeader;
  SCANCODE FAR *pScanCodes;
  int iBuffLen;


  if ( IsGetFunction( CallerRegs ) )
  {
    if ( CallerRegs->bx == SUI_UDHOTICON1 )
      pScanCodes = UIConfigData.aUDHotKeys1;
    else
      pScanCodes = UIConfigData.aUDHotKeys2;

    BuffHead.Buff = ( LPVOID )pScanCodes;
    BuffHead.iBuffLen = GetNumScanCodes(
pScanCodes ) * sizeof(
SCANCODE );
    BuffHead.iStructLen = sizeof( SCANCODE );

    CallerRegs->dx = SEG( &BuffHead );
    CallerRegs->si = OFF( &BuffHead );
    CallerRegs->ax = ERR_SUCCESS.
  }
  else
  {
    pBuffHeader = MK_FP( CallerRegs->dx,
CallerRegs->si );
    pScanCodes = ( SCANCODE FAR *
)pBuffHeader->Buff;

    if ( pBuffHeader == NULL || pScanCodes ==
NULL )
      CallerRegs->ax = ( WORD )ERR_INTERNAL;
    else if ( pBuffHeader->iStructLen == 0 ||
pBuffHeader->iBuffLen == 0 )
      CallerRegs->ax = ( WORD )ERR_INTERNAL;
    else
    {
      iBuffLen = pBuffHeader->iBuffLen >
SUI_MAXNUMSCANCODES *
sizeof( SCANCODE ) ?
              SUI_MAXNUMSCANCODES * sizeof(
SCANCODE ) :
pBuffHeader->iBuffLen;

      if ( CallerRegs->bx == SUI_UDHOTICON1 )
      {
        fl_chr( UIConfigData.aUDHotKeys1, 0,
              SUI_MAXNUMSCANCODES * sizeof(
SCANCODE ) );
        fmem_cp( ( LPVOID )pScanCodes, ( LPVOID
)UIConfigData.aUDHotKeys1,
              iBuffLen );
      }
      else
      {
        fl_chr( UIConfigData.aUDHotKeys2, 0,
              SUI_MAXNUMSCANCODES * sizeof(
SCANCODE ) );
        fmem_cp( ( LPVOID )pScanCodes, ( LPVOID
)UIConfigData.aUDHotKeys2,
              iBuffLen )
      }

      CallerRegs->ax = ERR_SUCCESS;
    }
  }

  SetForegroundRegs( CallerRegs );
}

APIFUNCRET GetSetSecurityID( struct REGW
*CallerRegs )
{
  LPSTR lpszNewSecurityID;
  int iLenSecurityID;

  if ( IsGetFunction( CallerRegs ) )
  {
    CallerRegs->dx = SEG(
UIConfigData.szSecurityID );
    CallerRegs->si = OFF( UIConfigData.szSecurityID
);
    CallerRegs->ax = ERR_SUCCESS;
  }
  else
  {
    if ( GetSCSCallProgress() ==
SMI_SCSDISCONNECTED )
    {
      lpszNewSecurityID = MK_FP( CallerRegs->dx,
CallerRegs->si
```

```
);
    lLenSecurityID = lstr_len( lpszNewSecurityID );

    if ( lpszNewSecurityID != NULL &&
         lLenSecurityID <=
SUI_MAXLENSECURITYSUI )
    {
        fmem_cp( ( LPVOID )lpszNewSecurityID, ( LPVOID
)UIConfigData.szSecurityID,
                lLenSecurityID + 1 );

      CallerRegs->ax = SetSecurityID(
UIConfigData.szSecurityID
);
    }
    else
      CallerRegs->ax = ( WORD )ERR_INTERNAL;
  }
  else
  {
    if ( !fSecurityWarning )
    {
      OpenMessageBox( STR_SUISECURITYID, 0,
SUI_LEFTJUSTIFIED,
SUI_OK );
      fSecurityWarning = TRUE;
    }

    CallerRegs->ax = ( WORD )ERR_INTERNAL;
  }
}

  SetForegroundRegs( CallerRegs );
}

APIFUNCRET GetSetDomainID( struct REGW
*CallerRegs )
{
  char nNewDomainID;

  if ( IsGetFunction( CallerRegs ) )
  {
    CallerRegs->ax = ( WORD
)UIConfigData.nDomainID;
  }
  else
  {
    nNewDomainID = LOBYTE( CallerRegs->bx );

    if ( nNewDomainID >= PRX_MINDOMAINID &&
nNewDomainID <=
PRX_MAXDOMAINID )
    {
      UIConfigData.nDomainID = nNewDomainID;

      if ( !fDomainWarning )
      {
        OpenMessageBox( STR_SUIDOMAINID, 0,
SUI_LEFTJUSTIFIED,
SUI_OK );
        fDomainWarning = TRUE;
      }

      CallerRegs->ax = ERR_SUCCESS;
    }
    else
      CallerRegs->ax = ( WORD )ERR_INTERNAL;
  }

  SetForegroundRegs( CallerRegs );
}

APIFUNCRET GetSetUILanguage( struct REGW
*CallerRegs )
{
  CallerRegs->ax = ( WORD )ERR_UIUSENGLISH;

  SetForegroundRegs( CallerRegs );
}

APIFUNCRET RebootHost( struct REGW
*CallerRegs )
{
  REG_W InArgs, OutArgs;

  fl_clr( ( NPSTR )&InArgs, 0, sizeof ( InArgs ) );

  InArgs.ax = SCS_REBOOTHOST;

  isan( &InArgs, &OutArgs, SCS_INTNUM );

  if ( OutArgs.ax == SCS_ACCEPTED )
    CallerRegs->ax = ERR_SUCCESS;
  else
    CallerRegs->ax = ( WORD )ERR_INTERNAL;

  SetForegroundRegs( CallerRegs );
}

APIFUNCRET GetPasswordStatus( struct REGW
*CallerRegs )
{
  CallerRegs->ax = ( WORD )IsPWRequired();

  SetForegroundRegs( CallerRegs );
}

APIFUNCRET GetSetPassword( struct REGW
*CallerRegs )
{
  LPSTR szNewPassword;

  if ( IsGetFunction( CallerRegs ) )
  {
    CallerRegs->dx = SEG( szPassword );
    CallerRegs->si = OFF( szPassword );
  }
  else
  {
    szNewPassword = ( LPSTR )MAKELP(
CallerRegs->ds,
CallerRegs->si );
    fmem_cp( ( LPVOID )szNewPassword, ( LPVOID
)sz~~.sword,
            SUI_MAXLENPASSWORD );
  }

  CallerRegs->ax = ERR_SUCCESS;

  SetForegroundRegs( CallerRegs );
}

APIFUNCRET UpdateHostList( struct REGW
*CallerRegs )
{
  CallerRegs->ax = ( WORD )RequestHostList();

  SetForegroundRegs( CallerRegs );
}

APIFUNCRET GetHostListStatus( struct REGW
*CallerRegs )
{


  if ( !GetSCSActiveStatus() )
    CallerRegs->ax = ( WORD
)ERR_NOTSUPPORTED;


  CallerRegs->ax = GetStatusHLListItem();

  SetForegroundRegs( CallerRegs );
}

APIFUNCRET LBGetSetHotGroup( struct REGW
*CallerRegs )
{
  if ( IsGetFunction( CallerRegs ) )
  {
    if ( GetStatusHLListItem() == SHI_BLANK )
    {
      CallerRegs->ax = ( WORD
)ERR_NOTSUPPORTED;
      goto exit;
    }

    if ( ( int )CallerRegs->bx > 0 )
    {
      ListBoxEntry.lpszEntry = ( LPSTR
)GetLBGroup(
CallerRegs->bx );
      ListBoxEntry.nAttribute =
SUI_LBENTRYENABLED;
      CallerRegs->dx = SEG( &ListBoxEntry );
      CallerRegs->si = OFF( &ListBoxEntry );
      CallerRegs->ax = ERR_SUCCESS;

    }
    else if ( ( int )CallerRegs->bx == 0 )
    {
      ListBoxEntry.lpszEntry = ( LPSTR
)GetLBGroup(-1 );
      ListBoxEntry.nAttribute =
SUI_LBENTRYENABLED;
      CallerRegs->dx = SEG( &ListBoxEntry );
      CallerRegs->si = OFF( &ListBoxEntry );
      CallerRegs->ax = GetLBCurrGroup();
    }
    else
      CallerRegs->ax = GetNumGroupEntries();
  }
  else
  {
    SetLBCurrGroup( CallerRegs->bx );
    CallerRegs->ax = ERR_SUCCESS;
  }

exit:
  SetForegroundRegs( CallerRegs );
}

APIFUNCRET LBGetSetHotHost( struct REGW
*CallerRegs )
{
  if ( IsGetFunction( CallerRegs ) )
  {
    if ( GetStatusHLListItem() == SHI_BLANK )
    {
      CallerRegs->ax = ( WORD
)ERR_NOTSUPPORTED;
      goto exit;
    }

    if ( ( int )CallerRegs->bx > 0 )
    {
      ListBoxEntry.lpszEntry = ( LPSTR )GetLBHost(
CallerRegs->bx
);
      ListBoxEntry.nAttribute = GetLBHostStatus(
CallerRegs->bx
);
      CallerRegs->dx = SEG( &ListBoxEntry );
      CallerRegs->si = OFF( &ListBoxEntry );
      CallerRegs->ax = 0;
    }
    else if ( ( int )CallerRegs->bx == 0 )
    {
      ListBoxEntry.lpszEntry = ( LPSTR )GetLBHost(
SUI_LBCURRENTRY );
      ListBoxEntry.nAttribute = GetLBHostStatus(
SUI_LBCURRENTRY
);
      CallerRegs->dx = SEG( &ListBoxEntry );
      CallerRegs->si = OFF( &ListBoxEntry );
      CallerRegs->ax = ( WORD )GetLBCurrHost();
    }
    else
      CallerRegs->ax = GetNumHostEntries();
  }
  else
  {
    SetLBCurrHost( CallerRegs->bx );
    CallerRegs->ax = 0;
  }

exit:
  SetForegroundRegs( CallerRegs );
}

APIFUNCRET UpdateDimenLoc( struct REGW
*CallerRegs )
{
  OCCLUDEUNION OccUnion;
  int iActualVidMode;

  CallerRegs->ax = ( WORD )ERR_SUCCESS;
  iActualVidMode = GetCurrVidMode();

  if ( !GetSCSActiveStatus() || IsSetupDlg(
wScreenCode ) ||
IsHelpScreen( wScreenCode ) )
  {
    CallerRegs->ax = ( WORD
)ERR_NOTSUPPORTED;
    goto exit;
  }

  if ( CallerRegs->bx == 0xFFFF && CallerRegs->cx
== 0xFFFF &&
       CallerRegs->si == 0xFFFF && CallerRegs->di
== 0xFFFF )
  {
    UnloadSUI( SUI_NOUNLOADSUI );
  }
  else
  {
    if ( iActualVidMode > SUI_TEXTVIDMODE )
    {
      if ( IsOSKWinGraphics( wScreenCode ) )
      {
        OccUnion.occWin.yULWin = CallerRegs->bx;
        OccUnion.occWin.xULWin = CallerRegs->cx;
        OccUnion.occWin.yLRWin = CallerRegs->si;
        OccUnion.occWin.xLRWin = CallerRegs->di;

        CallerRegs->ax = CreateOccludedArea(
&OccUnion,
SUI_OCCRWIN, SCS_OSKFREEMEMPERCENT );
        SetOSKMode( &OccUnion, SUI_OCCRWIN );
      }
      else
      {
        OccUnion.occDosGraph.yULDos =
CallerRegs->bx;
        OccUnion.occDosGraph.xULDos =
CallerRegs->cx;
        OccUnion.occDosGraph.yLRDos =
CallerRegs->si;
        OccUnion.occDosGraph.xLRDos =
CallerRegs->di;

        CallerRegs->ax = CreateOccludedArea(
&OccUnion,
SUI_OCCDOSGRAPHICS,
SCS_OSKFREEMEMPERCENT );

        if ( IsOSKAsSetupDlg( wScreenCode ) )

          SetOSKMode( &OccUnion,
SUI_OCCDOSGRAPHICS );
      }
    }
    else
    {
      OccUnion.occText.yULRow = CallerRegs->bx;
      OccUnion.occText.xULCol = CallerRegs->cx;
      OccUnion.occText.yLRRow = CallerRegs->si;
      OccUnion.occText.xLRCol = CallerRegs->di;

      CallerRegs->ax = CreateOccludedArea(
&OccUnion,
SUI_OCCDOSTEXT,
SCS_OSKFREEMEMPERCENT );
      SetOSKMode( &OccUnion, SUI_OCCDOSTEXT
);
    }
  }

exit:
  SetForegroundRegs( CallerRegs );
}

APIFUNCRET GetSetContrast( struct REGW
*CallerRegs )
{
  BYTE nContrastIdx;

  if ( IsGetFunction( CallerRegs ) )
    CallerRegs->ax = ( WORD
)UIConfigData.nContrastIdx;
  else
  {
    nContrastIdx = LOBYTE( CallerRegs->bx );

    if ( ( CallerRegs->ax = ( WORD )SetContrast(
nContrastIdx ) )
          == ERR_SUCCESS )
      UIConfigData.nContrastIdx = nContrastIdx;
  }

  SetForegroundRegs( CallerRegs );
}

APIFUNCRET GetSetBrightness( struct REGW
*CallerRegs )
{
  BYTE nBrightnessIdx;

  if ( IsGetFunction( CallerRegs ) )
    CallerRegs->ax = ( WORD
)UIConfigData.nBrightnessIdx;
  else
  {
    nBrightnessIdx = LOBYTE( CallerRegs->bx );

    if ( ( CallerRegs->ax = ( WORD )SetBrightness(
nBrightnessIdx
))
          == ERR_SUCCESS )
      UIConfigData.nBrightnessIdx = nBrightnessIdx;
  }

  SetForegroundRegs( CallerRegs );
}

APIFUNCRET GetSetAutoShutOff( struct REGW
*CallerRegs )
{
  if ( IsGetFunction( CallerRegs ) )
    CallerRegs->ax = ( WORD
)UIConfigData.bAutoShutoff;
  else
  {
    if ( LOBYTE( CallerRegs->bx ) == TRUE )
    {
      CallerRegs->ax = SetSuspendTimeout(
SSS_SUSPENDMINIMUM );
      UIConfigData.bAutoShutoff = TRUE;
    }
    else
    {
```

```
    CallerRegs->ax = SetSuspendTimeout(
SSS_SUSPENDDISABLED );

    UIConfigData.bAutoShutoff = FALSE;
  }
 }

 SetForegroundRegs( CallerRegs );
}

APIFUNCRET GetSetSleepTime( struct REGW
*CallerRegs )
{
 BYTE nSleepTimeIdx;

 if ( IsGetFunction( CallerRegs ) )
 {
  if ( UIConfigData.nSleepTimeIdx ==
SSS_SLEEPDISABLED )
   CallerRegs->ax = ( WORD
)SUI_NOSLEEPSLIDERIDX - 1;
  else
   CallerRegs->ax = ( WORD
)UIConfigData.nSleepTimeIdx - 1;
 }
 else
 {
  nSleepTimeIdx = LOBYTE( CallerRegs->bx ) + 1;

  if ( nSleepTimeIdx == SUI_NOSLEEPSLIDERIDX
)
   nSleepTimeIdx = ( BYTE
)SSS_SLEEPDISABLED;

  if ( ( CallerRegs->ax = SetSleepTimeout(
nSleepTimeIdx ) )
     == ERR_SUCCESS )
  {
   if ( nSleepTimeIdx == SSS_SLEEPDISABLED )
   {
    if ( ( CallerRegs->ax = SetPowerEnable(
SSS_POWERMANDISABLED ) )
      == ERR_SUCCESS )
    {
     if ( ( CallerRegs->ax = SetDozeTimeout(
SSS_DOZEDISABLED ) )
       == ERR_SUCCESS )
      UIConfigData.nSleepTimeIdx =
nSleepTimeIdx;
    }
   }
   else
   {
    if ( ( CallerRegs->ax = SetPowerEnable(
SSS_POWERMANENABLED ) )
      == ERR_SUCCESS )
    {
     if ( ( CallerRegs->ax = SetDozeTimeout(
SSS_DOZEDISABLED ) )
       == ERR_SUCCESS )
      UIConfigData.nSleepTimeIdx =
nSleepTimeIdx;
    }
   }
  }
 }

 SetForegroundRegs( CallerRegs );
}

int EnableBusyCursor( int fStatus )
{
 int rReturn;

 AX( SUI_SHOWHIDEBUSYCURSOR );
 BX( fStatus );

 rReturn = ( *lpfnSUICallBack )();

 return ( rReturn );
}

int DoMessageBox( NPSTR szMsgText, int
iSerNumber, char
nAlignment, int iButtons,
        MODALMSGBOXCB fnCallBack, int
iMsgBoxTimeOut )
{
 if ( !GetSUIReady() )
  return ( ERR_INTERNAL );

 if ( iMsgBoxTimeOut > 0 )
  iMsgBoxTimeOut += 2;

 if ( ( iProcMsgBoxThreadId =
GetTempEventItem() ) < ERR_SUCCESS
)
  return ( ERR_INTERNAL );

 A ( Thread( iProcMsgBoxThreadId, ( NEARPROC
)ProcessMessageBox,
NULL, SMO_POLLED,
        FALSE, SUI_PROCMSGBOXPOLLFREQ,
0 ),

 if ( fnCallBack != NULL )
  DoModalMsgBox( fnCallBack, iMsgBoxTimeOut );

 ProcessMessageBox( szMsgText, iSerNumber,
nAlignment, iButtons
);

 return ( ERR_SUCCESS );
}

void ProcessMessageBox( NPSTR szNewMsgText,
int iNewSerNumber,
char nNewAlignment, int iNewButtons )
{
 static NPSTR szMsgText;
 static char nAlignment;
 static int iButtons;
 static int iSerNumber;
 static int iProcMsgBoxState =
SUI_NOPROCMSGBOXSTATE;

 switch ( iProcMsgBoxState )
 {
  case SUI_NOPROCMSGBOXSTATE:
   szMsgText = szNewMsgText;
   iSerNumber = iNewSerNumber;
   nAlignment = nNewAlignment;
   iButtons = iNewButtons;
   iProcMsgBoxState = SUI_HIDEMSGBOX;
   break;

  case SUI_HIDEMSGBOX:
   HideMessageBox();
   iProcMsgBoxState = SUI_SHOWMSGBOX;
   break;

  case SUI_SHOWMSGBOX:
   OpenMessageBox( szMsgText, iSerNumber,
nAlignment, iButtons
);
   iProcMsgBoxState =
SUI_NOPROCMSGBOXSTATE;
   DelThread( iProcMsgBoxThreadId );
   break;
 }
}

int OpenMessageBox( NPSTR szMsgText, int
iSerNumber, char
nAlignment, int iButtons )
{
 int iSeg = 0, iOff = 0;
 int iMsgBoxTotalLines;

 if ( !GetSUIReady() )
  return ( ERR_INTERNAL );

 if ( szMsgText != NULL )
  iSerNumber = 0;
 else
  goto exit;

 if ( strlen( szMsgText ) > STR_STRMAXLINERR -
1 )
  return ( ERR_INTERNAL );

 iMsgBoxTotalLines = FillMsgBoxBuff( MsgBoxBuff,
szMsgText,
nAlignment );

 if ( *MsgBoxBuff[ 0 ].lpszText == NULL )
  return ( ERR_INTERNAL );

 SetHead.iBuffLen = sizeof( MSGBOXBUFF );
 SetHead.iBufLen = sizeof( MSGBOXBUFF ) *
iMsgBoxTotalLines;
 SetHead.lBuff = ( LPVOID )MsgBoxBuff;

 iSeg = SEG( &SetHead );
 iOff = OFF( &SetHead );

exit:

 AX( SUI_SHOWMSGBOX );
 BX( iButtons );
 CX( iSerNumber );
 DX( iSeg );
 SI( iOff );

 return ( ( *lpfnSUICallBack )() );
}

int FillMsgBoxBuff( MSGBOXBUFF MsgBoxBuff[]
char *szMsgText,
char nAlignment )
{
 int iTerminator, iMsgBoxLineIdx,
iMsgBoxTotalLines;
 char *szPtrTempStr = szTempMsgStr;

 strcpy( szTempMsgStr, szMsgText );

 _fmemset( MsgBoxBuff, 0, sizeof ( MSGBOXBUFF ) *
SUI_SUIMAXMSGBOXLINES );

 for ( iMsgBoxLineIdx = 0, iMsgBoxTotalLines = 0;
      iMsgBoxLineIdx <
SUI_SUIMAXMSGBOXLINES; ++iMsgBoxLineIdx
)
 {
  if ( ( iTerminator = str_pos( STR_SEPARATOR,
szPtrTempStr ) )
> 0 )
  {
   *( szPtrTempStr + ( iTerminator - 1 ) ) = NULL;
   MsgBoxBuff[ iMsgBoxLineIdx ].lpszText = (
LPSTR
)szPtrTempStr;
   MsgBoxBuff[ iMsgBoxLineIdx ].nAlignment =
nAlignment;
    szPtrTempStr += iTerminator;
    iMsgBoxTotalLines++;
  }
  else
   MsgBoxBuff[ iMsgBoxLineIdx ].lpszText =
szNullStr;
 }

 return ( iMsgBoxTotalLines );
}

int HideMessageBox( void )
{
 if ( !GetSUIReady() )
  return ( ERR_INTERNAL );

 AX( SUI_HIDEMSGBOX );

 return ( ( *lpfnSUICallBack )() );
}

int UpdateSUIConnectStatus( void )
{
 if ( !GetSUIReady() )
  return ( ERR_INTERNAL );

 SetUpdatingConnectStatus( TRUE );

 AX( SUI_UPDATECONNECTSTATUS );

 return ( ( *lpfnSUICallBack )() );
}

#if defined( _MSC_VER )
#pragma warning( default : 4704 )
#endif
Copr. 1995 Zenith Data Systems Corp.
#include "sr.h"
#include "frame.h"
#include "sysm.h"
#include "sm.h"

static BYTE fFrameWarning = FALSE;

static char aFrameTypes[][8]=
{
 "802.3",
 "802.2",
 "II",
 "SNAP",
};

APIFUNCRET LBGetSetNetFrameType( struct
REGW *CallerRegs )
{
 if ( IsGetFunction( CallerRegs ) )
 {
  int iCurFrameIdx = UIConfigData.nFrameType -
PRX_FRAMEBASE;
   CallerRegs->dx = SEG( &ListBoxEntry );
   CallerRegs->si = OFF( &ListBoxEntry );

   if ( ( int )CallerRegs->bx > 0 )
   {
    ListBoxEntry.lpszEntry = ( LPSTR
)aFrameTypes[
CallerRegs->bx - 1 ];
    ListBoxEntry.nAttribute =
SUI_LBENTRYENABLED;
    CallerRegs->ax = ERR_SUCCESS;
  }
  else if ( ( int )CallerRegs->bx == 0 )
  {
   ListBoxEntry.lpszEntry =
    ( LPSTR )aFrameTypes[ iCurFrameIdx ];
   ListBoxEntry.nAttribute =
SUI_LBENTRYENABLED;
   CallerRegs->ax = iCurFrameIdx + 1;
  }
  else
   CallerRegs->ax =
PRX_NUMOFAVAILFRAMES;
 }
 else
 {
  if ( !fFrameWarning )
  {
   OpenMessageBox( STR_SUIFRAMETYPE, 0,
SUI_LEFTJUSTIFIED,
SUI_OK );
    fFrameWarning = TRUE;
  }

  UIConfigData.nFrameType = PRX_FRAMEBASE
+ ( CallerRegs->bx -
1 );
  CallerRegs->ax = ERR_SUCCESS;
 }

 SetForegroundRegs( CallerRegs );
}

APIFUNCRET NotifyScreenCode( struct REGW
*CallerRegs )
{
 BYTE nLastOSKScreen;
 BYTE nLastSetupDlgScreen;

 if ( ( nLastOSKScreen = LOBYTE( CallerRegs->bx
) & SUI_OSKMASK
) > 0 )
 {
  if ( IsSetupDlg( GetCurrScrCode() ) )

    UIConfigData.nLastOSKDlgScreen =
nLastOSKScreen;
   else
    UIConfigData.nLastOSKScreen =
nLastOSKScreen;
 }

 if ( ( nLastSetupDlgScreen = LOBYTE(
CallerRegs->bx ) &
SUI_SETUPDLGMASK ) > 0 )
   UIConfigData.nLastSetupDlgScreen =
nLastSetupDlgScreen;

 CallerRegs->ax = ERR_SUCCESS;

 SetForegroundRegs( CallerRegs );
}
Copr. 1995 Zenith Data Systems Corp.
#include "sr.h"
#include "sis.h"
#include "sysm.h"
#include "t2.h"
#include "sm.h"

#if defined( _MSC_VER )
#pragma warning( disable : 4704 )
#endif

static int iCalibMode = -1;
static int iCalibThreadIdx = 0;
static int xCalibCol, yCalibRow;
static BOOL fCalibLowRight;

static CALIBPENSTATES PenCalibStates;

APIFUNCRET CalibratePen( struct REGW
*CallerRegs )
{
 if ( fCalibLowRight )
 {
   CallerRegs->ax = SUI_CALIBLOWRIGHT;
   CallerRegs->cx = SHC_XVGARES -
SUI_XCALIBPOINT;
   CallerRegs->bx = SHC_YVGARES -
SUI_YCALIBPOINT;
   fCalibLowRight = FALSE;
 }

 if ( IsGetFunction( CallerRegs ) )
   iCalibMode = PND_CALIBLR;
 else
 {
   fCalibLowRight = TRUE;
   iCalibMode = PND_CALIBUL;
 }
```

```
  if ( ( ICalibThreadId = GetTempEventNum() ) < 0 )
  {
   CallerRegs->ax = ( WORD )ERR_INTERNAL;
  }
  else
  {
   PenCalibStatus = SUI_INITIALCALIBSTATE;
   xCalibCol = CallerRegs->cx;
   yCalibRow = CallerRegs->bx;
   CallerRegs->ax = ERR_SUCCESS;

   AddThread( ICalibThreadId, WaitForPenCalib,
NULL,
SMO_POLLED, FALSE,
         SUI_CALIBPOLLFREQ, 0 );
  }

  SetForegroundRegs( CallerRegs );
}

APIFUNCRET CalibrateCancel( struct REGW
*CallerRegs )
{
  DelThread( ICalibThreadId );
  EnableNewCalib( FALSE );

  CallerRegs->ax = ERR_SUCCESS;

  SetForegroundRegs( CallerRegs );

  if ( GetCurrActionCode() ==
SUI_LASTCONNECTION )
    LoadSUI( SUI_SPECIFIEDSCREEN,
SUI_HOSTSELECTION );
}

void WaitForPenCalib( void )
{
  int xUpperCol, yUpperRow, xLowerCol,
yLowerRow
  int ICalibState;
  PENCALIB CurPenCalib;

  switch( PenCalibStatus )
  {
   case SUI_INITIALCALIBSTATE:
    if ( SetCalibMode( ICalibMode, xCalibCol,
yCalibRow ) == 0
    )
       PenCalibStatus = SUI_CHECKCALIB;
     else
       PenCalibStatus = SUI_CALIBERROR;
     break;

   case SUI_CHECKCALIB:
    ICalibState = GetCalibState( ICalibMode,
&xUpperCol,
&yUpperRow,
              &xLowerCol, &yLowerRow
);

    if ( ICalibState != PHD_CALIBNOTDONE )
    {
     if ( ICalibMode == PHD_CALIBLR )
     {
      if ( ICalibState == PHD_CALIBDONEVALID )
      {
        CurPenCalib.wXUpperPenCalib =
xUpperCol;
        CurPenCalib.wYUpperPenCalib =
yUpperRow;
        CurPenCalib.wXLowerPenCalib =
xLowerCol;
        CurPenCalib.wYLowerPenCalib =
yLowerRow;

        SetEEmouseConfig( &CurPenCalib );
        EnableNewCalib( TRUE );

        PenCalibStatus = SUI_CALIBSUCCESS;
      }
      else
        PenCalibStatus = SUI_CALIBERROR;
     }
     else
       PenCalibStatus = SUI_CALIBSUCCESS;
    }
    break;

   case SUI_CALIBERROR:
   case SUI_CALIBSUCCESS:
    AX( SUI_CALIBPOINTDONE );
    ( *lpfnSUICallback )();
    DelThread( ICalibThreadId );

    if ( ICalibMode == PHD_CALIBLR &&
  GetCurrActionCode() ==
SUI_DOPENCALIBRATION )
      LoadSUI( SUI_SPECIFIEDSCREEN,
SUI_HOSTSELECTION );
     break;
  }
}

#if defined( _MSC_VER )
#pragma warning( default : 4704 )
#endif



Copr 1995 Zenith Data Systems Corp.



#include "sr.h"
#include "sis.h"
#include "spcomm.h"
#include "k2.h"
#include "hm.h"
#include "im.h"
#include "sm.h"

#if defined( _MSC_VER )
#pragma warning( disable : 4704 )
#endif

static FLASHUPDATESTATES FlashUpdateState,
FlashStateOnError;
static MEM_REC MemRec;
static char far *sFlashImageBuff = NULL;
static char *szPathFlashFile = NULL;
static char *szHomeAstroUpdate = NULL;
static int IDoUpdateThreadId,
IAstroUpdateThreadId;
static int IFlashUpdateState;
static int ITmpFilePercent, IOldTmpFilePercent,
IOldTmpDispPercent;

static int ITotalFlashFiles,
static int ICurrFlashFile,
static LONG lLenCurrFlashFile;
static int ISectorFlashStatus;

APIFUNCRET DoUpdate( struct REGW *CallerRegs
)
{
  if ( GetSCSCallProgress() !=
SMI_SCSCONNECTED )
   CallerRegs->ax = ( WORD )ERR_INTERNAL;
  else
  {
   if ( ( IDoUpdateThreadId = GetTempEventNum()
) ==
ERR_INTERNAL )
   {
    CallerRegs->ax = ( WORD )ERR_INTERNAL;
   }
   else
   {
    if ( !sFlashSupported() )
    {
     FlashUpdateState = FLU_SAFETYCHECK;
     AddThread( IDoUpdateThreadId,
WaitForFlashUpdate, NULL,
SMO_MANYTIMES, FALSE,
           FLU_POLLFREQ, FLU_MAXRETRY );

     CallerRegs->ax = ( WORD )ERR_SUCCESS;
    }
    else
     CallerRegs->ax = ( WORD )ERR_INTERNAL;

   }
  }

  SetForegroundRegs( CallerRegs );
}

APIFUNCRET RequestAstroUpdate( struct REGW
*CallerRegs )
{
  char *szCurrentUpdate = GetHomeAstroUpdate();
  int MsgBoxTotalLines;
  WORD wReturn;
  FLASHUPDATESTATES PowerState;

  if ( *szCurrentUpdate != '' && *szCurrentUpdate !=
NULL )
  {
   if ( ( PowerState = CheckFlashPowerState() ) !=
FLU_NOFLUSTATE )
   {
    switch( PowerState )
    {
     case FLU_GETBATTERYINFOERROR:
      MsgBoxTotalLines = FillMsgBoxBuff(
MsgBoxBuff,
STR_FLUGETBATINFOERROR,

SUI_CENTERJUSTIFIED
);
      break;

     case FLU_NOTONACERROR:
      MsgBoxTotalLines = FillMsgBoxBuff(
MsgBoxBuff,
STR_FLUNOAC, SUI_CENTERJUSTIFIED );
      break;

     case FLU_BATNOTATTACHEDERROR:
      MsgBoxTotalLines = FillMsgBoxBuff(
MsgBoxBuff,
STR_FLUNOBATERROR, SUI_CENTERJUSTIFIED
);

      break;

     case FLU_BATCAPTOOLOWERROR:
      MsgBoxTotalLines = FillMsgBoxBuff(
MsgBoxBuff,
STR_FLUBATTOOLOWERROR,
SUI_CENTERJUSTIFIED );
      break;

     default:
      MsgBoxTotalLines = FillMsgBoxBuff(
MsgBoxBuff,
STR_FLUUNKNOWNBATERROR,
SUI_CENTERJUSTIFIED );
    }

    wReturn = ( WORD
)ERR_UPGRADENOTAVAIL;
   }
   else if ( GetSCSCallProgress() !=
SMI_SCSCONNECTED )
   {
    MsgBoxTotalLines = FillMsgBoxBuff(
MsgBoxBuff,
STR_FLUNOCONNECTERROR,
SUI_CENTERJUSTIFIED );
    wReturn = ( WORD
)ERR_UPGRADENOTAVAIL;
   }
   else if ( GetLinkQuality() != PRX_HIGHQUALITY
)
   {
    MsgBoxTotalLines = FillMsgBoxBuff(
MsgBoxBuff,
STR_FLULINKTOOLOWERROR,
SUI_CENTERJUSTIFIED );
    wReturn = ( WORD
)ERR_UPGRADENOTAVAIL;
   }
   else if ( GetCurrentModeId() != PHD_DOSAPP )
   {
    MsgBoxTotalLines = FillMsgBoxBuff(
MsgBoxBuff,
STR_FLUNOTINDOSAPP, SUI_CENTERJUSTIFIED
);
    wReturn = ( WORD
)ERR_UPGRADENOTAVAIL;
   }
   else
   {
    MsgBoxBuff[0].lpszText = ( LPSTR
)szCurrentUpdate;
    MsgBoxBuff[0].nAlignment =
SUI_CENTERJUSTIFIED;
    MsgBoxTotalLines = 1;
    wReturn = ERR_SUCCESS;
    TRACE( "NOTICE: Flash upgrade safety checks
passed.\n" );
   }
  }
  else
  {
   MsgBoxTotalLines = FillMsgBoxBuff(
MsgBoxBuff,
STR_FLUNOFLASHFILES,
SUI_CENTERJUSTIFIED );
   wReturn = ( WORD )ERR_UPGRADENOTAVAIL;
  }

  SetMsgd.lStructLen = sizeof( MSGBOXBUFF );
  SetMsgd.lBuffLen = sizeof( MSGBOXBUFF ) *
MsgBoxTotalLines;
  SetMsgd.Buff = ( LPVOID )MsgBoxBuff;

  CallerRegs->dx = SEG( &SetMsgd );
  CallerRegs->si = OFF( &SetMsgd );
  CallerRegs->ax = wReturn;

  SetForegroundRegs( CallerRegs );
}

void WaitForFlashUpdate( void )
{
  int IMaxFlashSector;
  int INumberOfFlash;
  int INewTmpFilePercent, INewTmpDispPercent;
  int IRetryLimit = GetRetryLimit(
IDoUpdateThreadId );
  FlashStateOnError = FlashUpdateState;

  switch ( FlashUpdateState )
  {
   case FLU_NOFLUSTATE:

   case FLU_SAFETYCHECK:
    FlashUpdateState = FLU_INITMEM;

    SetWaitingIcon( SSS_WAITINGICONON, TRUE
);

    if ( UIConfigData.nSleepTimeIdx !=
SSS_SLEEPDISABLED )
    {
     SetPowerEnable(
SSS_POWERMANDISABLED );
     TRACE( "NOTICE: Disabled powerman for
flash update\n" );
    }
    break;


   case FLU_INITMEM:
    TRACE( "NOTICE: Initializing and allocating
memory\n" );

    if ( ( szPathFlashFile = ( NPSTR )malloc(
SCS_MAXLENFILENAME + 1 ) ) == NULL )
     FlashUpdateState = FLU_MEMERROR;
    else
    {
     if ( SMDosBusy( GetFlashImageBuff ) !=
ERR_SUCCESS )
      FlashUpdateState = FLU_MEMERROR;
     else
     {
      FlashUpdateState = FLU_ALLOCDOSMEM;
      ResetRetryLimit( IDoUpdateThreadId );
     }
    }
    break;

   case FLU_ALLOCDOSMEM:
    if ( sFlashImageBuff == NULL )
    {
     if ( IRetryLimit == FLU_MAXDOSBUSY )
     {
      TRACE( "ERROR: Failed to allocate required
buffer\n" );
      FlashUpdateState = FLU_MEMERROR;
     }
    }
    else
    {
     TRACE( "NOTICE: Successfully acquired
memory\n" );

     ITotalFlashFiles = FLU_NUMBERUNKNOWN;
     ICurrFlashFile = 0;

     _fmemset( szPathFlashFile, 0,
SCS_MAXLENFILENAME );

     FlashUpdateState =
FLU_SENDREQFLASHUPD;
     ResetRetryLimit( IDoUpdateThreadId );

    }
    break;

   case FLU_SENDREQFLASHUPD:
    TRACE( "NOTICE: Requesting the flash
upgrade from the
Host\n" );
    IMaxFlashSector = FLU_SIZEFLASHSECTOR /
1024;

    if ( SendParcelMessage(
PMI_REQFLASHUPD, sizeof( int ),
        ( NPSTR )&IMaxFlashSector ) !=
ERR_SUCCESS )
     FlashUpdateState =
FLU_SENDPKIMSGERROR;
    else
```

```
      {
        if ( lRetryLimit == 0 )
          SetRetryLimit( lDoUpdateThreadIdx, 1 );

        SetTmpFilePercent( 0 );
        SetTimeLimit( lDoUpdateThreadIdx,
FLU_PRIMSGPOLLFREQ );
        FlashUpdateState =
FLU_WAITFORTMPFLASHFILES;
      }
      break;

    case FLU_WAITFORTMPFLASHFILES:
      lNewTmpFilePercent = GetTmpFilePercent();

      if ( lNewTmpFilePercent == 0 )
      {
        if ( lRetryLimit == FLU_MAXPCNTTMPFILE )

        {
          TRACE( "ERROR: Timeout waiting for first
percent of
temp files\r" );
          FlashUpdateState =
FLU_NOACKTEMPFILESERROR;
        }
        else if ( lRetryLimit %
FLU_MODPCNTTMPFILE == 0 )
        {
          TRACE( "ERROR: Requesting flash update
from host once
again\r" );
          FlashUpdateState =
FLU_SENDREQFLASHUPD;
        }
      }
      else
      {
        UpdateTmpFilePercentage(
lNewTmpFilePercent );
        lOldTmpFilePercent = lNewTmpFilePercent;
        lOldTmpDispPercent = lNewTmpDispPercent =
(
lNewTmpFilePercent * 2 ) / 100;
        FlashUpdateState =
FLU_UPDATETMPFILEPERCENT;
        ResetRetryLimit( lDoUpdateThreadIdx );
      }
      break;

    case FLU_UPDATETMPFILEPERCENT:
      lNewTmpFilePercent = GetTmpFilePercent();

      lNewTmpDispPercent = ( lNewTmpFilePercent *
2 ) / 100
      if ( lNewTmpFilePercent == lOldTmpFilePercent
)
      {
        if ( lRetryLimit == FLU_MAXPCNTTMPFILE ||
            lNewTmpFilePercent == 100 )
        {
          ResetRetryLimit( lDoUpdateThreadIdx );
          FlashUpdateState =
FLU_WAITFORNUMFILES;
          TRACE( "NOTICE: Done waiting for number
of files,
onwards\r" );

#if !defined( PROD )
          if ( lNewTmpFilePercent != 100 )
            TRACE( "ERROR: Timeout waiting for next
percent of
temp files\r" );
#endif
        }
      }
      else
      {
        ResetRetryLimit( lDoUpdateThreadIdx );
        lOldTmpFilePercent = lNewTmpFilePercent;

        if ( lNewTmpDispPercent !=
lOldTmpDispPercent )
        {
          TRACE( "NOTICE: Updating percentage of
tmp file
processing\r" );
          UpdateTmpFilePercentage(
lNewTmpFilePercent );
          lOldTmpDispPercent =
lNewTmpDispPercent;
        }
      }
      break;

    case FLU_WAITFORNUMFILES:
      TRACE( "NOTICE: Waiting for total number of
flash files\r"
);

      lNumberOfFlash = GetTotalFlashFiles();

      if ( lNumberOfFlash ==
FLU_NUMBERUNKNOWN )
      {
        if ( lRetryLimit == FLU_MAXUPDREQ )

        {
          TRACE( "ERROR: Timeout waiting for
number of flash
files\r" );
          FlashUpdateState =
FLU_NOACKNUMFILESERROR;
        }
      }
      else if ( lNumberOfFlash <=
FLU_ERRHOSTBASE )
      {
#if !defined( PROD )
        sprintf( szTempStr, "NOTICE: Number of flash
files
returned as an error code - %d\r", lNumberOfFlash );

        TRACE( szTempStr );
#endif
        switch ( lNumberOfFlash )
        {
          case FLU_ERRREADHOSTDAT:
            FlashUpdateState = FLU_READHOSTDAT;
            break;

          case FLU_ERRMISSINGFILE:
            FlashUpdateState = FLU_MISSINGFILE;
            break;

          case FLU_ERRNOFLASHFILES:
            FlashUpdateState = FLU_NOFLASHFILES;
            break;

          case FLU_ERROUTOFDISKSPACE:
            FlashUpdateState =
FLU_OUTOFDISKSPACE;
            break;

          case FLU_ERRFILECORRUPTED:
            FlashUpdateState =
FLU_FILECORRUPTED;
            break;

          case FLU_ERRNOCHECKSUM:
            FlashUpdateState = FLU_NOCHECKSUM;

            break;

          default:
            FlashUpdateState =
FLU_HOSTUNKNOWNERR;
            break;
        }
      }
      else
      {
        WORD wExtendedMem =
GetNumOfExtendedMem();

#if !defined( PROD )
        sprintf( szTempStr, "NOTICE: Number of flash
files - %d
\r", lNumberOfFlash );
        TRACE( szTempStr );
#endif
        if ( lNumberOfFlash >
FLU_2MEGTHRESHOLD &&
            wExtendedMem <
FLU_1MEGEXTENDEDRAM )
        {
          FlashUpdateState =
FLU_1MEGSYSTEMERROR;
        }
        else if ( lNumberOfFlash <=
FLU_2MEGTHRESHOLD &&
            wExtendedMem ==
FLU_1MEGEXTENDEDRAM )
        {
          FlashUpdateState =
FLU_2MEGSYSTEMERROR;

        }
        else
        {
          lCurrFlashFile = 1;

          FlashUpdateState = FLU_SENDREQPATH;
          Set2MegFlash( ( lNumberOfFlash >
FLU_2MEGTHRESHOLD )
);
          SetTimeLimit( lDoUpdateThreadIdx,
FLU_POLLFREQ );
          ResetRetryLimit( lDoUpdateThreadIdx );
        }
      }
      break;

    case FLU_SENDREQPATH:
      *szPathFlashFile = NULL;

      if ( SendPrivateMessage(
PM_REQPATHFROMHX, sizeof( int
),
                     ( NPSTR )&lCurrFlashFile )
!=
ERR_SUCCESS )
        FlashUpdateState =
FLU_SENDPRIMSGERROR;
      else
      {
        if ( lRetryLimit == 0 )
          SetRetryLimit( lDoUpdateThreadIdx, 1 );

        FlashUpdateState =
FLU_WAITFORPATHFLASHFILE;
        SetTimeLimit( lDoUpdateThreadIdx,
FLU_PRIMSGPOLLFREQ );
      }
      break;

    case FLU_WAITFORPATHFLASHFILE:
      if ( *GetPathFlashFile() == NULL )
      {
        if ( lRetryLimit < FLU_MAXPATHREQ )
        {
          TRACE( "ERROR: Timeout waiting for
response to path
request\r" );
          FlashUpdateState =
FLU_NOACKPATHERROR;
        }
        else if ( lRetryLimit % FLU_MODPATHREQ
== 0 )
        {
          TRACE( "NOTICE: Trying again to receive
the next path
name\r" );
          FlashUpdateState = FLU_SENDREQPATH;
        }
      }
      else
      {
        if ( *ParseForFileName( GetPathFlashFile() )
==
FLU_FLASHFILEID )
        {
          FlashUpdateState =
FLU_RECEIVEHOSTFILE;
          ResetRetryLimit( lDoUpdateThreadIdx );
          SetTimeLimit( lDoUpdateThreadIdx,
FLU_POLLFREQ );
        }
        else
        {
          TRACE( "NOTICE: Protected file
encountered, skipping to
the next file\r" );
          goto after_flash;
        }
      }
      break;

    case FLU_RECEIVEHOSTFILE:
#if !defined( PROD )
      sprintf( szTempStr, "NOTICE: File name
received - %s \r",
             GetPathFlashFile() );
      TRACE( szTempStr );
#endif
      if ( ReceiveHostFile( GetPathFlashFile(),
sFlashImageBuff,
FLU_SIZEFLASHSECTOR )
            != ERR_SUCCESS )
      {
        if ( lRetryLimit == FLU_MAXRECVFILEREQ )
        {
          if ( lCurrFlashFile > 1 )
          {
            TRACE( "ERROR: Timeout waiting for
successful
ReceiveHostFile() request, from sector\r" );
            FlashUpdateState =
FLU_NOACKRECEIVEFATALERROR;
          }
          else
          {
            TRACE( "ERROR: Timeout waiting for
successful
ReceiveHostFile() request\r" );
            FlashUpdateState =
FLU_NOACKRECEIVEFILEERROR;
          }
        }
      }
      else
      {
        TRACE( "NOTICE: Finally beginning refresh of
the
specified sector\r" );
        FlashUpdateState = FLU_FLASHIT;
        ResetRetryLimit( lDoUpdateThreadIdx );
      }
      break;

    case FLU_FLASHIT:
      if ( ( lSectorFlashStatus = FlashSector(
sFlashImageBuff,
             lCurrFlashFile ) ) !=
SSS_FLASHSUCCESS )
      {
        if ( lSectorFlashStatus ==
SSS_FLASHNOTATTACHED ||
             lRetryLimit == FLU_MAXFLASHIT )

          FlashUpdateState =
FLU_FLASHFATALERROR;
      }
      else
      {
after_flash:
        UpdateFlashPercentage( lCurrFlashFile );
        ResetRetryLimit( lDoUpdateThreadIdx );

        if ( ++lCurrFlashFile > lTotalFlashFiles )
          FlashUpdateState = FLU_CLEAREEROM;
        else
          FlashUpdateState = FLU_SENDREQPATH;

      }
      break;

    case FLU_CLEAREEROM:
      TRACE( "NOTICE: Clearing EEPROM\r" );

      if ( ClearEEPROM() != ERR_SUCCESS )
      {
        if ( lRetryLimit == FLU_MAXCLEAREEROM )

          FlashUpdateState =
FLU_EEROMNOCLRERROR;
      }
      else
      {
        ResetRetryLimit( lDoUpdateThreadIdx );
        FlashUpdateState =
FLU_FLASHUPDATECOMPLETE;
        SendPrivateMessage( PM_REQFLASHDONE,
0, NULL );
      }
      break;

    case FLU_FLASHUPDATECOMPLETE:
      SendPrivateMessage( PM_REQFLASHDONE,
0, NULL );
      FlashUpdateState = FLU_REBOOT;
      SetTimeLimit( lDoUpdateThreadIdx,
FLU_PRIMSGPOLLFREQ );
      break;

    case FLU_REBOOT:
      reboot( CRU_COLDBOOT );
      break;

    default:
      WaitForFlashError();
  }

  if ( FlashUpdateState >
FLU_BEGINERRORSTATES )
    WaitForFlashError();
}

void WaitForFlashError( void )
{
  SendPrivateMessage( PM_REQFLASHDONE, 0,
NULL );

  if ( sFlashImageBuff == NULL )
  {
    DelThread( lDoUpdateThreadIdx );
    SetWaitingIcon( SSS_WAITINGICONOFF, TRUE
);
  }
  else
  {
    SetRetryLimit( lDoUpdateThreadIdx, 1 );
    HideMessageBox();
    SitDoeBusy( ReleaseFlashMem );
    return;
  }
```

```
switch ( FlashUpdateState )
{
  case FLU_NOFLASHFILES:
    OpenMessageBox( STR_FLUNOFLASHFILES,
0, SUI_LEFTJUSTIFIED,
SUI_OK );
      break;

  case FLU_READHOSTDAT:
    OpenMessageBox( STR_FLUREADHOSTDAT,
0, SUI_LEFTJUSTIFIED,
SUI_OK );
      break;

  case FLU_MISSINGFILE:
    OpenMessageBox( STR_FLUMISSINGFLASH,
0, SUI_LEFTJUSTIFIED,
SUI_OK );
      break;

  case FLU_OUTOFDISKSPACE:
    OpenMessageBox(
STR_FLUOUTOFDISKSPACE, 0,
SUI_LEFTJUSTIFIED, SUI_OK );
      break;

  case FLU_FILECORRUPTED:
    OpenMessageBox(
STR_FLUFILECORRUPTED, 0,
SUI_LEFTJUSTIFIED,
SUI_OK );
      break;

  case FLU_NOCHECKSUM:
    OpenMessageBox( STR_FLUNOCHECKSUM,
0, SUI_LEFTJUSTIFIED,
SUI_OK );
      break;

  case FLU_NOACKTEMPFILEERROR:
    OpenMessageBox(
STR_FLUNOACKTMPERROR, 0,
SUI_LEFTJUSTIFIED,
SUI_OK );
      break;

  case FLU_NOACKNUMFILEERROR:
    OpenMessageBox(
STR_FLUNOACKNUMFILEERR, 0,
SUI_LEFTJUSTIFIED, SUI_OK );
      break;

  case FLU_NOACKPATHERROR:
    OpenMessageBox(
STR_FLUNOACKPATHERROR, 0,
SUI_LEFTJUSTIFIED, SUI_OK );
      break;

  case FLU_NOACKRECEIVEFILEERROR:
    OpenMessageBox(
STR_FLUNOACKRECVFILEERR, 0,
SUI_LEFTJUSTIFIED, SUI_OK );
      break;

  case FLU_NOACKRECEIVEFATALERROR:
    OpenMessageBox(
STR_FLUNOACKRECVFATAL, 0,
SUI_LEFTJUSTIFIED, SUI_OK );
      break;

  case FLU_SENDPRIMSGERROR:
    OpenMessageBox( STR_FLUSENDPRIMSG, 0,
SUI_LEFTJUSTIFIED,
SUI_OK );
      break;

  case FLU_1MEGSYSTEMERROR:
    OpenMessageBox(
STR_FLU1MEGSYSERROR, 0,
SUI_LEFTJUSTIFIED,
SUI_OK );
      break;

  case FLU_2MEGSYSTEMERROR:
    OpenMessageBox(
STR_FLU2MEGSYSERROR, 0,
SUI_LEFTJUSTIFIED,
SUI_OK );
      break;

  case FLU_FLASHFATALERROR:
    switch ( iSectorFlashStatus )
    {
    case SBS_FLASHNOTATTACHED:
      OpenMessageBox( STR_FLUNOAC, 0,
SUI_LEFTJUSTIFIED,
SUI_OK );
        break;

    case SBS_FLASHERASEERROR:
      OpenMessageBox( STR_FLUFLASHERASE,
0,
SUI_LEFTJUSTIFIED, SUI_OK );
        break;

    case SBS_FLASHPROGERROR:
      OpenMessageBox( STR_FLUFLASHPROG,
0, SUI_LEFTJUSTIFIED,
SUI_OK );
        break;

      default:
        OpenMessageBox(
STR_FLUFLASHUNKNOWN, 0,
SUI_LEFTJUSTIFIED, SUI_OK );
        break;
    }
    break;

  case FLU_EEROMNOCLRERROR:
    OpenMessageBox( STR_FLUEEROMNOCLR,
0, SUI_LEFTJUSTIFIED,
SUI_OK );
      break;

  case FLU_HOSTUNKNOWNERR:
    OpenMessageBox(
STR_FLUUNKNOWNHOSTERR, 0,
SUI_LEFTJUSTIFIED, SUI_OK );
      break;

  case FLU_MEMERROR:
    OpenMessageBox(
STR_FLURAMALLOCATION, 0,
SUI_LEFTJUSTIFIED,
SUI_OK );
      break;

    default:
      OpenMessageBox(
STR_FLUUNKNOWNERROR, 0,
SUI_LEFTJUSTIFIED,
SUI_OK );
  }
}

void GetFlashImageBuff( void )
{
  WORD wSector;

  TRACE( "NOTICE: Allocating memory from
Collession for the
reflash buffers" );

  SetSCSMemory( SCS_DLGFREEMEMPERCENT,
SCS_FREEMEM, ( BYTE
)SM_SCSNOWAITFORDOS );

  if ( ( wSector = GetFreeMCS( ( WORD )(
FLU_SIZEFLASHSECTOR / 16
) ) ) != 0 )
    sFlashImageBuff = MK_FP( wSector, 0 );
}

void ReleaseFlashMem( void )
{
  if ( szPathFlashFile != NULL )
  {
    free( szPathFlashFile );
    szPathFlashFile = NULL;
  }

  if ( sFlashImageBuff != NULL )
  {
    SetFreeMCS( SEG( sFlashImageBuff ) );
    sFlashImageBuff = NULL;
  }

  TRACE( "NOTICE: Returning memory to
Collession, used by the
reflash buffers" );

  SetSCSMemory( 0, SCS_FREEMEM, ( BYTE
)SM_SCSNOWAITFORDOS );


  if ( UIConfigData.nSleepTimeIdx !=
SBS_SLEEPDISABLED )
    SetPowerEnable( SBS_POWERMANENABLED );

}

int UpdateTmpFilePercentage( int
iNewTmpFilePercent )
{
  int iPercentage;

  iPercentage = ( iNewTmpFilePercent * 2 ) / 100;

  AX( SUI_UPDATEFLASHPRCNT );
  BX( iPercentage );

  ( *lpfnSUICallBack )();

  return ( ERR_SUCCESS );
}

int UpdateFlashPercentage( int iFlashFileNum )
{
  int iPercentage;

  if ( iTotalFlashFiles == 0 )
    return ( ERR_INTERNAL );

  iPercentage = ( iFlashFileNum * 100 ) /
iTotalFlashFiles;

  AX( SUI_UPDATEFLASHPRCNT );
  BX( iPercentage );

  ( *lpfnSUICallBack )();

  return ( ERR_SUCCESS );
}

int GetActiveUpdate( void )
{
  if ( GetSCSCallProgress() !=
SM_SCSCONNECTED )
    TRACE( "NOTICE: Not currently connected for
GetActiveUpdate(), sending PM anyway\r" );

  if ( IsFlashSupported() )
  {
    if ( szNameActiveUpdate == NULL )
      if ( ( szNameActiveUpdate = ( NPSTR )malloc(
SUI_MAXLENACTIVEUPD + 1 ) ) == NULL )
        return ( ERR_INTERNAL );

    _fmemset( szNameActiveUpdate, 0,
SUI_MAXLENACTIVEUPD + 1 );

    if ( SendPrivateMessage(
PM_REQACTIVEUPGRADE, 0, NULL ) !=
ERR_SUCCESS )
      return ( ERR_INTERNAL );

    TRACE( "NOTICE: Sent Private Message to
determine the name of
the active upgrade on the Host.\r" );

    if ( ( iActiveUpdateThreadIdx =
GetTempEventNum() ) ==
ERR_INTERNAL )
      return ( ERR_INTERNAL );

    AddThread( iActiveUpdateThreadIdx,
WaitForActiveUpdate, NULL,
SMC_MANYTIMES,
              FALSE, FLU_PRIMSGPOLLFREQ,
FLU_MAXRETRY );


  }
  else
  {
    TRACE( "ERROR: Flash not supported\r" );
    return ( ERR_INTERNAL );
  }

  return ( ERR_SUCCESS );
}

void WaitForActiveUpdate( void )
{
  int iRetryLimit = GetRetryLimit(
iActiveUpdateThreadIdx );

  if ( *GetNameActiveUpdate() == NULL )
  {
    if ( iRetryLimit < FLU_MAXACTUPDREQ )

      DelThread( iActiveUpdateThreadIdx );
    else if ( iRetryLimit % FLU_MODACTUPDREQ
== 0 )
    {
      if ( SendPrivateMessage(
PM_REQACTIVEUPGRADE, 0, NULL ) !=
ERR_SUCCESS )
        DelThread( iActiveUpdateThreadIdx );
    }
  }
  else
    DelThread( iActiveUpdateThreadIdx );
}

int SetPathFlashFile( LPSTR szNewPathFlashFile )
{
  if ( szPathFlashFile == NULL )
    return ( ERR_INTERNAL );
  PCS_BEGINCRITICAL;
  _fmem_cpy( ( LPVOID )szNewPathFlashFile, (
LPVOID
)szPathFlashFile,
          _fstr_len( szNewPathFlashFile ) + 1 );
  PCS_ENDCRITICAL;

  return ( ERR_SUCCESS );
}

char *GetPathFlashFile( void )
{
  return ( szPathFlashFile );
}

int SetTotalFlashFiles( int iNewTotalFlashFiles )
{
  iTotalFlashFiles = iNewTotalFlashFiles;

  return ( ERR_SUCCESS );
}

int GetTotalFlashFiles( void )
{
  int iReturn;

  PCS_BEGINCRITICAL;
  iReturn = iTotalFlashFiles;
  PCS_ENDCRITICAL;

  return ( iReturn );
}

int SetNameActiveUpdate( LPSTR
szNewActiveUpdate )
{
  if ( szNameActiveUpdate == NULL )
    return ( ERR_INTERNAL );

  PCS_BEGINCRITICAL;
  if ( szNewActiveUpdate == NULL )
    *szNameActiveUpdate = ' ';
  else
    _fmem_cpy ( LPVOID )szNewActiveUpdate, (
LPVOID
)szNameActiveUpdate,
          SUI_MAXLENACTIVEUPD );
  PCS_ENDCRITICAL;

  return ( ERR_SUCCESS );
}

char *GetNameActiveUpdate( void )
{
  if ( szNameActiveUpdate == NULL )
    return ( szNullStr );
  else
    return ( szNameActiveUpdate );
}

int SetTmpFilePercent( int iNewPercent )
{
  iTmpFilePercent = iNewPercent;

  return ( ERR_SUCCESS );
}

int GetTmpFilePercent( void )
{
  int iReturn;

  PCS_BEGINCRITICAL;
  iReturn = iTmpFilePercent;
  PCS_ENDCRITICAL;

  return ( iReturn );
}

FLASHUPDATESTATES CheckFlashPowerState(
void )
{
  LONG lBatteryInfo = GetBatteryInfo();

  if ( lBatteryInfo ==
SBS_GETBATTERYINFOERROR )
    return ( FLU_GETBATTERYINFOERROR );

  if ( ( lBatteryInfo & SBS_ACDCSTATEMASK ) !=
SBS_ACDCSTATEMASK
)
    return ( FLU_NOTONACERROR );

  if ( ( lBatteryInfo &
SBS_BATTERYATTACHEDMASK ) !=
SBS_BATTERYATTACHED )
    return ( FLU_BATNOTATTACHEDERROR );
```

```
  if ( HIBYTE( LOWORD( ( lBatteryInfo &
SSS_BATTERYCAPACITYMASK )
) ) < SSS_BATTERYFLASHMINCAP )
    return ( FLU_BATCAPTOOLOWERROR );

  return ( FLU_NOFLUSTATE );
}

#if defined( _MSC_VER )
#pragma warning( default : 4704 )
#endif
Copr. 1995 Zenith Data Systems Corp.
#include "sr.h"
#include "sio.h"
#include "spcom.h"
#include "sm.h"

#if defined( _MSC_VER )
#pragma warning( disable : 4704 )
#endif

TIMEOUT timeoutStatus = TIMEOUT_AVAILABLE;

static void TimeoutFire ( void );

static DOSBUSYCB fnDosBusyCallBack = NULL;
static VIDBUSYCB fnVidBusyCallBack1 = NULL;
static VIDBUSYCB fnVidBusyCallBack2 = NULL;
static MODALMSGBOXCB fnMsgBoxCallBack =
NULL;
static int iTempThreadId =
SMD_NOACTIVETHREAD;
static int iOnThreadId;
static int iVideoBusyThreadId =
SMD_NOACTIVETHREAD;
static int iSplrThreadId =
SMD_NOACTIVETHREAD;
BYTE aDummyPCB1[] = "\0
BYTE aDummyPCB2[] = "\0

static char *sVideoStateBuff;

void GetForegroundRegs( struct REGW *inRegs )
{
  register struct oreg *o;
  register struct REGW *r;
  struct glob_stk far *p;

  r = inRegs;
  o = _lst_frame

  r->ax = o->ax;
  r->bp = o->bp;
  r->di = o->di;
  r->si = o->si;
  r->ss = o->ss;

  *(word*)&p = o->saved_sp;
  *((word*)&p+1) = o->saved_ss;

  r->ds = p->ds;
  r->ds = p->ds;
  r->bx = p->bx;
  r->es = p->es;
}

void SetForegroundRegs( struct REGW *OutRegs )
{
  struct oreg *o;
  struct REGW *r;
  struct glob_stk far *p;

  r = OutRegs;
  o = _lst_frame;

  o->ax = r->ax;
  o->bp = r->bp;
  o->di = r->di;
  o->si = r->si;
  o->ss = r->ss;

  p = ( struct glob_stk far * )MK_FP( o->saved_ss,
o->saved_sp );

  p->ds = r->ds,
  p->ds = r->ds;
  p->bx = r->bx;
  p->es = r->es;
}

#if !defined( PROD )
void Trace( char *szOutStr )
{
  REQ_W InRegs, OutRegs,

  fill_char( ( NPSTR )&InRegs, 0, sizeof( REQ_W ) );

  InRegs.ax = SID_FUNCNUM | SID_OUTSTRING;
  InRegs.si = SID_SIGSI;
  InRegs.di = SID_SIGDI;
  InRegs.ds = SEG( szOutStr );
  InRegs.dx = OFF( szOutStr );

  intx( &InRegs, &OutRegs, SID_INTNUM );
}
#endif

void GetAPIFunction( APIFUNC aAPIFuncTable[] )
{
  APIFUNCPTR fpAPIFunction;
  struct REGW CallerRegs;

  PCS_BEGINCRITICAL
  GetForegroundRegs( &CallerRegs );
  PCS_ENDCRITICAL

  fpAPIFunction = ( APIFUNCPTR )GetAPIFunction(
aAPIFuncTable,
&CallerRegs );

  if ( fpAPIFunction != NULL )
    ( *fpAPIFunction )( &CallerRegs );
  else
  {
    CallerRegs.ax = ( WORD
)ERR_NOTSUPPORTED;
    SetForegroundRegs( &CallerRegs );
  }
}

NEARPROC GetAPIFunction( APIFUNC
aAPIFuncTable[], struct REGW
*pCallerRegs )
{
  WORD wFuncCode = pCallerRegs->ax & 0x7FFF;
  int iFuncIdx = 0;

  if ( aAPIFuncTable == NULL )
    return ( NULL );

  while ( TRUE )
  {
    if ( wFuncCode == aAPIFuncTable[ iFuncIdx
].wFuncCode )
      return( aAPIFuncTable[ iFuncIdx ].lpAPIFunc );

    if ( aAPIFuncTable[ ++iFuncIdx ].wFuncCode ==
0 &&
          aAPIFuncTable[ iFuncIdx ].lpAPIFunc ==
NULL )
      return ( NULL );
  }
}

int ErrorBeep( void )
{
  sound( SMU_ERRORFREQ, SMU_ERRORDUR );

  if ( iSplrThreadId >= 0 )
  {
    TRACE( "NOTICE: ErrorBeep() reentered\n" );
    return ( ERR_SUCCESS );
  }

  if ( ( iSplrThreadId = GetTempEventNum() ) < 0 )
    return ( ERR_INTERNAL );

  AddThread( iSplrThreadId, DoSplrRestore,
NULL, SMD_ONETIME,
FALSE, SMC_SPKRPOLLFREQ,
          0 );

  return ( ERR_SUCCESS );
}

void DoSplrRestore( void )
{
  DelThread( iSplrThreadId );

  iSplrThreadId = SMD_NOACTIVETHREAD;

  TRACE( "NOTICE: Speaker frequency restored for
POV" );

  SetPcnSplrFreq();
}

int SMDosBusy( DOSBUSYCB fnCallBack )
{
  if ( iTempThreadId >= 0 )
  {
    TRACE( "ERROR: SMDosBusy was reentered\n"
);
    DEBUG_BREAK;
    return ( 0 );
  }

  if ( ( iTempThreadId = GetTempEventNum() ) < 0
)
    return ( ERR_INTERNAL );

  fnDosBusyCallBack = fnCallBack;

  AddThread( iTempThreadId, SMCheckDosBusy,
NULL, SMD_MANYTIMES,
FALSE, DST_POLLFREQ,
          DST_MAXRETRY );

  return ( ERR_SUCCESS );
}

void SMCheckDosBusy( void )
{
  BOOL bModeDosBusy = FALSE;

  if ( *_inr_flg_ptr & ~SMD_SCHEDULERS )
    return;

  if ( dos_busy( 0 ) )
  {
    if ( GetBusyLimit( iTempThreadId ) == 0 )
    {
      TRACE( "ERROR: Timed out waiting for DOS
busy\n" );
      DEBUG_BREAK
    }
    else
      return;
  }

  DelThread( iTempThreadId );
  iTempThreadId = SMD_NOACTIVETHREAD;

  ( *fnDosBusyCallBack )();
}

int SMVideoBusy( VIDBUSYCB fnCallBack )
{
  if ( fnVidBusyCallBack1 != NULL )
  {
    if ( fnVidBusyCallBack2 != NULL )
    {
      TRACE( "NOTICE: SMVideoBusy() reentered
more than twice,
waiting for SU1 video busy\n" );
      DEBUG_BREAK,
      return ( ERR_INTERNAL );
    }
    else
    {
      TRACE( "NOTICE: SMVideoBusy() reentered
waiting for SU1
video busy\n" );
      fnVidBusyCallBack2 = fnCallBack;
    }
  }
  else
    fnVidBusyCallBack1 = fnCallBack;

  if ( iVideoBusyThreadId ==
SMD_NOACTIVETHREAD )
  {
    if ( ( iVideoBusyThreadId =
GetTempEventNum() ) < 0 )
      return ( ERR_INTERNAL );

    AddThread( iVideoBusyThreadId,
SMCheckVideoBusy, NULL,
SMD_POLLED, FALSE,
          SCE_VIDBLOCKPOLLFREQ, 0 );
  }

  return ( ERR_SUCCESS );
}

void SMCheckVideoBusy( void )
{
  static BYTE nCntVideoBlocked = 0;

  if ( !GetVideoBlocked() )
  {
    if ( ++nCntVideoBlocked >= 2 )
    {
      nCntVideoBlocked = 0;
      DelThread( iVideoBusyThreadId );
      iVideoBusyThreadId =
SMD_NOACTIVETHREAD;
      TRACE( "NOTICE: SU1 video not busy, notify
the threads\n"
);

      if ( fnVidBusyCallBack1 != NULL )
      {
        ( *fnVidBusyCallBack1 )();
        fnVidBusyCallBack1 = NULL;
      }

      if ( fnVidBusyCallBack2 != NULL )
      {
        ( *fnVidBusyCallBack2 )();
        fnVidBusyCallBack2 = NULL;
      }
    }
  }
  else
    nCntVideoBlocked = 0;
}

void SetReentrancy( BOOL fEnable )
{
  static BYTE bOldInrFlg;

  if ( fEnable )
  {
    PCS_BEGINCRITICAL;
    bOldInrFlg = *_inr_flg_ptr;
    *_inr_flg_ptr = SMD_NOREENTRANCE;
    PCS_ENDCRITICAL;
  }
  else
  {
    PCS_BEGINCRITICAL,
    *_inr_flg_ptr = bOldInrFlg;
    PCS_ENDCRITICAL;
  }
}

int RestoreVideoMode( void )
{

  if ( sVideoStateBuff == NULL )
    return ( ERR_INTERNAL );

  VideoState( sVideoStateBuff,
SHC_VIDEOHARDWARE |
SHC_VIDEODATAAREA | SHC_COLORPALREGS,
          SHC_RESTOREVIDEO );

  free( sVideoStateBuff );

  sVideoStateBuff = NULL;

  return ( ERR_SUCCESS );

}

WORD SetVideoMode( BYTE nRequestedMode )
{
  int AX;

  AX = MAKEWORD( nRequestedMode, 0 );
  int10( AX );

  return ( ERR_SUCCESS );
}

int VideoState( char *sVidBuff, char nDataType, char
nOperation )
{
  REQ_W InRegs, OutRegs;

  fill_char( ( NPSTR )&InRegs, 0, sizeof( REQ_W ) );

  if ( nOperation != SHC_SIZEOFBUFF )
  {
    if ( sVidBuff != NULL )
    {
      InRegs.es = SEG( sVidBuff );
      InRegs.bx = OFF( sVidBuff );
    }
    else
      return ( ERR_INTERNAL );
  }
```

```
  InRegs.ax = ( int )nDataType;
  InRegs.ax = MAKEWORD( nOperation,
SHC_VIDSTATEFUNC );

  intdx( &InRegs, &OutRegs, 0x10 );

  if ( nOperation == SHC_SIZEOFBUFF )
    return ( OutRegs.bx );
  else
    return ( ERR_SUCCESS );
}

int JimExec( char szProgName[], char
sCmdLineParm[] )
{
  int iReturn = 0;
  EXECPARAMS ep;
  BYTE sCmdLineTail[] = "\0\r";
  WORD wSegEP, wOffEP, wSegPN, wOffPN;
  WORD wOldPSP;

  ep.wSegEnv = 0;

  if ( sCmdLineParm == NULL )
  {
    ep.wOffCmdLineTail = OFF( sCmdLineTail );
    ep.wSegCmdLineTail = SEG( sCmdLineTail );
  }
  else
  {
    ep.wOffCmdLineTail = OFF( sCmdLineParm );
    ep.wSegCmdLineTail = SEG( sCmdLineParm );
  }

  ep.wOffFCB1 = OFF( sDummyFCB1 );
  ep.wSegFCB1 = SEG( sDummyFCB1 );
  ep.wOffFCB2 = OFF( sDummyFCB2 );
  ep.wSegFCB2 = SEG( sDummyFCB2 );

  wSegEP = SEG( &ep );
  wOffEP = OFF( &ep );
  wSegPN = SEG( szProgName );
  wOffPN = OFF( szProgName );

  wOldPSP = set_my_psp();

  AX( SMD_DOSEXEC );
  ES( wSegEP );
  BX( wOffEP );
  DS( wSegPN );
  DX( wOffPN );

  _asm
  {
    int 21h
    jnc success
    mov iReturn,ax
  };

success:
  restore_psp( wOldPSP );
  return ( iReturn );
}

WORD GetFreeMCB( WORD wNumPara )
{
  REG_W InRegs, OutRegs;
  WORD wReturn = 0, wFlags;

  fil_chr( ( NPSTR )&InRegs, 0, sizeof( REG_W ) );

  InRegs.ax = SMD_DOSALLOCMEM;
  InRegs.bx = wNumPara;

  PCS_BEGINCRITICAL;

  wFlags = intdx( &InRegs, &OutRegs, SMD_DOSINT
);

  PCS_ENDCRITICAL;

  if ( !( wFlags & GEN_CARRYFLAG ) )
    return ( OutRegs.ax );
  else
    return ( 0 );
}

int SetFreeMCB( WORD wSegment )
{
  REG_W InRegs, OutRegs;
  WORD wFlags;

  fil_chr( ( NPSTR )&InRegs, 0, sizeof( REG_W ) );

  InRegs.ax = SMD_DOSFREEMEM;
  InRegs.es = wSegment;

  PCS_BEGINCRITICAL;
```

```
  wFlags = intdx( &InRegs, &OutRegs, SMD_DOSINT
);

  PCS_ENDCRITICAL;

  if ( !( wFlags & GEN_CARRYFLAG ) )
    return ( ERR_SUCCESS );
  else
    return ( OutRegs.ax );
}

int StuffKeyStr( char *szStr )
{
  char *sKey = szStr;

  if ( strlen( szStr ) > SHC_MAXLENKBBUFF )
    return ( ERR_INTERNAL );

  while ( TRUE )
  {
    if ( *sKey )
      stuff_key( MAKEWORD( *sKey++, 0 ) );
    else
      return ( ERR_SUCCESS );
  }
}

BOOL IsGetFunction( struct REGW *CallerRegs )
{
  return ( CallerRegs->ax & 0x0000 );
}

char *ParseForFileName( char *szPathName )
{
  int iChar;

  for ( iChar = strlen( szPathName ) - 1; iChar >= 0;
--iChar )
  {
    if ( szPathName[ iChar ] == '\\' )
      return ( szPathName + iChar + 1 );
  }

  return ( NULL );
}

BOOL IsNodeAddressBlank( char *szNodeAddress )
{

  return ( strlen( szNodeAddress ) == 0 );


}

int DoModalMsgBox( MODALMSGBOXCB
fnCallBack, int iMsgBoxTimeOut )
{
  if ( ( fnMsgBoxCallBack = fnCallBack ) == NULL )
    return ( ERR_INTERNAL );

  if ( ( iOkThreadId = GetTempEventNum() ) <
ERR_SUCCESS )
    return ( ERR_INTERNAL );

  SetMsgBoxReturnCode( SUI_NOBUTTONS );

  if ( iMsgBoxTimeOut > 0 )
    AddThread( iOkThreadId, WaitForOK, NULL,
SMO_MANYTIMES,
FALSE, SUI_MSGBOXPOLLFREQ,
              iMsgBoxTimeOut );
  else
    AddThread( iOkThreadId, WaitForOK, NULL,
SMO_POLLED, FALSE,
SUI_MSGBOXPOLLFREQ,
              0 );

  return ( ERR_SUCCESS );
}

void WaitForOK( void )
{
  int iButtonCode;

  if ( ( iButtonCode = GetMsgBoxReturnCode() ) !=
SUI_NOBUTTONS )
  {
    SetThread( iOkThreadId );
    ( *fnMsgBoxCallBack )( iButtonCode );
  }
  else if ( GetThreadType( iOkThreadId ) ==
SMO_MANYTIMES )
  {
    if ( GetRetryLimit( iOkThreadId ) == 0 )
    {
      DelThread( iOkThreadId );
      ( *fnMsgBoxCallBack )( SUI_NOBUTTONS );
    }
```

```
  }
}

int AbsToZero( int iValue )
{
  return ( iValue < 0 ? 0 : iValue );
}

TIMEOUT TimerManager (TIMEOUT_FLAG
fTimeout, int iThreadId, long
lValue)
{
  static int iTimeoutThreadId;
  static int iThreadInUseId = -1;
  TIMEOUT timeoutReply;

  switch (fTimeout)
  {
    case TF_SET:
    if (timeoutStatus == TIMEOUT_AVAILABLE)
    {
      if ( ( iTimeoutThreadId =
GetTempEventNum() ) !=
ERR_INTERNAL )
      {
        AddThread( iTimeoutThreadId,
TimeoutFire, NULL,
SMO_ONETIME, FALSE,
                lValue, 0 );
          timeoutStatus = TIMEOUT_RUNNING;
          iThreadInUseId = iThreadId;

          timeoutReply = timeoutStatus;
      }
      else
        timeoutReply = TIMEOUT_ERROR;
    }
    break;

    case TF_RESET:
    if (iThreadInUseId == iThreadId)
    {
      timeoutStatus = TIMEOUT_AVAILABLE;
      timeoutReply = timeoutStatus;
      iThreadInUseId = -1;
    }
    else
      timeoutReply = TIMEOUT_NOTAVAILABLE;
    break;

    case TF_CHECK:
    if (iThreadInUseId == iThreadId ||
timeoutStatus ==
TIMEOUT_AVAILABLE)
        timeoutReply = timeoutStatus;
    else
        timeoutReply = TIMEOUT_NOTAVAILABLE;
    break;
  }

  return timeoutReply;
}

static void TimeoutFire ( void )
{
  timeoutStatus = TIMEOUT_FIRED;
}

#if defined( _MSC_VER )
#pragma warning( default : 4704 )
#endif



Copr. 1993 Zenith Data Systems Corp.
#include "sr.h"
#include "sio.h"
#include "sysum.h"
#include "sm.h"

#if defined( _MSC_VER )
#pragma warning( disable : 4704 )
#endif

static ZDSTRAPREC VIDTrapRec;
static char nXCharRes = -1;
static char nYCharRes = -1;
static int iYScreenRes = -1;
static iCurrVidMode = 0;

static iPanNotifyThreadId = -1;

void InitVIDTrapRec( void )
{
  fil_chr( ( NPSTR )&VIDTrapRec, 0, sizeof(
ZDSTRAPREC ) );

  VIDTrapRec.tr.tr_int = SSS_VIDINTNUM;
```

```
  VIDTrapRec.tr.tr_com_srv =
CRU_ONBUSYOLDINT;

  strcpy( VIDTrapRec.szSMAfterSignature,
szSMSignature );
}

TRAPREC *GetVIDTrapRec( void )
{
  return ( &VIDTrapRec.tr );
}

char GetYCharRes( void )
{
  if ( nYCharRes > 0 )
    return ( nYCharRes );
  else
    return ( SCS_HEIGHTOFTEXTCHAR );
}

char GetXCharRes( void )
{
  if ( nXCharRes > 0 )
    return ( nXCharRes );
  else
    return ( SCS_WIDTHOFTEXTCHAR );
}

int GetXScreenRes( int iVideoMode )
{
  switch ( iVideoMode )
  {
    case 0x00:
    case 0x01:
      return ( 320 );

    case 0x02:
    case 0x03:
      return ( 640 );

    case 0x04
    case 0x05:
      return ( 320 );

    case 0x06:
      return ( 640 );

    case 0x07:
      return ( 720 );

    case 0x08:
    case 0x09:
    case 0x0A
    case 0x0B
    case 0x0C:
      return ( ERR_INTERNAL );

    case 0x0D:
      return ( 320 );

    case 0x0E:
    case 0x0F:
    case 0x10:
    case 0x11:
    case 0x12:
      return ( 640 );

    default:
      return ( ERR_INTERNAL );
  }
}

int GetYScreenRes( int iVideoMode )
{
  if ( iVideoMode == SSS_HIGHTEXTVIDMODE &&
iYScreenRes > 0 )
    return ( iYScreenRes );
  else
  {
    switch ( iVideoMode )
    {
      case 0x00:
      case 0x01:
      case 0x02:
      case 0x03:
      case 0x04:
      case 0x05:
      case 0x06:
        return ( 400 );

      case 0x07:
        return ( 350 );

      case 0x08:
      case 0x09:
      case 0x0A:
      case 0x0B:
      case 0x0C:
        return ( ERR_INTERNAL );
```

```
    case 0x0D:
    case 0x0E:
      return ( 200 );

    case 0x0F
    case 0x10:
      return ( 350 );

    case 0x11:
    case 0x12:
      return ( 400 );

    default:
      return ( ERR_INTERNAL );
  }
 }
}

int GetCurrVidMode( void )
{
 return ( iCurrVidMode );
}

BOOL VIDTrapService( void )
{
 struct REGW Regs;
 BOOL fReturn = TRUE;

 GetForegroundRegs( &Regs );

 switch ( HIBYTE( Regs.ax ) )
 {
  case SSS_SETVIDEOMODEFUNCS:
    TRACE( "NOTICE: Set video mode intercepted\n" );

    iCurrVidMode = LOBYTE( Regs.ax ) &
~SSS_VIDMODEMASK;


     AlertModePenNotify();
     break;

  case SSS_CHARACTERGENFUNCS:
    TRACE( "NOTICE: Set text font after mode set intercepted\n"
);

    if ( iCurrVidMode ==
SSS_HIGHTEXTVIDMODE )
     AlertModePenNotify();
    break;

   default:
    return ( FALSE );
 }

 return ( TRUE );
}

void AlertModePenNotify( void )
{
 if ( iPenNotifyThreadIdx != 0 )
  return;

 if ( ( iPenNotifyThreadIdx = GetTempEventNum() )
< 0 )
  return;

 AddThread( iPenNotifyThreadIdx,
WaitForPenNotify, NULL,
SMC_ONETIME, FALSE,
        SSS_PENNOTIFYPOLLFREQ, 1 );
}

void WaitForPenNotify( void )
{
 char FAR *pNumScreenRows = ( char FAR *
)SMC_ADDSCREENROWS;
 char FAR *pNumCharScans = ( char FAR *
)SMC_ADDCHARSCANLINES;

 DelThread( iPenNotifyThreadIdx );
 iPenNotifyThreadIdx = -1;

 if ( iCurrVidMode == SSS_HIGHTEXTVIDMODE )
 {
  nYCharRes = *pNumCharScans;
  iYScreenRes = nYCharRes * (
*pNumScreenRows + 1 );
 }
 else
  iYScreenRes = -1;

 NotifyVideoMode( iCurrVidMode );
}

#if defined( _MSC_VER )
```

```
#pragma warning( default : 4704 )
#endif

Copr. 1995 Zenith Data Systems Corp.

MAX_STK_TOP  =  01790h

CMD_LINE_SZ  =  80h
MIN_STK_SZ  =  100h

_TEXT   segment  byte public 'CODE'
_TEXT   ends
_VTX segment byte public 'CODE'
_VTX ends
_ITEXT   segment  byte public 'CODE'
_ITEXT   ends
_ZTEXT   segment  byte public 'CODE'
_ZTEXT   ends
_FITEXT SEGMENT PARA PUBLIC 'CODE'
_FITEXT ENDS
_FXDATA  segment word public 'DATA'
_FXDATA  ends
_FDATA   segment word public 'DATA'
_FDATA   ends
_VDATA   segment word public 'DATA'
_VDATA   ends
_RDATA   segment word public 'DATA'
_RDATA   ends
_IDATA   segment word public 'DATA'
_IDATA   ends
_DATA    segment word public 'DATA'
_DATA    ends
_BSS segment word public 'BSS'
_BSS ends
_BSSEND segment byte public 'BSSEND'
_BSSEND ends

CGROUP   group _TEXT,_VTX,_ITEXT,_ZTEXT
DGROUP   group
_FDATA,_FXDATA,_VDATA,_RDATA,_IDATA,_DAT
A,_BSS,_BSSEND
    assume
cs:CGROUP,ds:DGROUP,ss:DGROUP

_STACK  SEGMENT WORD STACK 'STACK'
_STACK  ENDS

__acrtused   =  9876h
public __acrtused


dly    MACRO   n
    REPT n
       jmp  short $+2
    ENDM
       ENDM

inc2   MACRO   reg
       inc reg
       inc reg
       ENDM

dec2   MACRO   reg
       dec reg
       dec reg
       ENDM

OP_RET   =  0C3h
OP_CALN  =  0E8h

get MACRO   seg_reg
    push cs
    pop seg_reg
    ENDM


_DATA    segment word public 'DATA'
extrn
data_beg:byte,_ost_ptr:byte,idata_beg:byte,fr:data_b
eg:byte
extrn vdata_beg:byte,rdata_beg:byte,bss_top:byte

public __sdata,__scode
public __dummy_ret,exit_rtn,put_trei,__lsr_fg_ptr
__lsr_fg_ptr  dw  offset CGROUP:__lsr_fg
__scode      dw  CGROUP
__sdata      dw  DGROUP


put_tret  dw  offset CGROUP:__dummy_ret
_DATA    ends

_IDATA   segment word public 'DATA'
__heap       dw  offset DGROUP:bss_top
__psp        dw  0
_cmd_line dw  0
```

```
_icode_beg    dw  0
_idata_end    dw  0
vtx_size  dw  0
vtx_target    dw  0
vtx_ret      dw  offset CGROUP:__dummy_ret
exit_rtn  dw  offset CGROUP:__dummy_ret
target_data   dw  0
source_data   dw  0
data_gap  dw  0
res_size  dw  0
exit_rdy  dw  offset CGROUP:__dummy_ret
res_enabled   db  0
extrn _config_block:byte
extrn __lsr_name:byte
extrn idata_beg:byte
extrn __max_stack:word
public res_enabled,exit_rdy,__heap,__psv
public
target_data,source_data,data_gap,res_size,exit_res
public
_cmd_line,_icode_beg,_idata_end,vtx_size,vtx_target
,vtx_ret

_IDATA ends

_BSS segment word public 'BSS'
extrn bss_beg:byte
_resident db   2 dup(?)
__my_psp  dw   1 dup(?)
psp_tbl       dw   1 dup(?)

__stmt_tbl   dw   1 dup(?)
_res_stack_beg dw   1 dup(?)
_res_free_stack    dw   1 dup(?)
public _res_stack_beg,_res_free_stack,__stmt_tbl

public __my_psp,_cmd_line,_resident,psp_tbl
_BSS ends


_ITEXT   segment  byte public 'CODE'
    ASSUME
CS:CGROUP,DS:DGROUP,SS:DGROUP

extrn lsr_psp:word,lsr_stk:byte
extrn vtx_beg:byte
extrn itext_beg:byte
extrn gtx_beg:byte
extrn code_top:byte

public set_smem
set_smem  proc near
       cld
       pop si
       mov dx,ds
       mov ax,word ptr ds:[2ch]
       mov bp,DGROUP
       mov ds,bp
       mov es,bp
       mov [__psv],ax
       mov cx,offset DGROUP:bss_top
       mov di,offset DGROUP:bss_beg
       sub cx,di
       xor ax,ax
       mov es:[__lsr_ctl],ax
       shr cx,1
       rep stosw
       mov [__my_psp],dx


       mov es,dx
       mov bx,MAX_STK_TOP
       mov ax,[__max_stack]
       add ax,di
       jnc scmd
scmd_1:      mov ax,bx
scmd:        cmp ax,bx
       ja  scmd_1
       mov cl,4
       shr ax,cl
       add ax,CMD_LINE_SZ/16
       xchg ax,bx
       add bx,bp
       sub bx,dx
       mov ah,4Ah
       int 21h
       jnc scmt
       mov ah,4Ah
       int 21h
       jc  scm_err

scmt:        mov ax,bp
       add bx,dx
       sub bx,bp
       shl bx,cl
       sub bx,CMD_LINE_SZ
       mov [_cmd_line],bx
       cli
       mov ss,bp
```

```
       mov sp,bx
       sti
       cmp sp,offset
DGROUP:bss_top+MIN_STK_SZ
       jb  scm_err
       add dx,8
       mov es:[lsr_psp],dx
       mov [psp_tbl],dx
       mov ax,offset CGROUP:gtx_beg
       sub ax,offset CGROUP:vtx_beg
       mov [vtx_size],ax
       jmp si

scm_err:  mov ax,4c01h
       int 21h

set_smem  endp

_FITEXT  segment
assume cs:_FITEXT

public get_cmd_arg
get_cmd_arg    proc far
       cld


       mov di,[_cmd_line]
       mov ds,[__my_psp]
       get es
       mov si,80h
       mov cx,7fh
       and cl,[si]
       inc si
       rep movsb
       xor ax,ax
       stosb


       push ds
       pop es
       get ds
       mov di,102h
       mov si,offset DGROUP:_config_block+2
       movsw
       movsw
       movsw


       mov cx,32
       mov di,5ch
       mov si,offset DGROUP:__lsr_name
       rep movsb

       ret
get_cmd_arg    endp
_FITEXT  ends

assume cs:CGROUP

init_fdata:   cld


       mov si,offset DGROUP:fxdata_beg
       mov di,offset DGROUP:vdata_beg
init_fx:      cmp si,offset DGROUP:fdata_beg
       jae ifd1
       lodsw
       xchg ax,bx
       lodsw
       sub ax,bx
       mov es:[bx-2],ax
       mov byte ptr es:[bx-3],OP_CALN
       jmp init_fx

public init_rdata
init_rdata:   mov si,offset DGROUP:rdata_beg
       mov di,offset DGROUP:idata_beg

ifd1:         sti
       cld
       cmp si,di
       jae ifd_ex
       lodsw
       mov word ptr [si-2],offset
CGROUP:__dummy_ret
       push si
       push di
       call ax
       pop di
       pop si
       get ds
       jmp ifd1

ifd_ex:       ret

_TEXT   SEGMENT
public start
start         jmp start1
```

```
public go_res
go_res:        rep movsb
        int 21h
__dummy_ret:   ret
__dummy_ent:   iret
public __dummy_ret,__dummy_iret
extrn __ler_flgbyte:__fmt_ett:word
_TEXT   ENDS

extrn ler_data:word
extrn _main:near
start1:        call set_emem
        call get_cmd_arg
        call init_fonts
        call _main
        push ax
        mov byte ptr es:[__ler_flg],07h
        mov ax,[__env]
        mov ah,4ch
env_patch label word
public env_patch
        int 21h
        cmp [res_enabled],1
        jz int2

int1           xor bx,bx
        mov es:[bx],bx
        call word ptr [ext_rtn]
        pop ax
        mov ah,4ch
        int 21h
public _exit
_exit          pop ax
        jmp short int1

int2           mov ax,[__heap]
        add ax,0fh
        mov cl,4
        shr ax,cl
        add ax,DGROUP
        sub ax,[__my_psp]
        xchg ax,dx

        mov si,offset DGROUP:data_beg
        mov ax,_DATA
        mov bp,[_data_end]
        inc2 bp
        sub bp,offset DGROUP:data_beg
        jbe int3
        shr bp,cl
        add ax,bp
        shl bp,cl
        add si,bp

int3:          mov bx,offset CGROUP:vtx_beg
        mov bp,[vtx_size]
        mov di,[_loads_beg]
        or di,di
        jnz int3_1
        mov di,bx
int3_1:        cmp di,bx
        jbe int3_2
        mov di,bx
int3_2:        mov [vtx_target],di
        add di,bp
        add di,0fh
        shr di,cl
        mov bx,ax
        add bx,di

int4.          mov [target_data],bx
        mov [source_data],si
        sub ax,bx
        mov [data_gap],ax
        sub dx,ax
        mov [res_size],dx
        sub [__edata],ax
        mov byte ptr [_resident],0ffh
        call init_rtmts


        sti
        call word ptr [vtx_ovl]
        cli


        nop
        xchg bx,bx
fc_graph  label    word


        nop
        xchg bx,bx
fc_fmem_mv    label    word

        nop
        xchg bx,bx
fc_ega_gr label word


        nop
        xchg bx,bx
fc_uptrace    label word


        nop
        xchg bx,bx
fc_vpu_cpp    label    word


        nop
        xchg bx,bx
fc_vuptk  label word



        nop
        xchg bx,bx
fc_vpu_fn     label    word

        mov ax,[__edata]
        mov es:[ler_data],ax
        mov es,[target_data]
        mov si,[source_data]
        mov dx,[res_size]
        xor di,di
        mov ax,[__heap]
        add ax,0fh
        and al,0f0h
        mov [__heap],ax
        xchg ax,cx
        sub cx,si
        std
        cli
        mov es:[__ler_flg],0
        pop ax
        mov ah,31h
        nop
        xchg bx,bx
fc_lm_res     label word
        call go_res
fc_go_res label word

public
fc_go_res,fc_lm_res,fc_vpu_fn,fc_vpu_cpp,fc_uptrc
go,fc_graph
public fc_fmem_mv,fc_ega_gr,fc_vuptk

_ITEXT    ends

end start
Copr. 1995 Zenith Data Systems Corp.
tLISTBOXENTRY struc
lpszEntry dd 0
cAttribute db 0
ends

MB_LEFTJUSTIFIED equ 0
MB_CENTERED equ 1
MB_RIGHTJUSTIFIED equ 2

PENDRIVER_INTERRUPT equ 07h
SM_FUNCTION_INTERRUPT equ 00h

SM_GET_KEYBOARD_STATUS equ 062h
SM_GET_USER_INTERFACE_LANGUAGE equ
066h
SM_SET_ACTIVE_STATUS equ 000h
SM_GET_INITIAL_SCREEN equ 0000h
SM_GET_ABOUT_DIALOG equ 063h
SM_GET_NEXT_CREDITS_DIALOG equ 64h
SM_UPDATE_DIMENSIONS equ 062h
SM_REQUEST_UNLOAD equ 0063h
SM_REPORT_BUTTON_CLICKED equ 0000H
SM_CALIBRATE_UPPERLEFT equ 0ah
SM_CALIBRATE_LOWERRIGHT equ 000Ch
SM_CANCEL_CALIBRATION equ 00eh
SM_REBOOT_HOST equ 010h
SM_SET_KEYSTROKE equ 001h
SM_REQUEST_ACTIVE_FLASH_UPGRADE equ
12h
SM_PERFORM_FLASH_UPDATE equ 13h
SM_GET_CONNECTION_STATUS equ 22h
SM_GET_HOST_LIST_STATUS equ 21h
SM_UPDATE_HOST_LIST equ 20h
SM_GET_PASSWORD_STATUS equ 25h
SM_REQUEST_CONNECTION equ 23h
SM_REQUEST_DISCONNECTION equ 0023h
SM_ABORT_REQUEST_CONNECTION equ 24h

SM_TEST_FUNCTION equ 0FFFFh

UI_REQUEST_CLOSURE equ 063h
UI_REQUEST_DISPLAY equ 061h

UI_SHOW_MESSAGE_BOX equ 063h
UI_HIDE_MESSAGE_BOX equ 064h
UI_CALIBRATION_COMPLETE equ 65h
UI_FLASH_UPDATE_PERCENTAGE equ 14h
UI_GET_BUI_VERSION_NUMBER equ 66h
GET_HOST_LIST_STATUS      equ 021h


RES_NO_SCREEN         EQU 0
RES_OSK_ALPHA         EQU 1
RES_OSK_NUM           EQU 2
RES_OSK_FULL          EQU 3
RES_OSK_BIG           EQU 4
RES_OSK_BIG_ALPHA     EQU 5
RES_OSK_BIG_NUM       EQU 6
RES_OSK_BIG_FULL      EQU 7
RES_SETUPS_HOST       EQU 0h
RES_SETUPS_HOTKEYS    EQU 10h
RES_SETUPS_MAINTENANCE EQU 20h
RES_SETUPS_MODEM      EQU 30h
RES_SETUPS_POWER      EQU 40h
RES_SETUPS_SCREEN     EQU 48h

GETSET_AUTOMATIC_SHUTOFF      equ 0h
GETSET_BRIGHTNESS             equ 0bh
GETSET_CONTRAST               equ 0ah
GETSET_CUSTOM_AUTOANSWER_STRING equ
36h
GETSET_CUSTOM_CONNECT_STRING     equ 38h
GETSET_CUSTOM_DISCONNECT_STRING equ
37h
GETSET_CUSTOM_INIT_STRING     equ 035h
GETSET_HOST_CONNECTION_TYPE   equ 02ah
GETSET_MODEM_ANSWER_ON_RING   equ
032h
GETSET_MODEM_BAUD_RATE_ENTRY   equ
30h
GETSET_MODEM_HOST_DESC_ENTRY   equ
30h
GETSET_MODEM_HOST_PHONE_ENTRY   equ
37h
GETSET_MODEM_MANUFACTURER_ENTRY equ
30h
GETSET_MODEM_PREFIX           equ 034h
GETSET_MODEM_RETRY_DELAY      equ 034h
GETSET_MODEM_RETRY_LIMIT      equ 033h
GETSET_MODEM_SUFFIX           equ 031h
GETSET_MODEM_TONE_OR_PULSE    equ 03h
GETSET_NETWORK_GROUP_ENTRY    equ 2ah
GETSET_NETWORK_HOST_ENTRY     equ 20h
GETSET_PASSWORD               equ 00eh
GETSET_SLEEPMODE_PERIOD       equ 10h
GETSET_SECURITY_ID            equ 00h
GETSET_DOMAIN_ID              equ 07h
GETSET_LOCK_HOST_KEYBOARD     equ 00h
GETSET_BM_HOST_SCREEN         equ 0Ah
GETSET_USER_DEFINED_HOT_ICON  equ 0h
GETSET_USER_ID                equ 03ch



Copr. 1995 Zenith Data Systems Corp.
      .MODEL  small

SM_SUIEVENTNUM EQU 0

extrn _PushEventNum:near
extrn _lpfnForCallEntry:near

_TEXT SEGMENT WORD PUBLIC 'CODE'
ASSUME DS: DGROUP, SS: DGROUP

ASSUME CS: _TEXT

public _SUICallService
_SUICallService PROC far

      push    bp
      mov     bp,sp

      cli

      push    ds
      push    es
      push    bx
    push cx
      push    dx
      mov     ds, ss:0004h

      mov     ax, SM_SUIEVENTNUM
    push ax
      call    _PushEventNum
    add  sp,2

      pop     dx
      pop     es
      pop     bx

      pop     ax

      cli

      call  DWORD PTR _lpfnForCallEntry

      pop     ds
      mov     sp,bp
      pop     bp
      ret

_SUICallService     ENDP

public _GetPendingEvent
_GetPendingEvent PROC near

      push    bp
      mov     bp,sp

      mov     ax, es:00100h

      mov     sp,bp
      pop     bp
      ret

_GetPendingEvent ENDP

_TEXT ENDS

END
Copr. 1995 Zenith Data Systems Corp.
include pd.inc

      .MODEL  small

_TEXT SEGMENT WORD PUBLIC 'CODE'
ASSUME DS: DGROUP, SS: DGROUP

ASSUME CS: _TEXT

public _SetPenSplFreq
_SetPenSplFreq proc near
  push    bp
  mov     bp,sp

  mov     al, PD_TIMER2_100T_MODE
  cli
  out     43h, al
  jmp     short $+2
  mov     ax, PD_PSEO_FREQUENCY
  out     42h, al
  jmp     short $+2
  mov     al, ah
  out     42h, al
  sti

  mov     sp,bp
  pop     bp
  ret
_SetPenSplFreq endp

_TEXT ENDS

END

Copr. 1995 Zenith Data Systems Corp.
#define STR_PROMPT           "$L>"
#define STR_SMANPROGNAME     "sm.exe"
#define STR_SVIEWPROGNAME    "sv.exe"
#define STR_LSL              "lsl.com"
#define STR_IPXODI           "ipxodi.com"

#if defined( PCMCIA )
  #define STR_PROKIM         "kipcm.com"
#elif defined( CLISA ) || defined( MOUSE )
  #define STR_PROKIM         "kims.com"
#elif defined( PROO )
  #define STR_PROKIM         "k0com.com"
#else
  #define STR_PROKIM         "k0com.com"
#endif

#define STR_PDRVPROGNAME     "pd.exe"
#define STR_SDRVNETPROGNAME "sdrvnet.exe"
#define STR_RWINPROGNAME     "srwin.exe"
#define STR_COMMANDPROGNAME
"command.com"
#define STR_COMMANDPARM      " /c diag.bat"
#define STR_COMMANDDIR       "c:\"
#define STR_WELCOMESCREEN    " welcome.pcx
0x12V"

#define VAL_SPACE            0x20
#define MAX_WIDTHOFSCREEN    80
#define MAX_STACKSIZE        1024
#define MAX_BUILDLOADRETRY   3

#define KBD_CTRLMASK         0x0004
#define KBD_ALTMASK          0x0008
```

```
#define KBD_DSCAN          0x2000
#define KBD_ASCAN          0x1E00

#define SFR_NOSETFLAGS     0x00
#define SFR_SETFLAGS       0x01

#define ITR_NOSETVIDTRAP   0x00
#define ITR_SETVIDTRAP     0x01

typedef enum _tagACTIONKEYS
{
  KBD_NOACTIONKEY,
  KBD_DIAG,
  KBD_ABORTLOAD,
} ACTIONKEYS;

typedef int ( * STATETABLEPROC )();

int exit( int );

int      ProcessIdle( void );
int      ParseCommand( void );
int      ParseParameters( void );
int      ExecuteCommand( void );
int      ProcessSLExit( void );
int      ProcessStateUnknown( void );
void     DoExit( int );
int      GetFrameType( void );
int      GetMLIDStatus( void );
void     SetOldVidVector( LONG lOldVidVector );
int      RunProgram( char *szProgName, char
*szProgParms );
int      LoadMLID( char *szProgName );
int      LoadNetwork( void );
int      KeyProceeding( int iDelay );
int      KickSU( void );
int      EnableKbd( void );
ACTIONKEYS GetActionKey( void );
BOOL     RemoveVidTrap( void );
void     DisplayError( char *szEndStr );
void     InitTraps( BYTE *VidTrapStatus );
WORD     TrapService( struct trap_rec
*CurrTrapRec );
void     GetForegroundRegs( struct REGW *InRegs
);
void     SetForegroundRegsFlags( struct REGW
*OutRegs, BYTE
fSetFlags, WORD wFlags );
WORD     SetVideoMode( BYTE *RequestedMode
);
int      LoadSM( int iMemStrategy );

STATETABLEPROC fnStateTableProcs[] =
{
  ProcessIdle,
  ParseCommand,
  ParseParameters,
  ExecuteCommand,
  ProcessSLExit,
  ProcessStateUnknown,
};

typedef enum tagGENERALSTATEIDXS
{
  STM_IDLE,
  STM_COMMAND,
  STM_PARM,
  STM_EXECUTE,
  STM_EXIT,
  STM_UNKNOWN,
} GENERALSTATEIDXS;

typedef enum tagCOMMANDSTATEIDXS
{
  COM_UNKNOWN,
  COM_DISPOSUGSTRS,
  COM_RUNSM,
  COM_RUNPROG,
  COM_RUNDOSCOS,
  COM_RUNWINCOS,
} COMMANDSTATEIDXS;
Copr 1995 Zenith Data Systems Corp.
int  SortingList(int, int, int, int, char *);
long GetEntryOffset(int, int, int, int, char *);
int  DumpEntries( char *, char *, int);

#define SH_SWAP_BUFF_LEN 35
```

```
Copr. 1996 Zenith Data Systems Corp.

.model small

MINOR_VERSION =38
MAJOR_VERSION =1

.code

extrn UseNormalColors:near
extrn DoClickEvent:near
extrn FindRegionForControl:near
extrn CancelPenDown:near
extrn Bin2ASCII:near
extrn BlankenScreen:near
extrn ClearScreen:near
extrn DoInstallInterrupts:near
extrn DoHideOSK:near
extrn DrawColor:near
extrn DrawMessageBox:near
extrn DrawString:near
extrn ForceTotalRepaint:near
extrn ForceTotalRepaint1:near
extrn GetBitmapHeight:near
extrn GetListData:near
extrn GetStringWidth:near
extrn GetVGAState:near
extrn GetFirstControl:near
extrn GetNextControl:near
extrn GetNextControl:near
extrn HandleDelayedSet:near
extrn HideOSK:near
extrn IsNumericKey:near
extrn JumpOnAL:near
extrn JumpOnAX:near
extrn PenEntry:near
extrn PenExit:near
extrn PaintControlCaption:near
extrn PaintError:near
extrn PrepareMessageBox:near
extrn ReGrayOSKTypeButtons:near
extrn RemoveMessageBox:near
extrn RepaintOSK:near
extrn RepaintCursor:near
extrn RepaintAndSetTab:near
extrn RepaintForClick:near
extrn RepaintIndividualControl:near
extrn RepaintIndividualListBox:near
extrn RepaintUnderOSK:near
extrn RepaintWork:near
extrn ReportError:near
extrn RestVGAState:near
extrn RestoreRegion:near
extrn ReturnOSKRightAndShow:near
extrn SaveFormHeight:near
extrn SetInitialTab:near
extrn SetListCurrent:near
extrn SetNewTabItemWork:near
extrn SetOSKEnlargedButtons:near
extrn SetOSKReducedButtons:near
extrn StopProtecting:near
extrn UMain:far
extrn UndoCurrentTabItem:near
extrn UnprotectOSK:near
extrn SearchActiveRegions:near
extrn StopCursor:near
extrn ResumeCursor:near
extrn DefineNewOskArea:near

extrn GetPhysicalKeyState:near

include simsfed.inc

DATASEG_BEGIN
extrn AboutIcon:word
extrn ColoredAboutIcon:byte
extrn ControlDataStorageArea:byte
extrn OSK:Control
extrn ScanCodeHeader:BUFFHEADER
extrn ScanCodeParser:SCANCODES
extrn bAllNumberCount:byte
extrn bAwaitingMoveCompletion:byte
extrn bCurrentShadowColor:byte
extrn bCursorActive:byte
extrn bDoingEvents:byte
extrn bDontCenterOSK:byte
extrn bDontChangeProtection:byte
extrn bFormColor:byte
extrn bKeyChanged:byte
extrn bKeyState:byte
extrn bKeyboardCode:byte
extrn bLanguageToUse:byte
extrn bLeavePenOn:byte
extrn bLocalState:byte
extrn bMessageBoxID:byte
extrn bMessageBoxRequested:byte
extrn bModalFlag:byte
extrn bNewDisplayRequested:byte
extrn bNoDimensionUpdate:byte
extrn bOSKLastState:byte
extrn bPenShowing:byte
extrn bPenUpRequired:byte
extrn bRemoveMessageBoxRequested:byte
extrn bRepaintNeeded:byte
extrn bResetHotKeyDataLength:byte
extrn bScreenMode:byte
extrn bShadowColor:byte
extrn bSuppressHideShow:byte
extrn bTestMode:byte
extrn bTriggerPenOnForClick:byte
extrn cmdAbout:Control
extrn cmdCalibratePen:Control
extrn cmdClearHotKey1:CONTROL
extrn cmdClearHotKey2:CONTROL
extrn cmdDefault:Control
extrn cmdDisconnect:CONTROL
extrn cmdDisconnect:Control
extrn cmdDomainIDSpinUp:Control
extrn cmdEdit:Control
extrn cmdHost:CONTROL
extrn cmdHost:Control
extrn cmdHotKeys:CONTROL
extrn cmdHotKeys:Control
extrn cmdMaintenance:CONTROL
extrn cmdMaintenance:Control
extrn cmdModem:CONTROL
extrn cmdModem:Control
extrn cmdModemConnect:CONTROL
extrn cmdModemConnect:Control
extrn cmdModemConnect:Control
extrn cmdNetworkConnect:CONTROL
extrn cmdNetworkConnect:Control
extrn cmdNetworkUpdate:CONTROL
extrn cmdNetworkUpdate:Control
extrn cmdOSKAbout:Control
extrn cmdOSKAlphaKeyboard:Control
extrn cmdOSKEnlarge:Control
extrn cmdOSKFullKeyboard:Control
extrn cmdOSKNumKeyboard:Control
extrn cmdOSKReduce:CONTROL
extrn cmdOSKReduce:Control
extrn cmdPasswordOKCancel_Cancel:Control
extrn cmdPasswordOKCancel_OK:Control
extrn cmdPhoneBookOKCancel_Cancel:Control
extrn cmdPhoneBookOKCancel_OK:Control
extrn cmdPower:CONTROL
extrn cmdPower:Control
extrn cmdRebootHost:Control
extrn cmdScreen:CONTROL
extrn cmdScreen:Control
extrn cmdSerialConnect:Control
extrn cmdToolBarClose:Control
extrn cmdToolBarClose:Control
extrn cmdToolbarClose:CONTROL
extrn cmdUpgrade:Control
extrn cmdUseridOKCancel_Cancel:Control
extrn cmdUseridOKCancel_OK:Control
extrn fraConnectionOptions:CONTROL
extrn fraConnectionOptions:Control
extrn fraModemConnection:CONTROL
extrn fraModemConnection:Control
extrn fraModemCustom:CONTROL
extrn fraModemCustom:Control
extrn fraNetworkConnection:CONTROL
extrn fraNetworkConnection:Control
extrn fraSerialConnection:CONTROL
extrn fraSerialConnection:Control
extrn frmAlphaKeyboard:CONTROL
extrn frmHost:CONTROL
extrn frmHost:Control
extrn frmHotKey:CONTROL
extrn frmHotKey:Control
extrn frmMaintenance:CONTROL
extrn frmMaintenance:Control
extrn frmMessageBox:CONTROL
extrn frmMessageBox:Control
extrn frmMessageBox_End:byte
extrn frmModem:CONTROL
extrn frmModem:Control
extrn frmNumericKeyboard:CONTROL
extrn frmNumericKeyboard:Control
extrn frmPasswordBox:CONTROL
extrn frmPasswordBox:Control
extrn frmPhoneBookEdit:CONTROL
extrn frmPhoneBookEdit:Control
extrn frmPower:CONTROL
extrn frmPower:Control
extrn frmScreen:CONTROL
extrn frmScreen:Control
extrn frmUseridBox:Control
extrn lblMessageBox0:CONTROL
extrn lblMessageBox0:Control
extrn lblMessageBox0:CONTROL
extrn lblOSKBigCruiser:Control
extrn lblOSKChiselLine:CONTROL
extrn lblOSKChiselLine:Control
extrn lblOSKSmallCruiser:Control
extrn lblPasswordBox1:Control
extrn lblUseridBox1:Control
extrn lstHostPhones:CONTROL
extrn lstHostPhones:Control
extrn lstManufacturer:Control
extrn lstNetworkGroups:CONTROL
extrn lstNetworkGroups:Control
extrn lstNetworkHosts:CONTROL
extrn lstNetworkHosts:Control
extrn MainForm:Control
extrn mnuToolbar:CONTROL
extrn mnuToolbar:Control
extrn optModem:Control
extrn optNetwork:Control
extrn optPulse:Control
extrn optSerial:Control
extrn optTone:Control
extrn pClickRegion:word
extrn pCurrentFont:word
extrn pCurrentToolBarButton:word
extrn pEditBoxFont:word
extrn pFirstControl:word
extrn pGraphicFont:word
extrn pHostActiveRegion:word
extrn pNormFont:word
extrn pOSKFirstRegion:word
extrn pPenDownActiveRegion:word
extrn pPenUpListRegion:word
extrn pPenUpListRegion:word
extrn pPenUpListRegion:word
extrn pTabRegion:word
extrn pszProgressTable:word
extrn pszProgressTable_End:word
extrn rActiveRegions:Region
extrn rCalibrateLRCHeader:BUFFHEADER
extrn rCalibrateULCHeader:BUFFHEADER
extrn rCallProgressHeader:BUFFHEADER
extrn rCursorRegion:REGION
extrn rErrorMess1Header:BUFFHEADER
extrn rErrorMess2Header:BUFFHEADER
extrn rErrorMess3Header:BUFFHEADER
extrn rErrorMess4Header:BUFFHEADER
extrn rREGION:REGION
extrn rRebootHostHeader:BUFFHEADER
extrn rUpgradeCompHeader:BUFFHEADER
extrn rUpgradeHeader:BUFFHEADER
extrn rUpgradeIdAHeader:BUFFHEADER
extrn rUpgradeProgHeader:BUFFHEADER
extrn szCalibrationXString:byte
extrn szCallProgressFR:byte
extrn szCallProgressFR:byte
extrn szInvalidProgress:byte
extrn szInvalidProgress:byte
extrn szListItemBuffer1:byte
extrn szListItemBuffer2:byte
extrn szSerial:byte
extrn szUpgradeProgressPercent:byte
extrn txtCurrentHost:CONTROL
extrn txtCurrentHost:Control
extrn txtDomainID:control
extrn txtHotKey1:CONTROL
extrn txtHotKey2:CONTROL
extrn txtPBDescription:CONTROL
extrn txtPBDescription:Control
extrn txtPBPhoneNumber:CONTROL
extrn txtPBPhoneNumber:Control
extrn txtPassword:Control
extrn txtSecurityID:Control
extrn txtUserid:Control
extrn wBank:word
extrn wCurrentFormBottom:word
extrn wCurrentFormHeight:word
extrn wCurrentResource:word
extrn wCurrentResource:word
extrn wDisplayRequested:word
extrn wKeyPressed:word
extrn wListCurrentItem:word
extrn wMessageContinuationDX:word
extrn wMessageContinuationSI:word
extrn wNormFontHeight:word
extrn wPSPSegment:word
extrn wPenDownColumn:word
extrn wPreviousFormHeight:word
extrn wScreenSegment:word
extrn wWMCaption:word

bOSKMoveRequested db 0

bSuppressDimensionUpdate db 0

bNextOSKConfiguration db 0
  public bNextOSKConfiguration

bHourGlassMode db 0
  public bHourGlassMode

bHourGlassCursor label byte

dw 1000000000000011b
dw 1111111111111111b
dw 1000000000000011b
dw 1100000000000111b
dw 1100000000000111b
dw 1110000000001111b
dw 1111000000011111b
dw 1111100000111111b
dw 1111100000111111b
dw 1111000000011111b
dw 1110000000001111b
dw 1100000000000111b
dw 1100000000000111b
dw 1000000000000011b
dw 1111111111111111b
dw 1000000000000011b
dw 0000000000000000b
dw 0111111111111100b
dw 0011111111111000b
dw 0001111111110000b
dw 0001111111110000b
dw 0000101010100000b
dw 0000010101000000b
dw 0000001010000000b
dw 0000001010000000b
dw 0000011111000000b
dw 0000110101100000b
dw 0001101010110000b
dw 0001010101010000b
dw 0011111111111000b
dw 0111111111111100b
dw 0000000000000000b

bArrowCursor label byte

dw 0011111111111111b
dw 0001111111111111b
dw 0000111111111111b
dw 0000011111111111b
dw 0000001111111111b
dw 0000000111111111b
dw 0000000011111111b
dw 0000000001111111b
dw 0000000000111111b
dw 0000000000011111b
dw 0000000111111111b
dw 0000000111111111b
dw 0011000011111111b
dw 1111100001111111b
dw 1111100001111111b
dw 1111110000111111b

dw 0000000000000000b
dw 0100000000000000b
dw 0110000000000000b
dw 0111000000000000b
dw 0111100000000000b
dw 0111110000000000b
dw 0111111000000000b
dw 0111111100000000b
dw 0111111110000000b
dw 0111110000000000b
dw 0110110000000000b
dw 0100011000000000b
dw 0000011000000000b
dw 0000001100000000b
dw 0000001100000000b
dw 0000000000000000b

bHandMode db 0
  public bHandMode

bHandCursor label byte
dw 1111100011111111b
dw 1111000001111111b
dw 1111000001111111b
dw 1111000001111111b
dw 1111000001111111b
dw 1001000000001111b
dw 0000000000000111b
dw 0000000000000011b
dw 1000000000000011b
dw 1000000000000011b
dw 1100000000000011b
dw 1100000000000011b
dw 1110000000000011b
dw 1110000000000111b
dw 1111000000000111b
dw 1111100000001111b

dw 0000000000000000b
dw 0000011000000000b
dw 0000011000000000b
dw 0000011000000000b
dw 0000011000000000b
dw 0001011000000000b
dw 0110011010100000b
dw 0110011010101000b
```

```
dw 0011101010101000b
dw 0011111110101000b
dw 0001111111111000b
dw 0001111111111000b
dw 0000111111111000b
dw 0000111111110000b
dw 0000011111100000b
dw 0000000000000000b


surpalette db 00h,01h,02h,03h,04h,05h,14h,07h
        db 38h,39h,3ah,3bh,3ch,3dh,3eh,3fh,00h

cursclors label byte
db 00h, 00h, 00h
db 00h, 2Ah, 00h
db 2Fh, 00h, 00h
db 2Ah, 2Ah, 00h
db 00h, 00h  2Ah
db 00h, 2Ah, 2Ah
db 10h, 00h, 2Ah
db 2Dh, 20h, 20h
db 10h, 10h, 10h
db 1Ah, 3Fh, 10h
db 3Fh, 10h, 10h
db 3Fh, 3Fh, 10h
db 10h  10h  3Fh
db 0Eh  3Fh, 3Fh
db 3Fh  10h, 3Fh
db 3Fh, 3Eh, 3Fh
db 00h  00h, 00h

wHotKeyWork dw 0
bHotKeysShifted db 0
bHotKeyBuild db 30 dup(0)

bHotKeyAcoS db 0,0,0,0
bKeyWasShifted db 0
wHotKeyShiftKeyUps dw 7 dup(0)
bFuncWasAlt db 0
wHotKeyRightPixel dw 0
  public wHotKeyRightPixel

bCapsLockState db 0
bNumLockState db 0

bCalibrateOnly db 0

bPasswordOnly db 0

bConnectRequested db 0

bGetConnectionStatus db 0

wCurrentCallProgress dw 0

bFlashPercentageFlag db 0

wCountryCode  dw 0

bCalibrationCompleteFlag db 0

wAboutClickTimer  dw 0
bAboutClickActive db 0

bPollingTimer    db 0

bLastKeyboardState db 0
bUpdateOSKLockKeys db 0

wCurrentHostList dw 0


wClosureRequest dw 0

SMNotRunningError db 13,10,"SM Not
Running",13,10,"$"


SMFunctionDispatcher dd DummyFunction
  public SMFunctionDispatcher


bReportOskDimensions db 0
  public bReportOSKDimensions

DATASEG_END


.code

main proc far
  call VMain

  mov ax,4c00h
  int 21h
main endp

DoCustomStartup proc far
  public DoCustomStartup

  mov al,SM_FUNCTION_INTERRUPT
  mov ah,030h
  int 21h

  cmp word ptr es:[bx+13],"s"+256*"c"
  jnz main1a
  cmp word ptr es:[bx+13],"i"+256*"a"
  jnz main1a
  jmp main2
main1a:
  jmp InvalidStartup

main2:
  mov word ptr SMFunctionDispatcher[0],bx
  mov word ptr SMFunctionDispatcher[2],es

  SM_FUNCTION SM_GET_KEYBOARD_STATUS
  jc main3
  mov bKeyboardCode,al

main3:
  SM_FUNCTION
SM_GET_USER_INTERFACE_LANGUAGE
  jc main4
  mov bLanguageToUse,al

main4:
  mov si,offset UIFunctionDispatcher
  mov dx,cs
  SM_FUNCTION SM_SET_ACTIVE_STATUS
  jc main8

  test al,128
  jz main4a
  and al,not(128)
  mov bTextMode,-1

main4a:
  cmp ax,1
  jnz main8
  call HideModemOptions

main8:

  ret

InvalidStartup:
  mov dx,offset SMNotRunningError
  mov ah,9
  int 21h
  mov ax,4c01h
  int 21h
DoCustomStartup endp


DoSMFunction proc far
  public DoSMFunction

  or al,al
  jnz dsmf1
  xor ah,ah
  dec ax
  jc dsmf2
dsmf1:
  call dword ptr SMFunctionDispatcher
dsmf2:
  cmp ax,3
  ret
DoSMFunction endp

UIFunctionDispatcher proc far
  public UIFunctionDispatcher

  push ds
  push ax
  mov ax,OURDATASEG
  mov ds,ax
  pop ax

  inc bDoingEvents
  push si
  push bx
  or ax,ax
  jz ufd01
  call JumpOnAX

  dw
UI_GET_SM_VERSION_NUMBER,GetSMVersionN
umber
  dw UI_HIDE_MESSAGE_BOX,HideMessageBox
  dw UI_REQUEST_CLOSURE,RequestClosure
  dw UI_REQUEST_DISPLAY,RequestDisplay
  dw
UI_SHOW_MESSAGE_BOX,ShowSMMessageBox

  dw
UI_CALIBRATION_COMPLETE,CalibrationComplete
  dw
UI_FLASH_UPDATE_PERCENTAGE,FlashUpdateP
ercentage
  dw
UI_UPDATE_CONNECTION_STATUS,UpdateConn
ectionStatus
  dw
UI_SHOW_HIDE_BUSY_CURSOR,ShowHideBusyC
ursor
  dw UI_MOVE_OSK,DoOSKMoveRequest
  dw 0

ufd01:
  mov ax,-1
  jmp ReturnWithAX

DoOSKMoveRequest:

  mov OSK.TopPixel,bx
  mov OSK.LeftPixel,ax
  mov bOSKMoveRequested,-1
  mov bPopupRequired,-1
  jmp ReturnSuccess


GetSMVersionNumber:
  mov al,MINOR_VERSION
  mov ah,MAJOR_VERSION
  jmp ReturnWithAX

HideMessageBox:
  cmp bMessageBoxID,0
  jz hmb1

  mov bx,wCurrentResource
  test bx,0111111111111000b
  jnz hmb2

  call far ptr deinstallint09

hmb2:
  mov bRemoveMessageBoxRequested,-1
  mov ax,0
  mov bPopupRequired,-1
  jmp ReturnWithAX
hmb1:
  mov ax,-7
  jmp ReturnWithAX

RequestDisplay:

  mov bLocalState,1
  test bx,not(111b)
  jnz ooo1

  mov osk.TopPixel,si
  mov osk.LeftPixel,di
  mov bDontCenterOSK,-1

  or mouToolBar.ControlState,INVISIBLE
  mov pFirstControl,offset OSK

  push cx
  push bx
  call ResetPenRestart
  pop bx
  pop cx
  jmp orr1

ooo1:
  and al,111b
  mov bNextOSKConfiguration,al

orr1:
  mov ax,bx
  and al,111b
  cmp al,4
  jnz rdle1
  jmp ReturnInvalidParm

rdle1:
  mov ax,bx
  shr ax,1
  shr ax,1
  shr ax,1

  cmp ax,MAX_TOOLBARBUTTONS
  jbe rb3q
  jmp ReturnInvalidParm

rb3q:
  push bx
  mov ah,0Fh
  int 10h
  and al,1111111b
  pop bx
  mov bScreenMode,al

  cmp al,VGA_MODE
  jz rd1
  cmp al,3
  jz rd2b
  cmp al,7
  jz rd2

  jmp ReturnInvalidParm

rd2:
  mov ax,0b000h
  jmp rd2a
rd2b:

  mov ax,0b800h
rd2a:
  mov wScreenSegment,ax
  cmp bx,7
  jbe rd1
  jmp ReturnInvalidParm

rd1:
  test bx,1111111111111000b
  jz rd1a
  call far ptr installint09
  jmp rd1b

rd1a.
  mov bReportOSKDimensions,-1

rd1b.
  mov bNewDisplayRequested,-1
  mov wDisplayRequested,BX
  mov bPopupRequired,-1

  test wDisplayRequested,1111111000b
  jnz rd1bbe1

  mov bAwaitingMoveCompletion,-1
  mov bLeavePenOn,0
  jmp rd1bba

rd1bbe1:
  cmp bLeavePenOn,0
  jnz rd1bba
  mov bLeavePenOn,-1
  cmp bDoingEvents,1
  jz  rd1bba
  call PenExit

rd1bba
  xor ax,ax
  jmp ReturnWithAX

ShowSMMessageBox.

  cmp bMessageBoxID,0
  jz smg2
  cmp bRemoveMessageBoxRequested,-1
  jz smg2

  jmp smmb1

smg2:
  or cx,cx
  jz smg1
  cmp cx,0
  jz smg1
  cmp cx,0
  jz smg1
  mov ax,-3
  jmp ReturnWithAX

smg1:
  push bx
  push cx
  push dx
  push si
  push di
  push es
  or cx,cx
  jz smb1
  cmp cx,0
  jz smb3
  cmp cx,0
  jnz smb1

  mov bNewDisplayRequested,-1
  mov wDisplayRequested,8*1
  mov bPopupRequired,-1
  mov bPasswordOnly,-1
  jmp smb3xx

smb3:
  mov bNewDisplayRequested,-1
  mov wDisplayRequested,8*3
  mov bPopupRequired,-1
  mov bCalibrateOnly,-1
```

```
smb3a:
 xor bx,ax
 xor bx,bx
 jmp smb2

smb1:
 cmp wCurrentResource,0
 jnz smb11a
 or wCurrentResource,256*128

smb11a:
 mov bMessageBoxID,-1
 call PrepareMessageBox
 mov bMessageBoxRequested,-1

smb2:
 pop es
 pop di
 pop si
 pop ds
 pop cx
 pop bx
 or bx,bx
 jz somb2
 call far ptr InstallInt60

somb2:
 mov bPopupRequired,-1
 jmp ReturnSuccess

somb1:
 mov ax,-6
 jmp ReturnWithAX


CalibrationComplete:
 cmp bMessageBoxId,MS_CALIBRATEULC
 jz cc1
 cmp bMessageBoxId,MS_CALIBRATELRC
 jz cc2
 mov ax,-2
 jmp ReturnWithAx

cc1:
 mov bCalibrationCompleteFlag,1
 mov bPopupRequired,-1
 jmp ReturnSuccess

cc2:
 mov bCalibrationCompleteFlag,2
 mov bPopupRequired,-1
 jmp ReturnSuccess


FlashUpdatePercentage:
 cmp bl,bFlashPercentageFlag
 jz fup1
 mov bPopupRequired,-1
fup1:
 mov bFlashPercentageFlag,bl
 jmp ReturnSuccess


RequestClosure:

 push ax
 push bp
 push di
 mov wClosureRequest,bx
 cmp bx,1
 jnz rcl1

 call DisableInterrupts
 jmp rc11a

rcl1
 mov bRepaintNeeded,0
 call ForceTotalRepaint
 mov ax,479
 mov wCurrentFormBottom,ax
 inc ax
 mov wCurrentFormHeight,ax

rc11a:
 call far ptr deinstallInt60
 mov ah,0fh
 int 10h
 and al,1111111b
 cmp al,12h
 jnz rqc1a

 call SetVGAState
 push wCurrentResource
 call DeHideOSK
 pop wCurrentResource
 test wCurrentResource,not(111b)
 jz rqc1

 call unprotectosk

 end BlackenScreen

rqc1:
 call RestVGAState

rqc1a:
 call FreeScreen

 cmp wClosureRequest,1
 jnz rcl2
 mov bx,wPSPSegment
 mov ah,50h
 int 21h

rcl2.
 mov ax,wCurrentResource
 test al,111b
 jnz rcl

 mov ah,bOSKLastState
 and ah,111b
 or al,ah

rcl:
 cmp wClosureRequest,1
 jnz rcl3
 pop di
 pop bp
 pop ax

 mov ah,4ch
 int 21h

rcl3:
 call ResetForRestart
 xor ah,ah
 pop di
 pop bp
 pop ax

 test wCurrentResource,111111111b
 jnz rwt

 mov bLeavePenOn,0
 cmp bDoingEvents,0
 jnz ue1

 call PenEntry
ue1:
 jmp ReturnWithAX


UpdateConnectionStatus:

 SM_FUNCTION SM_GET_HOST_LIST_STATUS
 call GreyNetworkLists
 cmp ax,1
 jb ucs2a

 SM_FUNCTION SM_UPDATE_HOST_LIST
 mov bRepaintNeeded, PAINTALL

ucs2:
 mov bPopUpRequired,-1
ucs2a:
 mov bLeavePenOn,-1
 jmp ReturnSuccess


ShowHideBusyCursor:
 cmp bx,1
 jb shbc1
 ja ReturnInvalidParm
 call SetArrowCursor
 jmp ReturnSuccess

shbc1:
 call SetHourGlassCursor
 jmp ReturnSuccess

ReturnSuccess:
 xor ax,ax
 jmp ReturnWithAX

ReturnInvalidParm:
 mov ax,-3
 jmp ReturnWithAX


ReturnWithAX:
 pop bx
ReturnWithBX:
 pop si
ReturnWithSI:
 dec bDoingEvents
 pop ds
 ret
UIFunctionDispatcher endp

ResetForRestart proc near

 mov wCurrentResource,0
 mov pTabRegion,0
 push ax
 mov bShadowColor,SHADOW_COLOR
 mov bCurrentShadowColor,SHADOW_COLOR
 mov pOSKFirstRegion,-1
 call UseNormalColors
 pop ax
 ret
resetforrestart endp

DoCustomEvents proc far
 public DoCustomEvents
 cmp bUpdateOSKLockKeys,0
 jz dce0
 mov bUpdateOSKLockKeys,0
 call SetPhysicalKeyState
dce0:

 cmp bAboutClickActive,0
 jz sba4
 cmp wAboutClickTimer,0
 jb sba4
 mov bAboutClickActive,0
 call DeHideOSK
 call ShowAbout
sba4.

 cmp bOSKMoveRequested,0
 jz efe0
 mov bOSKMoveRequested,0
 mov bSuppressDimensionUpdate,-1
 mov bx,offset OSK
 and [bx].ControlState,not(INVISIBLE)
 mov pNextActiveRegion,offset bActiveRegions
 mov pOSKFirstRegion,-1
 call UnprotectOSK
 mov bDontChangeProtection,-1
 call RepaintOSK
 mov bDontChangeProtection,0
 mov bSuppressDimensionUpdate,0
 call ReportCurrentResource
 mov bAwaitingMoveCompletion,0

 cmp bScreenMode,12h
 jnz lpe1
 mov bTriggerPenOnForClick,-1
 jmp lpe2
lpe1:
 mov bLeavePenOn,-1
lpe2:

efe0:

 cmp bNewDisplayRequested,0
 jz efe1
 mov bAwaitingMoveCompletion,0
 call DoExternalDisplayRequest
efe1:


 cmp bRemoveMessageBoxRequested,0
 jz de4c
 mov bRemoveMessageBoxRequested,0
 cmp bMessageBoxID,MS_CALIBRATELRC
 jz de4e1
 cmp bMessageBoxID,MS_CALIBRATEULC
 jz de4e1
 cmp bMessageBoxRequested,0
 jz ev1
 call StopProtecting
 mov pFirstControl,offset MainForm
 mov wPreviousFormHeight,480
 mov bFormColor,FORM_COLOR
 call Repaint
 jmp ev2
ev1:



 call RemoveMessageBox
de4c:

 cmp bMessageBoxRequested,0
 jz de4b
ev2:
 call DeHideOSK
 call DrawMessageBox
 mov bMessageBoxRequested,0
de4b.


 cmp bCalibrationCompleteFlag,1
 jb de4f
 jz de4e1

 call DoCalibrateLRC
 jmp dce_quickout

de4e1:
 mov bCalibrationCompleteFlag,0
 mov bMessageBoxID,0
 call StopProtecting

 cmp bCalibrateOnly,-1
 jnz de4e2
 call BlackenScreen
 mov bCalibrateOnly,0
 mov wCurrentResource,0
 call FreeScreen
 call far ptr deinstallInt60
 mov bMessageBoxId,0
 call UnprotectOSK
 call ForceTotalRepaint
 mov bRepaintNeeded,0
 jmp de4f
de4e2:

 call ClearScreen
 call ForceTotalRepaint
de4f:
 mov bLeavePenOn,-1
de4ff:



 cmp bFlashPercentageFlag,0
 jz de4g
 xor bl,bl
 xchg bl,bFlashPercentageFlag
 xor ah,ah
 call ShowUpgradeProgress
de4g:

 call CheckUpdateHostList
 jnc de4h
 SM_FUNCTION SM_GET_HOST_LIST_STATUS
 jz de4h1
 jmp de4h
de4h1:
 call UngreyNetworkLists
 mov bRepaintNeeded,-1
de4h:

 cmp bGetConnectionStatus,0
 jz mcs1
 SM_FUNCTION
SM_GET_CONNECTION_STATUS

 cmp ax,wCurrentCallProgress
 jz mcs1

 or ax,ax
 jnz mcs3

 mov bGetConnectionStatus,0
 mov wCurrentCallProgress,ax
 mov bRepaintNeeded,0
 mov bPopUpRequired,0
 mov bLeavePenOn,0
 call far ptr deinstallInt60
 jmp mcs1


mcs3.
 cmp bMessageBoxID,0
 jz mcs2
 push ax
 call RemoveMessageBox
 pop ax
mcs2:
 call ShowCallProgress
mcs1:


 cmp bConnectRequested,0
 jz cfare1
 call RepaintAndSetTab

 mov wCurrentCallProgress,1234
 mov bGetConnectionStatus,-1
 mov bPopupRequired,-1
 mov bConnectRequested,0
 SM_FUNCTION SM_REQUEST_CONNECTION
 jge cfare1
cfare2:
 mov bGetConnectionStatus,0
 call ReportError
cfare1:


 cmp bMessageBoxRequested,0
 jz edrq1
 jmp dce0
```

```
ndrq1:

 clc
 ret
doc_quokzok:
 clc
 ret
DoCustomEvents endp

DoToolBarButtonClick proc far
 public DoToolBarButtonClick
 push si
 push ax

 cmp si,offset cmdHost
 jnz dibc1a
 call InitializeDefaults
 call UpdateHostList
 test fraNetworkConnection.ControlState,INVISIBLE
 jnz dorp1
 mov si,offset lstNetworkHosts
 mov ax,[si-1],si
 mov ax,-1
 call GetListData
 or dx,dx
 jnz dorp1

 or cmdDisconnect.ControlState,DISABLED or
GRAYED
 or cmdToolBarClose.ControlState,DISABLED or
GRAYED
 and txtSecurityID.ControlState,not(GRAYED or
DISABLED)
 or cmdRebootHost.ControlState,GRAYED or
DISABLED
 or cmdUpgrade.ControlState,GRAYED or
DISABLED
 or cmdNetworkConnect.ControlState,DISABLED or
GRAYED
dorp1:
 jmp dibc1b

dibc1a:
 call SetControlsForConnectState
 jmp dibc1b

dibc1c:
dibc1b:

 pop ax
 pop si
 ret
DoToolBarButtonClick endp

DummyFunction proc far
 mov ax,-1
 ret
DummyFunction endp

CheckScreenUpdateNeeded proc far
 public CheckScreenUpdateNeeded
 call CheckUpdateHostList
 ret
CheckScreenUpdateNeeded endp

CheckUpdateHostList proc near

 cmp bMessageBoxID,0
 jnz dothe
 cmp pCurrentToolBarButton,offset cmdHost
 jnz dothe
 test fraNetworkConnection.ControlState,INVISIBLE
 jnz dothe
 test cmdNetworkUpdate.ControlState,GRAYED or
DISABLED
 jz dothe
 stc
 ret
dothe:
 clc
 ret
CheckUpdateHostList endp


DoCalibrate proc near

 call UndoCurrentTabItem
 mov pTabRegion,0
 call DoHideOSK
 mov si,offset rCalibrateULCHeader
 mov dx,seg rCalibrateULCHeader
 mov bMessageBoxId,MB_CALIBRATEULC
 call CalibrateAny
 mov bLeavePenOn,-1
 call penend
 mov bx,4
 mov cx,4
 SM_FUNCTION SM_CALIBRATE_UPPERLEFT
 ret
DoCalibrate endp

DoCalibrateLRC proc near
 mov si,offset rCalibrateLRCHeader
 mov dx,seg rCalibrateLRCHeader
 mov bMessageBoxId,MB_CALIBRATELRC
 mov bCalibrationCompleteFlag,0
 call CalibrateAny
 mov bx,480-9+4
 mov cx,640-11+4
 SM_FUNCTION SM_CALIBRATE_LOWERRIGHT
 ret
DoCalibrateLRC endp

CalibrateAny proc near
 push dx
 push si

 call blankscreen
 xor cx,cx
 xor dx,dx
 mov si,offset szCalibrationXString
 mov pCurrentFont,offset UIFont
 mov bx,16
 call DrawString

 mov cx,640-11
 mov dx,480-9
 mov bx,16
 mov si,offset szCalibrationXString
 call DrawString
 pop si
 pop dx
 mov bx,MBX_CANCEL
 call PrepareMessageBox
 call DrawMessageBox
 ret
CalibrateAny endp

ShowUpgradeProgress proc near
 cmp bMessageBoxID,0
 jz sup0
 push ax
 call RemoveMessageBox
 pop ax
sup0:
 cmp ax,100
 jae sup4
 mov cl,3
 mov bx,offset szUpgradeProgressPercent
 call Bin2Asch

sup2:
 cmp bx,offset szUpgradeProgressPercent+3
 jae sup1
 mov byte ptr [bx]," "
 inc bx
 jmp sup2

sup1:
 call DoHideOSK
 mov si,offset rUpgradeProgHeader
 mov dx,seg rUpgradeProgHeader
 mov bMessageBoxId,MB_UPGRADE_PROGRESS

 mov bx,MBX_NOBUTTON
 call PrepareMessageBox
 call DrawMessageBox
 ret

sup4:
 call DoHideOSK
 mov si,offset rUpgradeCompHeader
 mov dx,seg rUpgradeCompHeader
 mov bMessageBoxId,MB_UPGRADE_COMPLETE

 mov bx,MBX_NOBUTTON
 call PrepareMessageBox
 call DrawMessageBox
 ret
ShowUpgradeProgress endp

DoExternalDisplayRequest proc near

 mov pNextActiveRegion,offset rActiveRegions
 mov pOSKFirstRegion,-1
 call DoHideOSK
 cmp bMessageBoxID,0
 jz dedr1
 call RemoveMessageBox
dedr1:
 mov ax,uDisplayRequested
dedr2:
 test ax,not(111b)
 jz dedr2a

 push ax
 call RestoreCurColors
 pop ax
dedr2a:
 test uCurrentResource,not(111b)
 jnz efs3
 test ax,not(111b)
 jz efs2

 mov osk.pixelheight,0
 push ax
 xor bx,bx
 xor cx,cx
 mov dx,SCREEN_WIDTH_PIXELS - 1
 mov si,SCREEN_HEIGHT_PIXELS - 1

 SM_FUNCTION SM_UPDATE_DIMENSIONS

 cmp bCalibrateOnly,-1
 jne efs2a
 pop ax
 mov uDisplayRequested,0
 mov uCurrentResource,0*256
 call far ptr InstallInt60
 call DoCalibrate
 jmp efs4
efs2a:

 cmp bPasswordOnly,-1
 jne efs2b
 pop ax
 mov uDisplayRequested,0
 mov uCurrentResource,0*256
 call far ptr InstallInt60
 call blankscreen
 mov
uCurrentHostList,GETSET_NETWORK_HOST_ENT
RY
 call GetPassword
 jmp efs4
efs2b:

 call ClearScreen
 pop ax

efs2:
 mov bl,not(BDOWN)
 and cmdHost.ControlState,bl
 and cmdHotKeys.ControlState,bl
 and cmdMaintenance.ControlState,bl
 and cmdModem.ControlState,bl
 and cmdPower.ControlState,bl
 and cmdScreen.ControlState,bl

 shr ax,1
 shr ax,1
 shr ax,1
 and ax,7
 jz efs3
 mov pOSKFirstRegion,-1
 or OSK.ControlState,INVISIBLE
 call ForceTotalRepaint

 mov si,offset cmdHost
 dec ax
 jz efs4
 mov si,offset cmdHotKeys
 dec ax
 jz efs4
 mov si,offset cmdMaintenance
 dec ax
 jz efs4
 mov si,offset cmdModem
 dec ax
 jz efs4
 mov si,offset cmdPower
 dec ax
 jz efs4
 mov si,offset cmdScreen
 dec ax
 jz efs4
 jmp efs3

efs4:
 or [si].ControlState,BDOWN
 and mnuToolbar.ControlState,not(INVISIBLE)
 call SaveFormHeight
 mov bRepaintNeeded,-1
 call RepaintAndSetTab

 cmp bCalibrateOnly,-1
 jnz eoif
 mov bCalibrateOnly,0
 call DoCalibrate
 jmp efs6
eoif:
 cmp bPasswordOnly,-1
 jnz eopg
 mov bPasswordOnly,0
 mov
uCurrentHostList,GETSET_NETWORK_HOST_ENT
RY
 call GetPassword
 jmp efs6
eopg:


 jmp efs6

efs3:
 test uCurrentResource,not(111b)
 jz efs3a
 call BlankenScreen
efs3a:
 or mnuToolbar.ControlState,INVISIBLE

efs5:
 mov ax,uDisplayRequested
 call ReconfigureOSK
efs6:
 mov bNewDisplayRequested,0
 ret
DoExternalDisplayRequest endp

restorecurcolors proc near

 mov ax,1002h
 push ds
 pop es
 mov dx,offset curpalette
 int 10h
 mov si,offset curpalette
 mov bx,offset curcolors
 mov cx,17
rrr:
 push cx
 lodsb
 mov ch,[bx]
 mov cl,[bx+1]
 mov dh,[bx+2]
 add bx,3
 push bx
 mov bl,al
 xor bh,bh
 mov ax,1010h
 int 10h
 pop bx
 pop cx
 loop rrr
 ret
restorecurcolors endp

ReconfigureOSK proc near
 public ReconfigureOSK

 and ax,111b
 jz efs6e
 mov bHostOSKConfiguration,0

 mov OSK.ID,ax
 test cmdOSKReduce.ControlState,INVISIBLE
 jnz efs7
 call SetOSKReducedButtons

efs7:
 test OSK.ID,RES_OSK_BIG
 jz efs8
 call SetOSKEnlargedButtons

efs8:
 mov ax,OSK.ID
 and al,11b
 cmp al,RES_OSK_ALPHA
 jz efs6a
 cmp al,RES_OSK_NUM
 jz efs6b
 cmp al,RES_OSK_FULL
 jmp efs6c
 jmp efs6e

efs6a:
 mov si,offset cmdOSKAlphaKeyboard
 call far ptr DoOSKSmallKeyboard
 jmp efs6e

efs6b:
 mov si,offset cmdOSKNumKeyboard
 call far ptr DoOSKNumKeyboard
 jmp efs6e

efs6c:
 mov si,offset cmdOSKFullKeyboard
 call far ptr DoOSKFullKeyboard
 jmp efs6e

efs6e:
 ret
ReconfigureOSK endp
```

```
 call RetainOSKRightAndShow
 call ReportCurrentResource
 ret

DoOSKSmallKeyboard1:
 call PrepUserResize

DoOSKSmallKeyboard:
 mov ax,OSK.ID
 and ax,not(RES_OSK_ALPHA + RES_OSK_NUM)

 or ax,RES_OSK_ALPHA
 mov OSK.ID,ax
 mov ax,uCurrentResource
 and ax,not(RES_OSK_ALPHA + RES_OSK_NUM)

 or ax,RES_OSK_ALPHA
 mov uCurrentResource,ax

 call ReGrayOSKTypeButtons
 or fbmNumericKeyboard.ControlState,INVISIBLE
 call RetainOSKRightAndShow
 call ReportCurrentResource
 ret

DoOSKNumKeyboard1:
 call PrepUserResize

DoOSKNumKeyboard:
 mov ax,OSK.ID
 and ax,not(RES_OSK_ALPHA + RES_OSK_NUM)

 or ax,RES_OSK_NUM
 mov OSK.ID,ax
 mov ax,uCurrentResource
 and ax,not(RES_OSK_ALPHA + RES_OSK_NUM)

 or ax,RES_OSK_NUM
 mov uCurrentResource,ax
 call ReGrayOSKTypeButtons
 or fbmAlphaKeyboard.ControlState,INVISIBLE
 call RetainOSKRightAndShow
 call ReportCurrentResource
 ret

DoOptNetwork:
 call SetNetworkFrame
 call UpdateHostList
 call RepaintForClick
 ret

DoOptModem:
 call SetModemFrame
 call RepaintForClick
 ret

DoOptSerial:
 call SetSerialFrame
 call RepaintForClick
 ret

DoListNetworkHosts:
 ret

DoCmdAbout:
 cmp bAboutClickActive,0
 jnz dca1
 mov wAboutClickTimer,0
 mov bAboutClickActive,-1
 ret
dca1:

 mov bAboutClickActive,0
 test cmdToolBarClose.ControlState,DISABLED or
GRAYED
 jnz dca2
 call far ptr TryUnload
dca2:
 ret

DoUpgrade:
 call DoHideOSK
 SM_FUNCTION
SM_REQUEST_ACTIVE_FLASH_UPGRADE
 jnc du1
 cmp ax,-8
 jnz du4

 or dx,dx
 jz du4a

 mov bMessageBoxID,-1
 mov bx,MBX_OK
 call PresentMessageBox
 mov bMessageBoxRequested,-1
 mov bPopupRequired,-1
 call far ptr InstallInt08
 ret

du4:
 call ReportError
du4a:
 ret

du1:
 or dx,dx
 jnz du2
 mov bMessageBoxID,MB_NOUPGRADE
 mov si,offset rUpgradeNAHeader
 mov ds,seg rUpgradeNAHeader
 mov bx,MBX_OK
 jmp du3
du2:

 mov wMessageContinuationSI,offset
rUpgradeHeader
 mov wMessageContinuationSX,seg
rUpgradeHeader
 mov bMessageBoxId,MB_UPGRADE
 mov bx,MBX_YESNO

du3:
 call PrepareMessageBox
 call DrawMessageBox
 ret

StartCalibrate:
 call DoCalibrate
 r.

DoReboot:
 call DoHideOSK
 mov si,offset rRebootHostHeader
 mov ds,seg rRebootHostHeader
 mov bMessageBoxId,MB_REBOOT
 mov bx,MBX_YESNO
 call PrepareMessageBox
 call DrawMessageBox
 ret

ClearHotKey1:
 mov bx,offset tdHotKey1
 xor ax,ax
 mov [bx].wDataLength,ax
 mov ScanCodeHeader.lBuff,ax,2
 mov word ptr ScanCodeParser,ax

 push bx
 call PassScanCodeList
 pop si
 call FindRegionForControl
 js chc1
 mov si,offset tdHotKey1
 call ResetHotKeyEditField
chc1:
 ret

ClearHotKey2:
 mov bx,offset tdHotKey2
 xor ax,ax
 mov [bx].wDataLength,ax
 mov ScanCodeHeader.lBuff,ax,2
 mov word ptr ScanCodeParser,ax
 push bx
 call PassScanCodeList
 pop si
 call FindRegionForControl
 js chc2
 mov si,offset tdHotKey2
 call ResetHotKeyEditField
chc2
 ret
HandleButtonClicks endp

ResetHotKeyEditField proc near
 mov pPenDownActiveRegion,bx
 mov pClickRegion,bx
 mov ax,[bx]
 call RepaintIndirectControl
 mov bResetHotKeyDataLength,-1
 mov wHotKeyRightPixel,0
 mov wPenDownColumn,0
 call DoClickEvent
 ret
ResetHotKeyEditField endp

HandleMessageBoxClick proc far
 public HandleMessageBoxClick
 call JumpOnAX
 dw MB_CALIBRATEULC or (MBB_CANCEL *
256),offset
CancelCalibrateULC
 dw MB_CALIBRATELRC or (MBB_CANCEL *
256),offset
CancelCalibrateLRC
 dw MB_SHOWCALLPROGRESS or
(MBB_CANCEL * 256),offset
AbortConnection
 dw MB_REBOOT or (MBB_YES * 256),offset
DoRebootYes
 dw MB_UPGRADE or (MBB_YES * 256),offset
DoUpgradeYes
 dw MB_ABOUT or (MBB_OK * 256),offset
DoAboutOK
 dw MB_CREDITS or (MBB_OK * 256),offset
DoAboutOK
 dw 0
 call RemoveMessageBox
 ret

CancelCalibrateULC:
 cmp bCalibrateOnly,-1
 jnz ccul1
 SM_FUNCTION SM_CANCEL_CALIBRATION
 mov bCalibrationCompleteFlag,2
 mov bpopuprequired,-1
 ret
ccul1:
 mov bMessageBoxID,0
 call StopPrinting
 call ClearScreen
 SM_FUNCTION SM_CANCEL_CALIBRATION

 call ForceTotalRepaint
 call repaint
 ret

CancelCalibrateLRC:
 call RemoveMessageBox
 call DoCalibrate
 ret

AbortConnection:
 SM_FUNCTION
SM_ABORT_REQUEST_CONNECTION
 jnc ac1
 cmp ax,-6
 jnz ac1
 ret
ac1:
 call RemoveMessageBox
 mov bNetConnectionStatus,0
 mov bRepaintNeeded,-1
 ret

DoRebootYes:
 call RemoveMessageBox
 SM_FUNCTION SM_REBOOT_HOST
 jz dry1
 call ReportError
 ret
dry1:
 mov bMenuDisplayRequested,-1
 mov wDisplayRequested,1*8
 ret

DoUpgradeYes:
 call RemoveMessageBox
 SM_FUNCTION SM_PERFORM_FLASH_UPDATE

 jz duy1
 call ReportError
 ret
duy1:
 xor ax,ax
 call ShowUpgradeProgress
 ret

DoAboutOK:
 call RemoveMessageBox
 SM_FUNCTION
SM_GET_NEXT_CREDITS_DIALOG
 jc daobok2
 mov ax,si
 or ax,dx
 jz daobok2
 mov bMessageBoxID,MB_CREDITS
 mov bx,MBX_OK
 call PrepareMessageBox
 call DrawMessageBox
daobok2:
 ret
HandleMessageBoxClick endp

HideModemOptions proc near

 or cmdModem.ControlState,INVISIBLE
 xor bx,bx
 mov ax,130

 mov cmdHost.PixelWidth,ax
 add bx,ax
 mov cmdHotKeys.LeftPixel,bx
 mov cmdHotKeys.PixelWidth,ax
 add bx,ax
 mov cmdMaintenance.LeftPixel,bx
 mov cmdMaintenance.PixelWidth,ax
 add bx,ax
 mov cmdPower.LeftPixel,bx
 mov cmdPower.PixelWidth,ax
 add bx,ax
 mov cmdScreen.LeftPixel,bx
 mov cmdScreen.PixelWidth,ax
 add bx,ax
 mov cmdToolbar.PixelWidth,bx
 mov fmHost.PixelWidth,bx
 mov fmHotKey.PixelWidth,bx
 mov fmMaintenance.PixelWidth,bx
 mov fmScreen.PixelWidth,bx
 mov fmPower.PixelWidth,bx

 sub bx,32
 mov cmdToolbarClose.LeftPixel,bx

 sub cmdDisconnect.LeftPixel,34
 sub cmdNetworkUpdate.LeftPixel,34
 sub cmdNetworkConnect.LeftPixel,34
 or fsConnectionOptions.ControlState,INVISIBLE
 sub fraNetworkConnection.TopPixel,40
 sub fmHost.PixelHeight,40
 sub lstNetworkHosts.LeftPixel,5

 ret
HideModemOptions endp

InitializeDefaults proc near

 mov ax,GETSET_HOST_CONNECTION_TYPE
 mov ah,00h
 SM_FUNCTION ax
 jl id1
 or bl,bl
 jz id1

 mov si,offset optModem
 call SetModemFrame
 cmp bl,1
 jz id2

 mov si,offset optSerial
 call SetSerialFrame
 cmp bl,2
 jz id2

id1
 mov si,offset optNetwork
 call SetNetworkFrame

id2:
 mov bx,[si].pStorageOffset
 mov byte ptr [bx],1

 call SetControlsForConnectState
 ret
InitializeDefaults endp

SetControlsForConnectState proc near

 or cmdDisconnect.ControlState,GRAYED or
DISABLED
 or cmdToolBarClose.ControlState,DISABLED or
GRAYED
 or cmdNetWorkConnect.ControlState,GRAYED or
DISABLED
 or cmdModemConnect.ControlState,GRAYED or
DISABLED

 and txtSecurityID.ControlState,not (GRAYED or
DISABLED)
 or cmdRebootHost.ControlState,GRAYED or
DISABLED
 or cmdUpgrade.ControlState,GRAYED or
DISABLED


 SM_FUNCTION
SM_GET_CONNECTION_STATUS
 jl id3

 or ax,ax
 jnz id3a

 and cmdDisconnect.ControlState,not(GRAYED or
DISABLED)
 and cmdToolBarClose.ControlState,not(DISABLED
or GRAYED)
 or txtSecurityID.ControlState,GRAYED or
DISABLED
 and cmdRebootHost.ControlState,not(GRAYED or
DISABLED)
 and cmdUpgrade.ControlState,not(GRAYED or
DISABLED)
```

```
  call GetHostName
  jmp id3

id2a:
  call ClearHostName
  and
wndNetworkConnect.ControlState,not(GRAYED or
DISABLED)
  and wndModemConnect.ControlState,not(GRAYED
or DISABLED)
  jmp id3

id3:
  ret
SetControlsForConnectState endp

SetModemFrame proc near

  call UndoAllHostTypes
  and
tbModemConnection.ControlState,not(INVISIBLE)
  ret
SetModemFrame endp


SetNetworkFrame proc near

  call UndoAllHostTypes
  and
tbNetworkConnection.ControlState,not(INVISIBLE)
  ret
SetNetworkFrame endp

SetSerialFrame proc near

  call UndoAllHostTypes
  and
tbSerialConnection.ControlState,not(INVISIBLE)
  ret
SetSerialFrame endp

ShowAbout proc near

  mov bMessageBoxID,MB_ABOUT
  SM_FUNCTION SM_GET_ABOUT_DIALOG
  jge sa1
  call PaintError
sa1:
  mov bx,MBX_OK
  call PrepareMessageBox

  and tbMessageBox0.ControlState,not(INVISIBLE)
  call DrawMessageBox
  or tbMessageBox0.ControlState,INVISIBLE

  push word ptr boxbackcolor
  mov boxbackcolor,11

  mov si,offset abouticon
  mov cx,tbMessageBox.LeftPixel
  mov dx,tbMessageBox.TopPixel
  add dx,15
  add cx,22
  call drawicolor
  pop word ptr boxbackcolor
  ret
ShowAbout endp

ShowCallProgress proc near


  mov wCurrentCallProgress,ax
  cmp ax,4
  jnz setcp0
  mov bGetConnectionStatus,0
  mov bLeavePanOn,-1
  mov bRepaintNeeded,-1
  ret

setcp0:
  mov si,ax
  add si,si
  add si,offset pszProgressTable
  cmp si,offset pszProgressTable_End
  jb setcp1
  mov si,offset szInvalidProgress
  jmp setcp2
setcp1:
  mov si,[si]
setcp2:
  push ds
  pop es
  mov di,offset szCallProgressFld
  mov cx,PROGRESS_MAXLEN
  rep movsb
  call DoHideOSK

  mov si,offset rCallProgressHeader
  mov dx,seg rCallProgressHeader
  mov bMessageBoxId,MB_SHOWCALLPROGRESS

  mov bx,MBX_CANCEL
  call PrepareMessageBox
  call DrawMessageBox
  ret
ShowCallProgress endp

ShowPasswordIDBox proc near


  push si
  push bx
  mov bx,wCurrentHostList
  or bx,bx
  jnz spid0
  mov si,offset szBlank
  jmp spid2
spid1:
  xor ax,ax
  call GetListData
spid2:
  pop bx
  push si
  mov si,bx
  call pointcontroloption
  add bx,3+14
  mov di,bx
  push ds
  pop es
  pop si
  mov cx,20
  rep movsb
  xor al,al
  stosb
  call DoHideOSK
  mov selc,topplxel,2

  pop si
  or [si].ControlState,not(INVISIBLE)
  cmp bPasswordOnly,-1
  jnz spid3
  cmp wCurrentResource,8*256
  jnz spid3
  call repaint
  mov si,offset tbPassword
  call setInitialtab


  ret
spid3:
  mov bModeFlag,-1
  call repaintwork

  mov si,offset tbPassword
  call setInitialtab
  ret
ShowPasswordIDBox endp

TryUnload proc far
  public TryUnload

  push ax
  push bx
  mov bx,wCurrentResource
  SM_FUNCTION SM_REQUEST_UNLOAD
  cmp ax,1
  jz tu1

  mov bLocalState,0
  mov bLeavePanOn,0
tu1:
  pop bx
  pop ax
  ret
TryUnload endp

UndoAllHostTypes proc near

  or tbNetworkConnection.ControlState,INVISIBLE
  or tbSerialConnection.ControlState,INVISIBLE
  or tbModemConnection.ControlState,INVISIBLE
  ret
UndoAllHostTypes endp

UpdateDimensions proc near
  public updatedimensions


  cmp bSuppressDimensionUpdate,0
  jz ud00
  ret
ud00:
  cmp bNoDimensionUpdate,0
  jz ud0
  ret
ud0:
  push bx
  push cx
  push di
  push si

  mov bx,rRegion.wCurrentTop
  mov cx,rRegion.wCurrentLeft
  mov di,rRegion.wCurrentRight
  mov si,rRegion.wCurrentBottom
  call UpdateDimensionsWork
  pop si
  pop di
  pop cx
  pop bx
  ret
UpdateDimensions endp


UpdateDimensionsWork proc near
  public UpdateDimensionsWork


  cmp bSuppressDimensionUpdate,0
  jz udw0
  ret

udw0:
  cmp bx,0
  jge ud1a
  xor bx,bx
ud1a:
  cmp si,0
  jge ud1b
  xor si,si
ud1b:
  cmp di,0
  jge ud1c
  xor di,di
ud1c:
  cmp cx,0
  jge ud1
  mov cx,0
ud1:

  cmp bScreenMode,VGA_MODE
  jz ud4

  push bx
  push es
  xor bx,bx
  mov es,bx
  mov bx,0484h
  mov bl,es:[bx]
  inc bl
  xor bh,bh
  shl bx,1
  shl bx,1
  shl bx,1
  cmp si,bx
  jb ud4a
  dec bx
  mov si,bx
ud4a:
  pop es
  pop bx

ud4:
  cmp di,640
  jb ud2
  mov di,640-1
ud2:
  cmp si,480
  jb ud3
  mov si,480-1
ud3:
  call restoregstate

  mov ax,sm_update_dimensions
  SM_FUNCTION SM_UPDATE_DIMENSIONS

  call getrgstate
  ret
UpdateDimensionsWork endp


DrawAboutIcon proc far
  public DrawAboutIcon

  push si
  mov si,offset ColoredAboutIcon
  mov cx,rRegion.wCurrentLeft
  mov dx,rRegion.wCurrentTop
  add dx,1
  add dx,wDlbMCaption
  call drawicolor
  pop si
  ret
DrawAboutIcon endp

DoCustomTimerProcedures proc far
  public DoCustomTimerProcedures


  inc wAboutClickTimer
  inc bPollingTimer


  cmp byte ptr cs:bWeOwnInt09,0
  jnz dctp1
  cmp pOSKFirstRegion,-1
  jz dctp1
  push es
  push bx
  mov bx,040h
  mov es,bx
  mov bx,17h
  mov bl,es:[bx]
  and bl,(SCROLL_LOCK_DOWN or
NUM_LOCK_DOWN or CAPS_LOCK_DOWN)
  cmp bl,bLastKeyboardState
  jz dctp2
  mov bLastKeyboardState,bl
  mov bPopupRequired,-1
  mov bUpdateOSKLockKeys,-1
dctp2:
  pop bx
  pop es
dctp1:


  ret
DoCustomTimerProcedures endp

GetCustomPopUpRequest proc far
  public GetCustomPopupRequest



  cmp bAboutClickActive,0
  jz gcpur3
  cmp wAboutClickTimer,4
  jae gcpur1
gcpur3:
  and bPollingTimer,1111b
  jnz gcpur2

  call CheckUpdateHostList
  jc gcpur1
  cmp bGetConnectionStatus,0
  jnz gcpur1
  jmp gcpur2

gcpur1:
  stc
  ret
gcpur2:
  clc
  ret
GetCustomPopUpRequest endp

GetGraphicCaptionForScanCode proc near
  cmp bx,30h
  jnz gcsc1

  push pGraphicFont
  pop pCurrentFont
  mov si,spacebar_icon
  mov ah,0
  stosw
  dec di
  clc
  ret

gcsc1:
  push dx
  push ax
  push si
  push rRegion.pCurrentControl
  push pFirstControl
  mov pFirstControl,offset OSK
  call GoFirstControl

dksc4:
  cmp [si].ControlType,KEYBUTTON
  jb dksc6
  cmp [si].ControlType,CAPSLOCKBUTTON
  ja dksc6
  cmp [si].id,bx
  jnz dksc6

  mov dx,[si].wDataLength
  call PointControlCaption
  jcxz dksc5a

  mov ah,byte ptr [si].id
  call IsNumericKey
  jnz dksc5a
```

```
  mov pTabRegion,0
  mov si,pPopUpListRegion
  call SetNewTabItemWork
  mov pCheckRegion,0
  jmp hlpu1x

dlm2
  jmp hlpu1x

hlpu1x:
  ret
DoCustomListPopUp endp

CheckListDataAvailable proc far
  public CheckListDataAvailable

  cmp ax,GETSET_NETWORK_HOST_ENTRY
  jz gld_upd
  cmp ax,GETSET_NETWORK_GROUP_ENTRY
  jz gld_upd
  jmp gld00
gld_upd:
  test cmdNetworkUpdate.ControlState,DISABLED or
GRAYED
  jz gld00
  stc
  ret
gld00
  clc
  ret
CheckListDataAvailable endp

DoCustomControlPenDown proc far
  public DoCustomControlPenDown

  cmp al,KEYEDITBOX
  jnz dpd2x
  mov bResetHotKeyDataLength,-1
  mov wHotKeyRightPixel,0
dpd2x
  ret
DoCustomControlPenDown endp

DoHotKeyEdit proc far
  public DoHotKeyEdit
LEFT_SHIFT_SCANCODE equ 42
RIGHT_SHIFT_SCANCODE equ 54
LEFT_CONTROL_SCANCODE equ 29
RIGHT_CONTROL_SCANCODE equ 0E0h*256+29
LEFT_ALT_SCANCODE equ 56
RIGHT_ALT_SCANCODE equ 0E0h*256+56

  push ax
  mov bx,pTabRegion
  mov bx,[bx].pCurrentControl
  cmp bResetHotKeyDataLength,0
  jz [illegible]
  mov bResetHotKeyDataLength,0
  mov [bx].wDataLength,0
[illegible]
  mov ax,[si].ID

  cmp wHotKeyRightPixel,[illegible]
  jb dhke0
  jmp dhke00

dhke0:
  cmp bNumlockState,0
  jz dke0x
  test bKeyState,ALT_DOWN
  jz dke0x
  push ax
  call IsNumericKey
  pop ax
  jnz dke0x
  jmp dke0x
dke0x:
  mov bAltNumberCount,0

dke0x:
  mov bKeyWasShifted,0
  push bx
  push ax
  mov di,offset wHotKeyShiftKeyups
  mov cx,[bx].wDataLength
  mov si,[bx].pStorageOffset
  add si,ax
dhk11:
  jcxz dhk10
  dec si
  dec si
  mov ax,[si]
  test al,80h
  jz dhk2
  and al,not(80h)
  call IsShiftKey
  jz dhk0b
  mov bKeyWasShifted,-1

dhk2:
  inc si
  inc si
  jmp dhk10
dhk0b:
  mov bFirstWasAlt,0
  call IsAltKey
  jnz dhk0c
  mov bFirstWasAlt,-1
dhk0c:
  std
  movsw
  dec si
  dec si
  dec si
  dec si
  jmp dhk11
dhk10:
  pop ax

  call IsShiftKey
  jnz dhk12
dhk12:
  add [bx].wDataLength,4
  mov [di],ax
  or al,80h
  inc di
  inc di
  mov [di],ax
  inc si
  inc si
  call RestoreShiftKeyups
  jmp dhk0

dhk12:
  cmp bKeyWasShifted,-1
  jz dhk16
  cmp di,offset wHotKeyShiftKeyups
  jz dhk16
dhk16:
  push ax
  call RestoreShiftKeyups
  pop ax
  mov [si],ax
  inc si
  inc si
  or al,80h
  mov [si],ax
  add [bx].wDataLength,4
  jmp dhk0

dhk0:
  mov cx,[bx].wDataLength
  mov si,[bx].pStorageOffset
  push ds
  pop es

  mov ScanCodeHeader.iBuffLen,cx
  mov di,offset ScanCodeParser
  jcxz jbc
  rep movsw
jbc:
  pop bx
  mov si,bx
  push si

  call ParseScanCodeList
  pop si

  call RepaintCurrent
dhke00:
  pop ax
  ret
DoHotKeyEdit endp

ParseScanCodeList proc near

  mov ax,[bx].ID
  mov bl,ah
  xor bh,bh
  xor ah,ah
  mov dx,seg ScanCodeHeader
  mov si,offset ScanCodeHeader
  SM_FUNCTION ax
  ret
ParseScanCodeList endp

RepaintCurrent proc near

  push pPenDownActiveRegion
  push pTabRegion
  pop pPenDownActiveRegion
  call RepaintIndividualControl
  pop pPenDownActiveRegion
  ret
RepaintCurrent endp

IsShiftKey proc near
  call IsLeftOrRightShift
  jz ilsk1
  cmp ax,LEFT_CONTROL_SCANCODE
  jz ilsk1
  cmp ax,RIGHT_CONTROL_SCANCODE
  jz ilsk1
  call IsAltKey
ilsk1:
  ret
IsShiftKey endp

IsAltKey proc near

  cmp ax,LEFT_ALT_SCANCODE
  jz ilak1
  cmp ax,RIGHT_ALT_SCANCODE
ilak1:
  ret
IsAltKey endp

IsLeftOrRightShift proc near

  cmp ax,LEFT_SHIFT_SCANCODE
  jz ilsrt
  cmp ax,RIGHT_SHIFT_SCANCODE
ilsrt:
  ret
IsLeftOrRightShift endp

GetCustomEditBoxContents proc far
  public GetCustomEditBoxContents

  cmp al,KEYEDITBOX
  jnz gcebc1
  call GetHotKeys
  clc
  ret
gcebc1:
  stc
  ret
GetCustomEditBoxContents endp

GetHotKeys proc near

  push di
  push si
  push ax
  push bx
  push dx
  push cx
  mov di,[si].pStorageOffset
  mov cx,[si].ID
  mov bl,ah
  xor bh,bh
  mov ah,80h
  push ds
  push si
  SM_FUNCTION ax
  jge ghk2
  pop si
  pop ds
  jmp ghk1
ghk2
  push ds
  pop es

  mov bx,dx
  mov cx,word ptr [si].iBuffLen
  lds si,dword ptr [si].pBuffOff
  push cx
  jcxz ghk2a
  rep movsb
ghk2a:
  pop cx
  pop si
  pop ds
  mov [si].wDataLength,cx
ghk1:
  pop cx
  pop dx
  pop bx
  pop ax
  pop si
  pop di
  ret
GetHotKeys endp

RepaintCustomEditBoxContents proc far
  public RepaintCustomEditBoxContents

  cmp al,KEYEDITBOX
  jnz dcrsb1
  call DrawKeyCombo
  cmp bCursorActive,0
  jz [illegible]
  mov di,offset rCursorRegion
  call [illegible]
[illegible]:
  clc
  ret
dcrsb1:
  clc
  ret
RepaintCustomEditBoxContents endp

DrawKeyCombo proc near

  push bp
  mov bp,[si].wDataLength
  mov si,[si].pStorageOffset
  mov bHotKeyIsShifted,0
  mov bCapsLockState,0
  mov bNumLockState,0
dhk2:
  dec bp
  jl dhk1x
  dec bp
  jl dhk1x
  jmp dhk2a
dhk1x:
  jmp dhk1

dhk2a:
  lodsw
  test al,10000000b
  jz dhk2d
  and al,01111111b
  call IsLeftOrRightShift
  jnz dhk2
  mov bHotKeyIsShifted,0
  jmp dhk2
dhk2d:
  cmp al,45h
  jnz dhk2e
  not bNumlockState
dhk2e:
  cmp al,3Ah
  jnz dhk2f
  not bCapsLockState
dhk2f:
  call IsLeftOrRightShift
  jz dhk2b
  jmp dhk2c
dhk2b:
  mov bHotKeyIsShifted,-1
dhk2c:
  push bx
  mov bx,ax
  push ds
  pop es
  mov di,offset bHotKeyBuild
  call GetGraphicCaptionForScanCode
  pop bx

  jz dhk2
  push si
  mov si,offset bHotKeyBuild
  call getstringwidth
  push ax
  push cx
  push dx
  push bx
  add dx,4
  push bx
  push ax
  mov al,[si]
  mov bx,pCurrentFont
  cmp bx,pGraphicFont
  jnz dhk5
  push dx
  call GetBitmapHeight
  pop dx
  cmp ax,wNormFontHeight
  jae dhk5
  sub cx,wNormFontHeight
  neg cx
  shr cx,1
  add dx,cx
dhk5:
  pop ax
  pop bx

  push ax
  push bp
  call DrawString
  pop bp
  pop ax

  pop bx
  pop dx
  pop cx
  add cx,ax
```

```
add sp,4
pop si
pop di
mov wHotKeyRightPanel,ax
jmp dkk2
dkk1:
pop bp
ret
DrawKeyCombo endp

RestoreShiftKeycaps proc near

rsku1:
dec di
dec di
cmp di,offset wHotKeyShiftKeycaps
jb rsku2
mov ax,[di]
mov [di],ax
inc si
inc si
jmp rsku1
rsku2:
ret
RestoreShiftKeycaps endp

FreeScreen proc near
public FreeScreen

mov bx,-1
mov cx,bx
mov si,bx
mov di,bx
SM_FUNCTION SM_UPDATE_DIMENSIONS
ret
FreeScreen endp

SetArrowCursor proc near

push ax
push bx
push cx
push ds
push es
mov bHourGlassMode,0

mov bx,0
mov ax,0
push ds
pop es
mov dx,offset bArrowCursor
mov cx,0
int 33h
pop es
pop ds
pop cx
pop bx
pop ax
ret
SetArrowCursor endp

SetHourGlassCursor proc near

push ax
push bx
push cx
push ds
push es
mov bHourGlassMode,1
mov bx,0
mov cx,0
push ds
pop es
mov dx,offset bHourGlassCursor
mov ax,9
int 33h
pop es
pop ds
pop cx
pop bx
pop ax
ret
SetHourGlassCursor endp

SetHandCursor proc near
public SetHandCursor

push ax
push bx
push cx
push ds
push si
push di
push es

cmp dx,OSK.topyloc
jl shc1
```

```
push dx
sub dx,OSK.pixelheight
cmp dx,OSK.toppixel
pop dx
jge shc1
cmp cx,OSK.leftpixel
jl shc1
push cx
sub cx,OSK.pixelwidth
cmp cx,OSK.leftpixel
pop cx
jge shc1

test OSK.ControlState,INVISIBLE
jnz shc1

cmp bHandMode,1
mov bHandMode,1
je shc3
jmp shc2

shc1:
cmp bHandMode,0
je shc3
mov bHandMode,0
cmp bHourGlassMode,0
jnz shc4
call SetArrowCursor
jmp shc3
shc4:
call SetHourGlassCursor
jmp shc3
shc2:
mov bx,5
mov cx,0
push ds
pop es
mov dx,offset bHandCursor
mov ax,9
int 33h
shc3:
pop es
pop di
pop si
pop ds
pop cx
pop bx
pop ax
ret
SetHandCursor endp
end main

Copr. 1996 Zenith Data Systems Corp.

ILISTBOXENTRY struc
lpszEntry dd 0
cAttribute db 0
ends

IMSGBOXBUFF struc
pTextOff dw 0
pTextSeg dw 0
cAlignment db 0
ends
IBUFFHEADER struc
dBuffLen dw 0
dBuffLen dw 0
pB...'CK dd 0
ends

IHOSTLIST struc
lpsNodeAddress dd 0
lpszGroupName dd 0
lpszHostName dd 0
HostVersion dw 0
lpsSerial dd 0
lpsReserved dd 0
ends

ISCANCODES struc
ScanCode dw 0
ends

MB_LEFTJUSTIFIED equ 0
MB_CENTERED equ 1
MB_RIGHTJUSTIFIED equ 2

PENDRIVER_INTERRUPT equ 67h
SM_FUNCTION_INTERRUPT equ [illegible]

SM_GET_KEYBOARD_STATUS equ [illegible]
SM_SET_ACTIVE_STATUS equ [illegible]
```

```
SM_GET_INITIAL_SCREEN equ [illegible]
SM_GET_ABOUT_DIALOG equ [illegible]
SM_GET_NEXT_CREDITS_DIALOG equ [illegible]
SM_UPDATE_DIMENSIONS equ [illegible]
SM_REQUEST_UNLOAD equ [illegible]
SM_REPORT_BUTTON_CLICKED equ [illegible]
SM_CALIBRATE_UPPERLEFT equ [illegible]
SM_CALIBRATE_LOWERRIGHT equ [illegible]
SM_CANCEL_CALIBRATION equ [illegible]
SM_REBOOT_HOST equ [illegible]
SM_GET_KEYSTROKE equ [illegible]
SM_REQUEST_ACTIVE_FLASH_UPGRADE equ
12h
SM_PERFORM_FLASH_UPDATE equ 13h
SM_GET_CONNECTION_STATUS equ 22h
SM_GET_HOST_LIST_STATUS equ 21h
SM_UPDATE_HOST_LIST equ [illegible]
SM_GET_PASSWORD_STATUS equ [illegible]
SM_REQUEST_CONNECTION equ [illegible]
SM_REQUEST_DISCONNECTION equ [illegible]
SM_ABORT_REQUEST_CONNECTION equ [illegible]
SM_GET_MODEM_DEFAULTS equ [illegible]
SM_BLOCK_VIDEO_ACCESS equ [illegible]
SM_UNBLOCK_VIDEO_ACCESS equ [illegible]

SM_TEST_FUNCTION equ [illegible]

UI_REQUEST_CLOSURE equ [illegible]
UI_REQUEST_DISPLAY equ [illegible]
UI_SHOW_MESSAGE_BOX equ [illegible]
UI_HIDE_MESSAGE_BOX equ [illegible]
UI_CALIBRATION_COMPLETE equ [illegible]
UI_FLASH_UPDATE_PERCENTAGE equ 14h
UI_GET_SM_VERSION_NUMBER equ [illegible]
UI_UPDATE_CONNECTION_STATUS equ [illegible]
GET_HOST_LIST_STATUS equ [illegible]
UI_MOVE_OSK equ [illegible]

RES_NO_SCREEN EQU 0
RES_OSK_ALPHA EQU 1
RES_OSK_NUM EQU 2
RES_OSK_FULL EQU 3
RES_OSK_SM EQU 4
RES_OSK_SM_ALPHA EQU 5
RES_OSK_SM_NUM EQU 6
RES_OSK_SM_FULL EQU 7
RES_SETUPS_HOST EQU [illegible]
RES_SETUPS_HOTKEYS EQU [illegible]
RES_SETUPS_MAINTENANCE EQU [illegible]
RES_SETUPS_MODEM EQU [illegible]
RES_SETUPS_POWER EQU [illegible]
RES_SETUPS_SCREEN EQU [illegible]

GETSET_AUTOMATIC_SHUTOFF equ [illegible]
GETSET_BRIGHTNESS equ [illegible]
GETSET_CONTRAST equ [illegible]
GETSET_CUSTOM_AUTOANSWER_STRING equ
[illegible]
GETSET_CUSTOM_CONNECT_STRING equ [illegible]
GETSET_CUSTOM_DISCONNECT_STRING equ
[illegible]
GETSET_CUSTOM_INIT_STRING equ [illegible]
GETSET_HOST_CONNECTION_TYPE equ [illegible]
GETSET_MODEM_ANSWER_ON_RING equ
[illegible]
GETSET_MODEM_BAUD_RATE_ENTRY equ
[illegible]
GETSET_MODEM_HOST_DESC_ENTRY equ
[illegible]
GETSET_MODEM_HOST_PHONE_ENTRY equ
27h
GETSET_MODEM_MANUFACTURER_ENTRY equ
[illegible]
GETSET_MODEM_PREFIX equ [illegible]
GETSET_MODEM_RETRY_DELAY equ [illegible]
GETSET_MODEM_RETRY_LIMIT equ [illegible]
GETSET_MODEM_SUFFIX equ [illegible]
GETSET_MODEM_TONE_OR_PULSE equ [illegible]
GETSET_NETWORK_GROUP_ENTRY equ [illegible]
GETSET_NETWORK_HOST_ENTRY equ [illegible]
GETSET_PASSWORD equ [illegible]
GETSET_SLEEPMODE_PERIOD equ [illegible]
GETSET_SECURITY_ID equ [illegible]
GETSET_DOMAIN_ID equ [illegible]
GETSET_LOCK_HOST_KEYBOARD equ [illegible]
GETSET_DIM_HOST_SCREEN equ [illegible]
GETSET_USER_DEFINED_HOT_ICON equ [illegible]
GETSET_USER_ID equ [illegible]
GETSET_FRAME_TYPE_ENTRY equ [illegible]
GETSET_USER_INTERFACE_LANGUAGE equ
[illegible]
Copr. 1996 Zenith Data Systems Corp.
```

```
.model small
include ulinclud.inc
DATASEG_BEGIN
extrn ControlDataStorageArea:byte
extrn b7smColor:byte
extrn bLightColor:byte
extrn bOutLineColor:byte
extrn bScreenMode:byte
extrn bShadowColor:byte

upbuttontable label word
db 9
dw offset upbuttonulc
dw offset upbuttontop
dw offset upbuttonurc
dw offset upbuttonleft
dw offset upbuttonmiddle
dw offset upbuttonright
dw offset upbuttonllc
dw offset upbuttonbottom
dw offset upbuttonlrc
UPBUTTONULC label byte
db 1
db 3
DS [illegible]
DS [illegible]
DS [illegible]
UPBUTTONTOP label byte
db 1
db BUTTONTOPHEIGHT
DS [illegible]
DS [illegible]
DS [illegible]
UPBUTTONURC label byte
db 1
db 3
DS [illegible]
DS [illegible]
DS [illegible]
UPBUTTONLEFT label byte
db 1
db 1
DS [illegible]

UPBUTTONMIDDLE label byte
db 1
db 1
DS [illegible]
UPBUTTONRIGHT label byte
db 1
db 1
DS [illegible]

UPBUTTONLLC label byte
db 1
db 3
DS [illegible]
DS [illegible]
DS [illegible]
UPBUTTONBOTTOM label byte
db 1
db BUTTONBOTTOMHEIGHT
DS [illegible]
DS [illegible]
DS [illegible]
UPBUTTONLRC label byte
db 1
db 3
DS [illegible]
DS [illegible]
DS [illegible]
dnbuttontable label word
db 9
dw offset dnbuttonulc
dw offset dnbuttontop
dw offset dnbuttonurc
dw offset dnbuttonleft
dw offset dnbuttonmiddle
dw offset dnbuttonright
dw offset dnbuttonllc
dw offset dnbuttonbottom
dw offset dnbuttonlrc
DNBUTTONULC label byte
db 1
db 3
DS [illegible]
DS [illegible]
DS [illegible]

DNBUTTONTOP label byte
db 1
db BUTTONTOPHEIGHT
DS [illegible]
DS [illegible]
DS [illegible]
DNBUTTONURC label byte
```

```
db 1
db 3
DB [illegible]
DB [illegible]
DB [illegible]

DNBUTTONLEFT label byte
db 1
db 1
DB [illegible]

DNBUTTONMIDDLE label byte
db 1
db 1
DB [illegible]

DNBUTTONRIGHT label byte
db 1
db 1
DB [illegible]

DNBUTTONLLC label byte
db 1
db 3
DB [illegible]
DB [illegible]
DB [illegible]
DNBUTTONBOTTOM label byte
db 1
db BUTTONBOTTOMHEIGHT
DB [illegible]
DB [illegible]
DB [illegible]
DNBUTTONLRC label byte
db 1
db 3
DB [illegible]
DB [illegible]
DB [illegible]
```

[illegible]

```
CHECKEDBOX label byte
  public CheckedBox
; CHECKMARK_CHECKBOXES eq 6
```

[illegible]

```
DB
[illegible]

endif
UNCHECKEDBOX label byte
 public UnCheckedBox

db 2
db 16
[illegible]
if DIAMOND_OPTBUTTONS eq 0
unseloptbutton label byte
 public UnSelOptButton
db 2
db 15
[illegible]
seloptbutton label byte
 public SelOptButton
db 2
db 15
[illegible]

[illegible]
else
unseloptbutton label byte
 public UnSelOptButton

db 2
db 15
[illegible]
seloptbutton label byte
 public SelOptButton

db 2
db 15
[illegible]

endif
bSpectrumPattern label byte
 public bSpectrumPattern
db 21*2

db 2
[illegible]
bTallNotchPattern label byte
 public bTallNotchPattern
db 1
db 8
[illegible]
bShortNotchPattern label byte
 public bShortNotchPattern
db 1
db 6
[illegible]

rectanglepointers label word
[illegible]
DATASEG_END
.code
extrn CheckIfCovered:near
extrn FillScreenArea:near
extrn NewRowForCheckIfCovered:near
extrn PointScreenDest:near

DrawColor proc near
 public DrawColor
 cmp bScreenMode,VGA_MODE
 jz d4c0
 ret
d4c0:
 push word ptr bLightColor
 push word ptr bFormColor
 push word ptr bShadowColor
 push word ptr bOutlineColor
 cmp byte ptr [si],-1
 jne d4c10
 lodsb
 lodsb
 mov bLightColor,al
 lodsb
 mov bFormColor,al
 lodsb
 mov bShadowColor,al
 lodsb
 mov bOutlineColor,al

d4c10:
 call pointscreendest
 lodsw

 mov bx,ax
 xor ah,ah
 mov bp,80
 sub bp,ax

 vgaloadlatches
d4c:
if need_ock eq 0
 call checkifcovered
 jne d4c1

 lodsb
 lodsb
 lodsb
 lodsb
 jmp d4d
endif
d4c1:
 mov al,es:[di]
 lodsb
 or al,al
 jz d4a
 vgawritecolor bLightColor
d4a:
 mov al,es:[di]
 lodsb
 or al,al
 jz d4b
 vgawritecolor bFormColor
d4b:
 mov al,es:[di]
 lodsb
 or al,al
 jz d4c
 vgawritecolor bShadowColor
d4c:
 mov al,es:[di]
 lodsb
 or al,al
 jz d4d
 vgawritecolor bOutlineColor
d4d:
 inc di
 dec bl
 jnz d4c
 add di,bp
 dec bh
 jz d4f
 mov ax,80
 sub ax,bp
 mov bl,al
if need_ock eq 0
 call NewRowForCheckIfCovered
endif
 jmp d4c
d4f:
 pop word ptr bOutlineColor
 pop word ptr bShadowColor
 pop word ptr bFormColor
 pop word ptr bLightColor
 ret
drawcolor endp

DrawRectangle proc near
 mov buttoncolumn,cx
 mov buttonrow,dx
 mov buttonheight,bh
 mov buttonlength,bl
 push ds
 pop es
 mov di,offset rectanglepointers
 mov cx,offset recend - offset rectanglepointers
 rep movsb
 mov al,recmiddle
 or al,al
```

```
jz drnomid
lodsb
lodsb

mov bl,11111111b
mov bh,bLightColor
lodsb
cmp al,bl
je drs1
mov bh,bFormColor
lodsb
cmp al,bl
je drs1
mov bh,bShadowColor
lodsb
cmp al,bl
je drs1
mov bh,bOutlineColor
lodsb
cmp al,bl
jnz drnomid
drs1:
mov recmiddle,0
mov si,recleft
mov bl,[si]
xor ah,ah
sal ax,1
sal ax,1
sal ax,1

add ax,buttoncolumn
mov cx,ax
mov dx,buttonrow
mov si,rectop
mov al,[si+1]
xor ah,ah
add dx,ax
mov al,buttonlength
xor ah,ah
mov al,ax
mov al,buttonheight
xor ah,ah
add ax,ax
jz drnomid


call Mouseonerase
drnomid:
cmp bScreenMode,VGA_MODE
jz ured
ret
drs0
mov dx,buttonrow
cmp buttonheight,0
jnz drs1
test recflags,1
jz drs1
mov cx,buttoncolumn
sub cx,8
jmp drs3
drs1
mov cx,buttoncolumn
mov si,recult
call drawlcolor
drs2:
mov cx,buttoncolumn
drs3:
mov bl,buttonlength
or bl,bl
jz drb1a
drb1
add cx,8
push bx
push cx
mov dx,buttonrow
mov si,rectop
call drawlcolor
pop cx
pop bx
dec bl
jnz drb1
drb1a:
add cx,8
cmp buttonheight,0
jnz drs4
test recflags,1
jz drs4
jmp drb00
drs4.
mov dx,buttonrow
mov si,recult
call drawlcolor
mov dx,buttonrow
add dx,3
mov bh,buttonheight
or bh,bh
jz drb4
push cx   -

call rectanglebody
pop bx
call rectanglebody
drb4:
mov cx,buttoncolumn
push cx
push dx
mov si,recllc
call drawlcolor
pop dx
pop cx
add cx,8
mov bl,buttonlength
or bl,bl
jz drb5a
drb5:
push bx
push cx
push dx
mov si,recbottom
call drawlcolor
pop dx
pop cx
pop bx
add cx,8
dec bl
jnz drb5
drb5a
mov si,recirc
call drawlcolor
drb00
ret
drawrectangle endp


rectanglebody proc near
drb3:
push bx
push dx
mov cx,buttoncolumn
push cx
mov si,recleft
call drawlcolor
pop cx
pop dx
pop bx
add cx,8
mov bl,buttonlength
or bl,bl
jz drb2a
drb2:
cmp recmiddle,0
jnz drb2b
mov al,buttonlength
xor ah,ah
sal ax,1
sal ax,1
sal ax,1
add cx,ax
jmp drb2a
drb2b
push bx
push cx
push dx
mov si,recmiddle
call drawlcolor
pop dx
pop cx
pop bx
add cx,8
dec bl
jnz drb2
drb2a
push bx
push dx
mov si,recright
call drawlcolor
pop dx
pop bx
inc dx
dec bh
jz drb4q
jmp drb3
drb4q:
ret

rectanglebody endp

DrawUpButton proc near
public DrawUpButton
public drawupbutton
push si
mov si,offset upbuttontable
call drawrectangle
pop si
ret
drawupbutton endp

DrawOnButton proc near
public DrawOnButton
public drawinbutton
push si
mov si,offset inbuttontable
call drawrectangle
pop si
ret
drawinbutton endp

DrawChiselBox proc near
public DrawChiselBox
public drawchiselbox
mov si,offset chiselboxtable
call drawrectangle
ret
drawchiselbox endp


DrawTextLine proc near
public DrawTextLine
push bx
call PaintScreenBest
pop bx
dtl2:
if need_csk ne 0
call CheckIfCovered
je dtl1
endif
mov ax,180+256*7
mov word ptr es:[di],ax
dtl1:
inc di
inc di
dec bl
jnz dtl2

ret
DrawTextLine endp

DrawTextForm proc near
public DrawTextForm
mov ax,223+15*256
push bx
call DrawTextHorizontalBar
pop bx
mov al,bh
xor ah,ah
add ax,ax
DIVIDE_BY_8 ax
mov bh,al
dec bh
dtf2:
add dx,8
cmp bh,0
je dtft
push bx
mov ax," "+15*256
call DrawTextHorizontalBar
pop bx
dec bh
jmp dtf2
dtft:
mov ax,220+15*256
call DrawTextHorizontalBar
ret
DrawTextForm endp

DrawTextHorizontalBar proc near
push ax
push dx
push cx
push bx
call PaintScreenBest
pop bx
pop cx
pop dx
pop ax

if need_csk ne 0
call CheckIfCovered
je dth1
endif
push ax
mov al,222
mov es:[di],ax
pop ax
dth1:
inc di
inc di

push bx
dth2:
if need_csk ne 0
call CheckIfCovered
je dth2
endif
mov es:[di],ax
dth3:
inc di
inc di
dec bl
jnz dth3
if need_csk ne 0
call CheckIfCovered
je dth4

endif
mov al,221
mov es:[di],ax
dth4:
pop bx
ret
DrawTextHorizontalBar endp

DrawButtonFrame proc near
public DrawButtonFrame
public drawbuttonframe
mov si,offset buttonframetable
call drawrectangle
ret
drawbuttonframe endp

DrawTextBox proc near
public DrawTextBox
public drawtextbox
push si
mov si,offset textboxtable
call drawrectangle
pop si
ret
drawtextbox endp


DrawSliderBox proc near
public DrawSliderBox
mov slideboxmiddle,offset textboxmiddle
push si
mov si,offset sliderboxtable
call drawrectangle
pop si
ret
DrawSliderBox endp

DrawSpectrumBox proc near
public DrawSpectrumBox
mov slideboxmiddle,offset somiddle
push si
mov si,offset sliderboxtable
call drawrectangle
pop si
ret
DrawSpectrumBox endp

DrawLinebox proc near
public DrawLinebox
public drawlinebox
mov si,offset lineboxtable
call drawrectangle
ret
drawlinebox endp
end
```

Copr. 1995 Zenith Data Systems Corp.

```
.model small
.code
extrn BlockVideo:near
extrn CancelOSKPenDown:near
extrn CheckHotKeyEdit:near
extrn CheckPenDownCoordinates:near
extrn DisinstallOSKFar
extrn DoCloseOSK:near
extrn DoHideOSK:near
extrn DoListSlide:near
extrn DoMessageBoxClick:near
extrn DoSlideBarPenDown:near
extrn DoSpinDown:near
extrn DoSpinUp:near
extrn DoVSBDnArrow:near
extrn DoVSBDnArrow:near
extrn DoVSBUpArrow:near
extrn DrawSolidKeyBox:near
extrn FindRegionForControl:near
extrn GetTabControlType:near
extrn GetTypeAndState:near
extrn GetNextControl:near
extrn GetNextControl:near
extrn GoPreviousControl:near
extrn GoPreviousControl:near
extrn HandleDelayedSet:near
extrn HandleOSKAlreadyDown:near
extrn HandleOSKKeyPenDown:near
extrn HandleOSKKeyPenUp:near
extrn HideForm:near
```

```
extrn HidePen:near
extrn IgnorePen:near
extrn IsItButton:near
extrn IsItCheckBox:near
extrn IsItEditBox:near
extrn IsItListBox:near
extrn IsItSlideBar:near
extrn ListItemClick:near
extrn ListItemClick:near
extrn ListItemClick:near
extrn Repaint:near
extrn RepaintIndividualControl:near
extrn RepaintUnderOSK:near
extrn RestorePenRegion:near
extrn RestoreRegion:near
extrn ResumeCursor:near
extrn ResumePen:near
extrn SaveFormHeight:near
extrn SearchActiveRegions:near
extrn SetNewTabItemWork:near
extrn SetPenColumnRegion:near
extrn SetPenRowRegion:near
extrn SetHandCursor:near


extrn SetTypeMode:near
extrn ShowOSK:near
extrn ShowOSKForClick:near
extrn ShowPen:near
extrn ShowTabBox:near
extrn UnlockVideo:near
extrn UndoCurrentTabItem:near
extrn UnprotectOSK:near
extrn UpdateDimensions:near
extrn UpdateDimensionsWork:near



include ulincled.inc



DATASEG_BEGIN
extrn bEnlargeFlag:byte


extrn ControlDataStorageArea:byte
extrn OSK:Control
extrn VSBBacking:Control
extrn VSBDnArrow:Control
extrn VSBSlider:Control
extrn VSBUpArrow:Control
extrn bAutoScrollMode:byte
extrn bAutoScrollMode:byte
extrn bAutoScrollMode:byte
extrn bDontShowOSK:byte
extrn bDrawStringPWFlag:byte
extrn bGetDataFromLocalStorage:byte
extrn bIgnoringMove:byte
extrn bIgnoringPen:byte
extrn bLeavePenOn:byte
extrn bMoveMode:byte
extrn bMoveMode:byte
extrn bPenEventHappened:byte
extrn bPenEventType:byte
extrn bPopUpRequired:byte
extrn bRepaintNeeded:byte
extrn bScreenMode:byte
extrn bShadowColor:byte
extrn bSuppressHideShow:byte
extrn bTypematicState:byte
extrn fmMessageBox:CONTROL
extrn fmMessageBox_end:CONTROL
extrn pClickRegion:word
extrn pCurrentToolBarButton:word
extrn pDelayedSetControl:word
extrn pNextActiveRegion:word
extrn pOSKFirstRegion:word
extrn pPenDownActiveRegion:word
extrn pPenDownLegendRegion:word
extrn pPenDownListItem:word
extrn pPenDownListItem:word
extrn pPenDownListItem:word
extrn pPenDownListRegion:word
extrn pPenDownListRegion:word
extrn pPenDownListRegion:word
extrn pPenUpListRegion:word
extrn pPenUpListRegion:word
extrn pPenUpListRegion:word
extrn pTabRegion:word
extrn rActiveRegions:Region
extrn rCursorRegion:REGION
extrn rMoveStartRegion:Region
extrn rMoveStartRegion:Region
extrn rREGION:REGION
extrn vsbBacking:Control
extrn vsbSlider:Control
extrn vsbUparrow:Control
extrn wAutoScrollTimer:word
extrn wAutoScrollTimer:word
extrn wCurrentResource:word
extrn wHotKeyRightPixel:word
extrn wListSlideRow:word
extrn wListSlideRow:word
extrn wListSlideRow:word
extrn wMoveModePenColumn:word
extrn wMoveModePenRow:word
extrn wOSKTitleBarBottomRow:word
extrn wPenCurrentColumn:word
extrn wPenCurrentRow:word
extrn wPenDownColumn:word
extrn wPenDownRow:word
extrn wPenUpColumn:word
extrn wPenUpRow:word


wHotKeyRightPixelSave dw 0


wPenColumnMin dw 0
wPenColumnMax dw 0
wPenRowMin dw 0
wPenRowMax dw 0

bAwaitingMoveCompletion db 0
  public bAwaitingMoveCompletion
bMoveModeBusy db 0
bBarShowing db 0
rBarRegion label tRegion

DATASEG_END

.code
DoToolBarButtonDown  proc near
  call HandleDelayedSet
  mov si,pCurrentToolBarButton
  and [si].ControlState,not(BDOWN)
  call SaveFormHeight
  mov pPenDownActiveRegion,0
  mov bRepaintNeeded, PAINTALL AND (NOT
PAINTTOOLBARS)
  mov bPopupRequired,-1
  ret
DoToolBarButtonDown  endp


CancelPenDown proc near
  public CancelPenDown

  mov si,pPenDownActiveRegion
  or si,si
  jz cpd1
  mov wPenUpRow,-1
  mov wPenUpColumn,-1
  call dopenuparound
cpd1:
  ret
CancelPenDown endp


DoButtonPenDown proc near

  cmp si,offset vsbBacking
  je dpe7c
  cmp si,offset vsbSlider
  je dpe7c
  or ah,BDOWN
  mov [si].ControlState,ah
  call RepaintIndividualControl
dpe7c:

  cmp si,offset vsbUpArrow
  jne dpe7d
  call UndoCurrentTabItem
  mov pTabRegion,0
  call SetTypeMode
  mov di,pPenDownActiveRegion
  call DoVSBUpArrow
  jmp dpe7x
dpe7d:

  cmp si,offset vsbDnArrow
  jnz dpe7e
  call UndoCurrentTabItem
  mov pTabRegion,0
  call SetTypeMode
  mov di,pPenDownActiveRegion
  call DoVSBDnArrow
  jmp dpe7x
dpe7e:

  cmp al,SPINUPBUTTON
  jnz dpe7a
  call SetTypeMode
  call DoSpinUp
  jmp dpe7x
dpe7a:
  cmp al,SPINDOWNBUTTON
  jnz dpe7b
  call SetTypeMode
  call DoSpinDown
  jmp dpe7x
dpe7b:

if need_osk ne 0
  call HandleOSKKeyPenDown
endif
dpe7x:
  ret
DoButtonPenDown endp


DoClickEvent proc near
  public DoClickEvent

  mov si,pClickRegion
  call PrepareClickRegisters

  call IsItEditBox
  jnz dce3
  push ax
  call ShowTabBox
  pop ax
if need_osk ne 0

  call ShowOSKForClick
endif
  ret
dce3:


  call IsItButton
  jnz dce4
  push si
  push di
  call ShowTabBox
  pop di
  pop si
  cmp si,offset fmMessageBox
  jb dce1a
  cmp si,offset fmMessageBox_end
  jb dce1a

  call DoMessageBoxClick
  ret

dce1a:
  cmp si,offset vsbBacking
  jz DoVsbBacking
  cmp si,offset vsbSlider
  jnz dce1b

DoVsbSlider:
  sub di,type rRegion * 3
DoVsbBacking:
  push wPenUpRow
  pop wListSlideRow
  call DoListSlide
  ret

dce1b:
  call HandleButtonClicks
  ret
dce4:

  call IsItCheckbox
  jnz dce2
dce4b:
  cmp al,OPTIONBUTTON
  jnz dce4f
  call UndoAllOptionButtons
dce4f:
  mov bx,[si].pStorageOffset
  not byte ptr [bx]
  and byte ptr [bx],1

  push ax
  cmp al,CHECKBOX
  je dce4h
  mov ax,[si].ID
  mov bl,ah
  xor bh,bh
  jmp dce4i
dce4h:

  mov ax,[si].ID
  mov bl,[bx]

dce4i:
  xor bh,bh
  SM_FUNCTION ax
  pop ax

  call RepaintIndividualControl
  call ShowTabBox
  call HandleButtonClicks
  ret

dce2:
  call IsItListBox
  jnz dce5
  call ListItemClick
  jnz dce2a
if need_osk ne 0
  call DoHideOSK
endif
  call HandleButtonClicks
dce2a:
  ret
dce5:

  ret
DoClickEvent endp


DoMoveQuit proc near

if need_osk ne 0
  test wCurrentResource,11111000b
  jnz lx0
  mov bAwaitingMoveCompletion,-1
lx0:
  mov bLeavePenOn,0
  call IgnorePen

  mov dx,wPenUpRow
  cmp dx,wPenRowMin
  jb lx1
  mov dx,wPenRowMin
  mov wPenUpRow,dx
lx1:
  cmp dx,wPenRowMax
  jb lx2
  mov dx,wPenRowMax
  mov wPenUpRow,dx
lx2:
  mov cx,wPenUpColumn
  cmp cx,wPenColumnMin
  jb cx1
  mov cx,wPenColumnMin
  mov wPenUpColumn,cx
cx1:
  cmp cx,wPenColumnMax
  jb cx2
  mov cx,wPenColumnMax
  mov wPenUpColumn,cx
cx2:
  call ShowMovedFormDestination

  call HideBox
  mov si,pPenDownActiveRegion

  test wCurrentResource,not(111b)
  jnz osdf1

  cmp [si].wCurrentLeft,0
  jge odf
  mov [si].wCurrentLeft,0
odf:

  cmp bScreenMode,12h
  jnz osqq1
  mov ax,[si].wCurrentTop
  round_to_byte_boundary ax
  add ax,[si].wCurrentHeight
  dec ax
  dec ax
  mov [si].wCurrentBottom,ax

  mov ax,[si].wCurrentLeft
  round_to_byte_boundary ax
  add ax,[si].wCurrentWidth
  dec ax
  mov [si].wCurrentRight,ax

osqq1:

  call peaseOSKDimensions
  mov di,offset rMoveStartRegion
  call HideForm
  jmp dpe3


osdf1:
  mov di,offset rMoveStartRegion
  call HideForm
  call RepaintUnderOSK
  mov si,pPenDownActiveRegion

  mov ax,[di].wCurrentTop
  sub ax,[si].wCurrentTop
  sub [bx].TopPixel,ax
  mov ax,[di].wCurrentLeft
  sub ax,[si].wCurrentLeft
  ROUND_TO_BYTE_BOUNDARY ax
```

```
 mov cx,[bx].LeftPixel
 test ch,100b
 jz hpo1
 or ch,11111000b
hpo1:
 sub cx,ax

 cmp cx,0
 jge fos1
 mov cx,0
fos1:

 ROUND_TO_BYTE_BOUNDARY cx
 mov [bx].LeftPixel,cx

 cmp bx,offset osk
 jnz dpo3
 or [bx].ControlState,INVISIBLE


 call ShowOSK
 mov bLeavePenOn,-1


 push wHotKeyRightPixelSave
 pop wHotKeyRightPixel

 mov si,pTabRegion
 push rCursorRegion.wCurrentLeft
 pop wPenDownColumn
 call SetNewTabItemWork

dpo3.
 mov pPenDownActiveRegion,0
 mov bMoveMode,0
 call RestorePenRegion
 call ResumePen
endif
 mov cx,wPenCurrentColumn
 mov dx,wPenCurrentRow
 call SetHandCursor

 ret
DoMoveQuit endp

PassOSKDimensions proc near
 public passOSKDimensions

 mov bx,[si].wCurrentTop
 ROUND_TO_BYTE_BOUNDARY bx
 mov cx,[si].wCurrentLeft
 ROUND_TO_BYTE_BOUNDARY cx
 mov di,[si].wCurrentRight
 mov si,[si].wCurrentBottom
      cmp bScreenMode,12h
      jnz pod1
      test wCurrentResource,4
      jnz pod1
      inc si
pod1:
 call UpdateDimensionsWork
 ret
PassOSKDimensions endp

DoPenDownEvent proc near

 call CancelPendown

if need_osk ne 0

 mov bDontShowOSK,0

endif

 call CheckPenDownCoordinates
 or si,si
 jnz dpe5a
 jmp dpdExit
dpe5a:

 cmp [si].wCurrentHeight,-1
 jnz dpe1a
 cmp [si].wListHandle,0
 jz dpe1b

dpe21:
 mov pPenDownListRegion,si
 cmp [si].wListItemIndex,0
 jnz dpe21a
 jmp dpdIgnore
dpe21a:
 mov pClickRegion,si
 mov pPenDownListItem,si
 jmp dpdExit

dpe1b.
 mov pPenDownLegendRegion,si
 sub si,type rActiveRegions
 mov pPenDownActiveRegion,si

dpe1a:
 call GetTypeAndState

 cmp al,FORM
 jz dpe1s
 test ah,MOVEABLE
 jnz dpe5e1
 jmp dpdIgnore
dpe5e1:

 push ax
 mov ax,[si].TopPixel
 add ax,10
 cmp dx,ax
 pop ax
 jbe dpe5e2
 cmp dx,wOSKTitleBarBottomRow
 jbe dpe5e2
 jmp dpdIgnore
dpe5e2:
 call PrepareToMoveForm
 jmp dpdExit

dpe1s:
 call IsButton
 jnz dpe0
 test ah,GRAYED
 jz dpe1g
 jmp dpdIgnore
dpe1g:
 mov bDrawStatePWFlag,0
 test ah,ISDOWN
 jz dpe5e1

dpe5a
if need_osk ne 0
 push ax
 call HandleOSKAlreadyDown
 pop ax
 jnz dpe5a2
 jmp dpdexit
endif
dpe5a2:
 jz dpdIgnore

dpe5e1:
 mov bx,pPenDownActiveRegion
 cmp bx,pTabRegion
 jnz dpe1f
dpe1d.
 mov pTabRegion,0
dpe1f:
 push si
 push ax
 call DoButtonPenDown
 pop ax
 pop si

 cmp al,TOOLBARBUTTON
 jnz doo1
 cmp si,pCurrentToolBarButton
 jz doo1
 call ForceDelayedSet
 call DoToolBarButtonClick
 call DoToolBarButtonDown
doo1:
 jmp dpdExit
dpe0.

 call IsItSlideBar
 jnz dpd2
 mov ax,wPenDownColumn
 call DoSlideBarPenDown
 jmp dpdExit
dpd2:

 call IsItCheckBox
 jnz dpd3
 call DoButtonPenDown
 jmp dpdExit

dpd3:
 call DoCustomControlPenDown
 jmp dpdExit

dpdIgnore:
 mov pPenDownActiveRegion,0
dpdExit:
 ret
DoPenDownEvent endp

ForceDelayedSet proc near

 push pTabRegion
 mov pTabRegion,0
 call HandleDelayedSet
 pop pTabRegion
 ret
ForceDelayedSet endp

DoPenEvent proc near
 public DoPenEvent
dpe1:
 xor al,al
 xchg al,bPenEventType
 mov bPenEventHappened,0

 cmp bIgnoringPen,0
 jz dpe0
 jmp dpe00
dpe0:

 test al,PENUP
 jz dpe2
 call DoPenUpEvent
 jmp dpe4

dpe2:
 test al,PENDOWN
 jz dpe3
 cmp bMoveMode,0
 jz dpe3a
 and al,not(PENDOWN)
 jmp dpe3
dpe3a:
 call DoPenDownEvent
 jmp dpe4

dpe3:
 test al,PENMOVED
 jz dpe4
 cmp bIgnoringMove,0
 jnz dpe00
dpe3y:
 cmp bMoveModeBusy,0
 jnz dpenomb
 mov bMoveModeBusy,-1

 call DoPenMoveEvent

 mov bMoveModeBusy,0
 and bPenEventType,not PENMOVED
dpenomb:

 jmp dpe4

dpe4:
 cmp bPenEventHappened,0
 jz dpe00
 jmp dpe1

dpe00:
 ret
DoPenEvent endp

DoPenMoveEvent proc near

 mov dx,wPenCurrentRow
 mov cx,wPenCurrentColumn

 cmp bMoveMode,-1
 jnz dpe25

 call ShowMovedFormDestination
 jmp dpmExit

dpe25:
 cmp pPenDownListRegion,0
 jz dpe30
 mov bAutoScrollMode,0
 call SearchActiveRegions
 mov si,pPenDownListRegion
 cmp di,si
 jnz dpe25a
 jmp dpmExit
dpe25a:
 or di,di
 jz dpe22
 mov ax,[si].wListHandle
 cmp ax,[di].wListHandle
 jnz dpe22
 mov si,di
 mov pPenDownActiveRegion,si
 mov pPenDownLegendRegion,0
 jmp dpe31

dpe22.
 mov si,pPenDownListRegion
 cmp dx,[si].wCurrentTop
 jb dpe23
 cmp dx,[si].wCurrentBottom
 ja dpe24
 jmp dpmExit

dpe23:
 mov wAutoScrollTimer,0
 mov bAutoScrollMode,-1
 jmp dpmExit

dpe24:
 mov wAutoScrollTimer,0
 mov bAutoScrollMode,1
 jmp dpmExit

dpe30:
 mov si,pPenDownActiveRegion
 or si,si
 jz dpmExit
 call GetTypeAndState

 call IsItSlideBar
 jnz dpe26
 call DoSlideBarPenDown
 jmp dpdExit
dpe26:

 cmp si,offset vabSlider
 jnz dpe27
 mov wListSlideRow,dx
 call UndoCurrentTabItem
 mov di,pPenDownActiveRegion
 mov pTabRegion,di
 sub di,type rRegion * 3
 call DoListSlide
 jmp dpmExit
dpe27:
dpmExit:

 ret
DoPenMoveEvent endp


DoPenUpEvent proc near
 public DoPenUpEvent

 mov bTypematicState,0
 push pPenDownListItem
 pop pPenUpListRegion
 mov pPenDownListRegion,0
 mov pPenDownListItem,0
 mov bAutoScrollMode,0

if need_osk ne 0
 cmp bMoveMode,-1
 jnz dpu1
 call DoMoveQuit
 call unblockvideo

 jmp dpuExit
dpu1:
endif

 mov si,pPenDownActiveRegion
 or si,si
 jnz dpu1c
 jmp dpuExit
dpu1c:

 mov di,si
 mov si,[si].pCurrentControl
 mov ax,[si]

 cmp al,CLOSEBUTTON
 jnz dpu4
 push pTabRegion
 mov pTabRegion,0
 call HandleDelayedSet
 pop pTabRegion
if need_osk ne 0
 cmp di,pOSKFirstRegion
 jb dpu4a
 call DoCloseOSK
 jmp dpuExit
dpu4a:
endif

 call TryUnload
 call UndoButtonDown
 jmp dpuExit
dpu4:


if need_osk ne 0
 call HandleOSKKeyPenUp
 jz dpuExit
endif

 cmp al,offset vabBacking
 jz dpu19
 cmp al,offset vabSlider
 jz dpu19
 cmp al,TOOLBARBUTTON
 jz dpu19
 call UndoButtonDown
```

```
dpe14


 mov dx,wPenUpRow
 mov cx,wPenUpColumn
 mov si,pPenDownLegendRegion
 or si,si
 jz dpe11
 cmp dx,[si].wCurrentTop
 jb dpe11
 cmp dx,[si].wCurrentBottom
 ja dpe11
 cmp cx,[si].wCurrentLeft
 jb dpe11
 cmp cx,[si].wCurrentRight
 ja dpe11
 jmp dpe12

dpe11:
 mov si,pPenDownActiveRegion
 cmp dx,[si].wCurrentTop
 jb dpe8
 cmp dx,[si].wCurrentBottom
 ja dpe8
 cmp cx,[si].wCurrentLeft
 jb dpe8
 cmp cx,[si].wCurrentRight
 ja dpe8

dpe12
 push pPenDownActiveRegion
 pop pClickRegion
 jmp dpeExit

dpe8
 cmp al,TOOLBARBUTTON
 jnz dpe8a
 mov si,pPenDownActiveRegion
 mov si,[si].pCurrentControl
 cmp si,pCurrentToolBarButton
 jz dpe8a
 call UndoButtonDown
dpe8a

dpeExit:
 mov pPenDownActiveRegion,0
 ret
DoPenUpEvent endp


DoSpacebar proc near
 public DoSpaceBar

 call GetTabControlType
 jnz dsb0a
 ret
dsb0a

 call IsItButton
 jnz dsb1

 cmp al,TOOLBARBUTTON
 jnz dsb0d
 test ah,ISDOWN
 jz dsb0c
 ret
dsb0c

 test ah,SKIPTAB
 jz dsb0b
 ret
dsb0b.

if need_osk ne 0
 call CancelOSKPenDown
endif

 or [si].ControlState,ISDOWN
 cmp [si].ControlType,ToolbarButton
 jz dsb0

 mov pPenDownActiveRegion,al
 push si
 call RepaintIndividualControl
 pop si
 mov pPenDownActiveRegion,0
 jmp dsb0d
dsb0:
 call DoToolBarButtonDown
 ret
dsb0d
 mov pClickRegion,si
 ret

dsb1:
 call IsItCheckBox
 jnz dsb2
if need_osk ne 0
 call CancelOSKPenDown
endif
 mov pClickRegion,si
 ret
dsb2
 ret
DoSpacebar endp


PrepareClickRegisters proc near
 public PrepareClickRegisters
 mov pPenDownActiveRegion,si
 mov di,si
 mov si,[si].pCurrentControl
 mov ax,[si]
 ret
PrepareClickRegisters endp

PrepareToMoveForm proc near

 push wHotKeyRightPixel
 pop wHotKeyRightPixelSave
if need_osk ne 0
ptm1:
 mov bMoveMode,-1
 mov bLeavePenOn,0
 call UndoCurrentTabItem
 push si
 mov si,pPenDownActiveRegion
 push si
 push ds
 pop es
 mov di,offset rMoveStartRegion
 mov cx,type rMoveStartRegion
 rep movsb
 pop si
 mov dx,wPenDownRow
 sub dx,[si].wCurrentTop
 mov wMoveModePenRow,dx

 mov cx,wPenDownColumn
 sub cx,[si].wCurrentLeft
 mov wMoveModePenColumn,cx
 push si
 call UnprotectOSK
 call blockvideo
 pop si
 call ShowBox
 mov cx,0
 add cx,wPenDownColumn
 sub cx,[si].wCurrentLeft

 mov dx,638-16
 mov wPenColumnMax,dx
 mov wPenColumnMin,cx
 cmp wPenDownColumn,dx
 jbe ooor
 call SetPenColumnRegion
ooor:
 mov cx,wMoveModePenRow
 call getmaxvalidscreenrow
 mov wPenRowMin,cx
 mov wPenRowMax,dx
 cmp wPenDownRow,dx
 jbe ptmr1
 call SetPenRowRegion
ptmr1:
 pop si
endif
 ret
PrepareToMoveForm endp


GetMaxValidScreenRow proc near
 public GetMaxValidScreenRow


 mov dx,479-16
 cmp bScreenMode,VGA_MODE
 jz pmrf1z

 push bx
 push es
 xor bx,bx
 mov es,bx
 mov bx,0484h
 mov bl,byte ptr es:[bx]
 xor bh,bh
 shl bx,1
 shl bx,1
 shl bx,1
 mov dx,bx
 sub dx,16
 pop es
 pop bx
pmrf1z:
 ret
GetMaxValidScreenRow endp

ShowMovedFormDestination proc near
 mov si,pPenDownActiveRegion
 mov bx,[si].pCurrentControl
 sub dx,wMoveModePenRow
 mov [si].wCurrentTop,dx
 add dx,[si].wCurrentHeight
 dec dx
 mov [si].wCurrentBottom,dx
 sub cx,wMoveModePenColumn
 mov [si].wCurrentLeft,cx
 add cx,[si].wCurrentWidth
 dec cx
 mov [si].wCurrentRight,cx
 call ShowBox
 ret
ShowMovedFormDestination endp

UndoAllOptionButtons proc near

 push si
 mov si,pPenDownActiveRegion
 mov si,[si].pCurrentControl
 mov rRegion.pCurrentControl,si

uaob2:
 call GoPreviousControl
 je uaob1a
 cmp [si].ControlType,LAST_ENDOFOBJECT
 je uaob2
uaob1:
 call GoNextControl
 jmp uaob1b
uaob1a:
 stc
uaob1b:
 jc uaob3
 mov al,[si].Controltype
 cmp al,LAST_ENDOFOBJECT
 jbe uaob3
 cmp [si].ControlType,OPTIONBUTTON
 jnz uaob1

 mov bx,[si].pStorageOffset
 mov byte ptr [bx],0
 call FindRegionForControl
 jc uaob1

 push pPenDownActiveRegion
 mov pPenDownActiveRegion,bx
 mov si,[bx].pCurrentControl
 mov ax,[si]
 mov bGetDataFromLocalStorage,-1
 call RepaintIndividualControl
 mov bGetDataFromLocalStorage,0
 pop pPenDownActiveRegion
 jmp uaob1

uaob3:
 mov si,pPenDownActiveRegion
 call RestoreRegion
 pop si
 ret
UndoAllOptionButtons endp


UndoButtonDown proc near
 public UndoButtonDown
 test ah,ISDOWN
 jz dpe10a
 and ah,not(ISDOWN)
 mov [si].ControlState,ah
 call RepaintIndividualControl
dpe10a:
 ret
UndoButtonDown endp

ShowBox proc near
 push si
 cmp bBoxShowing,0
 jz sbb1
 push si
 call HideBox
 pop si
sbb1:
 push ds
 pop es
 mov di,offset rBoxRegion
 mov cx,size rBoxRegion
 cld
 rep movsb
 mov bBoxShowing,-1
 mov si,offset rBoxRegion
 call DrawSolidXORBox
 pop si
 ret
ShowBox endp
HideBox proc near
 cmp bBoxShowing,0
 jz hb1
 mov si,offset rBoxRegion
 call DrawSolidXORBox
 mov bBoxShowing,0
hb1:
 ret
HideBox endp




end


Copr. 1995 Zenith Data Systems Corp.

.MODEL SMALL
.code
extrn getvgastate:near
extrn blockvideo:near
extrn unblockvideo:near
extrn FillScreenArea:near
extrn AddControlToActiveList:near
extrn AddLegendToActiveList:near
extrn AdjustBoxDimensions:near
extrn AdjustButtonDimensions:near
extrn AdjustFormHeight:near
extrn DrawColor:near
extrn DrawButtonCaption:near
extrn DrawCheckBox:near
extrn DrawDoButton:near
extrn DrawEditBoxCaption:near
extrn DrawLabel:near
extrn DrawLineBar:near
extrn DrawNotebox:near
extrn DrawOSKLegends:near
extrn DrawSliderBox:near
extrn DrawSpectrum:near
extrn DrawSpectrumBox:near
extrn DrawString:near
extrn DrawSunkenFrame:near
extrn DrawTextBox:near
extrn DrawTextForm:near
extrn DrawTextLine:near
extrn DrawUpButton:near
extrn GetCaptionHeight:near
extrn GetControlRegion:near
extrn GetAutomaticControl:near
extrn GetTextCenter:near
extrn InitButton:near
extrn InitCheckBox:near
extrn InitEditBox:near
extrn InitLegend:near
extrn InitListBox:near
extrn InitSlideBar:near
extrn PaintGraphicCaption:near
extrn PaintControlCaption:near
extrn PaintControlMiscItem:near
extrn PositionGraphicCaption:near
extrn Repaint:near
extrn RepaintListBox:near
extrn RestoreRegion:near
extrn SetColorsForControl:near
extrn SetFontForCaption:near
extrn SetProtectionForControl:near
extrn StartNewObjectLevel:near
extrn StartTextButtonObjectLevel:near
extrn UpdateLegendRegion:near
extrn UseGrayedColors:near
extrn UseNormalColors:near
extrn ResetVGAState:near


include ulimited.inc
DATASEG_BEGIN
wOSKTitleBarBottomRow dw 0
 public wOSKTitleBarBottomRow
extrn ControlDataStorageArea:byte
extrn rLegendRegion:REGION
extrn CheckedBox:byte
extrn DrawStringTextModeColor:byte
extrn OSKControl
extrn SetOptButton:byte
extrn SliderButton:byte
extrn UnCheckedBox:byte
extrn UnSetOptButton:byte
extrn bCaptionBackgroundColor:byte
extrn bCaptionForegroundColor:byte
extrn bCaptionForegroundColor:byte
extrn bDeskTopColor:byte
extrn bDoingSpin:byte
extrn bDrawStringPWFlag:byte
extrn bDummyBlank:byte
extrn bEditBoxFGColor:byte
extrn bEnlargeFlag:byte
```

```
extrn bFormColor:byte
extrn bGetDataFromLocalStorage:byte
extrn bModalFlag:byte
extrn bPreviewMode:byte
extrn bPreviousMode:byte
extrn bRepaintMode:byte
extrn bRepaintNeeded:byte
extrn bScreenMode:byte
extrn bTitleForegroundColor:byte
extrn bUnderlinedCharacter:byte
extrn IgnoreLevel:word
extrn iLeftAddon:word
extrn iTopAddon:word
extrn pCurrentFont:word
extrn pCurrentToolBarButton:word
extrn pCurrentToolButtonRegion:word
extrn pCurrentToolButtonRegion:word
extrn pEditBoxFont:word
extrn pNextActiveRegion:word
extrn pNormFont:word
extrn pPenDownActiveRegion:word
extrn pPenUpListRegion:word
extrn pPenUpListRegion:word
extrn pPenUpListRegion:word
extrn sActiveRegions:tRegion
extrn rREGION:REGION
extrn wCurrentFormBottom:word
extrn wCurrentFormHeight:word
extrn wCurrentFormLeft:word
extrn wCurrentFormRight:word
extrn wCurrentResource:word
extrn wCurrentResource:word
extrn wGraphicLegendRight:word
extrn wGraphicLegendRight:word
extrn wGraphicLegendRight:word
extrn wHeadTop:word
extrn wPreviousFormHeight:word
extrn wToolBarHeight:word
extrn wToolBarHeight:word
extrn pDelayedSetControl:word
extrn selectcontrol:control
DATASEG_END

.code

RepaintControl proc near
  public RepaintControl
  test ah,ISVISIBLE
  jz rc1

  cmp al,TOOLBARBUTTON
  jnz rc10
  inc IgnoreLevel
rc10:
  ret

rc1:
  call SetColorsForControl

  call GetControlRegion

  cmp bPreviewMode,0
  jz rc1a
  cmp al,TOOLBARBUTTON
  jnz rc0a
  call StartToolButtonObjectLevel
  mov pCurrentToolBarButton,si
rc0a:
  call AdjustFormHeight
  ret

rc1a:
  cmp al,FIRSTBUTTONTYPE
  jb rc2
  cmp al,LASTBUTTONTYPE
  ja rc2

  push ax
  push si
  call RepaintButton
  pop si
  pop ax

rc1b:
  cmp al,TOOLBARBUTTON
  jnz rc0
  test ah,ISDOWN
  jnz rc0a
  inc IgnoreLevel
  jmp rc0
rc0a:
  mov pCurrentToolBarButton,si
  call DoToolBarButtonClick
  call StartToolButtonObjectLevel
  push pNextActiveRegion
  pop pCurrentToolButtonRegion

rc0:

  call AddControlToActiveList
  cmp al,FIRSTFOCUSABLEBUTTONTYPE
  jb rc0b
  cmp al,LASTFOCUSABLEBUTTONTYPE
  ja rc0b
  call AddLegendToActiveList
rc0b:
  ret

rc2:
  call InitCheckBox
  jnz rc4
  call RepaintCheckBox
  call AddControlToActiveList
  call AddLegendToActiveList
  ret

rc4:
  call InitEditBox
  jnz rc5
  call RepaintEditBox
  call AddControlToActiveList
  ret

rc5:
  call InitListBox
  jnz rc6
  push si
  call RepaintListBox
  pop si
  mov si,pPenUpListRegion
  push rRegion.pCurrentControl
  call DoAfterRepaintingList
  pop rRegion.pCurrentControl
  ret

rc6:
  call InitLegend
  jnz rc7
  call RepaintLegend
  ret

rc7:
  cmp al,PROGRESSBAR
  jnz rc7a
  call repaintspectrumbar
  call addcontroltoactivelist
  ret
rc7a:
  call InitSlidebar
  jnz rc8
  call RepaintSpectrumBar
  call AddControlToActiveList
  call AddLegendToActiveList
  ret

rc8:
  cmp al,LINEBOX
  jnz rc12
  call RepaintLineBox
  ret

rc12:
  cmp al,CHISELBOX
  jnz rc14
  call RepaintChiselBox
  ret

rc14:

  cmp al,ICON
  jnz rc15
  call RepaintIcon
  call AddControlToActiveList

  ret

rc15:
  cmp al,SUNKENFRAME
  jnz rc16
  call RepaintSunkenFrame
  ret

rc16:
  ret
RepaintControl endp

RepaintIndividualControl proc near
  public RepaintIndividualControl

  push ax
  push si
  call SetProtectionForControl
  call blockvideo
  call getpenstate
  push ax
  mov ax,REMOVE_PEN_CURSOR
  int pen_function
  pop ax

  mov si,pPenDownActiveRegion
  call RestoreRegion
  call SetColorsForControl

  cmp al,ICON
  jnz ric1
  call repainticon
  jmp ri0
ric1:

  cmp al,CHECKBOX
  jz ri1
  cmp al,OPTIONBUTTON
  jz ri1
  jmp ri2
ri1:
  call RepaintCheckBox
  jmp ri0
ri2:

  call InitButton
  jnz ri3

if need_osk ne 0
  cmp si,offset OSK
  jb ri2a
  test OSK_ID,c
  jz ri2a
  mov bEnlargeFlag,-1
ri2a:
endif

  call RepaintButton
if need_osk ne 0
  mov bEnlargeFlag,0
endif
  jmp ri0
ri3:

  cmp al,SLIDEBAR
  jz ri3a
  cmp al,SPECTRUMBAR
  jz ri3a
  jmp ri4
ri3a:
  call RepaintSpectrumBar
ri4:

  cmp bDoingSen,-1
  jnz ri4a
  call InitEditBox
  jz ri4b
ri4a:
  cmp al,UNFRAMEDEDITBOX
  jz ri4b
  cmp al,KEYEDITBOX
  jnz ri5
ri4b:
  call RepaintEditBox
ri5:
  jmp ri0

ri0:
ri1:
  call restorpenstate
  push ax
  mov ax,DISPLAY_PEN_CURSOR
  INT PEN_FUNCTION
  pop ax
  call unblockvideo
  call UseNormalColors
  pop si
  pop ax
  ret
RepaintIndividualControl endp

RepaintGroupObject proc near
  public RepaintGroupObject
  test ah,ISVISIBLE
  jz rgo1

  inc IgnoreLevel
  ret

rgo1:

rgo0a:
  call GetControlRegion

rgo0:
  cmp al,TOOLBAR
  jnz rgo4
  push word ptr [si].PixelHeight
  pop wToolbarHeight

rgo4:
  call StartNewObjectLevel
  cmp bPreviewMode,0
  jz rgo4a
  call AdjustFormHeight
  ret

rgo4a:
  mov ax,word ptr [si].controltype

  cmp al,TOOLBAR
  jnz rgo2
  call RepaintToolbar
  ret

rgo2:
  cmp al,FORM
  jnz rgo3
  push ax
  push si
  call RepaintForm
  pop si
  pop ax

  test ah,MOVEABLE
  jz rgo2a
  call AddControlToActiveList
rgo2a:
  ret

rgo3:
  cmp al,GROUPBOX
  jnz rgo5
  call RepaintGroupBox
  ret

rgo5:
  ret
RepaintGroupObject endp

RepaintButton proc near
  public RepaintButton
  call AdjustButtonDimensions
  test ah,ISDOWN
  jnz rb1

  mov
DrawStringTextModeColor,TEXTMODE_KEY_UP_C
OLOR
  push ds
  call DrawUpbutton
  pop ds
  xor al,al
  jmp short rb2

rb1:
  mov
DrawStringTextModeColor,TEXTMODE_KEY_DOW
N_COLOR
  call DrawDnbutton
  mov al,2

rb2:
  push word ptr bDrawStringPWFlag
  mov bDrawStringPWFlag,0
  call DrawButtonCaption
  pop word ptr bDrawStringPWFlag
rb99:
  ret
RepaintButton endp

RepaintCheckBox proc near
  push ax
  test ah,ISDOWN
  jz rcb3
  call UseGrayedColors
rcb3:
  push si
  cmp bGetDataFromLocalStorage,0
  jz rcb3d
  mov bx,[si].pStorageOffset
  jmp rcb3e

rcb3d:
  push ax
  push cx
  mov cl,al
  mov ax,[si].ID
  mov ch,ah
  mov ah,0bh
  BM_FUNCTION ax
  mov bx,[si].pStorageOffset
  jb rcb3a

  cmp al,OPTIONBUTTON
  jnz rcb3b
  cmp al,ah
  jnz rcb3c
  mov al,1
```

```
 jmp rpcb3b
rpcb3c:
 xor bl,al

rpcb3b:
 mov [bx],al
rpcb3a:
 pop cx
 pop ax

rpcb3e

 cmp byte ptr [bx],0
 jnz rpcb1

 mov si,offset UncheckedBox
 cmp al,CHECKBOX
 je rpcb2
 mov si,offset UnselOptButton
 jmp rpcb2

rpcb1:
 mov si,offset CheckedBox
 cmp al,CHECKBOX
 je rpcb2
 mov si,offset SelOptButton

rpcb2
 call drawtcolor
 pop si

 call PaintControlCaption
 jz rpcb99
 or cx,cx
 jz rpcb4

 mov bx,cx
 jmp dlc

rpcb4:
 or bx,bx
 jz rpcb99

dlc:
 push si
 mov si,bx
 add si,3
 call SetFontForCaption
 call SetCaptionHeight
 mov dx,rRegion.wCurrentTop
 add ax,dx
 mov rLegendRegion.wCurrentBottom,ax
 mov cx,rRegion.wCurrentLeft
 add cx,20
 mov bl,bCaptionForegroundColor
 xor bh,bh

 sub cx,4
 call UpdateLegendRegion
 add cx,4
 add rLegendRegion.wCurrentRight,4
 call DrawLabel
 pop si

rpcb99:
 pop ax
 ret
RepaintCheckBox endp

RepaintChiselBox proc near
 dec rRegion.wCurrentHeight
 call AdjustBoxDimensions

 cmp si,offset osk
 jb rcb2
 push rRegion.wCurrentTop
 pop wOSKTitleBarBottomRow

rcb2:

 cmp bScreenMode,VGA_MODE
 je rcb1
 sub wOSKTitleBarBottomRow,3

 add wTextTop,7
 call DrawTextLine
 ret

rcb1:
 call DrawChiselBox
 ret
RepaintChiselBox endp

RepaintEditBox proc near

 push ax
 call AdjustButtonDimensions
 cmp al,UNFRAMEDEDITBOX
 jz reb66a
 call DrawTextBox
reb66a:
 call DrawEditBoxCaption

reb4:
 push si
 mov al,[si].ControlType
 cmp al,NUMEDITBOX
 jnz reb7

 call GetNumericControl
 jmp reb8

reb7:
 call GetCustomEditBoxContents
 jne reb8a
 jmp reb6aa
reb8a:
 cmp pDelayedSetControl,0
 jnz reb8
 call SetTextControl
reb8:
 cmp al,PWEDITBOX
 jnz reb5
 mov bDrawstringPWFlag,-1
reb5
 mov si,[si].pStorageOffset
reb5aa:
 mov bl,bEditBoxFGColor
 xor bh,bh
 push pEditBoxFont
 pop pCurrentFont
 mov dx,rRegion.wCurrentTop
 cmp al,UNFRAMEDEDITBOX
 je reb5a
 inc dx
 inc dx
 inc dx
 inc dx
reb5a:
 mov cx,rRegion.wCurrentLeft
 add cx,3
 call RepaintCustomEditBoxContents
 jz reb0

 cmp al,UNFRAMEDEDITBOX
 jnz reb6
 sub cx,5
 mov bh,bFormColor
 or bh,WITHBACKCOLOR
 mov ax,rRegion.wCurrentRight
 sub ax,cx
reb6:
 push word ptr bUnderlinedCharacter
 call DrawString
 pop word ptr bUnderlinedCharacter
reb0:
 pop si
reb66:
 pop ax
 ret
RepaintEditBox endp

RepaintForm proc near
 call DoBeforeRepaintingForm
 call AdjustButtonDimensions

 push rRegion.wCurrentRight
 pop wCurrentFormRight
 push rRegion.wCurrentLeft
 pop wCurrentFormLeft

if need_osk ne 0
 cmp si,offset osk
 je rf1
endif
 push word ptr [si].PixelHeight
 pop wCurrentFormHeight
 push rRegion.wCurrentBottom
 pop wCurrentFormBottom

rf1:
 test bRepaintMode,1
 jz rf0a
 jmp rf0
rf0a:

 cmp bScreenMode,VGA_MODE
 je rf0
 push ax
 mov ax,rRegion.wCurrentHeight
 sub ax,3
 sar ax,1
 mov bh,al

 pop ax
 call DrawTextForm
 jmp rf10

rf0:
 call DrawUpbutton

rf10:
if need_osk ne 0
 cmp si,offset osk
 jnz rf100
 cmp bScreenMode,VGA_MODE
 jnz rf101
 mov bl,byte ptr OSK.10
 and bl,11b
 cmp bl,10b
 jz rf101
 call DrawOskLegend
rf101:
 jmp rf66
endif

rf100:
 cmp bModalFlag,0
 jz rf100z
 or wCurrentResource,8000h
 mov
wPreviousFormHeight,SCREEN_HEIGHT_PIXELS
rf100z:

 mov ax,wPreviousFormHeight
 sub ax,wCurrentFormHeight
 jl rf66

 push si
 mov dx,rRegion.wCurrentBottom
 push word ptr bDeskTopColor
 test wCurrentResource,not(111b)
 jnz rf66
 mov bDeskTopColor,BLACK
rf66:
 CLEAR_RECTANGLE 0,dx,00,ax,bDeskTopColor
 pop word ptr bDeskTopColor
 pop si
rf66:
 ret
RepaintForm endp

RepaintGroupBox proc near
 call AdjustButtonDimensions
 push si
 call DrawChiselbox
 pop si

 call PaintControlCaption
 jz rgb66
 or bx,bx
 jz rgb66
 call SetFontForCaption

 push si
 mov si,bx
 add si,3
 mov bl,bCaptionForegroundColor
 mov bh,bCaptionBackgroundColor
 or bh,10
 mov dx,rRegion.wCurrentTop
 sub dx,4
 mov cx,rRegion.wCurrentLeft
 add cx,8
 call DrawString
 pop si
rgb66:
 ret
RepaintGroupBox endp

RepaintIcon proc near

 push si
 mov si,[si].id
 or si,si
 jz ri1
 push ax
 call DrawIColor
 pop ax
ri1:
 pop si
 ret
RepaintIcon endp

RepaintLegend proc near

 call PaintControlCaption
 jnz rl1a
 jmp rl1
rl1a:
 or bx,bx

 jnz rl3
 cmp bScreenMode,VGA_MODE
 je rl1aa

 push si
 push cx
 mov ah,16+1
 call PaintControlMnemonic
 pop ax
 pop si
 or bx,bx
 jnz rl3a
 jmp rl1
rl3a:
 push si
 push ax
 mov DrawStringTextModeColor,16
 mov si,bx
 mov dx,rRegion.wCurrentTop

 sub dx,8
 mov cx,rRegion.wCurrentLeft
 call DrawString
 pop ax
 pop si
 jmp rl1

rl1aa:
 mov bx,cx
 call SetFontForCaption
 xor cx,cx
 push cx
 jmp rl3a
rl3:
 push ax
 call SetFontForCaption
rl3a:
 add bx,3
 push si
 push bx
 mov bl,bCaptionForegroundColor
 mov al,[si].ControlType
 mov bh,32

 cmp al,LEFTLEGEND
 je rl2
 shl bh,1
 cmp al,CENTEREDLEGEND
 je rl2
 shl bh,1
rl2:
 test [si].ControlState,BACKFILL
 je rl4
 or bh,bCaptionBackgroundColor
 or bh,16
rl4:
 mov ax,[si].PixelWidth
 pop si
 mov dx,rRegion.wCurrentTop
 mov cx,rRegion.wCurrentLeft
 call DrawString
 pop si
 pop ax

 jmp rl1
rl6:

 push rRegion.wCurrentLeft
 pop wGraphicLegendRight
 mov bx,ax
 call PositionGraphicCaption
rl0:
 call PaintGraphicCaption
rl1:
 ret
RepaintLegend endp

RepaintLineBox proc near
 call AdjustBoxDimensions
 call drawlinebox
 ret
RepaintLineBox endp

RepaintSpectrumBar proc near

 call AdjustButtonDimensions
 cmp [si].controltype,progressbar
 je rsb21
 cmp [si].ControlType,SLIDEBAR
 je rsb21
 call DrawSpectrumBox
 call DrawSpectrum
```

```
  jmp rsb20
rsb21:
  call DrawSliderBox
rsb20:

  call DrawEditBoxCaption
  call DrawNotches
  mov ax,[si].10
  mov ah,300h
  SM_FUNCTION ax
  mov bx,[si].pStorageOffset
  jl rsb20a
  mov [bx],al
rsb20a:
  mov al,[bx]
  cmp [si].controltype,progressbar
  jz rsb20b
   mov ah,byte ptr [si].id[1]
   dec ah
  cmp al,ah
  jbe rsb20b
  mov al,ah
rsb20b:

  cmp ah,5-1
  jz rsb21c
  mov ah,8
  jmp rsb20d
rsb21c:
  mov ah,24
rsb21d:
  mov ah
  mov cx,rRegion.uCurrentLeft
  ADD CX,ax
  mov dx,rRegion.uCurrentTop
  cmp [si].controltype,PROGRESSBAR
  jz rsb60

  push pNormFont
  pop pCurrentFont
  mov si,offset bdummyblank
  mov ax,19
  mov bh,CENTERED
  add dx,3
  call UpdateLegendRegion
  sub dx,3
  mov ax,rLegendRegion.uCurrentTop
  add ax,7
  mov rLegendRegion.uCurrentBottom,ax

  mov si,offset sliderbutton
  call draw4color

rsb60:
  ret
RepaintSpectrumBar endp

RepaintButtonFrame proc near
  push si
  call AdjustButtonDimensions
  call DrawButtonFrame
  pop si
  ret
RepaintButtonFrame endp

RepaintToolbar proc near

  call AdjustButtonDimensions

  test bRepaintNeeded,PAINTTOOLBARS
  jz rtb60

  push bx
  push cx
  push dx
  call DrawUpbutton
  pop dx
  pop cx
  pop bx

  sub bl,64/8
  mov bh,13
  add cx,32
  call DrawUpButton

  call PaintControlCaption
  jz rtb60
  or bx,cx
  jz rt1
  mov bx,cx
  jmp rt2
rt1:
  or bx,bx
  jz rtb60

rt2:
  call SetFontForCaption
  push si
  add bx,3
  mov si,bx
  mov cx,rRegion.uCurrentLeft
  mov dx,rRegion.uCurrentTop
  add cx,32+8
  add dx,9

  mov bl,bTitleForegroundColor
  xor bh,bh
  call drawstring
  pop si
rtb60:
  ret
RepaintToolbar endp

end

Copr. 1995 Zenith Data Systems Corp.

.model small

SPTR = 0
include ulnded.inc

DATASEG_BEGIN
extrn ControlDataStorageArea:byte
extrn bScreenMode:byte
extrn pGraphicFont:word
extrn wScreenSegment:word
wScanAdder dw 0

bXORFill db 1
bPatternTable db 10101010b
downpattern db 10101010b
rightdownpattern db 10101010b

ColoredAboutIcon label byte
  public ColoredAboutIcon
db -1,WHITE,GRAY,CYAN,BLACK
AboutIcon label byte
  public AboutIcon
db 4,28
db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]

db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

db [illegible]
db [illegible]
db [illegible]
db [illegible]

SmallAboutIcon label byte
  public SmallAboutIcon
db 3,30-16

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

db [illegible]
db [illegible]
db [illegible]

DATASEG_END
.code

PaintScreenDest proc near
  public PaintScreenDest

if need_ssh ne 0

  mov bx,470

  sub bx,dx
  mov wLinesToBottom,bx
  mov bx,uCoveredAreaHeight
  mov wCoveredRowCountdown,bx
  mov bx,uCoveredAreaTop
  sub bx,dx
  jnb psd1
  mov bx,uCoveredAreaBottom
  sub bx,dx
  jnc psd2
  mov bx,-1
  jmp psd1
psd2:
  mov wCoveredRowCountdown,bx
  xor bx,bx
psd1:
  mov wUncoveredRowCountdown,bx
endif
  DIVIDE_BY_8 ax
if need_ssh ne 0
  mov wBytesToStart,ax
```

```
  mov wBytesToStartInit,cx

  mov bx,80
  sub bx,cx
  mov wBytesToRight,bx
  mov wBytesToRightInit,bx
  mov bx,wCoveredAreaWidth
  mov wCoveredByteCountdown,bx
  mov bx,wCoveredAreaLeft
  sub bx,cx
  jge pad1a
  mov bx,wCoveredAreaRight
  sub bx,cx
  jge pad2a
  mov bx,-1
  jmp pad1b
pad2a:
  inc bx
  mov wCoveredByteCountdown,bx
  xor bx,bx
pad1a:
  mov wUncoveredByteCountdown,bx
  mov wUncoveredByteInit,bx
  mov bx,wCoveredByteCountdown
  mov wCoveredByteInit,bx
pad1b:
  cmp bScreenMode,VGA_MODE
  jnz pad20
endif

  mov ax,SCREEN_WIDTH_BYTES
  mul dx
  mov bx,ax

  add bx,cx
  mov ax,VGASEGMENT
  mov es,ax
  mov di,bx
  ret
pad20:
  mov ax,dx
  mov bx,SPTR
  xor dx,dx
  div bx
  mov bx,160
  mul bx
  add ax,cx
  add ax,cx
  mov dx,ax
  mov bx,ax

  mov ax,wScreenSegment
  ret
pointscreendest endp

CheckIfCovered proc near
  public CheckIfCovered
  cmp wBytesToStart,0
  jge cic10
  inc wBytesToStart
  stc
  ret
cic10:
  cmp wBytesToRight,0
  jg cic0
  stc
  ret
cic0:
  dec wBytesToRight
  cmp wScansToBottom,1
  jg cic0b
  clc
  ret
cic0a:
  cmp wUncoveredRowCountdown,0
  jnz cic1

  cmp wUncoveredByteCountdown,0
  jnz cic2
  dec wCoveredByteCountdown
  jnz cic3
  mov wUncoveredByteCountdown,-1
cic3:
  cmp bCoveredAreaOnly,0
  jz cic3a
  clc
  ret
cic3a:
  stc
  ret
cic2:
  dec wUncoveredByteCountdown
cic1:
  cmp bCoveredAreaOnly,0
  jz cic1a
  stc
  ret
cic1a:
  clc
  ret
CheckIfCovered endp

NewRowForCheckIfCovered proc near
  public NewRowForCheckIfCovered
  dec wScansToBottom
  cmp wUncoveredRowCountdown,0
  jz nrfcic1
  dec wUncoveredRowCountdown
  jz nrfcic2
  push ax
  jmp nrfcic2b
  ret
nrfcic1:
  cmp wCoveredRowCountdown,0
  jz nrfcic3
  dec wCoveredRowCountdown

nrfcic2:
  push ax
  mov ax,wUncoveredByteInit
  mov wUncoveredByteCountdown,ax
  mov ax,wCoveredByteInit
  mov wCoveredByteCountdown,ax
  jmp nrfcic2b
nrfcic3:
  mov wUncoveredRowCountdown,-1
  push ax
nrfcic2b:
  mov ax,wBytesToRightInit
  mov wBytesToRight,ax
  mov ax,wBytesToStartInit
  mov wBytesToStart,ax
  pop ax
  ret
NewRowForCheckIfCovered endp

FillScreenArea proc near
  public FillScreenArea

if need_cek ne 0
  cmp bScreenMode,VGA_MODE
  jz fsa9
fsa4:
  push ax
  push si

  push cx
  push bx
  push dx
  call PointScreenDest
  pop dx
  pop bx
  pop cx
fsa1:
if need_cek ne 0
  call checkifcovered
  jc fsa2
endif
  mov al,' '
  mov ah,bh
  mov es:[di],ax
fsa2:
  inc di
  inc di
  dec si
  jnz fsa1

  pop si
  pop ax
  sub ax,SPTR
  jb fsa3
  add dx,SPTR
  jmp fsa4
fsa3:
  ret

endif
fsa9:

  or ax,ax
  jnz fsa2
  ret
fsa2:
  or si,si
  jnz fsa3
  ret
fsa3:
  push bp
  push di
  push ax
  push bx
  call pointscreendest
  pop bx
  if : + bp,SCREEN_WIDTH_BYTES
  ax : bp,si
  mov wScanAdder,bx

  vgaloadlatches

  mov ax,011111111b*256+8
  out dx,ax


  mov al,bh
  pop bx
fsa1:
  mov cx,si
  mov bp,ax

fsa5:
if need_cek ne 0
  call CheckIfCovered
  jnc fsa4a
else
  jmp fsa4a
endif
  inc di
  loop fsa5
  jmp fsa4b
fsa4a:
  vgaloadlatches
  mov ax,011111111b*256+8
  out dx,ax
  mov ax,bp
  mov ah,es:[di]
  stosb
fsa6:
  loop fsa5
fsa4b:
  add di,wScanAdder
if need_cek ne 0
  call NewRowForCheckIfCovered
endif
  dec bx
  jnz fsa1
  pop di
  pop bp


  ret

fillscreenarea endp

DATASEG_BEGIN
bCoveredAreaOnly  db 0,0
  public bCoveredAreaOnly
wCoveredAreaTopHold dw -1
  public wCoveredAreaTopHold
wCoveredAreaTop   dw -1
  public wCoveredAreaTop
wCoveredAreaBottom dw 250
  public wCoveredAreaBottom
wCoveredAreaLeft  dw 40
  public wCoveredAreaLeft
wCoveredAreaRight  dw 60
  public wCoveredAreaRight
wCoveredAreaWidth  dw 21
  public wCoveredAreaWidth
wCoveredAreaHeight dw 121
  public wCoveredAreaHeight

wScansToBottom dw 0
wBytesToRight dw 0
wBytesToRightInit dw 0



wUncoveredRowCountdown dw 0
wCoveredRowCountdown   dw 0
wUncoveredByteCountdown dw 0
wCoveredByteCountdown dw 0
wUncoveredByteInit    dw 0
wCoveredByteInit      dw 0
wBytesToStart dw 0
wBytesToStartInit dw 0
bDrawStringPWFlag  db 0,0
  public bDrawStringPWFlag
pCurrentFont dw 0
  public pCurrentFont
wCurrentFontHeight dw 0
  public wCurrentFontHeight
pDrawStringTabList dw 0
  public pDrawStringTabList
pNextTabItem dw 0
drawstringwidth  dw 0
finalch db 0
maxx0 dw 0
maxxl dw 0
bytestowrite db 0
startingmask db 0
endingmask db 0
PixelsToPadLeft dw 0
PixelsToPadRight dw 0
LeftPaddingCountdown dw 0
RightPaddingCountdown dw 0
drawstringsegment dw 0

drawstringbitflags db 0
DrawStringTextModeColor db 0
  public DrawStringTextModeColor
drawstringbackcolor db 0
drawstringcolumn dw 0
drawstringrow    dw 0
drawstringcolor  db 0
drawstringptr    dw 0
drawstringspacewidth db 0
drawstringheight db 0
donestringptr dw 0
scancountdown db 0
scansdone db 0
nextshiftjump dw 0
alreadydone db 0
bProcessUnderlines db 0
bUnderlinedCharacter db 0,0
  public bUnderlinedCharacter
bZeros db 5 dup(0)
bOnes  db 5 dup(-1)

scanbuffer db 80 dup(0)
DATASEG_END

.code

DrawLabel proc near
  public DrawLabel
  mov bProcessUnderlines,-1
  call drawstring
  mov bProcessUnderlines,0
  ret
DrawLabel endp

GetLabelWidth proc near
  public GetLabelWidth
  mov bProcessUnderlines,-1
  call GetStringWidth
  mov bProcessUnderlines,0
  ret
GetLabelWidth endp

DrawString proc near
  public DrawString


  mov bUnderlinedCharacter,0
  mov alreadydone,0
  mov drawstringwidth,ax
  mov drawstringbitflags,bh
  and bh,1111b
  mov drawstringbackcolor,bh
  mov drawstringcolumn,cx
  mov drawstringrow,dx
  mov drawstringptr,si
  mov drawstringcolor,bl
  mov bx,pCurrentFont
  mov ax,[bx]
  mov drawstringspacewidth,al
  mov drawstringheight,ah
  cmp bScreenMode,VGA_MODE
  jz ds1
  cmp bx,pGraphicFont
  jnz dst1
  ret
dst1:
dst7:
  push si
  push dx
  call PointScreenDest
  pop dx
  pop si
dst4:
  lodsb
  or al,al
  jz dst3
  cmp al,13
  jnz dst8
  add dx,8
  mov cx,DrawStringColumn
  jmp dst7
dst8:
if need_cek ne 0
  call checkifcovered
  jc dst2
endif
  mov ah,DrawStringTextModeColor
  cmp ax,222+32*256
  jnz dst5
  mov ax,221+2*256

dst5:
  mov word ptr es:[di],ax
dst2
  inc di
  inc di
  jmp dst4
dst3
  ret
```

```
 mov drawstringptr,si
 jmp de1

de0
 mov bDrawStringPWFlag,0
 ret
drawstring endp

GetStringWidth proc near
 public GetStringWidth
 call PrepareTabbing

 push si
 push di
 push dx
 push bx
 xor dx,dx
 mov di,pCurrentFont
gsw1:
 lodsb
 or al,al
 jz gsw2
 cmp al,13
 jz gsw2
 cmp al,9
 jnz gsw1a
 mov bx,pNextTabItem
 cmp word ptr [bx],0
 jz gsw1
 mov dx,[bx]
 inc bx
 inc bx
 mov pNextTabItem,bx
 jmp gsw1
gsw1a:
 cmp al,' '
 jb gsw1
 jz gsw3
gsw4:
 mov al,[di]
gsw5:
 xor ah,ah
 add dx,ax
 jmp gsw1
gsw3:
 cmp al,255
 jz gsw4
 cmp al,'&'
 jnz gsw5a
 cmp bProcessUnderlines,0
 jz gsw5a
 cmp byte ptr [si],'&'
 jz gsw5b
 cmp byte ptr [si],0
 jz gsw5a
 jmp gsw1
gsw5a:
 sub al,32
 xor ah,ah
 add bx,ax
 mov bx,di
 add bx,ax
 mov bx,[bx]
 mov al,[bx]
 jmp gsw5
gsw2:
 mov ax,dx
 pop bx
 pop dx
 pop di
 pop si
 ret
GetStringWidth endp

clearscreenbuffer proc near
 push ds
 pop es
 mov di,offset screenbuffer
 mov cx,80
 xor al,al
 rep stosb
 ret
clearscreenbuffer endp

PrepareTabbing proc near
 push pDrawStringTabList
 pop pNextTabItem
 ret
PrepareTabbing endp

LocateDrawStringPointer proc near
 mov dh,128
 and cl,111b
 ror dh,cl
 ret
LocateDrawStringPointer endp
```

```
DrawSolidXORBox proc near
 public DrawSolidXorBox
 mov al,11111111b
 call DrawXORBox
 ret
DrawSolidXORBox endp

DrawXORBox proc near
 public DrawXorBox
 mov bPatternToUse,al
 mov cx,[si].wCurrentLeft
 cmp cx,[si].wCurrentRight
 jz dxb7
 mov dx,[si].wCurrentTop
 cmp dx,[si].wCurrentBottom
 jz dxb0a
 cmp bXorFill,-1
 jz dxb10

 call XORHorizontal

 mov dx,[si].wCurrentBottom
 dec dx
dxb0:
 cmp bScreenMode,VGA_MODE
 jz dxb0b

 inc dx

 mov ax,dx
 sub ax,[si].wCurrentTop
 cmp ax,2
 jnz dxb0a
 jmp dxb0a
dxb0a:
 call XORHorizontal
dxb0b:
 mov cx,[si].wCurrentLeft
 jcxz dxb6
 cmp bScreenMode,VGA_MODE
 jnz dxb6
 dec cx
dxb6:
 call XORVertical
 mov cx,[si].wCurrentRight
 inc cx
dxb7:
 cmp bScreenMode,VGA_MODE
 jz dxb7a
 mov cx,[si].wCurrentRight
 sub cx,[si].wCurrentLeft
 cmp cx,2
 jl dxb13
 sub cx,2
 call XORVertical
 jmp dxb13
dxb7a:
 call XORVertical
dxb12:
dxb13:
 ret
dxb10:
 cmp dx,[si].wCurrentBottom
 jae dxb11
 push dx
 call XORHorizontal
 pop dx
 inc dx
 jmp dxb10
dxb11:
 mov bXorFill,0
 jmp dxb12
DrawXORBox endp

XORHorizontal proc near
 mov cx,[si].wCurrentLeft
 cmp bScreenMode,VGA_MODE
 jz xh0
 add cx,8
 call pointscreendest

 mov ax,[si].wCurrentRight
 DIVIDE_BY_8 ax
 neg ax,ax
 sub ax,ax
xh2:
 call XORTextByte

 inc di
 inc di
 loop xh2
 ret
xh0:
 call pointscreendest
 push cx
 mov al,bPatternToUse
```

```
 mov dashpattern,al
 mov cx,[si].wCurrentLeft
 and cl,111b
 jz xh1
 mov al,dashpattern
 shl al,cl
 shr al,cl
 mov dashpattern,al
xh1:
 pop ax
 mov ax,[si].wCurrentRight
 push ax
 push cx
 mov cl,ax
 mov al,bPatternToUse
 and cl,111b
 mov ch,7
 sub ch,cl
 jz xh3
 mov cl,ch
 xor al,al
 sal al,cl
xh3:
 mov rightdashpattern,al
 pop cx
 pop ax
 DIVIDE_BY_8 ax
 inc ax
 sub ax,cx
 jz dxb1
 mov cx,ax
 VGASETXOR
dxb2:
 if need_osk ne 0
 call CheckIfCovered
 jz dxb2a
 endif
 mov al,es:[di]
 mov al,dashpattern
 vgawritecolor 15
dxb2a:
 inc di
 mov al,bPatternToUse
 cmp cx,2
 jnz dxb3
 mov al,rightdashpattern
dxb3:
 mov dashpattern,al
 loop dxb2
dxb1:
 VGALOADLATCHES
 ret
XORHorizontal endp

DrawDashedXORBox proc near
 public DrawDashedXORBox

 mov al,10101010b

 call DrawXORBox
 ret
DrawDashedXORBox endp

XORTextByte proc near
 if need_osk ne 0
 call checkifcovered
 jz txb1
 endif
 mov al,es:[di+1]
 mov ah,al
 not ah
 and ah,01111111b
 and al,10000000b
 or al,ah
 mov es:[di+1],al
txb1:
 ret
XORTextByte endp

XORVertical proc near
 mov dx,[si].wCurrentTop
 cmp bScreenMode,VGA_MODE
 jz xv0
tmxv1:
 push dx
 push cx
 call pointscreendest
 pop cx
 pop dx
 call XORTextByte
 add dx,8

 cmp dx,[si].wCurrentBottom
 jl tmxv1
 ret
xv0:
 push cx
 call pointscreendest
 pop cx
```

```
 mov bl,10000000b
 and cl,111b
 jz xv1
 ror bl,cl

xv1
 VGASETXOR
 mov bl,bPatternToUse
 mov cx,[si].wCurrentTop
 inc cx
dxb5:
 cmp cx,[si].wCurrentBottom
 jae dxb4
 if need_osk ne 0
 call CheckIfCovered
 jz dxb5a
 endif
 mov al,es:[di]
 mov al,bl
 and al,bh
 vgawritecolor 15
dxb5a:
 add di,SCREEN_WIDTH_BYTES
 rol bl,1
 inc cx
 if need_osk ne 0
 call NewRowForCheckIfCovered
 endif
 jmp dxb5
dxb4:
 VGALOADLATCHES
 ret
XORVertical endp

end
Copr. 1995 Zenith Data Systems Corp.
.model small
include ctlmdef.inc
DATASEG_BEGIN
extrn ControlDataStorageArea:byte
extrn rRegion:REGION
extrn OSK:Control
extrn bCoveredAreaOnly:byte
extrn bDrawStringPWFlag:byte
extrn bHoldString:byte
extrn pCurrentFont:word
extrn pDrawStringTabList:word
extrn pMenuFont:word
extrn pTabHandler:word
extrn pTabRegion:word
extrn rCursorRegion:REGION
extrn wNull:word
extrn wCoveredAreaTop:word
extrn wCursorTimer:word
extrn wKeyPressed:word
extrn wPenDownColumn:word
extrn wShortCutKey:word
extrn wHotKeyRightPixel:word
extrn pDelayedSetControl:word
extrn pDelayedSetRegion:word
bCursorActive db 0
 public bCursorActive
bCursorState db 0
bCursorPWFlag db 0

bEditBoxType db 0
pEditBoxControl dw 0


pEditBoxFont dw offset0
 public pEditBoxFont

wEditBoxLeftPixel dw 0
wEditBoxRightPixel dw 0
wEditBoxTopPixel dw 0
bEditBoxFGColor db 0
 public bEditBoxFGColor
bEditBoxBGColor db 15
wEditBufferSize dw 0
pEditBufferStart dw 0
wEditBufferInsertPoint dw 0
DATASEG_END
.code
extrn CheckIfOnlyOSK:near
extrn DoListBoxKey:near
extrn DoSlideBarLeftArrow:near
extrn DoSlideBarRightArrow:near
extrn DoSpaceBar:near
extrn DoSpinDown:near
extrn DoSpinUp:near
extrn DoTab:near
extrn DrawSolidXorBox:near
extrn DrawString:near
extrn GetTabControlType:near
extrn GetNextControl:near
extrn GetNextControl:near
extrn GoPreviousControl:near
extrn GoPreviousControl:near
```

```
extrn IsButton:near
extrn IsCheckBox:near
extrn IsEditBox:near
extrn IsListBox:near
extrn IsSlideBar:near
extrn JumpOnAL:near
extrn PointNextTabControl:near
extrn PointPreviousTabControl:near
extrn ProtectOSK:near
extrn Repaint:near
extrn SetNumericControl:near
extrn SetTextControl:near

DrawEditBoxText proc near
if need_osk ne 0
 call ProtectOSK
endif

 mov si,pEditBufferStart
 mov bl,bEditBoxFGColor
 mov bh,bEditBoxBGColor
 or bh,WITHBACKCOLOR+LEFTJUSTIFIED
 mov dx,wEditBoxTopPixel
 mov cx,wEditBoxLeftPixel
 mov ax,wEditBoxRightPixel
 sub ax,cx
debt1
 mov pCurrentFont,offset altfont8
 mov pDrawStringTabList,offset bHusString
 call DrawString
 ret
DrawEditBoxText endp

ChangeCursorState proc near
 push wCoveredAreaTop
 push word ptr bCoveredAreaOnly

if need_osk ne 0
 call protectOSK
endif

 mov di,offset rCursorRegion
 call DrawSolidXORBox
 not bCursorState
 mov wCursorTimer,0
 pop word ptr bCoveredAreaOnly
 pop wCoveredAreaTop
 ret
ChangeCursorState endp

DeleteEditBufferCharacter proc near
 push ds
 pop es
 call PointEditBufferCurrent
 or al,al
 jz del1
 mov al,dl
 inc si
 mov cx pEditBufferStart
 add cx,wEditBufferSize
 dec cx
 sub cx,si
 inc cx
 jz del1
 rep movsb
del1:
 ret
DeleteEditBufferCharacter endp

DoBackSpaceEdit proc near

DoBackSpaceEdit1:
 call DoLeftArrowEdit
 jc bs1
 call DoDelKeyEdit
bs1:
 ret
DoBackSpaceEdit endp

DoCursorFlash proc near
 public DoCursorFlash

 cmp bCursorActive,0
 jz dcf1
 cmp wCursorTimer,10
 jb dcf1
 call ChangeCursorState
dcf1:
 ret
DoCursorFlash endp

DoDelKeyEdit proc near
 call DeleteEditBufferCharacter
 clc
 ret
DoDelKeyEdit endp

DoEditBoxKey proc near
 mov pEditBoxControl,bx

 cmp [bx].ControlType,PWEDITBOX
 jnz debk3
 mov bDrawStringPWFlag,-1
debk3:

 cmp al," "
 jae debk1
 call DoEditBoxSpecialKey
 jnc debk2
 ret
debk1:

 cmp bEditBoxType,NUMEDITBOX
 jnz debk1a
 cmp al,"0"
 jb debk99
 cmp al,"9"
 ja debk99
debk1a:

 push bx
 call InsertEditBufferCharacter
 pop bx

debk2:
 call StopCursor
 mov al,bEditBoxType
 mov si,pEditBoxControl

 cmp al,NUMEDITBOX
 jnz debk4
 push bx
 call SetNumericControl
 pop bx
 jmp debk10
debk4:

 cmp al,PWEDITBOX
 jz debk5
 call SetTextControl
 jmp debk6
debk5
 mov pDelayedSetControl,si
 push pTabRegion
 pop pDelayedSetRegion
debk6:
debk10:
 call DrawEditBoxText
 or = di,offset rCursorRegion
 c=1 ResumeCursor
debk99:
 clc
 ret
DoEditBoxKey endp

DoEditBoxSpecialKey proc near

 mov al,ah
 call JumpOnAL

 db UP_ARROW_SCAN_CODE
 dw offset debsUpArrow
 db DOWN_ARROW_SCAN_CODE
 dw offset debsDownArrow
 db LEFT_ARROW_SCAN_CODE
 dw offset debsLeftArrow
 db RIGHT_ARROW_SCAN_CODE
 dw offset debsRightArrow
 db DEL_SCAN_CODE
 dw offset debsDel
 db HOME_SCAN_CODE
 dw offset debsHome
 db END_SCAN_CODE
 dw offset debsEnd
 db BACKSPACE_SCAN_CODE
 dw offset debsBackSpace
 db 0
 stc
 ret

debsLeftArrow:
 call DoLeftArrowEdit
 ret
debsRightArrow:
 call DoRightArrowEdit
 ret
debsDel:
 call DoDelKeyEdit
 ret
debsHome:
 call DoHomeKeyEdit
 ret
debsEnd:
 call DoEndKeyEdit
 ret
debsBackSpace:
 call DoBackSpaceEdit
 ret

debsUpArrow
 mov si,pEditBoxControl
 mov rRegion,pCurrentControl,si
 call GoNextControl
 jc debsua1
 cmp [si].ControlType,SPINUPBUTTON
 jnz debsua2
 call DoSpinUp
debsua2:
 call GoPreviousControl
debsua1:
 clc
 ret

debsDownArrow:
 mov si,pEditBoxControl
 mov rRegion,pCurrentControl,si
 call GoNextControl
 jc debsda1
 call GoNextControl
 jc debsda2
 cmp [si].ControlType,SPINDOWNBUTTON
 jnz debsda3
 call DoSpinDown
debsda3:
 call GoPreviousControl
debsda2:
 call GoPreviousControl
debsda1:
 clc
 ret
DoEditBoxSpecialKey endp

DoEndKeyEdit proc near

deke2:
 call PointEditBufferCurrent
 or al,al
 jz deke1
 inc wEditBufferInsertPoint
 jmp deke2
deke1:
 stc
 ret
DoEndKeyEdit endp

DoHomeKeyEdit proc near

 mov wEditBufferInsertPoint,0
 clc
 ret
DoHomeKeyEdit endp

DoKeyEvent proc near
 public DoKeyEvent
dke1:
 mov ax,wKeyPressed
if need_osk ne 0
 call CheckIfOnlyOSK
 jne dke1b
 ret
dke1b:
endif

 cmp al,TABKEY
 jne dke3
 mov pTabHandler,offset PointNextTabControl
 call DoTab
 ret
dke3:

 cmp ax,SHIFTTABKEY
 jne dke4
 mov pTabHandler,offset PointPreviousTabControl
 call DoTab
 ret
dke4:

if NEED_ALTKEYS ne 0
 or al,al
 jnz dke4a
 call DoShortCutKey
 jnc dke4a
 ret
dke4a:
endif

 call GetTabControlType
 jne dke1c
 ret
dke1c:

 call IsEditBox
 jne dke4a
 mov bEditBoxType,al
 mov ax,wKeyPressed
 call DoEditBoxKey
 ret
dke4a:
 call IsListBox
 jnz dke4b
 mov ax,wKeyPressed
 call DoListBoxKey
 ret
dke4b

 call IsSlideBar
 jnz dke4c
 mov ax,wKeyPressed
 or al,al
 jnz dke4b1
 mov di,si
 mov al,ah
 cmp ah,LEFT_ARROW_SCAN_CODE
 jz dke4b2
 cmp ah,RIGHT_ARROW_SCAN_CODE
 jnz dke4b1
 call DoSlideBarRightArrow
 jmp dke4b1
dke4b2:
 call DoSlideBarLeftArrow
dke4b1:
 ret
dke4c:

 call IsCheckBox
 jz dke4e
 call IsButton
 jnz dke5
dke4e:
 mov ax,wKeyPressed
 cmp al," "
 jnz dke2
 call DoSpacebar
 ret
dke2:
 cmp al,13
 jnz dke5
 call DoSpaceBar
 ret
dke5

 ret
DoKeyEvent endp

DoShortCutKey proc near
if NEED_ALTKEYS ne 0
 push ds
 pop es
 mov di,offset ScanCodeTable_End - 1
 mov cx,offset ScanCodeTable_End - offset ScanCodeTable
 std
 push ax
 mov al,ah
 repnz scasb
 pop ax
 cld
 jnz dke8
 sub di,offset ScanCodeTable
 add di,offset AltKeyTable
 mov al,cs:[di+1]
 mov ah,128
 mov wShortCutKey,ax

 mov pTabHandler,offset PointNextTabControl
 call DoTab1
 mov wShortCutKey,0
 jnz dke8
 jmp dkeOret

dke8:
 call GetTabControlType
 call IsEditBox
 jnz dke7
 jmp dkeOret
dke7:
 mov ah,0
 mov al," "
 mov wKeyPressed,ax
 jmp dke1
dkeOret:
 clc
 ret
endif
dke8:
 clc
 ret
DoShortCutKey endp

DoLeftArrowEdit proc near

 cmp wEditBufferInsertPoint,0
 je la1
 stc
 jmp la2
la1.
```

```
dec wEditBufferInsertPoint
clc
lc3:
ret
DoLeftArrowEdit endp

DoRightArrowEdit proc near

call PointEditBufferCurrent
or al,al
jnz ewb0
stc
jmp short re1
ewb0:
mov bx,wEditBufferInsertPoint
ewb1:
inc wEditBufferInsertPoint
clc
re1:
ret
DoRightArrowEdit endp

GetInsertionPixelOffset proc near

push si
push dx
push cx
push bx
mov si,pEditBufferStart
mov bx,pEditBoxFont
mov cx,wEditBufferInsertPoint
xor dx,dx
jcxz gip1
gip2:
lodsb
or al,al
jz gip1
cmp al,' '
jne gip3
jb gip4
gip3:
cmp bDrawStringPWFlag,0
jz gip3a
mov al,'*'
gip3a:
sub al,' '
xor ah,ah
add ax,ax
mov bx,ax
add bx,pEditBoxFont
or ax,ax
jnz gip5
mov al,[bx]
jmp gip6
gip5:
mov bx,[bx]
mov al,[bx]
xor ah,ah
gip6:
add dx,ax
gip4:
loop gip2
gip1:
mov ax,dx
pop bx
pop cx
pop dx
pop si
ret
GetInsertionPixelOffset endp

InsertEditBufferCharacter proc near
push ds
pop es
mov di,pEditBufferStart
mov cx,wEditBufferSize
dec cx
add di,cx
dec di
cmp byte ptr [di],0
jnz ic2
mov si,di
dec si
mov bx,wEditBufferInsertPoint
sub cx,bx
jz ic2
dec cx
jl ic2
je ics1
std
rep movsb
cld
ics1:
inc wEditBufferInsertPoint
mov byte ptr [di],al
ic2:
ret
InsertEditBufferCharacter endp

PointEditBufferCurrent proc near
mov bx,word ptr wEditBufferInsertPoint
mov di,pEditBufferStart
add di,bx
mov al,[di]
ret
PointEditBufferCurrent endp

SetInsertionPointFromClick proc near

push si
push cx
push bx
push dx

cmp ax,wEditBoxLeftPixel
ja sipfc1
xor cx,cx
jmp sipfc30
sipfc1:

sub ax,wEditBoxLeftPixel
mov si,pEditBufferStart
sipfc2:
lodsb
or al,al
jz sipfc2
mov bx,pEditBoxFont
cmp bDrawStringPWFlag,0
jz sipfc6
mov al,'*'
sipfc6:
cmp al,' '
je sipfc4
jb sipfc3
sub al,' '
xor ah,ah
add ax,ax
add bx,ax
mov bx,[bx]
mov al,[bx]
jmp short sipfc5
sipfc4.
mov al,[bx]
sipfc5:
xor ah,ah
sub cx,ax
jge sipfc3
sipfc2:

dec si
sub si,pEditBufferStart
mov ax,si
sipfc30:
mov wEditBufferInsertPoint,ax
pop dx
pop bx
pop cx
pop si
ret
SetInsertionPointFromClick endp

StartCursor proc near
public StartCursor
mov si,pTabRegion
mov bx,[si].pCurrentControl
cmp [bx].ControlType,PWEDITBOX
jnz sc0
mov bDrawStringPWFlag,-1
mov bCursorPWFlag,-1
jmp short sc00
sc0
mov bCursorPWFlag,0
sc00.
mov ax,[bx].pStorageOffset
mov pEditBufferStart,ax
mov ax,[bx].uDataLength
mov wEditBufferSize,ax
mov ax,pNormalFont
mov pCurrentFont,ax
mov wEditBufferInsertPoint,0

mov di,offset rCursorRegion
mov ax,[si].uCurrentTop
inc ax
inc ax
inc ax
inc ax
mov [di].uCurrentTop,ax
mov wEditBoxTopPixel,ax
mov ax,[si].uCurrentBottom
dec ax
dec ax
dec ax
dec ax
mov [di].uCurrentBottom,ax
mov ax,[si].uCurrentRight
sub ax,3
mov wEditBoxRightPixel,ax
mov ax,[si].uCurrentLeft
add ax,3
mov wEditBoxLeftPixel,ax

mov ax,wPenDownColumn
call SetInsertionPointFromClick
call ResumeCursor
mov bDrawStringPWFlag,0
ret
StartCursor endp

ResumeCursor Proc Near
public ResumeCursor
mov al,bCursorPWFlag
mov bDrawStringPWFlag,al

push si
xor ax,ax
mov si,pTabRegion
mov si,[si].pCurrentControl
cmp byte ptr [si].ControlType,KEYEDITBOX
pop si
jne rsc1a
mov ax,wHotKeyRightPixel
or ax,ax
jz rsc1
jmp rsc1b
rsc1a.
call GetInsertionPixelOffset
rsc1:
add ax,wEditBoxLeftPixel
rsc1b:
mov [di].uCurrentLeft,ax
mov [di].uCurrentRight,ax
mov bCursorState,0
mov bCursorActive,-1
call ChangeCursorState
mov bDrawStringPWFlag,0
ret
ResumeCursor endp

StopCursor proc near
public StopCursor

cmp bCursorActive,0
jz sc1
cmp bCursorState,0
jz sc1
call ChangeCursorState
sc1:
mov bCursorActive,0
ret
StopCursor endp


end




Copr. 1995 Zenith Data Systems Corp.
.model small

include utilequ.inc
include uiincled.inc
DATASEG_BEGIN
extrn ControlDataStore:pxArea:byte


pfont0 label word
public pfont0
db 3
db 16


dw ch33,ch34,ch35,ch36,ch37,ch38,ch39
dw
ch40,ch41,ch42,ch43,ch44,ch45,ch46,ch47,ch48,ch4
9
dw
ch50,ch51,ch52,ch53,ch54,ch55,ch56,ch57,ch58,ch5
9
dw
ch60,ch61,ch62,ch63,ch64,ch65,ch66,ch67,ch68,ch6
9
dw
ch70,ch71,ch72,ch73,ch74,ch75,ch76,ch77,ch78,ch7
9
dw
ch80,ch81,ch82,ch83,ch84,ch85,ch86,ch87,ch88,ch8
9
dw
ch90,ch91,ch92,ch93,ch94,ch95,ch96,ch97,ch98,ch9
9
dw
ch100,ch101,ch102,ch103,ch104,ch105,ch106,ch107
,ch108,ch109
dw
ch110,ch111,ch112,ch113,ch114,ch115,ch116,ch117
,ch118,ch119
dw
ch120,ch121,ch122,ch123,ch124,ch125,ch126,ch127
,ch128,ch129
dw
ch130,ch131,ch132,ch133,ch134,ch135,ch136,ch137
,ch138,ch139
dw
ch140,ch141,ch142,ch143,ch144,ch145,ch146,ch147
,ch148,ch149
dw
ch150,ch151,ch152,ch153,ch154,ch155,ch156,ch157
,ch158,ch159
dw
ch160,ch161,ch162,ch163,ch164,ch165,ch166,ch167
,ch168,ch169
dw
ch170,ch171,ch172,ch173,ch174,ch175,ch176,ch177
,ch178,ch179
dw
ch180,ch181,ch182,ch183,ch184,ch185,ch186,ch187
,ch188,ch189
dw
ch190,ch191,ch192,ch193,ch194,ch195,ch196,ch197
,ch198,ch199
dw
ch200,ch201,ch202,ch203,ch204,ch205,ch206,ch207
,ch208,ch209
dw
ch210,ch211,ch212,ch213,ch214,ch215,ch216,ch217
,ch218,ch219
dw
ch220,ch221,ch222,ch223,ch224,ch225,ch226,ch227
,ch228,ch229
dw
ch230,ch231,ch232,ch233,ch234,ch235,ch236,ch237
,ch238,ch239
dw
ch240,ch241,ch242,ch243,ch244,ch245,ch246,ch247
,ch248,ch249
dw ch250,ch251,ch252,ch253,ch254,ch255


ch33 label byte
DB 4,021h
DB _XX_____
DB _XX_____
DB _XX_____
DB _XX_____
DB _XX_____
DB _XX_____
DB _XX_____
DB ________
DB _XX_____
DB _XX_____

ch34 label byte
DB 6,021h
DB XX__XX__
DB XX__XX__
DB XX__XX__
DB XX__XX__

ch35 label byte
DB 8,021h
DB __XX_XX_
DB __XX_XX_
DB _XXXXXXX
DB __XX_XX_
DB __XX_XX_
DB _XX_XX__
DB _XX_XX__
DB XXXXXXX_
DB _XX_XX__
DB _XX_XX__

ch36 label byte
DB 8,021h
DB ___XX___
DB __XXXX__
DB _XX__XX_
DB _XX__XX_
DB _XX_____
DB __XXXX__
DB _____XX_
DB _____XX_
DB _XX__XX_
DB __XXXX__
DB ___XX___

ch37 label byte
DB 11,022h
DB _XXX_____XX_____
DB XX_XX___XX______
DB XX_XX__XX_______
DB XX_XX_XX________
DB _XXX_XX_________
```

```
DB ____XX_X.XX______
DB ___XX_XX_XX______
DB __XX__XX_XX______
DB _XX___XX_XX______
DB XX_____X.XX______

ch38 label byte
DB 6,021h
DB ___XXX__
DB __XX_XX_
DB __XX_XX_
DB __XX_XX_
DB ___XXX__
DB __XXX___
DB _XX_XX_X
DB _XX__XXX
DB _XX__XX_
DB __XXXXXX

ch39 label byte
DB 4,021h
DB _XX_____
DB _XX_____
DB _XX_____
DB _XX_____

ch40 label byte
DB 4,021h
DB __XX____
DB _XX_____
DB _XX_____
DB _XX_____
DB _XX_____
DB _XX_____
DB _XX_____
DB _XX_____
DB _XX_____
DB _XX_____
DB _XX_____
DB _XX_____
DB __XX____

ch41 label byte
DB 4,021h
DB XX______
DB _XX_____
DB _XX_____
DB _XX_____
DB _XX_____
DB _XX_____
DB _XX_____
DB _XX_____
DB _XX_____
DB _XX_____
DB _XX_____
DB _XX_____
DB XX______

ch42 label byte
DB 6,021h
DB __XX____
DB XXXXXX__
DB __XX____
DB _XXXX___
DB _X__X___

ch43 label byte
DB 6,041h
DB ___XX___
DB ___XX___
DB ___XX___
DB _XXXXXX_
DB ___XX___
DB ___XX___
DB ___XX___

ch44 label byte
DB 4,0A1h
DB _XX_____
DB _XX_____
DB XX______

ch45 label byte
DB 5,071h
DB XXXX____

ch46 label byte
DB 4,0A1h
DB _XX_____
DB _XX_____

ch47 label byte
DB 4,021h
DB __XX____
DB __XX____
DB __XX____
DB __XX____
DB _XX_____
DB _XX_____

DB _XX_____
DB _XX_____
DB XX______
DB XX______
DB XX______
DB XX______

ch48 label byte
DB 6,021h
DB __XXXX__
DB _XX__XX_
DB _XX__XX_
DB _XX__XX_
DB _XX__XX_
DB _XX__XX_
DB _XX__XX_
DB _XX__XX_
DB _XX__XX_
DB _XX__XX_
DB __XXXX__

ch49 label byte
DB 6,021h
DB ___XX___
DB _XXXX___
DB ___XX___
DB ___XX___
DB ___XX___
DB ___XX___
DB ___XX___
DB ___XX___
DB ___XX___
DB ___XX___
DB ___XX___

ch50 label byte
DB 6,021h
DB __XXXX__
DB _XX__XX_
DB _XX__XX_
DB _____XX_
DB ____XX__
DB ___XX___
DB __XX____
DB _XX_____
DB _XX_____
DB _XX_____
DB _XXXXXX_

ch51 label byte
DB 6,021h
DB __XXXX__
DB _XX__XX_
DB _____XX_
DB _____XX_
DB ___XXX__
DB _____XX_
DB _____XX_
DB _____XX_
DB _XX__XX_
DB __XXXX__

ch52 label byte
DB 6,021h
DB _____XX_
DB ____XXX_
DB ___XXXX_
DB __XXXXX_
DB __XX_XX_
DB _XX__XX_
DB _XX__XX_
DB _XXXXXX_
DB _____XX_
DB _____XX_

ch53 label byte
DB 6,021h
DB _XXXXXX_
DB _XX_____
DB _XX_____
DB _XX_____
DB _XXXXX__
DB _XX__XX_
DB _____XX_
DB _____XX_
DB _XX__XX_
DB __XXXX__

ch54 label byte
DB 6,021h
DB __XXXX__
DB _XX__XX_
DB _XX_____
DB _XX_____
DB _XXXXX__
DB _XX__XX_
DB _XX__XX_
DB _XX__XX_
DB _XX__XX_
DB __XXXX__

ch55 label byte
DB 6,021h
DB _XXXXXX_
DB _____XX_
DB _____XX_
DB ____XX__
DB ___XX___
DB ___XX___
DB __XX____
DB __XX____
DB __XX____
DB __XX____

ch56 label byte
DB 6,021h
DB __XXXX__
DB _XX__XX_
DB _XX__XX_
DB _XX__XX_
DB __XXXX__
DB _XX__XX_
DB _XX__XX_
DB _XX__XX_
DB _XX__XX_
DB __XXXX__

ch57 label byte
DB 6,021h
DB __XXXX__
DB _XX__XX_
DB _XX__XX_
DB _XX__XX_
DB _XX__XX_
DB __XXXXX_
DB _____XX_
DB _____XX_
DB _XX__XX_
DB __XXXX__

ch58 label byte
DB 4,041h
DB _XX_____
DB _XX_____
DB ________
DB ________
DB ________
DB ________
DB _XX_____
DB _XX_____

ch59 label byte
DB 4,041h
DB _XX_____
DB _XX_____
DB ________
DB ________
DB ________
DB ________
DB _XX_____
DB _XX_____
DB XX______

ch60 label byte
DB 6,031h
DB _____XX_
DB ____XX__
DB ___XX___
DB __XX____
DB _XX_____
DB __XX____
DB ___XX___
DB ____XX__
DB _____XX_

ch61 label byte
DB 6,061h
DB _XXXXXX_
DB ________
DB ________
DB _XXXXXX_

ch62 label byte
DB 6,031h
DB _XX_____
DB __XX____
DB ___XX___
DB ____XX__
DB _____XX_
DB ____XX__
DB ___XX___
DB __XX____
DB _XX_____

ch63 label byte
DB 6,021h
DB __XXXX__
DB _XX__XX_
DB _XX__XX_
DB _____XX_
DB ____XX__

DB ___XX___
DB ___XX___
DB ________
DB ___XX___
DB ___XX___

ch64 label byte
DB 14,012h
DB _____XXX.X________
DB ___XXX___XXX______
DB __XX_______XX_____
DB __XX__XXX_XX______
DB _XX__XX_XX_XX_____
DB _XX__XX_XX_XX_____
DB _XX_XX__XX_XX_____
DB _XX_XX_XX__XX_____
DB _XX_XX_XX__XX_____
DB __XX_XX_XXXX______
DB __XX______________
DB ___XXX____XXX_____
DB _____XXXXXX_______

ch65 label byte
DB 8,021h
DB ___XX___
DB ___XX___
DB __XXXX__
DB __XXXX__
DB __X__X__
DB _XX__XX_
DB _XX__XX_
DB _XXXXXX_
DB XX____XX
DB XX____XX

ch66 label byte
DB 10,022h
DB _XXXXXXX__________
DB _XX____X.X________
DB _XX____X.X________
DB _XX____X.X________
DB _XXXXXXX__________
DB _XX____X.X________
DB _XX____X.X________
DB _XX____X.X________
DB _XX____X.X________
DB _XXXXXXX__________

ch67 label byte
DB 8,021h
DB ___XXXX_
DB __XX__XX
DB _XX____X
DB _XX_____
DB _XX_____
DB _XX_____
DB _XX_____
DB _XX____X
DB __XX__XX
DB ___XXXX_

ch68 label byte
DB 10,022h
DB _XXXXXX___________
DB _XX___XX__________
DB _XX____X.X________
DB _XX____X.X________
DB _XX____X.X________
DB _XX____X.X________
DB _XX____X.X________
DB _XX____X.X________
DB _XX___XX__________
DB _XXXXXX___________

ch69 label byte
DB 8,021h
DB _XXXXXXX
DB _XX_____
DB _XX_____
DB _XX_____
DB _XXXXXX_
DB _XX_____
DB _XX_____
DB _XX_____
DB _XX_____
DB _XXXXXXX

ch70 label byte
DB 8,021h
DB _XXXXXXX
DB _XX_____
DB _XX_____
DB _XX_____
DB _XXXXXX_
DB _XX_____
DB _XX_____
DB _XX_____
DB _XX_____
DB _XX_____
```

ch71 label byte
DB 10,022h
DB ___XXXXX_______
DB __XX___X.X______
DB _XX_____X______
DB _XX____________
DB _XX____________
DB _XX__XXX.X_____
DB _XX____X.X_____
DB _XX____X.X_____
DB __XX___X.X_____
DB ___XXXX_X______ ch72 label byte
DB 10,022h
DB _XX____X.X_____
DB _XX____X.X_____
DB _XX____X.X_____
DB _XX____X.X_____
DB _XXXXXXX.X_____
DB _XX____X.X_____
DB _XX____X.X_____
DB _XX____X.X_____
DB _XX____X.X_____
DB _XX____X.X_____ ch73 label byte
DB 4,021h
DB _XX____
DB _XX____
DB _XX____
DB _XX____
DB _XX____
DB _XX____
DB _XX____
DB _XX____
DB _XX____
DB _XX____ ch74 label byte
DB 7,021h
DB ____XX_
DB ____XX_
DB ____XX_
DB ____XX_
DB ____XX_
DB ____XX_
DB ____XX_
DB XX__XX_
DB XX__XX_
DB _XXXX__ ch75 label byte
DB 8,022h
DB _XX__XX________
DB _XX_XX_________
DB _XX_XX_________
DB _XXXX__________
DB _XXX___________
DB _XXXX__________
DB _XX_XX_________
DB _XX__XX________
DB _XX__XX________
DB _XX___XX_______ ch76 label byte
DB 8,021h
DB _XX_____
DB _XX_____
DB _XX_____
DB _XX_____
DB _XX_____
DB _XX_____
DB _XX_____
DB _XX_____
DB _XX_____
DB _XXXXXXX ch77 label byte
DB 12,022h
DB _XX______XX____
DB _XX______XX____
DB _XXX____XXX____
DB _XXX____XXX____
DB _XXXX__X.XXX___
DB _XXXX__X.XXX___
DB _XX_XXXX_XX____
DB _XX_XXXX._XX___
DB _XX__XX__XX____
DB _XX__XX__XX____ ch78 label byte
DB 10,022h
DB _XX____X.X_____
DB _XXX___X.X_____
DB _XXXX__X.X_____
DB _XXXX__X.X_____
DB _XX_XX_X.X_____
DB _XX_XX_X.X_____
DB _XX__XXX.X______
DB _XX__XXX.X______
DB _XX__XXX.X______
DB _XX___XX.X______ ch7C label byte
DB 10,022h
DB ___XXXX________
DB __XX__XX_______
DB _XX____X.X_____
DB _XX____X.X_____
DB _XX____X.X_____
DB _XX____X.X_____
DB _XX____X.X_____
DB _XX____X.X_____
DB __XX__XX_______
DB ___XXXX________ ch80 label byte
DB 8,022h
DB _XXXXXXX_______
DB _XX____X.X_____
DB _XX____X.X_____
DB _XX____X.X_____
DB _XX____X.X_____
DB _XXXXXXX_______
DB _XX____________
DB _XX____________
DB _XX____________
DB _XX____________
DB _XX____________ ch81 label byte
DB 10,022h
DB ___XXXX________
DB __XX__XX_______
DB _XX____X.X_____
DB _XX____X.X_____
DB _XX____X.X_____
DB _XX____X.X_____
DB _XX____X.X_____
DB _XX_XXXX.X_____
DB __XX__XX.X_____
DB ___XXXXX.X_____ ch82 label byte
DB 10,022h
DB _XXXXXXX_______
DB _XX____X.X_____
DB _XX____X.X_____
DB _XX____X.X_____
DB _XX____X.X_____
DB _XXXXXXX_______
DB _XX____X.X_____
DB _XX____X.X_____
DB _XX____X.X_____
DB _XX_____XX_____ ch83 label byte
DB 6,021h
DB __XXXXX_
DB _XX___XX
DB _XX___XX
DB _XX_____
DB __XXX___
DB ____XXX_
DB ______XX
DB _XX___XX
DB _XX___XX
DB __XXXXX_ ch84 label byte
DB 8,021h
DB XXXXXXXX
DB ___XX___
DB ___XX___
DB ___XX___
DB ___XX___
DB ___XX___
DB ___XX___
DB ___XX___
DB ___XX___
DB ___XX___ ch8a label byte
DB 10,022h
DB _XX____X.X_____
DB _XX____X.X_____
DB _XX____X.X_____
DB _XX____X.X_____
DB _XX____X.X_____
DB _XX____X.X_____
DB _XX____X.X_____
DB _XX____X.X_____
DB __XX__XX_______
DB ___XXXX________ ch86 label byte
DB 8,021h
DB XX____XX
DB XX____XX
DB _XX__XX_
DB _XX__XX_
DB _XX__XX_
DB __X__X__
DB __XXXX__
DB __XXXX__
DB ___XX___
DB ___XX___ ch87 label byte
DB 14,022h
DB XX____XX____XX__
DB XX____XX____XX__
DB XX____XX____XX__
DB _XX__XXXX_XX___
DB _XX__XXXX_XX___
DB __XX_X__X_XX___
DB __XXXX__XXXX___
DB ___XX____XX____
DB ___XX____XX____
DB ___XX____XX____ ch88 label byte
DB 8,022h
DB XX_____X.X_______
DB XX_____X.X_______
DB _XX___XX_______
DB __XX_XX________
DB ___XXX_________
DB ___XXX_________
DB __XX_XX________
DB _XX___XX_______
DB XX_____X.X_______
DB XX_____X.X_______ ch89 label byte
DB 10,022h
DB XX_______XX______
DB XX_______XX______
DB _XX____X.X_______
DB __XX__XX_______
DB ___XXXX________
DB ____XX_________
DB ____XX_________
DB ____XX_________
DB ____XX_________
DB ____XX_________ ch90 label byte
DB 8,022h
DB XXXXXXXX.X_______
DB ________X.X______
DB _______XX_______
DB ______XX________
DB _____XX_________
DB ____XX__________
DB __XX____________
DB _XX_____________
DB XX______________
DB XXXXXXXX.X_______ ch91 label byte
DB 4,021h
DB _XXX____
DB _XX_____
DB _XX_____
DB _XX_____
DB _XX_____
DB _XX_____
DB _XX_____
DB _XX_____
DB _XX_____
DB _XX_____
DB _XX_____
DB _XX_____
DB _XXX____ ch92 label byte
DB 4,021h
DB XX______
DB XX______
DB XX______
DB XX______
DB _XX_____
DB _XX_____
DB _XX_____
DB _XX_____
DB __XX____
DB __XX____
DB __XX____
DB __XX____ ch93 label byte
DB 4,021h
DB XXX_____
DB _XX_____
DB _XX_____
DB _XX_____
DB _XX_____
DB _XX_____
DB _XX_____
DB _XX_____
DB _XX_____
DB _XX_____
DB _XX_____
DB _XX_____
DB XXX_____ ch94 label byte
DB 5,021h
DB __X_____
DB _XXX____
DB XX_XX___ ch95 label byte
DB 8,0E1h
DB XXXXXXXX ch96 label byte
DB 5,011h
DB _XXX____
DB __XX____
DB ___XX___ ch97 label byte
DB 8,061h
DB __XXXX__
DB _XX__XX_
DB ___XXXX_
DB __XX_XX_
DB _XX__XX_
DB _XX__XX_
DB __XXXXX_ ch98 label byte
DB 8,021h
DB _XX_____
DB _XX_____
DB _XX_____
DB _XXXXX__
DB _XX__XX_
DB _XX__XX_
DB _XX__XX_
DB _XX__XX_
DB _XX__XX_
DB _XXXXX__ ch99 label byte
DB 7,061h
DB __XXXX__
DB _XX__XX_
DB _XX_____
DB _XX_____
DB _XX_____
DB _XX__XX_
DB __XXXX__ ch100 label byte
DB 8,021h
DB _____XX_
DB _____XX_
DB _____XX_
DB __XXXXX_
DB _XX__XX_
DB _XX__XX_
DB _XX__XX_
DB _XX__XX_
DB _XX__XX_
DB __XXXXX_ ch101 label byte
DB 8,061h
DB __XXXX__
DB _XX__XX_
DB _XXXXXX_
DB _XX_____
DB _XX_____
DB _XX__XX_
DB __XXXX__ ch102 label byte
DB 4,021h
DB __XX____
DB _XX_____
DB _XX_____
DB XXXX____
DB _XX_____
DB _XX_____
DB _XX_____
DB _XX_____
DB _XX_____
DB _XX_____ ch103 label byte
DB 8,051h
DB __XXXXX_
DB _XX__XX_

DB _XX__XX_
DB _XX__XX_
DB _XX__XX_
DB _XX__XX_
DB __XXXXX_
DB _____XX_
DB _XX__XX_
DB __XXXX__ ch104 label byte
DB 8,021h
DB _XX_____
DB _XX_____
DB _XX_____
DB _XXXXX__
DB _XX__XX_
DB _XX__XX_
DB _XX__XX_
DB _XX__XX_
DB _XX__XX_
DB _XX__XX_ ch105 label byte
DB 4,021h
DB _XX_____
DB _XX_____
DB ________
DB _XX_____
DB _XX_____
DB _XX_____
DB _XX_____
DB _XX_____
DB _XX_____
DB _XX_____ ch106 label byte
DB 4,021h
DB _XX_____
DB _XX_____
DB ________
DB _XX_____
DB _XX_____
DB _XX_____
DB _XX_____
DB _XX_____
DB _XX_____
DB _XX_____
DB _XX_____
DB _XX_____
DB XX______ ch107 label byte
DB 7,021h
DB _XX_____
DB _XX_____
DB _XX_____
DB _XX__XX_
DB _XX_XX__
DB _XXXX___
DB _XXX____
DB _XXXX___
DB _XX_XX__
DB _XX__XX_ ch108 label byte
DB 4,021h
DB _XX_____
DB _XX_____
DB _XX_____
DB _XX_____
DB _XX_____
DB _XX_____
DB _XX_____
DB _XX_____
DB _XX_____
DB _XX_____ ch109 label byte
DB 12,062h
DB _XXXXXXX_XX_____
DB _XX__XX__XX_____
DB _XX__XX__XX_____
DB _XX__XX__XX_____
DB _XX__XX__XX_____
DB _XX__XX__XX_____
DB _XX__XX__XX_____ ch110 label byte
DB 8,061h
DB _XXXXX__
DB _XX__XX_
DB _XX__XX_
DB _XX__XX_
DB _XX__XX_
DB _XX__XX_
DB _XX__XX_ ch111 label byte
DB 8,051h
DB __XXXX__
DB _XX__XX_
DB _XX__XX_
DB _XX__XX_
DB _XX__XX_
DB __XXXX__ ch112 label byte
DB 8,051h
DB _XXXXX__
DB _XX__XX_
DB _XX__XX_
DB _XX__XX_
DB _XX__XX_
DB _XX__XX_
DB _XXXXX__
DB _XX_____
DB _XX_____
DB _XX_____ ch113 label byte
DB 8,061h
DB __XXXXX_
DB _XX__XX_
DB _XX__XX_
DB _XX__XX_
DB _XX__XX_
DB _XX__XX_
DB __XXXXX_
DB _____XX_
DB _____XX_
DB _____XX_ ch114 label byte
DB 5,061h
DB _XXXX___
DB _XXX____
DB _XX_____
DB _XX_____
DB _XX_____
DB _XX_____
DB _XX_____ ch115 label byte
DB 8,061h
DB __XXXX__
DB _XX__XX_
DB _XX_____
DB __XXXX__
DB _____XX_
DB _XX__XX_
DB __XXXX__ ch116 label byte
DB 4,031h
DB _XX_____
DB _XX_____
DB XXXX____
DB _XX_____
DB _XX_____
DB _XX_____
DB _XX_____
DB _XX_____
DB __XX____ ch117 label byte
DB 8,061h
DB _XX__XX_
DB _XX__XX_
DB _XX__XX_
DB _XX__XX_
DB _XX__XX_
DB _XX__XX_
DB __XXXXX_ ch118 label byte
DB 8,061h
DB XX____XX
DB XX____XX
DB _XX__XX_
DB _XX__XX_
DB __XXXX__
DB ___XX___
DB ___XX___ ch119 label byte
DB 10,062h
DB XX______XX_____
DB XX__XX__XX_____
DB _XX_XX_XX______
DB _XX_XX_XX______
DB _XXXXXXX_______
DB __XX__XX_______
DB __XX__XX_______ ch120 label byte
DB 8,051h
DB XX____XX
DB _XX__XX_
DB __XXXX__
DB ___XX___
DB __XXXX__
DB _XX__XX_
DB XX____XX ch121 label byte
DB 8,061h
DB XX____XX
DB XX____XX
DB _XX__XX_
DB _XX__XX_
DB __XXXX__
DB __XXXX__
DB ___XX___
DB ___XX___
DB __XX____
DB _XX_____ ch122 label byte
DB 8,061h
DB _XXXXXX_
DB _____XX_
DB ____XX__
DB ___XX___
DB __XX____
DB _XX_____
DB _XXXXXX_ ch123 label byte
DB 5,021h
DB ___XX___
DB __XX____
DB __XX____
DB __XX____
DB __XX____
DB __XX____
DB _XX_____
DB __XX____
DB __XX____
DB __XX____
DB __XX____
DB __XX____
DB ___XX___ ch124 label byte
DB 4,021h
DB _XX_____
DB _XX_____
DB _XX_____
DB _XX_____
DB _XX_____
DB _XX_____
DB _XX_____
DB _XX_____
DB _XX_____
DB _XX_____
DB _XX_____
DB _XX_____
DB _XX_____ ch125 label byte
DB 5,021h
DB XX______
DB _XX_____
DB _XX_____
DB _XX_____
DB _XX_____
DB _XX_____
DB __XX____
DB _XX_____
DB _XX_____
DB _XX_____
DB _XX_____
DB _XX_____
DB XX______ ch126 label byte
DB 5,021h
DB XXX_X___
DB X_XXX___ ch127 label byte
DB 4,031h
DB _XX_____
DB _XX_____
DB _XX_____
DB _XX_____
DB _XX_____
DB _XX_____
DB _XX_____
DB _XX_____
DB _XX_____
DB _XX_____ ch128 label byte
DB 8,021h
DB __XXXX__
DB _XX__XX

DB _XX____X
DB _XX_____
DB _XX_____
DB _XX_____
DB _XX_____
DB _XX____X
DB __XX__XX
DB ___XXXX_
DB ____XX__
DB _____XX_
DB ___XXX__ ch129 label byte
DB 8,021h
DB _XX__XX_
DB _XX__XX_
DB ________
DB _XX__XX_
DB _XX__XX_
DB _XX__XX_
DB _XX__XX_
DB _XX__XX_
DB _XX__XX_
DB __XXXXX_ ch130 label byte
DB 8,011h
DB ___XXX__
DB ___XX___
DB __XX____
DB ________
DB __XXXX__
DB _XX__XX_
DB _XXXXXX_
DB _XX_____
DB _XX_____
DB _XX__XX_
DB __XXXX__ ch131 label byte
DB 8,011h
DB ___XX___
DB __XXXX__
DB _XX__XX_
DB ________
DB __XXXX__
DB _XX__XX_
DB ___XXXX_
DB __XX_XX_
DB _XX__XX_
DB _XX__XX_
DB __XXXXX_ ch132 label byte
DB 8,021h
DB _XX__XX_
DB _XX__XX_
DB ________
DB __XXXX__
DB _XX__XX_
DB ___XXXX_
DB __XX_XX_
DB _XX__XX_
DB _XX__XX_
DB __XXXXX_ ch133 label byte
DB 8,011h
DB __XXX___
DB ___XX___
DB ____XX__
DB ________
DB __XXXX__
DB _XX__XX_
DB ___XXXX_
DB __XX_XX_
DB _XX__XX_
DB _XX__XX_
DB __XXXXX_ ch134 label byte
DB 8,011h
DB ___XX___
DB __XXXX__
DB ___XX___
DB ________
DB __XXXX__
DB _XX__XX_
DB ___XXXX_
DB __XX_XX_
DB _XX__XX_
DB _XX__XX_
DB __XXXXX_ ch135 label byte
DB 7,051h
DB __XXXX__
DB _XX__XX_
DB _XX_____

```
DB _XX_____
DB _XX_____
DB _XX__XX_
DB __XXXX__
DB ___XX___
DB ____XX__
DB __XXX___

ch136 label byte
DB 8,011h
DB ___XX___
DB __XXXX__
DB _XX__XX_
DB ________
DB __XXXX__
DB _XX__XX_
DB _XXXXXX_
DB _XX_____
DB _XX_____
DB _XX__XX_
DB __XXXX__

ch137 label byte
DB 8,021h
DB _XX__XX_
DB _XX__XX_
DB ________
DB __XXXX__
DB _XX__XX_
DB _XXXXXX_
DB _XX_____
DB _XX_____
DB _XX__XX_
DB __XXXX__

ch138 label byte
DB 8,011h
DB __XXX___
DB ___XX___
DB ____XX__
DB ________
DB __XXXX__
DB _XX__XX_
DB _XXXXXX_
DB _XX_____
DB _XX_____
DB _XX__XX_
DB __XXXX__

ch139 label byte
DB 4,021h
DB X__X____
DB X__X____
DB ________
DB _XX_____
DB _XX_____
DB _XX_____
DB _XX_____
DB _XX_____
DB _XX_____
DB _XX_____

ch140 label byte
DB 4,011h
DB _XX_____
DB XXXX____
DB ________
DB ________
DB _XX_____
DB _XX_____
DB _XX_____
DB _XX_____
DB _XX_____
DB _XX_____
DB _XX_____

ch141 label byte
DB 4,011h
DB XXX_____
DB _XX_____
DB __XX____
DB ________
DB _XX_____
DB _XX_____
DB _XX_____
DB _XX_____
DB _XX_____
DB _XX_____
DB _XX_____

ch142 label byte
DB 6,001h
DB _XX__XX_
DB ________
DB ___XX___
DB ___XX___
DB __XXXX__
DB __XXXX__
DB __X__X__

DB _XX__XX_
DB _XX__XX_
DB _XXXXXX_
DB XX____XX
DB XX____XX

ch143 label byte
DB 8,001h
DB __XXXX__
DB ___XX___
DB ________
DB ___XX___
DB ___XX___
DB __XXXX__
DB __X__X__
DB _XX__XX_
DB _XX__XX_
DB _XXXXXX_
DB XX____XX
DB XX____XX

ch144 label byte
DB 6,001h
DB ____XX__
DB ___XX___
DB _XXXXXXX
DB _XX_____
DB _XX_____
DB _XX_____
DB _XXXXXX_
DB _XX_____
DB _XX_____
DB _XX_____
DB _XX_____
DB _XXXXXXX

ch145 label byte
DB 12,062h
DB __XXXXXX_XX_____
DB _XX__XX__XX_____
DB ___XXXXX_XXX____
DB __XX_XX_________
DB _XX__XX_________
DB _XX__XX__XX_____
DB __XXXXXX_XX_____

ch146 label byte
DB 13,022h
DB ___XXXXX_XXXX___
DB __XXXX__________
DB _XX_XX__________
DB _XX_XX__________
DB _XX_XXXXXXX_____
DB _XX__XX_________
DB _XX__XX_________
DB _XXXXXX_________
DB XX___XX_________
DB XX___XXX_XXXX___

ch147 label byte
DB 8,011h
DB ___XX___
DB __XXXX__
DB _XX__XX_
DB ________
DB __XXXX__
DB _XX__XX_
DB _XX__XX_
DB _XX__XX_
DB _XX__XX_
DB _XX__XX_
DB __XXXX__

ch148 label byte
DB 8,021h
DB _XX__XX_
DB _XX__XX_
DB ________
DB __XXXX__
DB _XX__XX_
DB _XX__XX_
DB _XX__XX_
DB _XX__XX_
DB _XX__XX_
DB __XXXX__

ch149 label byte
DB 8,011h
DB __XXX___
DB ___XX___
DB ____XX__
DB ________
DB __XXXX__
DB _XX__XX_
DB _XX__XX_
DB _XX__XX_
DB _XX__XX_
DB _XX__XX_
DB __XXXX__

ch150 label byte
DB 8,011h
DB ___XX___
DB __XXXX__
DB _XX__XX_
DB ________
DB _XX__XX_
DB _XX__XX_
DB _XX__XX_
DB _XX__XX_
DB _XX__XX_
DB _XX__XX_
DB __XXXXX_

ch151 label byte
DB 8,011h
DB __XXX___
DB ___XX___
DB ____XX__
DB ________
DB _XX__XX_
DB _XX__XX_
DB _XX__XX_
DB _XX__XX_
DB _XX__XX_
DB _XX__XX_
DB __XXXXX_

ch152 label byte
DB 8,021h
DB _XX__XX_
DB _XX__XX_
DB ________
DB XX____XX
DB XX____XX
DB _XX__XX_
DB _XX__XX_
DB __XXXX__
DB __XXXX__
DB ___XX___
DB ___XX___
DB __XX____
DB _XX_____

ch153 label byte
DB 10,062h
DB __XX__XX________
DB ________________
DB ___XXXX_________
DB __XX__XX________
DB _XX____XX_______
DB _XX____XX_______
DB _XX____XX_______
DB _XX____XX_______
DB _XX____XX_______
DB _XX____XX_______
DB __XX__XX________
DB ___XXXX_________

ch154 label byte
DB 10,062h
DB __XX__XX________
DB ________________
DB _XX____XX_______
DB _XX____XX_______
DB _XX____XX_______
DB _XX____XX_______
DB _XX____XX_______
DB _XX____XX_______
DB _XX____XX_______
DB _XX____XX_______
DB __XX__XX________
DB ___XXXX_________

ch155 label byte
DB 8,041h
DB ___XX___
DB __XXXX__
DB _XX_XXX_
DB _XX_X___
DB _XX_X___
DB _XXX____
DB _XXX_XX_
DB __XXXX__
DB __XX____

ch156 label byte
DB 8,021h
DB __XXX___
DB _XX_XX__
DB _XX_____
DB _XX_____
DB __XX____
DB _XXXX___
DB __XX____
DB __XX____
DB _XX__XX_
DB _XXXXX__

ch157 label byte
DB 8,021h
DB XX____XX
DB XX____XX
DB _XX__XX_
DB _XX__XX_
DB XXXXXXXX
DB ___XX___
DB XXXXXXXX
DB ___XX___
DB ___XX___
DB ___XX___

ch158 label byte
DB 8,061h
DB _XXXXX__
DB _XX__XX_
DB _XX__XX_
DB _XX__XX_
DB _XX__XX_
DB _XX__XX_
DB _XXXXX__
DB _XX_____
DB _XX_____
DB _XX_____

ch159 label byte
DB 4,021h
DB __XX____
DB _XX_____
DB _XX_____
DB XXXX____
DB _XX_____
DB _XX_____
DB _XX_____
DB _XX_____
DB _XX_____
DB _XX_____

ch160 label byte
DB 8,011h
DB ___XXX__
DB ___XX___
DB __XX____
DB ________
DB __XXXX__
DB _XX__XX_
DB ___XXXX_
DB __XX_XX_
DB _XX__XX_
DB _XX__XX_
DB __XXXXX_

ch161 label byte
DB 4,011h
DB _XXX____
DB _XX_____
DB XX______
DB ________
DB _XX_____
DB _XX_____
DB _XX_____
DB _XX_____
DB _XX_____
DB _XX_____
DB _XX_____

ch162 label byte
DB 8,011h
DB ___XXX__
DB ___XX___
DB __XX____
DB ________
DB __XXXX__
DB _XX__XX_
DB _XX__XX_
DB _XX__XX_
DB _XX__XX_
DB _XX__XX_
DB __XXXX__

ch163 label byte
DB 8,011h
DB ___XXX__
DB ___XX___
DB __XX____
DB ________
DB _XX__XX_
DB _XX__XX_
DB _XX__XX_
DB _XX__XX_
DB _XX__XX_
DB _XX__XX_
DB __XXXXX_

ch164 label byte
DB 8,021h
DB _XXXX_X_
DB _X_XXXX_
```

```
DB ________
DB _XXXXX__
DB _XX__XX_
DB _XX__XX_
DB _XX__XX_
DB _XX__XX_
DB _XX__XX_
DB _XX__XX_

ch165 label byte
DB 16,002h
DB __X_XXXX________
DB ________________
DB _XX___X_X_______
DB _XXX__X_X_______
DB _XXXX_X_X_______
DB _XXXX_X_X_______
DB _XX_XX_X_X______
DB _XX_XX_X_X______
DB _XX__XXX_X______
DB _XX__XXX_X______
DB _XX___XX_X______
DB _XX___X_X_______

ch166 label byte
DB 8,021h
DB __X_____
DB ___X____
DB __XX____
DB _X_X____
DB __XX____
DB ________
DB _XXX____

ch167 label byte
DB 8,021h
DB _XXX____
DB _X_X____
DB _X_X____
DB _X_X____
DB _XXX____
DB ________
DB _XXX____

ch168 label byte
DB 8,021h
DB ___XX___
DB ___XX___
DB ________
DB ___XX___
DB ___XX___
DB __XX____
DB _XX_____
DB _XX__XX_
DB _XX__XX_
DB __XXXX__

ch169 label byte
DB 8,0E1h
DB XXXXXXXX

ch170 label byte
DB 8,061h
DB _XXXXXX_
DB _____XX_
DB _____XX_

ch171 label byte
DB 11,032h
DB __XX_____XX_____
DB _XXX_____XX_____
DB __XX___X_X______
DB __XX__XX________
DB __XX_XX_________
DB _____XX_X_X_____
DB ___XX_X_XX______
DB __XX_____XX_____
DB _XX____X_X______
DB XX_____XX_XX____

ch172 label byte
DB 11,032h
DB __XX_____XX_____
DB _XXX_____XX_____
DB __XX___X_X______
DB __XX__XX________
DB __XX_XX_________
DB _____XX__XX_____
DB ___XX__X_XX_____
DB __XX__XX_X______
DB _XX___XX_XX_____
DB XX_______XX_____

ch173 label byte
DB 4,021h
DB _XX_____
DB _XX_____
DB ________
DB _XX_____
DB _XX_____
DB _XX_____
DB _XX_____
DB _XX_____
DB _XX_____
DB _XX_____

ch174 label byte
DB 7,061h
DB __XX_XX_
DB _XX_XX__
DB XX_XX___
DB _XX_XX__
DB __XX_XX_

ch175 label byte
DB 7,061h
DB XX_XX___
DB _XX_XX__
DB __XX_XX_
DB _XX_XX__
DB XX_XX___

ch176 label byte
DB 8,0E1h
DB XXXXXXXX

ch177 label byte
DB 8,0E1h
DB XXXXXXXX

ch178 label byte
DB 8,0E1h
DB XXXXXXXX

ch179 label byte
DB 4,031h
DB _XX_____
DB _XX_____
DB _XX_____
DB _XX_____
DB _XX_____
DB _XX_____
DB ________
DB _XX_____
DB _XX_____
DB _XX_____
DB _XX_____
DB _XX_____
DB _XX_____

ch180 label byte
DB 8,0E1h
DB XXXXXXXX

ch181 label byte
DB 8,0E1h
DB XXXXXXXX

ch182 label byte
DB 8,0E1h
DB XXXXXXXX

ch183 label byte
DB 8,0E1h
DB XXXXXXXX

ch184 label byte
DB 8,0E1h
DB XXXXXXXX

ch185 label byte
DB 8,0E1h
DB XXXXXXXX

ch186 label byte
DB 8,0E1h
DB XXXXXXXX

ch187 label byte
DB 8,0E1h
DB XXXXXXXX

ch188 label byte
DB 8,0E1h
DB XXXXXXXX

ch189 label byte
DB 8,0E1h
DB XXXXXXXX

ch190 label byte
DB 8,0E1h
DB XXXXXXXX

ch191 label byte
DB 8,0E1h
DB XXXXXXXX

ch192 label byte
DB 8,0E1h
DB XXXXXXXX

ch193 label byte
DB 8,0E1h
DB XXXXXXXX

ch194 label byte
DB 8,0E1h
DB XXXXXXXX

ch195 label byte
DB 8,0E1h
DB XXXXXXXX

ch196 label byte
DB 8,0E1h
DB XXXXXXXX

ch197 label byte
DB 8,0E1h
DB XXXXXXXX

ch198 label byte
DB 8,0E1h
DB XXXXXXXX

ch199 label byte
DB 8,0E1h
DB XXXXXXXX

ch200 label byte
DB 8,0E1h
DB XXXXXXXX

ch201 label byte
DB 8,0E1h
DB XXXXXXXX

ch202 label byte
DB 8,0E1h
DB XXXXXXXX

ch203 label byte
DB 8,0E1h
DB XXXXXXXX

ch204 label byte
DB 8,0E1h
DB XXXXXXXX

ch205 label byte
DB 8,0E1h
DB XXXXXXXX

ch206 label byte
DB 8,0E1h
DB XXXXXXXX

ch207 label byte
DB 8,0E1h
DB XXXXXXXX

ch208 label byte
DB 8,0E1h
DB XXXXXXXX

ch209 label byte
DB 8,0E1h
DB XXXXXXXX

ch210 label byte
DB 8,0E1h
DB XXXXXXXX

ch211 label byte
DB 8,0E1h
DB XXXXXXXX

ch212 label byte
DB 8,0E1h
DB XXXXXXXX

ch213 label byte
DB 8,0E1h
DB XXXXXXXX

ch214 label byte
DB 8,0E1h
DB XXXXXXXX

ch215 label byte
DB 8,0E1h
DB XXXXXXXX

ch216 label byte
DB 8,0E1h
DB XXXXXXXX

ch217 label byte
DB 8,0E1h
DB XXXXXXXX

ch218 label byte
DB 8,0E1h
DB XXXXXXXX

ch219 label byte
DB 8,0E1h
DB XXXXXXXX

ch220 label byte
DB 8,0E1h
DB XXXXXXXX

ch221 label byte
DB 8,0E1h
DB XXXXXXXX

ch222 label byte
DB 8,0E1h
DB XXXXXXXX

ch223 label byte
DB 8,0E1h
DB XXXXXXXX

ch224 label byte
DB 8,0E1h
DB XXXXXXXX

ch225 label byte
DB 8,021h
DB __XXXX__
DB _XX__XX_
DB _XX__XX_
DB _XX__XX_
DB _XX_XX__
DB _XX__XX_
DB _XX__XX_
DB _XX__XX_
DB _XX__XX_
DB _XX_XX__

ch226 label byte
DB 8,0E1h
DB XXXXXXXX

ch227 label byte
DB 7,021h
DB __XXXX__
DB _XXXXX__
DB _XXXXX__
DB _XXXXX__
DB _XXXXX__
DB __XXXX__
DB ____XX__
DB ____XX__
DB ____XX__
DB ____XX__

ch228 label byte
DB 8,0E1h
DB XXXXXXXX

ch229 label byte
DB 8,0E1h
DB XXXXXXXX

ch230 label byte
DB 8,041h
DB _XX__XX_
DB _XX__XX_
DB _XX__XX_
DB _XX__XX_
DB _XX__XX_
DB _XX__XX_
DB _XX__XX_
DB _XXXXXXX
DB _XX_____
DB _XX_____
DB _XX_____

ch231 label byte
DB 8,0E1h
DB XXXXXXXX

ch232 label byte
DB 8,0E1h
DB XXXXXXXX

ch233 label byte
DB 8,0E1h
DB XXXXXXXX

ch234 label byte
DB 8,0E1h
DB XXXXXXXX
```

```
ch235 label byte
DB 8,0E1h
DB XXXXXXXX

ch236 label byte
DB 8,0E1h
DB XXXXXXXX

ch237 label byte
DB 10,022h
DB __XXXXX_X______
DB __XX__XX_______
DB _XX__XX_X______
DB _XX_XX_X_X_____
DB _XX_XX_X_X_____
DB _XX_XX_X_X_____
DB _XXXX__X_X_____
DB _XXX__X_X______
DB __XX__XX_______
DB _XXXXXX________

ch238 label byte
DB 8,0E1h
DB XXXXXXXX

ch239 label byte
DB 8,0E1h
DB XXXXXXXX

ch240 label byte
DB 8,0E1h
DB XXXXXXXX

ch241 label byte
DB 8,081h
DB ___XX___
DB __XX____
DB _XXXXXX_
DB __XX____
DB __XX____
DB ________
DB _XXXXXX_

ch242 label byte
DB 8,0E1h
DB XXXXXXXX

ch243 label byte
DB 8,0E1h
DB XXXXXXXX

ch244 label byte
DB 8,0E1h
DB XXXXXXXX

ch245 label byte
DB 8,0E1h
DB XXXXXXXX

ch246 label byte
DB 8,0E1h
DB XXXXXXXX

ch247 label byte
DB 8,0E1h
DB XXXXXXXX

ch248 label byte
DB 5,021h
DB _XXX___
DB _X_X___
DB _X_X___
DB _XXX___

ch249 label byte
DB 4,061h
DB _XX____
DB _XX____

ch250 label byte
DB 4,061h
DB _XX____
DB _XX____

ch251 label byte
DB 8,0E1h
DB XXXXXXXX

ch252 label byte
DB 8,051h
DB _XXXXX__
DB _XX__XX_
DB _XX__XX_
DB _XX__XX_
DB _XX__XX_
DB _XX__XX_
DB _XX__XX_

ch253 label byte
DB 4,021h
DB _XX_____
DB X_XX____
DB __XX____
DB _XX_____
DB XXXX____

ch254 label byte
DB 8,0E1h
DB XXXXXXXX
ch255 label byte

DATASEG_END
end
Copr. 1995 Zenith Data Systems Corp.

.model small

include ctbitreqs.inc
include ctincled.inc
DATASEG_BEGIN
extrn ControlDataStorageArea:byte

offont1 label word
 public offont1
 db 2
 db 16

 dw ch33,ch34,ch35,ch36,ch37,ch38,ch39
 dw
ch40,ch41,ch42,ch43,ch44,ch45,ch46,ch47,ch48,ch4
9
 dw
ch50,ch51,ch52,ch53,ch54,ch55,ch56,ch57,ch58,ch5
9
 dw
ch60,ch61,ch62,ch63,ch64,ch65,ch66,ch67,ch68,ch6
9
 dw
ch70,ch71,ch72,ch73,ch74,ch75,ch76,ch77,ch78,ch7
9
 dw
ch80,ch81,ch82,ch83,ch84,ch85,ch86,ch87,ch88,ch8
9
 dw
ch90,ch91,ch92,ch93,ch94,ch95,ch96,ch97,ch98,ch9
9
 dw
ch100,ch101,ch102,ch103,ch104,ch105,ch106,ch107
,ch108,ch109
 dw
ch110,ch111,ch112,ch113,ch114,ch115,ch116,ch117
,ch118,ch119
 dw
ch120,ch121,ch122,ch123,ch124,ch125,ch126,ch127
,ch128,ch129
 dw
ch130,ch131,ch132,ch133,ch134,ch135,ch136,ch137
,ch138,ch139
 dw
ch140,ch141,ch142,ch143,ch144,ch145,ch146,ch147
,ch148,ch149
 dw
ch150,ch151,ch152,ch153,ch154,ch155,ch156,ch157
,ch158,ch159
 dw
ch160,ch161,ch162,ch163,ch164,ch165,ch166,ch167
,ch168,ch169
 dw
ch170,ch171,ch172,ch173,ch174,ch175,ch176,ch177
,ch178,ch179
 dw
ch180,ch181,ch182,ch183,ch184,ch185,ch186,ch187
,ch188,ch189
 dw
ch190,ch191,ch192,ch193,ch194,ch195,ch196,ch197
,ch198,ch199
 dw
ch200,ch201,ch202,ch203,ch204,ch205,ch206,ch207
,ch208,ch209
 dw
ch210,ch211,ch212,ch213,ch214,ch215,ch216,ch217
,ch218,ch219
 dw
ch220,ch221,ch222,ch223,ch224,ch225,ch226,ch227
,ch228,ch229
 dw
ch230,ch231,ch232,ch233,ch234,ch235,ch236,ch237
,ch238,ch239
 dw
ch240,ch241,ch242,ch243,ch244,ch245,ch246,ch247
,ch248,ch249
 dw ch250,ch251,ch252,ch253,ch254,ch255

ch33 label byte
DB 3,011h
DB _X______
DB _X______
DB _X______
DB _X______
DB _X______
DB _X______
DB ________
DB _X______

ch34 label byte
DB 4,011h
DB _X_X____
DB _X_X____

ch35 label byte
DB 5,011h
DB __X_X___
DB __X_X___
DB _XXXXX__
DB __X_X___
DB _XXXXX__
DB __X_X___
DB __X_X___

ch36 label byte
DB 5,011h
DB ___X____
DB __XXX___
DB _X______
DB __XX____
DB ____X___
DB _X__X___
DB __XX____
DB __X_____

ch37 label byte
DB 10,012h
DB __XX____X_______
DB _X__X__X________
DB _X__X_X_________
DB __XX_X_XX_______
DB _____X_X__X_____
DB ____X__X__X_____
DB ___X____XX______

ch38 label byte
DB 6,011h
DB __XX____
DB _X__X___
DB _X__X___
DB __XX__XX
DB _X__X_X_
DB _X___X__
DB __XXX_X_

ch39 label byte
DB 2,011h
DB _X______
DB _X______

ch40 label byte
DB 3,011h
DB __X_____
DB _X______
DB _X______
DB _X______
DB _X______
DB _X______
DB _X______
DB __X_____

ch41 label byte
DB 3,011h
DB _X______
DB __X_____
DB __X_____
DB __X_____
DB __X_____
DB __X_____
DB __X_____
DB _X______

ch42 label byte
DB 6,011h
DB _X__X___
DB __XX____
DB __XX____
DB _X__X___

ch43 label byte
DB 6,021h
DB ___X____
DB ___X____
DB _XXXXX__
DB ___X____
DB ___X____

ch44 label byte
DB 2,071h
DB _X______
DB _X______

ch45 label byte
DB 3,041h
DB _XX_____

ch46 label byte
DB 2,071h
DB _X______

ch47 label byte
DB 3,011h
DB __X_____
DB __X_____
DB __X_____
DB __X_____
DB _X______
DB _X______
DB _X______

ch48 label byte
DB 5,011h
DB __XX____
DB _X__X___
DB _X__X___
DB _X__X___
DB _X__X___
DB _X__X___
DB __XX____

ch49 label byte
DB 5,011h
DB ___X____
DB __XX____
DB ___X____
DB ___X____
DB ___X____
DB ___X____
DB __XXX___

ch50 label byte
DB 5,011h
DB __XX____
DB _X__X___
DB ____X___
DB ___X____
DB __X_____
DB _X__X___
DB _XXXX___

ch51 label byte
DB 5,011h
DB __XX____
DB _X__X___
DB ____X___
DB ___X____
DB ____X___
DB _X__X___
DB __XX____

ch52 label byte
DB 5,011h
DB ____X___
DB ___XX___
DB __X_X___
DB _X__X___
DB _XXXX___
DB ____X___
DB ____X___

ch53 label byte
DB 5,011h
DB _XXXX___
DB _X______
DB _X______
DB __XX____
DB ____X___
DB _X__X___
DB __XX____

ch54 label byte
DB 5,011h
DB __XX____
DB _X______
DB _X______
DB _XXX____
DB _X__X___
DB _X__X___
DB __XX____

ch55 label byte
DB 5,011h
DB _XXXX___
DB _X__X___
DB ___X____
DB ___X____
DB __X_____
DB __X_____
DB __X_____
```

```
ch56 label byte
DB 5,011h
DB __XX___
DB _X__X__
DB _X__X__
DB __XX___
DB _X__X__
DB _X__X__
DB __XX___

ch57 label byte
DB 6,011h
DB __XX___
DB _X__X__
DB _X__X__
DB __XXX__
DB ____X__
DB ____X__
DB __XX___

ch58 label byte
DB 2,031h
DB _X_____
DB _______
DB _______
DB _______
DB _X_____

ch59 label byte
DB 2,031h
DB _X_____
DB _______
DB _______
DB _______
DB _X_____
DB _X_____

ch60 label byte
DB 5,021h
DB _____X__
DB ___XX___
DB _XX_____
DB ___XX___
DB _____X__

ch61 label byte
DB 6,031h
DB _XXXX___
DB ________
DB _XXXX___

ch62 label byte
DB 5,021h
DB _X______
DB __XX____
DB ____XX__
DB __XX____
DB _X______

ch63 label byte
DB 5,011h
DB __XX____
DB _X__X___
DB ____X___
DB ___X____
DB __X_____
DB ________
DB __X_____

ch64 label byte
DB 9,012h
DB ___XXXX_________
DB __X____X________
DB _X__XXX__X______
DB _X_X__X__X______
DB _X_X__X__X______
DB _X__XX_X________
DB __X_____________
DB ___XXXX_________

ch65 label byte
DB 8,011h
DB ____X___
DB ____X___
DB ___X_X__
DB ___X_X__
DB __XXXXX_
DB __X___X_
DB _XXX_XXX

ch66 label byte
DB 7,011h
DB _XXXX___
DB __X__X__
DB __X__X__
DB __XXX___
DB __X__X__
DB __X__X__
DB _XXXX___

ch67 label byte
DB 7,011h
DB __XXXX_
DB _X___X_
DB _X_____
DB _X_____
DB _X_____
DB _X___X_
DB __XXX__

ch68 label byte
DB 6,011h
DB _XXXX__
DB _X__X_
DB _X__X_
DB _X__X_
DB _X__X_
DB _X__X_
DB _XXXX_

ch69 label byte
DB 7,011h
DB _XXXXX_
DB _X__X_
DB _X____
DB _XXX__
DB _X____
DB _X__X_
DB _XXXXX_

ch70 label byte
DB 6,011h
DB _XXXXX_
DB _X__X_
DB _X____
DB _XXX__
DB _X____
DB _X____
DB _XXX__

ch71 label byte
DB 8,011h
DB __XXXX_
DB _X___X_
DB _X_____
DB _X__XXX
DB _X___X_
DB _X___X_
DB __XXX__

ch72 label byte
DB 6,011h
DB _XXX_XXX
DB _X___X_
DB _X___X_
DB _XXXXX_
DB _X___X_
DB _X___X_
DB _XXX_XXX

ch73 label byte
DB 4,011h
DB _XXX__
DB _X____
DB _X____
DB _X____
DB _X____
DB _X____
DB _XXX__

ch74 label byte
DB 5,011h
DB __XXX_
DB ___X__
DB ___X__
DB ___X__
DB ___X__
DB _X_X__
DB _XX___

ch75 label byte
DB 8,011h
DB _XXX_XX_
DB _X_X__
DB _X_X__
DB _XX___
DB _X_X__
DB _X__X_
DB _XXX__XX

ch76 label byte
DB 6,011h
DB _XXX___
DB _X_____
DB _X_____
DB _X_____
DB _X_____
DB _X___X_
DB _XXXXX__

ch77 label byte
DB 10,013h
DB _XX_____XX______
DB __XX___XX_______
DB __XX___XX_______
DB __X_X_X_X_______
DB __X_X_X_X_______
DB __X__X__X_______
DB _XXX_X_XXX______

ch78 label byte
DB 8,011h
DB _XX__XXX
DB __XX__X_
DB __XX__X_
DB __X_X_X_
DB __X__XX_
DB __X__XX_
DB _XXX__X_

ch79 label byte
DB 8,011h
DB ___XXX__
DB __X___X_
DB __X___X_
DB __X___X_
DB __X___X_
DB __X___X_
DB ___XXX__

ch80 label byte
DB 6,011h
DB _XXXX___
DB __X__X__
DB __X__X__
DB __XXX___
DB __X_____
DB __X_____
DB _XXX____

ch81 label byte
DB 8,011h
DB ___XXX__
DB __X___X_
DB __X___X_
DB __X___X_
DB __X___X_
DB __X___X_
DB ___XXX__
DB _____XXX_

ch82 label byte
DB 7,011h
DB _XXXX___
DB __X__X__
DB __X__X__
DB __XXX___
DB __X_X___
DB __X__X__
DB _XXX_XX_

ch83 label byte
DB 6,011h
DB __XXX___
DB _X___X__
DB _X______
DB __XXX___
DB _____X__
DB _X___X__
DB _XXXX___

ch84 label byte
DB 6,011h
DB _XXXXX__
DB _X_X_X__
DB ___X____
DB ___X____
DB ___X____
DB ___X____
DB __XXX___

ch85 label byte
DB 8,011h
DB _XXX_XXX
DB __X___X_
DB __X___X_
DB __X___X_
DB __X___X_
DB __X___X_
DB ___XXX__

ch86 label byte
DB 8,011h
DB _XXX_XXX
DB __X___X_
DB __X___X_
DB ___X_X__
DB ___X_X__
DB ____X___

ch87 label byte
DB 10,012h
DB _XXX___X_XX______
DB __X__X__X________
DB __X__X__X________
DB __X_X_X_X________
DB __X_X_X_X________
DB ___X___X_________
DB ___X___X_________

ch88 label byte
DB 8,011h
DB _XX___XX
DB __X___X_
DB ___X_X__
DB ____X___
DB ___X_X__
DB __X___X_
DB _XX___XX

ch89 label byte
DB 8,011h
DB _XXX_XXX
DB __X___X_
DB ___X_X__
DB ___X_X__
DB ____X___
DB ____X___
DB ___XXX__

ch90 label byte
DB 6,011h
DB _XXXXX__
DB _X___X__
DB ____X___
DB ___X____
DB __X_____
DB _X___X__
DB _XXXXX__

ch91 label byte
DB 3,011h
DB _XX_____
DB _X______
DB _X______
DB _X______
DB _X______
DB _X______
DB _X______
DB _XX_____

ch92 label byte
DB 3,011h
DB _X______
DB _X______
DB _X______
DB _X______
DB __X_____
DB __X_____
DB __X_____

ch93 label byte
DB 3,011h
DB _XX_____
DB __X_____
DB __X_____
DB __X_____
DB __X_____
DB __X_____
DB __X_____
DB _XX_____

ch94 label byte
DB 5,001h
DB __XX____
DB _X__X___

ch95 label byte
DB 5,001h
DB XXXXX___

ch96 label byte
DB 3,001h
DB _X______
DB __X_____

ch97 label byte
DB 5,031h
DB __XX____
DB _____X__
DB __XXX___
DB _X__X___
DB __XXX___

ch98 label byte
DB 5,011h
DB XX______
```

DB _X____
DB _XXX___
DB _X__X__
DB _X__X__
DB _X__X__
DB __XX___ ch99 label byte
DB 5,031h
DB __XX___
DB _X__X__
DB _X_____
DB _X__X__
DB __XX___ ch100 label byte
DB 5,011h
DB __XX___
DB ____X__
DB __XXX__
DB _X__X__
DB _X__X__
DB _X__X__
DB __XXX__ ch101 label byte
DB 5,031h
DB __XX___
DB _X__X__
DB _XXXX__
DB _X_____
DB __XX___ ch102 label byte
DB 3,011h
DB __X____
DB _X_____
DB XXX____
DB _X_____
DB _X_____
DB _X_____
DB _XX____ ch103 label byte
DB 5,031h
DB __XXX__
DB _X__X__
DB _X__X__
DB __XXX__
DB ____X__
DB __XX___ ch104 label byte
DB 5,011h
DB XX_____
DB _X_____
DB _XXX___
DB _X__X__
DB _X__X__
DB _X__X__
DB _X__X__ ch105 label byte
DB 2,011h
DB _X_____
DB _______
DB XX_____
DB _X_____
DB _X_____
DB _X_____
DB _X_____ ch106 label byte
DB 2,011h
DB __X____
DB _______
DB XX_____
DB _X_____
DB _X_____
DB _X_____
DB _X_____
DB _X_____ ch107 label byte
DB 5,011h
DB XX_____
DB _X_____
DB _X__X__
DB _X_X___
DB _XXX___
DB _X_X___
DB _X__X__ ch108 label byte
DB 2,011h
DB XX_____
DB _X_____
DB _X_____
DB _X_____

DB _X____
DB _X____
DB _X____ ch109 label byte
DB 8,031h
DB X_XX_XX_
DB _X__X__X
DB _X__X__X
DB _X__X__X
DB _X__X__X ch110 label byte
DB 5,031h
DB X_XX___
DB _X__X__
DB _X__X__
DB _X__X__
DB _X__X__ ch111 label byte
DB 5,031h
DB __XX___
DB _X__X__
DB _X__X__
DB _X__X__
DB __XX___ ch112 label byte
DB 5,031h
DB X_XX___
DB _X__X__
DB _X__X__
DB _XXX___
DB _X_____
DB _XX____ ch113 label byte
DB 5,031h
DB __XX___
DB _X__X__
DB _X__X__
DB __XXX__
DB ____X__
DB ___XX__ ch114 label byte
DB 4,031h
DB X_XX___
DB _X_X___
DB _X_____
DB _X_____
DB _XX____ ch115 label byte
DB 4,031h
DB __XX___
DB _X_____
DB _XXX___
DB ___X___
DB _XX____ ch116 label byte
DB 3,021h
DB _X_____
DB XXX____
DB _X_____
DB _X_____
DB _X_____
DB __X____ ch117 label byte
DB 5,031h
DB XX_XX__
DB _X__X__
DB _X__X__
DB _X__X__
DB __XXX__ ch118 label byte
DB 5,031h
DB X___X__
DB _X_X___
DB _X_X___
DB __X____
DB __X____ ch119 label byte
DB 8,031h
DB _XX_X_XX
DB _X_X_X_X
DB _X_X_X_X
DB __X__X_
DB __X__X_ ch120 label byte
DB 5,031h
DB XX_XX__
DB _X_X___

DB __X____
DB _X_X___
DB XX_XX__ ch121 label byte
DB 5,031h
DB _X__X__
DB _X__X__
DB _X__X__
DB __XX___
DB __X____
DB _X_____ ch122 label byte
DB 5,001h
DB _XXXX__
DB ___X___
DB __X____
DB _X__X__
DB _XXXX__ ch123 label byte
DB 4,011h
DB __X____
DB _X_____
DB _X_____
DB _XX____
DB _X_____
DB _X_____
DB __X____ ch124 label byte
DB 2,011h
DB _X_____
DB _X_____
DB _X_____
DB _X_____
DB _X_____
DB _X_____
DB _X_____ ch125 label byte
DB 4,011h
DB _X_____
DB __X____
DB __X____
DB __XX___
DB __X____
DB __X____
DB _X_____ ch126 label byte
DB 5,011h
DB __XX_X__
DB _X_XX__ ch127 label byte
DB 4,011h
DB _XX____
DB _XX____
DB _XX____
DB _XX____
DB _XX____
DB _XX____
DB _XX____ ch128 label byte
DB 7,011h
DB ___XXXX_
DB __X__X_
DB __X____
DB __X____
DB __X____
DB __X__X_
DB ___XXX__
DB ____X__ ch129 label byte
DB 5,011h
DB _X__X__
DB _______
DB XX_XX__
DB _X__X__
DB _X__X__
DB _X__X__
DB __XXX__ ch130 label byte
DB 5,001h
DB ___X___
DB __X____
DB _______
DB __XX___
DB _X__X__
DB _XXXX__
DB _X_____
DB __XX___ ch131 label byte

DB 5,001h
DB ___X___
DB __X_X__
DB _______
DB __XX___
DB ____X__
DB __XXX__
DB _X__X__
DB __XXX__ ch132 label byte
DB 5,011h
DB __X_X__
DB _______
DB __XX___
DB ____X__
DB __XXX__
DB _X__X__
DB __XXX__ ch133 label byte
DB 5,001h
DB __X____
DB ___X___
DB _______
DB __XX___
DB ____X__
DB __XXX__
DB _X__X__
DB __XXX__ ch134 label byte
DB 5,001h
DB __X_X__
DB ___X___
DB _______
DB __XX___
DB ____X__
DB __XXX__
DB _X__X__
DB __XXX__ ch135 label byte
DB 5,031h
DB __XX___
DB _X__X__
DB _X_____
DB _X__X__
DB __XX___
DB ___X___ ch136 label byte
DB 5,001h
DB __XX___
DB _X__X__
DB _______
DB __XX___
DB _X__X__
DB _XXXX__
DB _X_____
DB __XX___ ch137 label byte
DB 5,011h
DB _X_X___
DB _______
DB __XX___
DB _X__X__
DB _XXXX__
DB _X_____
DB __XX___ ch138 label byte
DB 5,001h
DB __X____
DB ___X___
DB _______
DB __XX___
DB _X__X__
DB _XXXX__
DB _X_____
DB __XX___ ch139 label byte
DB 2,011h
DB XX_____
DB _______
DB XX_____
DB _X_____
DB _X_____
DB _X_____
DB _X_____ ch140 label byte
DB 2,011h
DB XX_____
DB _______
DB XX_____
DB _X_____

```
DB _X_____
DB _X_____
DB _X_____

ch141 label byte
DB 2,001h
DB X______
DB _X_____
DB _______
DB XX_____
DB _X_____
DB _X_____
DB _X_____
DB _X_____

ch142 label byte
DB 5,011h
DB ___X___
DB ___X___
DB __X_X__
DB __X_X__
DB _XXXXX_
DB _X___X_
DB XXX_XXX

ch143 label byte
DB 6,001h
DB __X_X__
DB ___X___
DB ___X___
DB __X_X__
DB __X_X__
DB _XXXXX_
DB _X___X_
DB XXX_XXX

ch144 label byte
DB 7,001h
DB __X___
DB _XXXXX_
DB _X__X_
DB _X____
DB _XXX__
DB _X____
DB _X__X_
DB _XXXXX_

ch145 label byte
DB 6,031h
DB __XX_XX_
DB ____X_X
DB _XXXXXX
DB _X__X__
DB __XX_XX_

ch146 label byte
DB 9,013h
DB ___XXXXX_X_______
DB ___XX___X_______
DB ___X_X_______
DB ___X_XXX_______
DB __XXXX_______
DB __X__X__X_______
DB _XX_XXXX_X_______

ch147 label byte
DB 5,001h
DB __XX___
DB _X__X__
DB _______
DB __XX___
DB _X__X__
DB _X__X__
DB _X__X__
DB __XX___

ch148 label byte
DB 5,011h
DB _X__X__
DB _______
DB __XX___
DB _X__X__
DB _X__X__
DB _X__X__
DB __XX___

ch149 label byte
DB 5,001h
DB __X____
DB ___X___
DB _______
DB __XX___
DB _X__X__
DB _X__X__
DB _X__X__
DB __XX___

ch150 label byte
DB 5,001h
DB __X____
DB _X_X___
DB _______
DB XX_XX__
DB _X__X__
DB _X__X__
DB _X__X__
DB __XXX__

ch151 label byte
DB 5,001h
DB _X_____
DB __X____
DB _______
DB XX_XX__
DB _X__X__
DB _X__X__
DB _X__X__
DB __XXX__

ch152 label byte
DB 5,011h
DB _X__X__
DB _______
DB _X__X__
DB _X__X__
DB _X__X__
DB __XX___
DB _X_____
DB _X_____

ch153 label byte
DB 6,011h
DB ___XXX__
DB _X___X_
DB _X___X_
DB _X___X_
DB _X___X_
DB __X__X_
DB ___XXX_

ch154 label byte
DB 6,011h
DB _XXX_XXX
DB _X___X_
DB _X___X_
DB _X___X_
DB _X___X_
DB _X___X_
DB ___XXX_

ch155 label byte
DB 5,021h
DB ___X___
DB __XX___
DB _X__X__
DB _X_____
DB _X__X__
DB __XX___
DB _X_____

ch156 label byte
DB 5,011h
DB _X_____
DB _X_X___
DB _X_____
DB _XXX___
DB _X_____
DB _X_____
DB _XXXX__

ch157 label byte
DB 5,011h
DB XX_XX__
DB X__X__
DB XXXXX__
DB _X_X___
DB _XXXX__
DB _X____
DB _XXX___

ch158 label byte
DB 6,031h
DB X_XX__
DB _X__X__
DB _X__X__
DB _XXX___
DB _X_____
DB _XX____

ch159 label byte
DB 3,011h
DB __X____
DB _X_____
DB XXX____
DB _X_____
DB _X_____
DB _X_____
DB _XX____

ch160 label byte
DB 5,001h
DB __X____
DB _X_____
DB _______
DB __XX___
DB ____X__
DB __XXX__
DB _X__X__
DB __XXX__

ch161 label byte
DB 2,001h
DB _X_____
DB X______
DB _______
DB XX_____
DB _X_____
DB _X_____
DB _X_____
DB _X_____

ch162 label byte
DB 5,001h
DB ___X___
DB __X____
DB _______
DB __XX___
DB _X__X__
DB _X__X__
DB _X__X__
DB __XX___

ch163 label byte
DB 6,001h
DB ___X___
DB __X____
DB _______
DB XX_XX__
DB _X__X__
DB _X__X__
DB _X__X__
DB __XXX__

ch164 label byte
DB 6,001h
DB __X_X__
DB _X_X___
DB _______
DB X_XX___
DB _X__X__
DB _X__X__
DB _X__X__
DB _X__X__

ch165 label byte
DB 4,001h
DB __X_XX__
DB _XX__XXX
DB __XX__X_
DB __XX__X_
DB __X_X_X_
DB __X__XX_
DB __X__XX_
DB _XXX__X_

ch166 label byte
DB 3,011h
DB _X_____
DB __X____
DB _XX____
DB _XX____
DB _______
DB _XX____

ch167 label byte
DB 3,011h
DB _XX____
DB _XX____
DB _XX____
DB _XX____
DB _______
DB _XX____

ch168 label byte
DB 5,021h
DB ___X___
DB _______
DB ___X___
DB __X____
DB _X_____
DB _X__X__
DB __XX___

ch169 label byte
DB 6,001h
DB XXXXX___

ch170 label byte
DB 6,041h
DB _XXXXX__
DB _____X__

ch171 label byte
DB 6,011h
DB __X____X
DB _XX____X_
DB __X__X__
DB _XXXXXX_
DB ____X___X
DB __X___X_
DB _X____XXX

ch172 label byte
DB 6,011h
DB __X____X
DB _XX____X_
DB __X__X__
DB _XXXX__X
DB ____X_X_X
DB __X__XXX
DB _X_____X

ch173 label byte
DB 3,021h
DB _X______
DB ________
DB _X______
DB _X______
DB _X______
DB _X______
DB _X______

ch174 label byte
DB 5,001h
DB __X_X___
DB _X_X___
DB __X_X___

ch175 label byte
DB 5,051h
DB _X_X____
DB __X_X___
DB _X_X____

ch176 label byte
DB 5,001h
DB XXXXX___

ch177 label byte
DB 5,001h
DB XXXXX___

ch178 label byte
DB 5,001h
DB XXXXX___

ch179 label byte
DB 2,011h
DB _X______
DB _X______
DB _X______
DB ________
DB _X______
DB _X______
DB _X______

ch180 label byte
DB 5,001h
DB XXXXX___

ch181 label byte
DB 5,001h
DB XXXXX___

ch182 label byte
DB 5,001h
DB XXXXX___

ch183 label byte
DB 5,001h
DB XXXXX___

ch184 label byte
DB 5,001h
DB XXXXX___

ch185 label byte
DB 5,001h
DB XXXXX___

ch186 label byte
DB 5,001h
DB XXXXX___

ch187 label byte
DB 5,001h
DB XXXXX___
```

```
ch188 label byte
DB 5,001h
DB XXXXX___

ch189 label byte
DB 5,001h
DB XXXXX___

ch190 label byte
DB 5,001h
DB XXXXX___

ch191 label byte
DB 5,001h
DB XXXXX___

ch192 label byte
DB 5,001h
DB XXXXX___

ch193 label byte
DB 5,001h
DB XXXXX___

ch194 label byte
DB 5,001h
DB XXXXX___

ch195 label byte
DB 5,001h
DB XXXXX___

ch196 label byte
DB 5,001h
DB XXXXX___

ch197 label byte
DB 5,001h
DB XXXXX___

ch198 label byte
DB 5,001h
DB XXXXX___

ch199 label byte
DB 5,001h
DB XXXXX___

ch200 label byte
DB 5,001h
DB XXXXX___

ch201 label byte
DB 5,001h
DB XXXXX___

ch202 label byte
DB 5,001h
DB XXXXX___

ch203 label byte
DB 5,001h
DB XXXXX___

ch204 label byte
DB 5,001h
DB XXXXX___

ch205 label byte
DB 5,001h
DB XXXXX___

ch206 label byte
DB 5,001h
DB XXXXX___

ch207 label byte
DB 5,001h
DB XXXXX___

ch208 label byte
DB 5,001h
DB XXXXX___

ch209 label byte
DB 5,001h
DB XXXXX___

ch210 label byte
DB 5,001h
DB XXXXX___

ch211 label byte
DB 5,001h
DB XXXXX___

ch212 label byte
DB 5,001h
DB XXXXX___

ch213 label byte
DB 5,001h
DB XXXXX___

ch214 label byte
DB 5,001h
DB XXXXX___

ch215 label byte
DB 5,001h
DB XXXXX___

ch216 label byte
DB 5,001h
DB XXXXX___

ch217 label byte
DB 5,001h
DB XXXXX___

ch218 label byte
DB 5,001h
DB XXXXX___

ch219 label byte
DB 5,001h
DB XXXXX___

ch220 label byte
DB 5,001h
DB XXXXX___

ch221 label byte
DB 5,001h
DB XXXXX___

ch222 label byte
DB 5,001h
DB XXXXX___

ch223 label byte
DB 5,001h
DB XXXXX___

ch224 label byte
DB 5,001h
DB XXXXX___

ch225 label byte
DB 7,011h
DB __XX____
DB _X__X___
DB _X__X___
DB _X_X____
DB _X__X___
DB _X__X___
DB _X_X____

ch226 label byte
DB 5,001h
DB XXXXX___

ch227 label byte
DB 7,011h
DB __XXX___
DB _XXX____
DB _XXX____
DB __XX____
DB ___X____
DB ___X____
DB ___X____

ch228 label byte
DB 5,001h
DB XXXXX___

ch229 label byte
DB 5,001h
DB XXXXX___

ch230 label byte
DB 5,041h
DB _X__X___
DB _X__X___
DB _X__X___
DB _XXX_X__
DB _X______

ch231 label byte
DB 5,001h
DB XXXXX___

ch232 label byte
DB 5,001h
DB XXXXX___

ch233 label byte
DB 5,001h
DB XXXXX___

ch234 label byte
DB 5,001h
DB XXXXX___

ch235 label byte
DB 5,001h
DB XXXXX___

ch236 label byte
DB 5,001h
DB XXXXX___

ch237 label byte
DB 7,011h
DB ___XXXX_
DB __X__XX_
DB __X__XX_
DB __X_X_X_
DB __XX__X_
DB __XX__X_
DB __XXXX__

ch238 label byte
DB 5,001h
DB XXXXX___

ch239 label byte
DB 5,001h
DB XXXXX___

ch240 label byte
DB 5,001h
DB XXXXX___

ch241 label byte
DB 7,011h
DB ___X____
DB ___X____
DB _XXXXX__
DB ___X____
DB ___X____
DB ________
DB _XXXXX__

ch242 label byte
DB 5,001h
DB XXXXX___

ch243 label byte
DB 5,001h
DB XXXXX___

ch244 label byte
DB 5,001h
DB XXXXX___

ch245 label byte
DB 5,001h
DB XXXXX___

ch246 label byte
DB 5,001h
DB XXXXX___

ch247 label byte
DB 5,001h
DB XXXXX___

ch248 label byte
DB 3,011h
DB _X______
DB X_X_____
DB _X______

ch249 label byte
DB 2,041h
DB _X______

ch250 label byte
DB 2,041h
DB _X______

ch251 label byte
DB 5,001h
DB XXXXX___

ch252 label byte
DB 5,031h
DB X_XX____
DB _X__X___
DB _X__X___
DB _X__X___
DB _X__X___

ch253 label byte
DB 3,011h
DB XX______
DB __X_____
DB _X______
DB XXX_____

ch254 label byte
DB 5,001h
DB XXXXX___
ch255 label byte

DATASEG_END
end
Copr. 1989 Zenith Data Systems Corp.

.model small

include ulibvga.inc
include ulstdseg.inc

DATASEG_BEGIN
extrn ControlDataStorageArea:byte

offset2 label word
public offset2
db 6
db 28

dw ch33,ch34,ch35,ch36,ch37,ch38,ch39
dw
ch40,ch41,ch42,ch43,ch44,ch45,ch46,ch47,ch48,ch49
dw
ch50,ch51,ch52,ch53,ch54,ch55,ch56,ch57,ch58,ch59
dw
ch60,ch61,ch62,ch63,ch64,ch65,ch66,ch67,ch68,ch69
dw
ch70,ch71,ch72,ch73,ch74,ch75,ch76,ch77,ch78,ch79
dw
ch80,ch81,ch82,ch83,ch84,ch85,ch86,ch87,ch88,ch89
dw
ch90,ch91,ch92,ch93,ch94,ch95,ch96,ch97,ch98,ch99
dw
ch100,ch101,ch102,ch103,ch104,ch105,ch106,ch107,ch108,ch109
dw
ch110,ch111,ch112,ch113,ch114,ch115,ch116,ch117,ch118,ch119
dw
ch120,ch121,ch122,ch123,ch124,ch125,ch126,ch127,ch128,ch129
dw
ch130,ch131,ch132,ch133,ch134,ch135,ch136,ch137,ch138,ch139
dw
ch140,ch141,ch142,ch143,ch144,ch145,ch146,ch147,ch148,ch149
dw
ch150,ch151,ch152,ch153,ch154,ch155,ch156,ch157,ch158,ch159
dw
ch160,ch161,ch162,ch163,ch164,ch165,ch166,ch167,ch168,ch169
dw
ch170,ch171,ch172,ch173,ch174,ch175,ch176,ch177,ch178,ch179
dw
ch180,ch181,ch182,ch183,ch184,ch185,ch186,ch187,ch188,ch189
dw
ch190,ch191,ch192,ch193,ch194,ch195,ch196,ch197,ch198,ch199
dw
ch200,ch201,ch202,ch203,ch204,ch205,ch206,ch207,ch208,ch209
dw
ch210,ch211,ch212,ch213,ch214,ch215,ch216,ch217,ch218,ch219
dw
ch220,ch221,ch222,ch223,ch224,ch225,ch226,ch227,ch228,ch229
dw
ch230,ch231,ch232,ch233,ch234,ch235,ch236,ch237,ch238,ch239
dw
ch240,ch241,ch242,ch243,ch244,ch245,ch246,ch247,ch248,ch249
dw ch250,ch251,ch252,ch253,ch254,ch255

ch33 label byte
DB 7,021h
DB ___X____
DB __XXX___
DB __XXX___
DB __XXX___
DB __XXX___
DB __XXX___
DB ___X____
```

```
DB [illegible bitmap rows]

ch88 label byte
DB 17,023h
DB [illegible bitmap rows]

ch89 label byte
DB 10,023h
DB [illegible bitmap rows]

ch90 label byte
DB 13,022h
DB [illegible bitmap rows]

ch91 label byte
DB 8,011h
DB [illegible bitmap rows]

ch92 label byte
DB 7,021h
DB [illegible bitmap rows]

ch93 label byte
DB 6,011h
DB [illegible bitmap rows]

ch94 label byte
DB 11,022h
DB [illegible bitmap rows]

ch95 label byte
ch96 label byte
DB 15,063h
DB [illegible bitmap rows]

ch96 label byte
DB 5,031h
DB [illegible bitmap rows]

ch97 label byte
DB 11,062h
DB [illegible bitmap rows]

ch98 label byte
DB 12,012h
DB [illegible bitmap rows]

ch99 label byte
DB 11,062h
DB [illegible bitmap rows]

ch100 label byte
DB 12,013h
DB [illegible bitmap rows]

ch101 label byte
DB 11,062h
DB [illegible bitmap rows]

ch102 label byte
DB 7,011h
DB [illegible bitmap rows]

ch103 label byte
DB 12,062h
DB [illegible bitmap rows]

ch104 label byte
DB 12,012h
DB [illegible bitmap rows]

ch105 label byte
DB 6,021h
DB [illegible bitmap rows]

ch106 label byte
DB 6,021h
DB [illegible bitmap rows]

ch107 label byte
DB 12,013h
DB [illegible bitmap rows]

ch108 label byte
DB 6,011h
DB [illegible bitmap rows]

ch109 label byte
DB 16,063h
DB [illegible bitmap rows]

ch110 label byte
DB 12,062h
DB [illegible bitmap rows]

ch111 label byte
DB 13,062h
DB [illegible bitmap rows]

ch112 label byte
DB 12,062h
DB [illegible bitmap rows]
```

```
DB _XXXX________

ch113 label byte
DB 13,062h
DB ___XXXX__X_____
DB __XX__X.XX_____
DB _XX____XX_____
DB _XX____XX_____
DB _XX____XX_____
DB _XX____XX_____
DB _XXX____XX_____
DB __XXX__X.XX____
DB ___XXXX_XX____
DB _______XX_____
DB _______XX_____
DB _______XX_____
DB ______X.XXX____

ch114 label byte
DB 8,061h
DB _XXX_XXX
DB __XXX_XX
DB _XX___
DB _XX___
DB _XX___
DB _XX___
DB _XX___
DB _XX___
DB _XXXX__

ch115 label byte
DB 10,062h
DB ___XXXX_X_____
DB _XX____X.X_____
DB _XX_____X_____
DB __XXX________
DB ___XXXX_______
DB ______XXX_____
DB _X______X.X_____
DB _XX_____X.X_____
DB _X_XXXX_______

ch116 label byte
DB 7,031h
DB __X___
DB __X___
DB _XX___
DB _XXXXX_
DB _XX___
DB _XX___
DB _XX___
DB _XX___
DB _XX___
DB _XX___
DB __XXX_

ch117 label byte
DB 12,062h
DB _XXX___X.XX_____
DB _XX____XX_____
DB _XX____XX_____
DB _XX____XX_____
DB _XX____XX_____
DB _XX____XX_____
DB _XX____XX_____
DB _XX___X.XX_____
DB __XXXX_XXX_____

ch118 label byte
DB 11,062h
DB XXXXX____XXX_____
DB _XX_____X______
DB _XX_____X______
DB __XX___X______
DB ___XX_X______
DB ___XX_X______
DB ____XXX______
DB ____XXX______
DB _____X_______

ch119 label byte
DB 17,062h
DB XXXX__XX.XXX__XXX.X______
DB _XX_____X.X______X______
DB __XX____XX___X______
DB __XX____XX___X______
DB ___XX_X_XX_X______
DB ___XX_X_XX_X______
DB ____XXX____XXX______
DB ____XXX____XXX______
DB _____X_____X________

ch120 label byte
DB 12,062h
DB _XXXX__X.XXX_____
DB ___XX___XX______
DB ____XX_X______
DB _____XXX______
DB _____XX_______
DB ____X_XX_______
DB ___X___XX______
DB _XXXX__X.XXX_____

ch121 label byte
DB 11,062h
DB XXXX____XXX_____
DB _XX______X______
DB __XX_____X______
DB __XX_____X______
DB ___XX__X_______
DB ___XX__X_______
DB ____XXX________
DB ____XXX________
DB _____X_________
DB ____XX_________
DB ____X__________
DB XX_X___________
DB XXX____________

ch122 label byte
DB 11,062h
DB _XXXXXXXX.XX_______
DB _XX____X.X_______
DB _X____XX________
DB ______XX________
DB _____XX_________
DB ____XX__________
DB ___XX_____X______
DB __XX______XX______
DB _XXXXXXXX.XX_______

ch123 label byte
DB 10,011h
DB _____XX_
DB ____XX__
DB ____XX__
DB ____XX__
DB ____XX__
DB ____XX__
DB ____XX__
DB ____XX__
DB ___XX___
DB ____XX__
DB ____XX__
DB ____XX__
DB ____XX__
DB ____XX__
DB ____XX__
DB ____XX__
DB _____XX_

ch124 label byte
DB 6,011h
DB __XX____
DB __XX____
DB __XX____
DB __XX____
DB __XX____
DB __XX____
DB __XX____
DB __XX____
DB __XX____
DB __XX____
DB __XX____
DB __XX____
DB __XX____
DB __XX____
DB __XX____
DB __XX____
DB __XX____

ch125 label byte
DB 10,011h
DB ___XX___
DB ____XX__
DB ____XX__
DB ____XX__
DB ____XX__
DB ____XX__
DB ____XX__
DB ____XX__
DB _____XX_
DB ____XX__
DB ____XX__
DB ____XX__
DB ____XX__
DB ____XX__
DB ____XX__
DB ____XX__
DB ___XX___

ch126 label byte
DB 12,022h
DB __XXXX_____X______
DB _XX__XX___XX______

DB _X____XX.XX______

ch127 label byte
DB 9,021h
DB __XXXX__
DB __XXXX__
DB __XXXX__
DB __XXXX__
DB __XXXX__
DB __XXXX__
DB __XXXX__
DB __XXXX__
DB __XXXX__
DB __XXXX__
DB __XXXX__
DB __XXXX__
DB __XXXX__

ch128 label byte
DB 15,022h
DB _____XXX.XXXX__X_
DB ___XXX_______XXXX_
DB __XX___________XX_
DB __XX____________X_
DB _XXX______________
DB _XX_______________
DB _XX_______________
DB _XX_______________
DB _XXX______________
DB __XX______________
DB __XX____________X_
DB ___XXX________XX__
DB _____XXX.XXXX_____
DB __________X_______
DB __________XXX_____
DB ____________XX____
DB __________X.XXX_____

ch129 label byte
DB 12,032h
DB ___XX__X.X_______
DB ___XX__X.X_______
DB _________________
DB _XXX____X.XX______
DB __XX_____XX______
DB __XX_____XX______
DB __XX_____XX______
DB __XX_____XX______
DB __XX_____XX______
DB __XX_____XX______
DB __XX___X.XX______
DB ___XXXX_XXX______

ch130 label byte
DB 11,032h
DB _____XXX________
DB ____XX__________
DB _________________
DB ____XXX_________
DB __XX___X.X_______
DB _XX______XX______
DB _XXXXXXXX.XX______
DB _XX______________
DB _XX______________
DB _XXX_____________
DB __XXX____XX______
DB ____XXXX_________

ch131 label byte
DB 11,022h
DB _____X__________
DB ____XXX_________
DB ___X___X________
DB _________________
DB ____XXXX________
DB __XX___X.X_______
DB __XX___X.X_______
DB ______XXX.X_______
DB __XXX__X.X_______
DB _XX____X.X_______
DB _XX____X.X_______
DB _XXX__XX.X_______
DB __XXXX_X.XX______

ch132 label byte
DB 11,032h
DB __XX___X.X_______
DB __XX___X.X_______
DB _________________
DB ____XXXX________
DB __XX___X.X_______
DB __XX___X.X_______
DB ______XXX.X_______
DB __XXX__X.X_______
DB _XX____X.X_______
DB _XX____X.X_______
DB _XXX__XX.X_______
DB __XXXX_X.XX______

ch133 label byte
DB 11,032h
DB ___XXX__________
DB _____XX_________
DB _________________
DB ____XXXX________
DB __XX___X.X_______
DB __XX___X.X_______
DB ______XXX.X_______
DB __XXX__X.X_______
DB _XX____X.X_______
DB _XX____X.X_______
DB _XXX__XX.X_______
DB __XXXX_X.XX______

ch134 label byte
DB 11,062h
DB ____XXX_________
DB ___XX_XX________
DB ___X___X________
DB ___XX_XX________
DB ____XXX_________
DB _________________
DB ____XXXX________
DB __XX___X.X_______
DB __XX___X.X_______
DB ______XXX.X_______
DB __XXX__X.X_______
DB _XX____X.X_______
DB _XX____X.X_______
DB _XXX__XX.X_______
DB __XXXX_X.XX______

ch135 label byte
DB 11,062h
DB ____XXXX________
DB __XX____X.XX______
DB _XX______XX______
DB _XX______________
DB _XX______________
DB _XX______________
DB _XXX_____________
DB __XXX____XX______
DB ____XXXX________
DB ______X_________
DB ______XXX_______
DB ________X.X_______
DB _____XXXX________

ch136 label byte
DB 11,022h
DB ______X_________
DB _____XXX________
DB ____X___X_______
DB _________________
DB _____XXX________
DB __XX____X.X_______
DB _XX______XX______
DB _XXXXXXXX.XX______
DB _XX______________
DB _XX______________
DB _XXX_____________
DB __XXX____XX______
DB ____XXXX________

ch137 label byte
DB 11,032h
DB __XX___X.X_______
DB __XX___X.X_______
DB _________________
DB ____XXX_________
DB __XX___X.X_______
DB _XX______XX______
DB _XXXXXXXX.XX______
DB _XX______________
DB _XX______________
DB _XXX_____________
DB __XXX____XX______
DB ____XXXX________

ch138 label byte
DB 11,032h
DB ___XXX__________
DB _____XX_________
DB _________________
DB ____XXX_________
DB __XX___X.X_______
DB _XX______XX______
DB _XXXXXXXX.XX______
DB _XX______________
DB _XX______________
DB _XXX_____________
DB __XXX____XX______
DB ____XXXX________

ch139 label byte
DB 6,031h
DB XX__XX__
DB XX__XX__
```

```
DB ______
DB _XXX___
DB _XX___
DB _XX___
DB _XX___
DB _XX___
DB _XX___
DB _XX___
DB _XX___
DB _XXXX__

ch140 label byte
DB 8,031h
DB _XXXX__
DB XX__XX_
DB _______
DB _XXX___
DB _XX___
DB _XX___
DB _XX___
DB _XX___
DB _XX___
DB _XX___
DB _XX___
DB _XXXX__

ch141 label byte
DB 8,031h
DB XXX____
DB __XX___
DB _______
DB _XXX___
DB _XX___
DB _XX___
DB _XX___
DB _XX___
DB _XX___
DB _XX___
DB _XX___
DB _XX___
DB _XXXX__

ch142 label byte
DB 17,003h
DB _____XX___XX________
DB ____________________
DB _______X____________
DB ______X.XX__________
DB ______XX.XXX________
DB ______X__XX_________
DB ______XX__XXX_______
DB _____X_____XX_______
DB ____XX____XXX_______
DB _____X______XX______
DB ____XXXXX.XXXXXX____
DB ____X__________XX___
DB ___XX__________XXX__
DB ___X____________XX__
DB XXXXX__________XXXXX.X__

ch143 label byte
DB 17,003h
DB ______XX_XX_________
DB ______X___X_________
DB ______XX_XX_________
DB _______X.XX_________
DB ______XX.XXX________
DB ______X__XX_________
DB _____XX___XXX_______
DB ______X_____XX______
DB _____XX_____XXX_____
DB ______X______XX_____
DB ____XXXXX.XXXXXX____
DB ____X__________XX___
DB ___XX__________XXX__
DB ___X____________XX__
DB XXXXX__________XXXXX.X__

ch144 label byte
DB 16,002h
DB ______X.X______
DB _______________
DB _XXXXXXX.XXXXXX_
DB __XX_______XX_
DB __XX________X_
DB __XX__________
DB __XX_____X____
DB __XX_____X____
DB __XXXXX.XXX____
DB __XX_____X____
DB __XX_____X____
DB __XX__________
DB __XX________X_
DB __XX_______XX_
DB _XXXXXXX.XXXXXX_

ch145 label byte
DB 17,002h
DB ____XXXX__XXX___
DB __XX___X.XX___XX_

DB __XX___X.X_____XX
DB _____XXX.XXXXXXXX
DB __XXX__X.X______
DB _XX____X.X______
DB _XX____X.XX_____
DB _XXX__XX.XXX__XX
DB __XXXX____XXXX__

ch146 label byte
DB 21,023h
DB ________X.XXXXXXXX.XXXX____
DB _______X_XX________XX____
DB ______XX_XX_________X____
DB ______X__XX________________
DB _____XX__XX________X_____
DB _____X___XX_______X______
DB ____XX___XXXXXXX.XX_______
DB ____X____XX_______X_______
DB ___XXXXX.XXX_______X______
DB ___X_____XX________________
DB __XX_____XX__________X_____
DB __X______XX__________XX____
DB XXXXX___X.XXXXXXXX.XXXX____

ch147 label byte
DB 12,022h
DB ________X__________
DB ______XXX__________
DB _____X___X_________
DB ___________________
DB ______XXXX_________
DB ___XX___X.XX_______
DB __XX_______XXX_____
DB __XX________XX_____
DB __XX________XX_____
DB __XX________XX_____
DB __XXX______XX______
DB ___XXX____XX_______
DB ______XXXX_________

ch148 label byte
DB 12,032h
DB _____XX_X.X________
DB _____XX_X.X________
DB ___________________
DB ______XXXX_________
DB ___XX___X.XX_______
DB __XX_______XXX_____
DB __XX________XX_____
DB __XX________XX_____
DB __XX________XX_____
DB __XXX______XX______
DB ___XXX____XX_______
DB ______XXXX_________

ch149 label byte
DB 12,032h
DB ______XXX__________
DB ________XX_________
DB ___________________
DB ______XXXX_________
DB ___XX___X.XX_______
DB __XX_______XXX_____
DB __XX________XX_____
DB __XX________XX_____
DB __XX________XX_____
DB __XXX______XX______
DB ___XXX____XX_______
DB ______XXXX_________

ch150 label byte
DB 12,032h
DB ______XXX__________
DB _____XX_XX_________
DB ___________________
DB __XXX_____X.XX_______
DB ___XX_______XX_______
DB ___XX_______XX_______
DB ___XX_______XX_______
DB ___XX_______XX_______
DB ___XX_______XX_______
DB ___XX_______XX_______
DB ___XX_____X.XX_______
DB _____XXXX_XXX_______

ch151 label byte
DB 12,032h
DB _____XXX___________
DB _______XX__________
DB ___________________
DB __XXX_____X.XX_______
DB ___XX_______XX_______
DB ___XX_______XX_______
DB ___XX_______XX_______
DB ___XX_______XX_______
DB ___XX_______XX_______
DB ___XX_______XX_______
DB ___XX_____X.XX_______
DB _____XXXX_XXX_______

ch152 label byte
DB 11,032h
DB ___XX__X.X_________
DB ___XX__X.X_________
DB ___________________
DB XXXX______XXX______
DB _XX_______X________
DB __XX______X________
DB __XX______X________
DB ___XX___X__________
DB ___XX___X__________
DB _____XXX___________
DB _____XXX___________
DB _______X___________
DB _____XX____________
DB _____X_____________
DB XX_X_______________
DB XXX________________

ch153 label byte
DB 17,003h
DB ______XX____XX______
DB ____________________
DB ________XXX.XXXX____
DB _____XXX_______XXX__
DB ___XX____________XX_
DB ___XX____________XX_
DB __XXX____________XXX
DB __XX______________XX
DB __XX______________XX
DB __XX______________XX
DB __XXX____________XXX
DB ___XX____________XX_
DB ___XX____________XX_
DB _____XXX_______XXX__
DB ________XXX.XXXX____

ch154 label byte
DB 17,003h
DB ______XX____XX______
DB ____________________
DB __XXXXXX______XXXXX
DB ____XX__________X___
DB ____XX__________X___
DB ____XX__________X___
DB ____XX__________X___
DB ____XX__________X___
DB ____XX__________X___
DB ____XX__________X___
DB ____XX__________X___
DB ____XX__________X___
DB _____XX________X____
DB ______XXX_____XX____
DB _________XX.XXX_____

ch155 label byte
DB 12,042h
DB __________X________
DB _________X_________
DB ______XXXX.X_______
DB ___XX____X.XX______
DB __XX_____X.XX______
DB __XX____X__________
DB __XX____X__________
DB __XX___X___________
DB __XXX_X____________
DB ___XXX______X______
DB _____XXXXX.X_______
DB _____X_____________
DB ___X_______________

ch156 label byte
DB 12,022h
DB ________XX.X_______
DB _______X____XX_____
DB _____XX______XX____
DB _____XX____________
DB _____XX____________
DB _____XX____________
DB ___XXXXXX.X________
DB _____XX____________
DB _____XX____________
DB _____XX____________
DB __XXXX________X____
DB XX___XXXX.XXX______
DB __XXXX_XX.XX_______

ch157 label byte
DB 12,022h
DB XXXXX_____XXXX_____
DB __XX_________X_____
DB ___XX_______X______
DB _____XX_____X______
DB ______XX_X_________
DB XXXXXXXXX.XXXX_____
DB ______XX___________
DB ______XX___________
DB XXXXXXXXX.XXXX_____
DB ______XX___________

DB ______XX___________
DB ______XX___________
DB ___XXXXX.X_________

ch158 label byte
DB 12,062h
DB _XXX_XXX__________
DB __XXX__X.XX_______
DB __XX_____XXX______
DB __XX_______XX_____
DB __XX_______XX_____
DB __XX_______XX_____
DB __XX_______XX_____
DB __XXX____XX_______
DB __XX_XXX.X________
DB __XX______________
DB __XX______________
DB __XX______________
DB _XXXX_____________

ch159 label byte
DB 7,011h
DB ____XXX_
DB ___X_XX_
DB __XX____
DB __XX____
DB __XX____
DB _XXXXX__
DB __XX____
DB __XX____
DB __XX____
DB __XX____
DB __XX____
DB __XX____
DB __XX____
DB _XXXXX__

ch160 label byte
DB 11,032h
DB ________XX.X_______
DB _______XX__________
DB ___________________
DB ______XXXX_________
DB ___XX____X.X_______
DB ___XX____X.X_______
DB _______XXX.X_______
DB ___XXX___X.X_______
DB __XX______X.X______
DB __XX______X.X______
DB __XXX___XX.X_______
DB ___XXXX_X.XX_______

ch161 label byte
DB 6,031h
DB __XXX___
DB _XX_____
DB ________
DB _XXX____
DB __XX____
DB __XX____
DB __XX____
DB __XX____
DB __XX____
DB __XX____
DB __XX____
DB _XXXX___

ch162 label byte
DB 12,032h
DB ________XX.X_______
DB _______XX__________
DB ___________________
DB _____XXXX__________
DB ___XX____X.XX______
DB __XX_______XXX_____
DB __XX________XX_____
DB __XX________XX_____
DB __XX________XX_____
DB __XXX______XX______
DB ___XXX____XX_______
DB _____XXXX__________

ch163 label byte
DB 12,032h
DB ________XX.X_______
DB _______XX__________
DB ___________________
DB __XXX_____X.XX_______
DB ___XX_______XX_______
DB ___XX_______XX_______
DB ___XX_______XX_______
DB ___XX_______XX_______
DB ___XX_______XX_______
DB ___XX_______XX_______
DB ___XX_____X.XX_______
DB _____XXXX_XXX_______

ch164 label byte
DB 12,032h
```

```
DB __XXX__X______
DB __X__XXX______
DB ______________
DB _XXX_XXX_X_____
DB __XXX___XX_____
DB __XX____XX_____
DB __XX____XX_____
DB __XX____XX_____
DB __XX____XX_____
DB __XX____XX_____
DB __XX____XX_____
DB _XXXX__X_XXX____

ch165 label byte
DB 17,022h
DB ____X__XXX_____
DB ________________
DB _XXX________XXXXX
DB __XXX_________X__
DB ___XXX________X__
DB ___XXXX_______X__
DB ___X_XXX______X__
DB ___X__XXX_____X__
DB ___X___XXX____X__
DB ___X_____XXX__X__
DB ___X______XXX_X__
DB ___X_______XXXX__
DB ___X_________XXX__
DB ___X__________XX__
DB _XXXXX_________X__

ch166 label byte
DB 8,021h
DB __XXXX__
DB _XX__XX_
DB _____XX_
DB __XXXXX_
DB _XX__XX_
DB _XX__XX_
DB __XXX_XX
DB ________
DB _XXXXXX_

ch167 label byte
DB 8,021h
DB __XXXX__
DB _XX__XX_
DB _XX__XX_
DB _XX__XX_
DB _XX__XX_
DB _XX__XX_
DB __XXXX__
DB ________
DB _XXXXXX_

ch168 label byte
DB 11,022h
DB ____XXX_________
DB ____XXX_________
DB ________________
DB ______X_________
DB ______X_________
DB _____X__________
DB ___XX___________
DB __XX____________
DB _XX_____________
DB _XX_______XX_____
DB _XX_______XX_____
DB __XX_____X_______
DB ____XXXXX________

ch169 label byte
DB 12,0F2h
DB ________________
DB XXXXXXXXX,XXXX____

ch170 label byte
DB 14,022h
DB _XXXXXXX,XXXXX___
DB ____________XX___
DB ____________XX___
DB ____________XX___

ch171 label byte
DB 16,022h
DB ___X___________XX_
DB _XXX___________XX__
DB __XX___________XX__
DB __XX__________XX___
DB __XX_________XX_____
DB _XXXX______XX_______
DB ___________X_X_______
DB _________XX____XXX__
DB ________XX____X__XX_
DB ______XX__________XX_
DB _____XX___________XX__
DB ___XX______________XX_X_
DB _XX_____________XXXXX_

ch172 label byte
DB 10,112h
DB ___X___________XX_
DB _XXX___________XX__
DB __XX__________XX___
DB __XX_________XX____
DB __XX_______XX______
DB _XXXX_____XX_______
DB __________X_X_______
DB ________XX________XX_
DB ______XX_________XXX_
DB ____XX__________X_XX_
DB ___XX__________X__XX_
DB __XX___________XXXXX_
DB _XX_____________XX_

ch173 label byte
DB 7,021h
DB __XXX___
DB __XXX___
DB ________
DB ___X____
DB ___X____
DB ___X____
DB ___X____
DB __XXX___
DB __XXX___
DB __XXX___
DB __XXX___
DB __XXX___
DB ___X____

ch174 label byte
DB 12,072h
DB ____XX___XX______
DB ___XX___XX_______
DB __XX___X_X_______
DB _XX___XX_________
DB __XX___X_X_______
DB ___XX___XX_______
DB ____XX___XX______

ch175 label byte
DB 12,072h
DB _XX___XX_________
DB __XX___X_X_______
DB ___XX___XX_______
DB ____XX___XX______
DB ___XX___XX_______
DB __XX___X_X_______
DB _XX___XX_________

ch176 label byte
DB 12,0F2h
DB ________________
DB XXXXXXXXX,XXXX____

ch177 label byte
DB 12,0F2h
DB ________________
DB XXXXXXXXX,XXXX____

ch178 label byte
DB 12,0F2h
DB ________________
DB XXXXXXXXX,XXXX____

ch179 label byte
DB 6,021h
DB __XX____
DB __XX____
DB __XX____
DB __XX____
DB __XX____
DB __XX____
DB __XX____
DB ________
DB ________
DB __XX____
DB __XX____
DB __XX____
DB __XX____
DB __XX____
DB __XX____
DB __XX____

ch180 label byte
DB 12,0F2h
DB ________________
DB XXXXXXXXX,XXXX____

ch181 label byte
DB 12,0F2h
DB ________________
DB XXXXXXXXX,XXXX____

ch182 label byte
DB 12,0F2h
DB ________________
DB XXXXXXXXX,XXXX____

ch183 label byte
DB 12,0F2h
DB ________________
DB XXXXXXXXX,XXXX____

ch184 label byte
DB 12,0F2h
DB ________________
DB XXXXXXXXX,XXXX____

ch185 label byte
DB 12,0F2h
DB ________________
DB XXXXXXXXX,XXXX____

ch186 label byte
DB 12,0F2h
DB ________________
DB XXXXXXXXX,XXXX____

ch187 label byte
DB 12,0F2h
DB ________________
DB XXXXXXXXX,XXXX____

ch188 label byte
DB 12,0F2h
DB ________________
DB XXXXXXXXX,XXXX____

ch189 label byte
DB 12,0F2h
DB ________________
DB XXXXXXXXX,XXXX____

ch190 label byte
DB 12,0F2h
DB ________________
DB XXXXXXXXX,XXXX____

ch191 label byte
DB 12,0F2h
DB ________________
DB XXXXXXXXX,XXXX____

ch192 label byte
DB 12,0F2h
DB ________________
DB XXXXXXXXX,XXXX____

ch193 label byte
DB 12,0F2h
DB ________________
DB XXXXXXXXX,XXXX____

ch194 label byte
DB 12,0F2h
DB ________________
DB XXXXXXXXX,XXXX____

ch195 label byte
DB 12,0F2h
DB ________________
DB XXXXXXXXX,XXXX____

ch196 label byte
DB 12,0F2h
DB ________________
DB XXXXXXXXX,XXXX____

ch197 label byte
DB 12,0F2h
DB ________________
DB XXXXXXXXX,XXXX____

ch198 label byte
DB 12,0F2h
DB ________________
DB XXXXXXXXX,XXXX____

ch199 label byte
DB 12,0F2h
DB ________________
DB XXXXXXXXX,XXXX____

ch200 label byte
DB 12,0F2h
DB ________________
DB XXXXXXXXX,XXXX____

ch201 label byte
DB 12,0F2h
DB ________________
DB XXXXXXXXX,XXXX____

ch202 label byte
DB 12,0F2h
DB ________________
DB XXXXXXXXX,XXXX____

ch203 label byte
DB 12,0F2h
DB ________________
DB XXXXXXXXX,XXXX____

ch204 label byte
DB 12,0F2h
DB ________________
DB XXXXXXXXX,XXXX____

ch205 label byte
DB 12,0F2h
DB ________________
DB XXXXXXXXX,XXXX____

ch206 label byte
DB 12,0F2h
DB ________________
DB XXXXXXXXX,XXXX____

ch207 label byte
DB 12,0F2h
DB ________________
DB XXXXXXXXX,XXXX____

ch208 label byte
DB 12,0F2h
DB ________________
DB XXXXXXXXX,XXXX____

ch209 label byte
DB 12,0F2h
DB ________________
DB XXXXXXXXX,XXXX____

ch210 label byte
DB 12,0F2h
DB ________________
DB XXXXXXXXX,XXXX____

ch211 label byte
DB 12,0F2h
DB ________________
DB XXXXXXXXX,XXXX____

ch212 label byte
DB 12,0F2h
DB ________________
DB XXXXXXXXX,XXXX____

ch213 label byte
DB 12,0F2h
DB ________________
DB XXXXXXXXX,XXXX____

ch214 label byte
DB 12,0F2h
DB ________________
DB XXXXXXXXX,XXXX____

ch215 label byte
DB 12,0F2h
DB ________________
DB XXXXXXXXX,XXXX____

ch216 label byte
DB 12,0F2h
DB ________________
DB XXXXXXXXX,XXXX____

ch217 label byte
DB 12,0F2h
DB ________________
DB XXXXXXXXX,XXXX____

ch218 label byte
DB 12,0F2h
DB ________________
DB XXXXXXXXX,XXXX____

ch219 label byte
DB 12,0F2h
DB ________________
DB XXXXXXXXX,XXXX____

ch220 label byte
DB 12,0F2h
DB ________________
DB XXXXXXXXX,XXXX____

ch221 label byte
DB 12,0F2h
DB ________________
DB XXXXXXXXX,XXXX____

ch222 label byte
```

```
DB 12,0F2h
DB ________ ________
DB XXXXXXXX XXXX___

ch223 label byte
DB 12,0F2h
DB ________________
DB XXXXXXXX XXXX___

ch224 label byte
DB 12,0F2h
DB ________ ________
DB XXXXXXXX XXXX___

ch225 label byte
DB 12,022h
DB ___XXXX________
DB __XX__X_X______
DB __XX____XX_____
DB __XX____XX_____
DB __XX__X_X______
DB __XX__XX_______
DB __XX__X_X______
DB __XX____XX_____
DB __XX_____XX____
DB __XX_____XX____
DB __XX_____XX____
DB __XX_XX_XX_____
DB _XXX__XX_X_____

ch226 label byte
DB 12,0F2h
DB ________________
DB XXXXXXXX XXXX___

ch227 label byte
DB 11,022h
DB ___XXXXX XX______
DB __XXXX__X_______
DB _XXXXX__X_______
DB _XXXXX__X_______
DB _XXXXX__X_______
DB __XXXX__X_______
DB ___XXX__X_______
DB _____X__X_______
DB _____X__X_______
DB _____X__X_______
DB _____X__X_______
DB _____X__X_______
DB _____X__X_______
DB _____X__X_______

ch228 label byte
DB 12,0F2h
DB ________________
DB XXXXXXXX XXXX___

ch229 label byte
DB 12,0F2h
DB ________________
DB XXXXXXXX XXXX___

ch230 label byte
DB 12,072h
DB _XX_____XX_____
DB _XX_____XX_____
DB _XX_____XX_____
DB _XX_____XX_____
DB _XX_____XX_____
DB _XX_____XX_____
DB _XXX___X_XX_____
DB _XXXXXXX_XXX____
DB _XX_____________
DB _XX_____________
DB _XX_____________
DB _XX_____________

ch231 label byte
DB 12,0F2h
DB ________ ________
DB XXXXXXXX XXXX___

ch232 label byte
DB 12,0F2h
DB ________________
DB XXXXXXXX XXXX___

ch233 label byte
DB 12,0F2h
DB ________________
DB XXXXXXXX XXXX___

ch234 label byte
DB 12,0F2h
DB ________________
DB XXXXXXXX XXXX___

ch235 label byte
DB 12,0F2h
DB ________________
DB XXXXXXXX XXXX___

ch236 label byte
DB 12,0F2h
DB ________________
DB XXXXXXXX XXXX___

ch237 label byte
DB 17,032h
DB ____XXX XXXX_XX_
DB __XXX______XXX_
DB __XX_______XXXX_
DB __XX_______XX_XX_
DB _XXX______XX__XXX
DB _XX______XX____XX
DB _XX______X_____XX
DB _XX_____X_X____XX
DB _XXX__XX_______XXX
DB __XX_XX________XX_
DB __XXXX_________XX_
DB ___XXX_______XXX__
DB __XX_XXX XXXX_____

ch238 label byte
DB 12,0F2h
DB ________________
DB XXXXXXXX XXXX___

ch239 label byte
DB 12,0F2h
DB ________________
DB XXXXXXXX XXXX___

ch240 label byte
DB 12,0F2h
DB ________________
DB XXXXXXXX XXXX___

ch241 label byte
DB 14,042h
DB ______XX________
DB ______XX________
DB ______XX________
DB ______XX________
DB _XXXXXXX XXXXX__
DB ______XX________
DB ______XX________
DB ______XX________
DB ______XX________
DB ________________
DB _XXXXXXX XXXXX__

ch242 label byte
DB 12,0F2h
DB ________________
DB XXXXXXXX XXXX___

ch243 label byte
DB 12,0F2h
DB ________________
DB XXXXXXXX XXXX___

ch244 label byte
DB 12,0F2h
DB ________ ________
DB XXXXXXXX XXXX___

ch245 label byte
DB 12,0F2h
DB ________________
DB XXXXXXXX XXXX___

ch246 label byte
DB 12,0F2h
DB ________________
DB XXXXXXXX XXXX___

ch247 label byte
DB 12,0F2h
DB ________________
DB XXXXXXXX XXXX___

ch248 label byte
DB 9,021h
DB __XXXX__
DB _XX__XX_
DB _XX__XX_
DB __XXXX__

ch249 label byte
DB 6,071h
DB __XX____
DB __XX____

ch250 label byte
DB 6,071h
DB __XX____
DB __XX____

ch251 label byte
DB 12,0F2h
DB ________________
DB XXXXXXXX XXXX___

ch252 label byte
DB 12,062h
DB _XXX_XXX X______
DB __XXX___XX______
DB __XX____XX______
DB __XX____XX______
DB __XX____XX______
DB __XX____XX______
DB __XX____XX______
DB __XX____XX______
DB _XXXX__X XXX_____

ch253 label byte
DB 7,021h
DB __XXX___
DB _X__XX_
DB ___XX__
DB ___XX__
DB __XX_X__
DB _XXXXX__

ch254 label byte
DB 12,0F2h
DB ________________
DB XXXXXXXX XXXX___
ch255 label byte

DATASEG_END
end
Copr. 1995 Zenith Data Systems Corp.

.model small
include utilequ.inc
include utilstruct.inc

DATASEG_BEGIN
extrn ControlDataStorageArea:byte

utfont3 label word
 public utfont3
 db 6
 db 9

 dw ch33,ch34,ch35,ch36,ch37,ch38,ch39
 dw
ch40,ch41,ch42,ch43,ch44,ch45,ch46,ch47,ch48,ch4
9
 dw
ch50,ch51,ch52,ch53,ch54,ch55,ch56,ch57,ch58,ch5
9
 dw
ch60,ch61,ch62,ch63,ch64,ch65,ch66,ch67,ch68,ch6
9
 dw
ch70,ch71,ch72,ch73,ch74,ch75,ch76,ch77,ch78,ch7
9
 dw ch80,ch81,ch82,ch83


ch33 label byte
DB 7,001h
DB ___X____
DB __XXX___
DB _XXXXX__
DB XXXXXXX_
DB __XXX___
DB __XXX___
DB __XXX___

ch34 label byte
DB 7,001h
DB __XXX___
DB __XXX___
DB __XXX___
DB XXXXXXX_
DB _XXXXX__
DB __XXX___
DB ___X____

ifneed_ext eq 0
ch35 label byte
else

ch35 label byte
db 16 , 2
db XXXXXXXX XXXXXXX_
db X______________X_
db X_XXXXXX_X_XXX_X_
db X_XXXXXX_X_XXX_X_
db X_XXXXXX_X_XXX_X_
db X_XXXXXX_X_XXX_X_
db X______________X_
db XXXXXXXX XXXXXXX_

ch36 label byte
db 11 , 2
db XXXXXXXX XXX_____
db X_________X_____
db X_XXXXXX_X_X_____
db X_XXXXXX_X_X_____
db X_XXXXXX_X_X_____
db X_XXXXXX_X_X_____
db X_________X_____
db XXXXXXXX XXX_____

ch37 label byte
db 13 , 2
db ___XXXX XXXXX__
db ___X______X__
db ___X______X__
db ___X______X__
db ___X______X__
db XXXXXXXX X___X__
db X_______XXXXX__
db X_______X______
db X_______X______
db X_______X______
db X_______X______
db XXXXXXXX X______

ch38 label byte
db 10 , 2
db _X______X______
db XXX_____XXX_____
db _XXX___X_XX_____
db __XXX_XX_X______
db ___XXXXX________
db ____XXX_________
db ___XXXXX________
db __XXX_XX_X______
db _XXX___X_XX_____
db XXX______XXX_____
db _X_______X______

ch39 label byte
db 16 , 2
db _XXXXX___________________
db _XX______________________
db _XX_____XXX___XX_X________
db _XXXX__X_X_XX_XX_XX________
db _XX______XXX__XX__________
db _XX_______XX_XX___________
db _XX____X_X_XX_XX_XX________
db _XXXXX__XXX___XX_X________

ch40 label byte
db 10 , 2
db _XXXXX__XX______
db _XX____X_XX_____
db _XX______XX_____
db _XXXX____XX_____
db _XX______XX_____
db _XX______XX_____
db _XX______XX_____
db _XX______XX_____

ch41 label byte
db 13 , 2
db _XXXXX__XXXX____
db _XX____X_X__XX__
db _XX_________XX__
db _XXXX_______XX__
db _XX_________XX__
db _XX_______XX____
db _XX____X_X______
db _XX____X_XXXXX___

ch42 label byte
db 13 , 2
db _XXXXX_X_XXXXX___
db _XX_________XX___
db _XX_________XX___
db _XXXX____XXXX____
db _XX_________XX___
db _XX_________XX___
db _XX____X_X__XX___
db _XX______XXXX____

ch43 label byte
db 14 , 2
db _XXXXX______XX___
db _XX________XXX___
db _XX_______XXXX___
db _XXXX____XX_XX___
db _XX____X_X__XX___
db _XX____X_XXXXXX__
db _XX_________XX___
db _XX_________XX___

ch44 label byte
db 13 , 2
db _XXXXX_X_XXXXX___
```

```
db _XX____X.X_______
db _XX____X.X_______
db _XXXX__X.XXXX____
db _XX__________XX___
db _XX__________XX___
db _XX____X.X__XX___
db _XX______XXXX____

ch43 label byte
db 13 , 2
db _XXXXX____XXX_____
db _XX______XX_______
db _XX_____X.X_______
db _XXXX__X.XXXX_____
db _XX_____X.X_XX____
db _XX_____X.X_XX____
db _XX_____X.X_XX____
db _XX______XXXX_____

ch44 label byte
db 13 , 2
db _XXXXX_X.XXXXX____
db _XX__________XX___
db _XX__________XX___
db _XXXX________XX___
db _XX_________XX____
db _XX_________XX____
db _XX_________XX____
db _XX_________XX____

ch47 label byte
db 13 , 2
db _XXXXX___XXXX_____
db _XX_____X.X_XX____
db _XX_____X.X_XX____
db _XXXX___XXXX______
db _XX_____X.X_XX____
db _XX_____X.X_XX____
db _XX_____X.X_XX____
db _XX______XXXX_____

ch4B label byte
db 13 , 2
db _XXXXX___XXXX_____
db _XX_____X.X_XX____
db _XX_____X.X_XX____
db _XXXX___X.X_XX____
db _XX______XXXXX____
db _XX__________XX___
db _XX_________XX____
db _XX_______XXX_____

ch48 label byte
db 17 , 3
db _XXXXX___XX__XXXX__________
db _XX_____X.XX_XX__X.X_______
db _XX_______XX_XX__X.X_______
db _XXXX_____XX_XX__X.X_______
db _XX_______XX_XX__X.X_______
db _XX_______XX_XX__X.X_______
db _XX_______XX_XX__X.X_______
db _XX_______XX__XXXX_________

ch50 label byte
db 14 , 2
db _XXXXX___XX__XX___
db _XX_____X.XX_XXX__
db _XX_______XX__XX__
db _XXXX_____XX__XX__
db _XX_______XX__XX__
db _XX_______XX__XX__
db _XX_______XX__XX__
db _XX_______XX__XX__

ch51 label byte
db 17 , 3
db _XXXXX___XX__XXXX__________
db _XX_____X.XX_XX__X.X_______
db _XX_______XX_____XX________
db _XXXX_____XX____XX_________
db _XX_______XX___XX__________
db _XX_______XX__XX___________
db _XX_______XX_XX____________
db _XX_______XX_XXXXX.X_______

ch52 label byte
db 18 , 3
db _XXXXX___________X.X_______
db _XX__XX__________X.X_______
db _XX__XX__XXXXX_XX.XX_______
db _XX__XX__XXX_____X.X_______
db _XXXXX___XX______X.X_______
db _XX______XX______X.X_______
db _XX______XX______X.X_______
db _XX______XX_______XX_______

ch53 label byte
db 12,2
db _XXXXXXXX.XXX_____

db XXXXX__X.XXXX____
db XXXXX__X.XXXX____
db XXXXX__X.XXXX____
db XXXXX__X.XXXX____
db XXXXX__X.XXXX____
db XXX______XXX_____
db XXXX_____XXXX____
db XXXXX__X.XXXX____
db _XXXXXXXX.XXX____

ch54 label byte
db 8 , 1
db XXX__XXX
db XXX__XXX
db XXX__XXX
db XXX__XXX
db XXX__XXX
db XXX__XXX

ch55 label byte
db 30 , 4
db _XXXXX_____________________XX_____
db _XX__XX____________________XX_____
db _XX__XX__XXXXX_XX.X__XXX__XX_XX___
db _XXXXX__XXX__XX_XX_XX_XX_XX_XXXX__
db _XX__XX_XX__XXX.XX_XXXX_XXX__XXX__
db _XX__XX_XX__XX__XX_XX_XX_XX_XXX___
db _XX__XX_XX__XX__XX_XX_XX_XX_XXXX__
db _XXXXX__XX___XX.X__XXXX_XX_XX_____

ch56 label byte
db 20 , 3
db _XXXX______________XXX
db _XX_XX_____________XX_
db _XX_____XX_XX__X.XX_XX_
db _XXXX__XX_XX_XX_XX_XX_
db ____XX_XX_XX___X.XX_XXX
db ____XX_XX_XX_____XX_XXX
db _XX_XX_XX_XX_XX_XX_XX_
db _XXXX___XXXX___X.XX__XX_
db __________XX__________
db __________XXX_________

ch57 label byte
db 17 , 3
db ____X______________
db ___XX______________
db ___XXX_____________
db __XXXXXXX.XXXXXXX.X_____
db __XXXXXXX.XXXXXXX.X_____
db __XXXXXXX.XXXXXXX.X_____
db __XXXXXXX.XXXXXXX.X_____
db ___XXX_____________
db ___XX______________
db ____X______________

ch58 label byte
db 15 , 2
db _XX____________
db _XX____________
db _XX_XXXX___XXX_
db _XX_XX_XX_XX_XX_
db _XX_XX_X.X__XXX_
db _XX_XX_X.X___XX_
db _XX_XX_X.X_XX_XX_
db _XX_XX_X.X__XXX_

ch59 label byte
db 12,2
db XXXXXXXXX.XXXX___
db XXXXXXXXX.XXXX___
db XX____________
db XX_XXX________
db XX_XXXXX______
db XX_XXXXX.XX___
db XX_XX_XX______
db XX_____X.X____
db XX______XX____
db XX_______XX___
db XX________XX__
db XX____________

ch60 label byte
db 8 , 1
db __XX__
db _XXXX_
db _XXXXX_
db XXXXXXXX
db __XX__
db __XX__
db __XX__
db _XXXXX_
db __XX__
db _XXXXX_
db __XX__
db _XXXXX_

ch61 label byte
db 12,2

db _XXXXXXX.XXX____
db XXXXX__X.XXXX____
db XXXX___X.XXXX____
db XXX____X.XXXX____
db XX_X__X.XXXX____
db XXXXX__X.XXXX____
db XXXXX__X.XXXX____
db XXXXX__X.XXXX____
db XXXXX__X.XXXX____
db _XXXXXXX.XXX____

ch62 label byte
db 10 , 2
db _X___XX________
db _X___XXX_______
db _X_XXXX________
db _X_XXXXX.XXXXXX_
db _X_XXXXX.XXXXXX_
db _X_XXXX________
db _X___XXX_X_____
db _X___XX_XX__X__
db ________X.XXX__X
db _________XXXX__X
db __XXXXXX.XXXXXX_X
db __________XXXX__X
db __________XXX___X
db __________XX____X
db ___________X____

ch63 label byte
db 15 , 2
db _XXXX________XXX
db _XX_XX_________XX
db _XX_XX__XXX__XX
db _XX_XX_XX_XX_XX
db _XX_XX_XXXXX_XX
db _XX_XX_XX____XX
db _XX_XX_XX_XX_XX
db _XXXX___XXX__XX

ch64 label byte
db 12,2
db ________XX____
db XX______XX____
db XX______XX____
db _XX_____XX____
db __XX____XX____
db ___XX_X.X_XX__
db __XXXXXX.X_XX__
db ____XXXX.X_XX__
db _____XX.X_XX__
db ________XX____
db XXXXXXXXX.XXXX__
db XXXXXXXXX.XXXX__

ch65 label byte
db 8 , 1
db _XXXXXX_
db __XX__
db _XXXXXX_
db __XX__
db _XXXXXX_
db __XX__
db __XX__
db __XX__
db XXXXXXXX
db _XXXXXX_
db __XXXX_
db __XX__

ch66 label byte
db 9 , 3
db ___XX________
db __XXXX_______
db _XXXXXX______
db XXXXXXXX.X_____
db ___XX________
db ___XX________
db ___XX________
db ___XX________
db ___XX________
db ___XX________

ch67 label byte
db 23,3
db _XXXXXXX.XXX______XX____
db XXXXX__X.XXXX__X.X__XX__
db XXXXX__X.XXXX__XX.X__XXX_
db XXXX___XXXX__XXX.XXXXXX_
db XXXX_XX__XXXX__XXX.XXXXXX_
db XXX__XX__XXX_X______X.
db XXX______XXX_X__X___X.
db XX_XXXX___XX_X___XX___X.
db XX_XX_XXXX_XX_X___X____
db _XXXXXXX.XXX______X.XXXXX__

ch68 label byte
db 30 , 4
db ___X______________________

db ___XX____________________XXX__
db ___XXX___________________XXX__
db ___XXXX__________________XXX__
db __XXXXXXXX.XXXXXXX.XXXXXXXX.XXXXXX__
db __XXXXXXXX.XXXXXXX.XXXXXXXX.XXXXXX__
db __XXXXXXXX.XXXXXXX.XXXXXXXX.XXXXXX__
db ___XXX___________________
db ___XX____________________
db ___X_____________________

ch69 label byte
db 10 , 2
db ___X_______
db ___XX______
db ___XXX_____
db __XXXXXXX.XX____
db __XXXXXXX.XX____
db ___XXX_____
db ___XX______
db ___X_______

ch70 label byte
db 10 , 2
db ______X_______
db ______XX______
db ______XX.X____
db __XXXXXXX.XX____
db __XXXXXXX.XX____
db ______XX.X____
db ______XX______
db ______X_______

ch71 label byte
db 15 , 2
db ______X.X_____
db _____XX.XX____
db ____XXX.XXX___
db ____XXX__XXX__
db ___XXX_____XXX__
db __XXXXXXX__XXXXXXX_
db __XXXXXXX__XXXXXXX_
db _____XX__XX____
db _____XX__XX____
db _____XXX.XXX____

ch72 label byte
db 15 , 2

db ___XX_X.XX_XX_
db ___XX__XX__XX_
db __XXXX__XX_XXXX_
db __XXXX__XX__XX_
db __XX__XX__XX__XX_
db __XXXXXX__XX__XX_
db __XX__XX__XX__XX_
db __XX__XX__XX__XX_

ch73 label byte
db 20 , 3

db _XXXX___XX_______XXX___
db _XX__XX_XX_______XX____
db _XX_____X.XXX_XXXX.X_XX___
db _XX_____XX__XXX____XX__
db _XX_____XX__XX_____XX__
db _XX_____XX__XX_____XX__
db _XX__XX_XX__XX_____XX__
db _XXXX___XX__XX_____XX__

ch74 label byte
db 9 , 2
db ___XX______
db ___XX______
db ___XX______
db ___XX______
db ___XX______
db _XXXXXXX.X____
db __XXXXXX____
db ___XXXX_____
db ____XX______

ch75 label byte
db 10 , 2
db ____X________
db ___XX_______XXX
db ___XXX______XXX
db ___XXXX_____XXX
db XXXXXXXX.XXXXXXXX
db XXXXXXXX.XXXXXXXX
db _XXXXXXX.XXXXXXX
db ___XXX______
db ___XX_______
db ___X________
```

```
ch7? label byte
DB 4,1
DB ________
DB ________
DB _XXX____
DB _XX_____
DB _XX_____
DB _XX_____
DB _XX_____
DB _XX_____
DB _XX_____
DB _XX_____
DB _XX_____
DB _XX_____
DB _XXX____

ch77 label byte
DB 4,01h
DB ________
DB ________
DB XXX_____
DB _XX_____
DB _XX_____
DB _XX_____
DB _XX_____
DB _XX_____
DB _XX_____
DB _XX_____
DB _XX_____
DB _XX_____
DB XXX_____

ch78 label byte
db 4,1
db ________

ch79 label byte
db 7,1
db XXXXXXX_
db X_____X_
db X_XXX_X_
db X_XXX_X_
db X_XXX_X_
db X_XXX_X_
db X_____X_
db XXXXXXX_

ch80 label byte
db 16,2
db XXXXXXXX,XXXXXXXX
db XXXXXXXX,XXXXXXXX

...

ch83 label byte

endif

DATASEG_END
end
Copr. 1993 Zenith Data Systems Corp.

.model small
include s8blequ.inc
include simstr.inc

DATASEG_BEGIN
extrn ControlDataStorageArea byte

offset label word
 public offset

db 0
db 0

dw ch33,ch34,ch35,ch36,ch37,ch38,ch39
dw
ch40,ch41,ch42,ch43,ch44,ch45,ch46,ch47,ch48,ch4
9
dw ch50,ch51,ch52,ch53,ch54

ch33 label byte
DB 16,002h
db XXXXXXXX,XXXXXXXX
db XXXXXXXX,XXXXXXXX

ch34 label byte

ch35 label byte
DP *,001h
db ... dup(XX______)

ch36 label byte
db 22,3
...

ch37 label byte
db 40,3
...

ch38 label byte
db 30,5
...

ch39 label byte
db 30,4
...

ch40 label byte
db 17,3
...

ch41 label byte
db 70,10
...
```

ch42 label byte

30 . 5 ch43 label byte

30 . 5 ch44 label byte

30 . 5 ch45 label byte

30 . 5

@ 30,5 ab47 label byte

@ 30,5 ab48 label byte

@ 36,6 ab46 label byte

```
ch49 label byte
db 36,5

ch50 label byte
db 71,16

ch51 label byte
db 36,5

ch52 label byte
db 16,2

ch53 label byte
db 11,2

ch54 label byte
DATASEG_END
end

Copr. 1995 Zenith Data Systems Corp.
.model small
include allsetup.inc

WORKBUF equ '                    ',0

VCENT=480/2

HCENT=640/2

DWIDE=MAXMESSAGELINE

DHIGH=348

DLEFT=HCENT-(DWIDE/2)

DTOP=VCENT-(DHIGH/2)

DATASEG_BEGIN
BEGIN_FORM_DEFINITIONS

mainform label tCONTROL
  public MainForm

mnuToolbar label tControl
  public mnuToolbar
  BEGIN_TOOLBAR %INVISIBLE,0,0,640,90
  FONT=SHIPFONT
  ENGLISH
  CAPTION "ChaiseePAD Setup"

cmdAbout label tControl
  public cmdAbout
  MAKE_ABOUTBUTTON %NORMSTATE,0,0,32,33

CmdHost label tCONTROL
  public CmdHost
  BEGIN_TOOLBARBUTTON %ISDOWN,0,0,144,54

  GRAPHIC_CAPTION HOST_ICON
  FONT=SMALLFONT
  ENGLISH
  CAPTION "Host"

FrmHost label tCONTROL
  public FrmHost
  NEXTCONTROL=RES_SETUPS_HOST
  BEGIN_FORM

txtCurrentHost label tCONTROL
  public txtCurrentHost
  MAKE_UNFRAMED_EDITBOX
DISABLED,104,11,304,10,48
  ENGLISH
  CAPTION "Current Host"

CmdDisconnect label tCONTROL
  public CmdDisconnect
  MAKE_COMMANDBUTTON
%NORMSTATE,520,%SAMETOP,90,34
  ENGLISH
  CAPTION "Disconnect"

ChkDimHost label tCONTROL
  public ChkDimHost
  NEXTCONTROL=GETSET_DIM_HOST_SCREEN
  MAKE_CHECKBOX 8,32,%NEXTTOP+8
  ENGLISH
  CAPTION "Dim host screen"

fraConnectionOptions label tControl
  public fraConnectionOptions
  BEGIN_FRAME
%NORMSTATE,8,%NEXTTOP+8,304,96
  MAKE_LINEBOX 8,18,0,304,1
  MAKE_LEFTLEGEND 8,32,12
  ENGLISH
  CAPTION "Connection:"

NEXTCONTROL=GETSET_HOST_CONNECTION_
TYPE + (0*256)
optNetwork label tCONTROL
  public optNetwork
  MAKE_OPTIONBUTTON 8,120,%SAMETOP
  ENGLISH
  CAPTION "Network"

optModem label tCONTROL
  public optModem

NEXTCONTROL=GETSET_HOST_CONNECTION_
TYPE + (1*256)
  MAKE_OPTIONBUTTON 8,200,%SAMETOP
  ENGLISH
  CAPTION "Modem"

NEXTCONTROL=GETSET_HOST_CONNECTION_
TYPE + (2*256)
optSerial label tCONTROL
  public optSerial
  MAKE_OPTIONBUTTON 8,280,%SAMETOP
  ENGLISH
  CAPTION "Serial"
END_FRAME

HOSTFRAMETOP=128

fraNetworkConnection label tControl
  public fraNetworkConnection
  BEGIN_FRAME
%NORMSTATE,32,HOSTFRAMETOP,488,88

lstNetworkGroups label tCONTROL
  public lstNetworkGroups

NEXTCONTROL=GETSET_NETWORK_GROUP_E
NTRY
  MAKE_LISTBOX %NORMSTATE,8,8,224,86+16
  ENGLISH
  CAPTION "Groups"

lstNetworkHosts label tCONTROL
  public lstNetworkHosts

NEXTCONTROL=GETSET_NETWORK_HOST_ENT
RY
  MAKE_LISTBOX %NORMSTATE,248,8,224,86+16
  ENGLISH
  CAPTION "Hosts"

cmdNetworkUpdate label tCONTROL
  public cmdNetworkUpdate
  MAKE_COMMANDBUTTON
%NORMSTATE,520-32,%SAMETOP+40,90,34
  ENGLISH
  CAPTION "Update List"

cmdNetworkConnect label tControl
  public cmdNetworkConnect
  MAKE_COMMANDBUTTON
%NORMSTATE,520-32,%NEXTTOP+8,90,34
  ENGLISH
  CAPTION "Connect"

END_FRAME
```

```
fraModemConnection label lControl
  public fraModemConnection
BEGIN_FRAME
%INVISIBLE,32,HOSTFRAMETOP,480,96

lstHostPhones label lCONTROL
  public lstHostPhones
NEXTCONTROL=GETSET_MODEM_HOST_DESC
_ENTRY
+(256*GETSET_MODEM_HOST_PHONE_ENTRY)
  MAKE_LISTBOX_NOSCROLL
%NORMSTATE,8,8,400,96+16
  SETTAB 300
  HOSTPHONECAPTION EQU "Hosts",9,"Phone"
  ENGLISH
  CAPTION HOSTPHONECAPTION

cmdEdit label lCONTROL
  public cmdEdit
  MAKE_COMMANDBUTTON
%NORMSTATE,520-32,%SAMETOP+40,88,24
  ENGLISH
  CAPTION "Edit..."

cmdModemConnect label lCONTROL
  public cmdModemConnect
  MAKE_COMMANDBUTTON
%NORMSTATE,520-32,%NEXTTOP+8,88,24
  ENGLISH
  CAPTION "Connect"

END_FRAME

fraSerialConnection label lControl
  public fraSerialConnection
BEGIN_FRAME
%INVISIBLE,32,HOSTFRAMETOP,480,96

cmdSerialConnect label lCONTROL
  public cmdSerialConnect
  MAKE_COMMANDBUTTON
%NORMSTATE,520-32,8,88,24
  ENGLISH
  CAPTION "Connect"

END_FRAME

lstSerialHost label lCONTROL
  public lstSerialHost


END_FORM
END_TOOLBARBUTTON


cmdHotKeys label lControl
  public cmdHotKeys
  BEGIN_TOOLBARBUTTON
0,%TBBNEXTLEFT,%TBBSAMETOP,%TBBSAMEW
IDE,%TBBSAMEHIGH
  GRAPHIC_CAPTION HOTKEY_ICON
  FONT=SMALLFONT
  ENGLISH
  CAPTION "Hot Keys"

FrmHotKey label lCONTROL
  public FrmHotKey
  NEXTCONTROL=RES_SETUPS_HOTKEYS
  BEGIN_FORM

txtHOTKEY1 label lCONTROL
  public txtHOTKEY1

NEXTCONTROL=GETSET_USER_DEFINED_HOT_
ICON + 256*1
  MAKE_KEY_EDITBOX
%SKIPTAB,84+56-48-16,24,400-48,32
  GRAPHIC_CAPTION HAND1_ICON

cmdClearHotKey1 label lCONTROL
  public cmdClearHotKey1
  MAKE_COMMANDBUTTON
%SKIPTAB,%NEXTLEFT+8,%SAMETOP,48,32
  ENGLISH
  CAPTION "Clear"

txtHOTKEY2 label lCONTROL
  public txtHOTKEY2

NEXTCONTROL=GETSET_USER_DEFINED_HOT_
ICON + 256*2
  MAKE_KEY_EDITBOX
%SKIPTAB,84+56-48-16,%NEXTTOP+24,400-48,32
  GRAPHIC_CAPTION HAND2_ICON

cmdClearHotKey2 label lCONTROL
  public cmdClearHotKey2
  MAKE_COMMANDBUTTON
%SKIPTAB,%NEXTLEFT+8,%SAMETOP,48,32
  ENGLISH
  CAPTION "Clear"

END_FORM
END_TOOLBARBUTTON

cmdMaintenance label lControl
  public cmdMaintenance
  BEGIN_TOOLBARBUTTON
0,%TBBNEXTLEFT,%TBBSAMETOP,%TBBSAMEW
IDE,%TBBSAMEHIGH
  GRAPHIC_CAPTION MAINT_ICON
  FONT=SMALLFONT
  ENGLISH
  CAPTION "Maintenance"

FrmMaintenance label lCONTROL
  public FrmMaintenance
  NEXTCONTROL=RES_SETUPS_MAINTENANCE
  BEGIN_FORM

CmdCalibratePen label lCONTROL
  public CmdCalibratePen
  MAKE_COMMANDBUTTON
%NORMSTATE,8+40,16+8,96,24
  ENGLISH
  CAPTION "Calibrate Pen"

CmdRebootHost label lCONTROL
  public CmdRebootHost
  MAKE_COMMANDBUTTON
%NORMSTATE,%SAMELEFT,%NEXTTOP+20,%SA
MEWIDE,%SAMEHIGH
  ENGLISH
  CAPTION "Reboot Host"

CmdUpgrade label lCONTROL
  public CmdUpgrade
  MAKE_COMMANDBUTTON
%NORMSTATE,%SAMELEFT,%NEXTTOP+20,%SA
MEWIDE,%SAMEHIGH
  ENGLISH
  CAPTION "Upgrade"

  BEGIN_GROUPBOX
%NORMSTATE,312+8-88-40,24,304-8-16-8+88,96-1
6-24+32+64-24
  ENGLISH
  CAPTION "Network"

txtSecurityID label lCONTROL
  public txtSecurityID
  NEXTCONTROL=GETSET_SECURITY_ID
  MAKE_PW_EDITBOX
%NORMSTATE,72+8,16+8,24+88,24,20
  ENGLISH
  CAPTION "Security ID"

txtDomainID label lCONTROL
  public txtDomainID
  NEXTCONTROL=GETSET_DOMAIN_ID
  MAKE_NUM_EDITBOX
%NORMSTATE,%SAMELEFT,%SAMETOP+32+8,3
2,%SAMEHIGH,2
  ENGLISH
  CAPTION "Domain ID"

  MAKE_SPINUPBUTTON
%NORMSTATE+SKIPTAB,%NEXTLEFT,%SAMETO
P-4 16,16
  GRAPHIC_CAPTION UPARROWBITMAP

cmdDomainIDSpinUp label lCONTROL
  public cmdDomainIDSpinUp
  MAKE_SPINDOWNBUTTON
%NORMSTATE+SKIPTAB,%SAMELEFT,%NEXTTO
P,16,16
  GRAPHIC_CAPTION DNARROWBITMAP

lstFrameType label lCONTROL
  public lstFrameType

NEXTCONTROL=GETSET_FRAME_TYPE_ENTRY
  MAKE_LISTBOX_NOSCROLL
%NORMSTATE,72+72+88,16,88+16,88+16-24+4
  ENGLISH
  CAPTION "Frame Type"

  END_GROUPBOX

END_FORM
END_TOOLBARBUTTON

cmdModem label lControl
  public cmdModem
  BEGIN_TOOLBARBUTTON
0,%TBBNEXTLEFT,%TBBSAMETOP,%TBBSAMEW
IDE,%TBBSAMEHIGH
  GRAPHIC_CAPTION MODEM_ICON
  FONT=SMALLFONT
  ENGLISH
  CAPTION "Modem"

frmModem label lCONTROL
  public frmModem
  NEXTCONTROL=RES_SETUPS_MODEM
  BEGIN_FORM
  BEGIN_GROUPBOX
%NORMSTATE,16,24,200+8,64+8
  ENGLISH
  CAPTION "Dialing"

optTone label lCONTROL
  public optTone
  NEXTCONTROL=
GETSET_MODEM_TONE_OR_PULSE +(0*256)
  MAKE_OPTIONBUTTON 8,16,16
  ENGLISH
  CAPTION "Tone"

  NEXTCONTROL=
GETSET_MODEM_TONE_OR_PULSE +(1*256)
optPulse label lCONTROL
  public optPulse
  MAKE_OPTIONBUTTON
%NORMSTATE,%SAMELEFT,%NEXTTOP+12
  ENGLISH
  CAPTION "Pulse"

TxtPrefix label lCONTROL
  public TxtPrefix
  NEXTCONTROL=GETSET_MODEM_PREFIX
  MAKE_EDITBOX
%NORMSTATE,136,12,168,24,16
  ENGLISH
  CAPTION "Prefix"

TxtSuffix label lCONTROL
  public TxtSuffix
  NEXTCONTROL=GETSET_MODEM_SUFFIX
  MAKE_EDITBOX
%NORMSTATE,%SAMELEFT,%NEXTTOP+4,%SA
MEWIDE,%SAMEHIGH,%SAMELEN
  ENGLISH
  CAPTION "Suffix"

  END_GROUPBOX

LstManufacturer label lCONTROL
  public LstManufacturer


NEXTCONTROL=GETSET_MODEM_MANUFACTU
RER_ENTRY
  MAKE_LISTBOX
%NORMSTATE,336,24,140,104+4
  ENGLISH
  CAPTION "Manufacturer"

LstBaudRate label lCONTROL
  public LstBaudRate

NEXTCONTROL=GETSET_MODEM_BAUD_RATE_
ENTRY
  MAKE_LISTBOX
%NORMSTATE,400-16,%SAMETOP,%SAMEWIDE,
%SAMEHIGH
  ENGLISH
  CAPTION "Baud Rate"

  ANSWERONRINGCAPTION EQU "Answer",13,"on
Ring"
TxtAnswerOnRing label lCONTROL
  public TxtAnswerOnRing

NEXTCONTROL=GETSET_MODEM_ANSWER_ON
_RING
  MAKE_NUM_EDITBOX
%NORMSTATE,136-56-8,88+16+8,24,24,1
  ENGLISH
  CAPTION ANSWERONRINGCAPTION
  HOLDSAMETOP=SAMETOP
  MAKE_SPINUPBUTTON
%NORMSTATE+SKIPTAB,%NEXTLEFT,%SAMETO
P-4,16,16
  GRAPHIC_CAPTION UPARROWBITMAP
  MAKE_SPINDOWNBUTTON
%NORMSTATE+SKIPTAB,%SAMELEFT,%NEXTTO
P,16,16
  GRAPHIC_CAPTION DNARROWBITMAP

  RETRYLIMITCAPTION EQU "Retry",13,"Limit"
TxtRetryLimit label lCONTROL
  public TxtRetryLimit

NEXTCONTROL=GETSET_MODEM_RETRY_LIMIT
  MAKE_NUM_EDITBOX
%NORMSTATE,%NEXTLEFT+40,%SAMETOP-12,3
2,24,2
  ENGLISH
  CAPTION RETRYLIMITCAPTION
  HOLDSAMEWIDE=SAMEWIDE
  MAKE_SPINUPBUTTON
%NORMSTATE+SKIPTAB,%NEXTLEFT,%SAMETO
P-4,16,16
  GRAPHIC_CAPTION UPARROWBITMAP
  MAKE_SPINDOWNBUTTON
%NORMSTATE+SKIPTAB,%SAMELEFT,%NEXTTO
P,16,16
  GRAPHIC_CAPTION DNARROWBITMAP

  RETRYDELAYCAPTION EQU "Retry",13,"Delay"
TxtRetryDelay label lCONTROL
  public TxtRetryDelay

NEXTCONTROL=GETSET_MODEM_RETRY_DELA
Y
  MAKE_NUM_EDITBOX
%NORMSTATE,%SAMELEFT+64,SAMETOP-12,40,
24,3
  ENGLISH
  CAPTION RETRYDELAYCAPTION
  MAKE_SPINUPBUTTON
%NORMSTATE+SKIPTAB,%NEXTLEFT,%SAMETO
P-4,16,16
  GRAPHIC_CAPTION UPARROWBITMAP
  MAKE_SPINDOWNBUTTON
%NORMSTATE+SKIPTAB,%SAMELEFT,%NEXTTO
P,16,16
  GRAPHIC_CAPTION DNARROWBITMAP


fraModemCustom label lControl
  public fraModemCustom
BEGIN_FRAME
%INVISIBLE,32,%NEXTTOP+16,480,96

NEXTCONTROL=GETSET_CUSTOM_INIT_STRIN
G
  MAKE_EDITBOX
%NORMSTATE,184-8,8,320,24,48
  ENGLISH
  CAPTION "Initialization"


NEXTCONTROL=GETSET_CUSTOM_AUTOANSW
ER_STRING
  MAKE_EDITBOX
%NORMSTATE,%SAMELEFT,%NEXTTOP+4,300,2
4,16
  ENGLISH
  CAPTION "Auto Answer"


NEXTCONTROL=GETSET_CUSTOM_DISCONNEC
T_STRING
  MAKE_EDITBOX
%NORMSTATE,%SAMELEFT,%NEXTTOP+4,300,2
4,16
  ENGLISH
  CAPTION "Disconnect"


NEXTCONTROL=GETSET_CUSTOM_CONNECT_
STRING
  MAKE_EDITBOX
%NORMSTATE,%SAMELEFT,%NEXTTOP+4,300,2
4,16
  ENGLISH
  CAPTION "Connect Resp"

CmdDefault label lCONTROL
  public CmdDefault
  MAKE_COMMANDBUTTON
%NORMSTATE,520-33,%SAMETOP,88,24
  ENGLISH
  CAPTION "Default"

  END_FRAME

END_FORM
END_TOOLBARBUTTON


cmdPower label lControl
  public cmdPower
  BEGIN_TOOLBARBUTTON
0,%TBBNEXTLEFT,%TBBSAMETOP,%TBBSAMEW
IDE,%TBBSAMEHIGH
  GRAPHIC_CAPTION POWER_ICON
  FONT=SMALLFONT
  ENGLISH
  CAPTION "Power"

frmPower label lCONTROL
```

```
public frmPower
NEXTCONTROL=RES_SETUPS_POWER
BEGIN_FORM

MAKE_LEFTLEGEND 0,312,32
GRAPHIC_CAPTION %VLINE2X64

MAKE_LEFTLEGEND 0,312,SAMETOP+24
GRAPHIC_CAPTION %VLINE2X64

MAKE_LEFTLEGEND 0,312,SAMETOP+24+32
GRAPHIC_CAPTION %VLINE2X64

MAKE_LEFTLEGEND 0,72+4,32
GRAPHIC_CAPTION SLEEP_ICON
ENGLISH
CAPTION "Sleep Delay"

hsbSleep label tCONTROL
public hsbSleep

NEXTCONTROL=GETSET_SLEEPMODE_PERIOD
+(0*256)
MAKE_SLIDEBAR
0,%SAMELEFT-4,%SAMETOP+34,224+0-40,16+2

MAKE_LEFTLEGEND
0 %SAMELEFT+6,%NEXTTOP+10
CAPTION "1   2   4   6   8   12   16
Never"

MAKE_LEFTLEGEND
0,%SAMELEFT+32,%SAMETOP+24
CAPTION "Minutes of inactivity"

MAKE_LEFTLEGEND 0,16,%SAMETOP+24
CAPTION "Sleep is a low power state that
extends"

MAKE_LEFTLEGEND
0,%SAMELEFT,%SAMETOP+10
CAPTION "battery life. CruisePad will wake up
from sleep"

MAKE_LEFTLEGEND
0,%SAMELEFT,%SAMETOP+10
CAPTION "immediately after the display is
touched."

MAKE_LEFTLEGEND 0,320+24+10+16,32
GRAPHIC_CAPTION HIBERNATE_ICON
ENGLISH
CAPTION "Hibernate"

chkAutoShutoff label tCONTROL
public chkAutoShutoff

NEXTCONTROL=GETSET_AUTOMATIC_SHUTOF
F
MAKE_CHECKBOX 0,320+16,80
ENGLISH
HIBLEGEND equ "Auto hibernate after 60
minutes",13,"of sleep"
CAPTION HIBLEGEND

MAKE_LEFTLEGEND
0,%SAMELEFT,%SAMETOP+40
CAPTION "Hibernate is a very low power state"

MAKE_LEFTLEGEND
0,%SAMELEFT,%SAMETOP+16
CAPTION "that consumes almost no battery"

MAKE_LEFTLEGEND
0,%SAMELEFT,%SAMETOP+16
CAPTION "power. CruisePad will wake up from"

MAKE_LEFTLEGEND
0,%SAMELEFT,%SAMETOP+16
CAPTION "hibernate about 10 seconds after"

MAKE_LEFTLEGEND
0,%SAMELEFT,%SAMETOP+16
CAPTION "the display is touched."

END_FORM
END_TOOLBARBUTTON

cmdScreen label tControl
public cmdScreen
BEGIN_TOOLBARBUTTON
0,%TBBNEXTLEFT,%TBBSAMETOP,%TBBSAMEW
IDE,%TBBSAMEHIGH
GRAPHIC_CAPTION SCREEN_ICON
FONT=SMALLFONT
ENGLISH
CAPTION "Screen"

FrmScreen label tCONTROL

public FrmScreen
NEXTCONTROL=RES_SETUPS_SCREEN
BEGIN_FORM

MAKE_LEFTLEGEND 0,72+4,32
GRAPHIC_CAPTION BRIGHTNESS_ICON
ENGLISH
CAPTION "Brightness"

HsbBrightness label tCONTROL
public HsbBrightness
NEXTCONTROL=GETSET_BRIGHTNESS +
(0*256)
MAKE_SPECTRUMBAR
0,%SAMELEFT-4,%SAMETOP+34,224+0-40+16,16
+2

MAKE_LEFTLEGEND
0,%SAMELEFT-32,%NEXTTOP+0
ENGLISH
CAPTION "Dark"

MAKE_LEFTLEGEND
0,%SAMELEFT+200,%SAMETOP
ENGLISH
CAPTION "Light"

MAKE_LEFTLEGEND 0,312,32
ENGLISH
GRAPHIC_CAPTION %VLINE2X64

MAKE_LEFTLEGEND 0,320+40+4,32
GRAPHIC_CAPTION CONTRAST_ICON
ENGLISH
CAPTION "Contrast"

HsbContrast label tCONTROL
public HsbContrast
N*:TCONTROL= GETSET_CONTRAST
+(0*256)
MAKE_SPECTRUMBAR
0,%SAMELEFT-4,%SAMETOP+34,224+0-40+16,16
+2
MAKE_LEFTLEGEND
0,%SAMELEFT-32,%NEXTTOP+0
ENGLISH
CAPTION "Low"

MAKE_LEFTLEGEND
0,%SAMELEFT+200,%SAMETOP
ENGLISH
CAPTION "High"

END_FORM
END_TOOLBARBUTTON

cmdToolBarClose label tControl
public cmdToolBarClose
MAKE_CLOSEBUTTON
%NORMSTATE,184*8+64+0,0,32,33
GRAPHIC_CAPTION BIG_X_ICON

ADJUST_TOOLBAR_WIDTH %TBBNEXTLEFT
END_TOOLBAR

frmFirstModalForm label tControl
public frmFirstModalForm

frmPasswordBox label tControl
public frmPasswordBox
NEXTCONTROL=8000h

CONTROL
FORM,%INVISIBLE,DLEFT,%DTOP+DHIGH/2-80
,DWIDE,%DHIGH*3/3+16,0

lblPasswordBox1 label tControl
public lblPasswordBox1
MAKE_CENTEREDLEGEND
%NORMSTATE,0,32,DWIDE,16
CAPTION "Connect to:

txtPassword label tControl
public txtPassword
NEXTCONTROL=GETSET_PASSWORD
MAKE_PW_EDITBOX
%NORMSTATE,140,%NEXTTOP+16,80,24,16
CAPTION "Password"

BEGIN_FRAME
%NORMSTATE,0,%NEXTTOP+16,DWIDE,34
cmdPasswordOKCancel_OK label tControl
public cmdPasswordOKCancel_OK
MAKE_COMMANDBUTTON
%NORMSTATE,DWIDE/2-64-16-34,0,64+24,34
CAPTION "OK"

cmdPasswordOKCancel_Cancel label tControl
public cmdPasswordOKCancel_Cancel
MAKE_COMMANDBUTTON
%NORMSTATE,DWIDE/2+16-0,%SAMETOP,64+24,
34
CAPTION "Cancel"

END_FRAME
MAKE_CENTEREDLEGEND
%NORMSTATE,0,%NEXTFRAMETOP+16,DWIDE,1
0
caption "Press 'OK' if no password."

END_FORM

frmPhoneBookEdit label tControl
public frmPhoneBookEdit
NEXTCONTROL=8000h
CONTROL
FORM,%INVISIBLE,40+20,%DTOP+DHIGH/2-40,34
0-200,%DHIGH/2,0

txtPSDescription label tControl
public txtPSDescription
MAKE_EDITBOX
%NORMSTATE,80,16,34+80+40,24,20
CAPTION "Description"

txtPSPhoneNumber label tControl
public txtPSPhoneNumber
MAKE_EDITBOX
%NORMSTATE,%SAMELEFT,%NEXTTOP+8,%SA
MEWIDE,%SAMEHIGH,20
CAPTION "Phone #"

BEGIN_FRAME
%NORMSTATE,0,%NEXTTOP+16,DWIDE,34
cmdPhoneBookOKCancel_OK label tControl
public cmdPhoneBookOKCancel_OK
MAKE_COMMANDBUTTON
%NORMSTATE,DWIDE/2-64-16-34,0,64+24,34
CAPTION "OK"

cmdPhoneBookOKCancel_Cancel label tControl
public cmdPhoneBookOKCancel_Cancel
MAKE_COMMANDBUTTON
%NORMSTATE,DWIDE/2+16-0,%SAMETOP,64+24,
34
CAPTION "Cancel"

END_FRAME
END_FORM

END_FORM_DEFINITIONS

ControlDataStorageArea label byte
public ControlDataStorageArea
db TOTALSTORAGE dup(0)

DATASEG_END
end

Copr. 1995 Zenith Data Systems Corp.

.MODEL SMALL
include cincled.inc
DATASEG_BEGIN
extrn ControlDataStorageArea:byte
extrn FirstStandardControl:tCONTROL
extrn FontTable:word
extrn LastStandardControl:tCONTROL
extrn OSK:tControl
extrn bCurrentControlType:byte
extrn pNormalFont:word
extrn rREGION:tREGION
extrn offsetId:word
extrn wCurrentFormBottom:word
extrn wCurrentFormHeight:word
extrn wGraphicCaptionHeight:word
extrn wNormalFontHeight:word
extrn wPreviousFormBottom:word
extrn wPreviousFormHeight:word
extrn frmMessageBox:tCONTROL
extrn frmMessageBox_end:tCONTROL

bPreviousMode db 0
public bPreviousMode
pLastForm dw 0
public pLastForm
wLastFormTop dw 0
wLastFormHeight dw 0
wFormWidth dw 0
public wFormWidth
DATASEG_END

.code
extrn DrawOnButton:near
extrn DrawUpButton:near
extrn GetStringWidth:near
extrn PaintControlCaption:near
extrn SetFontForCaption:near

GetBitMapHeight proc near
public GetBitMapHeight

or al,al
jz gah1
sub al,32
xor ah,ah
add ax,ax
add bx,ax
mov di,[bx+2]
mov bx,[bx]
mov ah,[bx]
mov al,[bx+1]
cmp ah,128
jae gah5
and al,1111b
gah5:
xor ah,ah
inc bx
inc bx
sub di,bx
xchg ax,di
xor dx,dx
or di,di
jz gah2
div di
jmp short gah3
gah2:
xor al,al
gah1:
xor ah,ah
gah3:
ret
GetBitMapHeight endp

GetCaptionHeight proc near
public GetCaptionHeight

push di
push si
push bx
push dx
or bx,bx
jnz gch4
xor ax,ax
jmp gch1a
gch4:
mov al,[bx]
shl al,1
shr al,1
shr al,1
shr al,1
shr al,1
shr al,1
xor ah,ah
cmp al,11b * 2
jnz gch8
cmp bCurrentControlType,LEFTLEGEND
jb gch9

cmp bx,offset osk
jne gch8

cmp bx,offset frmMessageBox
jb gch10
cmp bx,offset frmMessageBox_end
jb gch16
jmp gch9
gch10:
cmp bx,offset FirstStandardControl
jb gch7
cmp bx,offset LastStandardControl
jb gch8
gch7:
cmp bCurrentControlType,SPINUPBUTTON
je gch8
cmp bCurrentControlType,SPINDOWNBUTTON
jz gch8
gch8:
mov si,offset sitemId
jmp gch6
gch9:
mov si,ax
mov si,[si+offset FontTable]
gch6:
mov al,[si+1]
xor ah,ah
or al,al
jnz gch1a
```

```
    xchg bx,si
    add si,3

    lodsb
    call GetBitMapHeight
gch1a:
    pop dx
    pop bx
    pop si
    pop ds
    ret
GetCaptionHeight endp

GetCaptionWidth proc near
    public GetCaptionWidth

    add bx,3
    push bx
    push si
    mov si,bx
    call GetStringWidth
    pop si
    pop bx
    ret
GetCaptionWidth endp

GetCombinedCaptionHeight proc near
    public GetCombinedCaptionHeight

    push bx
    push cx
    mov bx,cx
    call GetCaptionHeight
    mov wGraphicCaptionHeight,ax
    pop cx
    pop bx
    mov dx,ax
    push cx
    push dx
    call GetCaptionHeight
    pop dx
    pop cx
    add ax,dx
    ret
GetCombinedCaptionHeight endp

GetLegendHeight proc near
    public GetLegendHeight
    push ax
    push si
    push ds
    push cx
    call PointControlCaption
    jz glh1
    push ax
    or bx,bx
    jz glh2

    push si
    call GetItemIterator
    mov ax,bx
    add bx,3
    mov si,bx
    mov bx,ax

glh4:
    lodsb
    or al,al
    jz glh3
    cmp al,13
    jnz glh4
    add bx,ax
    jmp glh4
glh3:
    pop si
glh2:
    pop cx
    push bx
    mov bx,cx
    call GetCaptionHeight
    pop bx
    cmp ax,bx
    jb glh6
    mov bx,ax
glh5:
    jmp short glh6
glh1:
    xor bx,bx
glh6:
    pop cx
    pop ds
    pop si
    pop ax
    ret
GetLegendHeight endp

GetNormFontHeight proc near
    public GetNormFontHeight
    push bx
    mov bx,pNormFont
    mov al,[bx+1]
    pop bx
    xor ah,ah
    mov wNormFontHeight,ax
    ret
GetNormFontHeight endp

SaveFormHeight proc near
    public SaveFormHeight

    push wCurrentFormHeight
    pop wPreviousFormHeight
    push wCurrentFormBottom
    pop wPreviousFormBottom
    ret
SaveFormHeight endp

AdjustBoxDimensions proc near
    public AdjustBoxDimensions
    mov ax,rRegion.wCurrentLeft
    mov dx,rRegion.wCurrentTop
    mov ax,rRegion.wCurrentWidth
    DIVIDE_BY_8 ax
    mov bl,al
    mov ax,rRegion.wCurrentHeight
    sar ax,1
    mov bh,al
    ret
AdjustBoxDimensions endp

AdjustButtonDimensions proc near
    public AdjustButtonDimensions
    push ax
    mov ax,rRegion.wCurrentHeight
    sub ax,BUTTONTOPHEIGHT +
BUTTONBOTTOMHEIGHT
    sar ax,1
    mov bh,al
    mov ax,rRegion.wCurrentWidth
    sub ax,BUTTONLEFTPIXELS +
BUTTONRIGHTPIXELS
    DIVIDE_BY_8 ax
    mov bl,al
    pop ax
    ret
AdjustButtonDimensions endp

AdjustFormHeight proc near
    public AdjustFormHeight


    mov al,[si].ControlType
    cmp al,FORM
    jnz rgo6b

    mov pLastForm,si
    mov bx,rRegion.wCurrentTop
    mov wLastFormTop,bx
    mov wLastFormHeight,0
    jmp rgo6aa

rgo6b:
    cmp al,FRAME
    je rgo6bb
    mov bx,rRegion.wCurrentRight
    add bx,16
    and bl,11111000b
    cmp bx,wFormWidth
    jbe rgo6bb
    mov wFormWidth,bx

rgo6bb:
    mov bx,rRegion.wCurrentBottom
    sub bx,wLastFormTop
    cmp bx,wLastFormHeight
    jbe rgo6aa
    mov wLastFormHeight,bx
    add bx,24
    push si
    mov si,pLastForm
    or si,si
    jz rgo6ab
    test [si].ControlState,EXPLICITSIZE
    jnz rgo6ab
    mov [si].PixelHeight,bx
rgo6ab:
    pop si
rgo6aa:
    ret
AdjustFormHeight endp
end


Copr 1995 Zenith Data Systems Corp.

.model small

.code
extrn Ascii2Bin:near
extrn Bin2ASCII:near

include uiinclud.inc

DATASEG_BEGIN
extrn ControlDataStorageArea:byte
DATASEG_END

.code

SetNumericControl proc near
    public SetNumericControl

    push ax
    push si
    mov ax,[si].ID
    push ax
    mov si,[si].pStorageOffset
    call Ascii2Bin
    pop ax
    SM_FUNCTION ax
    pop si
    pop ax
    ret
SetNumericControl endp

GetNumericControl proc near
    public GetNumericControl

    push ax
    mov ax,[si].ID
    mov ah,80h
    SM_FUNCTION ax
    jl rnb4a

    push cx
    push bx
    mov cl,byte ptr [si].wDataLength
    dec cl
    mov bx,[si].pStorageOffset
    call bin2ascii
    mov byte ptr [bx],0
    pop bx
    pop cx

rnb4a:
    pop ax
    ret
GetNumericControl endp

SetTextControl proc near
    public SetTextControl
    push ax
    push si
    mov ax,[si].ID
    mov si,[si].pStorageOffset
    mov dx,ds
    SM_FUNCTION ax
    pop si
    pop ax
    ret
SetTextControl endp

GetTextControl proc near
    public GetTextControl

    push si
    push ax
    push dx
    push cx
    push di
    mov cx,[SI].wDataLength
    mov di,[SI].pStorageOffset
    dec cx
    jle gtxct1
    mov ax,[SI].ID
    mov ah,80h
    SM_FUNCTION ax
    jl gtxct1

    push es
    push ds
    push ds
    pop es
    mov ds,dx
    rep movsb
    pop ds
    pop es
gtxct1:
    pop di
    pop cx
    pop dx
    pop ax
    pop si
    ret
GetTextControl endp
end


Copr. 1995 Zenith Data Systems Corp

.MODEL SMALL
.code
extrn AddControlToActiveList:near
extrn AdjustButtonDimensions:near
extrn DoPenEvent:near
extrn DrawLabel:near
extrn DrawString:near
extrn DrawButtonFrame:near
extrn DrawTextbox:near
extrn FindRegionForControl:near
extrn GetNormFontHeight:near
extrn JumpOnAL:near
extrn PointControlCaption:near
extrn PopRegion:near
extrn PushRegion:near
extrn Repaint:near
extrn RepaintButton:near
extrn RestoreRegion:near
extrn SetControlTabList:near
extrn SetFontForCaption:near
extrn SetNewTabItem:near
extrn SetNewTabItem:near
extrn ShowTabBox:near
extrn StoreRegion:near
extrn UndoCurrentTabItem:near
include uiinclud.inc


DATASEG_BEGIN
extrn ControlDataStorageArea:byte
extrn bButtonForegroundColor:byte
extrn bCaptionForegroundColor:byte
extrn bCaptionForegroundColor:byte
extrn bCaptionForegroundColor:byte
extrn bIgnoringMove:byte
extrn bInString:byte
extrn pClickRegion:word
extrn pCurrentFont:word
extrn pHostActiveRegion:word
extrn pNormFont:word
extrn pTabRegion:word
extrn rActiveRegion:rRegion
extrn rREGION:REGION
extrn rTabRegion:REGION
extrn wNormFontHeight:word
extrn wPenCurrentRow:word

FirstStandardControl label ICONTROL
    public FirstStandardControl

VScrollControls label ICONTROL
NEXTCONTROL=32000
VsbBacking label IControl
    public vsbBacking
    MAKE_COMMANDBUTTON
%NORMSTATE,0,0,16,16*2

VsbUpArrow label IControl
    public vsbUparrow
    MAKE_SYMBOLBUTTON
%NORMSTATE,0,0,16,16
    GRAPHIC_CAPTION UPARROWBITMAP

VsbSlider label IControl
    public vsbSlider
    MAKE_COMMANDBUTTON
%NORMSTATE,0,%NEXTTOP,16,16

VsbDnArrow label IControl
    public VSBDnArrow
    MAKE_SYMBOLBUTTON
%NORMSTATE,0,%NEXTTOP,16,16
    GRAPHIC_CAPTION DNARROWBITMAP

LastStandardControl label ICONTROL
    public LastStandardControl



bListItemNormForeground db BLACK
bListItemNormBackground db WHITE
bListItemGrayedForeground db GRAY
bListItemGrayedBackground db WHITE
bListItemSelectedForeground db WHITE
bListItemSelectedBackground db BLACK


wListCurrentItem dw 0
    public wListCurrentItem

bListItemHoldItem db 0

wHoldCurrentListIndex dw 0

wListGotSel dw 0
wListIndex dw 0
```

```
bListItemAttribute db 1

wListSlideRow dw 0
 public wListSlideRow

LISTITEMBUFFERSIZE equ 80


rListBoxItem tListBoxEntry <szListItemBuffer,0>
rListBoxItem1 tListBoxEntry <szListItemBuffer1,0>
rListBoxItem2 tListBoxEntry <szListItemBuffer2,0>

szListItemBuffer label byte
  db LISTITEMBUFFERSIZE+1 dup(0)
szListItemBuffer1 label byte
  public szListItemBuffer1
  db LISTITEMBUFFERSIZE+1 dup(0)
szListItemBuffer2 label byte
  public szListItemBuffer2
  db LISTITEMBUFFERSIZE+1 dup(0)

pPenDownListRegion dw 0
  public pPenDownListRegion
pPenUpListRegion dw 0
  public pPenUpListRegion
pPenDownListItem dw 0
  public pPenDownListItem
rListItemRegion tRegion <0,0,0,0,0,-1,0,0>

wAutoScrollTimer  dw 0
  public wAutoScrollTimer
bAutoScrollMode   db 0
  public bAutoScrollMode
bRepaintItemsOnly db 0
  public bRepaintItemsOnly

wCurrentMaxListItem dw 0
  public wCurrentMaxListItem
wCurrentTopListItem dw 0
wCurrentScrollBarHeight dw 0
bListRepaintNeeded  db 0
pListGrayedItemSkipped dw 0
DATASEG_END

.code

AddListItemToActiveList proc near
 push si
 mov si,offset rListItemRegion
 call StoreRegion
 pop si
 ret
AddListItemToActiveList endp

RepaintListBox proc near
  public RepaintListBox


  cmp al,LISTBOX
  jz rlb1
  cmp al,LISTBOXNOSCROLL
  jz rlb1
  ret
rlb1:

  push si
  push ax
  call GetListMaxAndTop
  push pNextActiveRegion
  pop pPenUpListRegion
  mov rRegion.bListItemFlags,128
  call AddControlToActiveList
  mov rRegion.bListItemFlags,0
  pop ax
  pop si

  call SetControlTabList

  push ax
  call AdjustButtonDimensions

rlb3a:
  cmp bRepaintItemsOnly,0
  mov bRepaintItemsOnly,0
  jnz rlb3c

  push dx
  push cx
  push bx
  add dx,20
  sub bh,10
 cmp al,LISTBOXNOSCROLL
  jz rlb2
  sub bl,2
rlb2:
  call DrawTextBox
  pop bx
  pop cx
  pop dx
```

```
 push si
 push di
 push es
 push bx
 call DrawSunkenFrame
 pop bx
 pop es
 pop di
 pop si

 push ax
 call PaintControlCaption
 pop ax
 jz rlb3
 or bx,bx
 jz rlb3
 call SetFontForCaption

 push si
 mov si,bx
 and si,3
 and cx,12
 add dx,4
 mov bl,bButtonForegroundColor
 xor bh,bh
 call drawlabel
 pop si

rlb3c:
 pop bx
 push cx
 cmp al,LISTBOXNOSCROLL
 jz rlb3
 push si
 call PushRegion
 call DrawVerticalScrollBar
 call PopRegion
 pop si
rlb3:
 mov bx,si
 or bx,bx
 pop ax
 jnz rlb16
 jmp rlb4
rlb16:

 call GetListItemItem

 push pNextActiveRegion
 pop [bx].pFirstRegionRecord

 mov rListItemRegion.pCurrentControl,si
 mov dx,rRegion.wCurrentTop
 add dx,21+3
 mov rListItemRegion.wCurrentTop,dx
 add dx,wMenuFontHeight
 dec dx
 mov rListItemRegion.wCurrentBottom,dx
 mov cx,rRegion.wCurrentLeft
 add cx,4+4+1
 mov rListItemRegion.wCurrentLeft,cx
 mov cx,rRegion.wCurrentRight
 sub cx,(21+4+4+1)-8
 cmp [si].ControlType,LISTBOXNOSCROLL
 jnz rlb11
 add cx,18
rlb11:
 mov rListItemRegion.wCurrentRight,cx
 mov cx,[bx].ID
 mov cx,[bx].wTopVisible
 inc cx
 mov rListItemRegion.wListItemIndex,cx
rlb14:
 mov cx,rListItemRegion.wListItemIndex
 mov cx,[bx].ID
 mov rListItemRegion.wListHandle,cx
 mov rListItemRegion.wCurrentHeight,-1
 push bx
 push si
 or cx,cx
 jz rlb16a
 cmp cx,wCurrentMaxListItem
 jbe rlb15
rlb16a:
 mov rListItemRegion.wListItemIndex,0
 mov bl,0
 jmp rlb12
rlb15:
 call getlistdata
 cmp wCurrentMaxListItem,dx
 jna rlb12
 or bl,4
rlb12:
 mov rListItemRegion.bListItemFlags,bl
 mov si,pNextActiveRegion
 call AddListItemToActiveList
 call DrawListItem
 pop si
 pop bx
```

```
 mov ax,wMenuFontHeight
 push ax
 add ax,rListItemRegion.wCurrentBottom
 cmp ax,rRegion.wCurrentBottom
 pop ax
 jz rlb13
 add rListItemRegion.wCurrentTop,ax
 add rListItemRegion.wCurrentBottom,ax
 cmp rListItemRegion.wListItemIndex,0
 jz rlb14a
 inc rListItemRegion.wListItemIndex
rlb14a:
 jmp rlb14
rlb13:
 mov ax,[si]
rlb4:
rlb00:
 ret
RepaintListBox endp

RepaintIndividualListBox proc near
 public RepaintIndividualListBox
 call FindRegionForControl
 jnc dlng1
 ret

dlng1:
 push pNextActiveRegion
 mov pNextActiveRegion,bx
 mov si,bx
 call RestoreRegion
 mov ax,[si]
 call RepaintListBox
 pop pNextActiveRegion
 clc
 ret
RepaintIndividualListBox endp

CopyListItemFromStd proc near
 push ds
 pop es
 mov ds,dx
 mov al,[si].cAttribute
 mov es:bListItemAttribute,al
 push cx
 mov cx,LISTITEMBUFFERSIZE
 or dx,dx
 jz glr04
 lds si,[si].lpszEntry
 mov ax,ds
 or ax,si
 jz glr04
 rep movsb

glr04:
 pop cx
 xor al,al
 stosb
 push es
 pop ds
 ret
CopyListItemFromStd endp

DoAutoScrollEvent proc near
 public DoAutoScrollEvent
 cmp wAutoScrollTimer,1
 jb dase00

 mov wAutoScrollTimer,0
 mov si,pTabRegion
 cmp bAutoScrollMode,1
 jne dase1
 mov ax,[si].wCurrentBottom
 cmp wPenCurrentRow,ax
 jbe dase00
 call DoListDownArrow
 jmp short dase2
dase1:
 mov ax,[si].wCurrentTop
 cmp wPenCurrentRow,ax
 jae dase00
 call DoListUpArrow
dase2:
 jc dase00
 mov pClickRegion,si
dase00:
 ret
DoAutoScrollEvent endp

DoListBoxKey proc near
 public DoListBoxKey
 cmp al,' '
 jne dlbk1
 mov al,ah

 call JumpOnAL
 db UP_ARROW_SCAN_CODE
 dw offset dlbua
 db DOWN_ARROW_SCAN_CODE
```

```
 dw offset dlbda
 db 0
dlbk1:
 ret

dlbua:
 call DoListUpArrow
 jc dlbda1
 mov pClickRegion,si
 mov pPenUpListRegion,si
dlbda1:
 ret

dlbda:
 call DoListDownArrow
 jc dlbda2
 mov pClickRegion,si
 mov pPenUpListRegion,si
dlbda2:
 ret
DoListBoxKey endp

DoListDownArrow proc near


 mov si,pTabRegion
 or si,si
 jnz dlda1a
 jmp dlda1
dlda1a:

 cmp [si].wListHandle,0
 jnz dlda1aa
 jmp dlda1
dlda1aa:
 cmp [si].wListItemIndex,0
 jnz dlda1x
 jmp dlda1
dlda1x:
 test [si].bListItemFlags,4
 jz dlda3
 jmp dlda1
dlda3:
 mov ax,[si].wListHandle
 mov bx,type rTabRegion
 cmp ax,[si+bx].wListHandle
 jnz dlda2
 add si,bx
 test [si].bListItemFlags,1
 jnz dlda3

dlda2a:
 stc
 ret
dlda2:
 push si
 mov bx,[si].pCurrentControl
 inc [bx].wTopVisible
 mov ax,[bx].pFirstRegionRecord
 mov cx,si
 mov si,ax
dlda3a:
 cmp si,cx
 jb dlda4
 mov di,si
 add si,type rRegion
 mov dx,[si].wListItemIndex
 mov [di].wListItemIndex,dx
 mov dl,[si].bListItemFlags
 mov [di].bListItemFlags,dl
 jmp short dlda3a

dlda4:
 inc [si].wListItemIndex
 mov ax,[si].wListItemIndex
 mov bx,[si].wListHandle
 push si
 call GetListData
 pop si
 mov [si].bListItemFlags,bl
 mov ax,LIST_LAST_ITEM
 mov ax,[si].wListHandle
 push si
 call GetListData
 pop si
 cmp dx,[si].wListItemIndex
 jnz dlda5
 or [si].bListItemFlags,4
dlda5:
 mov bListRepaintNeeded,-1
 pop si
 sub si,type rTabRegion
 jmp dlda3
dlda1:
 stc
 ret
DoListDownArrow endp

DoListSlide proc near
```

```
 public DoListSlide


 push di
 call FindListBoxForVSB
 pop di

 call GetListMaxAndTop
 call GetListTopItemRange
 cmp cx,1
 jle dvs1
 mov bx,ax
 mov ax,wListSlideRow
 mov dx,[di].wCurrentBottom
 sub dx,28
 cmp ax,dx
 jle dvs3
 mov ax,dx
dvs3:
 sub ax,[di].wCurrentTop
 sub ax,16
 jge dvs2
 xor ax,ax
dvs2:
 mov dx,100
 mul dx
 mov cx,[di].wCurrentHeight
 sub cx,2*16
 div cx
 mul bx
 mov cx,100
 div cx
 cmp [si].wTopVisible,ax
 jz dvs1
 mov [si].wTopVisible,ax
 mov bRepaintItemsOnly,-1
 call RepaintIndividualListBox
dvs1:
 ret
DoListSlide endp

DoListUpArrow proc near

 mov si,pTabRegion
 mov pListGrayedItemSkipped,si
 or si,si
 jnz dlua1a
 jmp dlua1
dlua1a:
 cmp [si].wListHandle,0
 jnz dlua3
 jmp dlua1
dlua3:
 cmp [si].wListItemIndex,1
 jnz dlua1b
 jmp dlua1
dlua1b:
 cmp si,offset aActiveRegions
 jbe dlua2
 mov bx,type rTabRegion
 neg bx
 mov ax,[si].wListHandle
 cmp [si+bx].wListHandle,ax
 jnz dlua2
 add si,bx
 test [si].bListItemFlags,1
 jz dlua1s
 cmp [si].wListItemIndex,1
 jz dlua1

 cmp [si+bx].wListHandle,ax
 jz dlua1s
 call ScrollDownList
 mov si,pListGrayedItemSkipped
 add si,type rTabRegion
 jmp dlua1c
dlua1d:
 jmp dlua3
dlua1c:
 clc
 ret
dlua2:

 call ScrollDownList
 jmp dlua3
dlua1:
 stc
 ret
DoListUpArrow endp

DoVsbDnArrow proc near
 public doVSBDnArrow
 call FindListBoxForVSB
 mov ax,[di].wListHandle
dvda3:
 cmp [di].wListHandle,ax
 jnz dvda1
 cmp [di].wListItemIndex,0
 jz dvda2
 test [di].bListItemFlags,4
 jnz dvda2
 add di,type rRegion
 jmp dvda3
dvda1:
 inc [si].wTopVisible
 mov bRepaintItemsOnly,-1
 call RepaintIndividualListBox
dvda2:
 ret
DoVsbDnArrow endp

DoVsbUpArrow proc near
 public doVSBUpArrow

 call FindListBoxForVSB
 cmp [si].wTopVisible,1
 jb dvua2
 dec [si].wTopVisible
 mov bRepaintItemsOnly,-1
 call RepaintIndividualListBox
dvua2:
 ret
DoVsbUpArrow endp

FindListBoxForVSB proc near

dvua1:
 add di,type rRegion
 cmp [di].wLISTHANDLE,0
 jz dvua1
 mov si,[di].pCurrentControl
 ret
FindListBoxForVSB endp

GetListData proc near
 public GetListData
LIST_CURRENT_ITEM equ 0
LIST_LAST_ITEM   equ -1
 push di
 cmp cx,-1
 jnz glx1
 call GetListDataWork
 jmp gls90
glx1:
 cmp cx,0
 jnz gls2
 call GetListDataWork

 mov wListCurrentItem,dx
 not bl
 and bl,1
 or bl,2
 jmp gls90

gls2:
 mov bListItemNoStore,-1
 push ax
 push cx
 xor cx,cx
 call GetListDataWork
 mov wHoldCurrentListIndex,dx
 pop cx
 pop ax
 call GetListDataWork
 not bl
 and bl,1
 cmp dx,wHoldCurrentListIndex
 jnz gls3
 or bl,2
gls3:
 jmp gls90
gls90:
 pop di
 ret
GetListData Endp

GetListDataWork proc near
 call CheckListDataAvailable
 jnc gld00

gld_wait1:
 mov dx,0
 stc
gld00:
 mov wListGetSel,cx
 mov bx,ax
 mov ah,80h
 SM_FUNCTION sx
 jl gld1
 cmp cx,-1
 jnz gld2
 mov dx,ax
 ret
gld1:
 mov dx,0
 ret
gld2:
 cmp cx,0
 jz tmp1
 mov ax,cx
tmp1:
 cmp bListItemNoStore,0
 jz gld2a
 mov bListItemNoStore,0
 ret
gld2a:
 mov wListIndex,ax
 mov ax,wListGetSel
 mov di,offset szListItemBuffer
 cmp ah,0
 jz gld3
 mov di,offset szListItemBuffer1
gld3:
 call CopyListItemFromSM
 mov ax,wListGetSel
 or ah,ah
 jz gld6

 mov byte ptr szListItemBuffer2,0
 mov al,ah
 mov ah,80h
 mov bx,ax
 SM_FUNCTION sx
 jl gld6
 mov ax,dx
 or ax,ax
 jz gld6
 mov di,offset szListItemBuffer2
 call CopyListItemFromSM

gld6:
 push ds
 pop es
 mov si,offset szListItemBuffer1
 mov di,offset szListItemBuffer
gld6a:
 cmp di,offset szListItemBuffer +
LISTITEMBUFFERSIZE
 jae gld6b
 lodsb
 or al,al
 jz gld6b
 stosb
 jmp gld6a
gld6b:
 mov si,offset szListItemBuffer2
gld6c:
 cmp di,offset szListItemBuffer +
LISTITEMBUFFERSIZE
 jae gld6d
 mov al,0
 stosb
gld6e:
 cmp di,offset szListItemBuffer +
LISTITEMBUFFERSIZE
 jae gld6d
 lodsb
 stosb
 or al,al
 jnz gld6e

gld6d:


gld5:
 mov bl,bListItemAttribute
 mov dx,wListIndex
 mov si,offset szListItemBuffer
 ret
GetListDataWork endp

HandleListPenUp proc near
 public HandleListPenUp

 mov si,pPenUpListRegion
 or si,si
 jnz hlpu1a
 jmp hlpu1
hlpu1a:
 mov ax,[si].pCurrentControl
 or ax,ax
 jnz hlpu1b
 jmp hlpu1
hlpu1b:
 call DoCustomListPenUp

hlpu1:
 mov pPenUpListRegion,0
 ret
HandleListPenUp endp

ListItemClick proc near
 public ListItemClick


 test [di].wListItemIndex,07FFh
 jnz lic1
 jmp lic11
lic1:
 test [di].bListItemFlags,1
 jz lic2
 jmp lic11
lic2:
 cmp bListRepaintNeeded,-1
 jz lic7

 test [di].bListItemFlags,2
 jz lic3
 call ShowTabBox
 jmp lic11
lic3:
 call UndoCurrentTabItem
 call ChangeListItem
 mov si,di
 call DrawListItem
 call SetNewTabItem
 jmp lic10

lic7:
 mov bListRepaintNeeded,0
 call UndoCurrentTabItem
 inc bIgnoringMove
 call ChangeListItem
 mov si,[di].pCurrentControl
 mov bRepaintItemsOnly,-1
 call RepaintIndividualListBox
 call SetNewTabItem
 dec bIgnoringMove

lic10:
 stc
 jmp short lic12
lic11:
 clc
lic12:
 ret
ListItemClick endp


ChangeListItem proc near

 call UndoOldCurrentListItem
 or [di].bListItemFlags,2
 mov cx,[di].wListItemIndex
 mov ax,[di].wListHandle
 push ax
 push cx
 call GetListData
 pop cx
 pop ax
 call SetListCurrent
 ret
ChangeListItem endp

ScrollDownList proc near

 push si
 mov bx,[si].pCurrentControl
 dec [bx].wTopVisible
 mov cx,si
 mov ax,[si].wListHandle
 mov bx,type rTabRegion
dlus7:
 cmp [si+bx].wListHandle,ax
 jnz dlus8
 add si,bx
 jmp dlus7

dlus8:
 neg bx
dlus9:
 cmp si,cx
 jz dlus0
 mov dx,[si+bx].wListItemIndex
 mov [si].wListItemIndex,dx
 mov dl,[si+bx].bListItemFlags
 mov [si].bListItemFlags,dl
 add si,bx
 jmp short dlus9
dlus0:
 dec [si].wListItemIndex
 mov cx,[si].wListItemIndex
 mov ax,[si].wListHandle
 push si
 call GetListData
 pop si
 mov [si].bListItemFlags,bl
 mov cx,LIST_LAST_ITEM
 mov ax,[si].wListHandle
 push si
 call GetListData
 pop si
 cmp dx,[si].wListItemIndex
 jnz dlus5
 or [si].bListItemFlags,4
```

```
dlsc6:

 mov bListRepaintNeeded,-1
 pop si
 add si,type rTabRegion
 ret
ScrollDownList endp

SetListCurrent proc near
 public SetListCurrent
 cmp ah,0
 jnz slc1

 mov si,offset rListBorItem
 push bx
 mov dx,ds
 mov ah,bListItemAttribute
 mov [si].cAttribute,ah
 mov word ptr [si].lpszEntry[0],offset
szListItemBuffer
 mov word ptr [si].lpszEntry[2],ds
 xor ah,ah
 mov bx,ax
 SM_FUNCTION ax
 pop ax
 ret

slc1
 mov si,offset rListBorItem1
 push si
 mov dx,ds
 mov ah,bListItemAttribute
 mov [si].cAttribute,ah
 mov word ptr [si].lpszEntry[0],offset
szListItemBuffer1
 mov word ptr [si].lpszEntry[2],ds
 xor ah,ah
 mov bx,ax
 SM_FUNCTION ax
 pop ax
 mov si,offset rListBorItem2
 push ax
 mov al,ah
 mov dx,ds
 mov ah,bListItemAttribute
 mov [si].cAttribute,ah
 mov word ptr [si].lpszEntry[0],offset
szListItemBuffer2
 mov word ptr [si].lpszEntry[2],ds
 xor ah,ah
 mov bx,ax
 SM_FUNCTION ax
 pop ax
 ret
SetListCurrent endp

DrawVerticalScrollBar proc near
 public DrawVerticalScrollBar

 mov si,offset VsbBacking
 mov rRegion.pCurrentControl,si
 mov cx,rRegion.wCurrentRight
 sub cx,23
 ROUND_TO_BYTE_BOUNDARY cx

 mov rRegion.wCurrentLeft,cx
 push cx
 add cx,12
 dec cx
 mov rRegion.wCurrentRight,cx
 pop cx
 add rRegion.wCurrentTop,21
 mov dx,rRegion.wCurrentTop
 mov ax,rRegion.wCurrentHeight
 mov [si].TopPixel,dx
 sub ax,34
 mov rRegion.wCurrentHeight,ax
 mov wCurrentScrollBarHeight,ax
 mov [si].PixelHeight,ax
 mov ax,16
 mov rRegion.wCurrentWidth,ax
 mov ax,[si]
 call RepaintButton
 mov rRegion.bListItemFlags,128
 call AddControlToActiveList


 mov si,offset VsbUpArrow
 mov rRegion.pCurrentControl,si
 mov ax,16
 mov rRegion.wCurrentHeight,ax
 add ax,rRegion.wCurrentTop
 mov rRegion.wCurrentBottom,ax
 mov ax,[si]
 mov bx rRegion.wCurrentTop
 mov cx rRegion.wCurrentLeft
 call RepaintButton
 mov rRegion.bListItemFlags,128
 call AddControlToActiveList
 push rRegion.wCurrentBottom


 mov si,offset VsbDnArrow
 mov rRegion.pCurrentControl,si
 mov dx,VsbBacking.TopPixel
 add dx,VsbBacking.PixelHeight
 mov rRegion.wCurrentBottom,dx
 mov ax,16
 sub dx,ax
 mov rRegion.wCurrentTop,dx
 mov rRegion.wCurrentHeight,ax
 mov [si].TopPixel,dx
 mov cx,rRegion.wCurrentLeft
 mov ax,[si]
 call RepaintButton
 mov rRegion.bListItemFlags,128
 call AddControlToActiveList
 pop rRegion.wCurrentBottom


 mov si,offset VsbSlider
 mov rRegion.pCurrentControl,si

 call GetListTopItemRange
 jz dvs3
dvs4:
 xor ax,ax
 jmp dvs1
dvs3:
 mov ax,100
 mov bx,wCurrentTopListItem
 or bx,bx
 jz dvs4
 inc bx
 mul bx
 div cx
 mov dx,wCurrentScrollBarHeight
 sub dx,16*2
 mul dx
 mov cx,100
 div cx
dvs1:
 add ax,rRegion.wCurrentBottom
 mov bx,rRegion.wCurrentTop
 sub bx,16
 cmp ax,bx
 jbe dvs2
 mov ax,bx
dvs2:
 mov rRegion.wCurrentTop,ax
 mov dx,ax
 add ax,rRegion.wCurrentHeight
 dec ax
 mov rRegion.wCurrentBottom,ax
 mov ax,rRegion.wCurrentLeft
 mov ax,[si]
 call RepaintButton
 mov rRegion.bListItemFlags,128
 call AddControlToActiveList
 ret
DrawVerticalScrollBar endp

GetListTopItemRange proc near

 call GetNormFontHeight
 mov cx,ax
 mov ax,wCurrentScrollBarHeight
 xor dx,dx
 div cx
 mov cx,wCurrentMaxListItem
 sub cx,ax
 inc cx
 ret
GetListTopItemRange endp

DrawListItem proc near
 public DrawListItem

 push si
 push bx
 push di
 mov di,si
 mov ax,[di].wListHandle
 mov cx,[di].wListItemIndex
 or cx,cx
 jnz dli1

 mov si,offset bNullString
 mov bl,0
 jmp dli2
dli1:
 call GetListData
dli2:
 mov al,[di].bListItemFlags
 mov bl,bListItemNormForeground
 mov bh,bListItemNormBackground
 test al,1
 jz dli3
 mov bl,bListItemGrayedForeground
 mov bh,bListItemGrayedBackground
 jmp dli4
dli3:
 test al,2
 jz dli4
 mov bl,bListItemSelectedForeground
 mov bh,bListItemSelectedBackground
dli4:
 or bh,LEFTJUSTIFIED+WITHBACKCOLOR
 mov cx,[di].wCurrentRight
 mov ax,[di].wCurrentLeft
 sub cx,ax
 inc cx
 mov dx,[di].wCurrentTop
 push pNormFont
 pop pCurrentFont
 call DrawString
 pop di
 pop bx
 pop si
 ret
DrawListItem endp

GetListMaxItem proc near
 public GetListMaxItem

 push ax
 mov ax,[bx].ID
 mov cx,LIST_LAST_ITEM
 push dx
 push bx
 push si

 call GetListData
 mov wCurrentMaxListItem,dx
 pop si
 pop bx
 pop dx
 pop ax
 ret
GetListMaxItem endp

GetListMaxAndTop proc near
 public GetListMaxAndTop

 mov bx,si
 call GetListMaxItem
 push [si].wTopVisible
 pop wCurrentTopListItem
 ret
GetListMaxAndTop endp

UndoOldCurrentListItem proc near
 push si
 mov bx,[di].pCurrentControl
 mov si,[bx].pFirstRegionRecord
lsd1:
 test [si].bListItemFlags,2
 jnz lsd4
 mov ax,[si].wListHandle
 add si,type rRegion
 cmp ax,[si].wListHandle
 jz lsd1

 jmp short lsd3

lsd4:
 and [si].bListItemFlags, not(2)
 call DrawListItem
lsd3:
 pop si
 ret
UndoOldCurrentListItem endp

end

Copr. 1996 Zenith Data Systems Corp.

.MODEL SMALL
.CODE
extrn PenOff:near
extrn PenOn:near
extrn HidePen:near
extrn ActivatePen:near
extrn CheckIfOnlyOSK:near
extrn DoAutoScrollEvent:near
extrn DoClickEvent:near
extrn DoCursorFlash:near
extrn DoKeyEvent:near
extrn DoPenEvent:near
extrn DoSpinDown:near
extrn DoSpinUp:near
extrn DoVSBDnArrow:near
extrn FillScreenArea:near
extrn GetNormFontHeight:near
extrn GetTabControlType:near
extrn HandleListPenUp:near
extrn Repaint:near
extrn RepaintAndSetTab:near
extrn RepaintOSKInMemory:near
extrn SendKey:near
extrn SendKeyDownScanCode:near
extrn SetFormHeights:near
extrn ShowPen:near
extrn DoVSBDnArrow:near
extrn DoVSBUpArrow:near

include ulmdef.inc

if need_tsr ne 0
ProgEnd segment public 'stack'
ProgEnd ends
endif

DATASEG_BEGIN
extrn ControlDataStorageArea:byte
extrn MainFormsControl
extrn OSKControl
extrn VSBDnArrowControl
extrn VSBUpArrowControl
extrn bAutoScrollMode:byte
extrn bAutoScrollMode:byte
extrn bAutoScrollMode:byte
extrn bCursorActive:byte
extrn bPenEventHappened:byte
extrn bSuppressShow:byte
extrn pPenUpListRegion:word
extrn pPenUpListRegion:word
extrn pPenUpListRegion:word
extrn wFont0:word
extrn wFont1:word
extrn wFont2:word
extrn wFont3:word
extrn vsbUpArrowControl
extrn wAutoScrollTimer:word
extrn wAutoScrollTimer:word
extrn wCoveredAreaTop:word
DATASEG_END


if need_tsr eq 0
 SET_PEN_EVENT_HANDLER = 5ah
 PEN_ACTIVATE_FUNCTION = 33h
endif

INSTALL_INT macro intnum
 jmp short $ + 6
old&intnum&int dd 0
 push ds
 mov ah,35h
 mov al,&intnum&h
 int 21h
 mov word ptr cs:old&intnum&int,bx
 mov word ptr cs:old&intnum&int[2],es
 push cs
 pop ds
 mov dx,offset new&intnum&int
 mov ah,25h
 mov al,&intnum&h
 int 21h
 pop ds
endm
REMOVE_INT macro intnum
 push ds
 mov dx,word ptr cs:old&intnum&int
 mov ds,word ptr cs:old&intnum&int[2]
 mov al,intnum&h
 mov ah,25h
 int 21h
 pop ds
endm

DATASEG_BEGIN

wPSPSegment dw 0
 public wPSPSegment


bTestMode db 0
 public bTestMode

bLanguageToUse db 0
 public bLanguageToUse

wCurrentResource dw 0
 public wCurrentResource
bNewDisplayRequested db 0
 public bNewDisplayRequested
wDisplayRequested dw 0
 public wDisplayRequested
bMessageBoxRequested db 0
 public bMessageBoxRequested
bRemoveMessageBoxRequested db 0
 public bRemoveMessageBoxRequested
bMessageBoxID db 0
 public bMessageBoxID
```

```
bMessageBoxResult db 0
  public bMessageBoxResult
bGetDataFromLocalStorage db 0
  public bGetDataFromLocalStorage
bDummyBlank db " ",0
  public bDummyBlank

wDivisors label word
dw 10000
dw 1000
wDivisors100 label word
dw 100
wTenWord label word
dw 10
dw 1

bNullString db 0,0
  public bNullString

wJumpTableBase dw 0

wCursorTimer dw 0
  public wCursorTimer

wTypematicTimer dw 0
pTypematicOSKControl dw 0
bTypematicState db 0
  public bTypematicState

bDoingEvents db 0
  public bDoingEvents
bPopUpRequired db 0
  public bPopUpRequired

wVideoStateBuffer dw 0 dup(0)
bOrgScreenMode db 0
bScreenMode db 0
  public bScreenMode
wScreenSegment dw 0
  public wScreenSegment

bMoveMode db 0
  public bMoveMode
wMoveModePenRow dw 0
  public wMoveModePenRow
wMoveModePenColumn dw 0
  public wMoveModePenColumn

bNoDimensionUpdate db 0
  public bNoDimensionUpdate

wKeyPressed dw 0
  public wKeyPressed
bKeyChanged db 0
  public bKeyChanged

wShortCutKey dw 0
  public wShortCutKey

rActiveRegions label tRegion
  public rActiveRegions
  db MAX_ACTIVE_CONTROLS * type tRegion dup(0)

rMoveStartRegion tRegion <0,0,0,0,0,0,0,0>
  public rMoveStartRegion
rPushedRegion tRegion <0,0,0,0,0,0,0,0>
  public rPushedRegion
rRegion tRegion <0,0,0,0,0,0,0,0>
  public rREGION
rLegendRegion tRegion <0,0,0,0,-1,0,0>
  public rLegendRegion
rTabRegion tRegion <0,0,0,0,-1,0,0>
  public rTabRegion
rCursorRegion tRegion <0,0,0,0,0,0,0,0>
  public rCursorRegion

pPenDownActiveRegion dw 0
  public pPenDownActiveRegion
pPenDownLegendRegion dw 0
  public pPenDownLegendRegion

pClickRegion dw 0
  public pClickRegion

pOSKFirstRegion dw -1
  public pOSKFirstRegion

pNextActiveRegion dw 0
  public pNextActiveRegion
pCurrentToolButtonRegion dw 0
  public pCurrentToolButtonRegion
pOrgTabRegion dw 0

pCurrentToolBarButton dw 0
  public pCurrentToolBarButton
pFirstControl dw 0
  public pFirstControl

bLocalState db 1
  p..lic bLocalState

FontTable label word
  public FontTable
pNormFont dw offset uifont0
  public pNormFont
pSmallFont dw offset uifont1
pBigFont dw offset uifont2
pGraphicFont dw offset uifont3
  public pGraphicFont

wNormFontHeight dw 0
  public wNormFontHeight

bFormColor db FORM_COLOR,0
  public bFormColor
bShadowColor db SHADOW_COLOR,0
  public bShadowColor
bOutLineColor db OUTLINE_COLOR,0
  public bOutLineColor
bLightColor db LIGHT_COLOR,0
  public bLightColor

bDesktopColor db BLUE,0
  public bDeskTopColor
bIconForegroundColor db BLACK,0
  public bIconForegroundColor
bIconBackgroundColor db
WHITE+WITHBACKCOLOR,0
  public bIconBackgroundColor
bButtonForegroundColor db BLACK,0
  public bButtonForegroundColor
bCaptionForegroundColor db BLACK,0
  public bCaptionForegroundColor
bCaptionBackgroundColor db GRAY,0
  public bCaptionBackgroundColor
bTitleForegroundColor db BLACK,0
  p..lic bTitleForegroundColor

bRepaintNeeded db 0
  public bRepaintNeeded
bRepaintMode db 0
  public bRepaintMode
bDontChangeProtection db 0
  public bDontChangeProtection
bDoingSpin db 0
  public bDoingSpin
bModalFlag db 0
  public bModalFlag
bModalFlagHold db 0
  public bModalFlagHold

pGraphicsCaption dw 0
  public pGraphicsCaption
pTextCaption dw 0
  public pTextCaption
wShiftCaption dw 0
  public wShiftCaption
wCaptionTop dw 0
  public wCaptionTop
wGraphicCaptionHeight dw 0
  public wGraphicCaptionHeight
wGraphicLegendRight dw 0
  public wGraphicLegendRight

IgnoreLevel dw 0
  public IgnoreLevel
IObjectLevel dw 0
  public IObjectLevel

ITopAdders label word
  public ITopAdders
        dw 10 dup(0)
ILeftAdders label word
  public ILeftAdders
        dw 10 dup(0)
wDeltaLeft dw 0
  public wDeltaLeft
wDeltaTop dw 0
  public wDeltaTop

if NEED_ALTKEYS ne 0
AltKeyTable label byte
  db "1234567890"
  db "QWERTYUIOP"
  db "ASDFGHJKL"
  db "ZXCVBNM"
AltKeyTable_end label byte

ScanCodeTable label byte
  db 120,121,122,123,124,125,126,127,128,129
  db 16,17,18,19,20,21,22,23,24,25
  db 30,31,32,33,34,35,36,37,38
  db 44,45,46,47,48,49,50
ScanCodeTable_end label byte
endif
DATASEG_END
.CODE
uimain proc far
  public UIMain

  mov ax,CURDATASEG
  mov ds,ax
  mov ax,5100h
  int 21h
  mov wPSPsegment,bx

  mov ah,0fh
  int 10h
  and al,1111111b
  mov bScreenMode,al
  mov bOrgScreenMode,al

if need_tsr eq 0
  mov ah,0
  mov al,12h
  mov bScreenMode,al
  int 10h
endif

  call ActivatePen

  call far ptr DoCustomStartups

  mov pFirstControl,offset MainForm
  call GetNormFontHeight
  call SetFormHeights

  call InstallInterrupts

if need_tsr eq 0
  call showpen
  mov bRepaintNeeded,-1
  call doevents
  mov ah,0
  mov al,bOrgScreenMode
  and al,1111111b
  int 10h
  call DeinstallInterrupts
  mov ax,0
  int 33h
  ret
else
  mov dx,ProgEnd
  sub dx,wPspSegment
  inc dx
  mov ax,3100h
  int 21h
endif

uimain endp

DoEvents proc near
  public DoEvents

  mov bLocalState,1
doloop:

  call far ptr DoCustomEvents
  jnc dolp1
  jmp do100
dolp1:

  cmp bRepaintNeeded,0
  jz doda
  call RepaintAndSetTab
if need_osk ne 0
  call RepaintOSKInMemory
endif
doda:

  call DoCursorFlash

  cmp bPenEventHappened,0
  jz do2
  call DoPenEvent
do2:

if need_tsr eq 0
  mov ah,1
  int 16h
  jz dph1
  mov ah,0
  int 16h
  mov bKeyChanged,-1
  mov wKeyPressed,ax
endif
dph1:

  cmp bTestMode,0
  jz do1
  cmp bKeyChanged,0
  jz do1
  call DoTestModeEvent
do1:

  call CheckTypematicState
  jnc ete3
  call DoTypematicEvent
ete3:
  cmp bAutoScrollMode,0
  jz ete1
  call DoAutoScrollEvent
ete1:

  cmp wKeyPressed,0
  jz do6
  call GetTabControlType
  cmp al,KEYEDITBOX
  jz do6
  call DoKeyEvent
  mov wKeyPressed,0
do6:

  cmp pClickRegion,0
  jz do5
  call DoClickEvent
  mov pClickRegion,0
  mov pPenDownActiveRegion,0
do5:
  cmp pPenUpListRegion,0
  jz do5a
  call HandleListPenUp
do5a:

do99:

if need_tsr ne 0
  cmp bRepaintNeeded,0
  jz do101
  jmp doloop
do101:
  cmp bPopupRequired,0
  jz do100
endif

  cmp bLocalState,0
  jz do100
  mov bPopupRequired,0
  jmp doloop
do100:
  ret
DoEvents endp

DoTestModeEvent proc near

  mov ax,wKeyPressed
  cmp al,0
  jne dke1a

  cmp ah,78h
  jb ckk1
  cmp ah,7eh
  jb ckk1
  jmp ckk2
ckk1:
  cmp ah,47h
  jne dke1a
ckk2:
  mov bl,ah
  SM_FUNCTION SM_TEST_FUNCTION
dke1a:
  ret
DoTestModeEvent endp
```

```
CheckTypematicState proc near
 cmp bTypematicState,1
 je dte1
 jz dte1a
dte1b:
 clc
 ret
dte1a:
 cmp wTypematicTimer,8
 jb dte1b
 inc bTypematicState
 jmp dte1b
dte1:
 cmp wTypematicTimer,4
 jb dte1b
 stc
 ret
CheckTypematicState endp

DoTypematicEvent proc near


 mov si,pTypematicOSKControl

if need_osk ne 0
 cmp si,offset OSK
 jb dte3
 call CheckIfOnlyOSK
 jnz dte3a
 call SendKeyDownScanCode
 jmp dte08
dte3a:
 call SendKey
 jmp dte08
dte3:
endif

 mov al,[si].ControlType

 cmp al,SPINUPBUTTON
 jnz dte3a
 call DoSpinUp
 jmp dte08
dte3a:

 cmp al,SPINDOWNBUTTON
 jnz dte3b
 call DoSpinDown
 jmp dte08
dte3b:

 cmp si,offset vsbUpArrow
 jnz dte3c
 mov di,pPenDownActiveRegion
 call DoVSBUpArrow
 jmp dte08
dte3c:

 cmp si,offset vsbDnArrow
 jnz dte3d
 mov di,pPenDownActiveRegion
 call DoVSBDnArrow
 jmp dte08
dte3d:

 jmp dte08

dte08:
 mov wTypematicTimer,0
dte09:
 ret
DoTypematicEvent endp

SetTypeMatic proc near
 public SetTypeMatic
 mov pTypematicOSKControl,si
 mov wTypematicTimer,0
 mov bTypematicState,1
 ret
SetTypematic endp


ClearScreen proc near
 public ClearScreen

 CLEAR_RECTANGLE
0,0,SCREEN_WIDTH_BYTES,SCREEN_HEIGHT_P
IXELS,bDesktopColor
 ret
ClearScreen endp

BlankenScreen proc near
 public BlankenScreen
 cmp bScreenMode,VGA_MODE
 jnz bls1

 CLEAR_RECTANGLE
0,0,SCREEN_WIDTH_BYTES,SCREEN_HEIGHT_P
IXELS,0
bls1:
 ret
BlankenScreen endp


GetVGAState proc near

 public GetVGAState
if need_tsr ne 0
 cmp bScreenMode,VGA_MODE
 je gvs0
 ret
gvs0:
 push ax
 push cx
 push bx
 push dx
 mov bx,offset wVideoStateBuffer
 mov dx,03ceh
 xor cl,cl
gvs1:
 mov al,cl
 out dx,al
 inc dx
 in al,dx
 dec dx
 mov ah,al
 mov al,cl
 mov [bx],ax
 inc bx
 inc bx
 inc cl
 cmp cl,8
 jbe gvs1
 pop dx
 pop bx
 pop cx
 pop ax
endif
 ret
getvgastate endp


RestVGAState proc near
 public RestVGAState
 if need_tsr ne 0
 cmp bScreenMode,VGA_MODE
 je rvs0
 ret
rvs0:
 push ax
 push cx
 push bx
 push dx
 mov bx,offset wVideoStateBuffer
 mov cx,9
 mov dx,03ceh
rvs1:
 mov ax,[bx]
 out dx,ax
 inc bx
 inc bx
 loop rvs1
 pop dx
 pop bx
 pop cx
 pop ax
endif
 ret
restvgastate endp

Ascii2Bin proc near
 public Ascii2Bin

 push cx
 xor bx,bx
 xor cx,cx
a2b1:
 lodsb
 cmp al,' '
 je a2b1
 jb a2b3
a2b2:
 cmp al,'0'
 jb a2b3
 cmp al,'9'
 ja a2b3
 xor ah,ah
 sub al,'0'
 xchg bx,ax
 mul word ptr wTenWord
 push dx
 xchg ax,bx
 mul word ptr wTenWord
 xchg bx,cx
 pop dx
 add cx,dx
 add ax,bx
 adc cx,0
 xchg bx,ax
 lodsb
 jmp a2b2
a2b3:
 dec si
 mov dx,cx
 pop cx
 ret
ascii2bin endp

Bin2Ascii proc near
 public Bin2ASCII

 push si
 push dx
 xor ah,ah
m4d0:
 mov si,offset wDivisors
 cmp al,5
 jz m4d1
 inc si
 inc si
 cmp al,4
 jz m4d1
 inc si
 inc si
 cmp al,3
 jz m4d1
 inc si
 inc si
 cmp al,2
 jz m4d1
 inc si
 inc si
 cmp al,1
 jz m4d1
 jmp m4dx
m4d1:
 xor dx,dx
 div word ptr [si]
 or al,30h
 cmp al,'0'
 jnz m4d2a
 cmp cl,1
 je m4d2
 cmp ah,-1
 je m4d2
 jmp m4d3
m4d2a:
 mov ah,-1
m4d2:
 mov [bx],al
 inc bx
m4d3:
 inc si
 inc si
 mov ax,dx
 dec cl
 jnz m4d1
m4dx:
 pop dx
 pop si
 ret
Bin2Ascii endp


JumpOnAL proc near
 public JumpOnAL
          pop     wJumpTableBase
          push    si
          push    ax
          mov     si,wJumpTableBase
joal_lp:     mov     ah,cs:[si]
          or      ah,ah
          jz      joal_nm
          cmp     ah,al
          je      joal_m
          add     si,3
          jmp     joal_lp
joal_nm:     inc     si
joal_nmr:    mov     wJumpTableBase,si
          pop     ax
          pop     si
          push    wJumpTableBase
          ret
joal_m:      mov     ax,cs:[si+1]
          mov     si,ax
          jmp     joal_nmr
JumpOnAL     endp

JumpOnAX proc near
 public JumpOnAX
          pop     wJumpTableBase
          push    si
          push    ax
          push    bx
          mov     si,wJumpTableBase
joax_lp:     mov     bx,cs:[si]
          or      bx,bx
          jz      joax_nm
          cmp     ax,bx
          je      joax_m
          add     si,4
          jmp     joax_lp
joax_nm:     inc     si
          inc     si
joax_nmr     mov     wJumpTableBase,si
          pop     bx
          pop     ax
          pop     si
          push    wJumpTableBase
          ret
joax_m:      mov     ax,cs:[si+2]
          mov     si,ax
          jmp     joax_nmr
JumpOnAX     endp


DisinstallInterrupts proc near
 public DisinstallInterrupts

 REMOVE_INT 1c

if NEED_CRITICAL ne 0
 remove_int 0
 remove_int 24
 remove_int 23
endif

if need_tsr ne 0
 REMOVE_INT 10
endif


 ret
DisinstallInterrupts endp


InstallInterrupts proc near
 INSTALL_INT 1c

if NEED_CRITICAL ne 0
 INSTALL_INT 0
 INSTALL_INT 24
 INSTALL_INT 23
endif

if need_tsr ne 0
 INSTALL_INT 10
endif
 ret
InstallInterrupts endp


New1Cint proc far

if need_tsr ne 0
 jmp n1ci1
int1Cactive dw 0
n1ci1:
 inc cs:int1Cactive
 pushf
 call dword ptr cs:old1Cint
 dec cs:int1Cactive
 jnz n1ci2


 push ax
 push ds
 mov ax,CURDATASEG
 mov ds,ax
 call DoPopUp
 pop ds
 pop ax

n1ci2:
endif
 iret

New1Cint endp


New1cint proc far
 push ax
 push ds
 mov ax,CURDATASEG
 mov ds,ax

 inc wCursorTimer
 inc wTypematicTimer
 inc wAutoScrollTimer
 call far ptr DoCustomTimerProcedures
```

```
if need_for ne 0
  call CheckTypematicState
  jne n0l4
  jmp n0l6
n0l4:
  cmp bAutoScrollMode,0
  jnz n0l6

  cmp bCursorActive,0
  jz n0l6
  cmp wCursorTimer,10
  jne n0l6
n0l6:
  call far ptr GetCustomPopUpRequest
  jz n0l6
n0l6:
  jmp n0l6
n0l5:
  mov bPopupRequired,-1
n0l6:
  call DoPopup
endif
n0l7:
  pop ds
  pop es
  jmp dword ptr cs:OldIclnt
NewIclnt    endp

DoPopUp proc near
  public DoPopUp

if need_for ne 0
  cmp bPopupRequired,0
  jz n0l1a

  cmp cs:int13active,0
  jnz n0l1a
  cmp bDoingEvents,0
  jnz n0l1a
  cmp bLocalState,0
  jz n0l1a

  pushf
  cli
  inc bDoingEvents
  mov bPopupRequired,0
  sti

  push es
  push bp
  push bx
  push cx
  push dx
  push di
  push si

n0l2:

  extrn penentry:near
  call penentry

  sti
  call GetVgaState
  call DoEvents
  call ResetVgaState
  extrn penexit:near
  call penexit
  pop si
  pop di
  pop dx
  pop cx
  pop bx
  pop bp
  pop es
  cli
  dec bDoingEvents
  popf
n0l1a:
endif
  ret
DoPopUp endp

if NEED_CRITICAL ne 0
fatal_error_code dw 0

New24int     proc     far
  mov cs:fatal_error_code,di

  pop     bx
  pop     cx
  pop     si
  pop     ax
  pop     bx
  pop     cx
  pop     dx
```

```
pop     si
pop     di
pop     bp
pop     ds
pop     es
mov     bp,sp
mov     ax,[bp+4]
push    ax
popf
mov     ax,[bp+2]
mov     [bp]+4,ax
mov     ax,[bp+0]
mov     [bp+2],ax
pop     ax
mov     ax,1
stc
ret
New24int        endp

New0int     proc far
        mov  ax,0
        mov  dx,0
        iret
New0int         endp

control_c_pressed db 0

New23int proc far
        mov cs:control_c_pressed,-1
        iret
New23int endp

endif

end
Copr. 1996 Zenith Data Systems Corp.

.MODEL SMALL
.code
extrn freezescreen:near
extrn UpdateDimensions:near
extrn StashonScreen:near
extrn DefineCoveredArea:near
extrn FindRegionForControl:near
extrn GoFirstControl:near
extrn GoNextControl:near
extrn GoNextControl:near
extrn InitLegend:near
extrn JumpOnAX:near
extrn PaintControlCaption:near
extrn Repaint:near
extrn SetNewTabItemWork:near
extrn SetProtectionForControl:near
extrn UndoCurrentTabItem:near
extrn CancelPenDown:near

include stnded.inc
WORKBUF equ '            ',0
VCENT=480/2
HCENT=640/2
DWIDE=MAXMESSAGELINE
DHIGH=240
DLEFT=HCENT-(DWIDE/2)
DTOP=VCENT-(DHIGH/2)
DATASEG_BEGIN
extrn ControlDataStorageArea:byte
extrn MainForm:IControl
extrn bCoveredAreaOnly:byte
extrn bDontChangeProtection:byte
extrn bFormColor:byte
extrn bMessageBoxID:byte
extrn bMessageBoxResult:byte
extrn bModalFlag:byte
extrn bModalFlagHold:byte
extrn pFirstControl:word
extrn pTabRegion:word
extrn pTabRegionHold:word
extrn wCoveredAreaTop:word
extrn wCoveredAreaTopHold:word
extrn wCurrentResource:word
extrn wCurrentResource:word
extrn wPreviousFormHeight:word
extrn rErrorMess1Header:BUFFHEADER
extrn rErrorMess2Header:BUFFHEADER
extrn rErrorMess3Header:BUFFHEADER
extrn rErrorMess4Header:BUFFHEADER
extrn rRegion:Iregion

iSMBrowLen dw 0
pSMBufferStart dw 0,0
pSMBufferEnd   dw 0

wMessageBoxHeight dw 0
  public wMessageBoxHeight
pMessageBoxButtonFrame dw 0
```

```
  public pMessageBoxButtonFrame

wMessageContinuationSI dw 0
  public wMessageContinuationSI
wMessageContinuationDX dw 0
  public wMessageContinuationDX

BEGIN_FORM_DEFINITIONS

frmMessageBox label IControl
  public frmMessageBox
CURRENTFORM=0
 CONTROL
FORM,%NORMSTATE,DLEFT,DTOP,DWIDE,DHIG
H,0
lblMessageBox0 label IControl
 public lblMessageBox0
 MAKE_CENTEREDLEGEND
%INVISIBLE,0,16,DWIDE,16
 GRAPHIC_CAPTION SMALL_CRUZER

lblMessageBox1 label IControl
 MAKE_CENTEREDLEGEND
%NORMSTATE,0,32,DWIDE,16
 CAPTION %WORKBUF

lblMessageBox2 label IControl
 MAKE_CENTEREDLEGEND
%NORMSTATE,0,32+16*1,DWIDE,16
 CAPTION %WORKBUF

lblMessageBox3 label IControl
 MAKE_CENTEREDLEGEND
%NORMSTATE,0,32+16*2,DWIDE,16
 CAPTION %WORKBUF

lblMessageBox4 label IControl
 MAKE_CENTEREDLEGEND
%NORMSTATE,0,32+16*3,DWIDE,16
 CAPTION %WORKBUF

lblMessageBox5 label IControl
 MAKE_CENTEREDLEGEND
%NORMSTATE,0,32+16*4,DWIDE,16
 CAPTION %WORKBUF

lblMessageBox6 label IControl
 MAKE_CENTEREDLEGEND
%NORMSTATE,0,32+16*5,DWIDE,16
 CAPTION %WORKBUF

lblMessageBox7 label IControl
 MAKE_CENTEREDLEGEND
%NORMSTATE,0,32+16*6,DWIDE,16
 CAPTION %WORKBUF

lblMessageBox8 label IControl
 MAKE_CENTEREDLEGEND
%NORMSTATE,0,32+16*7,DWIDE,16
 CAPTION %WORKBUF

fraMessageBoxOK label IControl
 public fraMessageBoxOK
BEGIN_FRAME
%INVISIBLE,0,%NEXTTOP+8,DWIDE,34
cmdMessageBoxOK_OK label IControl
 public cmdMessageBoxOK_OK
 MAKE_COMMANDBUTTON
%NORMSTATE,DWIDE/2-32,1,64,24
 CAPTION "OK"
END_FRAME
fraMessageBoxCancel label IControl
 public fraMessageBoxCancel
BEGIN_FRAME
%INVISIBLE,0,%NEXTTOP+8,DWIDE,34
cmdMessageBoxCancel_Cancel label IControl
 public cmdMessageBoxCancel_Cancel
 MAKE_COMMANDBUTTON
%NORMSTATE,DWIDE/2-32,0,64,24
 CAPTION "Cancel"
END_FRAME
fraMessageBoxOKCancel label IControl
 public fraMessageBoxOKCancel
BEGIN_FRAME
%INVISIBLE,0,%NEXTTOP+8,DWIDE,34
cmdMessageBoxOKCancel_OK label IControl
 public cmdMessageBoxOKCancel_OK
 MAKE_COMMANDBUTTON
%NORMSTATE,DWIDE/2-64-16-34,0,64+34,24
 CAPTION "OK"
cmdMessageBoxOKCancel_Cancel label IControl
 public cmdMessageBoxOKCancel_Cancel
 MAKE_COMMANDBUTTON
%NORMSTATE,DWIDE/2+16-8,%SAMETOP,64+34,
24
 CAPTION "Cancel"
```

```
END_FRAME
fraMessageBoxARI label IControl
  public fraMessageBoxARI
BEGIN_FRAME
%INVISIBLE,0,%NEXTTOP+8,DWIDE,34
cmdMessageBoxARI_Abort label IControl
 public cmdMessageBoxARI_Abort
 MAKE_COMMANDBUTTON
%NORMSTATE,DWIDE/2-64-16-16,0,56,24
 CAPTION "Abort"
cmdMessageBoxARI_Retry label IControl
 public cmdMessageBoxARI_Retry
 MAKE_COMMANDBUTTON
%NORMSTATE,%NEXTLEFT+8,0,64,24
 CAPTION "Retry"
cmdMessageBoxARI_Ignore label IControl
 public cmdMessageBoxARI_Ignore
 MAKE_COMMANDBUTTON
%NORMSTATE,%NEXTLEFT+8,0,64,24
 CAPTION "Ignore"
END_FRAME
fraMessageBoxYNC label IControl
  public fraMessageBoxYNC
BEGIN_FRAME
%INVISIBLE,0,%NEXTTOP+8,DWIDE,34
cmdMessageBoxYNC_Yes label IControl
 public cmdMessageBoxYNC_Yes
 MAKE_COMMANDBUTTON
%NORMSTATE,DWIDE/2-64-16-16,0,56,24
 CAPTION "Yes"
cmdMessageBoxYNC_No label IControl
 public cmdMessageBoxYNC_No
 MAKE_COMMANDBUTTON
%NORMSTATE,%NEXTLEFT+8,0,56,24
 CAPTION "No"
cmdMessageBoxYNC_Cancel label IControl
 public cmdMessageBoxYNC_Cancel
 MAKE_COMMANDBUTTON
%NORMSTATE,%NEXTLEFT+8,0,56,24

 CAPTION "Cancel"
END_FRAME
fraMessageBoxYNR label IControl
  public fraMessageBoxYNR
BEGIN_FRAME
%INVISIBLE,0,%NEXTTOP+8,DWIDE,34
cmdMessageBoxYNR_Yes label IControl
 public cmdMessageBoxYNR_Yes
 MAKE_COMMANDBUTTON
%NORMSTATE,DWIDE/2-64-16-16,0,56,24
 CAPTION "Yes"
cmdMessageBoxYNR_No label IControl
 public cmdMessageBoxYNR_No
 MAKE_COMMANDBUTTON
%NORMSTATE,%NEXTLEFT+8,0,56,24
 CAPTION "No"
cmdMessageBoxYNR_Retry label IControl
 public cmdMessageBoxYNR_Retry
 MAKE_COMMANDBUTTON
%NORMSTATE,%NEXTLEFT+8,0,56,24
 CAPTION "Retry"
END_FRAME
fraMessageBoxYesNo label IControl
  public fraMessageBoxYesNo
BEGIN_FRAME
%INVISIBLE,0,%NEXTTOP+8,DWIDE,34
cmdMessageBoxYesNo_Yes label IControl
 public cmdMessageBoxYesNo_Yes
 MAKE_COMMANDBUTTON
%NORMSTATE,DWIDE/2-64-16-34,0,64+34,24
 CAPTION "Yes"
cmdMessageBoxYesNo_No label IControl
 public cmdMessageBoxYesNo_No
 MAKE_COMMANDBUTTON
%NORMSTATE,DWIDE/2+16-8,%SAMETOP,64+34,
24
 CAPTION "No"
END_FRAME
fraMessageBoxRetryCancel label IControl
  public fraMessageBoxRetryCancel
BEGIN_FRAME
%NORMSTATE,0,%NEXTTOP+8,DWIDE,34
cmdMessageBoxRetryCancel_Retry label IControl
 public cmdMessageBoxRetryCancel_Retry
 MAKE_COMMANDBUTTON
%NORMSTATE,DWIDE/2-64-16-34,0,64+34,24
 CAPTION "Retry"
cmdMessageBoxRetryCancel_Cancel label IControl
 public cmdMessageBoxRetryCancel_Cancel
 MAKE_COMMANDBUTTON
%NORMSTATE,DWIDE/2+16-8,%SAMETOP,64+34,
24
 CAPTION "Cancel"
END_FRAME
frmMessageBox_end label byte
 public frmMessageBox_end
END_FORM

END_FORM_DEFINITIONS
```

```
DATASEG_END

code

CopyMessageToMessageBox proc near

 push word ptr pFirstControl
 mov pFirstControl,offset frmMessageBox
 call GoFirstControl
cmb0:
 mov si,[si].ControlType
 call InitLegend
 jnz cmb4
 mov di,si
 call pointControlCaption
 or bx,bx
 jz cmb4
cbmdo:
 push ds
 call ReadNextMessageLine
 jz cmb0

 cmp al,2
 jbe cbmdo
 xor al,al
cbmdo:
 add al,LEFTLEGEND
 mov es:[di].ControlType,al
 and es:[di].ControlState,not(INVISIBLE)
 mov ax,es:[di].TopPixel
 add ax,es:[di].PixelHeight
 mov es:wMessageBoxHeight,ax
 add bx,3
 mov dx,bx
 mov es,ax

 rep movsb
 xor al,al
 stosb
 jmp cmb7

cmb8:
 cmp es:wMessageContinuationDX,0
 jz cbmdo
 pop ds
 push es
 push di
 xor dx,dx
 xchg dx,wMessageContinuationDX
 xor si,si
 xchg si,wMessageContinuationSI
 push ax
 push bx
 call PrepareMessageForReading
 pop bx
 pop ax
 pop es
 pop di
 jmp cbmdo

cbmdo:
 or es:[di].ControlState,INVISIBLE

cmb7:
 pop ds
cmb4:
 call GoNextControl
 jnc cmb5

 pop word ptr pFirstControl
 ret
CopyMessageToMessageBox endp

DrawMessageBox proc near
 public DrawMessageBox
 call CancelPenDown

 call UndoCurrentTabItem
 mov pFirstControl,offset frmMessageBox
 mov wPreviousFormHeight,0
 mov bFormColor,LT_CYAN
 call Repaint

 call GoFirstControl
dmb3:
 cmp [si].ControlType,FRAME
 jnz dmb5
 test [si].ControlState,INVISIBLE
 jz dmb5

dmb5:
 call GoNextControl
 jz dmb3
 cmp [si].ControlType,ENDFRAME
 jnz dmb4
 jmp dmb4

dmb5:
 cmp [si].ControlType,COMMANDBUTTON
 jz dmb1
dmb4:
 call GoNextControl
 jnc dmb2
 jmp dmb3

dmb1:
 call FindRegionForControl
 mov di,bx
 call SetNewTabItemWork
dmb3:
 ret
DrawMessageBox endp

PaintError proc near
 public PaintError

 mov si,offset rErrorMess1Header
 inc ax
 jz ae1
 mov si,offset rErrorMess2Header
 inc ax
 jz ae1
 mov si,offset rErrorMess3Header
 inc ax
 jz ae1
 mov si,offset rErrorMess4Header
ae1:
 mov ax,seg rErrorMess1Header
 ret
PaintError endp

PrepareMessageBox proc near
 public PrepareMessageBox
 mov al,bModalFlag
 mov bModalFlagHold,al
 mov bModalFlag,0
 push pTabRegion
 pop pTabRegionHold

 push ds
 push si
 push bx
 call UndoCurrentTabItem
 mov pTabRegion,0
 pop bx
 pop si
 pop ds

 call SetMBXButtons
 call PrepareMessageForReading
 call CopyMessageToMessageBox
 mov ax,wMessageBoxHeight
 add ax,10
 mov bx,pMessageBoxButtonFrame
 or bx,bx
 jz pmb0
 mov [bx].TopPixel,ax
 add ax,[bx]+15
pmb0:
 mov frmMessageBox.PixelHeight,ax
 ret
PrepareMessageBox endp

PrepareMessageForReading proc near
 push ds
 pop es
 mov di,ds
 mov ax,[si].lStructLen
 mov es:lSMStructLen,ax
 mov ax,[si].lBufLen
 mov ax,word ptr [si].pBufOff
 add ax,bx
 mov es:pSMBufferStart,ax
 mov es:pSMBufferEnd,ax
 mov ax,word ptr [si].pBufOff[2]
 mov es:pSMBufferStart[2],ax
 push es
 pop ds
 ret
PrepareMessageForReading endp

ReadNextMessageLine proc near
 push ds
 pop es
 mov ax,pSMBufferStart
 cmp ax,pSMBufferEnd
 jb rnml1
 stc
 ret
rnml1:
 mov ax,lSMStructLen
 lds si,dword ptr pSMBufferStart
 add es:pSMBufferStart,ax
 mov al,[si].sAlignment
 lds si,dword ptr [si].pTextOff
 clc
 ret
ReadNextMessageLine endp

RemoveMessageBox proc near
 public RemoveMessageBox
 mov al,bModalFlagHold
 mov bModalFlag,al

 mov bMessageBoxID,0
 mov bDontChangeProtection,-1
 mov bx,offset frmMessageBox
 call DefineCoveredArea
 push uCoveredAreaTopHold
 pop uCoveredAreaTop
 mov bCoveredAreaOnly,-1
 mov pFirstControl,offset MainForm
 mov wPreviousFormHeight,480
 mov bFormColor,FORM_COLOR
 and uCurrentResource, not(200*128)
 cmp uCurrentResource,0
 jnz rmb1
 call BlankenScreen

 mov pTabRegion,0
 call Recursion
rmb1:

 call CheckScreenUpdateNeeded
 jnc rmb3
 call StopProtecting
rmb3:
 call Repaint
rmb2:
 call StopProtecting

 push pTabRegionHold
 pop si

 call SetNewTabItemWork
 ret
RemoveMessageBox endp

StopProtecting proc near
 public StopProtecting
 mov bDontChangeProtection,0
 mov uCoveredAreaTop,-1
 mov bCoveredAreaOnly,0
 ret
StopProtecting endp

ReportError proc near
 public ReportError
 call PaintError
 mov bx,MBX_OK
 call PrepareMessageBox
 call DrawMessageBox
 ret
ReportError endp

ReportMessageClick proc near
 public ReportMessageClick
 mov al,bMessageBoxID
 push ax
 push bx
 cmp al,-1
 jnz rmc1
 mov bl,bMessageBoxResult
 xor bh,bh
 SM_FUNCTION
SM_REPORT_BUTTON_CLICKED
rmc1:
 pop bx
 pop ax
 cmp al,-1
 ret
ReportMessageClick endp

SetMBXButtons proc near

  push si
  push bx
  push word ptr pFirstControl
  mov pFirstControl,offset frmMessageBox

  call GoFirstControl
smb2:
  cmp [si].ControlType,FRAME
  jnz smb1
  or [si].ControlState,INVISIBLE
smb1:
  call GoNextControl
  jnc smb2
  pop word ptr pFirstControl
  pop bx
  pop si

mov ax,bx
or ax,ax
jz smb100

 call JumpOnAX
 dw MBX_OK,offset smb_OK
 dw MBX_CANCEL,offset smb_CANCEL
 dw MBX_OKCANCEL,offset smb_OKCANCEL
 dw MBX_ABORTRETRYIGNORE,offset
smb_ABORTRETRYIGNORE
 dw MBX_YESNOCANCEL,offset
smb_YESNOCANCEL
 dw MBX_YESNORETRY,offset
smb_YESNORETRY
 dw MBX_YESNO,offset smb_YESNO
 dw MBX_RETRYCANCEL,offset
smb_RETRYCANCEL
 dw 0
 xor bx,bx
 jmp smb100

smb_OK:
 mov bx,offset frmMessageBoxOK
 jmp smb99

smb_CANCEL:
 mov bx,offset frmMessageBoxCancel
 jmp smb99

smb_OKCANCEL:
 mov bx,offset frmMessageBoxOKCancel
 jmp smb99

smb_ABORTRETRYIGNORE
 mov bx,offset frmMessageBoxARI
 jmp smb99

smb_YESNOCANCEL:
 mov bx,offset frmMessageBoxYNC
 jmp smb99

smb_YESNORETRY:
 mov bx,offset frmMessageBoxYNR
 jmp smb99

smb_YESNO:
 mov bx,offset frmMessageBoxYesNo
 jmp smb99

smb_RETRYCANCEL:
 mov bx,offset frmMessageBoxRetryCancel
 jmp smb99


smb99:
 and [bx].ControlState,not(INVISIBLE)

smb100:
 mov pMessageBoxButtonFrame,bx
 ret
SetMBXButtons endp

DoMessageBoxClick proc near
 public DoMessageBoxClick
 mov ax,si
 call JumpOnAX
 dw offset cmdMessageBoxOK_OK,offset
DoCmdMessageBoxOK
 dw offset cmdMessageBoxCancel_Cancel,offset
DoCmdMessageBoxCancel
 dw offset cmdMessageBoxOKCancel_OK,offset
DoCmdMessageBoxOK
 dw offset cmdMessageBoxOKCancel_Cancel,offset
DoCmdMessageBoxCancel
 dw offset cmdMessageBoxARI_Abort,offset
DoCmdMessageBoxAbort
 dw offset cmdMessageBoxARI_Retry,offset
DoCmdMessageBoxRetry
 dw offset cmdMessageBoxARI_Ignore,offset
DoCmdMessageBoxIgnore
 dw offset cmdMessageBoxYNC_Yes,offset
DoCmdMessageBoxYes
 dw offset cmdMessageBoxYNC_No,offset
DoCmdMessageBoxNo
 dw offset cmdMessageBoxYNC_Cancel,offset
DoCmdMessageBoxCancel
 dw offset cmdMessageBoxYNR_Yes,offset
DoCmdMessageBoxYes
 dw offset cmdMessageBoxYNR_No,offset
DoCmdMessageBoxNo
 dw offset cmdMessageBoxYNR_Retry,offset
DoCmdMessageBoxRetry
 dw offset cmdMessageBoxYesNo_Yes,offset
DoCmdMessageBoxYes
 dw offset cmdMessageBoxYesNo_No,offset
DoCmdMessageBoxNo
 dw offset
cmdMessageBoxRetryCancel_Retry,offset
DoCmdMessageBoxRetry
```

```
widen,%NEXTFRAMELEFT,%SAMEFRAMETOP,30,
100*8

escktrow label tCONTROL
   public escktrow
   MAKE_KEYBUTTON %NORMSTATE or WIDEN
or COMPENSATE,8,0,24,IDH
   GRAPHIC_CAPTION ESC_KEY
   TEXTMODE_CAPTION "Esc"
   DEFINE_KEY 1,27,27,27,256


   MAKE_KEYBUTTON
%NORMSTATE,%NEXTLEFT+8,%SAMETOP,24,IDH

   GRAPHIC_CAPTION F1_KEY
   TEXTMODE_CAPTION "F1"
   DEFINE_KEY 59,59,84,94,104


   MAKE_KEYBUTTON
%NORMSTATE,%NEXTLEFT,%SAMETOP,24,IDH
   GRAPHIC_CAPTION F2_KEY
   TEXTMODE_CAPTION "F2"
   DEFINE_KEY 60,60,85,95,105

   MAKE_KEYBUTTON
%NORMSTATE,%NEXTLEFT,%SAMETOP,24,IDH
   GRAPHIC_CAPTION F3_KEY
   TEXTMODE_CAPTION "F3"
   DEFINE_KEY 61,61,86,96,106

   MAKE_KEYBUTTON
%NORMSTATE,%NEXTLEFT,%SAMETOP,24,IDH
   GRAPHIC_CAPTION F4_KEY
   TEXTMODE_CAPTION "F4"
   DEFINE_KEY 62,62,87,97,107

   MAKE_KEYBUTTON
%NORMSTATE,%NEXTLEFT+8,%SAMETOP,24,IDH

   GRAPHIC_CAPTION F5_KEY
   TEXTMODE_CAPTION "F5"
   DEFINE_KEY 63,63,88,98,108

   MAKE_KEYBUTTON
%NORMSTATE,%NEXTLEFT,%SAMETOP,24,IDH
   GRAPHIC_CAPTION F6_KEY
   TEXTMODE_CAPTION "F6"
   DEFINE_KEY 64,64,89,99,109

   MAKE_KEYBUTTON
%NORMSTATE,%NEXTLEFT,%SAMETOP,24,IDH
   GRAPHIC_CAPTION F7_KEY
   TEXTMODE_CAPTION "F7"
   DEFINE_KEY 65,65,90,100,110

   MAKE_KEYBUTTON
%NORMSTATE,%NEXTLEFT,%SAMETOP,24,IDH
   GRAPHIC_CAPTION F8_KEY
   TEXTMODE_CAPTION "F8"
   DEFINE_KEY 66,66,91,101,111

   MAKE_KEYBUTTON
%NORMSTATE,%NEXTLEFT+8,%SAMETOP,24,IDH

   GRAPHIC_CAPTION F9_KEY
   TEXTMODE_CAPTION "F9"
   DEFINE_KEY 67,67,92,102,112

   MAKE_KEYBUTTON %NORMSTATE or
WIDEN,%NEXTLEFT,%SAMETOP,24,IDH
   GRAPHIC_CAPTION F10_KEY
   TEXTMODE_CAPTION "F10"
   DEFINE_KEY 68,68,93,103,113

   MAKE_KEYBUTTON %NORMSTATE or
WIDEN,%NEXTLEFT,%SAMETOP,24,IDH
   GRAPHIC_CAPTION F11_KEY
   TEXTMODE_CAPTION "F11"
   DEFINE_KEY 87h,133,135,137,139

   MAKE_KEYBUTTON %NORMSTATE or
WIDEN,%NEXTLEFT,%SAMETOP,24,IDH
   GRAPHIC_CAPTION F12_KEY
   TEXTMODE_CAPTION "F12"
   DEFINE_KEY 88h,134,136,138,140

escsecondrow label tCONTROL
   public escsecondrow
   MAKE_KEYBUTTON %NORMSTATE or WIDEN
or
COMPENSATE,8,%NEXTTOP+8,24,IDH
   DEFINE_KEY 41,96,126,255,256

   MAKE_KEYBUTTON
%NORMSTATE,%NEXTLEFT,%SAMETOP,24,IDH
   DEFINE_KEY 2,49,33,255,120

   MAKE_KEYBUTTON
%NORMSTATE,%NEXTLEFT,%SAMETOP,24,IDH
   DEFINE_KEY 3,50,64,3,121

   MAKE_KEYBUTTON
%NORMSTATE,%NEXTLEFT,%SAMETOP,24,IDH
   DEFINE_KEY 4,51,35,255,122

   MAKE_KEYBUTTON
%NORMSTATE,%NEXTLEFT,%SAMETOP,24,IDH
   DEFINE_KEY 5,52,36,255,123

   MAKE_KEYBUTTON
%NORMSTATE,%NEXTLEFT,%SAMETOP,24,IDH
   DEFINE_KEY 6,53,37,255,124

   MAKE_KEYBUTTON
%NORMSTATE,%NEXTLEFT,%SAMETOP,24,IDH
   DEFINE_KEY 7,54,94,30,125

   MAKE_KEYBUTTON
%NORMSTATE,%NEXTLEFT,%SAMETOP,24,IDH
   DEFINE_KEY 8,55,38,255,126

   MAKE_KEYBUTTON
%NORMSTATE,%NEXTLEFT,%SAMETOP,24,IDH
   DEFINE_KEY 9,56,42,255,127

   MAKE_KEYBUTTON
%NORMSTATE,%NEXTLEFT,%SAMETOP,24,IDH
   DEFINE_KEY 10,57,40,255,128

   MAKE_KEYBUTTON
%NORMSTATE,%NEXTLEFT,%SAMETOP,24,IDH
   DEFINE_KEY 11,48,41,255,129

   MAKE_KEYBUTTON
%NORMSTATE,%NEXTLEFT,%SAMETOP,24,IDH
   DEFINE_KEY 12,45,95,31,130

   MAKE_KEYBUTTON
%NORMSTATE,%NEXTLEFT,%SAMETOP,24,IDH
   DEFINE_KEY 13,61,43,255,131

   MAKE_KEYBUTTON %NORMSTATE
,%NEXTLEFT,%SAMETOP,-1,IDH
   GRAPHIC_CAPTION BS_KEY
   DEFINE_KEY 14,8, 8,127,255
   BACKSPACECAPTION equ 32,17,196,196
   TEXTMODE_CAPTION BACKSPACECAPTION
   SETWIDTHS 40,56,48,48

   MAKE_KEYBUTTON %NORMSTATE or WIDEN
or
COMPENSATE,8,%NEXTTOP,32,IDH
   GRAPHIC_CAPTION TAB_KEY
   TEXTMODE_CAPTION " Tab"
   DEFINE_KEY 15,9,15,255,256

   MAKE_KEYBUTTON
%NORMSTATE,%NEXTLEFT,%SAMETOP,24,IDH
   DEFINE_KEY 16,113,81,17,16

   MAKE_KEYBUTTON
%NORMSTATE,%NEXTLEFT,%SAMETOP,24,IDH
   DEFINE_KEY 17,119,87,23,17

   MAKE_KEYBUTTON
%NORMSTATE,%NEXTLEFT,%SAMETOP,24,IDH
   DEFINE_KEY 18,101,69, 5,18

   MAKE_KEYBUTTON
%NORMSTATE,%NEXTLEFT,%SAMETOP,24,IDH
   DEFINE_KEY 19,114,82,18,19

   MAKE_KEYBUTTON
%NORMSTATE,%NEXTLEFT,%SAMETOP,24,IDH
   DEFINE_KEY 20,116,84,20,20

   MAKE_KEYBUTTON
%NORMSTATE,%NEXTLEFT,%SAMETOP,24,IDH
   DEFINE_KEY 21,121,89,25,21

   MAKE_KEYBUTTON
%NORMSTATE,%NEXTLEFT,%SAMETOP,24,IDH
   DEFINE_KEY 22,117,85,21,22

   MAKE_KEYBUTTON
%NORMSTATE,%NEXTLEFT,%SAMETOP,24,IDH
   DEFINE_KEY 23,105,73, 9,23

   MAKE_KEYBUTTON
%NORMSTATE,%NEXTLEFT,%SAMETOP,24,IDH
   DEFINE_KEY 24,111,79,15,24

   MAKE_KEYBUTTON
%NORMSTATE,%NEXTLEFT,%SAMETOP,24,IDH
   DEFINE_KEY 25,112,80,16,25

   MAKE_KEYBUTTON
%NORMSTATE,%NEXTLEFT,%SAMETOP,24,IDH
   GRAPHIC_CAPTION LEFT_BRAKET_KEY
   TEXTMODE_CAPTION " ["
   DEFINE_KEY 26,91,123,27,256

   MAKE_KEYBUTTON
%NORMSTATE,%NEXTLEFT,%SAMETOP,24,IDH
   GRAPHIC_CAPTION RIGHT_BRAKET_KEY
   TEXTMODE_CAPTION " ]"

   DEFINE_KEY 27,93,125,29,256

   MAKE_KEYBUTTON %NORMSTATE
,%NEXTLEFT,%SAMETOP,-1,IDH
   DEFINE_KEY 43,92,124,28,256
   SETWIDTHS 32,40,40,32

OSKCapsLock label TControl
   public OSKCapsLock

   MAKE_CAPSLOCKBUTTON %NORMSTATE or
WIDEN or
COMPENSATE,8,%NEXTTOP,40,IDH
   GRAPHIC_CAPTION CAPS_KEY
   TEXTMODE_CAPTION " Caps"
   DEFINE_KEY 58,256,256,256,258

   MAKE_KEYBUTTON
%NORMSTATE,%NEXTLEFT,%SAMETOP,24,IDH
   DEFINE_KEY 30,97,65, 1,30

   MAKE_KEYBUTTON
%NORMSTATE,%NEXTLEFT,%SAMETOP,24,IDH
   DEFINE_KEY 31,115,83,19,31

   MAKE_KEYBUTTON
%NORMSTATE,%NEXTLEFT,%SAMETOP,24,IDH
   DEFINE_KEY 32,100,68, 4,32

   MAKE_KEYBUTTON
%NORMSTATE,%NEXTLEFT,%SAMETOP,24,IDH
   DEFINE_KEY 33,102,70, 6,33

   MAKE_KEYBUTTON
%NORMSTATE,%NEXTLEFT,%SAMETOP,24,IDH
   DEFINE_KEY 34,103,71, 7,34

   MAKE_KEYBUTTON
%NORMSTATE,%NEXTLEFT,%SAMETOP,24,IDH
   DEFINE_KEY 35,104,72, 8,35

   MAKE_KEYBUTTON
%NORMSTATE,%NEXTLEFT,%SAMETOP,24,IDH
   DEFINE_KEY 36,106,74,10,36

   MAKE_KEYBUTTON
%NORMSTATE,%NEXTLEFT,%SAMETOP,24,IDH
   DEFINE_KEY 37,107,75,11,37

   MAKE_KEYBUTTON
%NORMSTATE,%NEXTLEFT,%SAMETOP,24,IDH
   DEFINE_KEY 38,108,76,12,38

   MAKE_KEYBUTTON
%NORMSTATE,%NEXTLEFT,%SAMETOP,24,IDH
   DEFINE_KEY 39,59,58,255,256

   MAKE_KEYBUTTON
%NORMSTATE,%NEXTLEFT,%SAMETOP,24,IDH
   DEFINE_KEY 40,39,34,256,256

   MAKE_KEYBUTTON %NORMSTATE
,%NEXTLEFT,%SAMETOP,-1,IDH
   GRAPHIC_CAPTION ENTER_KEY
   ENTERKEYCAPTION equ
32,17,196,217,32,32,32
   TEXTMODE_CAPTION ENTERKEYCAPTION
   DEFINE_KEY 28,13,13,10,256
   SETWIDTHS 48,64,56,56

   MAKE_LSHIFTKEYBUTTON %NORMSTATE or
WIDEN or
COMPENSATE,8,%NEXTTOP,64,IDH
   GRAPHIC_CAPTION SHIFT_KEY
   TEXTMODE_CAPTION " Shift  "
   DEFINE_KEY 42,256,256,256,256

   MAKE_KEYBUTTON
%NORMSTATE,%NEXTLEFT,%SAMETOP,24,IDH
   DEFINE_KEY 44,122,90,26,44

   MAKE_KEYBUTTON
%NORMSTATE,%NEXTLEFT,%SAMETOP,24,IDH
   DEFINE_KEY 45,120,88,24,45

   MAKE_KEYBUTTON
%NORMSTATE,%NEXTLEFT,%SAMETOP,24,IDH
   DEFINE_KEY 46,99,67, 3,46

   MAKE_KEYBUTTON
%NORMSTATE,%NEXTLEFT,%SAMETOP,24,IDH
   DEFINE_KEY 47,118,86,22,47

   MAKE_KEYBUTTON
%NORMSTATE,%NEXTLEFT,%SAMETOP,24,IDH
   DEFINE_KEY 48,98,66, 2,48

   MAKE_KEYBUTTON
%NORMSTATE,%NEXTLEFT,%SAMETOP,24,IDH
   DEFINE_KEY 49,110,78,14,49

   MAKE_KEYBUTTON
%NORMSTATE,%NEXTLEFT,%SAMETOP,24,IDH
   DEFINE_KEY 50,109,77,13,50

   MAKE_KEYBUTTON
%NORMSTATE,%NEXTLEFT,%SAMETOP,24,IDH
   DEFINE_KEY 51,44,60,256,256

   MAKE_KEYBUTTON
%NORMSTATE,%NEXTLEFT,%SAMETOP,24,IDH
   DEFINE_KEY 52,46,62,256,256

   MAKE_KEYBUTTON
%NORMSTATE,%NEXTLEFT,%SAMETOP,24,IDH
   DEFINE_KEY 53,47,63,256,256

   MAKE_RSHIFTKEYBUTTON %NORMSTATE
,%NEXTLEFT,%SAMETOP,-1,IDH
   GRAPHIC_CAPTION SHIFT_KEY
   TEXTMODE_CAPTION " Shift  "
   DEFINE_KEY 54,256,256,256,256
   SETWIDTHS 56,72,64,64

ctrlkey1 label tcontrol
   public ctrlkey1
   MAKE_CTRLKEYBUTTON %NORMSTATE or
WIDEN or
COMPENSATE,8,%NEXTTOP,32,IDH
   GRAPHIC_CAPTION CTRL_KEY
   TEXTMODE_CAPTION " Ctl"
   DEFINE_KEY 29,256,256,256,256

altkey1 label tcontrol
   public altkey1
   MAKE_ALTKEYBUTTON
%NORMSTATE,%NEXTLEFT+32,%SAMETOP,32,K
H
   GRAPHIC_CAPTION ALT_KEY
   DEFINE_KEY 56,256,256,256,256
   TEXTMODE_CAPTION "Alt "

   MAKE_KEYBUTTON
%NORMSTATE,%NEXTLEFT,%SAMETOP,7*24,IDH
   DEFINE_KEY 57,32,32,32,32

altkey2 label tcontrol
   public altkey2
   MAKE_ALTKEYBUTTON
%NORMSTATE,%NEXTLEFT,%SAMETOP,32,IDH
   GRAPHIC_CAPTION ALT_KEY
   TEXTMODE_CAPTION "Alt "
   DEFINE_KEY 0E0h*256+56,256,256,256,256

ctrlkey2 label tcontrol
   public ctrlkey2
   MAKE_CTRLKEYBUTTON %NORMSTATE
,%NEXTLEFT+24,%SAMETOP,-1,IDH
   GRAPHIC_CAPTION CTRL_KEY
   TEXTMODE_CAPTION "Ctl"
   DEFINE_KEY 0E0h*256+29,256,256,256,256
   SETWIDTHS 32,40,40,40

   END_FRAME


tasthometicKeyboard label tControl
   public tasthometicKeyboard
BEGIN_FRAME %NORMSTATE or
components,%NEXTFRAMELEFT,%SAMEFRAMET
OP,86,%H100*8

   MAKE_KEYBUTTON %NORMSTATE or
WIDEN,0,0,24,IDH
   GRAPHIC_CAPTION PRT_KEY
   TEXTMODE_CAPTION "Prt"
   DEFINE_KEY 0E00h,256,256,256,256

OSKScrollLock label TControl
   public OSKScrollLock

   MAKE_SCROLLLOCKBUTTON %NORMSTATE
or
WIDEN,%NEXTLEFT,%SAMETOP,24,IDH
   GRAPHIC_CAPTION SLK_KEY
   TEXTMODE_CAPTION "SLk"
   DEFINE_KEY 046h,256,256,256,255
```

```
  MAKE_KEYBUTTON %NORMSTATE or
WIDEN,%NEXTLEFT,%SAMETOP,34,KH
  GRAPHIC_CAPTION PSE_KEY
  TEXTMODE_CAPTION "Pse"
  DEFINE_KEY 0E046h,255,255,255,255

  MAKE_KEYBUTTON %NORMSTATE or
WIDEN,%NEXTLEFT,%SAMETOP,34,KH
  GRAPHIC_CAPTION SYSREQ_KEY
  TEXTMODE_CAPTION "Sys"
  DEFINE_KEY 100,255,255,255,255

OSKNumLock label TControl
  public OSKNumLock

  MAKE_NUMLOCKBUTTON %NORMSTATE or
WIDEN,0,%NEXTTOP,0,34,KH
  GRAPHIC_CAPTION NLK_KEY
  TEXTMODE_CAPTION "NLk"
  DEFINE_KEY 045h,255,255,255,255

  MAKE_KEYBUTTON %NORMSTATE or
WIDEN,%NEXTLEFT,%SAMETOP,34,KH
  DEFINE_KEY 0E035h,47,47,255,255

  MAKE_KEYBUTTON %NORMSTATE or
WIDEN,%NEXTLEFT,%SAMETOP,34,KH
  DEFINE_KEY 37h,42,42,255,255

  MAKE_KEYBUTTON %NORMSTATE or
WIDEN,%NEXTLEFT,%SAMETOP,34,KH
  DEFINE_KEY 4Ah,45,45,255,255

  MAKE_KEYBUTTON %NORMSTATE or
WIDEN,0,%NEXTTOP,34,KH
  GRAPHIC_CAPTION HM_KEY
  TEXTMODE_CAPTION "Hm"
  DEFINE_KEY 71,71,55,77h,255

  MAKE_KEYBUTTON %NORMSTATE or
WIDEN,%NEXTLEFT,%SAMETOP,34,KH
  GRAPHIC_CAPTION UA_KEY
  UACAPTION equ ' ',24
  TEXTMODE_CAPTION UACAPTION
  DEFINE_KEY 72,72,56,255,255

  MAKE_KEYBUTTON %NORMSTATE or
WIDEN,%NEXTLEFT,%SAMETOP,34,KH
  GRAPHIC_CAPTION PGUP_KEY
  TEXTMODE_CAPTION TEXTMODEPGUP
  DEFINE_KEY 73,73,57,84h,255

 MAKE_KEYBUTTON %NORMSTATE or
WIDEN,%NEXTLEFT,%SAMETOP,34,KH*2
  DEFINE_KEY 4eh,43,43,255,255
  GRAPHIC_CAPTION PLUS_KEY
  PLUSCAPTION equ 32,43,32,222,13,32,32,32
  TEXTMODE_CAPTION PLUSCAPTION

  MAKE_KEYBUTTON %NORMSTATE or
WIDEN,0,%NEXTTOP or
PRIORFLAG,34,KH
  GRAPHIC_CAPTION LA_KEY
  LACAPTION equ ' ',27
  TEXTMODE_CAPTION LACAPTION
  DEFINE_KEY 75,75,52,73h,255

  MAKE_KEYBUTTON %NORMSTATE or
WIDEN,%NEXTLEFT,%SAMETOP,34,KH
  GRAPHIC_CAPTION GRAPHIC_SPACER
  TEXTMODE_CAPTION ' '

  DEFINE_KEY 76,76,53,255,255

 MAKE_KEYBUTTON %NORMSTATE or
WIDEN,%NEXTLEFT,%SAMETOP,34,KH
  GRAPHIC_CAPTION RA_KEY
  RACAPTION equ ' ',26
  TEXTMODE_CAPTION RACAPTION
  DEFINE_KEY 77,77,54,74h,255

  MAKE_KEYBUTTON %NORMSTATE or
WIDEN,0,%NEXTTOP,34,KH
  GRAPHIC_CAPTION END_KEY
  TEXTMODE_CAPTION "End"
  DEFINE_KEY 79,79,49,75h,255

  MAKE_KEYBUTTON %NORMSTATE or
WIDEN,%NEXTLEFT,%SAMETOP,34,KH
  GRAPHIC_CAPTION DA_KEY
  DACAPTION equ ' ',25
  TEXTMODE_CAPTION DACAPTION
  DEFINE_KEY 80,80,50,255,255

  MAKE_KEYBUTTON %NORMSTATE or
WIDEN,%NEXTLEFT,%SAMETOP,34,KH
  GRAPHIC_CAPTION PGDN_KEY
  TEXTMODE_CAPTION TEXTMODEPGDN
```

```
  DEFINE_KEY 81,81,51,76h,255

 MAKE_KEYBUTTON %NORMSTATE or
WIDEN,%NEXTLEFT,%SAMETOP,34,KH*2
  GRAPHIC_CAPTION ENT_KEY
  ENTCAPTION equ 60,110,110,232,13,32,32,32
  TEXTMODE_CAPTION ENTCAPTION

  DEFINE_KEY 0e01ch,13,13,10,255

  MAKE_KEYBUTTON
%NORMSTATE,0,%NEXTTOP or
PRIORFLAG,-1,KH
  GRAPHIC_CAPTION INS_KEY
  TEXTMODE_CAPTION "Ins  "
  DEFINE_KEY 82,82,48,255,255
  SETWIDTHS 48,64,64,64

  MAKE_KEYBUTTON %NORMSTATE or
WIDEN,%NEXTLEFT,%SAMETOP,34,KH
  GRAPHIC_CAPTION DEL_KEY
  TEXTMODE_CAPTION "Del"
  DEFINE_KEY 83,83,46,255,255

  END_FRAME

  END_FORM
END_FORM_DEFINITIONS

DATASEG_END

end

Copr 1993 Zenith Data Systems Corp

.MODEL SMALL
.code
extrn AdjustButtonDimensions:near
extrn Asci2Bin:near
extrn CheckIfCovered:near
extrn DefineCoveredArea:near
extrn DoPenUpEvent:near
extrn DrawColor:near
extrn DrawString:near
extrn DrawUpButton:near
extrn FillScreenArea:near
extrn SetTabControlType:near
extrn GetFirstControl:near
extrn GetNextControl:near
extrn GetNextControl:near
extrn Repaint:near
extrn RepaintWork:near
extrn ResetVGAState:near
extrn SetCaptionPointers:near
extrn SetFormHeights:near
extrn SetNewTabItemWork1:near
extrn SetNewTabItemWork:near
extrn SetProtectionForControl:near
extrn SetTypeMode:near
extrn UndoButtonDown:near
extrn UndoCurrentTabItem:near
extrn [illegible]:near
extrn [illegible]:near
extrn [illegible]:near
extrn repaintindividualcontrols:near

include [illegible].inc

DATASEG_BEGIN
extrn bRepaintOSKDimensions:byte
extrn bNextOSKConfiguration:byte
extrn cmdHotKeys:CONTROL
extrn fmNumericKeyboard:CONTROL
extrn rCursorRegion:REGION
extrn cmdOSKFullKeyboard:CONTROL
extrn cmdOSKReduce:CONTROL
extrn cmdOSKEnlarge:CONTROL
extrn cmdOSKFullKeyboard:CONTROL
extrn fmOSKAlphaKeyboard:CONTROL
extrn fmOSKNumericKeyboard:CONTROL
extrn bOSKSmallCruzer:CONTROL
extrn bOSKChisel[illegible]:CONTROL
extrn cmdOSKAbout:CONTROL
extrn cmdOSKNumKeyboard:CONTROL
extrn cmdOSKAlphaKeyboard:CONTROL
extrn fmAlphaKeyboard:CONTROL
extrn ControlDataStorageArea:byte
extrn OSK:Control

extrn OSKCapsLock:Control
extrn OSKNumLock:Control
extrn OSKScrollLock:Control
```

```
extrn AboutIcon:byte
extrn SmallAboutIcon:byte
extrn bCoveredAreaOnly:byte
extrn bDontTopColor:byte
extrn bDontChangeProtection:byte
extrn bKeyChanged:byte
extrn bModalFlag:byte
extrn bNoDimensionUpdate:byte
extrn bPopUpRequired:byte
extrn bRepaintMode:byte
extrn bRepaintNeeded:byte
extrn bScreenMode:byte
extrn bShadowColor:byte
extrn pCurrentFont:word
extrn pCurrentToolBarSelect:word
extrn pFirstControl:word
extrn pGraphicFont:word
extrn pNextActiveRegion:word
extrn pOSKFirstRegion:word
extrn pPenDownActiveRegion:word
extrn pTabRegion:word
extrn rActiveRegion:Region
extrn rREGION:REGION
extrn rTabRegion:REGION
extrn uBestX:word
extrn uCoveredAreaLeft:word
extrn uCoveredAreaTop:word
extrn uCoveredAreaTopHold:word
extrn uCurrentResource:word
extrn uCurrentResource:word
extrn uFontWidth:word
extrn uKeyPressed:word
extrn uHotKeyRightPixel:word
extrn ctlKey1:CONTROL
extrn ctlKey2:CONTROL
extrn altKey1:CONTROL
extrn altKey2:CONTROL


bDontCenterOSK db 0
 public bDontCenterOSK

bIgnoreOSKShow db 0

ScanCodeParser label SCANCODES
 public ScanCodeParser
      dw 400 dup(0)
SCANCODESIZE equ $-ScanCodeParser

ScanCodeHeader tBUFFHEADER <type
SCANCODES,SCANCODESIZE,ScanCodeParser>
 public ScanCodeHeader

bResetHotKeyDataLength db 0

 public bResetHotKeyDataLength
bKeyboardCode db 0
 public bKeyboardCode

bKeyStatePrev dw 0

bOSKLastState db 0
 public bOSKLastState

bReleaseShift db 0
 public bReleaseShift

bKeyState db 0,0
 public bKeyState

bAltNumberCount db 0
 public bAltNumberCount

bAltNumberAccum db 0,0,0,0

bDontShowOSK db 0
 public bDontShowOSK

bEnlargeFlag db 0,0
 public bEnlargeFlag


wKeyWidth dw 0
 public wKeyWidth

bCaptionLetter db ' ',0,0
 public bCaptionLetter

bDummyCaption db 0,80 dup(0)
 public bDummyCaption

bBigCruzerWork db BIG_CRUZER,0
bSmallCruzerWork db SMALL_CRUZER,0
bKeyDownType db 0
DATASEG_END
.code
```

```
ShowOSKForClick proc near
 public ShowOSKForClick




 cmp bNextOSKConfiguration,0
 je sofc1
 push ax
 mov al,bNextOSKConfiguration
 and al,111b
 xor ah,ah
 mov bIgnoreOSKShow,-1
 call ReconfigureOSK
 mov bIgnoreOSKShow,0
 pop ax

sofc1:
 cmp bDontShowOSK,0
 jnz dso4d

 cmp al,PWEDITBOX
 je sof

 cmp al,KEYEDITBOX
 je sof
 cmp bKeyboardCode,0
 jnz dso4d
sof:

 test osk.ControlState,INVISIBLE
 jz dso4d

 mov ax,rCursorRegion.uCurrentTop


 cmp ax,400/2
 jae dso4d1
 mov ax,400
 sub ax,osk.PixelHeight
 jmp dso4d2
dso4d1:
 mov ax,0
dso4d2:
 mov osk.TopPixel,ax
 call ShowOSK
dso4d:
 ret
ShowOSKForClick endp

CancelOSKPenDown proc near
 public CancelOSKPenDown

 push si
 push bx
 push ax
 mov si,pPenDownActiveRegion
 cmp si,pOSKFirstRegion
 jb sopd1

 call DoPenUpEvent
sopd1:
 pop ax
 pop bx
 pop si
 ret
CancelOSKPenDown endp

SetOSKReducedButtons proc near
 public SetOSKReducedButtons



 or cmdOSKReduce.ControlState,INVISIBLE
 and cmdOSKEnlarge.ControlState,not(INVISIBLE)
 ret
SetOSKReducedButtons endp

SetOSKEnlargedButtons proc near
 public SetOSKEnlargedButtons


 or cmdOSKEnlarge.ControlState,INVISIBLE
 and cmdOSKReduce.ControlState,not(INVISIBLE)
 ret
SetOSKEnlargedButtons endp

ReGreyOSKTypeButtons proc near
 public ReGreyOSKTypeButtons

 call hideOSK
 call RepaintUnderOSK
 or OSK.ControlState,INVISIBLE
 mov al,not(GRAYED+ISDOWN)
 and cmdOSKFullKeyboard.ControlState,al
 and cmdOSKAlphaKeyboard.ControlState,al
 and cmdOSKNumKeyboard.ControlState,al
 or [bx].ControlState,GRAYED+ISDOWN
```

```
 and frmAlphaKeyboard.ControlState,not(INVISIBLE)
 and
frmNumericKeyboard.ControlState,not(INVISIBLE)
 ret

ReGrayOSKTypeButtons endp

ReturnOSKRightAndShow proc near
 public ReturnOSKRightAndShow

 cmp bIgnoreOSKShow,-1
 jnz rorso1
 ret
rorso1:
 call SetOSKCoordinates
 cmp bReportOSKDimensions,0
 jz rorso1b
   mov si,offset rREGION
    mov di,offset osk
    mov ax,[di].toppixel
     push dx
     extrn getmaxvalidscreenrow:near
     call getmaxvalidscreenrow
     cmp ax,dx
     jbe oooo
     mov ax,dx
      mov [di].toppixel,ax



oooo
     pop dx
     mov [si].wCurrentTop,ax
     add ax,[di].pixelheight
     dec ax
     mov [si].wCurrentBottom,ax
     mov ax,[di].leftpixel
     mov [si].wCurrentLeft,ax
     add ax,[di].pixelwidth
     dec ax
     mov [si].wCurrentRight,ax
     cmp bScreenMode,12h
     jz rgr
     mov ax,16
     add [si].wCurrentRight,ax
      add ax,8
     add [si].wCurrentBottom,ax
rgr
     extrn PassOSKDimensions:near
   call PassOSKDimensions
   jmp oor
rorso1b:
 call ShowOSK

 cmp pTabRegion,0
 jz oor
 mov si,offset rTabRegion
 call SetNewTextItemWork1
oor
 ret
ReturnOSKRightAndShow endp


setoskcoordinates proc near
 public setoskcoordinates
 mov bx,offset OSK
 mov [bx].PixelHeight,0
 push osk.LeftPixel
 mov [bx].LeftPixel,0

 call ComputeOSKHeight
 pop osk.LeftPixel


 mov bx,OSK.PixelHeight

 cmp bDontCenterOSK,-1
 jz rorso1a
 mov ax,640
 sub ax,OSK.PixelWidth
 sar ax,1
  ROUND_TO_BYTE_BOUNDARY ax
 mov OSK.LeftPixel,ax
rorso1a:
 mov ax,OSK.TopPixel
 add ax,bx
 cmp bScreenMode,12h
 jz rorso3
 cmp ax,25*8
 jbe rorso2
 mov ax,25*8
 sub ax,bx
 jmp rorso4
rorso3:
 cmp ax,480
 jbe rorso2
 mov ax,480
 sub ax,bx
rorso4.
   cmp bDontCenterOSK,-1
   mov bDontCenterOSK,0
   jz rorso3
 mov OSK.TopPixel,ax
rorso2:
 ret
setoskcoordinates endp

DoHideOSK proc near
 public DoHideOSK

 test osk.ControlState,INVISIBLE
 jnz dho1

 call HideOSK
 call RepaintUnderOSK
 or OSK.ControlState,INVISIBLE
dho1:
 and wCurrentResource,not(111b)
 ret
DoHideOSK endp

HideOSK proc near
 public HideOSK

 test osk.ControlState,INVISIBLE
 jnz hook1
 push ax
 push si
 push bx
 mov di,pOSKFirstRegion
 cmp di,-1
 jz hok1
 call HideForm
 push pOSKFirstRegion
 pop pHostActiveRegion
 mov pOSKFirstRegion,-1
hok1:
 pop bx
 pop si
 pop ax
hook1:
 ret
HideOSK endp


HideForm proc near
 public HideForm

 push di
 mov bx,[di].pCurrentControl
 push bx
 or [bx].ControlState,INVISIBLE
 call UnprotectOSK

 mov dx,[di].wCurrentTop
 mov cx,[di].wCurrentLeft
 mov bh,bDeskTopColor
 test wCurrentResource,not(111b)
 jnz hf1
  jmp noclear

 mov bh,0
 cmp bScreenMode,12h
 jz hf1

 mov bh,7

hf1:
 mov ax,[di].wCurrentHeight
 mov si,[di].wCurrentRight
 sub si,cx
 inc si
 DIVIDE_BY_8 si

 call FillScreenArea
noclear:
 pop bx
 pop di
 ret
HideForm endp


InterpretShift proc near
 public InterpretShift

 or1 IsNumericKey
 jnz is1
 test bl,NUM_LOCK_DOWN
 jz is1

 test bl,L_SHIFT_DOWN or R_SHIFT_DOWN
 jnz sld1
   mov al,dh
   ret
sld1:

 and bl,not(L_SHIFT_DOWN or R_SHIFT_DOWN)
 mov bh,0
 xor al,al
 ret

if 0
 mov bh,bl
 and bl,not(L_SHIFT_DOWN or R_SHIFT_DOWN)
 not bh
 and bh,L_SHIFT_DOWN or R_SHIFT_DOWN
 or bl,bh
endif

is1:
 mov bh,dl
 sub bh,dh
 cmp bh,32
 jz sk2a
is2:
 test bl,L_SHIFT_DOWN or R_SHIFT_DOWN
 jnz sk2a
 mov al,dl
 ret
sk2a:
 mov al,dh
   cmp ah,dl
   jnz sk2c2
   mov ah,dh
   xor al,al
   jmp sk2c1
sk2c2:
  cmp al,ah
  jnz sk2c1
  xor al,al
sk2c1:


 ret

sk2x:
 xor bh,bh
 test bl,CAPS_LOCK_DOWN
 jz sk2b
 mov bh,-1
sk2b:
 test bl,L_SHIFT_DOWN or R_SHIFT_DOWN
 jz sk2d
 not bh
sk2d:
 or bh,bh
 jz sk2e
 mov al,dh
 ret
sk2e:
 mov al,dl
 ret
InterpretShift endp

ReShowOSK proc near
 public ReshowOSK

 push ax
 push si
  cmp pOSKFirstRegion,-1
  jnz ossz
  mov pOSKFirstRegion,offset aActiveRegions
ossz:
 push pOSKFirstRegion
 pop pHostActiveRegion
 or osk.ControlState,INVISIBLE
 mov bRepaintMode,1

 call ShowOSK
 pop si
 pop ax
 ret
ReShowOSK endp

RepaintOSK proc near
 public RepaintOSK

 push bx
 push pHostActiveRegion
 pop pOSKFirstRegion
 push pFirstControl
 mov pFirstControl,offset OSK
  test OSK.ID,4
  jz red1
  mov bEnlargeFlag,-1
red1:
 call RepaintWork
 mov bEnlargeFlag,0
 pop pFirstControl
 mov bx,wCurrentResource
 and bx,not(111b)
 or bx,OSK.ID
 mov wCurrentResource,bx
 pop bx
 ret
RepaintOSK endp

DrawOSKLegend proc near
 public DrawOSKLegend

 push si
 push ax
 push rRegion.wCurrentHeight
 push rRegion.wCurrentWidth

 mov si,offset rRegion
 mov al,byte ptr OSK.ID
 and al,11b
 cmp al,2
 jnz red0

 jmp red2a
red0:
 mov dx,[si].wCurrentTop
 mov ax,[si].wCurrentLeft

 add ax,34
 mov bx,20
 mov cx,OSK.PixelWidth
 sub cx,34*8
 cmp bEnlargeFlag,0
 jz red3
 add bx,20-8
 sub cx,5*8
 add ax,8
red3
 push si
 push bx
 mov rRegion.wCurrentHeight,bx
 mov rRegion.wCurrentWidth,cx
 call adjustbuttondimensions
 pop bx
 pop si
 mov ax,34
 cmp bEnlargeFlag,0
 jz red4
 add ax,8
red4:
 mov rRegion.wCurrentHeight,bx
 mov rRegion.wCurrentWidth,cx
 mov dx,[si].wCurrentTop
 mov cx,[si].wCurrentLeft
 call adjustbuttondimensions
 push si
 pop si
 push word ptr bshadowcolor
 mov bshadowcolor,3
 mov cx,[si].wCurrentLeft
 mov dx,[si].wCurrentTop
 add ax,8


 inc dx
 inc dx
 inc dx
 inc dx

 mov si,offset abouticon
 cmp bEnlargeFlag,0
 jnz red8
 mov si,offset smallabouticon


red8:
 push ax
 push dx
 call drawicolor
 pop dx
 pop ax
 pop word ptr bshadowcolor
 cmp bEnlargeFlag,0
 jnz red7
 mov si,offset bSmallCruzerWork
 add ax,32
 add dx,2
 jmp red6
red7:
 mov si,offset bBigCruzerWork
 add dx,4
 add ax,48

red6:


 mov pCurrentFont,offset UIFont
 call drawstring




red2a:
 pop rRegion.wCurrentWidth
 pop rRegion.wCurrentHeight
 pop ax
 pop si
```

```
 ret
DrawOSKLegend endp

ShowOSK proc near
 public ShowOSK
 test osk.ControlState,INVISIBLE
 jz sosk1

 call DefineNewOSKArea


 call UseNormalColors
 call RepaintOSK
sosk1:
 ret
ShowOSK endp


DefineNewOSKArea proc near
 public DefineNewOSKArea
 mov bx,offset osk
 and [bx].ControlState,not(INVISIBLE)
 call ComputeOSKHeight
 mov ax,480
 cmp osk.TopPixel,ax
 jb se1a
 sub ax,OSK.PixelHeight
 mov osk.TopPixel,ax
se1a:
 call DefineCoveredArea
 ret
DefineNewOSKArea endp

ComputeOSKHeight proc near
 push bx
 test OSK.ID,4
 jz coh1
 mov bEnlargeFlag,-1
coh1.
 or cmdOSKAbout.ControlState,INVISIBLE
 or lblOSKSmallCruzer.ControlState,INVISIBLE
 mov lblOSKChiselLine.PixelWidth,8
 mov OSK.PixelWidth,0
 push pFirstControl
 mov pFirstControl,bx
 call SetFormHeights
 mov bEnlargeFlag,0
 mov ax,wFormWidth
 sub ax,OSK.LeftPixel
 ROUND_TO_BYTE_BOUNDARY ax
 cmp bScreenMode,12h
 jz coh2
 sub ax,16
coh2
 mov OSK.PixelWidth,ax
 cmp bScreenMode,12h
 jnz se2a
 sub ax,15
 mov lblOSKChiselLine.PixelWidth,ax
 mov lblOSKChiselLine.LeftPixel,0
 sub osk.PixelHeight,16
 jmp se2
se2a:
 mov lblOSKChiselLine.PixelWidth,ax
 mov lblOSKChiselLine.LeftPixel,8
 mov al,byte ptr OSK.ID
 and al,11b
 cmp al,2
 jz se2a1
 and cmdOSKAbout.ControlState,not(INVISIBLE)
 and
lblOSKSmallCruzer.ControlState,not(INVISIBLE)
 mov cmdOSKAbout.TopPixel,8
se2a1
 sub osk.PixelHeight,24+8
 cmp bEnlargeFlag,0
 jz se2
 sub osk.PixelHeight,8
se2:
 pop pFirstcontrol
se1:
 pop bx
 ret
ComputeOSKHeight endp

RepaintOSKInMemory proc near
 public RepaintOSKInMemory
 test osk.ControlState,INVISIBLE
 jnz do4


 mov bDontChangeProtection,-1
 call ProtectOSK
 call RepaintOSK
 mov bDontChangeProtection,0
do4.
 ret
RepaintOSKInMemory endp

SendKey proc near
 public SendKey


 push ax
 call SetKeyRegisters

 cmp cx,0FFFFh
 jnz sk01
 cmp dx,0FFFFh
 jnz sk01
 mov al,0


 jmp sk8a
sk01:
 test bl,ALT_DOWN
 jz sk1
 cmp ah,256
 jnc skn1
 test bl,NUM_LOCK_DOWN
 jz skn1
 cmp ah,"0"
 jb skn1
 cmp ah,"9"
 ja skn1
 mov bl,bAltNumberCount
 xor bh,bh
 add bx,offset bAltNumberAccum
 mov [bx],ah
 mov byte ptr [bx+1],0
 inc bAltNumberCount
 cmp bAltNumberCount,3
 jz skn2
 cmp byte ptr bAltNumberAccum,"3"
 jb skn4
 cmp bAltNumberCount,2
 jb skn4
skn2:
 call GetAltNumberValue
 cmp bx,256
 jbe skn3
skn4:
 jmp sk10
skn3:
 mov ax,bx
 jmp sk8a
skn1:
 cmp ah,256
 jz sk10
 mov ah,ah
 xor al,al
 jmp sk8
sk1
 mov bAltNumberCount,0

 test bl,CTRL_DOWN
 jz sk2
 cmp al,84
 jae sk1b



 cmp ah,al
 jnz sk1a
sk1b:
 mov ah,al
 xor al,al
 jmp sk8
sk1a
 mov al,al
 jmp sk8
sk2
 test bl,NUM_LOCK_DOWN
 jz sk3
 call IsNumericKey
 jz sk11

sk3:
 cmp ah,75
 jz sk11
 cmp ah,74
 jz sk11
 cmp ah,58+10
 jb sk11a
 jmp sk8a
sk11a:
 test bl,L_SHIFT_DOWN or R_SHIFT_DOWN
 jnz sk11


 cmp ah,58
 jb sk11
 mov al,0
 jmp sk8a
sk11:
 call InterpretShift
sk7
 cmp al,256
 jz sk10
sk8a:
 mov wKeyPressed,ax
sk8:
 mov bKeyChanged,-1
sk10:
 pop ax
 ret
SendKey endp

GetAltNumberValue proc near
 public GetAltNumberValue

 mov bAltNumberCount,0
 push si
 mov si,offset bAltNumberAccum
 call Asc2Bin
 pop si
 mov byte ptr bAltNumberAccum,0
 ret
GetAltNumberValue endp


SetKeyRegisters proc near
 public SetKeyRegisters

 mov cx,[si].pStorageOffset
 mov dx,[si].wDataLength

 mov ax,[si].ie
 xchg ah,al
 mov bl,bKeyState
 ret
SetKeyRegisters endp

ProtectOSK proc near
 public ProtectOSK


 cmp pOSKFirstRegion,-1
 jz pos1
 test osk.ControlState,INVISIBLE
 jnz pos1
 push wCoveredAreaTopHold
 pop wCoveredAreaTop
 mov bCoveredAreaOnly,0
pos1:
 ret
ProtectOSK endp



ResetShiftKeys proc near

 push cx
 push si
 push rRegion.pCurrentControl
 push pFirstControl
 mov pFirstControl,offset OSK
 call GoFirstControl
 jz rsk1
rsk3:
 mov al,[si].ControlType
 cmp al,RSHIFTKEYBUTTON
 jb rsk2
 cmp al,ALTKEYBUTTON
 ja rsk2
 jne rsk3b
 cmp bAltNumberCount,0
 jz rsk3b

 jmp rsk2
rsk3b:
 test [si].ControlState,ISDOWN
 jz rsk2
 call CheckIfOnlyOSK
 jne rsk3a
 call SendKeyUpScanCode
rsk3a:
 and [si].ControlState,not(ISDOWN)
rsk2:
 call GoNextControl
 jne rsk3
rsk1:
 pop pFirstControl
 pop rRegion.pCurrentControl
 pop si
 pop cx
 ret
ResetShiftKeys endp




UnprotectOSK proc near
 public UnprotectOSK
 mov wCoveredAreaTop,-1
 mov bCoveredAreaOnly,0
 ret
UnprotectOSK endp

IsNumericKey proc near
 public IsNumericKey


 cmp ah,71
 jb lnk2
 cmp ah,83
 ja lnk2
 cmp ah,74
 jz lnk2
 cmp ah,78
 jz lnk2
 cmp ah,ah
 jmp lnk1
lnk2:
 or ah,ah
lnk1:
 ret
IsNumericKey endp

IsNumericOnNumKeyPad proc near
 public IsNumericOnNumKeypad
 test bKeyState,NUM_LOCK_DOWN
 jz lne1
 test bKeyState,L_SHIFT_DOWN or
R_SHIFT_DOWN
 jnz lne1
 call SetKeyRegisters
 call IsNumericKey
 jz lne2
lne1:
 stc
 ret
lne2:
 clc
 ret
IsNumericOnNumKeyPad endp

SetOSKKeyCaptionString proc near
 public SetOSKKeyCaptionString
 call SetKeyRegisters
 call InterpretShift

 cmp bScreenMode,VGA_MODE
 jnz dbc3a

 mov bx,offset bDummyCaption
 xor ah,ah
 mov [bx+3],ax
 jmp dbc3b

dbc3a:

 push si
 mov di,si
 mov si,offset bCaptionLetter
 mov byte ptr [si+1],al
 call SetKeyCaption
 pop si

dbc3b:
 xor ax,ax
 call SetCaptionPointers
 ret
SetOSKKeyCaptionString endp

SetKeyCaption proc near
 public SetKeyCaption


 push ax
 mov dx,rRegion.wCurrentHeight
 DIVIDE_BY_8 dx
 mov dh,dl
 mov bx,offset bDummyCaption
 mov ax,rRegion.wCurrentWidth
 mov ah,222
 cmp [di].ControlType,KEYBUTTON
 jne skc5
 mov ah,'T'
skc5:
 DIVIDE_BY_8 ax
 dec ax
 cmp bEnlargeFlag,0
 jz skc0
 test [di].ControlState,WIDEN
 jnz skc0
 dec cx
skc0:
 test [di].ControlState,DOUBLEWIDEN
 jz skc0a
 inc cx
skc0a:
 mov wKeyWidth,cx
```

```
 xor di,di
 push ds
 pop es
 mov di,offset bDummyCaption+3

sks2:
 lodsb
 or al,al
 jz sks1
 stosb
 inc di
 loop sks2

sks2a:

 cmp byte ptr [si],222
 jnz sks1

sks2aa:
 add ax,wKeyWidth
 inc ax
 inc cx
 jmp sks2

sks1:

 jcxz sks3
 mov al,' '
sks4:
 stosb
 inc di
 loop sks4
sks3:
 cmp bEnlargeflag,0
 je sks3a

 mov al,' '
 cmp byte ptr [si],0
 je sks3aa
 lodsb
sks3aa:
 stosb
 inc di
sks3ab:
 dec dh
 jz sks3b
 mov al,13
 stosb
 mov al,220
 cmp dh,1
 jz sks3ab1
 mov al,' '
sks3ab1:
 mov cl,dl
 xor ch,ch
 rep stosb
 jmp sks3ab

sks3a:
 mov al,ah
 stosb
sks3b:
 xor ax,ax
 stosb
 pop es
 ret
SetKeyCaption endp

HandleOSKKeyPenUp proc near
 public HandleOSKKeyPenUp

 cmp al,FIRSTKEYTYPE
 jbe dpu10b
 cmp al,LASTKEYTYPE
 ja dpu10b

 cmp bReleaseShift,0
 mov bReleaseShift,0
 jz dpu8bb
 call GetBitForShiftKey
 cmp bl,ALT_DOWN
 jnz dpu20
 cmp bAltNumberCount,0
 jz dpu20
 push bx
 push ax
 call GetAltNumberValue
 cmp bx,255
 ja ars1
 mov wKeyPressed,bx
 mov bKeyChanged,-1
 mov bPopUpRequired,-1
ars1:
 pop ax
 pop bx

dpu20
 xor bl

 and bKeyState,bl
 call UndoButtonDown
 call CheckIfOnlyOSK
 jnz dpu21
 call SendKeyUpScanCode
dpu21:
 mov bNoDimensionUpdate,-1

 call SetBiosLockState

 call ReShowOSK
 mov bNoDimensionUpdate,0
 mov bKeyChanged,-1
dpu10b:
 jmp hopu1

dpu10b:
 cmp al,KEYBUTTON
 jne hopu2
 push word ptr bKeyState
 pop word ptr bKeyStatePrev

 test bKeystate, L_SHIFT_DOWN +
R_SHIFT_DOWN + CTRL_DOWN +
ALT DOWN
 jz , nopu3
 call UndoButtonDown
 call CheckIfOnlyOSK
 jnz hopu4
 call SendKeyUpScanCode
hopu4:
 jmp hopu1
hopu3:
 call undobuttondown
 call CheckIfOnlyOSK
 jnz hopu5
 call SendKeyUpScanCode
hopu5:
 and bKeystate, not( L_SHIFT_DOWN +
R_SHIFT_DOWN + CTRL_DOWN +
ALT_DOWN )
 cmp bAltNumberCount,0
 jz dpu10ba
 or bKeystate,ALT_DOWN
dpu10ba:
 call ResetShiftKeys
 mov bNoDimensionUpdate,-1

 test bKeyStatePrev,L_SHIFT_DOWN +
R_SHIFT_DOWN
 jnz hopu5a
 call repaintstriandalt
 jmp hopu5b
hopu5a:
 call ReShowOSK
hopu5b:
 mov bNoDimensionUpdate,0
 jmp hopu1
hopu2:
 clc
 ret
hopu1:
 mov pPenDownActiveRegion,0
 stc
 ret
HandleOSKKeyPenUp endp

repaintstriandalt proc near
 cmp ctrl.id,2
 jz rcaa1
 cmp ctrl.id,6
 jz rcaa1
 push si
 push pPenDownActiveRegion
 mov si,offset ctrlkey1
 call repaintspecifickey
 mov si,offset ctrlkey2
 call repaintspecifickey
 mov si,offset altkey1
 call repaintspecifickey
 mov si,offset altkey2
 call repaintspecifickey
 pop pPenDownActiveRegion
 pop si
rcaa1:
 ret
repaintstriandalt endp

repaintspecifickey proc near
 mov bx,pOSKFirstRegion
 cmp bx,-1
 je rpok2
rpok1:
 cmp bx,pNextActiveRegion
 jae rpok2
 cmp [bx].pCurrentControl,si
 je rpok3
 add bx,type sActiveRegions
 jmp rpok1
rpok3:
 mov pPenDownActiveRegion,bx
 mov ax,[si]
 call repaintindividualcontrol

rpok2:
 ret
repaintspecifickey endp

HandleOSKKeyPenDown proc near
 public HandleOSKKeyPenDown
 mov bKeyDownType,al

 cmp al,KEYBUTTON
 jb dpd8b
 cmp al,CAPSLOCKBUTTON
 ja dpd8b
 call CheckHotKeyEdit
 jnz dpd8gg
 call far ptr GoHotKeyEdit
 cmp al,KEYBUTTON
 je dpd8b
 jmp dpd8z
dpd8gg:
 cmp al,KEYBUTTON
 jnz dpd8b
 call SetTypeMatic
 call CheckIfOnlyOSK
 jnz dpd8g
 call SendKeyDownScanCode
 jmp dpd8z
dpd8g:
 call SendKey
 jmp dpd8z
dpd8bv:
 cmp al,KEYBUTTON
dpd8b:
 jb dpd8z
 cmp al,CAPSLOCKBUTTON
 ja dpd8z

 call GetBitForShiftKey
 or bKeyState,bl
 call CheckHotKeyEdit
 je dpd8z
 mov bNoDimensionUpdate,-1
 call CheckIfOnlyOSK
 jnz dpd8h
 call SendKeyDownScanCode
dpd8h:
 cmp bKeyDownType,ALTKEYBUTTON
 jz dpd8hh
 cmp bKeyDownType,CTRLKEYBUTTON
 jnz dpd8hi
dpd8hh:
 call repaintstrlandalt
 jmp dpd8hj
dpd8hi:
 call SetBiosLockState
 call ReShowOSK
dpd8hj:
 mov bNoDimensionUpdate,0
 mov bKeyChanged,-1
dpd8z:
 ret
HandleOSKKeyPenDown endp

CheckHotKeyEdit proc near
 public CheckHotKeyEdit

 cmp pCurrentToolBarButton,offset sendHotKeys
 jnz qqll2
 call CheckIfOnlyOSK
 je qqll2
 cmp wHotKeyRightPixel,640-48-8
 jne qqll2
 push ax
 push si
 call GetTabControlType
 cmp al,KEYEDITBOX
 pop si
 pop ax
 je qqll1
qqll2:
 clc
 ret
qqll1:
 stc
 ret
CheckHotKeyEdit endp

HandleOSKAlreadyDown proc near
 public HandleOSKAlreadyDown

 cmp al,KEYBUTTON
 jbe dpd8ax
 cmp al,CAPSLOCKBUTTON
 ja dpd8ax
 mov bReleaseShift,-1
 push ax
 call checkhotkeyedit
 pop ax
 jne xxdd
 cmp al,SCROLLLOCKBUTTON
 jb xxdd

 call far ptr DoHotKeyEdit

xxdd:
 clc
 ret
dpd8ax:
 stc
 ret
HandleOSKAlreadyDown endp

GetBitForShiftKey proc near

 push cx

 mov bl,R_SHIFT_DOWN
 sub al,RSHIFTKEYBUTTON
dpd8d:
 jz dpd8c
 shl bl,1
 dec al
 jmp dpd8d
dpd8c:
 pop cx
 ret
GetBitForShiftKey endp

CheckIfOnlyOSK proc near
 public CheckIfOnlyOSK

 test uCurrentResource,not(111b)
 jnz dho1ba
 cmp bModalFlag,-1
 jz dho1ba
 stc
 ret
dho1ba:
 clc
 ret
CheckIfOnlyOSK endp

SendKeyDownScanCode proc near
 public SendKeyDownScanCode
 push bx
 push ax

 call RestVgaState

 mov bx,[si].ID

 SM_FUNCTION SM_SET_KEYSTROKE
 call IsItLockKey
 jnz skdc1
 or bl,80h
 SM_FUNCTION SM_SET_KEYSTROKE
skdc1:
 pop ax
 pop bx
 ret
SendKeyDownScanCode endp

IsItLockKey proc near
 push bx
 and bl,01111111b
 cmp bx,58
 jz iilkr1
 cmp bx,46h
 jz iilkr1
 cmp bx,45h
iilkr1:
 pop bx
 ret
IsItLockKey endp

SendKeyUpScanCode proc near
 push ax
 push bx

 call restvgastate

 mov bx,[si].ID
```

```
 call IsNumLockKey
 jnz skuse1
 SM_FUNCTION SM_SET_KEYSTROKE
skuse1:
 or bl,10000000b
 SM_FUNCTION SM_SET_KEYSTROKE
 pop bx
 pop ax
 ret
SendKeyUpScanCode endp

DoCloseOSK proc near
 public DoCloseOSK

 call UndoCurrentTabItem
 and [si].ControlState,not(ISDOWN)
 call RaiseAllOSKKeys


 mov ax,wCurrentResource
 and al,111b
 mov bOSKLastState,al


 test wCurrentResource,not(111b)
 jnz dk1
 and wCurrentResource,not(111b)
  call Rescreen
  jmp dk13

dk1:

 push wCurrentResource
 call DoHideOSK
 cmp wCurrentResource,0
 jnz dk11
 call FreeScreen
 jmp dk12
dk11:
 mov bDontShowOSK,-1
dk12:
 pop wCurrentResource
 mov si,pTabRegion
 call SetNewTabItemWork
dk13:
 ret
DoCloseOSK endp



RaiseAllOSKKeys proc near

 push si
 push pFirstControl
 mov si,offset OSK
 mov pFirstControl,si
rao1:
 mov al,[si].ControlType
 cmp al,KEYBUTTON
 jb rao2
 cmp al,ALTKEYBUTTON
 ja rao2
 and [si].Controlstate,not(ISDOWN)
rao2:
 call GetNextControl
 jnc rao1
 pop pFirstControl
 pop si
 ret
RaiseAllOSKKeys endp

RepaintUnderOSK proc near
 public RepaintUnderOSK

if need_osk ne 0
 push si
 push di
 push bx
 push wCoveredAreaTopHold
 pop wCoveredAreaTop
 mov bCoveredAreaOnly,-1
 or OSK.ControlState,INVISIBLE
 mov bRepaintNeeded,-1
 call Repaint
 and OSK.ControlState,not(INVISIBLE)
 pop bx
 pop di
 pop si
 call UnprotectOSK
endif
 ret
RepaintUnderOSK endp


GetPhysicalKeyState proc near
 public GetPhysicalKeyState
 push ds
 push es
 push bx
 push ax
 mov ax,OURDATASEG
 mov ds,ax
 mov bx,40h
 mov es,bx
 mov bx,017h
 mov al,es:[bx]
 and al,SCROLL_LOCK_DOWN or
NUM_LOCK_DOWN or CAPS_LOCK_DOWN
 mov ah,bKeyState
 mov bl,ah
 and ah,SCROLL_LOCK_DOWN or
NUM_LOCK_DOWN or CAPS_LOCK_DOWN
 cmp ah,al
 je gpks4

 and bl,not (SCROLL_LOCK_DOWN or
NUM_LOCK_DOWN or
CAPS_LOCK_DOWN)
 or bl,al
 mov bKeyState,al

 and OskCapsLock.ControlState,not ISDOWN


 and OskNumLock.ControlState,not ISDOWN
 and OskScrollLock.ControlState,not ISDOWN

 test al,CAPS_LOCK_DOWN
 je gpks1
 or OskCapsLock.ControlState,ISDOWN


gpks1:
 test al,NUM_LOCK_DOWN
 jz gpks2
 or OskNumLock.ControlState,ISDOWN
gpks2:
 test al,SCROLL_LOCK_DOWN
 jz gpks3
 or OskScrollLock.ControlState,ISDOWN
gpks3:
  cmp pOSKFirstRegion,-1
  je gpks0
  call ReshowOSK


gpks0:
 pop ax
 pop bx
 pop es
 pop ds
 ret
GetPhysicalKeyState endp

SetBiosLockState proc near
 push es
 push bx
 push ax
 mov bx,40h
 mov es,bx
 mov bx,017h
 mov al,bKeyState
 and al,SCROLL_LOCK_DOWN or
NUM_LOCK_DOWN or CAPS_LOCK_DOWN
 mov ah,es:[bx]
 and ah,not(SCROLL_LOCK_DOWN or
NUM_LOCK_DOWN or
CAPS_LOCK_DOWN)
 or ah,al
 mov es:[bx],ah
 pop ax
 pop bx
 pop es
 ret
SetBiosLockState endp




end

Copr. 1995 Zenith Data Systems Corp.


.MODEL SMALL
include olinclud.inc
DATASEG_BEGIN
bCurrentShadowColor db DARKGRAY
 public bCurrentShadowColor
extrn wCurrentResource:word
extrn ControlDataStorageArea:byte
extrn rLegendRegion:REGION
extrn FirstStandardControl:CONTROL
extrn FontTable:word
extrn LastStandardControl:CONTROL
extrn MainForm:Control
extrn OSK:Control
extrn bButtonForegroundColor:byte
extrn bCaptionForegroundColor:byte
extrn bCaptionForegroundColor:byte
extrn bCaptionForegroundColor:byte
extrn bCoveredAreaOnly:byte
extrn bCursorActive:byte
extrn bDontChangeProtection:byte
extrn bFormColor:byte
extrn bIconBackgroundColor:byte
extrn bIconForegroundColor:byte
extrn bLanguageToUse:byte
extrn bLightColor:byte
extrn bMultiString:byte
extrn bOutLineColor:byte
extrn bPreviousMode:byte
extrn bPreviousMode:byte
extrn bRepaintMode:byte
extrn bRepaintNeeded:byte
extrn bScreenMode:byte
extrn bShadowColor:byte
extrn bShortNotchPattern:byte
extrn bSpectrumPattern:byte
extrn bTabNotchPattern:byte
extrn IgnoreLevel:word
extrn LeftAddress:word
extrn lObjectLevel:word
extrn lTopAddress:word
extrn pClickRegion:word
extrn pCurrentFont:word
extrn pCurrentToolButtonRegion:word
extrn pCurrentToolButtonRegion:word
extrn pDrawStringTabList:word
extrn pFirstControl:word
extrn pGraphicsCaption:word
extrn pLastForm:word
extrn pLastActiveRegion:word
extrn pTabHandler:word
extrn pTabRegion:word
extrn pTextCaption:word
extrn rActiveRegion:REGION
extrn rREGION:REGION
extrn uResId:word
extrn wCaptionTop:word
extrn wCaptionTop:word
extrn wCaptionTop:word
extrn wCurrentFontHeight:word
extrn wCurrentFormBottom:word
extrn wCurrentFontHeight:word
extrn wDeltaLeft:word
extrn wDeltaTop:word
extrn wFormWidth:word
extrn wGraphicCaptionHeight:word
extrn wGraphicLegendRight:word
extrn wGraphicLegendRight:word
extrn wGraphicLegendRight:word
extrn wShiftCaption:word
extrn wToolBarHeight:word
extrn wToolBarHeight:word
extrn frmMessageBar:CONTROL
extrn frmMessageBar_end:CONTROL
extrn UIFont3:word

extrn osdmessagedraw:control

bCurrentControlType db 0
 public bCurrentControlType
DATASEG_END
.code
extrn blockvideo:near
extrn unblockvideo:near

extrn DoClickEvent:near
extrn DoTab:near
extrn DrawIColor:near
extrn DrawLabel:near
extrn DrawString:near
extrn FindRegionForControl:near
extrn GetCaptionHeight:near
extrn GetCaptionWidth:near
extrn GetCombinedCaptionHeight:near
extrn GetControlRegion:near
extrn GetLabelWidth:near
extrn IsNumericOnNumKeypad:near
extrn PaintNextTabControl:near
extrn PrepareClickRegisters:near
extrn ProtectOSK:near
extrn RepaintControl:near
extrn RepaintGroupObject:near
extrn RepaintOSKInMemory:near
extrn SetKeyCaption:near
extrn SetNewTabItem:near
extrn SetNewTabItem:near
extrn SetOSKKeyCaptionString:near
extrn ShowTabBox:near
extrn UnprotectOSK:near
extrn UpdateLegendRegion:near

DrawButtonCaption proc near
 public DrawButtonCaption

 xor ah,ah
 mov wShiftCaption,ax

 mov wGraphicCaptionHeight,0

 push si
 mov al,[si].ControlType
if need_osk ne 0
 cmp al,KEYBUTTON
 jnz dbc6

 call IsNumericOnNumKeyPad
 je dbc7

endif
dbc6:
 call PaintControlCaption
 jnz dbc00a


 mov al,[si].ControlType
if need_osk ne 0
 cmp al,KEYBUTTON
 jnz dbc3

dbc7
 call SetOSKKeyCaptionString
 jmp dbc00a

endif

dbc3:
if need_abouticon ne 0
 cmp al,ABOUTBUTTON
 jne dbc4
 call DrawAbouticon
 jmp dbc00
endif

dbc4
 jmp dbc00

dbc00a:
 cmp bScreenMode,VGA_MODE
 je dbc00d


 mov dx,rRegion.wCurrentTop
 and dl,11111000b
 jmp dbc00e

dbc00d:
 call GetCombinedCaptionHeight
 jnz dbc00b
 jmp dbc00

dbc00b:
 mov dx,rRegion.wCurrentHeight
 sub dx,ax
 jge dbc00c
 jmp dbc00
dbc00c:
 sar dx,1
 add dx,rRegion.wCurrentTop
 add dx,wShiftCaption
dbc00e:
 mov wCaptionTop,dx
 mov bx,pGraphicsCaption
 or bx,bx
 jnz dbc1zz
 jmp dbc1
dbc1zz:
if need_osk ne 0
 cmp bScreenMode,VGA_MODE
 jz dbc0

 mov ah,15+1
 call PaintControlMechanism
 or bx,bx
 jz dbc1
 call SetFontForCaption

 push si
 mov di,si
 mov si,bx
 call SetKeyCaption
 pop si
 add bx,3

 mov ax,rRegion.wCurrentLeft
 mov dx,rRegion.wCurrentTop
 jmp dbc0



 dbc0:
```

```
endif

 call SetFontForCaption

 call GetCaptionWidth
 or ax,ax
 jz dbc1
 mov cx,rRegion.wCurrentWidth
 sub cx,ax
 jl dbc1
 sar cx,1
 jns dbc8
 inc cx
dbc8:
 mov dx,rRegion.wCurrentLeft
 ROUND_TO_BYTE_BOUNDARY dx
 add cx,dx
 dec cx
 add cx,wShiftCaption
 mov dx,wCaptionTop

dbc9:
 push si
 push ax
 mov al,[si].ControlType
 mov di,si
 mov si,bx
 mov bl,bIconForegroundColor
 test [di].ControlState,DISABLED or GRAYED
 jz dbc2a
 mov bl,bShadowColor
dbc2a:
 mov bh,bIconBackgroundColor
 cmp al,SYMBOLBUTTON
 jb dbc2
 xor bh,bh
dbc2:
 pop ax
 call DrawString
 pop si

dbc1:
 mov bx,pTextCaption
 or bx,bx
 jz dbc88
 call SetFontForCaption
 mov dx,wCaptionTop
 add dx,wGraphicCaptionHeight
 add ax,dx
 mov rLegendRegion.wCurrentBottom,ax
 add bx,3
 push si
 mov ax,rRegion.wCurrentLeft
 ROUND_TO_BYTE_BOUNDARY ax
 add ax,wShiftCaption
 mov ax,rRegion.wCurrentWidth
 mov si,bx
 mov bl,bButtonForegroundColor
 mov bh,CENTERED
 call UpdateLegendRegion
 call DrawLabel
 pop si
dbc88:
 pop si
 ret
DrawButtonCaption endp

DrawEditBoxCaption proc near
 public DrawEditBoxCaption

 push rRegion.wCurrentLeft
 pop wGraphicLegendRight
 call PaintControlCaption
 jnz rnb0db
 jmp debc1
rnb0db:
 or bx,bx
 jz rnb3

 push cx
 call SetFontForCaption
 add bx,3
 push si
 mov si,bx
 call getlabelwidth
 mov dx,rRegion.wCurrentTop
 mov cx,rRegion.wCurrentLeft
 sub cx,ax
 mov wGraphicLegendRight,cx

 mov ax,rRegion.wCurrentHeight
 sar ax,1
 add dx,ax
 mov ax,wCurrentFontHeight
 sar ax,1
 sub dx,ax

 mov bl,bCaptionForegroundColor
 xor bh,bh
 call DrawLabel
 pop si
 pop cx

rnb3:
 jcxz debc1
 mov bx,cx
 push rRegion.wCurrentHeight
 pop wCurrentFontHeight
 call PositionGraphicCaption
 call PaintGraphicCaption

debc1:
 ret
DrawEditBoxCaption endp

DrawNotches proc near
 public DrawNotches

 push si
 push ax
 sub rRegion.wCurrentRight,8
 mov al,byte ptr [si+1].id
 mov cx,rRegion.wCurrentLeft
 cmp al,8
 mov ax,24
 je rnb3
 mov ax,8

rnb2:
 mov si,offset bTallNotchPattern
 cmp cx,rRegion.wCurrentLeft
 je rnb4
 add cx,ax
 cmp cx,rRegion.wCurrentRight
 jae rnb4a
 mov si,offset bShortNotchPattern
rnb4a:
 sub cx,ax
rnb4:
 mov dx,rRegion.wCurrentBottom
 inc dx
 push cx
 push ax
 call drawicolor
 pop ax
 pop cx
 add cx,ax
 cmp cx,rRegion.wCurrentRight
 jl rnb2
rnb3:
 add rRegion.wCurrentRight,8

 pop ax
 pop si
 ret
DrawNotches endp

DrawSpectrum proc near
 public DrawSpectrum

 push si
 mov dx,rRegion.wCurrentTop
 mov cx,rRegion.wCurrentLeft
 mov ax,rRegion.wCurrentBottom
 sub ax,3
 add cx,8
 add dx,5
rsb1:
 push ax
 push cx
 push dx
 mov si,offset bSpectrumPattern
 call drawicolor
 pop dx
 pop cx
 pop ax

 inc dx
 inc dx
 cmp dx,ax
 jb rsb1
 pop si
 ret
DrawSpectrum endp

ForceTotalRepaint proc near
 public ForceTotalRepaint
 call ForceTotalRepaint1
 mov bRepaintNeeded,-1
 ret
ForceTotalRepaint endp


ForceTotalRepaint1 proc near
 public ForceTotalRepaint1

 mov pFirstControl,offset MainForm
 mov bFormColor,FORM_COLOR
 mov wCurrentFormHeight,0
 mov wCurrentFormBottom,0
 ret
ForceTotalRepaint1 endp


GetTabControlType proc near
 public GetTabControlType
 xor ax,ax
 mov si,pTabRegion
 or si,si

 jz gtct1
 mov bx,[si].pCurrentControl
 mov ax,[bx]
 or ax,ax
gtct1:
 ret
GetTabControlType endp

GetTypeAndState proc near
 public GetTypeAndState

 mov di,si
 mov si,[si].pCurrentControl
 mov al,[si].ControlType
 mov ah,[si].ControlState
 ret
GetTypeAndState endp

GoFirstControl proc near
 public GoFirstControl


 mov si,pFirstControl
 mov rRegion.pCurrentControl,si
 clc
 ret
GoFirstControl endp

GoNextControl proc near
 public GoNextControl

 mov si,rRegion.pCurrentControl
 add si,type tControl
gnc3:
 test byte ptr [si],128
 jz gnc1
 mov si,[si+1]
 jmp gnc3

gnc1:
 cmp byte ptr [si],0
 jnz gnc2
 mov si,rRegion.pCurrentControl
 stc
 ret
gnc2:
 mov rRegion.pCurrentControl,si
 clc
 ret
GoNextControl endp

GoPreviousControl proc near
 public GoPreviousControl


 mov si,rRegion.pCurrentControl
gpc2:
 mov al,[si-1]
 or al,al
 jnz gpc3
 stc
 ret
gpc3:
 cmp al,255
 jz gpc1

 mov si,[si-3]
 jmp gpc2
gpc1:
 sub si,type tControl
 mov rRegion.pCurrentControl,si
 clc
 ret
GoPreviousControl endp


IgnoreObject proc near
 cmp al,FIRST_ENDOFOBJECT
 jb io2
 cmp al,LAST_ENDOFOBJECT
 jbe io1
 cmp al,TOOLBARBUTTON
 jz io2
 ret
io1:
 dec IgnoreLevel
 ret
io2:
 inc IgnoreLevel
 ret
IgnoreObject endp

PaintGraphicCaption proc near
 public PaintGraphicCaption

 push si
 mov si,bx
 mov bl,bCaptionForegroundColor
 xor bh,bh
 call drawstring
 pop si
 ret
PaintGraphicCaption endp

PaintControlCaption proc near
 public PaintControlCaption
 push di
 push si

 xor cx,cx
 xor di,di
 mov bx,si
 mov al,[bx]
 mov bCurrentControlType,al
 add bx,type tControl
pcc4:
 mov al,[bx]
 test al,128
 jnz pcc1
 or di,di
 jnz pcc6
 xor bx,bx
 jmp pcc2
pcc6:
 mov bx,di
 jmp short pcc2

pcc1:
 test al,16
 jnz pcc3

 mov ah,al
 and ah,GRAPHICFONT
 cmp ah,GRAPHICFONT
 jnz pcc5
 mov cx,bx
 jmp pcc3

pcc5:
 mov ah,al
 and ah,11110
 cmp ah,bLanguageToUse
 jz pcc2
 or ah,ah
 jnz pcc3
 mov di,bx
pcc3:
 mov bx,[bx+1]
 jmp short pcc4
pcc2:
 mov ax,bx
 or ax,ax
 call SetCaptionPointers
 pop si
 pop di
 ret
PaintControlCaption endp

PaintControlSelection proc near
 public PaintControlSelection


 mov bx,si
 add bx,type tControl
pib4:
 mov al,[bx]

 test al,128
 jnz pib1
 sub bx,bx
 ret

pib1:
 and al,ah
 cmp al,ah
```

```
 jz pih2
 mov bx,[bx+1]
 jmp short pin4
pih2:
 add bx,3
 or bx,bx
 ret
PointControlAtBottom endp

PositionGraphicCaption proc near
 public PositionGraphicCaption

 call GetCaptionHeight
 mov wGraphicCaptionHeight,ax
 push wCurrentFontHeight
 call SetFontForCaption
 pop wCurrentFontHeight
 call GetCaptionWidth
 mov ax,wGraphicLegendRight
 sub ax,bx
 sub ax,8
 mov dx,[Region.wCurrentTop
 mov ax,wGraphicCaptionHeight
 sar ax,1
 sub dx,ax
 mov ax,wCurrentFontHeight
 sar ax,1
 add dx,ax
 ret
PositionGraphicCaption endp

RePaint proc near
 public Repaint
 mov bCursorActive,0
 mov pHotActiveRegion,offset sActiveRegions
 call RepaintWork
 ret
Repaint Endp

RepaintAndSetTab proc near
 public RepaintAndSetTab
 call Repaint
 mov pTabRegion,0
 push pCurrentToolbuttonRegion
 pop pClickRegion

 cmp pClickRegion,0
 jnz rast1
 push pNextActiveRegion
 pop pTabRegion
 mov pTabHandler,offset PointNextTabControl
 call DoTab
 ret
rast1:
 call ShowTabBox
 mov pClickRegion,0
 ret
RepaintAndSetTab endp

RepaintForClick proc near
 public RepaintForClick

 push si
 mov bRepaintNeeded,-1
 call repaint

if need_osk ne 0
 call RepaintOSKInMemory
endif

 pop si

 call FindRegionForControl
 mov si,bx
 mov pClickRegion,si
 call PrepareClickRegisters
 call SetNewTabItem
 ret
RepaintForClick endp

RepaintWork proc near
 public RepaintWork

 mov iObjectLevel,0
 mov IgnoreLevel,0
 call blockvideo

 call GoFirstControl
 jmp rp2

rp0:
 call GoNextControl
rp2:
 jnz rp1

 call unblockvideo
 mov bRepaintNeeded,0
 mov bRepaintMode,0
 mov bPreviewMode,0
 ret

rp1:
 mov al,[si].ControlType
 cmp IgnoreLevel,0
 jz rp6
 call IgnoreObject
 jmp rp0

rp6:
 mov al,[si].ControlState
 cmp al,FIRST_ENDOFOBJECT
 jb rp8
 cmp al,LAST_ENDOFOBJECT
 ja rp7
 dec iObjectLevel
 jmp rp0

rp8:
 call SetProtectionForControl
 call RepaintGroupObject
 jmp rp0

rp7:
 call SetProtectionForControl
 call RepaintControl
 jmp rp0
RepaintWork endp

SetCaptionPointers proc near
 public SetCaptionPointers
 mov pTextCaption,bx
 mov pGraphicsCaption,ax
 ret
SetCaptionPointers endp

SetColorsForControl proc near
 public SetColorsForControl

 call UseNormalColors
 test ah,DISABLED or GRAYED
 jz rs13
 call UseGrayedColors
rs13:
 ret
SetColorsForControl endp

SetControlTabList proc near
 public SetControlTabList

 push ax
 push bx
 mov ah,10+2
 call PointControlAtBottom
 jnz scl1
 mov bx,offset blankString
scl1:
 mov pDrawStringTabList,bx
 pop bx
 pop ax
 ret
SetControlTabList endp

SetFontForCaption proc near
 public SetFontForCaption
 push bx
 mov al,[bx]
 and al,ANYFONT
 rol al,1
 rol al,1
 rol al,1
 rol al,1
 xor ah,ah
 cmp al,11b * 2
 jnz sfc1
 cmp bCurrentControlType,LEFTLEGEND
 je sfc4
 cmp bx,offset OSK
 jne sfc1

 cmp bx,offset lbmMessageBox
 jb sfc5
 cmp bx,offset lbmMessageBox_end
 ja sfc5
 jmp sfc4
sfc5:
 cmp bx,offset FirstStandardControl
 jb sfc2
 cmp bx,offset LastStandardControl
 jb sfc1
sfc2:
 cmp bCurrentControlType,SPINUPBUTTON
 je sfc1
 cmp bCurrentControlType,SPINDOWNBUTTON
 je sfc1
sfc4:
 mov bx,offset sfbold
 jmp sfc3
sfc1:
 mov bx,offset FontTable
 add bx,ax
 mov bx,[bx]
sfc3:
 mov pCurrentFont,bx
 mov ax,[bx]
 mov al,ah
 xor ah,ah
 mov wCurrentFontHeight,ax
 pop bx
 ret
SetFontForCaption endp

SetFormHeights proc near
 public SetFormHeights
 mov bPreviewMode,-1
 mov si,pFirstControl
 push word ptr [si]
 and [si].ControlState,not(INVISIBLE)
 mov pLastForm,0
 mov wFormWidth,0
 push si
 call RepaintWork
 pop si
 pop word ptr [si]
 ret
SetFormHeights endp

SetProtectionForControl proc near
 public SetProtectionForControl

 cmp bDontChangeProtection,0
 jnz rp6b

if need_osk ne 0
 cmp si,offset OSK
 jne rp6a
 mov bCurrentShadowColor,DARKGRAY
 call protectOSK
 ret

rp6a:
 mov bCurrentShadowColor,DARKGRAY
 test wCurrentResource,not(11 lb)
 jnz rp6c

 mov bCurrentShadowColor,DARKGRAY+1

rp6c:
 call unprotectOSK
endif

rp6b:
 ret
SetProtectionForControl endp

StartNewObjectLevel proc near
 public StartNewObjectLevel

 push dx
 push cx
 inc iObjectLevel
 mov bx,iObjectLevel
 add bx,bx
 mov dx,wDeltaTop
 mov iTopAdders[bx],dx
 mov cx,wDeltaLeft
 mov iLeftAdders[bx],cx
 pop cx
 pop dx
 ret
StartNewObjectLevel endp

StartToolbuttonObjectLevel proc near
 public StartToolbuttonObjectLevel
 push wToolBarHeight
 pop wDeltaTop
 mov wDeltaLeft,0
 call StartNewObjectLevel
 ret
StartToolbuttonObjectLevel endp

UseGrayedColors proc near
 public UseGrayedColors
 push ax
 mov al,bCurrentShadowColor

 mov bShadowColor,al

 mov bOutlineColor,al

 mov bLightColor,FORM_COLOR
 mov bButtonForeGroundColor,al
 pop ax
 ret
UseGrayedColors endp

UseNormalColors proc near
 public UseNormalColors

 push word ptr bCurrentShadowColor
 pop word ptr bShadowColor
 mov bOutlineColor,OUTLINE_COLOR
 mov bLightColor,LIGHT_COLOR
 mov bButtonForeGroundColor,OUTLINE_COLOR
 ret
UseNormalColors endp
end

Copr. 1996 Zenith Data Systems Corp.
.model small
.code
extrn DoPopUp:near
extrn RestVGAState:near

extrn SetHandCursor:near

include sltmdef.inc

DATASEG_BEGIN
extrn ControlDataStorageArea:byte
extrn bAwaitingMoveCompletion:byte
extrn bDoingEvents:byte
extrn bHourGlassMode:byte
extrn bLocalState:byte
extrn bMessageBoxID:byte
extrn bPopUpRequired:byte
extrn bScreenMode:byte

bTimesHidden db 1

bTriggerPenOnForClick db 0
 public bTriggerPenOnForClick

bLeavePenOn db 0
 public bLeavePenOn

bPenEventHappened db 0
 public bPenEventHappened
bPenEventType db 0
 public bPenEventType

bIgnoringPen db 0
 public bIgnoringPen

bIgnoringMove db 0
 public bIgnoringMove

wPenCurrentColumn dw 0
 public wPenCurrentColumn
wPenCurrentRow dw 0
 public wPenCurrentRow
wPenDownColumn dw 0
 public wPenDownColumn
wPenDownRow dw 0
 public wPenDownRow
wPenUpColumn dw 0
 public wPenUpColumn
wPenUpRow dw 0
 public wPenUpRow

DATASEG_END

.code

ActivatePen proc near
 public ActivatePen
 push es
 mov ax,SET_PEN_EVENT_HANDLER
 mov dx,offset PenEventHandler
 push cs
 pop es
 mov cx,PENMOVED or PENUP or PENDOWN
 int PEN_ACTIVATE_FUNCTION
 pop es
 ret
ActivatePen endp

BlockVideo proc near
 public blockvideo

 push ax
 BM_FUNCTION BM_BLOCK_VIDEO_ACCESS
 pop ax
 ret
BlockVideo endp

UnblockVideo proc near
 public unblockvideo
 push ax
```

```
SM_FUNCTION SM_UNBLOCK_VIDEO_ACCESS

pop ax
ret
UnblockVideo endp

PenEventHandler proc far

push ds
push bx
push dx
mov bx,OURDATASEG
mov ds,bx

cmp bTriggerPenOnForClick,0
jz peh00
mov bLeavePenOn,-1
mov bTriggerPenOnForClick,0
peh00:

cmp bAwaitingMoveCompletion,0
jnz peh21

cmp bIgnoringPen,0
jnz peh21

cmp bHourGlassMode,0
jnz peh21

cmp bLocalState,0
jnz peh20

peh21:
jmp peh3e


peh20
cmp bScreenMode,VGA_MODE
jz mmm

ROUND_TO_BYTE_BOUNDARY dx
jmp nnn

mmm:
call SetHandCursor
nnn:


cmp al,PENMOVED
jne peh0a
mov bx,wPenCurrentColumn
sub bx,cx
jge peh0b
neg bx
peh0b:
cmp bx,4
jge peh0c
mov bx,wPenCurrentRow
sub bx,dx
jge peh0c
neg bx
peh0c:
cmp bx,2
jge peh0a
mov wPenCurrentColumn,cx
mov wPenCurrentRow,dx
jmp peh3e

peh0a
mov bPenEventHappened,-1
test al,(PENUP or PENDOWN)
jz peh1

peh1.
or bPenEventType,al
mov wPenCurrentColumn,cx
mov wPenCurrentRow,dx
test al,PENDOWN
jz peh2
mov wPenDownColumn,cx
mov wPenDownRow,dx
peh2.
test al,PENUP
jz peh3
mov wPenUpColumn,cx
mov wPenUpRow,dx
peh3:

if need_tsr eq 0
mov bPopupRequired,-1
pushf
cli
push ax
call DoPopUp
pop ax

popf

endif

peh3e:
pop dx
pop bx
pop ds
ret
PenEventHandler endp

IgnorePen proc near
public IgnorePen

inc bIgnoringPen
ret
IgnorePen endp

SetPenRowRegion proc near
public SetPenRowRegion

push ax
mov ax,06h
int PEN_FUNCTION
pop ax
ret
SetPenRowRegion endp

SetPenColumnRegion proc near
public SetPenColumnRegion
push ax
mov ax,07h
int PEN_FUNCTION
pop ax
ret
SetPenColumnRegion endp

ResumePen proc near
public ResumePen
dec bIgnoringPen
ret
ResumePen endp

PenEntry proc near
public PenEntry

cmp bLeavePenOn,0
jz p1
cmp bTimeoutHidden,0
jnz p1
push cx
mov ax,REMOVE_PEN_CURSOR
int PEN_FUNCTION
inc bTimeoutHidden
pop cx
p1:
ret
PenEntry endp

PenExit proc near
public penexit

cmp bLeavePenOn,0
jz pex1
cmp bTimeoutHidden,0
jz pex1
push ax
push cx

mov cx,5
agn:
mov ax,DISPLAY_PEN_CURSOR
int PEN_FUNCTION
loop agn
pop cx
mov bTimeoutHidden,0
pop ax
pex1:
ret
PenExit endp

end


Copr. 1995 Zenith Data Systems Corp.

.MODEL SMALL
include ulimited.inc
DATASEG_BEGIN
extrn lLeftAdders:word
extrn lTopAdders:word
extrn ControlDataStorageArea:byte
extrn OSK:tControl
extrn bSliderButton:byte
extrn bCoveredAreaOnly:byte
extrn bEnlargeFlag:byte
extrn bModalFlag:byte
extrn bPreviousMode:byte
extrn bPreviousMode:byte
extrn bScreenMode:byte
extrn bUnderlinedCharacter:byte
extrn fmFirstModalForm:tControl
extrn lObjectLevel:word
extrn pNextActiveRegion:word
extrn pOSKFirstRegion:word
extrn pPenDownActiveRegion:word
extrn pPenDownLegendRegion:word
extrn rActiveRegion:tRegion
extrn rLegendRegion:tRegion
extrn rPushedRegion:tRegion
extrn rREGION:REGION
extrn wCoveredAreaBottom:word
extrn wCoveredAreaHeight:word
extrn wCoveredAreaLeft:word
extrn wCoveredAreaRight:word
extrn wCoveredAreaTop:word
extrn wCoveredAreaTopHold:word
extrn wCoveredAreaWidth:word
extrn wDeltaLeft:word
extrn wDeltaTop:word
extrn wPenDownColumn:word
extrn wPenDownRow:word


wToolbarHeight dw 0
  public wToolbarHeight
wCurrentFormHeight dw 0
  public wCurrentFormHeight
wCurrentFormBottom dw 0
  public wCurrentFormBottom
wPreviousFormHeight dw 0
  public wPreviousFormHeight
wPreviousFormBottom dw 0
  public wPreviousFormBottom

wCurrentFormLeft dw 0
  public wCurrentFormLeft
wCurrentFormRight dw 0
  public wCurrentFormRight


wNextTop dw 0
  public wNextTop
wPriorNextTop dw 0
wPriorPriorNextTop dw 0
wNextFrameTop dw 0
wNextLeft dw 0
wNextFrameLeft dw 0
wSameLeft dw 0
wSameHigh dw 0
wSameWide dw 0
wSameTop dw 0
wPriorSameTop dw 0
wPriorPriorSameTop dw 0
wSameFrameTop dw 0
extrn setfirstrow:tControl
extrn setsecondrow:tControl

DATASEG_END
.code
extrn GetLabelWidth:near
extrn GetLegendHeight:near
extrn InitLegend:near
extrn PaintControlNoBottom:near
extrn ProtectOSK:near
extrn Repaint:near
extrn SetPenColumnRegion:near
extrn SetPenRowRegion:near


GetControlRegion proc near
 public GetControlRegion

 mov dx,[si].TopPixel
 call HandleTopConstants
 mov wDeltaTop,dx

 mov ax,wPriorSameTop
 mov wPriorPriorSameTop,ax
 mov ax,wPriorNextTop
 mov wPriorPriorNextTop,ax
 mov ax,wSameTop
 mov wPriorSameTop,ax
 mov ax,wNextTop
 mov wPriorNextTop,ax

 mov wSameTop,dx
 mov wNextTop,dx

 xor cx,cx

 cmp bScreenMode,VGA_MODE
 jz hmm1
 cmp al,FORM
 jz hmm1
 add cx,8
 add dx,8

hmm1:

 mov bx,lObjectLevel
 add bx,bx
gcl2:
 add cx,lLeftAdders[bx]
 add dx,lTopAdders[bx]
 or bx,bx
 jz gcl1
 dec bx
 dec bx
 jmp short gcl2
gcl1:

 mov bx,[si].LeftPixel


 cmp al,FORM
 jnz gcl1d

 test bh,10h
 jz gcl1a
 or bh,11111000b
 jmp short gcl1e

gcl1d:
 call HandleLeftConstants


 test [si].LeftPixel,FROMRIGHT
 jz gcl1a
 cmp al,FORM
 jz gcl1a

if need_osk ne 0
 cmp bEnlargeFlag,0
 jz gsu5

 push ax
 push dx
 mov ax,4
 mul bx
 mov bx,3
 div bx
 mov bx,ax
 pop dx
 pop ax

endif

gsu5:
 cmp bPreviousMode,0
 jz gsu6a
 xor bx,bx
 jmp gcl1f

gsu6a:
 neg bx
 add bx,wCurrentFormRight
 sub bx,wCurrentFormLeft

if need_osk ne 0
 cmp bScreenMode,VGA_MODE
 jz gcl1e
 add bx,8
 cmp bEnlargeFlag,0
 jnz gcl1e
 sub bx,16

endif
gcl1e:
 cmp bScreenMode,VGA_MODE
 jz gcl1f

 mov ax,[si]

if need_osk ne 0

 test ah,COMPENSATE
 jz gcl1f
 cmp al,FORM
 jz gcl1f
 sub bx,8
 cmp bEnlargeFlag,0
 jz gcl1f
 sub bx,8
endif

gcl1f:
 mov wDeltaLeft,bx
 add cx,bx
```

```
gcl1b
 mov rRegion.wCurrentTop,dx
 mov rRegion.wCurrentLeft,cx
 mov wSameLeft,bx
 mov wNextLeft,bx

 mov bx,[si].PixelWidth

if need_ock ne 0

 cmp bx,-1
 jnz gcl4e

 push ax
 mov ah,16+3
 call PointControlRecTom
 pop ax
 or bx,bx
 jz gcl4e4

 cmp bScreenMode,VGA_MODE
 jz gcl4e1
 cmp bEnlargeFlag,0
 jnz gcl4e3
 mov bx,[bx+4]
 jmp gcl4f
gcl4e3
 mov bx,[bx+6]
 jmp gcl4f

gcl4e1

 cmp bEnlargeFlag,0
 jnz gcl4e2
 mov bx,[bx]
 jmp gcl4f
gcl4e2
 mov bx,[bx+2]
gcl4f
 jmp glc4a
gcl4e4
 mov bx,-1

endif

gcl4e
 cmp bx,SAMEWIDE
 jnz gcl4
 mov bx,wSameWide
 jmp glc4a

gcl4
if need_ock ne 0

 cmp bEnlargeFlag,0
 jz gcl1e

 cmp al,FORM
 jz gcl1e
 cmp al,CHISELBOX
 jz gcl1e

 push dx
 push ax
 mov ax,4
 mul bx
 mov bx,3
 div bx
 mov bx,ax
 test bl,11b

 jz owe
 add bx,8
 and bl,11111000b

owe
 pop dx
 pop ax

gcl1e
 cmp bScreenMode,VGA_MODE
 jz glc4a

 cmp bEnlargeFlag,0
 jnz glc4a

 test [si].ControlState,WIDEN
 jz glc4a
 test [si].ControlState,DOUBLEWIDEN
 jz glc4c
 add bx,8
glc4c:
 add bx,8

endif

glc4a:
 and bl,11111100b
 mov wSameWide,bx
 mov rRegion.wCurrentWidth,bx
 add wNextLeft,bx
 add bx,ax
 dec bx
 mov rRegion.wCurrentRight,bx

if need_ock ne 0
 cmp bScreenMode,VGA_MODE
 jz gcu10

 test [si].ControlState,COMPENSATE
 jz glc4r
 test [si].LeftPixel,FROMRIGHT
 jnz glc4r
 sub wNextLeft,8

glc4r:

 test [si].ControlState,WIDEN
 jz gcu10
 test [si].ControlState,COMPENSATE
 jz gcu10a

 add wNextLeft,8
gcu10a:

 cmp bEnlargeFlag,0
 jz gcu10
gcu10a:
 sub rRegion.wCurrentWidth,8
 sub rRegion.wCurrentRight,8
endif

gcu10:

 mov bx,[si].PixelHeight
 or bx,bx
 jnz gcu1

 call IsInLegend
 jnz gcu1

 call GetLegendHeight
 jmp short gcu2

gcu1:

 call HandleHeightConstants

gcu2:
 mov rRegion.wCurrentHeight,bx
 mov wSameHigh,bx
 add wNextTop,bx
 add bx,dx
 dec bx
 mov rRegion.wCurrentBottom,bx

if need_ock ne 0
 cmp al,FORM
 jnz hlf1
 cmp bScreenMode,VGA_MODE
 jz hlf1
 mov bx,16
 add rRegion.wCurrentRight,bx
 add rRegion.wCurrentWidth,bx
 add bx,8
 add rRegion.wCurrentBottom,bx
 add rRegion.wCurrentHeight,bx

endif

hlf1:
 cmp al,FRAME
 jnz glc4b
 push wNextLeft
 pop wNextFrameLeft
 push wNextTop
 pop wNextFrameTop
 push wSameTop
 pop wSameFrameTop

glc4b:
 ret
GetControlRegion endp

AddControlToActiveList proc near
 public AddControlToActiveList
 test ah,DISABLED
 jnz actal1

if NEED_ALTKEYS ne 0

 push ax
 mov al,bUnderLinedCharacter
 mov ah,128
 cmp al,'a'
 jb atal1
 cmp al,'z'
 jb atal1
 sub al,32
atal1:
 mov rRegion.wListIndex,ax
 pop ax
endif

 mov si,offset rRegion
 call StoreRegion

if NEED_ALTKEYS ne 0
 mov rRegion.wListIndex,0
 mov bUnderLinedCharacter,0
endif
actal1:
 ret
AddControlToActiveList endp

AddLegendToActiveList proc near
 public AddLegendToActiveList

 test ah,DISABLED or GRAYED
 jnz alla1

 push rRegion.pCurrentControl
 pop rLegendRegion.pCurrentControl

 mov rLegendRegion.wCurrentHeight,-1
 mov si,offset rLegendRegion
 call StoreRegion
alla1:
 ret
AddLegendToActiveList endp

CheckHeightEnlarge proc near
if need_ock ne 0

 cmp bEnlargeFlag,0
 jz gcl3e
 cmp bScreenMode,VGA_MODE
 jz che1

 cmp al,ABOUTBUTTON
 jz che1
 cmp al,COMMANDBUTTON
 jb che1
 jmp gcl3e

che1:
 push ax
 push dx
 mov ax,3
 mul bx
 mov bx,3
 div bx
 mov bx,ax
 pop dx
 pop ax

endif

gcl3e:
 ret
CheckHeightEnlarge endp

CheckPenDownCoordinates proc near
 public CheckPenDownCoordinates

 mov pPenDownActiveRegion,0
 mov pPenDownLegendRegion,0
 mov si,wPenDownColumn
 mov di,wPenDownRow
 call SearchActiveRegions
 mov pPenDownActiveRegion,di
 mov si,di
 ret
CheckPenDownCoordinates endp

DefineCoveredArea proc near
 public DefineCoveredArea

 push bx
 mov ax,[bx].TopPixel

 mov wCoveredAreaTopHold,ax
 mov wCoveredAreaTop,-1
 add ax,[bx].PixelHeight
 mov wCoveredAreaBottom,ax
 mov ax,[bx].LeftPixel
 test ah,100b
 jz dca3
 or ah,11111000b
dca3:
 push ax
 DIVIDE_BY_8 ax
 mov wCoveredAreaLeft,ax
 pop ax
 add ax,[bx].PixelWidth
 dec ax
 DIVIDE_BY_8 ax
 mov wcoveredAreaRight,ax
 mov ax,[bx].PixelHeight
 mov wCoveredAreaHeight,ax
 mov ax,[bx].PixelWidth
 DIVIDE_BY_8 ax
 mov wCoveredAreaWidth,ax
 mov bCoveredAreaOnly,0
 pop bx
 ret
DefineCoveredArea endp

FindRegionForControl proc near
 public FindRegionForControl

 mov bx,offset rActiveRegions
uaab0:
 cmp bx,pOSKFirstRegion
 jae uaab4
 cmp bx,pNextActiveRegion
 jae uaab4
 cmp [bx].pCurrentControl,si
 jz uaab8
 add bx,type rActiveRegions
 jmp uaab0

uaab8:
 clc
 ret

uaab4:
 stc
 ret
FindRegionForControl endp

HandleHeightConstants proc near

 cmp bx,SAMEHIGH
 jnz gcl3
 cmp al,FRAME
 jz gcl3a
 mov bx,wSameHigh
gcl3a
 ret

gcl3:
 cmp bx,H100
 jae gcl5
 ret

gcl5:
 cmp bScreenMode,VGA_MODE
 jz gcl6

 cmp bx,H50
 jnz gcl5e
 mov bx,H50TEXTHEIGHT
 ret

gcl5e:
 call CheckHeightEnlarge

 cmp bx,H100
 jnz gcl5a
 mov bx,H100TEXTHEIGHT
 ret

gcl5a:
 cmp bx,H166
 jnz gcl5b
 mov bx,H166TEXTHEIGHT
 ret

gcl5b:
 cmp bx,H200
 jnz gcl5c
 mov bx,H200TEXTHEIGHT
 ret

gcl5c:
 cmp bx,H333
 jnz gcl5d
 mov bx,H333TEXTHEIGHT
 ret

gcl5d:

 push dx
 push ax
 mov ax,bx
 xor dx,dx
```

```
mov bx,1200
div bx
mov bx,H100TEXTHEIGHT
mul bx
mov bx,ax
pop ax
pop dx
ret

gcl0
cmp bx,H50
jnz gcl0a
mov bx,H50VGAHEIGHT
ret
gcl0a:
call CheckHeightEnlarge
cmp bx,H100
jnz gcl0b
mov bx,H100VGAHEIGHT
ret

gcl0b:
cmp bx,H150
jnz gcl0c
mov bx,H150VGAHEIGHT
ret

gcl0c:
cmp bx,H200
jnz gcl0d
mov bx,H200VGAHEIGHT
ret

gcl0d:
cmp bx,H333
jnz gcl0e
mov bx,H333VGAHEIGHT
ret

gcl0e

push dx
push ax
mov ax,bx
xor dx,dx
mov bx 1200
div bx
mov bx,H100VGAHEIGHT
mul bx
mov bx,ax
pop ax
pop dx
ret
HandleHeightConstants endp

HandleLeftConstants proc near

test bh,11111100b
jnz hlc1
ret

hlc1
and bh,not(FROMRIGHT/256)

cmp bx,SAMELEFT - 511
jb hlc8

cmp bx,NEXTLEFT - 511
jb hlc4

cmp bx NEXTFRAMELEFT - 511
jb hlc5

jmp hlc6

hlc4:

sub bx,SAMELEFT
add bx,wSameLeft
jmp hlc8

hlc5:
sub bx,NEXTLEFT
add bx,wNextLeft
jmp hlc8

hlc6.
sub bx,NEXTFRAMELEFT
add bx,wNextFrameLeft
jmp hlc8

hlc8
ret
HandleLeftConstants endp

HandleTopConstants proc near
test dh,11111100b
jnz htc1
ret
htc1:
test dh,80h
jz htc2
test dh,40h
jz htc1a

push wPriorPriorNextTop
pop wNextTop
push wPriorPriorSameTop
pop wSameTop
jmp htc1b

htc1a:
push wPriorNextTop
pop wNextTop
push wPriorSameTop
pop wSameTop

htc1b:
and dh,not(80h+40h)

htc2:

and dh,not(FROMRIGHT/256)

cmp dx,SAMETOP - 511
jb htc8

cmp dx,NEXTTOP - 511
jb htc4

cmp dx,SAMEFRAMETOP - 511
jb htc5

cmp dx,NEXTFRAMETOP - 511
jb htc6

cmp dx,NEXTTOP50 - 511
jb htc7

jmp htc9
htc4.

sub dx,SAMETOP
add dx,wSameTop
jmp htc8

htc5:
sub dx,NEXTTOP
add dx,wNextTop
jmp htc8

htc6:
sub dx,SAMEFRAMETOP
add dx,wSameFrameTop
jmp htc8

htc7:
sub dx,NEXTFRAMETOP
add dx,wNextFrameTop
jmp htc8

htc9:
sub dx,NEXTTOP50
add dx,wNextTop
cmp bScreenMode,VGA_MODE
jnz htc9a
add dx,H50VGAHEIGHT
jmp htc8

htc9a:
add dx,H50TEXTHEIGHT
jmp htc8
htc8:
ret
HandleTopConstants endp

PaintAssociatedLegend proc near
public PaintAssociatedLegend

push ax
mov ax,[si].pCurrentControl
add si,type rRegion
cmp ax,[si].pCurrentControl
pop ax
ret
PaintAssociatedLegend endp

PopRegion proc near
public PopRegion
mov si,offset rPushedRegion
call RestoreRegion
ret
PopRegion endp

PushRegion proc near
public PushRegion
push si
push di
push ds
pop es
mov si,offset rRegion
mov di,offset rPushedRegion
mov cx,type rRegion
rep movsb
pop di
pop si
ret
PushRegion endp

RestorePenRegion proc near
public RestorePenRegion
xor ax,ax
mov dx,639
call SetPenColumnRegion
xor ax,ax
mov dx,479
call SetPenRowRegion
ret
RestorePenRegion endp

RestoreRegion proc near
public RestoreRegion

mov di,offset rRegion
push ds
pop es
mov cx,type rRegion
rep movsb
mov ax,rRegion.wCurrentLeft
mov dx,rRegion.wCurrentTop
mov si,rRegion.pCurrentControl
mov ax,[si]
ret
RestoreRegion endp

SearchActiveRegions proc near
public SearchActiveRegions

push si
xor di,di
mov si,offset rActiveRegions

spdc2:
cmp si,pNextActiveRegion
jae spdc3

cmp bModalFlag,0
jz spdc2a
cmp [si].pCurrentControl,offset frmFirstModalForm
jb spdc1
spdc2a:

cmp cx,[si].wCurrentLeft
jl spdc1
cmp cx,[si].wCurrentRight
jg spdc1
cmp dx,[si].wCurrentTop
jl spdc1
cmp dx,[si].wCurrentBottom
jg spdc1

mov di,si

spdc1:
add si,type rActiveRegions
jmp short spdc2

spdc3
or di,di
pop si
ret
SearchActiveRegions endp

StoreRegion proc near
public StoreRegion

mov di,pNextActiveRegion
push ds
pop es
mov cx,type rRegion
rep movsb
mov pNextActiveRegion,di
ret
StoreRegion endp

UpdateLegendRegion proc near
public UpdateLegendRegion

push bp
push bx
push ax
mov bp,sp
mov rLegendRegion.wCurrentTop,dx
mov rLegendRegion.wCurrentLeft,ax
call GetLabelWidth
test bh,CENTERED
jz ulr1

mov bx,[bp]
sar bx,1
add bx,rLegendRegion.wCurrentLeft
push ax
sar ax,1
sub bx,ax
mov rLegendRegion.wCurrentLeft,bx
pop ax
add ax,bx
jmp ulr2

ulr1:
add ax,cx
ulr2:
mov rLegendRegion.wCurrentRight,ax
pop ax
pop bx
pop bp
ret
UpdateLegendRegion endp
end
Copr. 1995 Zenith Data Systems Corp.

.model small
.code
extrn Repaint:near
extrn RepaintIndividualControl:near
extrn SetNewTabItem:near
extrn SetNewTabItem:near
extrn StoreRegion:near
extrn UndoCurrentTabItem:near


include pinclud.inc
DATASEG_BEGIN
extrn ControlDataStorageArea:byte
extrn pClickRegion:word
extrn pNextActiveRegion:word
extrn pPenDownActiveRegion:word
extrn rActiveRegions:REGION
extrn rLegendRegion:REGION
extrn rREGION:REGION

DATASEG_END


.code

DoSlideBarPenDown proc near
public DoSlideBarPenDown


mov bx,[di].PixelWidth
sub cx,[di].wCurrentLeft
jge dsbpd2
xor cx,cx
dsbpd2:
sub bx,8
cmp cx,bx
jbe dsbpd4
mov cx,bx
dsbpd4:


mov ax,100
mul cx
div bx
mov cl,byte ptr [di].Id[1]
xor ch,ch
dec cx
mul cx
mov cx,100
div cx
cmp dx,50
jb dsbpd1
inc ax
dsbpd1:

mov bx,[di].pStorageOffset
cmp byte ptr [bx],al
jz dsbpd3
call SetSlideBarPosition
dsbpd3:

ret
DoSlideBarPenDown endp

SetSlideBarPosition proc near
push bx
push ax
call UndoCurrentTabItem
mov pClickRegion,di
```

```
pop ax
pop bx

mov byte ptr [bx],al
mov bl,al
xor bh,bh
mov ax,[si].ID
    xor ah,ah
SM_FUNCTION ax
mov ax,[si]
call RepaintIndividualControl

push pNextActiveRegion
mov di,pClickRegion
add di,type rRegion
mov pNextActiveRegion,di
mov rLegendRegion.pCurrentControl,si
mov si,offset rLegendRegion
call StoreRegion
pop pNextActiveRegion

call SetNewTabItem
mov pClickRegion,0
ret
SetSlideBarPosition endp

DoSlideBarRightArrow proc near
 public DoSlideBarRightArrow

 mov pPenDownActiveRegion,si
 mov bx,[si].pStorageOffset
 mov al,byte ptr [bx]
  push ax
  mov ah,byte ptr [si+1],al
  dec ah
 cmp al,ah
  pop ax
 jae dsbra1
 inc al
 call SetSlideBarPosition
dsbra1:
 mov pPenDownActiveRegion,0
  ret
DoSlideBarRightArrow endp

DoSlideBarLeftArrow proc near
 public DoSlideBarLeftArrow
  mov pPenDownActiveRegion,si
  mov pClickRegion,si
  mov bx,[si].pStorageOffset
  mov al,byte ptr [bx]
  or al,al
  jz dsbla1
  dec al
  call SetSlideBarPosition
dsbla1:
  mov pPenDownActiveRegion,0
  ret
DoSlideBarLeftArrow endp
end


Copr. 1995 Zenith Data Systems Corp.
.MODEL SMALL
include uiincted.inc
DATASEG_BEGIN
extrn ControlDataStorageArea:byte
extrn bDoingSpin:byte
extrn pPenDownActiveRegion:word
extrn rActiveRegions:rRegion
extrn rRegion:rRegion
DATASEG_END

.code
extrn FindRegionForControl:near
extrn GoPreviousControl:near
extrn GoPreviousControl:near
extrn InitEditBox:near
extrn RepaintIndividualControl:near
extrn SetNumericControl:near


DoSpinDown proc near
 public DoSpinDown
 push si
 call SetPreviousEditFieldForSpin
 je dsd1

 cmp cx,4
 jb dsd13

 mov cx,10
dsd14:
 call DecrementAsciiField
 loop dsd14
 jmp dsd15

dsd13:
 call DecrementAsciiField
dsd15:
 call RepaintSpinnedEditBox
dsd1:
 pop si
 mov rRegion.pCurrentControl,si
 ret
DoSpinDown endp

DecrementAsciiField proc near


 push di
dsd11:
 dec di
 cmp di,bx
 jb dsd10
 mov al,[di]
 cmp al,'9'
 ja dsd11
 cmp al,'0'
 jb dsd11
 je dsd12
 dec byte ptr [di]
 jmp dsd10
dsd12:
 mov byte ptr [di],'9'
 jmp dsd11
dsd10:
 pop di
 ret
DecrementAsciiField endp

DoSpinUp proc near
 public DoSpinUp

 push si
 call SetPreviousEditFieldForSpin
 je dsu1
 cmp cx,4
 jb dsu13


 mov cx,10
dsu14:
 call IncrementAsciiField
 loop dsu14
 jmp dsu15

dsu13:
 call IncrementAsciiField

dsu15:
 call RepaintSpinnedEditBox
dsu1:
 pop si
 mov rRegion.pCurrentControl,si
 ret
DoSpinUp endp

SetPreviousEditFieldForSpin proc near


 mov rRegion.pCurrentControl,si
dsu2:
 call GoPreviousControl
 jne dsu2a
 ret
dsu2a:
 mov ax,[si]
 call InitEditBox
 jne dsu2

 push ds
 pop es
 mov di,[si].wDataLength

 mov cx,di
 mov bx,[si].pStorageOffset
 add di,bx
 dec di
 push di

 push si
 mov si,bx
dsu4:
 cmp si,di
 jz dsu6
 lodsb
 or al,al
 jnz dsu4
dsu3:
 dec si

 std
dsu5:
 lodsb
 cmp al,bx
 jne dsu6
 mov al,'0'
dsu7:
 cmp di,bx
 jb dsu8
 stosb
 jmp dsu7
dsu8:
 cld
 pop si
 pop di
 clc
 ret
SetPreviousEditFieldForSpin endp

RepaintSpinnedEditBox proc near
 call SetNumericControl
 call FindRegionForControl
 je dsu1z

 push pPenDownActiveRegion
 mov pPenDownActiveRegion,bx
 mov bDoingSpin,1
 call RepaintIndividualControl
 mov bDoingSpin,0
 pop pPenDownActiveRegion
dsu1z:
 ret
RepaintSpinnedEditBox endp

IncrementAsciiField proc near

 push di
dsu11:
 dec di
 cmp di,bx
 jb dsu10
 mov al,[di]
 cmp al,'9'
 ja dsu11
 cmp al,'0'
 jb dsu11
 je dsu12
 inc byte ptr [di]
 jmp dsu10
dsu12:
 mov byte ptr [di],'0'
 jmp dsu11
dsu10:
 pop di
 ret
IncrementAsciiField endp
end


Copr. 1995 Zenith Data Systems Corp.

.MODEL SMALL
include uiincted.inc
DATASEG_BEGIN
extrn wHotKeyRightPart:word
extrn ControlDataStorageArea:byte
extrn OBK:Control
extrn VBSBacking1Control
extrn VBSDnArrowControl
extrn VBSSliderControl
extrn bModeFlag:byte
extrn bPenEventHappened:byte
extrn bmFirstModelForceControl
extrn pClickRegion:word
extrn pNextActiveRegion:word
extrn pOBKFirstRegion:word
extrn rActiveRegions:rRegion
extrn rTabRegion:REGION
extrn vsbBacking:Control
extrn vsbSlider:Control
extrn wPenDownColumn:word
extrn wPenDownRow:word
extrn wShortCutKey:word
extrn bMoveModeByte
pTabHandler  dw 0
  public pTabHandler

pOrgTabRegion dw 0
pTabRegion dw 0
  public pTabRegion


pTabRegionHold dw 0
  public pTabRegionHold
wTabLoopCount  dw 0
pDelayedSetControl dw 0
  public pDelayedSetControl
pDelayedSetRegion dw 0
  public pDelayedSetRegion
  extrn rCursorRegion:REGION

DATASEG_END

.CODE
extrn DoClickEvent:near
extrn DrawDashedXORBox:near
extrn DrawSolidXorBox:near
extrn FindRegionForControl:near
extrn PointAssociatedLegend:near
extrn ProtectOBK:near
extrn RetainOBKRightAndShow:near
extrn SetProtectionForControl:near
extrn ShowOBKForClick:near
extrn StartCursor:near
extrn StopCursor:near
extrn SetTextControl:near

DoTab proc near
 public DoTab


 mov wShortCutKey,0

DoTab1.

 mov wTabLoopCount,0

 mov wPenDownColumn,-1
 mov wPenDownRow,-1
 mov bPenEventHappened,0

 mov ax,pTabRegion
 or ax,ax
 jnz hat3
 mov wShortCutKey,0
 stc
 ret

hat3.
 call word ptr pTabHandler


hat1:


if NEED_ALTKEYS ne 0
 cmp si,pTabRegion
 jnz hat6
 push ax
 mov ax,wShortCutKey
 cmp ax,[si].wListItemIndex
 pop ax
 je hat2
 push pClickRegion
 mov pClickRegion,si
 call ShowTabBox
 pop pClickRegion
 clc
 ret
hat6:
 inc wTabLoopCount
 cmp wTabLoopCount,MAX_ACTIVE_CONTROLS
 jbe hat8
 stc
 ret
hat8:
 cmp wShortCutKey,0
 je hat1b
 push ax
 mov ax,wShortCutKey
 cmp ax,[si].wListItemIndex
 pop ax
 jnz hat3
 mov wShortCutKey,0
hat1b.
endif

 test [si].bListItemFlags,128
 jnz hat1a
 cmp [si].wCurrentHeight,-1
 jnz hat2
 test [si].bListItemFlags,2
 jnz hat2
hat1a:
 call word ptr pTabHandler
 jnc hat1c
 ret

hat1c:
 jmp hat1

hat2:
 push pClickRegion
 mov pClickRegion,si
 call ShowTabBox
 pop pClickRegion
 clc
 ret
DoTab endp

InitButton proc near
 public InitButton
```

```
 cmp al,FIRSTBUTTONTYPE
 jb lib1
 cmp al,LASTBUTTONTYPE
 ja lib1
 cmp ax,ax
lib1:
 ret
IsItButton endp

IsItCheckBox proc near
 public IsItCheckBox

 cmp al,CHECKBOX
 je lcb1
 cmp al,OPTIONBUTTON
lcb1:
 ret
IsItCheckBox endp

IsItEditBox proc near
 public IsItEditBox

 cmp al,FIRSTEDITBOXTYPE
 jb leb1
 cmp al,LASTEDITBOXTYPE
 ja leb1
 cmp ax,ax
leb1
 ret
IsItEditBox endp

IsItLegend proc near
 public IsItLegend
 cmp al,FIRSTLEGENDTYPE
 jb ll1
 cmp al,LASTLEGENDTYPE
 ja ll1
 cmp ax,ax
ll1
 ret
IsItLegend endp

IsItListBox proc near
 public IsItListBox

 cmp al,FIRSTLISTBOXTYPE
 jb ilb1
 cmp al,LASTLISTBOXTYPE
 ja ilb1
 cmp ax,ax
ilb1:
 ret
IsItListBox endp

IsItSlideBar proc near
 public IsItSlideBar
 cmp al,SLIDEBAR
 je lsb1
 cmp al,SPECTRUMBAR
lsb1:
 ret
IsItSlideBar endp

PointNextTabControl proc near
 public PointNextTabControl
 mov pOrgTabRegion,si
 jmp dlw2bb
dlw2b:
 cmp si,pOrgTabRegion
 jnz dlw2bb
 stc
 ret
dlw2bb:
 add si,size rActiveRegions
 cmp si,pOSKFirstRegion
 jae dlw2aa
 cmp si,pNextActiveRegion
 jb dlw2a

dlw2aa:
 mov si,offset rActiveRegions

dlw2a:
 call CheckSkipTab
 jnz dlw2b
 clc
 ret
PointNextTabControl endp

PointPreviousTabControl proc near
 public PointPreviousTabControl
pptc2:
 sub si,size rActiveRegions
 cmp si,offset rActiveRegions
 jae pptc1
 mov si,pNextActiveRegion
 sub si,size rActiveRegions
 cmp si,pOSKFirstRegion
 jb pptc1
 mov si,pOSKFirstRegion
 sub si,size rActiveRegions
pptc1:
 call CheckSkipTab
 jnz pptc2
 ret
PointPreviousTabControl endp

SetInitialTab proc near
 public SetInitialTab
 call FindRegionForControl
 jc sit1
 mov pClickRegion,bx
  push [bx].wCurrentTop
  pop rCursorRegion.wCurrentTop

 call DoClickEvent
sit1:
 ret
SetInitialTab endp

SetNewTabItem proc near
 public SetNewTabItem

 mov si,pClickRegion
 or si,si
 jz sntl1
 call SetNewTabItemWork
sntl1:
 ret
SetNewTabItem endp

SetNewTabItemWork proc near
 public SetNewTabItemWork
 or si,si
 jz dccd4
 call SetTabControl
SetNewTabItemWork1:
 public SetNewTabItemWork1
 push si
 mov si,[si].pCurrentControl
 call SetProtectionForControl
 mov bx,si
 pop si
 mov ax,[bx]

 call ISITEDITBOX
 jnz dccd4c
 push ax
  push wHotKeyRightPixel
  call ShowOSKForClick
  pop wHotKeyRightPixel
 call STARTCURSOR
 pop ax
if need_osk ne 0
endif
 jmp dccd4
dccd4c:

 call ISITLISTBOX
 jnz dccd4a
 call DrawDashedXORBox
 jmp dccd4
dccd4a:

 call ShowCommandButtonTabBox
 push bx
 mov bx,[si].pCurrentControl
 cmp [bx].ControlType,Toolbarbutton
 pop bx
 je dccd4
 call PointAssociatedLegend
 jnz dccd4
dccd4g:
 call DrawDashedXORBox
dccd4:

 ret
SetNewTabItemWork endp

SetTabControl proc near
 push si
 mov pTabRegion,si
 mov cx,type rTabRegion
 mov di,offset rTabRegion
 push ds
 pop es
 rep movsb
 pop si
 ret
SetTabControl endp

ShowCommandButtonTabBox proc near
 push bx
 push si
 mov bx,[si].pCurrentControl
 mov al,[bx]
 call ISITBUTTON
 jnz scbt1x
 cmp al,TOOLBARBUTTON
 je scbt1a
 cmp al,SYMBOLBUTTON
 je scbt1z
scbt1x:
 cmp al,closebutton
 jz scbt1q
 cmp al,aboutbutton
 jz scbt1q

 jmp scbt1
scbt1z:
 cmp bx,offset vobSlider
 jnz scbt4
 add [si].wCurrentTop,4
 sub [si].wCurrentBottom,4
 add [si].wCurrentLeft,8
 sub [si].wCurrentRight,4
 call DrawDashedXorBox
 add [si].wCurrentRight,4
 sub [si].wCurrentLeft,8
 add [si].wCurrentBottom,4
 sub [si].wCurrentTop,4
 jmp scbt1
scbt4:

 cmp bx,offset vobSeeking
 jb scbt2
 cmp bx,offset vobOnArrow
 ja scbt2
 jmp scbt1
scbt1r:
 mov cx,3
 mov dx,1
 jmp scbt1aa
scbt1q:
 mov cx,4
 mov dx,8
 jmp scbt1aa
scbt1a:
 mov cx,3
 mov dx,28
scbt1aa:
 xor ax,ax
 test [bx].ControlState,ISDOWN
 jz scbt2b
 inc ax
 inc ax
scbt2b:
 add cx,ax
 add dx,ax
 mov ax,-1

 jmp scbt2a
scbt2:

 mov cx,-1
 mov dx,0
 xor ax,ax
scbt2a:
 add [si].wCurrentTop,cx
 sub [si].wCurrentBottom,cx
 add [si].wCurrentLeft,dx
 sub [si].wCurrentRight,dx

 push dx
 push cx

 or ax,ax
 jz scbt5
 call DrawDashedXORBox
 jmp scbt6
scbt5:
 call DrawSolidXORBox
scbt6:
 pop cx
 pop dx
 sub [si].wCurrentTop,cx
 add [si].wCurrentBottom,cx
 sub [si].wCurrentLeft,dx
 add [si].wCurrentRight,dx

scbt1:
 pop si
 pop bx
 ret

ShowCommandButtonTabBox endp

ShowTabBox proc near
 public ShowTabBox

 push ax
 mov ax,pClickRegion
 cmp ax,pOSKFirstRegion
 pop ax
 jae stbx1
 call UndoCurrentTabItem
 call SetNewTabItem
 call HandleDelayedSet
stbx1:
 ret
ShowTabBox endp

UndoCurrentTabItem proc near
 public UndoCurrentTabItem


if need_osk ne 0
 call ProtectOSK
endif

 push si
 push di
 mov si,pTabRegion
 or si,si
 jz stb1
 push si
 call StopCursor
 call ShowCommandButtonTabBox
 pop si
stb3
 push si
 mov si,[si].pCurrentControl
 mov al,[si].ControlType
 pop si
 cmp al,Toolbarbutton
 je stb1
 call IsItListBox
 jz stb2

 call PointAssociatedLegend
 jnz stb1
stb2:
 call DrawDashedXORBox

stb1.
 pop di
 pop si
 ret
UndoCurrentTabItem endp

CheckSkipTab proc near
 push bx
 mov bx,[si].pCurrentControl
 cmp bModalFlag,0
 je cst1
 cmp bx,offset bmFirstModalForm
 jb cst2
cst1:
 mov bl,[bx].ControlState
 test bl,SKIPTAB or DISABLED or GRAYED
cst2:
 pop bx
 ret
CheckSkipTab endp

HandleDelayedSet proc near
 public HandleDelayedSet

 cmp pDelayedSetControl,0
 je hds1
 push ax
 push si
 cmp bMoveMode,0
 jnz hst2
 mov ax,pTabRegion
 cmp ax,pDelayedSetRegion
 jz hst2
 xor si,si
 xchg si,pDelayedSetControl
 call SetTextControl
 mov pDelayedSetControl,0
hst2:
 pop si
 pop ax
hds1:
 ret
HandleDelayedSet endp
END
```

Copr. 1996 Zenith Data Systems Corp.

```
________ equ 0
_______X equ 1
______X_ equ 2
______XX equ 3
```

```
_____X__ equ 4
_____X_X equ 5
_____XX_ equ 6
_____XXX equ 7
____X___ equ 8
____X__X equ 9
____X_X_ equ 10
____X_XX equ 11
____XX__ equ 12
____XX_X equ 13
____XXX_ equ 14
____XXXX equ 15
___X____ equ 16
___X___X equ 17
___X__X_ equ 18
___X__XX equ 19
___X_X__ equ 20
___X_X_X equ 21
___X_XX_ equ 22
___X_XXX equ 23
___XX___ equ 24
___XX__X equ 25
___XX_X_ equ 26
___XX_XX equ 27
___XXX__ equ 28
___XXX_X equ 29
___XXXX_ equ 30
___XXXXX equ 31
__X_____ equ 32
__X____X equ 33
__X___X_ equ 34
__X___XX equ 35
__X__X__ equ 36
__X__X_X equ 37
__X__XX_ equ 38
__X__XXX equ 39
__X_X___ equ 40
__X_X__X equ 41
__X_X_X_ equ 42
__X_X_XX equ 43
__X_XX__ equ 44
__X_XX_X equ 45
__X_XXX_ equ 46
__X_XXXX equ 47
__XX____ equ 48
__XX___X equ 49
__XX__X_ equ 50
__XX__XX equ 51
__XX_X__ equ 52
__XX_X_X equ 53
__XX_XX_ equ 54
__XX_XXX equ 55
__XXX___ equ 56
__XXX__X equ 57
__XXX_X_ equ 58
__XXX_XX equ 59
__XXXX__ equ 60
__XXXX_X equ 61
__XXXXX_ equ 62
__XXXXXX equ 63
_X______ equ 64
_X_____X equ 65
_X____X_ equ 66
_X____XX equ 67
_X___X__ equ 68
_X___X_X equ 69
_X___XX_ equ 70
_X___XXX equ 71
_X__X___ equ 72
_X__X__X equ 73
_X__X_X_ equ 74
_X__X_XX equ 75
_X__XX__ equ 76
_X__XX_X equ 77
_X__XXX_ equ 78
_X__XXXX equ 79
_X_X____ equ 80
_X_X___X equ 81
_X_X__X_ equ 82
_X_X__XX equ 83
_X_X_X__ equ 84
_X_X_X_X equ 85
_X_X_XX_ equ 86
_X_X_XXX equ 87
_X_XX___ equ 88
_X_XX__X equ 89
_X_XX_X_ equ 90
_X_XX_XX equ 91
_X_XXX__ equ 92
_X_XXX_X equ 93
_X_XXXX_ equ 94
_X_XXXXX equ 95
_XX_____ equ 96
_XX____X equ 97
_XX___X_ equ 98
_XX___XX equ 99
_XX__X__ equ 100
_XX__X_X equ 101
_XX__XX_ equ 102

_XX__XXX equ 103
_XX_X___ equ 104
_XX_X__X equ 105
_XX_X_X_ equ 106
_XX_X_XX equ 107
_XX_XX__ equ 108
_XX_XX_X equ 109
_XX_XXX_ equ 110
_XX_XXXX equ 111
_XXX____ equ 112
_XXX___X equ 113
_XXX__X_ equ 114
_XXX__XX equ 115
_XXX_X__ equ 116
_XXX_X_X equ 117
_XXX_XX_ equ 118
_XXX_XXX equ 119
_XXXX___ equ 120
_XXXX__X equ 121
_XXXX_X_ equ 122
_XXXX_XX equ 123
_XXXXX__ equ 124
_XXXXX_X equ 125
_XXXXXX_ equ 126
_XXXXXXX equ 127
X_______ equ 128
X______X equ 129
X_____X_ equ 130
X_____XX equ 131
X____X__ equ 132
X____X_X equ 133
X____XX_ equ 134
X____XXX equ 135
X___X___ equ 136
X___X__X equ 137
X___X_X_ equ 138
X___X_XX equ 139
X___XX__ equ 140
X___XX_X equ 141
X___XXX_ equ 142
X___XXXX equ 143
X__X____ equ 144
X__X___X equ 145
X__X__X_ equ 146
X__X__XX equ 147
X__X_X__ equ 148
X__X_X_X equ 149
X__X_XX_ equ 150
X__X_XXX equ 151
X__XX___ equ 152
X__XX__X equ 153
X__XX_X_ equ 154
X__XX_XX equ 155
X__XXX__ equ 156
X__XXX_X equ 157
X__XXXX_ equ 158
X__XXXXX equ 159
X_X_____ equ 160
X_X____X equ 161
X_X___X_ equ 162
X_X___XX equ 163
X_X__X__ equ 164
X_X__X_X equ 165
X_X__XX_ equ 166
X_X__XXX equ 167
X_X_X___ equ 168
X_X_X__X equ 169
X_X_X_X_ equ 170
X_X_X_XX equ 171
X_X_XX__ equ 172
X_X_XX_X equ 173
X_X_XXX_ equ 174
X_X_XXXX equ 175
X_XX____ equ 176
X_XX___X equ 177
X_XX__X_ equ 178
X_XX__XX equ 179
X_XX_X__ equ 180
X_XX_X_X equ 181
X_XX_XX_ equ 182
X_XX_XXX equ 183
X_XXX___ equ 184
X_XXX__X equ 185
X_XXX_X_ equ 186
X_XXX_XX equ 187
X_XXXX__ equ 188
X_XXXX_X equ 189
X_XXXXX_ equ 190
X_XXXXXX equ 191
XX______ equ 192
XX_____X equ 193
XX____X_ equ 194
XX____XX equ 195
XX___X__ equ 196
XX___X_X equ 197
XX___XX_ equ 198
XX___XXX equ 199
XX__X___ equ 200
XX__X__X equ 201

XX__X_X_ equ 202
XX__X_XX equ 203
XX__XX__ equ 204
XX__XX_X equ 205
XX__XXX_ equ 206
XX__XXXX equ 207
XX_X____ equ 208
XX_X___X equ 209
XX_X__X_ equ 210
XX_X__XX equ 211
XX_X_X__ equ 212
XX_X_X_X equ 213
XX_X_XX_ equ 214
XX_X_XXX equ 215
XX_XX___ equ 216
XX_XX__X equ 217
XX_XX_X_ equ 218
XX_XX_XX equ 219
XX_XXX__ equ 220
XX_XXX_X equ 221
XX_XXXX_ equ 222
XX_XXXXX equ 223
XXX_____ equ 224
XXX____X equ 225
XXX___X_ equ 226
XXX___XX equ 227
XXX__X__ equ 228
XXX__X_X equ 229
XXX__XX_ equ 230
XXX__XXX equ 231
XXX_X___ equ 232
XXX_X__X equ 233
XXX_X_X_ equ 234
XXX_X_XX equ 235
XXX_XX__ equ 236
XXX_XX_X equ 237
XXX_XXX_ equ 238
XXX_XXXX equ 239
XXXX____ equ 240
XXXX___X equ 241
XXXX__X_ equ 242
XXXX__XX equ 243
XXXX_X__ equ 244
XXXX_X_X equ 245
XXXX_XX_ equ 246
XXXX_XXX equ 247
XXXXX___ equ 248
XXXXX__X equ 249
XXXXX_X_ equ 250
XXXXX_XX equ 251
XXXXXX__ equ 252
XXXXXX_X equ 253
XXXXXXX_ equ 254
XXXXXXXX equ 255
Copr. 1996 Zenith Data Systems Corp.
NEED_ABOUTICON equ 1
NEED_OSK equ 1
NEED_TSR equ 1
NEED_GETSET equ 1
NEED_EDIT equ 1
NEED_LISTS equ 1
NEED_ALTKEYS equ 0
NEED_CRITICAL equ 0
DIAMOND_OPTBUTTONS equ 1
CHECKMARK_CHECKBOXES equ 1

PENDRIVER_INTERRUPT equ 07h
SM_FUNCTION_INTERRUPT equ 60h

MAX_TOOLBARBUTTONS equ 9
PIXELS_PER_NOTCH equ 24
NOTCH_COUNT equ 8
MAXMESSAGELINE = 320
PROGRESS_MAXLEN equ 30

MB_ABOUT equ 1
MB_CREDITS equ 2
MB_CALIBRATEULC equ 3
MB_CALIBRATELRC equ 4
MB_REBOOT equ 5
MB_UPGRADE equ 6
MB_UPGRADE_PROGRESS equ 7
MB_UPGRADE_COMPLETE equ 8
MB_NOUPGRADE equ 9
MB_SHOWCALLPROGRESS equ 10

SM_ABORT_REQUEST_CONNECTION equ 24h
SM_BLOCK_VIDEO_ACCESS equ 50h
SM_CALIBRATE_LOWERRIGHT equ 000Ch
SM_CALIBRATE_UPPERLEFT equ 0ah
SM_CANCEL_CALIBRATION equ 00eh
SM_GET_ABOUT_DIALOG equ 003h
SM_GET_CONNECTION_STATUS equ 22h
SM_GET_HOST_LIST_STATUS equ 21h
SM_GET_INITIAL_SCREEN equ 0001bh
SM_GET_KEYBOARD_STATUS equ 062h
SM_GET_MODEM_DEFAULTS equ 38h

SM_GET_NEXT_CREDITS_DIALOG equ 04h
SM_GET_PASSWORD_STATUS equ 25h
SM_GET_USER_INTERFACE_LANGUAGE equ
06Fh
SM_PERFORM_FLASH_UPDATE equ 13h
SM_REBOOT_HOST equ 011h
SM_REPORT_BUTTON_CLICKED equ 0060H
SM_REQUEST_ACTIVE_FLASH_UPGRADE equ
12h
SM_REQUEST_CONNECTION equ 23h
SM_REQUEST_DISCONNECTION equ 0023h
SM_REQUEST_UNLOAD equ 00063h
SM_SET_ACTIVE_STATUS equ 060h
SM_GET_KEYSTROKE equ 061h
SM_UNBLOCK_VIDEO_ACCESS equ 0050h
SM_UPDATE_DIMENSIONS equ 063h
SM_UPDATE_HOST_LIST equ 20h
SM_NOTIFY_NEW_SETUP equ 00eh

UI_CALIBRATION_COMPLETE equ 0Dh
UI_FLASH_UPDATE_PERCENTAGE equ 14h
UI_GET_SM_VERSION_NUMBER equ 00h
UI_HIDE_MESSAGE_BOX equ 065h
UI_MOVE_OSK equ 000h
UI_REQUEST_CLOSURE equ 063h
UI_REQUEST_DISPLAY equ 061h
UI_SHOW_MESSAGE_BOX equ 064h
UI_UPDATE_CONNECTION_STATUS equ 030h
UI_SHOW_HIDE_BUSY_CURSOR equ 066h

RES_NO_SCREEN        EQU 0
RES_OSK_ALPHA        EQU 1
RES_OSK_NUM          EQU 2
RES_OSK_FULL         EQU 3
RES_OSK_BIG          EQU 4
RES_OSK_BIG_ALPHA    EQU 5
RES_OSK_BIG_NUM      EQU 6
RES_OSK_BIG_FULL     EQU 7
RES_SETUPS_HOST      EQU 1*8
RES_SETUPS_HOTKEYS   EQU 2*8
RES_SETUPS_MAINTENANCE EQU 3*8
RES_SETUPS_MODEM     EQU 4*8
RES_SETUPS_POWER     EQU 5*8
RES_SETUPS_SCREEN    EQU 6*8

GETSET_AUTOMATIC_SHUTOFF        equ 0Ah
GETSET_BRIGHTNESS               equ 08h
GETSET_CONTRAST                 equ 0ah
GETSET_CUSTOM_AUTOANSWER_STRING equ
36h
GETSET_CUSTOM_CONNECT_STRING    equ 38h
GETSET_CUSTOM_DISCONNECT_STRING equ
37h
GETSET_CUSTOM_INIT_STRING       equ 030h
GETSET_OSK_HOST_SCREEN          equ 0AAh
GETSET_DOMAIN_ID                equ 07h
GETSET_HOST_CONNECTION_TYPE     equ 03ah
GETSET_LOCK_HOST_KEYBOARD       equ 00h
GETSET_MODEM_ANSWER_ON_RING     equ
032h
GETSET_MODEM_BAUD_RATE_ENTRY    equ
20h
GETSET_MODEM_HOST_DESC_ENTRY    equ
28h
GETSET_MODEM_HOST_PHONE_ENTRY   equ
27h
GETSET_MODEM_MANUFACTURER_ENTRY equ
26h
GETSET_MODEM_PREFIX             equ 030h
GETSET_MODEM_RETRY_DELAY        equ 034h
GETSET_MODEM_RETRY_LIMIT        equ 033h
GETSET_MODEM_SUFFIX             equ 031h
GETSET_MODEM_TONE_OR_PULSE      equ 02h
GETSET_NETWORK_GROUP_ENTRY      equ 2ah
GETSET_NETWORK_HOST_ENTRY       equ 2bh
GETSET_PASSWORD                 equ 03ah
GETSET_SECURITY_ID              equ 08h
GETSET_SLEEPMODE_PERIOD         equ 09h
GETSET_USER_DEFINED_HOT_ICON    equ 06h
GETSET_USER_ID                  equ 03ah
GETSET_FRAME_TYPE_ENTRY         equ 2eh

global AboutIconStyle
global ColoredAboutIconStyle

HLINE16X3       equ 33
VLINE2X04       equ 35
CONTRAST_ICON   equ 36
BRIGHTNESS_ICON equ 37
SLEEP_ICON      equ 38
ABOUT_ICON      equ 39
BIG_X_ICON      equ 40
BIG_CRUZER      equ 41
HOST_ICON       equ 42
HOTKEY_ICON     equ 43
MAINT_ICON      equ 44
MODEM_ICON      equ 45
POWER_ICON      equ 46
SCREEN_ICON     equ 47
```

```
HAND1_ICON      equ 48
HAND2_ICON      equ 49
SMALL_CRUZER    equ 50
HIBERNATE_ICON  equ 51
SMALL_ABOUT     equ 52
CALIBRATION_X   equ 53

SPACEBAR_ICON   equ 62

Copr 1996 Zenith Data Systems Corp

SM_TEST_FUNCTION equ 0FFFFh
MB_LEFTJUSTIFIED equ 0
MB_CENTERED equ 1
MB_RIGHTJUSTIFIED equ 2

UPARROWBITMAP   equ 33
DNARROWBITMAP   equ 34

FULL_KEYBOARD_ICON equ 35
SMALL_KEYBOARD_ICON equ 36
REDUCE_KEYBOARD_ICON equ 37
KEYBOARD_EXIT_ICON equ 38
ESC_KEY equ 39
F1_KEY equ 40
F2_KEY equ 41
F3_KEY equ 42
F4_KEY equ 43
F5_KEY equ 44
F6_KEY equ 45
F7_KEY equ 46
F8_KEY equ 47
F9_KEY equ 48
F10_KEY equ 49
F11_KEY equ 50
F12_KEY equ 51
PRT_KEY equ 52
SLK_KEY equ 53
PSE_KEY equ 54
BREAK_KEY equ 55
SYSREQ_KEY equ 56
BS_KEY equ 57
INS_KEY equ 58
HM_KEY equ 59
PGUP_KEY equ 60
NLK_KEY equ 61
TAB_KEY equ 62
DEL_KEY equ 63
END_KEY equ 64
PGDN_KEY equ 65
UA_KEY equ 66
CAPS_KEY equ 67
ENTER_KEY equ 68
LA_KEY equ 69
RA_KEY equ 70
SHIFT_KEY equ 71
ALT_KEY equ 72
CTRL_KEY equ 73
DA_KEY equ 74
SNT_KEY equ 75
LEFT_BRAKET_KEY equ 76
RIGHT_BRAKET_KEY equ 77
GRAPHIC_SPACER equ 78
NUM_KEYBOARD_ICON equ 79
ENLARGE_KEYBOARD_ICON equ 80
PLUS_KEY equ 81

BUTTONTOPHEIGHT equ 3
BUTTONBOTTOMHEIGHT equ 3
BUTTONLEFTPIXELS equ 8
BUTTONRIGHTPIXELS equ 8
TITLEBARHEIGHT equ 32

RESET_PEN_DRIVER      equ 00h
DISPLAY_PEN_CURSOR    equ 01h
REMOVE_PEN_CURSOR     equ 02h
SET_PEN_EVENT_HANDLER = 20h
GET_CURSOR_HOTSPOT    equ 3Ah

PEN_FUNCTION equ 33h
PEN_ACTIVATE_FUNCTION = 07h

PENMOVED    equ 1
PENDOWN     equ 2
PENUP       equ 4

FORM_COLOR equ gray
SHADOW_COLOR equ darkgray
OUTLINE_COLOR equ black
LIGHT_COLOR equ white

TEXTMODE_KEY_UP_COLOR equ 112
TEXTMODE_KEY_DOWN_COLOR equ 32
```

```
WITHBACKCOLOR equ 16
LEFTJUSTIFIED equ 32
CENTERED      equ 64
RIGHTJUSTIFIED equ 128

LEFT_ARROW_SCAN_CODE   equ 75
RIGHT_ARROW_SCAN_CODE  equ 77
DEL_SCAN_CODE          equ 83
HOME_SCAN_CODE         equ 71
END_SCAN_CODE          equ 79
UP_ARROW_SCAN_CODE     equ 72
DOWN_ARROW_SCAN_CODE   equ 80

BACKSPACE_SCAN_CODE    equ 14

SHIFTTABKEY   equ 0F00h
BACKSPACE     equ 8
TABKEY        equ 9

PAINTALL      equ 255
PAINTTOOLBARS equ 2
PAINTFORMS    equ 4
MAX_ACTIVE_CONTROLS equ 220

NORMSTATE     equ 0
GRAYED        equ 1
SIOPTAB       equ 2
DISABLED      equ 4
INVISIBLE     equ 8
ISDOWN        equ 16
WIDEN         equ 32
MOVEABLE      equ 64
COMPENSATE    equ 64
BACKFILL      equ 128
DOUBLEWIDEN   equ 128
EXPLICITSIZE  equ 128

TOOLBAR       equ 1
FORM          equ 2
DIALOGBOX     equ 3
FRAME         equ 4
GROUPBOX      equ 5

ENDFRAME      equ 6
ENDDIALOGBOX  equ 7
ENDFORM       equ 8
ENDTOOLBAR    equ 9
ENDTOOLBARBUTTON equ 10
ENDOFOBJECT   equ 11

FIRST_ENDOFOBJECT equ ENDFRAME
LAST_ENDOFOBJECT equ ENDOFOBJECT

COMMANDBUTTON equ 12
CANCELBUTTON  equ 13
TOOLBARBUTTON equ 14
SYMBOLBUTTON  equ 15
SPINUPBUTTON  equ 16
SPINDOWNBUTTON equ 17

CLOSEBUTTON   equ 18
ABOUTBUTTON   equ 19
KEYBUTTON     equ 20

RSHIFTKEYBUTTON equ 21
LSHIFTKEYBUTTON equ 22
CTRLKEYBUTTON   equ 23
ALTKEYBUTTON    equ 24
SCROLLLOCKBUTTON equ 25
NUMLOCKBUTTON   equ 26
CAPSLOCKBUTTON  equ 27

FIRSTBUTTONTYPE equ COMMANDBUTTON
LASTBUTTONTYPE equ CAPSLOCKBUTTON

FIRSTFOCUSABLEBUTTONTYPE equ
COMMANDBUTTON
LASTFOCUSABLEBUTTONTYPE equ
TOOLBARBUTTON

FIRSTKEYTYPE equ KEYBUTTON
LASTKEYTYPE equ CAPSLOCKBUTTON

CHECKBOX      equ 28
OPTIONBUTTON  equ 29

EDITBOX       equ 30
UCEDITBOX     equ 31
PWEDITBOX     equ 32
NUMEDITBOX    equ 33
KEYEDITBOX    equ 34
UNFRAMEDEDITBOX equ 35
```

```
FIRSTEDITBOXTYPE equ EDITBOX
LASTEDITBOXTYPE equ UNFRAMEDEDITBOX

LISTBOX       equ 36
LISTBOXNOSCROLL equ 37
SPINBUTTON    equ 38

FIRSTLISTBOXTYPE equ LISTBOX
LASTLISTBOXTYPE equ LISTBOXNOSCROLL

VSCROLLBAR    equ 39
SLIDEBAR      equ 40
SPECTRUMBAR   equ 41
PROGRESSBAR   equ 42

FIRSTSCROLLBARTYPE equ VSCROLLBAR
LASTSCROLLBARTYPE equ PROGRESSBAR

TITLEBAR      equ 43

LEFTLEGEND    equ 44
CENTEREDLEGEND equ 45
RIGHTLEGEND   equ 46

CHISELBOX     equ 47

LINEBOX       equ 48
ICON          equ 49
SUNKENFRAME   equ 50

FIRSTLEGENDTYPE equ LEFTLEGEND
LASTLEGENDTYPE equ RIGHTLEGEND

NORMFONT      equ 0
SMALLFONT     equ 32
BIGFONT       equ 64
GRAPHICFONT   equ 32+64
ANYFONT       equ 32+64

ENGLISH_LANGUAGE equ 0
FRENCH_LANGUAGE equ 1
GERMAN_LANGUAGE equ 2

NORMFONT equ 0
SMALLFONT equ 32
BIGFONT equ 64
GRAPHICFONT equ 32+64

VGA_MODE equ 12h
VGASEGMENT =0A000h
SCREEN_HEIGHT_PIXELS =480
SCREEN_WIDTH_BYTES =80
SCREEN_WIDTH_PIXELS = 640

SAMETOP       equ 4000
NEXTTOP       equ 4000+1024
SAMEFRAMETOP  equ 4000+1024*2
NEXTFRAMETOP  equ 4000+1024*3
NEXTTOP50     equ 4000+1024*4

PRIORFLAG     equ 8000h
PRIORPRIORFLAG equ 0C000h

SAMELEFT      equ 4000
NEXTLEFT      equ 8192
NEXTFRAMELEFT equ 4000+8192
FROMRIGHT     equ 16384

SAMEHIGH      equ 0

H100          equ 1200
H100TEXTHEIGHT equ 8
H100VGAHEIGHT equ 38
H180          equ 2000
H180TEXTHEIGHT equ 16
H180VGAHEIGHT equ 33
H200          equ 2400
H200TEXTHEIGHT equ 18
H200VGAHEIGHT equ 40
H333          equ 4000
H333TEXTHEIGHT equ 32
H333VGAHEIGHT equ 64

H60           equ 8000h
H60TEXTHEIGHT equ 8
H60VGAHEIGHT equ 8

SAMEWIDE      equ 0
W100          equ 1200
W200          equ 2400
W300          equ 3600

MBS_OK        equ 001h
MBS_CANCEL    equ 002h
MBS_ABORT     equ 004h
MBS_RETRY     equ 008h
```

```
MBS_IGNORE equ 010h
MBS_YES    equ 020h
MBS_NO     equ 040h

MBX_NOBUTTON equ 0
MBX_OK      equ MBS_OK
MBX_CANCEL  equ MBS_CANCEL
MBX_OKCANCEL equ MBS_OK or MBS_CANCEL
MBX_ABORTRETRYIGNORE equ MBS_ABORT or
MBS_RETRY or MBS_IGNORE
MBX_YESNOCANCEL equ MBS_YES or MBS_NO
or MBS_CANCEL
MBX_YESNORETRY equ MBS_YES or MBS_NO or
MBS_RETRY
MBX_YESNO equ MBS_YES or MBS_NO
MBX_RETRYCANCEL equ MBS_RETRY or
MBS_CANCEL

R_SHIFT_DOWN equ 1
L_SHIFT_DOWN equ 2
CTRL_DOWN equ 4
ALT_DOWN equ 8
SCROLL_LOCK_DOWN equ 16
NUM_LOCK_DOWN equ 32
CAPS_LOCK_DOWN equ 64
INS_STATE_ACTIVE equ 128

BLACK      equ 0
BLUE       equ 1
GREEN      equ 2
CYAN       equ 3
RED        equ 4
MAGENTA    equ 5
BROWN      equ 6
GRAY       equ 7
DARKGRAY   equ 8
LT_BLUE    equ 9
LT_GREEN   equ 10
LT_CYAN    equ 11
LT_RED     equ 12
LT_MAGENTA equ 13
YELLOW     equ 14
WHITE      equ 15

Copr. 1996 Zenith Data Systems Corp.
ifndef MAJOR_VERSION
.code
extrn CheckListDataAvailable:far
extrn CheckScreenUpdateNeeded:far
extrn DisinstallInt09:far
extrn DoAfterRepaintingList:far
extrn DoBeforeRepaintingForm:far
extrn DoCustomControlPenDown:far
extrn DoCustomEvents:far
extrn DoCustomListPenUp:far
extrn DoCustomStartups:far
extrn DoCustomTimerProcedures:far
extrn DoHotKeyEdit:far
extrn DoNUFunction:far
extrn DoToolBarButtonClick:far
extrn DrawAboutIcon:far
extrn GetCustomEditBoxContents:far
extrn GetCustomPopupRequest:far
extrn HandleButtonClicks:far
extrn HandleMessageBoxClick:far
extrn RepaintCustomEditBoxContents:far
extrn TryUnload:far
endif
Copr. 1995 Zenith Data Systems Corp.
include siforest.inc

DATASEG_BEGIN macro
UIDATA segment public 'data'
assume ds:UIDATA
ENDM

DATASEG_END macro
UIDATA ends
endm
CURDATASEG EQU UIDATA

include sicustom.inc
include sirequste.inc
include sistruce.inc
include simacros.inc

Copr. 1996 Zenith Data Systems Corp

NEXTSTORAGE = offset ControlDataStorageArea
TOTALSTORAGE = 0
NEXTCONTROL = 1
FRAMETOP = 0
```

```
FRAMELEFT = 0

SM_FUNCTION macro fnum
  mov ax,fnum
  call far ptr DoSMFunction
endm

ROUND_TO_BYTE_BOUNDARY macro r
 sar r,1
 sar r,1
 sar r,1
 sal r,1
 sal r,1
 sal r,1
endm

DIVIDE_BY_8 macro r
 sar r,1
 sar r,1
 sar r,1
endm

TEXTMODEINIT macro
  mov ax,0003h
  int 10h
endm

DEBUGGER macro
   push ax
   push ax
    textmodeinit
   pop ax
   pop ax
   int 3
endm

CLEAR_RECTANGLE macro
CLX,CTop,CWh,CHt,Colr
  mov cx,CLX
  mov dx,CTop
  mov si,CWh
  mov ax,CHt
  mov bh,Colr
  call FillScreenArea
endm


vgainit macro
  mov ax,VGA_MODE
  int 10h
endm

vgaloadlatches macro
  mov dx,3ceh
  mov ax,0305h
  out dx,ax
  mov ax,0003h
  out dx,ax
endm

VGASETXOR macro
  mov dx,3ceh
  mov ax,0705h
  out dx,ax
  mov ax 0003h or (00011000b * 256)
  out dx,ax
endm

vgawritecolor macro colr
  mov ah,al
  mov al,0
  out dx,ax
  mov al,colr
  mov es:[di],al
endm


ENGLISH macro
LANGUAGE=ENGLISH_LANGUAGE
endm

FRENCH macro
LANGUAGE=FRENCH_LANGUAGE
endm

GERMAN macro
LANGUAGE=GERMAN_LANGUAGE
endm

ADJUST_FORM_HEIGHT MACRO NewHeight
CURRENTLOCATION=$
org CURRENTFORM + PixelHeight
  dw NewHeight + FRAMETOP
org CURRENTLOCATION
endm


ADJUST_FORM_WIDTH MACRO NewWidth
CURRENTLOCATION=$
org CURRENTFORM + PixelWidth
  dw NewWidth + FRAMELEFT
org CURRENTLOCATION
endm


ADJUST_FRAME_WIDTH macro NewWidth
CURRENTLOCATION=$
org CURRENTFRAME + PixelWidth
  dw NewWidth
org CURRENTLOCATION
endm

ADJUST_TOOLBAR_WIDTH MACRO NewWidth
CURRENTLOCATION=$
org CURRENTTOOLBAR + PixelWidth
  dw NewWidth
org CURRENTLOCATION
endm

MAKE_CAPTION_STRUCTURE macro CaptionText
CAPTION_END_POINTER=$
 dw 0
 db CaptionText
 db 0
 dw THIS_CAPTION_START
 db 254
THIS_CAPTION_END=$
org CAPTION_END_POINTER
dw THIS_CAPTION_END
org THIS_CAPTION_END
LANGUAGE=0
endm

GRAPHIC_CAPTION macro CaptionText
THIS_CAPTION_START=$
 db 128 or GRAPHICFONT
 MAKE_CAPTION_STRUCTURE CaptionText
endm

CAPTION macro CaptionText
THIS_CAPTION_START=$
 db 128 or LANGUAGE or FONT
 MAKE_CAPTION_STRUCTURE CaptionText
endm


TEXTMODE_CAPTION macro tmstring
THIS_MISC_ITEM_START =$
 db 128 or 16 or 1
MISC_ITEM_END_POINTER=$
 dw 0
 db tmstring
 db 0
 dw THIS_MISC_ITEM_START
 db 253
THIS_MISC_ITEM_END=$
org MISC_ITEM_END_POINTER
dw THIS_MISC_ITEM_END
org THIS_MISC_ITEM_END
endm

SETTAB macro tabstop
THIS_MISC_ITEM_START =$
 db 128 or 16 or 3
MISC_ITEM_END_POINTER=$
 dw 0
 dw tabstop
 dw 0
 dw THIS_MISC_ITEM_START
 db 252
THIS_MISC_ITEM_END=$
org MISC_ITEM_END_POINTER
dw THIS_MISC_ITEM_END
org THIS_MISC_ITEM_END
endm


SETWIDTHS macro
graphwidth,textwidth,agraphwidth,atextwidth
THIS_MISC_ITEM_START =$
 db 128 or 16 or 3
MISC_ITEM_END_POINTER=$
 dw 0
 dw graphwidth
 dw textwidth
 dw agraphwidth
 dw atextwidth
 dw THIS_MISC_ITEM_START
 db 251
THIS_MISC_ITEM_END=$
org MISC_ITEM_END_POINTER
dw THIS_MISC_ITEM_END
org THIS_MISC_ITEM_END
endm

CONTROL macro
CTyp,CSta,CLX,CTop,CWI,CHI,CLen

STOREOFF = NEXTSTORAGE
if (CTyp eq CHECKBOX ) or (CTyp eq
OPTIONBUTTON )
  STORESZ = 1
elseif (CTyp ge FIRSTLISTBOXTYPE) and (CTyp le
LASTLISTBOXTYPE)
  STORESZ = 0
  STOREOFF=0
elseif (CTyp ge FIRSTEDITBOXTYPE) and (CTyp le
LASTEDITBOXTYPE)
  STORESZ = CLen + 1
elseif (CTyp ge FIRSTSCROLLBARTYPE) and
(CTyp le
LASTSCROLLBARTYPE)
  STORESZ = 1
else
  STORESZ = 0
endif
 CURRENTCONTROL=$
 %CONTROL
 <CTyp,CSta,NEXTCONTROL,CLX,CTop,CWI,CHI,S
TORESZ,STOREOFF,0FFh>
 NEXTCONTROL=0
 FONT=NORMFONT
 LANGUAGE=0

SAMESTATE=CSta
SAMELEN=CLen
 NEXTSTORAGE = NEXTSTORAGE + STORESZ
 TOTALSTORAGE = TOTALSTORAGE +
STORESZ
endm


BEGIN_FORM_DEFINITIONS MACRO
 db 0
endm

END_FORM_DEFINITIONS MACRO
 db 0
endm


BEGIN_TOOLBAR macro CSta,CLX,CTop,CWI,CHI
CURRENTTOOLBAR=$
 CONTROL TOOLBAR,CSta,CLX,CTop,CWI,CHI,0
TBBOTTOM=CTop+CHI
TBLEFT=CLX
TBWIDE=CWI
endm

BEGIN_TOOLBARBUTTON macro
CSta,CLX,CTop,CWI,CHI
 CONTROL
TOOLBARBUTTON,CSta,CLX,CTop+TITLEBARHEI
GHT,CWI,CHI,0
 TBSNEXTLEFT=CLX+CWI
 TBSSAMETOP=CTop
 TBSSAMEHIGH=CHI
 TBSSAMEWIDE=CWI
endm

BEGIN_FORM macro
 CURRENTFORM=$
 CONTROL FORM,0,0,0,0,0,0
endm

BEGIN_GROUPBOX macro
CSta,CLX,CTop,CWI,CHI
 CONTROL
GROUPBOX,CSta,CLX,CTop,CWI,CHI,0
endm


BEGIN_FRAME macro CSta,CLX,CTop,CWI,CHI
 FRAMETOP=CTop
 FRAMELEFT=CLX
 CURRENTFRAME=$
 CONTROL FRAME,CSta,CLX,CTop,CWI,CHI,0
endm

END_FORM macro
 CONTROL ENDFORM,0,0,0,0,0,0
endm

END_TOOLBARBUTTON macro
 CONTROL ENDTOOLBARBUTTON,0,0,0,0,0,0
endm

END_GROUPBOX macro
 CONTROL ENDOFOBJECT,0,0,0,0,0,0
endm

END_FRAME macro
 FRAMETOP=0
 FRAMELEFT=0
 CONTROL ENDFRAME,0,0,0,0,0,0
endm

END_TOOLBAR macro
 CONTROL ENDTOOLBAR ,0,0,0,0,0,0
endm

MAKE_UNFRAMED_EDITBOX macro
CSta,CLX,CTop,CWI,CHI,CLen
  CONTROL
UNFRAMEDEDITBOX,CSta,CLX,CTop,CWI,CHI,CLe
n
endm

MAKE_PW_EDITBOX macro
CSta,CLX,CTop,CWI,CHI,CLen
  CONTROL
PWEDITBOX CSta,CLX,CTop,CWI,CHI,CLen
endm

MAKE_KEY_EDITBOX macro
CSta,CLX,CTop,CWI,CHI
  CONTROL
KEYEDITBOX,CSta,CLX,CTop,CWI,CHI,0

endm

MAKE_NUM_EDITBOX macro
CSta,CLX,CTop,CWI,CHI,CLen
  CONTROL
NUMEDITBOX,CSta,CLX,CTop,CWI,CHI,CLen
endm

MAKE_EDITBOX macro
CSta,CLX,CTop,CWI,CHI,CLen
  CONTROL
EDITBOX,CSta CLX,DTop,CWI,CHI,CLen
endm

MAKE_COMMANDBUTTON macro
CSta,CLX,CTop,CWI,CHI
  CONTROL
COMMANDBUTTON CSta,CLX,CTop,CWI,CHI,0
endm

MAKE_SYMBOLBUTTON macro
CSta,CLX,CTop,CWI,CHI
  CONTROL
SYMBOLBUTTON,CSta,CLX,CTop,CWI,CHI,0
endm

MAKE_SPINUPBUTTON macro
CSta,CLX,CTop,CWI,CHI
  CONTROL
SPINUPBUTTON,CSta,CLX,CTop,CWI,CHI,0
endm

MAKE_SPINDOWNBUTTON macro
CSta,CLX,CTop,CWI,CHI
  CONTROL
SPINDOWNBUTTON,CSta,CLX,CTop,CWI,CHI,0
endm

MAKE_ABOUTBUTTON macro
CSta,CLX,CTop,CWI,CHI
  CONTROL
ABOUTBUTTON,CSta,CLX,CTop,CWI,CHI,0
endm

make_closebutton macro CSta,CLX,CTop,CWI,CHI
  control
CLOSEBUTTON,CSta,CLX,CTop,CWI,CHI,0
endm

MAKE_KEYBUTTON macro
CSta,CLX,CTop,CWI,CHI
  CURRENTKEY=$
  CONTROL
KEYBUTTON,CSta,CLX,CTop,CWI,CHI,0
endm

MAKE_LSHIFTKEYBUTTON macro
CSta,CLX,CTop,CWI,CHI
  CURRENTKEY=$
  CONTROL
LSHIFTKEYBUTTON,CSta,CLX,CTop,CWI,CHI,0
endm

MAKE_RSHIFTKEYBUTTON macro
CSta,CLX,CTop,CWI,CHI
  CURRENTKEY=$
  CONTROL
RSHIFTKEYBUTTON,CSta,CLX,CTop,CWI,CHI,0
endm

MAKE_CTRLKEYBUTTON macro
CSta,CLX,CTop,CWI,CHI
  CURRENTKEY=$
  CONTROL
CTRLKEYBUTTON,CSta,CLX,CTop,CWI,CHI,0
endm
```

```
MAKE_ALTKEYBUTTON macro
CSta,CL8,CTop,CWI,CHt
  CURRENTKEY=6
  CONTROL
ALTKEYBUTTON,CSta,CL8,CTop,CWI,CHI,0
endm

MAKE_CAPSLOCKBUTTON macro
CSta,CL8,CTop,CWI,CHI
  CURRENTKEY=8
  CONTROL
CAPSLOCKBUTTON,CSta,CL8,CTop,CWI,CHI,0
endm

MAKE_NUMLOCKBUTTON macro
CSta,CL8,CTop,CWI,CHI
  CURRENTKEY=6
  CONTROL
NUMLOCKBUTTON,CSta,CL8,CTop,CWI,CHI,0
endm

MAKE_SCROLLLOCKBUTTON macro
CSta,CL8,CTop,CWI,CHI
  CURRENTKEY=0
  CONTROL
SCROLLLOCKBUTTON,CSta,CL8,CTop,CWI,CHI,0
endm

MAKE_CHECKBOX macro CSta,CL8,CTop
  CONTROL CHECKBOX,CSta,CL8,CTop,16,16,0
endm

MAKE_OPTIONBUTTON macro CSta,CL8,CTop
  CONTROL
OPTIONBUTTON,CSta,CL8,CTop,16,16,0
endm

MAKE_LEFTLEGEND macro CSta,CL8,CTop
  CONTROL LEFTLEGEND,CSta,CL8,CTop,0,0,0
endm

MAKE_CHISELBOX macro CSta,CL8,CTop,CWI,CHI
  CONTROL
CHISELBOX,CSta,CL8,CTop,CWI,CHI,0
endm

MAKE_SUNKENFRAME macro
CSta,CL8,CTop,CWI,CHI
  CONTROL
SUNKENFRAME,CSta,CL8,CTop,CWI,CHI,0
endm

MAKE_CENTEREDLEGEND macro
CSta,CL8,CTop,CWI,CHI
  CONTROL
CENTEREDLEGEND,CSta,CL8,CTop,CWI,CHI,0
endm

MAKE_ICON macro CSta,CL8,CTop
  CONTROL ICON,CSta,CL8,CTop,16,16,0
endm

MAKE_LISTBOX_NOSCROLL macro
CSta,CL8,CTop,CWI,CHI,CLen
  CONTROL
LISTBOXNOSCROLL,CSta,CL8,CTop,CWI,CHI,0
endm

MAKE_LISTBOX macro
CSta,CL8,CTop,CWI,CHI,CLen
  CONTROL LISTBOX,CSta,CL8,CTop,CWI,CHI,0
endm

MAKE_SPINBUTTON macro
CSta,CL8,CTop,CWI,CHI,CLen
  CONTROL
SPINBUTTON,CSta,CL8,CTop,CWI,CHI,0
endm

MAKE_SPECTRUMBAR macro
CSta,CL8,CTop,CWI,CHI,CLen
  CONTROL
SPECTRUMBAR,CSta,CL8,CTop,CWI,CHI,0
endm

MAKE_SLIDEBAR macro
CSta,CL8,CTop,CWI,CHI,CLen
  CONTROL SLIDEBAR,CSta,CL8,CTop,CWI,CHI,0
endm

MAKE_LINEBOX macro CSta,CL8,CTop,CWI,CHI
  CONTROL LINEBOX,CSta,CL8,CTop,CWI,CHI,0
endm

DEFINE_KEY macro
ScanCode,NormVal,ShftVal,CtrlVal,AltVal
 THIS_MISC_ITEM_START =$
  org CURRENTKEY + ID
  db ScanCode
  org CURRENTKEY + wDATALENGTH
  dw NormVal+ShftVal*256
  org CURRENTKEY + pStorageOffset
  dw CtrlVal+AltVal*256
  org THIS_MISC_ITEM_START
endm

DEFINE_ICON macro IconAddr
 THIS_MISC_ITEM_START = $
 org CURRENTCONTROL + ID
 dw IconAddr
 org THIS_MISC_ITEM_START
endm

tControl struc
ControlType    db ?
ControlState   db ?
ID             dw ?
LeftPixel      dw ?
TopPixel       dw ?
PixelWidth     dw ?
PixelHeight    dw ?
wDataLength    dw ?
pStorageOffset dw ?
ControlEOC     db ?
ends

wTopVisible equ pStorageOffset

pFirstRegionRecord equ wDataLength

tRegion struc
pCurrentControl dw ?
wCurrentTop     dw ?
wCurrentBottom  dw ?
wCurrentLeft    dw ?
wCurrentRight   dw ?
wCurrentHeight  dw ?
wCurrentWidth   dw ?
wListHandle     dw ?
wListItemIndex  dw ?
bListItemFlags  db ?
ends
tLISTBOXENTRY struc
lpszEntry dd ?
cAttribute db 0
ends

tMSGBOXBUFF struc
pTextOff dw 0
pTextSeg dw 0
cAlignment db 0
ends
tBUFFHEADER struc
tStructLen dw 0
tBuffLen   dw 0
pBuffOff   dd 0
ends

tHOSTLIST struc
lpszNodeAddress dd 0
lpszGroupName   dd 0
lpszHostName    dd 0
lHostVersion    dw 0
lpszSerial      dd 0
lpszReserved    dd 0
ends

tSCANCODES struc
tScanCode dw 0
ends
```

Copr. 1996 Zenith Data Systems Corp.

```
Copr. 1996 Zenith Data Systems Corp.

#define N_DIG (16)
#define BCD_BYTES (2+(N_DIG/2))
#define BCD_TOP (1+(N_DIG/2))
#define BCD_WORDS (1+(N_DIG/4))
#define BCD_BIAS (0x4000)

typedef word bcd[BCD_WORDS];
extern char _bcd_buf[];

#define bdbs(p,q1,q2,q3,q4,sp) \
{(sp<<BCD_BIAS-1)<<(1 bs
(-1))<<14),0x00q1,0x00q2,0x00q3,0x00q1}

#define bl0 {0,0,0,0,0}
#define bl1 bl(+,1000,0,0,0,1)

#define bcdv(n,bs,q1,q2,q3,q4,sp) \
bcd v=({sp<<BCD_BIAS-1)<<(1 bs
(-1))<<14),0x00q1,0x00q2,0x00q3,0x00q1}

#define bcd2dec(x,i,integer,frac)
bcd2d(p,s,i(integer)<<0)(frac))

#define bc_abs(x) *((byte*)(x)+1)&~0x7f
#define bc_chs(x) *((byte*)(x)+1)^=0x80
#define bc_neg(x) *((byte*)(x)+1)|=0x80
#define bc_sgn(x) (short)(*(int*)(x)<0)?-1:1
#define bc_isneg(x) (*(int*)(x)<0)
#define bc_ispos(x) (*(int*)(x)>0)
#define bc_iszero(x) (*(char*)(x)+BCD_TOP))
#define bc_notz(x) (*(char*)(x)+BCD_TOP)
#define bc_abs(x)
*(word*)(x)+*(word*)(x)+BCD_WORDS-1)+0
#define bc_m10(x) (*(word*)(x))++
#define bc_d10(x) (*(word*)(x))--
#define bc_m100(x) (*(word*)(x))+=2
#define bc_d100(x) (*(word*)(x))-=2
#define bc_mp(x,n) *(word*)(x)+=(n)
#define bc_dp(x,n) *(word*)(x)-=(n)
#define bc_bld(x)
((int)(*(int*)(x))&0x7fff)-BCD_BIAS+1)
#define bc_sld(x)
((int)(*(int*)(x))&0x7fff)-BCD_BIAS-1+N_DIG)
#define bc_lsd(x)
(char)(*(byte*)(x)+BCD_TOP)>>4)
#define bc_lsd(x) (char)(*(byte*)(x)+2)&0x0f)


void bcsub(bcd x,bcd y);
void bcdd(bcd x,bcd y, bcd z);
void bcmb(bcd x,bcd y, bcd z);
void bcmul(bcd x,bcd y, bcd z);
void bdiv(bcd x,bcd y, bcd z);
void bcmp(bcd x, bcd y);
void bcs(bcd x,bcd y);
int bcmp(bcd x, bcd y);
void bcround(bcd x, int n);
void bcrnd(bcd x, bcd y);
void bround(bcd x, bcd y);

char *bcd2a(bcd x, char *s, int nd);
char *bcd2d(bcd x, char *s, word fmt);
int bcd2asc(bcd x, int nd);
long bcd2l(bcd x);
char *asc2bcd(char *s, bcd x);
void i2bcd(int n, bcd x);
void w2bcd(word w, bcd x);
void l2bcd(long n, bcd x);
void ul2bcd(ulong ulw, bcd x);
Copr. 1996 Zenith Data Systems Corp.

#define HW_BACKSP 0x0008
#define HW_ENTER 0x000D
#define HW_INVALID_KEY 0x00FE
#define HM_WIN_DONE_PW 0x00E0
#define HM_WIN_GET_STA 0x00E1
#define HM_WIN_GET_HOST 0x00E2
#define HM_OSKOCC_DEFINE_ACK_TO_HM
0x00E3
#define HM_OSKOCC_CLOSE_ACK_TO_HM
0x00E4
#define HM_OSKOCC_CLOSE_UNI_TO_HM
0x00E5

#define WM_POST_MSG (0x0400 + 0x1000)
#define WM_WN_KEY (WM_USER + 0x1002)

#define WM_OSKOCC_DEFINE_ACK (WM_USER
+ 0x1003)
#define WM_OSKOCC_CLOSE_ACK (WM_USER
+ 0x1004)
#define WM_OSKOCC_CLOSE_UNI (WM_USER
+ 0x1005)

#define WM_ENABLE_CLOSE (WM_USER +
0x1010)

void FAR PASCAL SetHook(HWND);
void FAR PASCAL RemoveHook(void);
void FAR PASCAL SwitchFlier(int);
LRESULT CALLBACK CheckKeys (int nCode,
WORD wParam, LONG lParam);


void FAR PASCAL UnloadOSKOCCACK(void);

Copr. 1996 Zenith Data Systems Corp.


#define HSE_VERI_BAD_PARM1 1
#define HSE_VERI_BAD_PARM2 2
#define HSE_VERI_BAD_PARM3 3
#define HSE_VERI_BAD_PARM4 4
#define HSE_VERI_BAD_PARM5 5
#define HSE_VERI_BAD_PARM6 6
#define HSE_CORRECT_SERIAL_NUMBER 0

#define HSE_CRC_RAND_LEN 8
#define HSE_SERIAL_LEN 16
Copr. 1996 Zenith Data Systems Corp.



#define SL_FT_E882_2 10
#define SL_FT_E882_3 11
#define SL_FT_EI 12
#define SL_FT_ESNAP 13


#define SL_FT_LEN_NVRAM 7
#define SL_FIELDOFFSET(struct, field) ((int)(
(&(struct)->field)) - ((char NEAR*)(struct))) )


#define SL_LSL_CMD_E882_2
"/C=ETH8822.CFG\r"
#define SL_LSL_CMD_E882_3
"/C=ETH8823.CFG\r"
#define SL_LSL_CMD_EI "/C=ETHEI.CFG\r"
#define SL_LSL_CMD_ESNAP
"/C=ETHSNAP.CFG\r"


#define SL_LSL_CMD_LENGTH 16
Copr. 1996 Zenith Data Systems Corp.


typedef struct CALLVXDPARASTRUC
{
 int ICmd;
 int SessOrFuncID;
 int Int2FAPI;
};

typedef struct Win386_Startup_Info_Struc
{
 unsigned char SIS_Version_Major;
 unsigned char SIS_Version_Minor;
 unsigned long SIS_Next_Dev_Ptr;
 unsigned long SIS_Virt_Dev_File_Ptr;
 unsigned long SIS_Reference_Data;
 unsigned long SIS_Instance_Data_Ptr;
};

typedef struct HostSysStatus
{
 char cVideoMode;
 char cUserName[11];
 char cConnStatus;
 char cProtocolID;
};

#define HM_FLASH_FNSIZE 14
#define HM_FLASH_FNUM 32
#define HM_FILEBUFF_LEN 2048
#define HM_FLASH_NAME_LEN 40

typedef struct FILESET
{
 unsigned int iCheckSum[HM_FLASH_FNUM];
 int iErrorCode;
 char cFlashName[HM_FLASH_NAME_LEN];
 int iFlashNameLen;
 int iTotalProtectFiles;
 unsigned char cFileAttr[HM_FLASH_FNUM];
 int iProtectFileNum[HM_FLASH_FNUM];
 int iTotalPieces;
 int iTotalFiles;
 int iFileLen[HM_FLASH_FNUM];
 int iFileNameLen[HM_FLASH_FNUM];
 char
cFileName[HM_FLASH_FNUM][HM_FLASH_FNSIZE
];
};

#define HM_ERR_LOG_MAX 10
typedef struct ERRORLOG
{
 char cErrorCode[5];
 char lLineNumber[5];
 char cModuleName[8];
 char cMsec[10];
 char cMinute;
 char cHour;
 char cDay;
 char cMonth;
};

#define HM_BRCAST_RESP 30
#define HM_SERIAL_NUM_DEFA 1

#define HM_VERSION 100

#define HM_PATH_LEN 80



#define FALSE 0
#define TRUE 1
#define HM_OFF 0
#define ON 1
#define NULL 0

#define HM_DOS_MODE 0
#define HM_WINDOWS_MODE 1

#define HM_PM_DOSWIN 0
#define HM_PM_DOSWIN_ACK 1
#define HM_PM_FILEREQ 10
#define HM_PM_TOTALFILES 12
#define HM_PM_PATHREQ 13
#define HM_PM_PATHREP 14
#define HM_PM_FLASHOK 15
#define HM_PM_FLASH_NAMQ 20
#define HM_PM_FLASH_NAMP 21
#define HM_PM_FLASH_BREAK 22
#define HM_PM_HOSTCON 30
#define HM_PM_BLANKSCR 40
#define HM_PM_UNBLANKSCR 41
#define HM_PM_LOCKKBMO 42
#define HM_PM_UNLOCKKBMO 43
#define HM_PM_BLANKSCR_ACK 46
#define HM_PM_UNBLANKSCR_ACK 47
#define HM_PM_LOCKKBMO_ACK 48
#define HM_PM_UNLOCKKBMO_ACK 49
#define HM_PM_ERRORRN 50
#define HM_PM_ERRORREQ 51
#define HM_PM_OSK_DEFINE 60
#define HM_PM_OSK_DEFINE_ACK 61
#define HM_PM_OSK_CLOSE 62
#define HM_PM_OSK_CLOSE_ACK 63
#define HM_PM_OSK_CLOSE_UNI 64
#define HM_PM_OSK_CLOSE_UNI_ACK 65

#define HM_PASSWORD_LEN 20+1

#define HM_PM_LEN_ONE 64
#define HM_PM_LEN 100
#define HM_SC_LEN 30

#define HM_PM_FLASH_UNIT 8

#define HMUI_UNLOAD_HCS 0x01
#define HMUI_DISCONNECT 0x10
#define HMUI_WAIT_CALL_SNT 0x20
#define HMUI_GRP_HOST_NAME 0x30
#define HMUI_GET_STATUS 0x40
#define HMUI_PW_PROTECT 0x41
#define HMUI_RST_STATUS 0x42
#define HMUI_GET_ERRORNESS 0x50
#define HMUI_SET_SECU_ID 0x60
#define HMUI_GET_SECU_ID 0x61
#define HMUI_GET_SESSION 0x70

#define HM_EXIST_SI 0xf8a7
#define HM_EXIST_DI 0x3a4d
#define HM_EXIST_CX 0x3131

#define HM_GET_CUR_SS 30

#define HM_HMWIN_OSK 0x06A1
#define HM_HMWIN_OSKOCC_UNI_ACK 0x06A2

#define STK_SZ 5120

#define GetStack(p) ((void far*)(*(long
*)&(p->saved_ss)))

#define _FP_SEG(fp) (*((unsigned __far *)&(fp)+1))

#define _FP_OFF(fp) (*((unsigned __far *)&(fp)))

#define HM_CONNECT 3
#define HM_DISCONNECT 0
#define HM_WAITING 1

#define HM_PHN_REC_LEN 257
#define HM_PHN_NAME_OFF 3
#define HM_PHN_NAME_LEN 19
#define HM_PHN_PW_OFF 92
#define HM_PHN_PW_END 113

#define DWORD long
#define WORD unsigned short
#if defined( LOWORD )
 #undef LOWORD
#endif
#define LOWORD(l) ((WORD)(DWORD)(l))

#if defined( HIWORD )
 #undef HIWORD
#endif

#define HIWORD(l) ((WORD)((((DWORD)(l))
>> 16) &
0xFFFF))

#define HM_VHMCD_ID 0x3306

#define HM_VHMCD_SV 0
#define HM_VHMCD_MSG 1

#define HM_WIN_DONE_PW 0xe0
#define HM_WIN_GET_STA 0x00e1
#define HM_WIN_GET_HOST 0x00e2
#define HM_OSKOCC_DEFINE_ACK_TO_HM
0x00E3
#define HM_OSKOCC_CLOSE_ACK_TO_HM
0x00E4
#define HM_OSKOCC_CLOSE_UNI_TO_HM
0x00E5
#define HM_VXD_GET_PROC 0x0

#define HM_TEMP_FILE_NAME_LEN 8
#define HM_SARA_FLASH_BUFF 64
#define HM_FLASH_BUFF 1024
#define HM_DEFAULT_ICON 0x0015
#define HM_CONN_ICON 0x0020
#define HM_DISCONN_ICON 0x0030
#define HM_FLASH_ICON 0x0040
#define HM_FLASH_ICON_END 0x0041
#define HM_WAIT_ICON 0x0050
#define HM_HOST_CNT_ICON 0x0060

#define HM_SWITCH_OFF 0x0100

#define HM_ERROR_LOG_FILE "ERROR.LOG"
#define HM_PHONEBOOK_FILE "SESSION.PHN"
#define HM_SIG_STRING "host_manager"
#define HM_HOSTCS_SIG "DOS-HOST"
#define HM_HOSTDAT_NMAPI "NMAPI"
#define HM_HOSTDAT_CONFIG "configuration"
#define HM_HOSTDAT_GRP "GROUPNAME"
#define HM_HOSTDAT_HOST "HOSTNAME"
#define HM_HOSTDAT_VER "VERSION"
#define HM_HOSTDAT_SERIAL "SERIALNUMBER"
#define HM_HOSTDAT_LEFT "["
#define HM_HOSTDAT_RIGHT "]"
#define HM_SESSION_CFG_FN "SESSION.CFG"

#define HM_HCS_API 0x00
#define HM_HCS_SCRON 0xDE30
#define HM_HCS_SCROFF 0xDE31
#define HM_HCS_KBON 0xDE32
#define HM_HCS_KBOFF 0xDE33
#define HM_HCS_SENDPRI 0xDD00
#define HM_HCS_SYSPTR 0xDF00
#define HM_HCS_BROAD 0xE000
#define HM_HCS_UNLOAD 0xE300
#define HM_HCS_DISC 0xE200
#define HM_HCS_WAIT 0xE100
#define HM_HCS_SESSION 0xE400

#define HM_VER_STR "Version 1.1"

#define ZX 8
#define HM_FILE_NOT_FOUND 2

#define HM_FLASH_READ_NBAT -10
#define HM_FLASH_POS_NBAT -11
#define HM_FLASH_NOT_SOURCE -21
#define HM_FLASH_OPEN_SOURCE -22
#define HM_FLASH_CLOSE_SOURCE -23
#define HM_FLASH_READ_SOURCE -24
#define HM_FLASH_POS_SOURCE -25
#define HM_FLASH_CREATE_TEMP -30
#define HM_FLASH_WRITE_TEMP -31
#define HM_FLASH_CLOSE_TEMP -32
#define HM_FLASH_NO_FILES -40
```

```
#define HM_FLASH_NO_CHECKSUM -50
#define HM_FLASH_BAD_CHECKSUM -51

#define HM_STUFF_ENTER      0x000D

#define HM_DOS_BUSY_TRY_TICKS   4

#define HM_INT_2F_START       0x1605
#define HM_INT_2F_TERM        0x1606
#define HM_INT2F_ENTRY_API    0x1604

#define HM_DOS_WIN_TRIES      5*8+3
#define HM_UNI_CLOSE_TRIES    5*8+2
#define HM_TICKS_PER_TRY      8
#define HM_TICKS_PER_SECOND   18
#define HM_TICKS_TWO_SECOND   36
#define HM_WIN_STATUS_CHG_TRY   3

typedef struct sTrapRec80t
{
  struct trap_rec sTrapRec80;
  char a[8];
  char b[36];
};

Copr. 1995 Zenith Data Systems Corp

#define MOVE_DATA 1
#define MOVE_CODE 2
#define MOVE_BOTH 3

extern    int lim_error;
extern    int _prog_handle;
int move_to_lim(int MinPages,int MaxPages,int
Method);
void _m2l_no_wait(void);
void _adjust_tim(void);
extern    word _lim_top;

typedef   struct lim_ctl {
    int sys_handle;
    int page_cnt;
    int tot_pages;
    char active[2];
    word reserved1;
    word bl_code;
    word reserved2;
    word lc_data;
} LIM_CTL;

extern _lim_ctl();
#define   TSR_LIM_CTL()  *(word
far*)MK_FP(parent_code,(word)_lim_ctl)

int lim_present(void);
int lim_status(void);
word lim_window(void);
int lim_alloc(void);
int lim_alloc(int NoPages);
void lim_dealloc(int Handle);
void lim_map(int Handle,int Page,int Position);
int lim_version(void);
void lim_save_map(int Handle);
void lim_restore_map(int Handle);
int lim_tot_pages(void);
int lim_handles(void);
int lim_h_pages(int Handle);
int lim_h_search(int *ResultOfs,word ResultSeg);
void lim_get_map(void *Ofs,word Seg);
void lim_set_map(void *Ofs,word Seg);
void lim_swap_map(void *NewOfs,word
NewSeg,void *OldOfs,word
OldSeg);
int lim_map_size(void);

word Read(int Handle,void far *Buf,word Cnt);
word Write(int Handle,void far *Buf,word Cnt);
char far *lmem_find(int PatLen,void far *Pat,int
AreaLen,void far
*Area);
word far_len(void far *Str);
word far_cp(void far *Src,void far *Dest);
word far_pos(char c,void far *s);
word lmem_cmp(void far *s1,void far *s2,word cnt);
char far *lmem_swap(void far *s1,void far *s2,word
cnt);
void get_fill(int x_size, int y_size, word far *buf);
void put_fill(int x_size, int y_size, word far *buf);
void swap_fill(int x_size, int y_size, word far *buf);

typedef struct pctl_rec {
    char *Buf;
    word BufSize;
    word BufHgh;
    word BufCnt;
    char Flags.
    char ErCode,
    char PutWr,PutStr;
} PCTL_REC;

#define PF_ON    1
#define PF_PRINT  2
#define PF_DIRTY 0x40
#define PF_OVF   0x80

#define PXC_RDY      0x90
#define PXC_PAPER   0x20
#define PXC_SEL      0x10
#define PXC_ERR    0x08
#define PXC_TMO       0x01

install_strap(int service,word stack_size,byte
task_mask,PCTL_REC
*p);
extern PCTL_REC *_pctl;
extern word _printer_mask;
Copr. 1995 Zenith Data Systems Corp.

#define   CLASS_MAGIC     0x434E
#define   MENU_MAGIC      0x4D4D

#define   ERR_SUCCESS     0
#define   ERR_INTERNAL    -1

#define   OSK_NOTCLOSING   0
#define   OSK_UNICLOSING   1
#define   OSK_MOVEALLOWED  0
#define   OSK_NOMOVEALLOWED 1

typedef struct
{
  HANDLE  hsNext,
  WORD    wSig;
  ATOM    atomCls;
  HANDLE  hDCE;
  WORD    cClsWnds.
  WNDCLASS wc;
  WORD    cExtra[1];
} CLASS, NEAR * HCLASS;

typedef struct
{
  HWND     hwndNext;
  HWND     hwndChild;
  HCLASS   hClass,
  HANDLE   hProp;
  HWND     hwndLastActive;
  HANDLE   hScroll;
  HANDLE   hmemTaskQ;
  HRGN     hrgnUpdate;
  HANDLE   hDCE;
  HMENU    hmenuSystem;
  HWND     hwndOwner;
  RECT     rectWindow;
  RECT     rectClient;
  HPALETTE hPalette,
  WORD     wFlags.
  DWORD    dwExStyle.
  DWORD    dwStyle;
  WORD     wID_Menu;
  HANDLE   hText;
  HWND     hwndParent,
  HANDLE   hInstance;
  FARPROC  lpfnWndProc;
} WND_3_0 ;

typedef struct
{
  HWND     hwndNext;
  HWND     hwndChild;
  HWND     hwndParent;
  HWND     hwndOwner;
  RECT     rectWindow;
  RECT     rectClient;
  HANDLE   hmemTaskQ;
  HRGN     hrgnUpdate;
  HCLASS   hClass;
  HANDLE   hInstance;
  FARPROC  lpfnWndProc;
  DWORD    dwFlags;
  DWORD    dwStyle;
  DWORD    dwExStyle;
  WORD     wID_Menu;
  HWND     hText;
  HANDLE   hScroll;
  HANDLE   hProp;
  HWND     hwndLastActive;
  HMENU    hmenuSystem;
} WND_3_1 ;

typedef struct
{
  WORD   wFlags;
  WORD   hSubPopup;
  RECT   rectCapture;
  WORD   xTab;
  HANDLE hCheckedBmp;
  HANDLE hUncheckedBmp;
  HANDLE hItemBmp;
  WORD   xAltStart;
  WORD   cchAltLen;
  WORD   cbItemLen;
} MENUITEM, FAR *LPMENUITEM;

typedef struct
{
  WORD wFlags;
  WORD iCurSel;
  WORD iCurPopup;
  WORD cbItems;
  WORD cxWidth;
  WORD cyHeight;
  WORD cItems;
  HWND hwndOwner;
  MENUITEM *pItems;
} MENU_3_0 ;

typedef struct
{
  HMENU  hmenuNext;
  WORD   wFlags;
  WORD   wMagic;
  HANDLE hTaskQ;
  WORD   cxWidth;
  WORD   cyHeight;
  WORD   cItems;
  HWND   hwndOwner;
  HANDLE hItems;
  WORD   w12;
} MENU_3_1 ;

typedef void FAR *LPMENU;

typedef struct
{
  ATOM   atomID,
  HANDLE hData,
  WORD   wFlags.
} PROPERTY;
typedef struct
{
  WORD cProps,
} PROPLIST;

typedef struct
{
  HANDLE hdceNext;
  HWND   hwnd;
  HDC    hDC;
  BYTE   byFlags;
  BYTE   byInUse;
  BYTE   byDirty;
  BYTE   byXX;
  WORD   xOrigin;
  WORD   yOrigin;
  HWND   hwndTop;
  HRGN   hVisRgn;
} DCE, *HDCE;

typedef struct tagCALLWNDPROCPARMS
{
  LONG lParam;
  WORD wParam;
  WORD message,
  HWND hwnd;
} CALLWNDPROCPARMS, FAR
*LPCALLWNDPROCPARMS;

typedef enum tagWMCODES
{
  WM_OSKDOCOBEFINSCOMPLETE = WM_USER
+ 0x0000,
  WM_OSKDOCCLOSECOMPLETE,
  WM_OSKDOCUNICLOSEDCOMPLETE,
} WMCODES;

int CALLBACK              LibMain( HINSTANCE
hInstance,
WORD wDataSeg, WORD cbHeapSize,
                          LPSTR
lpszCmdLine);
int CALLBACK __export __loadds WEP( int
nExitType );
long WINAPI __export __loadds OscWndProc(
HWND hWnd, UINT
message, WPARAM wParam, LPARAM lParam );

HINSTANCE GetLibInst( void );
BYTE     IsMoveActive( void );
BOOL     InitLibrary( HINSTANCE hInstance );
HWND      GetHotPointWindow( void );
int      MoveOcclusion( LPRECT lprcCheckPos,
LPRECT lprcNewDimen
);
int      CreateOcclusion( LPRECT lprcCheckPos,
LPRECT
lprcNewDimen );
int      UniCloseOcclusion( void );
int      CheckWindowPos( LPRECT lprcPopupPos );
int      CheckOSKWindowPos( LPRECT
lprcNewHotPointPos );

LPRECT GetMenuPos( HMENU hPopupMenu );
int    LocateMenuHeap( void );
BOOL   ContainsLocalHeap( WORD wSeg );
BOOL   IsMenuHeap( WORD wSel );
int    FindAddress( WORD wSel, HANDLE hHandle,
WORD FAR *pOfs,
WORD FAR *pSize );

BOOL IsMsgHookInstalled( void );
int  InstallMsgHook( void );
int  UninstallMsgHook( void );
LRESULT CALLBACK __export __loadds
OSKGetMsgProc( int iCode,
WPARAM wParam, LPARAM lParam );

int WINAPI __export __loadds DefineOcclusion( int
xPos, int yPos,
int nWidth, int yHeight );
int WINAPI __export __loadds CloseOcclusion( void
);
int WINAPI __export __loadds RegisterOSKDesk(
HWND hWndOSK );

Copr. 1995 Zenith Data Systems Corp.
#ifndef __RPARM_H__

   #define __RPARM_H__

#define MAXLEN_ENTRY_NAME          16
#define MAXLEN_DIALOUT_LOGIND      16
#define MAXLEN_DIALOUT_PASSWORD     20
#define MAXLEN_TELEPHONE_NUMBER     36
#define MAXLEN_DIALIN_LOGIND       16
#define MAXLEN_DIALIN_PASSWORD      20
#define MAXLEN_REMOTE_DESCRIPTION  37
#define MAXLEN_DIRECTORY           64
#define MAXLEN_SERVICE             22
#define MAXLEN_NETBIOS_IP_ADDRESS  36
#define MAXLEN_TCP_IP_ADDRESS      12
#define MAXLEN_NETBIOS_CALL_NAME   16
#define MAXLEN_RPARM_SPARE         16

#define OPTIONS_DIALBACK          (1<<0)
#define OPTIONS_FILEACCESS_ALL      (0x00)
#define OPTIONS_FILEACCESS_SENDONLY
(0x01)
#define OPTIONS_FILEACCESS_RCVONLY
(0x10)
#define OPTIONS_FILEACCESS_NONE     (0x11)
#define OPTIONS_PHONEBOOK_ENCRYPT
(1<<3)

#define PORT_COM0             0
#define PORT_COM1             1
#define PORT_COM2             2
#define PORT_SPECIAL           3

#define BAUDRATE_300          0
#define BAUDRATE_1200         1
#define BAUDRATE_2400         2
#define BAUDRATE_4800         3
#define BAUDRATE_7200         4
#define BAUDRATE_9600         5
#define BAUDRATE_14400        6
#define BAUDRATE_19200        7
#define BAUDRATE_38400        8
#define BAUDRATE_57600        9
#define BAUDRATE_115200        10

#define TERMTYPE_REMOTE        0
#define TERMTYPE_TTY          1
#define TERMTYPE_VT100        2
#define TERMTYPE_VT102        3

#define DIAL_TONE            0
#define DIAL_PULSE           1

#define PROTOCOL_SPX           6
#define PROTOCOL_ASYNCH          7

#define INT14_COACS          8
```

```
#define INT14_EBIOS          1
#define INT14_CROSS          2
#define INT14_MID            3
#define INT14_BANYAN         4
#define INT14_CONTECH        5
#define INT14_PROTO          6

#define NETBIOS_ADAPTER_1        0
#define NETBIOS_ADAPTER_2        1

struct rparm
{
  char rpsone;
  char rpaphon;

  char rpnl[MAXLEN_ENTRY_NAME + 1];

  char rpdund[MAXLEN_DIALOUT_LOGINID + 1];

  char rpdopw[MAXLEN_DIALOUT_PASSWORD +
1];

  char rptelno[MAXLEN_TELEPHONE_NUMBER +
1];

  char rpdnd[MAXLEN_DIALIN_LOGINID + 1];

  char rpdipw[MAXLEN_DIALIN_PASSWORD + 1];

  char rpdesc[MAXLEN_REMOTE_DESCRIPTION +
1];

  char rpcom;

  char rpptyp;

  char rpbrate;

  char rptermtyp;

  char rpdltyp;

  char rpprotocol;

  char rpdirec[MAXLEN_DIRECTORY + 1];

  char rpserv[MAXLEN_SERVICE + 1];

  char rpnetname[MAXLEN_NETBIOS_IP_ADDRESS
+ 1];

  char rptype

  char rptcpnet[MAXLEN_TCP_IP_ADDRESS + 1];

  char
rpnetbname[MAXLEN_NETBIOS_CALL_NAME + 1];

  char rpautodeal;

  char rpspare[MAXLEN_RPARM_SPARE];
```

```
};

typedef struct rparm RPARM;

#endif
Copr. 1995 Zenith Data Systems Corp.

#define MAXLEN_DEFAULT_PATH          26
#define MAXLEN_FASTACCESS_REMOTEID 10
#define MAXLEN_DIRECTORY         66
#define MAXLEN_CALLID        10
#define MAXLEN_NETBIOS_NAME        16
#define MAXLEN_SPARE         21

#define MISC_USE_SOUND             (1<<0)
#define MISC_COM_DRIVER            (1<<1)
#define MISC_CLOCK_DISPLAY           (1<<2)
#define MISC_SCREEN_SIZE           (1<<3)
#define MISC_FAST_GRAPHICS             (1<<4)
#define MISC_FULL_SPEED            (1<<5)
#define MISC_SCREEN_BLANK_XS_DISABLED
(1<<6)
#define MISC_FILE_OVERWRITE_CHECK_OFF
(1<<7)

#define BPLANE_NONE             0
#define BPLANE_1            1
#define BPLANE_2            2
#define BPLANE_3            3
#define BPLANE_4            4

#define CTRL_ALT_RSHIFT            0
#define CTRL_ALT             1
#define CTRL_LSHIFT            2
#define CTRL_RSHIFT            3
#define CTRL_ALT_LSHIFT            4
#define ALT_LSHIFT            5
#define ALT_RSHIFT            6
#define LSHIFT_RSHIFT           7

#define DEFAULT_DRIVE_A          0
#define DEFAULT_DRIVE_B          1
#define DEFAULT_DRIVE_C          2

#define REBOOTONHANGUP_NEVER          0
#define REBOOTONHANGUP_ALWAYS          1
#define REBOOTONHANGUP_NORMAL          2
#define REBOOTONHANGUP_ABNORMAL          3

#define OPTIONS_COMPRESS_FILE_ON_XFER
(1<<0)
#define OPTIONS_CONSOLE_DRIVER
(1<<1)
#define OPTIONS_AUTO_DETERMINE_ANSI
(1<<2)
#define OPTIONS_REMOTE_MOUSE_SUPPORT
(1<<3)
#define OPTIONS_COM_PORT_MONITOR
(1<<4)

struct cfsd_cfg
{
  char dwdl;

  char dtype;

  char dscon;

  char bcdr;
  char bgrd;
  char fgrd;
  char utlbgrd;
  char utlfgrd;
  char appm;
  char options;

  char adlm;
  char keys;

  char drvt;

  char pdir[MAXLEN_DEFAULT_PATH + 1];

  char fasr[MAXLEN_FASTACCESS_REMOTEID
+ 1];
```

```
  char sound;

  char pout;

  char mboot;

  char setup;

  char adrdb;
  char dirs[MAXLEN_DIRECTORY + 1];

  char vmode;

  char scid[MAXLEN_CALLID + 1];

  char target;

  char inactiv

  char cpfx;

  char se_rate;

  int upall;
  char slrq;
  char onlinec;

  char netname[MAXLEN_NETBIOS_NAME + 1];

  char spare[MAXLEN_SPARE];

};
Copr. 1995 Zenith Data Systems Corp

#define VOID        void
#define APIFUNCRET   VOID

#define FAR       _far
#define NEAR      _near
#define PASCAL     _pascal
#define CDECL      _cdecl

typedef int       BOOL;

#if defined( TRUE )
  #undef TRUE
#endif
```

```
#if defined( FALSE )
  #undef FALSE
#endif

#if defined( FON )
  #undef ON
#endif

#if defined( FOFF )
  #undef OFF
#endif

#define TRUE       1
#define FALSE      0
#define FON       1
#define FOFF       0

typedef unsigned char       BYTE;

#if defined( WORD )
  #undef WORD
#endif

#if defined( DWORD )
  #undef DWORD
#endif
typedef unsigned long       DWORD;

typedef unsigned short      WORD;
typedef unsigned int       UINT;
typedef signed long        LONG;
typedef void *            PVOID;
typedef void FAR*         LPVOID;

#define LOBYTE(w)           ((BYTE)(w))
#define HIBYTE(w)           ((BYTE)(((UINT)(w) >> 8)
& 0xFF))

#if defined( LOWORD )
  #undef LOWORD
#endif
#define LOWORD(l)
((WORD)(DWORD)(LPVOID)(l))

#if defined( HIWORD )
  #undef HIWORD
#endif

#define HIWORD(l)
((WORD)(((DWORD)(LPVOID)(l) >> 16)
& 0xFFFF))

#define MAKELONG(low, high)
((LONG)(((WORD)(low)) |
(((DWORD)((WORD)(high))) << 16)))
#define MAKEWORD(low, high) ((WORD)(low) |
((WORD)(high) << 8))

#if defined( OFF )
  #undef OFF
#endif

#define OFF(fp)           (LOWORD( ( DWORD )(
BYTE FAR * )(fp ))
#define SEG(fp)           (HIWORD( ( DWORD )(
BYTE FAR * )(fp ))

#ifndef NOMINMAX
#ifndef max
#define max(a,b)           (((a) > (b)) ? (a) : (b))
#endif
#ifndef min
#define min(a,b)           (((a) < (b)) ? (a) : (b))
#endif
#endif

typedef UINT WPARAM;
typedef LONG LPARAM;
typedef LONG LRESULT;

#define MAKELPARAM(low, high)
((LPARAM)MAKELONG(low, high))
#define MAKELRESULT(low, high)
((LRESULT)MAKELONG(low, high))

#ifndef NULL
#define NULL          0
#endif

typedef char NEAR*       PSTR;
typedef char NEAR*       NPSTR;

typedef char FAR*       LPSTR;
typedef const char FAR*    LPCSTR;

typedef BYTE NEAR*       PBYTE;
```

```
typedef BYTE FAR*        LPBYTE;

typedef int NEAR*        PINT;
typedef int FAR*         LPINT;

typedef WORD NEAR*       PWORD;
typedef WORD FAR*        LPWORD;

typedef long NEAR*       PLONG;
typedef long FAR*        LPLONG;

typedef DWORD NEAR*      PDWORD;
typedef DWORD FAR*       LPDWORD;

#define MAKELP(sel, off)   ((void
FAR*)MAKELONG((off), (sel)))


#define STRFIELDOFFSET( struct, field )
((NPSTR)&(struct.field)-(NPSTR)&(struct))
#define WORDFIELDOFFSET( struct, field )
((NPSTR)&(struct.field)-(NPSTR)&(struct))


#define AX( value ) _asm mov ax, value
#define BX( value ) _asm mov bx, value
#define CX( value ) _asm mov cx, value
#define DX( value ) _asm mov dx, value
#define ES( value ) _asm mov es, value
#define DS( value ) _asm mov ds, value
#define SI( value ) _asm mov si, value
#define DI( value ) _asm mov di, value

#define PSP_PARENT_PSP( psp ) *( int far * )( (
long )psp << 16
) + 0x16 )
#define PSP_TERMINATE( psp ) *( long far * )( (
long )psp << 16
) + 0x0A )

#if defined( PROD )
#define DEBUG_BREAK _asm nop
#define TRACE( s ) _asm nop
#else
#define DEBUG_BREAK _asm int 3
#define TRACE( s ) Trace( s )
#endif

typedef void ( FAR * FARPROC )();
typedef void ( FAR * FARCALLENTRY )();
typedef void ( * NEARPROC )();
typedef APIFUNCRET ( * APIFUNCPTR )( struct
REGW * );
typedef void ( * SCSBUSYCB )( void );
typedef void ( * VIDBUSYCB )( void );
typedef void ( * MODALMSGBOXCB )( int );
typedef int ( FAR * SUICB )( void );
typedef int ( FAR * PRXCB )( void );

#define SIG_SMSIGNATURE       "tetralogy manager,
copyright info"
#define SIG_RLNOEMSIGNATURE "Proxim OEM
Interface Enabler"
#define SIG_POSOFFSET          16
#define SIG_MSGOFFSET          18

#define SUI_MAXLENUSERID       10
#define SUI_MAXLENPASSWORD     20
#define SUI_MAXLENSECURITYID   20
#define SUI_MAXLENSECURITYIDLA 20
#define SUI_MAXLENSENTRY       80
#define SUI_MAXLENACTIVEUPD    80
#define SUI_MAXNUMSCANCODES    32

#define RLN_MAXLENNODEADDRESS 20

#define PRX_EVENTNUM  5
#define PRX_POLLFREQ  6

#define PRX_MAXLENROMVERSION  0x07
#define PRX_MAXLENMASTERNAME  11
#define PRX_MAXLENNODEADDRESS 6

#define PRX_CSBUSPEND         0x0000
#define PRX_CSREADLINE        0x0001
#define PRX_CSPRXVARIABLES    0x0002
#define PRX_CSSETSECUREID     0x0003

#define PRX_NUMOFAVAILFRAMES 4
#define PRX_NOFRAMETYPE      0
#define PRX_FRAME8022        ( SL_FT_E802_2 )
#define PRX_FRAME8023        ( SL_FT_E802_3 )
#define PRX_FRAMEEN          ( SL_FT_EN )
#define PRX_FRAMESNAP        ( SL_FT_ESNAP )
#define PRX_FRAMEBASE        (
PRX_FRAME8022 )

#define PRX_NOLINKQUALITY  -1
#define PRX_DISCONNECTED   0x0000
#define PRX_LOWQUALITY     0x0001
#define PRX_HIGHQUALITY    0x0002

#define PRX_DOMAIN0        0
#define PRX_DOMAIN1        1
#define PRX_DOMAIN7        7

#define PRX_MAXDOMAINID    15
#define PRX_MINDOMAINID    0

#define SCS_MAXLENMSGBUFF     160
#define SCS_MAXLENNODEADD     21
#define SCS_MAXLENHOSTDATA    35
#define SCS_MAXLENPHONEBOOK   11
#define SCS_MAXLENGROUPNAME   9
#define SCS_MAXLENHOSTNAME    8
#define SCS_MAXLENHOSTVERSION 3
#define SCS_MAXLENSERIALNUM   10
#define SCS_MAXLENRESERVED    1
#define SCS_MAXLENFILENAME    128

#define SCS_OFFGROUPKEY   (
SCS_MAXLENNODEADD )
#define SCS_OFFHOSTKEY    (
SCS_MAXLENNODEADD +
SCS_MAXLENGROUPNAME + 1 )
#define SCS_OFFSERIALNUM  (
SCS_MAXLENNODEADD +
SCS_MAXLENGROUPNAME + 1 +
SCS_MAXLENHOSTNAME + 1 + 3 * sizeof(
BYTE ) )

typedef struct tagSCANCODE
{
  WORD wScanCode;
} SCANCODE;

typedef struct tagUICONFIGDATA
{
  WORD wBuildLen;
  BYTE nMajorVersionNum;
  BYTE nMinorVersionNum;
  unsigned int bAutoShutoff      : 1;
  unsigned int bConnectType      : 2;
  unsigned int bLockKbdMouse     : 1;
  unsigned int bDimScreen        : 1;
  unsigned int bLastConnPassword : 1;
  unsigned int bReserved         : 10;
  BYTE nContrastIdx;
  BYTE nBrightnessIdx;
  BYTE nSleepTimeIdx;
  BYTE nDomainID;
  WORD wXUpperPenCalib;
  WORD wYUpperPenCalib;
  WORD wXLowerPenCalib;
  WORD wYLowerPenCalib;
  WORD wUILanguage;
  WORD wLastVersion;
  BYTE nLastOSKScreen;
  BYTE nLastOSKDigScreen;
  BYTE nLastSetupDigScreen;
  int  xPosLastOSKScreen;
  int  yPosLastOSKScreen;
  char szLastHostName[ SCS_MAXLENHOSTNAME
+ 1 ];
  char szSecurityID[ SUI_MAXLENSECURITYID + 1
];
  char szLastNodeAddress[
RLN_MAXLENNODEADDRESS + 1 ];
  BYTE nFrameType;
  SCANCODE aUDHotkey1[
SUI_MAXNUMSCANCODES + 1 ];
  SCANCODE aUDHotkey2[
SUI_MAXNUMSCANCODES + 1 ];
} UICONFIGDATA;

#define PHD_OFFCALIB ( sizeof( WORD ) + sizeof(
BYTE ) * 2 +
sizeof( unsigned int ) + sizeof( BYTE ) * 4 );


typedef enum tagTHREADTYPEID
{
  SMD_NOTHREAD,
  SMD_ALLTHREADTYPES,
  SMD_POLLED,
  SMD_ONETIME,
  SMD_MANYTIMES,
  SMD_ONDEMAND,
} THREADTYPEID;

typedef enum tagSUIACTIONCODE
{
  SUI_NOACTION,
  SUI_NOSCREEN,
  SUI_LASTOSKSCREEN,
  SUI_LASTSETUPDLGSCREEN,
  SUI_LASTCONNECTION,
  SUI_SPECIFIEDSCREEN,
  SUI_DOPENCALIBRATION,
  SUI_BADVIDEOMSG,
} SUIACTIONCODE;

typedef enum tagPREPSUISTATES
{
  SUI_NOPREPSTATE,
  SUI_SETINITHOSTOCC,
  SUI_CHECKMONITOROFF,
  SUI_DOMEMREALLOC,
  SUI_DOMEMDEALLOC,
  SUI_CHECKMEMDEALLOC,
  SUI_CHECKMEMREALLOC,
  SUI_CHECKFULLREPAINT,
  SUI_PREPSUCCESS,
  SUI_PREPERROR,
} PREPSUISTATES;

typedef enum tagUNLOADSUISTATES
{
  SUI_NOUNLOADSUISTATE,
  SUI_GETACTIVEUPDATE,
  SUI_DIMSCREEN,
  SUI_LOCKKBDMOUSE,
  SUI_UNLOADSUISUCCESS,
} UNLOADSUISTATES;

typedef enum tagCLEANUPSUISTATES
{
  SUI_NOCLEANUPSTATE,
  SUI_CHECKLMEMCLEANUP,
  SUI_CHECKMONITORON,
  SUI_CHECKFULLPAINTCLEANUP,
  SUI_FULLSCREENREPAINT,
  SUI_CLEANUPSUCCESS,
  SUI_CLEANUPERROR,
} CLEANUPSUISTATES;

typedef enum tagCALIBPENSTATES
{
  SUI_INITIALCALIBSTATE,
  SUI_CHECKCALIB,
  SUI_CALIBSUCCESS,
  SUI_CALIBERROR,
} CALIBPENSTATES;

typedef enum tagFLASHUPDATESTATES
{
  FLU_NOFLUSTATE,
  FLU_SAFETYCHECK,
  FLU_INITMEM,
  FLU_ALLOCDOSMEM,
  FLU_SENDREQFLASHUPD,
  FLU_WAITFORTMPFLASHFILES,
  FLU_UPDATETMPFILEPERCENT,
  FLU_WAITFORNUMFILES,
  FLU_SENDREQPATH,
  FLU_WAITFORPATHFLASHFILE,
  FLU_RECEIVEHOSTFILE,
  FLU_FLASHIT,
  FLU_FLASHUPDATECOMPLETE,
  FLU_CLEARERROR,
  FLU_REBOOT,
  FLU_BEGINERRORSTATES,
  FLU_RELEASEMEM,
  FLU_NOFLASHFILES,
  FLU_READHOSTDAT,
  FLU_MISSINGFILE,
  FLU_OUTOFDISKSPACE,
  FLU_FILECORRUPTED,
  FLU_NOCHECKSUM,
  FLU_HOSTUNKNOWNERR,
  FLU_NOACKTEMPFILESERROR,
  FLU_NOACKNUMFILESERROR,
  FLU_NOACKPATHERROR,
  FLU_NOACKRECEIVEFILEERROR,
  FLU_NOACKRECEIVEFATALERROR,
  FLU_FLASHFATALERROR,
  FLU_SENDPRIMEERROR,
  FLU_ERRONNOCLRERROR,
  FLU_MEMERROR,
  FLU_GETBATTERYINFOERROR,
  FLU_BATNOTATTACHEDERROR,
  FLU_BATCAPTOOLOWERROR,
  FLU_NOTONACERROR,
  FLU_NOCONNECTERROR,
  FLU_LIMITTOOLOWERROR,
  FLU_1MEGSYSTEMERROR,
  FLU_2MEGSYSTEMERROR,
} FLASHUPDATESTATES;

typedef enum tagPROCMSGBOXSTATES
{
  SUI_NOPROCMSGBOXSTATE,
  SUI_HIDEMSGBOX,
  SUI_SHOWMSGBOXSTATE,
};

typedef enum tagSMSCANCODES
{
  SM_SF1   = 0x003B,
  SM_SF2,
  SM_SF3,
  SM_SF4,
  SM_SF5,
  SM_SF6,
  SM_SF7,
  SM_SF8,
  SM_SF9,
  SM_SF10,
  SM_SALTQ = 0x0010,
} SMSCANCODES;


typedef struct tagAPIFUNC
{
  WORD        wFuncCode;
  APIFUNCPTR  fpAPIFunc;
} APIFUNC;

typedef struct tagEVENT
{
  NEARPROC     fpThread;
  APIFUNC      *nAPIFuncTable;
  THREADTYPEID ThreadTypeId;
  LONG         lTimeLimit;
  LONG         lTimeCurrent;
  int          InitRetryLimit;
  int          RetryLimit;
  BYTE         nReenterCount;
  unsigned int bReentrant : 1;
  unsigned int bReserved  : 15;
} EVENT;

typedef struct tagPENCALIB
{
  WORD wXUpperPenCalib;
  WORD wYUpperPenCalib;
  WORD wXLowerPenCalib;
  WORD wYLowerPenCalib;
  WORD wHITopMargin;
  WORD wHIRightMargin;
  WORD wHIVertSpace;
  WORD wHIXWidth;
  WORD wHIYHeight;
} PENCALIB;

typedef struct trap_rec TRAPREC;

typedef struct tagZDSTRAPREC
{
  TRAPREC tr;

  char nAfterFill[ SIG_POSOFFSET - 8 ];

  char szSMAfterSignature[ sizeof(
SIG_SMSIGNATURE ) + 1 ];
} ZDSTRAPREC;

typedef struct tagPROXIMTRAPREC
{
  char cFill;
  char szFillBeforeSignature[ sizeof(
SIG_RLNOEMSIGNATURE ) - 8 ];

  TRAPREC tr;

} PROXIMTRAPREC;

typedef struct tagPROXIMVARIABLES
{
  LPSTR lpszSynchronizeFlag;
  LPSTR lpszRomVersion;
  LPSTR lpszLinkQuality;
} PROXIMVARIABLES;

typedef struct tagPROXIMNETCONFIGDATA
{
  BYTE nIRQ;
  BYTE nDomainID;
  BYTE nChannel;
  BYTE nSubChannel;
  BYTE nNodeType;
  WORD wPortAdd;
  WORD wInactivityTime;
  char szMasterName[
PRX_MAXLENMASTERNAME + 1 ];
  char sNodeAddress[
PRX_MAXLENNODEADDRESS ];
  BYTE nSocket;
  BYTE fIN285;
  WORD wMemAddress;
  BYTE nSniffTime;
} PROXIMNETCONFIGDATA;

typedef struct tagPROXIMVERSIONINFO
{
```

```
  WORD wMajorVersion;
  WORD wMinorVersion;
  LPSTR lpszModuleName;
} PROXINVERSIONINFO;

typedef struct tagCALLREC
{
  char sFarCallOpCode;
  char zCallBuf[ sizeof( FARPROC ) ];
  char sFarRetOpCode;

  char sAfterFill[ SIG_POSOFFSET - ( sizeof(
FARPROC ) + 2 ) ];
  char szSMMerSignature[ sizeof(
SIG_SMSIGNATURE ) + 1 ];
} CALLREC;

typedef struct tagEXECPARMS
{
  WORD wSegEnv;
  WORD wOffCmdLineTail;
  WORD wSegCmdLineTail;
  WORD wOffFCB1;
  WORD wSegFCB1;
  WORD wOffFCB2;
  WORD wSegFCB2;
} EXECPARMS;

typedef struct tagBUFFHEADER
{
  int  iStructLen;
  int  iBuffLen;
  LPVOID lpBuff;
} BUFFHEADER;

typedef struct tagPRIVATEMSGBUFF
{
  int iMsgID;
  int iBuffLen;
  char aMsgBuff[ SCS_MAXLENMSGBUFF ];
} PRIVATEMSGBUFF;

typedef struct tagCURRHOSTNAME
{
  LPSTR lpszNodeAddress;
  LPSTR lpszGroupName;
  LPSTR lpszHostName;
  UINT  iHostVersion;
  LPSTR lpsSerial;
  LPSTR lpsReserved;
} CURRHOSTNAME;

typedef struct tagHOSTDATABUFF
{
  char szGroupName[ SCS_MAXLENGROUPNAME
+ 1 ];
  char szHostName[ SCS_MAXLENHOSTNAME + 1
];
  BYTE nMinorVersion;
  BYTE nMajorVersion;
  char sHostSerial[ SCS_MAXLENSERIALNUM ];

  unsigned char bPasswordProtect : 1;
  unsigned char bNotInUseYet : 7;
  char cReserved[ SCS_MAXLENRESERVED ];
  char nHostStatus;
} HOSTDATABUFF;

typedef struct tagHOSTLISTBUFF
{
  char szNodeAddress[ SCS_MAXLENNODEADD ];
  HOSTDATABUFF HostDataBuff;
} HOSTLISTBUFF;

typedef struct tagHOSTLISTENTRIES
{
  int iNumEntries;
  HOSTLISTBUFF *aHostListBuff;
} HOSTLISTENTRIES;

typedef struct tagHOSTLISTBOXENTRY
{
  HOSTLISTBUFF HostListBuff;
  char nAttribute;
} HOSTLISTBOXENTRY;

typedef struct tagHOSTLISTBOXENTRIES
{
  int iNumEntries;
  HOSTLISTBOXENTRY aHostListBoxEntries[];
} HOSTLISTBOXENTRIES;

typedef struct tagLISTBOXENTRY
{
  char far *pszEntry;
  char nAttribute;
} LISTBOXENTRY;

#pragma pack(1)
typedef struct tagMSGBOXBUFF
{
  char far *pszText;
  char nAlignment;
} MSGBOXBUFF;
#pragma pack()

typedef struct tagSYSTEMSTATUSBUFF
{
  BYTE nCurrentAdMode;
  char szLastConnect[ SCS_MAXLENPHONEBOOK
];
  BYTE nCallProgress;
  BYTE nProtocolId;
  BYTE tbSentRequestConnect;
} SYSTEMSTATUSBUFF;

typedef struct tagOCCLUDETEXT
{
  int yULRow;
  int xULCol;
  int yLRRow;
  int xLRCol;
} OCCLUDETEXT;

typedef struct tagOCCLUDEDOSGRAPHICS
{
  int xULDos;
  int yULDos;
  int xLRDos;
  int yLRDos;
} OCCLUDEDOSGRAPHICS;

typedef struct tagOCCLUDERWIN
{
  int xULWin;
  int yULWin;
  int xLRWin;
  int yLRWin;
} OCCLUDERWIN;

typedef union tagOCCLUDEUNION
{
  OCCLUDETEXT occText;
  OCCLUDEDOSGRAPHICS occDosGraph;
  OCCLUDERWIN occRWin;
} OCCLUDEUNION;

#pragma pack(1)
typedef struct tagMCB
{
  unsigned char cType;
  WORD      wOwner;
  WORD      wSize;
  unsigned char aUnused[3];
  unsigned char sDOS4[8];
} MCB;
#pragma pack()

#define SHC_SPKRPOLLFREQ       0x0006

#define SHC_HVRAMSEG           0xF800
#define SHC_HVRAMOFF           0x0000
#define SHC_MAXLENHVRAM        0x1458
#define SHC_SEDEGLUPTABLE      0x0040
#define SHC_OFFSCREENROWS      0x0004
#define SHC_OFFCHARSCANLINES   0x0005
#define SHC_ADDSCREENROWS      0x00000484
#define SHC_ADDCHARSCANLINES   0x00000485

#define SHC_MAXLENHEAP         20000
#define SHC_MAXLENKBBUFF       16

#define SHC_VIDSTATEFUNC       0x1C

#define SHC_VIDEOHARDWARE      0x01
#define SHC_VIDEODATAAREA      0x02
#define SHC_COLORPALREGS       0x04

#define SHC_SIZEOFBUFF         0x00
#define SHC_SAVEVIDEO          0x01
#define SHC_RESTOREVIDEO       0x02

#define SHC_VIDSTATEBLOCKSIZE  0x44

#define SHC_XVGARES            640
#define SHC_YVGARES            480

#define SHC_DEFCONTRASTIDX     11
#define SHC_DEFBRIGHTNESSIDX   23

#define SHC_HIMEMSEG           0xC000

#define SMD_SCHEDULERS         0x01
#define SMD_HOTKEYS            0x02
#define SMD_GENERALTRAPS       0x04
#define SMD_COMMSVCS           0x08
#define SMD_INTSSVCS           0x10

#define SMD_MOUSEXWATCH        0x20
#define SMD_FARCALLS           0x40
#define SMD_SYSMASK            0x80

#define SMD_FULLREENTER   SMD_INTSSVCS
#define SMD_NOREENTRANCE  (
SMD_SCHEDULERS | SMD_HOTKEYS |
SMD_GENERALTRAPS | \
                  SMD_COMMSVCS |
SMD_INTSSVCS |
SMD_MOUSEXWATCH | \
                  SMD_FARCALLS )

#define SMD_REENTERSCHED (
SMD_HOTKEYS | SMD_FARCALLS |
SMD_GENERALTRAPS | \
                  SMD_COMMSVCS |
SMD_INTSSVCS |
SMD_MOUSEXWATCH )

#define SMD_MAXRECOUNTSCHED  1
#define SMD_MAXTHREADS       17
#define SMD_REUSETHREADS     12

#define SMD_DISPATFREQ    ( DWORD )1

#define SMD_IRET     0
#define SMD_CLDINT   1
#define SMD_EITHER   2

#define SMD_EVENTSTACKLIMIT 10

#define SMD_DOSINT          0x21
#define SMD_DOSEXEC         0x4B00
#define SMD_DOSALLOCMEM     0x4800
#define SMD_DOSFREEMEM      0x4900
#define SMD_GETLISTOFLISTS  0x5200

#define SMD_GETSETALLOCSTRAT 0x5800
#define SMD_GETALLOCSTRAT    0x5800
#define SMD_SETALLOCSTRAT    0x5801
#define SMD_ALLOCFIRSTFIT    0x0000
#define SMD_ALLOCBESTFIT     0x0001
#define SMD_ALLOCLASTFIT     0x0002

#define SMD_CALLOPCODE    ( BYTE )0x9A
#define SMD_RETOPCODE     ( BYTE )0xCB

#define SMD_THREADACTIVE    0xFFFF

#define SMD_NOACTIVETHREAD  -1

#define PCS_BEGINCRITICAL  disable_intq()
#define PCS_ENDCRITICAL    enable_intq()

#define SMI_GETMASK         0x0000

#define SMI_SUBINTHAND      0x0000
#define SMI_SUBPOLLFREQ     0
#define SMI_SUBEVENTNUM     0

#define SMI_SUBNOTLOADED    0
#define SMI_SUBLOADING      1
#define SMI_SUBUNLOADING    2
#define SMI_SUBLOADED       3
#define SMI_SUBDEACTIVATING 4
#define SMI_SUBINACTIVE     5

#define SMI_SUBMAXNUMBOXLINES [illegible]

#define SMI_SETCONTRAST      0x000A
#define SMI_GETCONTRAST      0x000A
#define SMI_SETBRIGHTNESS    0x000B
#define SMI_GETBRIGHTNESS    0x000B
#define SMI_SETAUTOSHUTOFF   0x000F
#define SMI_GETAUTOSHUTOFF   0x000F
#define SMI_SETSLEEPTIME     0x0010
#define SMI_GETSLEEPTIME     0x0010
#define SMI_REBOOTHOST       0x0011
#define SMI_ACTIVSUPDATE     0x0012
#define SMI_OCUPDATE         0x0013

#define SMI_UPDATEHOSTLIST   0x0020

#define SMI_GETHOSTLISTSTAT  0x0021
#define SMI_AVAILABLE        0x0000
#define SMI_INPROGRESS       0x0001
#define SMI_BLANK            0x0002

#define SMI_CALIBUPLEFT      0x000C
#define SMI_CALIBLOWRIGHT    0x000C
#define SMI_CALIBCANCEL      0x000E
#define SMI_CALIBPOLLFREQ    0x0001

#define SMI_GETCONNECTSTAT   0x0022
#define SMI_SCSDISCONNECTED  0x01
#define SMI_SCSWAITINGFORCONNECT 0x01

#define SMI_SCSDIALING       0x02
#define SMI_SCSCONNECTED     0x03
#define SMI_SCSLOGGINGON     0x04
#define SMI_SCSNETWARESPX    0x06
#define SMI_SCSASYNC         0x07
#define SMI_CONNECTED        0x00
#define SMI_DIALING          0x01
#define SMI_WAITINGFORCONNECT 0x02
#define SMI_LOGGINGON        0x03
#define SMI_DISCONNECTED     0x04
#define SMI_INVALIDHOST      0x05
#define SMI_INVALIDPASSWORD  0x06
#define SMI_CONNECTTIMEOUT   0x07
#define SMI_BUSY             0x08
#define SMI_NOCARRIER        0x09
#define SMI_NODIALTONE       0x0A
#define SMI_WAITINGFORREDIAL 0x0B
#define SMI_NETWARESPX       0x00
#define SMI_MODEM            0x01
#define SMI_SERIAL           0x02

#define SMI_REQUESTCONNECT   0x0023

#define SMI_REQUESTDISCO     0x0023
#define SMI_ABORTREQCONNECT  0x0024
#define SMI_GETPASSWORDSTAT  0x0025
#define SMI_LBSETMODEMDESC   0x0026
#define SMI_LBGETMODEMDESC   0x0026
#define SMI_LBSETPHONELIST   0x0027
#define SMI_LBGETPHONELIST   0x0027
#define SMI_LBSETMODEMMANU   0x0028
#define SMI_LBGETMODEMMANU   0x0028
#define SMI_LBSETMODEMBAUD   0x0029
#define SMI_LBGETMODEMBAUD   0x0029
#define SMI_LBSETNETGROUP    0x002A
#define SMI_LBGETNETGROUP    0x002A
#define SMI_LBSETNETHOST     0x002B
#define SMI_LBGETNETHOST     0x002B

#define SMI_SETCONNECTTYPE   0x002C
#define SMI_GETCONNECTTYPE   0x002C
#define SMI_NETWORKCONNECT   0x0000
#define SMI_MODEMCONNECT     0x0001
#define SMI_SERIALCONNECT    0x0002

#define SMI_SETUSERID        0x002D
#define SMI_GETUSERID        0x002D
#define SMI_SETPASSWORD      0x002E
#define SMI_GETPASSWORD      0x002E
#define SMI_SETMODEMTONE     0x002F
#define SMI_GETMODEMTONE     0x002F
#define SMI_SETMODEMPREFIX   0x0030
#define SMI_GETMODEMPREFIX   0x0030
#define SMI_SETMODEMSUFFIX   0x0031
#define SMI_GETMODEMSUFFIX   0x0031
#define SMI_SETMODEMRINGS    0x0032
#define SMI_GETMODEMRINGS    0x0032
#define SMI_SETMODEMRETRY    0x0033
#define SMI_GETMODEMRETRY    0x0033
#define SMI_SETMODEMDELAY    0x0034
#define SMI_GETMODEMDELAY    0x0034
#define SMI_SETMODEMINITSTR  0x0035
#define SMI_GETMODEMINITSTR  0x0035
#define SMI_SETMODEMAUTOSTR  0x0036
#define SMI_GETMODEMAUTOSTR  0x0036
#define SMI_SETMODEMDISCOSTR 0x0037
#define SMI_GETMODEMDISCOSTR 0x0037
#define SMI_SETCONNECTRSPSTR 0x0038
#define SMI_GETCONNECTRSPSTR 0x0038
#define SMI_GETMODEMDEFAULTS 0x0039
#define SMI_LBGETNETFRAMETYPE 0x003A
#define SMI_LBSETNETFRAMETYPE 0x003A

#define SMI_UPDATESMMLOC     0x0002
#define SMI_REQUESTUNLOAD    0x0003
#define SMI_UNLOADDENIED     0x0001
#define SMI_UNLOADACCEPTED   0x0000

#define SMI_SETMSGBOXRETCODE 0x0006
#define SMI_SETUILANGUAGE    0x0007
#define SMI_GETUILANGUAGE    0x0007
#define SMI_UKENGLISH        0x00

#define SMI_SETVIDEOBLOCK    0x0008
#define SMI_CLEARVIDEOBLOCK  0x0008

#define SMI_NOTIFYSCRCODE    0x000A

#define SMI_SETACTIVESTAT    0x0000
#define SMI_SETKEYSTROKE     0x0001

#define SMI_GETKEYBOARDSTAT  0x0002
#define SMI_KBDNOTPRESENT    0x00
#define SMI_KBDPRESENT       0x01

#define SMI_GETABOUTDIALOG   0x0003
#define SMI_GETNEXTCREDITS   0x0004
#define SMI_SETUDNOTICON     0x0005
```

```
#define SM_GETUIDNOTICON      0x0000
#define SM_SETSECURITYID      0x0004
#define SM_GETSECURITYID      0x0000
#define SM_SETDOMAINID        0x0007
#define SM_GETDOMAINID        0x0007
#define SM_SETLOCKKBDMOUSE    0x1001
#define SM_GETLOCKKBDMOUSE    0x0000
#define SM_DISABLEDLOCKKBDMOUSE 0x0000
#define SM_ENABLEDLOCKKBDMOUSE  0x0001

#define SM_SETDIMSCREEN       0x000A
#define SM_GETDIMSCREEN       0x000A
#define SM_DISABLEDDIMSCREEN  0x0000
#define SM_ENABLEDDIMSCREEN   0x0001

#define SM_SCSINTNUM          0x0000
#define SM_SCSPOLLFREQ        0
#define SM_SCSEVENTNUM        1

#define SM_SCSLOADING         0x0100
#define SM_SCSINACTIVE        0x0000
#define SM_SCSACTIVE          0x0001

#define SM_SCSNOWAITFORDOS    FALSE
#define SM_SCSWAITFORDOS      TRUE

#define SM_SCSABORTCOMM       { 0x1b, 0x1b,
0x1a }

#define SM_SLLOADSUI          0x1000
#define SM_SLPOLLFREQ         2

#define SM_SLENABLEKBD        0x0001
#define SM_SLGETFRAMETYPE     0x0002
#define SM_SLGETFINECLOSVIDVECTOR 0x0003
#define SM_SLGETMLIDSTATUS    0x0004

#define SM_EVENTLOOPBASE      0x4000
#define SM_UNLOADOSK          (
SM_EVENTLOOPBASE + 1 )
#define SM_CHANGETOBADVIDEO (
SM_EVENTLOOPBASE + 2 )
#define SM_CHANGETOGOODVIDEO (
SM_EVENTLOOPBASE + 3 )

#define SM_PRIMSGBASE         0x1000
#define SM_REQFLASHUPD        (
SM_PRIMSGBASE + HM_PM_FILEREQ )
#define SM_ACKFLASHBREAK      (
SM_PRIMSGBASE +
HM_PM_FLASH_BREAK )
#define SM_ACKTOTALFILES      (
SM_PRIMSGBASE + HM_PM_TOTALFILES
)
#define SM_REQPATHPROMDX      (
SM_PRIMSGBASE + HM_PM_PATHREQ )
#define SM_ACKPATHASSTRING    (
SM_PRIMSGBASE + HM_PM_PATHREP )
#define SM_REQACTIVEUPDATE    (
SM_PRIMSGBASE + HM_PM_FLASH_NAMQ
)
#define SM_ACKACTIVEUPDATE    (
SM_PRIMSGBASE + HM_PM_FLASH_NAMP
)
#define SM_REQFLASHDONE       (
SM_PRIMSGBASE + HM_PM_FLASHOK )
#define SM_REQNOTIFYDOWN      (
SM_PRIMSGBASE + HM_PM_DOWNIN )
#define SM_REQOCCDEFINE       (
SM_PRIMSGBASE + HM_PM_OSK_DEFINE
)
#define SM_ACKOCCDEFINE       (
SM_PRIMSGBASE +
HM_PM_OSK_DEFINE_ACK )
#define SM_REQOCCCLOSE        (
SM_PRIMSGBASE + HM_PM_OSK_CLOSE
)
#define SM_ACKOCCCLOSE        (
SM_PRIMSGBASE +
HM_PM_OSK_CLOSE_ACK )
#define SM_REQUNHOCCCLOSE     (
SM_PRIMSGBASE +
HM_PM_OSK_CLOSE_UNH )
#define SM_ACKUNHOCCCLOSE     (
SM_PRIMSGBASE +
HM_PM_OSK_CLOSE_UNH_ACK )

#define SM_SEQRLMNTNUM        0x0000
#define SM_ENDRLMNTNUM        0x0005
#define SM_RLNPOLLFREQ        0
#define SM_RLNEVENTNUM        3

#define SM_PNDINTNUM          0x000A
#define SM_PNDPOLLFREQ        0
#define SM_PNDEVENTNUM        2

#define SM_PNDLOADING         0x0001

#define SM_PRXINTNUM          0x0000

#define SM_PRXEVENTNUM        0
#define SM_PRXPOLLFREQ        0

#define SM_PRXPOWERMANCE      0x0000
#define SM_PRXUNLOADING       0x0001
#define SM_PRXNETCONFIG       0x0002
#define SM_PRXICHGREVINFO     0x0003

#define SUI_INTNUM            0x0005
#define SUI_POLLFREQ          0
#define SUI_EVENTNUM          4
#define SUI_CLEANUPEVENTNUM   10
#define SUI_PRIMSGPOLLFREQ    5
#define SUI_MSGBOXPOLLFREQ    3
#define SUI_PROCMSGBOXPOLLFREQ 1

#define SUI_MSGBOXCONNECTTIMEOUT 20
#define SUI_LOGINTIMEOUT      120

#define SUI_CALIBPOINTDONE    0x0000
#define SUI_XCALIBPOINT       4
#define SUI_YCALIBPOINT       4

#define SUI_UPDATEFLASHPRCNT  0x0014
#define SUI_DISPLAYDIALOG     0x0001

#define SUI_CLOSEDIALOG       0x0000
#define SUI_NOUNLOADSUI       0
#define SUI_UNLOADSUI         1

#define SUI_SHOWMSGBOX        0x0000

#define SUI_NOSLEEPSLIDERBOX  0

#define SUI_UPDATECONNECTSTATUS 0x0030

#define SUI_HIDEMSGBOX        0x0014
#define SUI_LEFTJUSTIFIED     0
#define SUI_CENTERJUSTIFIED   1
#define SUI_RIGHTJUSTIFIED    2
#define SUI_NOBUTTONS         0x0000
#define SUI_OK                0x0001
#define SUI_CANCEL            0x0002
#define SUI_ABORT             0x0004
#define SUI_RETRY             0x0008
#define SUI_IGNORE            0x0010
#define SUI_YES               0x0020
#define SUI_NO                0x0040

#define SUI_SHOWHIDEBUSYCURSOR 0x0000
#define SUI_BUSYCURSORON      0
#define SUI_BUSYCURSOROFF     1

#define SUI_MOVEOSK           0x0000

#define SUI_GETSUIVERSION     0x0000

#define SUI_PARTIALDIALOGSET  0x0001
#define SUI_FULLDIALOGSET     0x0000

#define SUI_OSKASSETUPDIALOGMASK 0x0000
#define SUI_OSKUNCLOSEMASK    0x0000
#define SUI_OSKVIDCHANGEMASK  0x2000
#define SUI_OSKWINGRAPHICSMASK 0x1000

#define SUI_NOSCREEN          0x0000

#define SUI_SMALLALPHA        0x0001
#define SUI_YULSMALLALPHA     0x0040
#define SUI_XULSMALLALPHA     0x0000
#define SUI_YLRSMALLALPHA     0x00E3
#define SUI_XLRSMALLALPHA     0x01F7

#define SUI_SMALLNUMERIC      0x0002
#define SUI_YULSMALLNUMERIC   0x0040
#define SUI_XULSMALLNUMERIC   0x0100
#define SUI_YLRSMALLNUMERIC   0x00E3
#define SUI_XLRSMALLNUMERIC   0x017F

#define SUI_SMALLFULL         0x0003
#define SUI_YULSMALLFULL      0x0040
#define SUI_XULSMALLFULL      0x0000
#define SUI_YLRSMALLFULL      0x00E3
#define SUI_XLRSMALLFULL      0x023F

#define SUI_BIGALPHA          0x0005
#define SUI_YULBIGALPHA       0x0040
#define SUI_XULBIGALPHA       0x0040
#define SUI_YLRBIGALPHA       0x013E
#define SUI_XLRBIGALPHA       0x0237

#define SUI_BIGNUMERIC        0x0006
#define SUI_YULBIGNUMERIC     0x0040
#define SUI_XULBIGNUMERIC     0x00E0
#define SUI_YLRBIGNUMERIC     0x013E
#define SUI_XLRBIGNUMERIC     0x018F

#define SUI_BIGFULL           0x0007
#define SUI_YULBIGFULL        0x0040
#define SUI_XULBIGFULL        0x0000
#define SUI_YLRBIGFULL        0x013E
#define SUI_XLRBIGFULL        0x027F

#define SUI_WINDOWSOSK        0x01
#define SUI_DOSOSK            0x02
#define SUI_SETUPDLG          0x03

#define SUI_PENCALIBRATION    0x0000

#define SUI_LOGIN             0x0000

#define SUI_HOSTSELECTION     0x0000
#define SUI_HOTKEYS           0x0010
#define SUI_MAINTANENCE       0x0010
#define SUI_POWER             0x0020
#define SUI_MODEM             0x0020
#define SUI_SCREEN            0x0030

#define SUI_SETUPDLGMASK      0x00F0
#define SUI_OSKMASK           0x0007

#define SUI_UGNOTICON1        0x0001
#define SUI_UGNOTICON2        0x0002
#define SUI_UGNOTICON1DEF     { 0x0011,
0x0001, 0x0017, 0x0007,
0x0031, 0x0001, 1
                    0x001C, 0x000C }
#define SUI_MAXLENDEFNOTICON  0x0010

#define IsOSK( code )         ( LOBYTE( code ) <=
SUI_BIGFULL
&& \
                    LOBYTE( code ) >
SUI_NOSCREEN
)
#define IsOSKAsSetupDlg( code ) ( ( code &
SUI_OSKASSETUPDIALOGMASK ) && IsOSK(
code ) )
#define IsOSKUnClose( code )  ( ( code &
SUI_OSKUNCLOSEMASK )
&& IsOSK( code ) )
#define IsOSKVidChange( code ) ( ( code &
SUI_OSKVIDCHANGEMASK
) && IsOSK( code ) )
#define IsOSKWinGraphics( code ) ( ( code &
SUI_OSKWINGRAPHICSMASK ) && IsOSK(
code ) )
#define IsSetupDlg( code )    ( LOBYTE( code ) >
SUI_BIGFULL )
#define IsNoScreen( code )    ( LOBYTE( code )
== SUI_NOSCREEN
)

#define IsOSKVideoSupported( code ) ( code ==
SUI_TEXTVIDMODE )

#define SUI_LOADSUINTNUM      0
#define SUI_LOADSUIPOLLFREQ   1L
#define SUI_LOADSUIMAXRETRY   10
#define SUI_CLEANUPMAXRETRY   1000
#define SUI_LOADSUI
#define SUI_CANCELCONNPOLLFREQ 0
#define SUI_CANCELCONNMAXRETRY 25
#define SUI_UNLOADSUIPOLLFREQ 1L

#define SUI_EXECNAME          "SARULEXE"

#define SUI_INITIALVIDMODE    0x12
#define SUI_TEXTVIDMODE       0x03
#define SUI_CLEARBIT          0x80

#define SUI_OSKNOTVISIBLE     0x00
#define SUI_OSKVISIBLE        0x01

#define SUI_LBENTRYENABLED    1
#define SUI_LBENTRYDISABLED   0

#define SUI_LBCURRENTRY       -1

typedef enum tagOCCTYPE
{
  SUI_NOOCCTYPE,
  SUI_OCCDOSTEXT,
  SUI_OCCDOSGRAPHICS,
  SUI_OCCRWIN,
} OCCTYPE;

#define SCS_INTNUM            0x0000
#define SCS_ACCEPTED          1
#define SCS_REJECTED          0
#define SCS_DISCOEVENTNUM     7
#define SCS_DISCOPOLLFREQ     3
#define SCS_LOADSCSPOLLFREQ   1
#define SCS_PRIMSGEVENTNUM    0
#define SCS_PRIMSGPOLLFREQ    1
#define SCS_FILEMEMPOLLFREQ   1
#define SCS_VIDBLOCKPOLLFREQ  1
#define SCS_VIDBLOCKMAXRETRY  32

#define SCS_HOSTCTRLPOLLFREQ  2
#define SCS_HOSTCTRLMAXRETRY  15
#define SCS_WAITSUIPOLLFREQ   1
#define SCS_WAITACKPOLLFREQ   1
#define SCS_WAITACKMAXRETRY   20
#define SCS_DOHOSTOCCPOLLFREQ 1
#define SCS_DOHOSTOCCMAXRETRY 3
#define SCS_SENDPWPOLLFREQ    2
#define SCS_SENDPWMAXRETRY    3

#define SCS_REQUESTHOSTLIST   0x3000
#define SCS_HOSTLISTNUMOFFSET 2

#define SCS_CANCELREQHOSTLIST 0x3A00

#define SCS_ENABLEDCON        0x0001

#define SCS_DISCODISABLECON   0x0000

typedef enum tagCONNERROR
{
  SCS_NOCONNERROR,
  SCS_ERRMAKECON,
  SCS_ERRMONITITOR,
  SCS_ERRFULLSCRPAINT,
  SCS_ERRTIMEOUT,
  SCS_ERRUSERABORT,
  SCS_ERRPASSWORD,
  SCS_ERRLOGINID,
  SCS_ERRUNSUPVIDMODE,
  SCS_ERRUNKNOWN,
} CONNERROR;

typedef enum tagSCOSCONNERROR
{
  SCS_NOLOGINERROR = 0,
  SCS_PASSWORDREJECTED = 15,
  SCS_LOGINIDREJECTED,
  SCS_LOGINUSERREJECTED,
  SCS_REMOTEDISCONNECTED,
  SCS_RESPONSETIMEOUT,
  SCS_UNSUPPORTEDVIDMODE = 47,
  SCS_OUTSIDERANGE = 256,
} SCOSCONNERROR;

#define SCS_SCSREMOTECTRL     0
#define SCS_SCSTTY            1
#define SCS_SCSVT100          2
#define SCS_SCSVT102          3
#define SCS_SPX               0
#define SCS_ASYNCH            7

#define SCS_STRDEFUSERID      "DEFAULT___"

#define SCS_FREEMEM           0x4200

#define SCS_FREEOSKMEM        0x4300

#define SCS_SETBUSY           0x4400
#define SCS_SETIDLE           0x4000

#define SCS_FULLREPAINT       0x4000

#define SCS_SETSCROLLING      0x4700
#define SCS_DISABLESCROLL     0x00
#define SCS_ENABLESCROLL      0x01

#define SCS_OCCLUDE2          0x4C00

#define SCS_DLGFREEMEMPERCENT 100
#define SCS_OSKFREEMEMPERCENT 30

#define SCS_WIDTHOFTEXTCHAR   8
#define SCS_HEIGHTOFTEXTCHAR  16
#define SCS_OSKTEXTCHARHEIGHT 6
#define SCS_OSKTEXTCHARWIDTH  6

#define SCS_SCOSVIDEO         0x3D00
#define SCS_SCOSVIDBLOCK      1
#define SCS_SCOSVIDUNBLOCK    0

#define SCS_SETUPKEYBSTATEBUFF 0x3E00

#define SCS_REBOOTHOST        0x4100

#define SCS_MONITOROFF        0x1E00
#define SCS_MONITORON         0x2000
#define SCS_LOCALKBOFF        0x0001
#define SCS_LOCALKBON         0x0000

#define SCS_SENDKBSCANCODE    0x2b00

#define SCS_XFERFILE          0x3000
#define SCS_TOHOST            0x0000
#define SCS_TOSARATOGA        0x0001
```

```
#define SCS_REBOOTHOST 0x4100

#define SCS_LOCKHOST 0x0200
#define SCS_UNLOCKKBDMOUSE 0x0000
#define SCS_LOCKKBDMOUSE 0x0001
#define SCS_UNBLANKDISPLAY 0x0002
#define SCS_BLANKDISPLAY 0x0003

#define SCS_PINGPRIMSG 0x3000

#define SCS_ZIUNOLOCATION 0xFF00

#define SCS_REPAINTREQUIRED 0x0001
#define SCS_NOREPAINTREQUIRED 0x0000

#define SCS_NOUPDATEICON 0
#define SCS_UPDATEICON 1
#define SCS_NOCONNECTREQUESTED FALSE
#define SCS_CONNECTREQUESTED TRUE

#define SCS_RETAINERROR FALSE
#define SCS_CLEARERROR TRUE

#define SCS_HOSTNOSTATUS 0
#define SCS_HOSTAVAILABLE 'a'
#define SCS_HOSTCONNECTED 'c'
#define SCS_HOSTUNAVAILABLE 'u'

#define FLU_POLLFREQ 1
#define FLU_PRIMSGPOLLFREQ 4
#define FLU_MAXRETRY 30
#define FLU_MAXACTUPDREQ (
FLU_MAXRETRY - 6 )
#define FLU_NODACTUPDREQ 5
#define FLU_NODPCNTTMPFILE 7
#define FLU_MAXPCNTTMPFILE (
FLU_MAXRETRY / 2 )
#define FLU_MAXUPDREQ (
FLU_MAXRETRY / 2 )
#define FLU_NODPATHREQ 5

#define FLU_MAXPATHREQ (
FLU_MAXRETRY / 2 )
#define FLU_MAXRECVFILEREQ (
FLU_MAXRETRY - 3 )
#define FLU_MAXFLASHIT ( FLU_MAXRETRY
- 3 )
#define FLU_MAXCLEARESROM (
FLU_MAXRETRY - 3 )
#define FLU_MAXDOSBUSY (
FLU_MAXRETRY - 5 )
#define FLU_TIMEOUTPRIMSG 2

#define FLU_SIZEFLASHSECTOR 0x10000L

#define FLU_FLASHFILEID 'F'

#define FLU_NUMBERUNKNOWN -1
#define FLU_ERRHOSTBASE (
HM_FLASH_READ_HDAT )
#define FLU_ERRREADHOSTDAT (
HM_FLASH_READ_HDAT )
#define FLU_ERRMISSINGFILE (
HM_FLASH_NOT_SOURCE )
#define FLU_ERRNOFLASHFILES (
HM_FLASH_NO_FILES )
#define FLU_ERROUTOFDISKSPACE (
HM_FLASH_CREATE_TEMP )
#define FLU_ERRFILECORRUPTED (
HM_FLASH_BAD_CHECKSUM )
#define FLU_ERRNOCHECKSUM ( .
HM_FLASH_NO_CHECKSUM )

#define FLU_2MEGTHRESHHOLD 10
#define FLU_1MEGEXTENDEDRAM 1000

#define PNO_INTNUM 0x0007
#define PNO_POLLFREQ 2
#define PNO_EVENTNUM 0

#define PNO_SLEEPPOLLFREQ 0
#define PNO_GETDATA 0x0010
#define PNO_PENUP 0x00
#define PNO_PENDOWN 0x01
#define PNO_PENDOWNMOVE 0x03.
#define PNO_NOICON -1
#define PNO_ICONSLEEP 0x0000
#define PNO_ICONSETUP 0x0001
#define PNO_ICONOSK 0x0002
#define PNO_ICONPALLETTE 0x0003
#define PNO_ICONSPEAKER 0x0004
#define PNO_ICONLRMOUSE 0x0005
#define PNO_ICONHOSTCTRLMODE 0x0006
#define PNO_UDEF1 0x0007
#define PNO_UDEF2 0x0008

#define PNO_SETDEVICEMODE 0x0011
#define PNO_MOUSEMODE 0
#define PNO_PENMODE 1

#define PNO_SETVIDEOMODE 0x0012

#define PNO_SETUPDLGMODE 0x0013
#define PNO_SETUPDLGOFF 0
#define PNO_SETUPDLGON 1

#define PNO_SETMOUSEBUTTON 0x0016
#define PNO_LEFTMOUSE 0x0000
#define PNO_RIGHTMOUSE 0x0001

#define PNO_OSKDIMEN 0x0018

#define PNO_HOSTMODE 0x0019
#define PNO_DOSAPP 0x0000
#define PNO_MSWINDOWS3X 0x0001
#define PNO_MSNTW 0x0002
#define PNO_MSPENWINDOWS 0x0003
#define PNO_MSWINDOWS95 0x0004

#define PNO_SETEVENTHANDLER 0x0020

#define PNO_SETCALIBMODE 0x0030
#define PNO_CALIBUL 0x00
#define PNO_CALIBLR 0x01

#define PNO_GETCALIBSTAT 0x0031
#define PNO_CALIBULSTAT 0x0001
#define PNO_CALIBLRSTAT 0x0002
#define PNO_CALIBVALID 0x0004
#define PNO_CALIBDONEINVALID 1
#define PNO_CALIBDONEVALID 0
#define PNO_CALIBNOTDONE -1

#define PNO_ENABLENEWCALIB 0x0032

#define PNO_NOTICONCONFIG 0x0041
#define PNO_MAXXDIGITIZER 3600
#define PNO_MAXYDIGITIZER 3500
#define PNO_NUMNOTICONS 6
#define PNO_TOPMARGIN 60
#define PNO_RIGHTMARGIN 4
#define PNO_VERTSPACING 76
#define PNO_HEIGHT 200
#define PNO_WIDTH 400

#define PNO_XUPPERPENCALIB 0x0252
#define PNO_YUPPERPENCALIB 0x037F
#define PNO_XLOWERPENCALIB 0x0C30
#define PNO_YLOWERPENCALIB 0x0070

#define SMU_ERRORFREQ 1000
#define SMU_ERRORDUR 94
#define SMU_OSCAN 0x10
#define SMU_ALTOSCAN ( SMU_OSCAN +
M_LA )

#define DST_INTNUM 0
#define DST_POLLFREQ 1
#define DST_MAXRETRY 10

#define INI_INTNUM 0
#define INI_POLLFREQ 0

#define HLD_POLLFREQ 15
#define HLD_MAXRETRIES 6

#define HLD_MAXNUMHOSTENTRIES 100
#define HLD_MAXLENHOSTENTRY (
SCS_MAXLENHOSTADD +
SCS_MAXLENHOSTDATA )

#define HLD_VALIDSERIALS 0
#define HLD_DUPLICATESERIALS 1
#define HLD_INVALIDSERIALS 2

#define HLD_NOHOSTAVAIL -1
#define HLD_NOTINGROUP -1
#define HLD_NOHOSTSELECTED 0

#define PMS_WINDOWSLOADED 0x0001

#define SSS_INTNUM 0x0015
#define SSS_SLINTNUM 0x0000
#define SSS_PENNOTIFYPOLLFREQ 2
#define SSS_SARATOGAFUNC 0x0000
#define SSS_MEMORYTOEEPROM 0x0003
#define SSS_EEPROMTOMEMORY 0x0004
#define SSS_ADJUSTBRIGHTNESS 0x0006
#define SSS_ADJUSTCONTRAST 0x0007
#define SSS_SUSPENDFLAGPTR 0x0010
#define SSS_ENADISSPEAKER 0x000A
#define SSS_ENADISRIGHTMOUSE 0x000B

#define SSS_GETBATTERYINFO 0x0005
#define SSS_GETBATTERYINFOERROR 0L
#define SSS_ISPSTATEMASK 0x00000000

#define SSS_ACDCSTATEMASK
0x00400000
#define SSS_SLOWCHARGEMASK
0x00200000
#define SSS_FASTCHARGEMASK
0x00100000
#define SSS_BATTERYATTACHEDMASK
0x000000FF
#define SSS_BATTERYCAPACITYMASK
0x0000FF00

#define SSS_VIDMODEMASK 0x30

#define SSS_BATTERYATTACHED 1L
#define SSS_BATTERYFLASHMINCAP 40

#define SSS_NOENTRYBATTERYINFO (
SSS_ACDCSTATEMASK | 0x00000001 |
0x00000400 )

#define SSS_GETSYSRESUMEBIT 0x001E
#define SSS_CLEARSYSRESUMEBIT 0x0017
#define SSS_NORMALBOOT 0x0000
#define SSS_RESUMING 0x0001

#define SSS_GOTOSLEEP 0x0012
#define SSS_GOTOSUSPEND 0x000E
#define SSS_GOTOSUSPENDSAVE 0x000F

#define SSS_WAITINGICON 0x000C
#define SSS_WAITINGICONOFF 0
#define SSS_WAITINGICONON 1

#define SSS_ENABLEKBD 0x0015

#define SSS_TOWERWAVESICON 0x000D
#define SSS_TOWEROFF 0x0000
#define SSS_TOWERON 0x0001
#define SSS_TOWERSLOWBLINK 0x0003
#define SSS_TOWERMEDBLINK 0x0005
#define SSS_TOWERHIGHBLINK 0x0007
#define SSS_WAVESOFF 0x0000
#define SSS_WAVESON 0x0001
#define SSS_WAVESLOWBLINK 0x0003
#define SSS_WAVESMEDBLINK 0x0005
#define SSS_WAVESHIGHBLINK 0x0007

#define SSS_VIDINTNUM 0x0010
#define SSS_VIDEO 0x1200
#define SSS_VIDEOPALLETTE 0x0005

#define SSS_ENABLEDISABLEWRITE 0x0000
#define SSS_ENABLEWRITE 0x0001
#define SSS_DISABLEWRITE 0x0000

#define SSS_SARATOGAFLASH 0xE100
#define SSS_FLASHNOTEXT 0x0000
#define SSS_FLASHWITHTEXT 0x0001
#define SSS_FLASHAVAILABLE 0x0002
#define SSS_FLASHAVAILRETCODE 0x00E1

#define SSS_1MEGBASESECTOR 0x70
#define SSS_2MEGBASESECTOR 0x60

#define SSS_FLASHSUCCESS 0x00
#define SSS_FLASHACNOTATTACHED 0x01
#define SSS_FLASHERASEERROR 0x02
#define SSS_FLASHPROGERROR 0x03

#define SSS_SETPOWERENABLE 0x0017
#define SSS_POWERMANDISABLED 0
#define SSS_POWERMANENABLED 1
#define SSS_POWERMANCKDCONLY 2

#define SSS_SETDOZETIMEOUT 0x0019
#define SSS_DOZEDISABLED 0
#define SSS_DOZE1SECONDS 1
#define SSS_DOZE4SECONDS 2
#define SSS_DOZE8SECONDS 3
#define SSS_DOZE16SECONDS 4

#define SSS_SETSLEEPTIMEOUT 0x001b
#define SSS_SLEEPDISABLED 0
#define SSS_SLEEPIN1MIN 1
#define SSS_SLEEPIN2MIN 2
#define SSS_SLEEPIN4MIN 3
#define SSS_SLEEPIN6MIN 4
#define SSS_SLEEPIN8MIN 5
#define SSS_SLEEPIN12MIN 6
#define SSS_SLEEPIN16MIN 7

#define SSS_SETSUSPENDTIMEOUT 0x001C
#define SSS_SUSPENDDISABLED 0
#define SSS_SUSPENDIN5MIN 1
#define SSS_SUSPENDIN10MIN 2
#define SSS_SUSPENDIN15MIN 3
#define SSS_SUSPENDIN20MIN 4
#define SSS_SUSPENDIN30MIN 5
#define SSS_SUSPENDIN40MIN 6

#define SSS_SUSPENDIN60MIN 7

#define SSS_LENMOUSECFGDATA 0
#define SSS_OFFMOUSECFGDATA 0
#define SSS_OFFUICFGDATA 0

#define SSS_DEFVIDPALLETTE 0x[illegible]
#define SSS_INVVIDPALLETTE 0x03
#define SSS_MAXNUMVIDPAL 0x06

#define SSS_GETNOSVERSION 0x0000

#define SSS_SIZEOFEXTENDEDMEM 0x0000

#define SSS_SETVIDEOMODEFUNCS 0x00
#define SSS_LOWTEXTVIDMODE 0x00
#define SSS_HIGHTEXTVIDMODE 0x03

#define SSS_MISCELLANEOUSFUNCS 0x12
#define SSS_SETSCANLINESTEXTMODE 0x30
#define SSS_200SCANLINES 0
#define SSS_350SCANLINES 1
#define SSS_400SCANLINES 2

#define SSS_CHARACTERGENFUNCS 0x11
#define SSS_8X14FONTAFTERMODE 0x11
#define SSS_8X8FONTAFTERMODE 0x12
#define SSS_8X16FONTAFTERMODE 0x14

#define SSS_CMOSREADHIGHBYTE 0x31
#define SSS_CMOSREADLOWBYTE 0x30
#define SSS_CMOSPORT 0x0070
#define SSS_CMOSEXTENDEDMEM 0x0071

#define SSS_TELETYPE 0x0E
#define SSS_RELOCATEDSCRADD 0xFE

#define SSS_DRIVERSLOADING 1
#define SSS_BUILOADING 2

#define CRU_RETURNWITHIRET 0
#define CRU_REFLECTINT 2

#define CRU_ONBUSYIRET 0
#define CRU_ONBUSYOLDINT 1
#define CRU_ONBUSYEITHER 2

#define CRU_COLDBOOT 1
#define CRU_WARMBOOT 0

#define PHA_NOTFOUND -1

#define SRT_MAXLENSWAPBUFF 35

#define PM_REQSCSBLANKSCR (
HM_PM_BLANKSCR )
#define PM_REQSCSUNBLANKSCR (
HM_PM_UNBLANKSCR )
#define PM_REQSCSLOCKKBMO (
HM_PM_LOCKKBMO )
#define PM_REQSCSUNLOCKKBMO (
HM_PM_UNLOCKKBMO )

#define PM_REQFLASHINFO (
HM_PM_FILEREQ )
#define PM_ACKTOTALFILES (
HM_PM_TOTALFILES )
#define PM_REQPATHFROMIDX (
HM_PM_PATHREQ )
#define PM_ACKPATHASSTRING (
HM_PM_PATHREP )
#define PM_REQFLASHDONE (
HM_PM_FLASHOK )
#define PM_REQACTIVEUPGRADE (
HM_PM_FLASH_NAMQ )
#define PM_ACKACTIVEUPGRADE (
HM_PM_FLASH_NAMP )

#define PM_REQHOSTCONTROL (
HM_PM_HOSTCON )

#define PM_ACKNOTIFYDOSWIN (
HM_PM_DOSWIN_ACK )

#define PM_REQOCCDEFINE (
HM_PM_OSK_DEFINE )
#define PM_ACKOCCDEFINE (
HM_PM_OSK_DEFINE_ACK )
#define PM_REQOCCCLOSE (
HM_PM_OSK_CLOSE )
#define PM_ACKOCCCLOSE (
HM_PM_OSK_CLOSE_ACK )
#define PM_REQUNIOCCCLOSE (
HM_PM_OSK_CLOSE_UNI )
#define PM_ACKUNIOCCCLOSE (
HM_PM_OSK_CLOSE_UNI_ACK )

#define PM_NOACK 0
#define PM_ACKEDTRUE 1
```

```
extern THREADTYPEID ActiveThreadType;
extern char szSMSignature[];
extern char szSMVersionName[];
extern char szSMVersionNum[];
extern char szSMModuleName[];
extern char szSUIExecName[];
extern char szLNMName;
extern char szTempStr[];
extern char szTempMsgStr[];
extern char szMailStr[];
extern char szPassword[ SUI_MAXLENPASSWORD
+ 1 ];
extern char szSCSAbortCond[];
extern UICONFIGDATA UIConfigData;
extern WORD aHotKeys[];
extern WORD RDATA;
extern MREG MEventOutArgs;
extern FARCALLENTRY lpfnFarCallEntry;
extern BUICB lpfnSUICallBack;
extern LISTBOXENTRY ListBoxEntry;
extern MSGBOXBUFF MsgBoxBuff[];
extern BUFFHEADER BuffHead;
extern WORD uScreenCode;
extern WORD uOldScreenCode;

#define ERR_SUCCESS        0
#define ERR_NOTSUPPORTED   -1
#define ERR_INTERNAL       -2
#define ERR_INVALIDPARM    -3
#define ERR_OUTOFMEM       -4
#define ERR_VERSIONMISMATCH -5
#define ERR_UPGRADENOTAVAIL -6
#define ERR_SCSBUSY        -7
#define ERR_SCSOCCFAILED   -8
#define ERR_SCSSCROLLING   -9
#define ERR_SCSIDLE        -10
#define ERR_SCSFULLREPAINT -11
#define ERR_INPROGRESS     -15000

#define ERR_PNDINTERNAL    -2

typedef enum
{
   TIMEOUT_ERROR,
   TIMEOUT_AVAILABLE,
   TIMEOUT_NOTAVAILABLE,
   TIMEOUT_RUNNING,
   TIMEOUT_FIRED

} TIMEOUT;

typedef enum
{
   TF_SET,
   TF_RESET,
   TF_CHECK

} TIMEOUT_FLAG;

TIMEOUT TimerManager (TIMEOUT_FLAG
fTimeout, int iThreadIdx, long
lData);
Copr 1995 Zenith Data Systems Corp.
typedef struct mem_rec {
      word block_type;
      word owner;
      word size;
      word hdr_seg;
} MEM_REC;
extern char _dos_version[];
word   get_master_env(void);
void   keep_env(void);
word   get_command_psp(void);
int    get_app_name(word AppPSP,void
*AppFname);
extern char far *_cur_app_name;
word   get_dos_mem(word MinSize,MEM_REC
*State);
void   rel_dos_mem(MEM_REC *State);
extern word mouse_size;
word   max_app_mem(void);
dword  calc_app_mem(void);
word   get_app_mem(void *MouseBuf,int
Handle,word LimSeg,word
Min,word Max);
extern word app_MCB,_cpu_switch;
extern byte _load_mask[];
void   far *get_app_ptr(void);
void   rel_app_mem(void *MouseBuf,int Handle,fp
ErrorFunc);
int    get_lim_mem(int Handle,int Page,int Cnt,word
Loc,word
LimSeg);
extern word lim_MCB;
int    rel_lim_mem(word Cif);

int    spawn(void *Program,void *CmdLn,word
Env,word FreeMCB);

int    spawn_a(void *Program,void *CmdLn);
word   shrink_mem(word NewBlockSize);

int    spawn_b(void *Program,word Env,int
SetHandle);
void   prep_shared_mem(word SharedSize);
extern void *shared_mem;
void   far *get_shared_mem(void);
word   split_mcb(word OrigMCB,word NoPara);
void   far *fill_wnd(void far *Mem,word Filler,word
Cnt);

int    make_dos_idle(void *DosStateBuf);
void   undo_dos_idle(void *DosStateBuf);
extern word _dos_idle_loc;
void   _no_dos_idle(void);

word   save_gs(word Handle,word LimSeg,word
Mode,dword Fpos,void
far *TmpBuf);
word   restore_gs(word Handle,word LimSeg,word
Mode,dword
Fpos,void far *TmpBuf);
void   saved_gs_on(void);
extern word _min_vram,_max_vram,_min_graphics;
int    is_graphics(void);
extern word _MinVram,_MaxVram,_MinGraphics;
void   init_video(fp SetRetrace);
void   toggle_blinks(void);
void   get_rgb_colors(void *RGB_buf,int StartReg,int
RegCnt);
void   set_rgb_colors(void *RGB_buf,int StartReg,int
RegCnt);
char   *save_com(word BasePort,void *Buff);
char   *restore_com(word BasePort,void *Buff);

typedef struct Mreg { word ax,bx,cx,dx,si,di,ds,es; }
MREG;
word   mouse(MREG *InArgs,MREG *OutArgs);
void   get_mouse(void *StateBuffer);
void   set_mouse(void *StateBuffer);
    install_mouse(fp Service,word StkSize,byte
LockMask);
word   mouse_event(word Trigger);

int    is_network(void);
char   network_swap_eoj(char NewEOJ);
int    get_spl_convert(void);
void   set_spl_convert(int Server);
Copr. 1995 Zenith Data Systems Corp.

#define MAX_CHANNELS 16

typedef struct chain {
  char *ch_buf;
  word ch_size;
  word ch_crit;
} CHAIN;

typedef struct buf_ctl {
  char *Buf;
  char *Top;
  char *Put;
  char *Get;
  word Size;
  word Cnt;
  word CritCnt;
  CHAIN *Chain;
} BUF_CTL;

typedef struct ser_ctl {
  int SerPort2;
  char IRQ;
  char SerChanNum;
  char XmitCtl,RcvCtl;
  char ErrCtl;
  char RingCtl;
  char SerIntMask;
  char ServReq;
  int UserField;
  fp RingService;
  fp XmitService;
  fp RcvService;
  fp ErrService;
  fp KeyEntry[4];
  int LibWord[4];
  int StatusWord;
  BUF_CTL rcv;
  BUF_CTL xmt;
} SER_CTL;

typedef struct ser_pctl {
  int SerPort2;
  char *SetPtr;
  word ReqCnt;
  word PollCnt;
  word StartTable;
  int ErrorSts;
  char XmitCtl;
  char PollCtl;
} SER_PCTL;

#define BD_50   0x900
#define BD_75   0x600
#define BD_110  0x417
#define BD_134  0x360
#define BD_150  0x300
#define BD_300  0x180
#define BD_600  0xc0
#define BD_1200    0x60
#define BD_1800    0x40
#define BD_2000    0x3a
#define BD_2400    0x30
#define BD_3600    0x20
#define BD_4800    0x18
#define BD_7200    0x10
#define BD_9600    0xc
#define BD_19200 0x6
#define BD_38400 0x3
#define BD_56K   0x2
#define BD_115K  0x1

#define DF_PAR_N 0
#define DF_PAR_O 0x8
#define DF_PAR_E 0x18
#define DF_PAR_M 0x28
#define DF_PAR_S 0x38

#define DF_STOP1 0
#define DF_STOP2 4

#define DF_D5 0
#define DF_D6 1
#define DF_D7 2
#define DF_D8 3

#define DF_8N1 (DF_D8+DF_PAR_N+DF_STOP1)

#define IFC_DTR         1
#define IFC_RTS         2
#define IFC_DTR_DROPPED 4
#define IFC_XOFF    8
#define IFC_XOFF_SENT    0x10

#define OFC_WATCH_XOFF  0x20
#define OFC_GOT_XOFF    0x40
#define OFC_LOCK   0x80

#define SR_RCV_M  0x01
#define SR_RCV_OVF 0x02
#define SR_XMT_LO 0x04
#define SR_XMT_EMP 0x08
#define SR_RING   0x10
#define SR_ERR    0x20

#define SM_RCV      1
#define SM_XMT      2
#define SM_ERR    4
#define SM_RING   8

#define SID_RING   0
#define SID_XMT      1
#define SID_RCV      2
#define SID_ERR      3

#define MC_LOOP   0x10
#define MC_OP2  0x08
#define MC_OP1  0x04
#define MC_RTS 0x02
#define MC_DTR 0x01

#define STA_TXE       0x4000
#define STA_TBE       0x2000
#define STA_BREAK   0x1000
#define STA_FRAM_ERR    0x0800
#define STA_PAR_ERR 0x0400
#define STA_OVR_ERR 0x0200
#define STA_RxRDY  0x0100

#define STA_DCD       0x80
#define STA_RING   0x40
#define STA_DSR       0x20
#define STA_CTS       0x10
#define STA_D_DCD  0x08
#define STA_D_RING 0x04
#define STA_D_DSR  0x02
#define STA_D_CTS  0x01

#define STA_RCV_ERR 0x1E00

#define NUL   0
#define SOH   1
#define STX   2
#define ETX   3
#define EOT   4
#define ENQ   5
#define ACK   6
#define BEL   7
#define BS    8
#define HT    9
#define LF    0xA
#define VT    0xB
#define FF    0xC
#define CR    0xD
#define SO    0xE
#define SI    0xF
#define DLE   0x10
#define DC1   0x11
#define DC2   0x12
#define DC3   0x13
#define DC4   0x14
#define NAK   0x15
#define SYN   0x16
#define ETB   0x17
#define CAN   0x18
#define EM    0x19
#define SUB   0x1A
#define ESC   0x1B
#define FS    0x1C
#define GS    0x1D
#define RS    0x1E
#define US    0x1F
#define SP    0x20
#define DEL   0x7F
#define CTLQ  0x11
#define CTLS  0x13
#define XON   0x11
#define XOFF  0x13

extern SER_CTL *scd;
extern int _sleep_frame;

install_ser(word stk_sz,byte mask,SER_CTL *sc);
install_2ser(word stk_sz,byte mask,SER_CTL *sc);
install_serial(word stk_sz,byte mask,SER_CTL
*sc,int NoChan);
install_ser2a(word stk_sz,byte mask,SER_CTL
*sc,int No1,int
No2);
install_mser(word stk_sz,byte mask,SER_CTL *sc,int
NoChan,int
IdPort);
install_mbser(word stk_sz,byte mask,SER_CTL
*sc,int NoChan,int
IdPort);

void uninstall_ser(void);
void break_on(void);
void break_off(void);
void set_baud(word BaudDivisor, byte DataFormat);
void set_dtr_rts(char ModemControl);
char get_dtr_rts(void);
void prog_8250(void *CommandList);
char fifo_ctl(char FifoCmd);
int  ser_sts(void);
int  ser_in(void);
int  ser_out(char c);
int  ser_inw(word WaitTicks);
int  ser_outw(char c, word WaitTicks);
int  ser_rcv_test(SER_PCTL *CurrentPol);
int  ser_xmt_test(SER_PCTL *CurrentPol);
void set_ibuf(void *InBuf,word BufSize,word CritCnt);
void set_ichain(CHAIN *InChain);
char *load_ichain(void *InBlock,word InCnt);
int  wrap_ichain(CHAIN *InChain,void *OvStart);
void set_obuf(void *OutBuf,word BufSize,word
CritCnt);
```

```
void set_echain(CHAIN *OutChain);
void enable_rsvr(void);
int send_ser(void);
void enable_rsv(void);
void disable_rsv(void);
void enable_xmtr(void);
void enable_rcv(void);
void disable_xmtr(void);
void ser_intr_on(void);
void ser_intr_off(void);
int flush_ser(void);
void restart_xmt(void);
void restart_intr(void);
int ser_get(void);
int ser_get_full(void);
int ser_put(char c);
char *ser_puts(void *s);
int ser_snd_blk(word ByteCnt,word WaitTicks);
int ser_rcv_blk(dword ByteCnt,word WaitTicks);
int blk_get(void *BitMap,int BitNum);
void blk_set(void *BitMap,int BitNum);
int blk_tog(void *BitMap,int BitNum);
dword set_quick_tmr(void);
void set_quick_tmr(dword OldIntVect);
void upd_quick_tmr(void);
dword set_quick_kbd(void);
void rst_quick_kbd(dword OldIntVect);
void lt_int_off(char IntMask);
void lt_int_on(void);
void set_ltr_lev(char TapLevel);
word cm_chsum(void *Buf,word ByteCnt);
word cm_crc(void *Buf,word ByteCnt);
void sleep(void);
void awake(void);
int sleeping(void);
#define reset_sleep() _sleep_flag=0;

char pak_ser_buf(word *SerBuf,int WordCnt);
void unpak_ser_buf(word *SerBuf,int WordCnt,char ValAr);
int remove_blanks(void *Str);
char *ser_n(void *StrList,int N_th);
char *str2beep(void *Str);
char *num2beep(void *Str,int Cnt);
void _oven_beep(void);

extern _dummy_rst();

void set_ser_len(int NoLines);
void reset_ansi(void);
void save_ansi(dword *AnsiState);
void restore_ansi(dword *AnsiState);
void ansi_chr(char c);
int is_ansi_end(void);

extern fp ansi_stra;
extern int ansi_no_args;
extern char ansi_args[];

void reset_vt100(void);
void save_vt100(dword *VT100State);
void restore_vt100(dword *VT100State);
void vt100_chr(char c);
int is_vt100_end(void);

extern fp vt100_stra;
extern int vt100_no_args;
extern char vt100_args[];
Copr 1986 Zenith Data Systems Corp.

PD_PSEO_FREQUENCY    EQU 0000h
PD_TIMER2_16BIT_MODE EQU 0B6h
PD_SPK_DELAY         EQU 4

PD_CURSOR_TOTAL_LEN EQU 3
PD_CURSOR_TOTAL_HGT EQU 10
PD_CUR_IMAGE_SAVE_BUFF EQU 00F00h
PD_CUR_IMAGE_PROC_BUFF EQU 00F30h

PD_REDUCE_MAX       EQU 2

PD_OBRUICALL_PT_80_X EQU 16
PD_OBRUICALL_PT_80_Y EQU 10

PD_TOP_MARGIN      EQU 5
PD_RIGHT_MARGIN    EQU 24
PD_ICON_LENGTH     EQU 1000
PD_ICON_SPACE      EQU 5
PD_HOT_ICON_NUMBER EQU 5

PD_DELAY_PITCH     EQU 1
```

```
PD_TIME_TICK_SEG EQU 0040h
PD_TIME_TICK_OFF EQU 006Ch
PD_TIME_TICK_80  EQU 18

PD_PIXEL_80      EQU 16

PD_SM_INT        EQU 0001h
PD_SM_NOTIFY     EQU 0002h

PD_CALL_OFF_MIN EQU 190

PD_SM_SIG_OFF   EQU 10
PD_SM_INT       EQU 006Ah

PD_IRQ_5        EQU 5
PD_23679        EQU 23679

PD_CXD          EQU 4000
PD_CYD          EQU 4000
PD_CXD          EQU 1000
PD_CYD          EQU 1000

PD_10000        EQU 10000

PD_NO_HOT_ICON  EQU -1

PD_01_PAGE_SIZE EQU 11
PD_23_PAGE_SIZE EQU 13
PD_80           EQU 80
PD_40           EQU 40
PD_01_LENGTH    EQU 80
PD_23_LENGTH    EQU 100
PD_123H_LENGTH  EQU 80
PD_01_SHIFT     EQU 4
PD_23_SHIFT     EQU 3
PD_0123_SHIFT   EQU 3

PD_B000H        EQU 0B000h
PD_BC00H        EQU 0B800h
PL_A000H        EQU 0A000h
PD_45_PAGE1     EQU 0B000h
PD_45_PAGE2     EQU 0BA00h
PD_8K           EQU 0200h
PD_16K          EQU 0400h
PD_32K          EQU 0800h

PD_SENSE_X      EQU 50
PD_SENSE_X      EQU 50
PD_THRESHOLD    EQU 04

PD_0            EQU 0
PD_842          EQU 640
PD_833          EQU 630
PD_834          EQU 634
PD_200          EQU 200
PD_150          EQU 150
PD_350          EQU 350
PD_348          EQU 348
PD_480          EQU 480
PD_479          EQU 479
PD_464          EQU 464
PD_400          EQU 400
PD_320          EQU 320
PD_310          EQU 310
PD_304          EQU 304

PD_ON           EQU 1
PD_OFF          EQU 0
PD_YES          EQU 1
PD_NO           EQU 0
PD_RIGHT        EQU 1
PD_LEFT         EQU 0
PD_DOWN         EQU 1
PD_UP           EQU 0
PD_ZERO         EQU 0
PD_ONE          EQU 1
PD_TWO          EQU 2
PD_NONE         EQU -1

PD_HOT_SPOT_X   EQU 7
PD_HOT_SPOT_Y   EQU 0

PD_P82          EQU 4

PD_SEQUE_ADDR_REG EQU 03C4h
PD_SEQUE_DATA_REG EQU 03C5h
PD_GRAPH_ADDR_REG EQU 03CEh
PD_GRAPH_DATA_REG EQU 03CFh

PD_TXT_SCR_MASK EQU 077FFh
PD_TXT_CUR_MASK EQU 07700h

PD_HALF640      EQU 320
PD_HALF480      EQU 240
PD_HALF300      EQU 150
PD_HALF350      EQU 175

PD_FUNC50MK     EQU 0FC2Ch
```

```
PD_MOUSE_TYPE   EQU 0400h
PD_MOUSE_VER    EQU 0030h

PD_VERSION         EQU '1.0'
PD_VER_MAJOR       EQU '0'
PD_VER_MINOR       EQU '1'
PD_ALREADY_IN      EQU 0
PD_REMOVE_MESSAGE  EQU 1
PD_NOT_IN_MEM      EQU 2
PD_REMOVE_ERROR    EQU 3
PD_CMD_LINE_ERR    EQU 4
PD_LOAD_OK         EQU 5
PD_SM_NOT          EQU 6

sIntVectorReplace struc
 IntNum       db ?
 lOldISROffset dw ?
 lOldISRSeg    dw ?
 lNewISROffset dw ?
sIntVectorReplace ends

mIntVectorReplace MACRO IntNum, lpmOldISR,
lpmNewISR
     db   &IntNum
lpmOldISR  dd  0
     dw   &lpmNewISR
ENDM

sPanelConfig struc
 xUL          dw ?
 yUL          dw ?
 xLR          dw ?
 yLR          dw ?
 nTopMargin   dw ?
 nRightMargin dw ?
 nVertSpace   dw ?
 nHILength    dw ?
 nHIWidth     dw ?
sPanelConfig ends

SetEGAWriteReadMode macro
 mov dx, PD_GRAPH_ADDR_REG
 mov al, 5
 out dx, al
 inc dx
 mov al, ah
 out dx, al
 endm

SetEGABitMask macro
 mov dx, PD_GRAPH_ADDR_REG
 mov al, 8
 out dx, al
 inc dx
 mov al, ah
 out dx, al
 endm

SetEGAColorMask macro
 mov dx, PD_SEQUE_ADDR_REG
 mov al, 2
 out dx, al
 inc dx
 mov al, 0Fh
 out dx, al
 endm

SaveEGARegister macro
 mov dx, PD_GRAPH_ADDR_REG
 in al, dx
 mov es:[bx+2], al
 mov al, 5
 out dx, al
 inc dx
 in al, dx
 mov es:[bx], al
 dec dx
 mov al, 8
 out dx, al
 inc dx
 in al, dx
 mov es:[bx+1], al
 mov dx, PD_SEQUE_ADDR_REG
 in al, dx
 mov es:[bx+4], al
 mov al, 2
 out dx, al
 inc dx
 in al, dx
 mov es:[bx+3], al
 endm

RestoreEGARegister macro
 mov dx, PD_GRAPH_ADDR_REG
 mov al, 5
 out dx, al
 inc dx
 mov al, es:[bx]
```

```
 out dx, al
 dec dx
 mov al, 8
 out dx, al
 inc dx
 mov al, es:[bx+1]
 out dx, al
 dec dx
 mov al, es:[bx+2]
 out dx, al
 mov dx, PD_SEQUE_ADDR_REG
 mov al, 2
 out dx, al
 inc dx
 mov al, es:[bx+3]
 out dx, al
 dec dx
 mov al, es:[bx+4]
 out dx, al
 endm

SaveEntryRegisters macro
 push ax
 push bx
 push cx
 push dx
 push di
 push si
 endm

RestoreEntryRegisters macro
 pop si
 pop di
 pop dx
 pop cx
 pop bx
 pop ax
 endm

Copr. 1986 Zenith Data Systems Corp.
 page ,80
 title PENDRV.ASM - Pen Driver of Sewings
 .286

.model small

include pd.inc
.stack
.code

ORG 100h

startaddr     label  byte
lmTxtScrMask  dw  077FFh
lmTxtCurMask  dw  07700h
lHardstart    dw  0
lHardEnd      dw  7

lVertBarPixels dw 200
lVertcharPixels dw 0

lVideoMode    dw  5
lLanguage     dw  0

lCrtPage      dw  0
lCursorFlag   dw  -1

lHotspotX     dw  1
lHotspotY     dw  0

lHorMin       dw  0
lHorMax       dw  639
lVertMin      dw  0
lVertMax      dw  199

lMaxX         dw  2133
lMaxY         dw  800

lXpos         dw  0
lYpos         dw  0
lLastX        dw  0
lLastY        dw  0

lLastTickCount dw -1000

lLeftTouchCount dw 0
lRightTouchCount dw 0
lLeftInTouchCount dw 0
lRightInTouchCount dw 0
lMouse        dw 0
lMouseBUI     dw 0
lCallMask     dw 0
lpMouseEventHandler dd 0
lpSaveMouseHandler dd 0

lXposFSL      dw  0
```

```
mov lCRTPage,PD_ZERO

cmp lVideoMode,0064h
jge setvmdetohigh

mov lGraResX,PD_639

cmp si,PD_ZERO
je not_chg_scan_lines
mov lVertSerPixels,di
and ax,000h
mov lVertshorPixels,ax

mov ax,di
div al
cmp al,25
jne not_25_line_mode
mov lVertSerPixels,PD_200
mov lVertshorPixels,PD_8

not_25_line_mode:

not_chg_scan_lines:
 mov ax,lVertSerPixels
 dec ax
 mov lGraResY,ax

 jmp endofi712
setvmdetohigh:

 mov lGraResX,PD_639
 mov lGraResY,PD_479
 mov lGraCurDiffX,PD_624
 mov lGrateniX,PD_88

 cmp bx,0000h
 jne end005
 mov lGraResX,PD_319
 mov lGraCurDiffX,PD_304
 mov lGraResY,PD_199
 mov lGrateniX,PD_40
 mov lPagesize,PD_8K
 jmp gfs6712
end005
 cmp bx,0000h
 je mo840200
 cmp bx,0006h
 jg mochith
mo840200.
 mov lGraResY,PD_199
 mov lPagesize,PD_16K
 jmp gfs6712
mochith:
 cmp bx,000Fh
 jne @F
 mov lGraResY,PD_341
 mov lPagesize,PD_32K
 jmp gfs6712
@@.
 cmp bx,0010h
 jne gfs6712
 mov lGraResY,PD_349
 mov lPagesize,PD_32K
gfs6712:
 mov ax,lGraResY
 sub ax,16
 mov lGraCurDiffY,ax
endof6712:

 call _SetModeData
 call _ShowCursor

endofi712:
 jmp end67ier

after6712
 cmp ax,0013h
 jne end6713
 cmp bx, lUIActive
 je notdo6712
 mov lUIActive,bx
 add lOSKUICell, bx
 cmp bx, PD_ZERO
 jne notdo6712
 dec lOSKUICell
notdo6712:
 jmp end67ier
end6713:

 cmp ax,0010h
 jne end6711
 cmp lLeftRight,PD_LEFT
 je @f
 mov lLeftRight,PD_LEFT
 mov lButtonDown,1
 mov lButtonDownTrigger,3
 mov lButtonUpTrigger,4
 jmp end67ier
@@
 mov lLeftRight,PD_RIGHT
 mov lButtonDown,3
 mov lButtonDownTrigger,8
 mov lButtonUpTrigger,10
 jmp end67ier

end6716:
 cmp ax,001Ah
 je lSelect6718h
 jmp end6718h
lSelect6718h:
 mov ax,al
 add ax,bx
 add cx,ax
 add ax,dx
 cmp ax,PD_ZERO
 jne noreset10
 mov lOSKActive,PD_ZERO
 jmp end67ier
noreset10:
 mov lOSKActive,PD_ONE
 mov lOSKULX,bx
 mov lOSKULY,ax
 mov lOSKLRX,dx
 mov dx,al
 mov lOSKLRY,dx
 push ax
 push bx
 push cx
 push dx
 push si
 push di

 mov ax, lOSKUICell
 mov lOSKUICell, PD_OFF
 push ax

 mov ax, PD_479
 sub ax, dx
 mov dx, 1
 cmp ax, cx
 je @F
 mov dx, PD_400
@@:
 mov ax, lButtonMoveTrigger
 mov bx, 0
 mov cx, PD_320
 push cx
 push dx
 sub cx, lXpos
 sub dx, lYpos
 sal dx, 1
 mov si, cx
 mov di, dx
 pop dx
 pop cx
 call _CellHandler
 cli
 pop bx
 mov lOSKUICell, ax

 pop di
 pop si
 pop dx
 pop cx
 pop bx
 pop ax
 jmp end67ier
end6718h.
 cmp ax,0018h
 jne end6719h
 mov lWindows,bx
 jmp end67ier
end6719h:
 cmp ax,0020h
 jne end6720h

 mov lHookBUI,PD_OK
 mov bx,ax
 cmp dx,PD_ZERO
 jne @F
 cmp ax,PD_ZERO
 jne @F
 mov lHookBUI,PD_OFF
@@:
 mov lCallHookUI,ax
 mov word ptr lpSerialMouseHandler+2,ax
 mov word ptr lpSerialMouseHandler,dx
 jmp end67ier

end6720h:
 cmp ax,0030h
 jne end6730
 cmp bx,PD_ONE
 je noch6730
 cmp bx,PD_ZERO
 jl noch6730
 inc lOSKUICell
 ... lCallstate,bx
 mov lCellState,PD_ZERO
 cmp bx,PD_ONE
 je lSecallr
 call _RestoreCursor
 mov lCellORULX,cx
 mov lCellORULY,dx
 mov ax, 0
 jmp tojmpend67ier
lSecallr:
 mov lCellORLRX,cx
 mov lCellORLRY,dx
 sub cx, lCellORULX
 cmp cx, PD_Cell_OFF_MIN
 jl celloffdbad
 sub dx, lCellORULY
 cmp dx, PD_Cell_OFF_MIN
 jl celloffdbad
 mov ax, 0
 jmp tojmpend67ier
celloffdbad:
 mov ax, 2
 jmp tojmpend67ier
noch6730:
 mov ax, 1
tojmpend67ier:
 jmp end67ier
end6730:

 cmp ax,0031h
 jne end6731
 mov bx,lCellState
 test bx,0002h
 jz @F
 mov cx,lMinXTmp
 mov dx,lMinYTmp
 mov cx,lMaxXTmp
 mov si,cx
 mov bx,lMaxYTmp
 mov di,bx
@@
 jmp end67ier
end6731:
 cmp ax,0032h
 jne end6732
 cmp bx,PD_ONE
 jne @F
 mov bx,lMinXTmp
 mov lMinX,bx
 mov bx,lMaxXTmp
 mov lMaxX,bx
 mov bx,lMinYTmp
 mov lMinY,bx
 mov bx,lMaxYTmp
 mov lMaxY,bx

   mov lHotIconspace, PD_ICON_spACE
   push ax
   push dx
   mov ax, bx
   sub ax, lMinYTmp
   mov dx, 0
   mov bx, PD_HOT_ICON_NUMBER
   div bx
   mov lHotIconWidth, ax
   pop dx
   pop ax

 call _CalcCell
@@:
 jmp end67ier
end6732:

end67ier:
 iret
lpMouseInt67h endp

public _CalcCell
_CalcCell proc near
 push ax
 push bx
 push dx

 cmp lVideoMode,000Eh
 je @F
 mov lMinXTmp,PD_199
 jmp endsetmes
@@:
 cmp lVideoMode,0010h
 je @F
 mov lMinXTmp,PD_349
 jmp endsetmes
@@:
 mov lMinXTmp,PD_479
endsetmes:
 mov ax,PD_10000
 mov bx,PD_639
 mul bx
 mov bx,lMaxX
 sub bx,lMinX
 cmp bx, dx
 jle calcoshdiv0
 div bx
 push ax

 mov ax,PD_10000
 mul lMinXTmp
 mov bx,lMaxY
 sub bx,lMinY
 cmp bx, dx
 jle calcoshdiv01
 div bx
 mov lMaY,ax
 pop bx
 mov lMaX,ax
 clc
 jmp calcoshdivok
calcoshdiv01:
 pop bx
calcoshdiv0:
 stc
calcoshdivok:
 pop dx
 pop bx
 pop ax

 ret
_CalcCell endp

public lpMouseInt0Ch
lpMouseInt0Ch proc far
 push ax
 push bx
 push cx
 push dx
 push es
 push ds
 push si
 push di
 push bp

 mov dx, lComPort
 in al,dx

 push ax

 mov dx, 32
 mov al, 32
 out dx, al

 cmp bSpeaker, 0
 je sp_no_spk_toggle

 inc bSpeakerCount
 cmp bSpeakerCount, PD_SPK_DELAY
 jne sp_no_spk_toggle

 mov al, bport61h
 out 61h, al
 mov bSpeaker, 0
 mov bSpeakerCount, 0

sp_no_spk_toggle:

 pop ax

 cli

 call _AssembleByte
 jncz not_complete_podd_pt
 call _MouseManager
not_complete_podd_pt:

 pop bp
 pop di
 pop si
 pop ds
 pop es
 pop dx
 pop cx
 pop bx
 pop ax

 cli

 iret

lpMouseInt0Ch      endp

_MouseManager proc near

 cmp lMouEmuBusy, 1
 je exitmousemanager

 mov lMouEmuBusy, 1
```

```
mov ax, IXposRawBak
mov IXposRaw, ax
mov ax, IYposRawBak
mov IYposRaw, ax
mov ax, ITouchBak
mov ITouch, ax

neg ax
inc ax
sub X_up_or_not, ax

call _MouseEmulator

cmp X_up_or_not, 1
jne 9comouseemulator
mov ITouch, 0
mov X_up_or_not, 0

cli
call _MouseEmulator

9comouseemulator:
mov iMouEmuBusy, 0

exitmousemanager:
ret

_MouseManager endp

_AssembleByte proc near

cmp InputFlag,1
je char_2nd
cmp InputFlag,2
je char_3rd
cmp InputFlag,3
je char_4th
cmp al,80h
jae over_bad_char
jmp bad_char
over_bad_char:
cmp al,0C0h
jae char_1st

cmp ITouchBak, 0
je not_use_2nd_up

cmp bSpeaker, 0
je up_no_spk_tog
mov al, bport61h
out 61h, al
mov bSpeaker, 0
mov bSpeakerCount, 0
up_no_spk_tog:

mov ITouchBak,0
mov X_up_or_not, 1
mov InputFlag,0
mov ax, PD_ONE
ret
not_use_2nd_up:
mov ax, 0
ret

char_1st:
mov bByte1,al

jmp goodnotlast

char_2nd:
cmp al,128
jae bad_char

mov bByte2,al

jmp goodnotlast

char_3rd
cmp al,32
jae bad_char

mov bByte3,al

jmp goodnotlast

char_4th
cmp al,128
jae bad_char

mov bByte4,al

mov ah bByte1
shr ax,1
and ax,3F80h
or al,bByte2
mov IXposRawBak,ax

mov ah,bByte3
shr ax,1
and ax,3F80h
or al,bByte4
mov IYposRawBak,ax
mov InputFlag,0
mov ITouchBak,PD_DOWN

mov ax,PD_ONE
ret
goodnotlast:
inc InputFlag
mov ax,PD_ZERO
ret
bad_char:
mov InputFlag,0
mov ax,PD_ZERO
ret
_AssembleByte endp

public _spkTone
_spkTone proc near
cli
in al, 61h
mov bport61h, al
or al, 3
out 61h, al
mov bSpeaker, 1
;
sti
ret
_spkTone endp

_MouseEmulator proc near

cmp ITouch,PD_ZERO
jne over_upproproc
jmp upproproc
over_upproproc:

mov ax,IYposRaw
sub ax,IMinY
cmp ax,PD_ZERO
jge @F
xor ax,ax
@@:
mul IMulY
mov bx,PD_10000
div bx
cmp ax, IGraResY
jl @F
mov ax, IGraResY
dec ax
@@:
mov IYpos,ax

mov ax,IXposRaw
sub ax,IMinX
cmp ax,PD_ZERO
jge @F
xor ax,ax
@@:
mul IMulX
mov bx,PD_10000
div bx
cmp ax, IGraResX
jl @F
mov ax, IGraResX
dec ax
@@:
mov IXpos,ax

cmp IDragMode,PD_ON
jne over_predropmode
jmp predropmode
over_predropmode:

cmp ILastTouch,PD_DOWN
jne over_not_h_c_s
jmp not_h_c_s
over_not_h_c_s:

cmp ICalibrate,PD_NONE
je notcalibnotu
mov IDropMode,PD_ON

call _spkTone

ret
notcalibnotu:

mov ax,IMinX
cmp ax,IXposRaw
jle endchkhoticon

mov IDropMode,PD_ON
sub ax,IXposRaw
cmp ax,IHotRightMargin
jl endnothoticon
sub ax,IHotRightMargin
cmp ax,IHotIconLength
jg endnothoticon
mov ax,IYposRaw
sub ax,IMinY
sub ax,IHotTopMargin
cmp ax,0
jl endnothoticon
mov bx,IHotIconWidth
add bx,IHotIconspace
xor dx,dx
div bx
cmp dx,IHotIconWidth
jge endnothoticon
mov IHIdsave,ax
jmp endyeshoticon
endnothoticon:
mov IHIdsave,PD_23679
endyeshoticon:
ret
endchkhoticon:

call _spkTone

cmp IOSKActive,PD_ZERO
je endoskchk
mov ax,IXpos
cmp ax,IOSKULX
jl endoskchk
cmp ax,IOSKLRX
jg endoskchk
mov ax,IYpos
cmp ax,IOSKULY
jl endoskchk
cmp ax,IOSKLRY
jg endoskchk
mov IOSKMode,PD_ON
inc IOSKUICall
jmp afterchk
endoskchk:

not_h_c_s:

mov ax,IHorMax
cmp ax,IXpos
jge @F
mov IXpos,ax
@@:
mov ax,IHorMin

cmp ax,IXpos
jle @F
mov IXpos,ax
@@:
mov ax,IVerMax
cmp ax,IYpos
jge @F
mov IYpos,ax
@@:
mov ax,IVerMin
cmp ax,IYpos
jle @F
mov IYpos,ax
@@:
afterchk:

cmp ILastTouch,PD_ZERO
je over_stilldown
jmp stilldown
over_stilldown:

endchkstch:

cmp ILeftRight,PD_LEFT
jne addright
inc ILeftTouchCount
mov ax, IXpos
mov IXposPSL,ax
mov ax,IYpos
mov IYposPSL,ax
jmp endcountlet
addright:
inc IRightTouchCount
mov ax, IXpos
mov IXposPSR,ax
mov ax,IYpos
mov IYposPSR,ax
endcountlet:

cli
call _RestoreCursor
call _ShowCursor
sti

mov ax,IButtonMoveTrigger
mov bx,0
mov cx,IXpos
sub cx,ILastX
mov dx,IYpos
sub dx,ILastY
sal dx,1
mov si,cx
mov di,dx
mov cx,IXpos
mov dx,IYpos
call _CallHandler

butdownmess:
mov ax,IButtonDownTrigger
mov bx,IButtonDown
mov si,0
mov di,0
mov cx,IXpos
mov dx,IYpos
call _CallHandler

mov IReduceFactor,PD_ONE
jmp updateptrel

downdragpt:
mov IReduceFactor, PD_ZERO
jmp jumprel

stilldown:

cmp IReduceFactor, PD_ZERO
jne downdragpt
mov IReduceFactor, PD_ONE

mov cx,IXpos
sub cx,ILastX
mov dx,IYpos
sub dx,ILastY
sal dx,1
mov si,cx
mov di,dx

cmp IOSKUICall, 0
je not_oskuicall_for_move
cmp cx, 0
jge @F
neg cx
@@:
cmp cx, PD_OSKUICALL_PT_BD_X
jg oskuicall_not_close_down
cmp dx, 0
jge @F
neg dx
@@:
cmp dx, PD_OSKUICALL_PT_BD_Y
jg over_after_update_xy
jmp after_update_xy
over_after_update_xy:

oskuicall_not_close_down:
mov dx, di
mov cx, si

not_oskuicall_for_move:
cmp dx,PD_ZERO
jne notsamepos
jmp samepos
notsamepos:

mov cx,IXpos
mov dx,IYpos
mov ax,IButtonMoveTrigger
mov bx,IButtonDown
call _CallHandler

cli
call _RestoreCursor
call _ShowCursor
sti

samepos:
jmp updateptrel

upproproc:
mov IReduceFactor,0
mov IDropMode,PD_OFF

cmp IHIdsave,PD_NO_HOT_ICON
je endpdgchk
cmp IHIdsave,PD_23679
je @F
mov ax,IMinX
cmp ax,IXposRaw
jl @F
mov ax,IHIdsave
mov IHotIconID,ax
@@:
```

```
mov lHidsave,PD_NO_HOT_ICON
mov lHotReducImut,PD_ZERO
mov lLastTouch,PD_ZERO
ret
endjudgeleft:
cmp lLeftRight,PD_LEFT
je addleftun
inc lRightUnTouchCount
mov ax,lLastX
mov lXposFSR,ax
mov ax,lLastY
mov lYposFSR,ax
jmp endaddun
addleftun:
inc lLeftUnTouchCount
mov ax,lLastX
mov lXposFSL,ax
mov ax,lLastY
mov lYposFSL,ax
endaddun:
mov ax,lButtonUpTrigger
mov bx,8
mov cx,lXpos
mov dx,lYpos
mov si,0
mov di,0
call _CallHandler

cmp lCalibrate,PD_NONE
je @F
call _Calibration
dec lOSKUICab
mov lCalibrate,PD_NONE
jmp updateptrret
@@:

cmp lOSKMode,PD_ON
jne uposkmodeloff
mov ax,lXpos
cmp ax,lOSKULX
jl uposhourhide
cmp ax,lOSKLRX
jg uposhourhide
mov ax,lYpos
cmp ax,lOSKULY
jl uposhourhide
cmp ax,lOSKLRY
jle setuposkmodeopen
uposhourhide:
cli
Call _RestoreCursor
sti
setuposkmodeopen:
mov lOSKMode,PD_OFF
dec lOSKUICab
uposkmodeloff:

updateptrret:
mov ax,lXpos
mov lLastX,ax
mov ax,lYpos
mov lLastY,ax
after_update_xy:

jl4stlet:
mov ax,lTouch
mov lLastTouch,ax

jumpret:
ret
predropmode:
cmp lHidsave,PD_NO_HOT_ICON
je realdrop
mov ax,lMinX
cmp ax,lXposRaw
jge realdrop

mov lHidsave,PD_23170

inc lHotReducImut

cmp lHotReducImut,4
jne realdrop
mov lHotReducImut,PD_ZERO

cmp lWindows,PD_ONE
jne @F

mov ax,lButtonMoveTrigger
mov bx,8
mov cx,lXpos
sub cx,lLastX
mov dx,lYpos
sub dx,lLastY
sal ax,1
mov si,cx
mov di,dx
mov cx,lXpos
mov dx,lYpos

call _CallHandler
jmp updateptrret

@@:
cli
call _RestoreCursor
call _ShowCursor
sti
jmp updateptrret

realdrop:
ret
_MouseEmulator endp

_Calibration proc near

cmp lCalibrate,PD_ZERO
jne notcalbt
mov ax,lXposRaw
mov lMinXTmp,ax
mov ax,lYposRaw
mov lMinYTmp,ax
mov lCalStatus,0000h
jmp retcalb
notcalbt:
cmp lCalibrate,PD_ONE
je over_retcalb
jmp retcalb
over_retcalb:
mov ax,lYposRaw
cmp ax,lMinYTmp
jge @F
mov bx,lMinYTmp
mov lMinYTmp,ax
xchg ax,bx
@@:
mov lMaxYTmp,ax
mov ax,lXposRaw
cmp ax,lMinXTmp
jge @F
mov bx,lMinXTmp
mov lMinXTmp,ax
xchg ax,bx
@@:
mov lMaxXTmp,ax

sub ax,lMinXTmp
mul lCalIORULX
mov bx,lCalIORLRX
sub bx,lCalIORULX
div bx
push ax
mov ax,lMaxYTmp
sub ax,lMinYTmp
mul lCalIORULY
mov bx,lCalIORLRY
sub bx,lCalIORULY
div bx
push ax
mov ax,lMaxXTmp
sub ax,lMinXTmp
mov bx,PD_639
sub bx,lCalIORLRX
mul bx
mov bx,lCalIORLRX
sub bx,lCalIORULX
div bx
push ax
mov ax,lMaxYTmp
sub ax,lMinYTmp
mov bx,PD_479
sub bx,lCalIORLRY
mul bx
mov bx,lCalIORLRY
sub bx,lCalIORULY
div bx
add lMaxYTmp,ax
pop ax
add lMaxXTmp,ax
pop ax
sub lMinYTmp,ax
pop ax
sub lMinXTmp,ax

mov ax,lMaxXTmp
sub ax,lMinXTmp
cmp ax,PD_CXD
jl notrecal
mov ax,lMaxYTmp
sub ax,lMinYTmp
cmp ax,PD_CYD
jl notrecal

mov ax,lMinX
sub ax,lMinXTmp
cmp ax,PD_ZERO
jge @F
mov ax,lMinXTmp
sub ax,lMinX
@@:
cmp ax,PD_CXD
jg notrecal

mov ax,lMinY
sub ax,lMinYTmp
cmp ax,PD_ZERO
jge @F
mov ax,lMinYTmp
sub ax,lMinY
@@:
cmp ax,PD_CYD
jg notrecal

mov lCalStatus,0000h
jmp endcalc
notrecal:
mov lCalStatus,0002h
endcalc:
retcalb:
ret
_Calibration endp

_CallHandler proc near

push di
push si
push bp
push ds
push es

push ax
mov ax,@data
mov ds,ax
pop ax

cmp lOSKUICab,PD_ON
jl mouboos
cmp lHookSUI,PD_OFF
je endmoubcall

call dword ptr lpSendMouseHandler
cli
jmp endmoubcall

mouboos:
cmp lMouse,PD_OFF
je endmoubcall
call dword ptr lpMouseEventHandler
endmoubcall:
pop es
pop ds
pop bp
pop si
pop di
ret
_CallHandler endp

public lpMouseInt33h
lpMouseInt33h proc far
push es
push ds
push si
push di

cmp ax,PD_ZERO
jge over_end33ier
jmp end33ier
over_end33ier:
cmp ax,52
jle over1_end33ier
jmp end33ier
over1_end33ier:

shl ax,PD_ONE
lea di,wCmd33Table
add di,ax
jmp word ptr cs:[di]

func330:
mov lMouse,PD_OFF
mov lCallMask,0

    call _RestoreCursor

mov lCursorFlag,-1

mov lnTxtScrMask,PD_TXT_SCR_MASK
mov lnTxtCurMask,PD_TXT_CUR_MASK

mov lHotspotX,PD_HOT_spOT_X
mov lHotspotY,PD_HOT_spOT_Y

push cx
mov cx,32
xor bx,bx
f330loop:
mov ax,lnGSMaskData[bx]
mov lmScr12Mask[bx],ax
add bx,PD_TWO
loop f330loop
pop cx

push ds
push es
pop ds
call _build_cursor_image
pop ds

mov lRatioHM,8
mov lRatioVM,16

mov lXposFSL,PD_ZERO
mov lYposFSL,PD_ZERO
mov lXposFSL,PD_ZERO
mov lYposFSL,PD_ZERO
mov lXposFSR,PD_ZERO
mov lYposFSR,PD_ZERO
mov lXposFSR,PD_ZERO
mov lYposFSR,PD_ZERO
mov lLeftTouchCount,PD_ZERO
mov lRightTouchCount,PD_ZERO
mov lLeftUnTouchCount,PD_ZERO
mov lRightUnTouchCount,PD_ZERO

call _SetModeData

mov lThreshold,PD_THRESHOLD
cmp si,33
je @F
mov lCrtPage,PD_ZERO
@@:
mov ax,-1
mov bx,2
jmp end33ier

func331:
cmp lCursorFlag,0
je n_c_cur
inc lCursorFlag
call _ShowCursor
n_c_cur:
jmp end33ier

func332:
call _RestoreCursor
dec lCursorFlag
jmp end33ier

func333:
mov bx,lTouch
cmp lLeftRight,PD_LEFT
je @F
shl bx,1
@@:
mov cx,lXpos
mov dx,lYpos
jmp end33ier

func334:
cmp cx,lHorMin
jge @F
mov cx,lHorMin
@@:
cmp cx,lHorMax
jle @F
mov cx,lHorMax
@@:
cmp dx,lVertMin
jge @F
mov dx,lVertMin
@@:
cmp dx,lVertMax
jle @F
mov dx,lVertMax
@@:
mov lXpos,cx
mov lLastX,cx
mov lYpos,dx
mov lLastY,dx

call _RestoreCursor
call _ShowCursor
jmp end33ier

func335:
xor ax,ax
cmp bx,PD_ZERO
jne fbright
mov bx,lLeftTouchCount
mov lLeftTouchCount,0
mov cx,lXposFSL
mov dx,lYposFSL
cmp lLeftRight,PD_LEFT
jne fbright
mov ax,lTouch
jmp endfl
fbright:
```

```
 cmp bx,1
 jne lfcenter
 mov bx,wRightTouchCount
 mov wRightTouchCount,0
 mov cx,wXposFSR
 mov dx,wYposFSR
 cmp wLeftRight,PD_Right
 jne lfcenter
 mov ax,wTouch
 sal ax,1
 jmp endl8
lfcenter:
 xor bx,bx
 xor cx,cx
 xor dx,dx
endl8:
 jmp end33ler

func336:
 xor ax,ax
 cmp bx,0
 jne lfright
 mov bx,wLeftUnTouchCount
 mov wLeftUnTouchCount,0
 mov cx,wXposFSL
 mov dx,wYposFSL
 cmp wLeftRight,PD_LEFT
 jne lfright
 mov ax,wTouch
 jmp endl8
lfright:
 cmp bx,1
 jne lfcenter
 mov bx,wRightUnTouchCount
 mov wRightUnTouchCount,0
 mov cx,wXposFSR
 mov dx,wYposFSR
 cmp wLeftRight,PD_Right
 jne lfcenter
 mov ax,wTouch
 sal ax,1
 jmp endl8
lfcenter:
 xor bx,bx
 xor cx,cx
 xor dx,dx
endl8:
 jmp end33ler

func337:
 mov wHorMin,cx
 mov wHorMax,dx
 cmp dx,cx
 jge @F
 mov wHorMin,dx
 mov wHorMax,cx
@@:
 shr cx, 1
 shr cx, 1
 shr cx, 1
 mov wMinXByte12h, cx
 shr dx, 1
 shr dx, 1
 shr dx, 1
 mov wMaxXByte12h, dx
 jmp end33ler

func338:
 mov wVertMin,cx
 mov wVertMax,dx
 cmp dx,cx
 jge @F
 mov wVertMin,dx
 mov wVertMax,cx
@@:
 jmp end33ler

func339:
 mov wHotspotX,bx
 mov wHotspotY,cx

 mov cx,32
 mov di,dx
 xor bx,bx
f339loop:
 mov ax, word ptr es:[di]
 mov bmSer12Mask[bx], ax
 add di,2
 add bx,2
 loop f339loop

 push ds
 push es
 pop ds
 call _build_cursor_image
 pop ds

 cli
 call _RestoreCursor
 call _ShowCursor
 sti

 jmp end33ler

func3310:
 cmp bx,0
 jne setbrmsr
 mov bmTxtScrMask,cx
 mov bmTxtCurMask,dx
 jmp endfnc10
setbrmsr:
 mov wHardstart,cx
 mov wHardEnd,dx
 mov bx,cx
 mov cx,8
 sal bx,cl
 mov cx,bx
 and dx,00ffh
 or cx,dx
 mov ax,0100h
 int 10h
endfnc10:
 jmp end33ler


func3311:
 cmp wFirstF11,1
 je firstf11c
 mov cx,wXpos
 sub cx,wXMickey11
 mov dx,wYpos
 sub dx,wYMickey11
 sal dx,1
 jmp endf11p
firstf11c:
 mov cx,0
 mov dx,0
 mov wFirstF11,0
endf11p:
 mov ax,wXpos
 mov wXMickey11,ax
 mov ax,wYpos
 mov wYMickey11,ax
 jmp end33ler

func3312:
 mov ax,es
 mov wHookes,PD_ON
 cmp dx,PD_ZERO
 jne @F
 cmp ax,PD_ZERO
 jne @F
 mov wHookes,PD_OFF
@@:
 mov wCallMask,cx
 mov word ptr lpMouseEventHandler+2,ax
 mov word ptr lpMouseEventHandler,dx
 jmp end33ler

func3318:
 mov wRatioHM,cx
 mov wRatioVM,dx
 jmp end33ler

func3319:
 jmp end33ler

func3319:
 cmp dx,0
 je @F
 mov dx,PD_THRESHOLD
@@:
 mov wThreshold,dx
 jmp end33ler

func3320:
 mov wHookes,PD_ON
 mov ax,wCallMask
 mov wCallMask,cx
 mov cx,ax
 push bx
 mov bx,es
 cmp dx,PD_ZERO
 jne @F
 cmp bx,PD_ZERO
 jne @F
 mov wHookes,PD_OFF
@@:
 mov ax,word ptr lpMouseEventHandler+2
 mov word ptr lpMouseEventHandler+2,bx
 mov es,ax
 pop bx
 mov ax,word ptr lpMouseEventHandler
 mov word ptr lpMouseEventHandler,dx
 mov dx,ax
 jmp end33ler

func3321:
 mov bx,PD_STATE_SIZE
 jmp end33ler

func3322:
 push cx
 pushf
 cld
 mov di,dx
 lea si,startaddr
 mov cx,PD_STATE_SIZE
 rep movsb
 popf
 pop cx
 jmp end33ler

func3323:
 push cx
 lea di,startaddr
 mov cx,PD_STATE_SIZE
 mov si,dx
f23copy:
 mov al,es:[si]
 mov [di],al
 inc di
 inc si
 loop f23copy
 pop cx
 jmp end33ler

func3324:
 inc ax
 jmp end33ler

func3325:
 mov ax,0
 jmp end33ler

func3326:
 mov wSensitivityX,bx
 mov wSensitivityY,cx
 mov wThreshold,dx
 jmp end33ler

func3327:
 mov bx,wSensitivityX
 mov cx,wSensitivityY
 mov dx,wThreshold
 jmp end33ler

func3328:
 mov wCrtPage,bx
 jmp end33ler

func3330:
 mov bx,wCrtPage
 jmp end33ler

func3331:
 mov ax,-1
 jmp end33ler

func3332:
 jmp end33ler

func3334:
 mov wLanguage,bx
 jmp end33ler

func3335:
 mov bx,wLanguage
 jmp end33ler

func3336:
 mov bx,PD_MOUSE_VER
 mov cx,PD_MOUSE_TYPE
 jmp end33ler

func3337:
 mov ax,0100h
 jmp end33ler

func3338:
 mov bx,0
 mov cx,wHorMax
 mov dx,wVertMax
 jmp end33ler

func3339:
 cmp wVideoMode,3
 jne @F
 cmp wCursorFlag,PD_ZERO
 jne @F
 mov ax,bmTxtScrMask
 mov bx,bmTxtCurMask
 jmp gm3339
@@:
 mov ax,wHardstart
 mov bx,wHardEnd
gm3339:
 xor cx,cx
 xor dx,dx
 jmp end33ler

func3340:
 cmp cx,1
 jl endf40
 cmp cx,0012h
 jg endf40
 cmp cx,000dh
 jge goodf40
 cmp cx,0007h
 jge endf40
goodf40:
 mov wVideoMode,cx
 call _SetModeData
 mov cx,0
endf40:
 jmp end33ler

func3341:
 cmp cx,0
 jne @F
 mov cx,1
 jmp endf41list
@@:
 inc wMouseVideoList
 cmp wMouseVideoList,7
 jne @F
 mov wMouseVideoList,13
@@:
 cmp wMouseVideoList,20
 jne @F
 mov wMouseVideoList,0
@@:
 mov cx,wMouseVideoList
endf41list:
 mov bx,0
 mov dx,0
 jmp end33ler

func3342:
 mov ax,wCursorFlag
 mov bx,wHotspotX
 mov cx,wHotspotY
 mov dx,PD_PS2
 jmp end33ler

func3347:
 mov wCrtPage,0
 mov ax,-1
 mov wHardstart,0
 mov wHardEnd,7
 jmp end33ler

func3349:
 mov ax,wHorMin
 mov bx,wVertMin
 mov cx,wHorMax
 mov dx,wVertMax
 jmp end33ler

func3366:
 mov ax,PD_FUNC666
 jmp end33ler

end33ler:
 pop di
 pop si
 pop ds
 pop es
 iret

fpMouseInt33h endp

_ShowCursor proc near

 cmp wCursorFlag,PD_ZERO
 je @F
 ret
@@:
 cmp wOSKUICall,PD_ON
 jge notshowcursor
 cmp wWindows,PD_ZERO
 je doeshowcursor
 ret
notshowcursor:
 cmp wCalibrate, PD_NONE
 je doeshowcursor
 ret
doeshowcursor:
 cmp wVideoMode,0012h
 jne showcursor12h
 cli
 call _PositionCursor
 sti
 call _show_12h_cursor
 ret
```

```
showcursor12h:
 push ax
 push bx
 push cx
 push dx
 push es
 push si
 push di

 cmp fVideoMode,0003h
 jle over_showgcur
 jmp showgcur
over_showgcur:

 mov ax,PD_B800H
 mov es,ax
 mov ax,lCrtPage

 cmp fVideoMode,1
 jg showm23

 mov cl,PD_01_PAGE_SIZE
 shl ax,cl
 mov bx,ax

 mov ax, lYpos
 mov cx, lVertcharPixels
 div cl
 and ax, 00ffh

 mov cl,PD_01_LENGTH
 mul cl
 add bx,ax
 mov ax,lXpos
 mov cl,PD_01_SHIFT
 shr ax,cl
 shl ax,1
 add ax,bx
 mov si,ax
 mov lCurRecOffset,ax
 mov ax,es:[si]
 mov lCursorCover,ax
 and ax,lmTxtScrMask
 xor ax,lmTxtCurMask
 mov es:[si],ax
 jmp endshowc
showm23:
 mov cl,PD_23_PAGE_SIZE
 shl ax,cl
 mov bx,ax

 mov ax, lYpos
 mov cx, lVertcharPixels
 div cl
 and ax, 00ffh

 mov cl,PD_23_LENGTH
 mul cl
 add bx,ax
 mov ax,lXpos
 mov cl,PD_23_SHIFT
 shr ax,cl
 shl ax,1
 add ax,bx
 mov si,ax
 mov lCurRecOffset,ax
 mov ax,es:[si]
 mov lCursorCover,ax
 and ax,lmTxtScrMask
 xor ax,lmTxtCurMask
 mov es:[si],ax
 jmp endshowc
showgcur:

 mov ax,lXpos
 sub ax,lHotspotX
 cmp ax,lHorMin
 jge @F
 mov ax,lHorMin
@@:
 mov lCursorX,ax

 mov ax,lYpos
 sub ax,lHotspotY
 cmp ax,lVertMin
 jge @F
 mov ax,lVertMin
@@:
 mov lCursorY,ax

 mov ax,PD_A000H
 mov es,ax

 cmp fVideoMode,0011h
 jne begega

 cmp fVideoMode,0006h
 je @F
 mov ax,lCRTPage
 mul lPagesize
 add ax,PD_A000H
 mov es,ax
 mov ax,lSavePageOff
@@:
 cmp fVideoMode,0005h
 ja @F
 and lCursorX,0fffeh
@@:
 cmp fVideoMode,000Ch
 jne not640320
 mov ax,lXpos
 shr ax,PD_ONE
 sub ax,lHotspotX
 cmp ax,lHorMin
 jge @F
 mov ax,lHorMin
@@:
 mov lCursorX,ax
not640320:

begega:
 mov ax,lCursorY
 mul lBraionX
 mov bx,ax
 mov ax,lCursorX
 mov cl,3
 shr ax,cl
 add ax,bx

 mov si,ax
 mov lCurRecOffset,ax
 mov ax,lCursorX
 and ax,0007h
 mov lBitPosCur,ax
 mov bx,8
 sub bx,ax
 mov lCountBitCur,bx

 mov lRealCurWidth,16
 mov ax,lGraCurdXX
 cmp ax,lCursorX
 jge @F
 mov ax,lOrgResX
 sub ax,lCursorX
 mov lRealCurWidth,ax
@@:

 mov lCursorBytes,1
 mov ax,lCountBitCur
 cmp ax,lRealCurWidth
 jge @F
 add ax,8
 inc lCursorBytes
 cmp ax,lRealCurWidth
 jge @F
 inc lCursorBytes
@@:

 mov lRealCurHeight,16
 mov ax,lGraCurdYY
 cmp ax,lCursorY
 jc @F
 mov ax,lOrgResY
 sub ax,lCursorY
 mov lRealCurHeight,ax
@@:

 call _SaveVGARegister

 mov di,lBitPosCur
 mov dl,bLeftBit12h[di]

 cmp lCursorBytes,1
 ja @F
 mov ax,lCountBitCur
 sub ax,lRealCurWidth
 mov di,ax
 mov al,bRightBit12h[di]
 and al,dl
 mov bBitMask12h,al
 jmp endbit12h
@@:
 mov bBitMask12h,dl

 cmp lCursorBytes,2
 ja @F
 mov ax,lCountBitCur
 add ax,8
 sub ax,lRealCurWidth
 mov di,ax
 mov dl,bRightBit12h[di]
 mov bBitMask12h+1,dl
 jmp endbit12h
@@:
 mov bBitMask12h+1,0ffh

 mov ax,lCountBitCur
 add ax,16
 sub ax,lRealCurWidth
 mov di,ax
 mov dl,bRightBit12h[di]
 mov bBitMask12h+2,dl
endbit12h:


 mov cx,3
 cmp fVideoMode,0012h
 je curvalid
 cmp fVideoMode,0006h
 je over_eodie12h
 jmp eodie12h
over_eodie12h:
 cmp fVideoMode,000Fh
 jne @F
 mov cx,2
@@:
 cmp fVideoMode,0011h
 jne curvalid
 xor cx,cx
curvalid:
 mov cl,0
bitplaneloop:
 push cx

 mov ah,cl
 mov al,4
 mov dx,PD_GRAPH_addR_REG
 out dx,ax

 mov ax,0100h
 shl ax,cl
 mov al,2
 mov dx,PD_SEQUE_addR_REG
 out dx,ax

 mov si,lCurRecOffset
 push si

 mov cx,lCursorBytes
 mov lColumnCount12h,0
columnloop:
 push cx

 mov di,0
 mov bx,lColumnCount12h
 mov ah,bBitMask12h[bx]
 mov dx,PD_GRAPH_addR_REG
 out dx,ax

 mov cx,lRealCurHeight
 mov lRowCount12h,0
byteloop:
 push cx

 mov dl,es:[si]

 mov bCurSave12h[di],dl
 inc di

 mov bx,lRowCount12h
 mov ax,lmScr12Mask[bx]
 cmp lColumnCount12h,0
 jne @F
 mov cx,lBitPosCur
 shr ah,cl
 and dl,ah

 mov ax,lmCur12Mask[bx]
 shr ah,cl
 xor ah,dl
 mov es:[si],ah
 jmp end12hdm
@@:
 mov cx,lCountBitCur
 cmp lColumnCount12h,1
 jne @F
 shl ax,cl
 and dl,ah

 mov ax,lmCur12Mask[bx]
 shl ax,cl
 xor ah,dl

 mov es:[si],ah
 jmp end12hdm
@@:
 add cl,8
 shl ax,cl
 and dl,ah

 mov ax,lmCur12Mask[bx]
 shl ax,cl
 xor ah,dl
 mov es:[si],ah

end12hdm:
 add si,lBraionX

 inc lRowCount12h
 inc lRowCount12h

 pop cx
 dec cx
 cmp cx,0
 jne byteloop


 inc lColumnCount12h
 add si,lColumnCount12h

 pop cx
 pop si
 inc si
 push si
 dec cx
 cmp cx,0
 je over_columnloop
 jmp columnloop
over_columnloop:
 pop si

 pop cx
 dec cx
 cmp fVideoMode,000Fh
 jne @F
 dec cx
@@:
 cmp cx,0
 jl over_bitplaneloop
 jmp bitplaneloop
over_bitplaneloop:

 call _ResVGARegister
 jmp endshowc

eodie12h:

 mov ax,lCursorY
 mov bx,ax
 and bx,0001h
 mov lEvenOddRow,bx
 mov bCurSave12h,bl
 shr ax,1
 mov cx,PD_50
 mul cx
 add ax,2000h
 mov lOddOff450,ax

 mov ax,lCursorY
 inc ax
 shr ax,1
 mov cx,PD_50
 mul cx
 mov lEvenOff450,ax

 mov ax,lCursorX
 mov cl,3
 shr ax,cl
 mov lColNum,ax

 mov lBit1Off450,ax

 mov ax,lColNum
 and ax,0001h
 mov lColNum,ax
 mov bCurSave12h+1,al

 mov ax,PD_B800H
 mov es,ax

 mov cl,3
 mov ax,lCursorBytes
 mov lColumnCount12h,0
bitplanedh:
 push ax
 mov ax,lColNum

 cmp fVideoMode,0006h
 jne @F
 mov ax,PD_ZERO
@@:

 mov cl,0
 shl ax,cl
 mov al,ah
 mov al,4
 mov dx,PD_GRAPH_addR_REG
 out dx,ax

 mov ax,0100h
 shl ax,cl
 mov al,2
 mov dx,PD_SEQUE_addR_REG
 out dx,ax
```

```
 ret
_ResVGARegister endp

_show_12h_cursor proc near
 SaveEntryRegisters
 push bp
 push es
 push ds
 mov bx, offset bEGARegBuff
 SaveEGARegister

 mov ah, 1
 SetEGAWriteReadMode
 SetEGAColorMask

 mov di, PD_CUR_IMAGE_SAVE_BUFF
 mov bx, PD_CUR_IMAGE_PROC_BUFF
 mov si, [CurOffset12h]
 mov dx, [LineSkip12hCur]

 mov ax, PD_A000H
 mov es, ax
 mov ch, byte ptr [CurHeight12h]
 mov cx, [CurWidth12h]
 push es
 pop ds

 mov bp, sp
backup_image_12h:
 mov cx bx
backup_image_12h_line:
 movsb
 mov [bx], al
 inc bx
 loop backup_image_12h_line
 add si, dx
 dec ch
 jnz backup_image_12h

 pop es
 mov ah, 0
 SetEGAWriteReadMode
 mov si, [OffsetIntoANDMask]
 mov bx, [OffsetIntoXORMask]
 mov di, PD_CUR_IMAGE_PROC_BUFF
 mov bp, [CurHeight12h]

Cursor12hLines
 push es
 pop ds
 mov cx, [CurWidth12h]
Cursor12hOneLine
 mov ah, byte ptr es:[di]
 lodsb
 mov ah, al
 not ah
 SetEGABitMask
 mov byte ptr es:[di], 0
 SetEGAColorMask
 mov al, byte ptr es:[bx]
 inc bx
 stosb
 SetEGAColorMask
 loop Cursor12hOneLine

 add si, [CurMaskSkip12h]
 add bx, [CurMaskSkip12h]
 dec bp
 jnz Cursor12hLines

 push ds
 mov ah, 1
 SetEGAWriteReadMode
 mov ah, 0ffh
 SetEGABitMask
 mov si, PD_CUR_IMAGE_PROC_BUFF
 mov di, [CurOffset12h]
 mov dx, [CurHeight12h]
 mov bx, [LineSkip12hCur]
 mov ax, [CurWidth12h]
 mov ax, es
 mov ds, ax
 mov cx ax
Cursor12hWrite
 mov cx ax
 rep movsb
 add di, bx
 dec dx
 jnz Cursor12hWrite

 pop ds
 pop es

 mov bx, offset bEGARegBuff
 RestoreEGARegister
 pop bp
 RestoreEntryRegisters
 ret
_show_12h_cursor endp

_restore_12h_cursor proc near
 SaveEntryRegisters
 mov bx, offset bEGARegBuff
 SaveEGARegister
 mov ah, 1
 SetEGAWriteReadMode
 SetEGAColorMask
 mov si, PD_CUR_IMAGE_SAVE_BUFF
 mov di, [CurOffset12h]
 mov dx, [CurHeight12h]
 mov bx, [LineSkip12hCur]
 mov ax, [CurWidth12h]

 push ds
 push es
 mov ax, PD_A000H
 mov ds, ax
 mov es, ax
 mov ax, cx

restore_12h_loop1:
 mov cx, ax
 rep movsb
 add di, bx
 dec dx
 jnz restore_12h_loop1

 pop es
 pop ds
 mov bx, offset bEGARegBuff
 RestoreEGARegister
 RestoreEntryRegisters
 ret
_restore_12h_cursor endp

_PositionCursor proc near
 push bp
 mov bp, sp
 SaveEntryRegisters

 mov ax,[Xpos
 sub ax,[HotspotX
 mov bx, ax
 mov dx, ax
 and dx, 7
 push dx

 sar ax, 1
 sar ax, 1
 sar ax, 1

 mov cx, ax
 dec cx
 add cx, PD_CURSOR_TOTAL_LEN

 cmp ax, [MinXByte12h]
 jl clipxleft12h

 cmp cx, [MaxXByte12h]
 jg clipxright12h

 push ax
 mov [CurWidth12h], PD_CURSOR_TOTAL_LEN
 xor bx, bx
 push bx
 jmp clipx12hover

clipxleft12h:
 push [MinXByte12h]
 mov dx, [MinXByte12h]
 sub dx, ax
 mov ax, PD_CURSOR_TOTAL_LEN
 sub ax, dx
 mov [CurWidth12h], ax
 push dx
 jmp clipx12hover

clipxright12h:
 sub cx, [MaxXByte12h]
 push ax
 mov dx, PD_CURSOR_TOTAL_LEN
 sub dx, cx
 mov [CurWidth12h], dx
 xor ax, ax
 push ax
clipx12hover

 mov ax,[Ypos
 sub ax,[HotspotY

 mov bx, ax
 add bx, PD_CURSOR_TOTAL_HGT
 dec bx

 cmp ax, [VertMin]
 jl clipytop12h

 mov ax, [VertMax]
 cmp bx, ax
 jg clipybottom12h

 push ax
 mov [CurHeight12h], PD_CURSOR_TOTAL_HGT
 xor ax, ax
 push ax
 jmp clipy12hover

clipytop12h:
 push [VertMin]
 mov dx, [VertMin]
 sub dx, ax
 mov ax, PD_CURSOR_TOTAL_HGT
 sub ax, dx
 mov [CurHeight12h], ax
 push dx
 jmp clipy12hover

clipybottom12h:
 push ax
 sub bx, ax
 mov dx, PD_CURSOR_TOTAL_HGT
 sub dx, bx
 mov [CurHeight12h], dx
 xor ax, ax
 push ax
clipy12hover:

 mov bp, sp
 mov ax, [bp+2]
 mov cx, PD_80
 mul cx
 add ax, [bp+6]
 mov [CurOffset12h], ax

 mov ax, PD_80
 sub ax, [CurWidth12h]
 mov [LineSkip12hCur], ax

 mov ax, PD_CURSOR_TOTAL_LEN
 sub ax, [CurWidth12h]
 mov [CurMaskSkip12h], ax

 lea bx, bCurImageBuffer
 mov ax, PD_CURSOR_TOTAL_LEN *
PD_CURSOR_TOTAL_HGT * 2
 mov cx, [bp+8]
 mul cx
 add bx, ax
 add bx, [bp+4]

 mov ax, [bp+0]
 mov cx, PD_CURSOR_TOTAL_LEN
 mul cx
 add bx, ax
 mov [OffsetIntoANDMask], bx

 add bx, PD_CURSOR_TOTAL_LEN *
PD_CURSOR_TOTAL_HGT
 mov [OffsetIntoXORMask], bx

 add sp, 10
 RestoreEntryRegisters
 pop bp
 ret
_PositionCursor endp

_SetModeData proc near
 mov HorMin,0
 mov VertMin,0
 mov Xpos,PD_HalfP640
 mov LastX,PD_HalfP640
 mov HorMax,PD_639

 mov MinXByte12h, 0
 mov MaxXByte12h, 79

 cmp VideoMode,14
 jg v14_or_higher
 cmp VideoMode, 3
 jg set_lv_0123
 mov ax, VertScrPixels
 dec ax
 mov VertMax, ax
 mov MaxY, ax
 shr ax, 1
 mov Ypos, ax
 mov LastY, ax
 jmp m_v_mode

set_lv_0123:
 mov VertMax,PD_199
 mov MaxY,PD_199
 mov Ypos,PD_HalfP200
 mov LastY,PD_HalfP200
 jmp m_v_mode

v14_or_higher
 cmp VideoMode,16
 je @F
 mov VertMax,PD_349
 mov MaxY,PD_349
 mov Ypos,PD_HalfP350
 mov LastY,PD_HalfP350
 jmp m_v_mode
@@:
 mov VertMax,PD_479
 mov MaxY,PD_479
 mov Ypos,PD_HalfP480
 mov LastY,PD_HalfP480
m_v_mode:
 push ax
 push bx
 push dx
 mov ax,PD_10000
 mul MaxY
 mov bx,MaxY
 sub bx,MinY
 cmp bx, PD_ZERO
 je setmodedata0
 div bx
 mov MaxY,ax

 mov ax,PD_10000
 mov bx,PD_639
 mul bx
 mov bx,MaxX
 sub bx,MinX
 cmp bx, PD_ZERO
 je setmodedata0
 div bx
 mov MaxX,ax
 clc
 jmp setmodedataok
setmodedata0:
 stc
setmodedataok:
 pop dx
 pop bx
 pop ax
 ret
_SetModeData endp

_build_cursor_image proc far
 push bp
 mov bp, sp
 SaveEntryRegisters
 push ds
 push es

 push ds
 pop es
 lea dx, lpCur12Mask

 mov cx, 16
 lea di, bCurImageBuffer
 mov si, dx
 mov bl, 0ffh
build_cur_swap_xor:
 lodsw
 xchg al, ah
 stosw
 mov al, bl
 stosb
 loop build_cur_swap_xor
 mov cx, 16
build_cur_swap_mask:
 lodsw
 xchg al, ah
 stosw
 mov al, 0
 stosb
 loop build_cur_swap_mask

 mov ax, es
 mov ds, ax
 lea si, bCurImageBuffer
 mov cx, 16*2*7
build_cur_image:
 mov dx, 3
 mov bx, di
 clc
build_cur_image_x:
 lodsb
 rcr al, 1
 stosb
 dec dx
 jnz build_cur_image_x
 jnc build_cur_image_zend
 or byte ptr es:[bx], 10000000b
build_cur_image_zend:
 loop build_cur_image

 pop es
 pop ds
 RestoreEntryRegisters
 pop bp
 ret
```

```
_build_cursor_image endp

InstallTSR SEGMENT public 'CODE'
    assume cs:InstallTSR, ds:@code

public MouInstall
MouInstall proc far
  mov ax,@code
  mov ds,ax
  mov wTSRorigPsp,es

  cld
  call checkCommandLine
  jc ins_remove
  call Existcheck
  jc ins_error

  call Interfacecall
  jc  sm_not
  call InstallISR

  mov al,PD_LOAD_OK
  call PrintInstallMsg

  call _build_cursor_image

  call _SetPenspktFreq

  mov dx,InstallTSR
  sub dx wTSRorigPsp
  add dx 3
  mov ax,3100h
  int 21h
ins_remove:
  or  al,al
  jge prn_err
  call RemoveDriver
  jmp prn_err
sm_not:
  mov al,PD_SM_not
  jmp prn_err
ins_error:
  mov al,PD_alREADY_IN
prn_err:
  call PrintInstallMsg
  inc al
  mov ah,4ch
  int 21h
MouInstall endp

checkCommandLine proc near
    push ds
    push es
    push es
    pop ds
    mov es,@data
    mov es,ax

    mov si,0080h
    lodsb
    cbw
    xchg cx,ax
    jcxz dlexpars
dlsearch:
    lodsb
    cmp al,' '
    jb dlexpars
    je dlsearch
    cmp al,'/'
    jne notvalid

    lodsb
    or al,' '
    cmp al,'r'
    je  doinstall
notvalid:
    mov al,PD_CMD_LINE_ERR
    jmp dlerror
doinstall:
    mov al,-1
dlerror:
    stc
    jmp dlreturn
dlexpars:
    clc
dlreturn:
    pop es
    pop ds
    ret
checkCommandLine endp

Existcheck proc near
  push bx
  push cx
  push dx
  push di
  push si
  push ds
  push es

  mov cs,@code
  mov ds,ax
  mov dx,0000h
  mov bx,dx
ai_0:
  mov si,offset bsponsignature
  inc byte ptr [si]
  mov ax,[si]
ai_1:
  mov es,dx
  cmp ax,es:[si]
  je ai_3
ai_2:
  inc dx
  cmp dx,bx
  jb ai_1
  clc
  jmp short ai_ret

ai_3:
  mov cx,PD_SIG_LEN
  mov di,si
  push si
  repe cmpsb
  pop si
  je  ai_4
  jmp ai_4
  jmp ai_2
ai_4:
  mov ax,es
  stc
ai_ret:
  pop es
  pop ds
  pop si
  pop di
  pop dx
  pop cx
  pop bx
  ret
Existcheck endp

Interfacecall proc near
  push bx
  push cx
  push dx
  push di
  push si
  push ds
  push es

  mov ax,360ah
  int 21h
  add bx,PD_SM_sIG_OFF
  mov si,offset sSMsignature
  or  si,bx
  clc
  mov cx,PD_SM_sIG_LEN
  repe cmpsb
  jnz smsignot
  mov ax,PD_SM_INIT
  int 0ah
  mov es,dx
  mov ax,word ptr es:[bx]
  mov MinX,ax
  mov ax,word ptr es:[bx+2]
  mov MinY,ax
  mov ax,word ptr es:[bx+4]
  mov MaxX,ax
  mov ax,word ptr es:[bx+6]
  mov MaxY,ax
  mov ax,word ptr es:[bx+8]
  mov ax,word ptr es:[bx+10]
  mov ax,word ptr es:[bx+12]
  mov ax,word ptr es:[bx+14]
  mov ax,word ptr es:[bx+16]

    mov ax, MaxY
    sub ax, MinY
    mov dx, 0
    mov bx, PD_HOT_ICON_NUMBER
    div bx
    mov StaticonWidth, ax

  mov ax,PD_10000
  mov bx,PD_630
  mul bx
  mov bx,MaxX
  sub bx,MinX
  cmp bx, PD_ZERO
  je  smsignot
  div bx
  mov MulX,ax

  mov ax,PD_10000
  mov bx,PD_100
  mul bx
  mov bx,MaxY
  sub bx,MinY
  cmp bx, PD_ZERO
  je  smsignot
  div bx
  mov MulY,ax
  clc
  jmp smlibsorst
smsignot:
  stc
smlibsorst:
  pop es
  pop ds
  pop si
  pop di
  pop dx
  pop cx
  pop bx
  ret
Interfacecall endp

public InstallISR
InstallISR  proc  near
  push es
  mov si,offset wTSRreplacedVectorTable
  mov cx,PD_TSR_repLACE_NUM
initvec:
  mov al,[si].IntNum
  mov ah,35h
  int 21h
  mov [si].OldISRoffset,bx
  mov [si].OldISRseg,es

  mov dx [si].NewISRoffset
  mov ah,25h
  int 21h

  add si,size strVectorreplace
  loop initvec
  pop es

  mov dx,0021h
  jmp short $+2
  jmp short $+2
  jmp short $+2
  in  al,dx
  and al,0DFh
  mov dx,0021h
  jmp short $+2
  jmp short $+2
  jmp short $+2
  out dx,al

  ret
InstallISR endp

RemoveDriver proc near
  call Existcheck
  jnc notinmem

  mov es,ax

  mov ax,PD_SM_notIFY
  int 0ah

  call DeinstallISR

  push es
  mov es,es:wTSRorigPsp
  mov es,ax
  mov es,es:[2ch]
  mov ah,49h
  int 21h
  pop es

  mov ax,es:wTSRorigPsp
  push es
  mov es,ax
  mov ah,49h
  int 21h
  pop es
  jc  removebad
  mov al,PD_REmovE_MesSAGE
  jmp removeret

removebad:
  mov al,PD_REmovE_ERRor
  jmp removeret

notinmem:
  mov al,PD_not_IN_MEM
removeret:
  ret
RemoveDriver endp

public _SetPenspktFreq
_SetPenspktFreq proc near
  mov al, PD_TIMER2_16BIT_MODE
  cli
  out 43h, al
  jmp short $+2
  mov ax, PD_FREQ_FREQUENCY
  out 42h, al
  jmp short $+2
  mov al, ah
  out 42h, al
  sti
  ret
_SetPenspktFreq endp

public DeinstallISR
DeinstallISR proc near
  push ax
  push ds
  push di
  push si
  push ds

  mov dx,0021h
  jmp short $+2
  jmp short $+2
  jmp short $+2
  in  al,dx
  or  al,20h
  mov dx,0021h
  out dx,al

  mov cx,PD_TSR_repLACE_NUM
  mov si,offset wTSRreplacedVectorTable
dsoloop:
  mov al,es:[si].IntNum
  lds dx,dword ptr es:[si].OldISRoffset
  mov ah,25h
  int 21h
  add si,size strVectorreplace
  loop dsoloop

  pop ds
  pop si
  pop di
  pop ds
  pop ax
  ret
DeinstallISR endp

PrintInstallMsg proc near
  push ax
  push ds

  push cs
  pop ds

  push ax

  mov ax,cs:install_msg_title[2]
  mov dx,cs:install_msg_title[0]
  sub ax,dx
  mov bx,1
  mov ah,40h
  int 21h

  pop ax
  xor bx,bx
  mov bl,al
  shl bx,1
  mov ax,cs:install_msg_index[bx+2]
  mov dx,cs:install_msg_index[bx]
  sub ax,dx
  mov bx,1
  mov ah,40h
  int 21h
  pop ds
  pop ax
  ret
PrintInstallMsg endp

install_msg_title label word
  dw msgtitle
  dw msgtitleend

msgtitle  db 0Dh,0ah,'Saratoga Pen Driver Version '
    db PD_VERsION
    db 0Dh,0ah
    db 'Copyright (C) 1995 Zenith Data Systems
Corp. All rights
reserved.',0Dh,0ah
    db 0Dh,0ah
msgtitleend label byte

install_msg_index label word
  dw msg0, msg1, msg2, msg3
  dw msg4, msg5, msg6
  dw msgend

msg0  db 'Saratoga Pen Driver was already
loaded.',0Dh,0ah
msg1  db 'Saratoga Pen Driver was removed from
memory.',0Dh,0ah
```

```
msg2  db 'Saratoga Pen Driver is not in memory
now.',0Dh,0ah
msg3  db 'Error for attempting remove.',0Dh,0ah
msg4  db 'Unknown command line option.',0Dh,0ah

msg5  db 'Saratoga Pen Driver was successfully
loaded.',0Dh,0ah
msg6  db 'Saratoga Pen Driver was not loaded.
Saratoga Manager
was not detected.',0Dh,0ah
msgend label byte

InstallTSR ends
    end MainInstall
```

```
Copr. 1996 Zenith Data Systems Corp

#include "pcx.h"
#include <stdio.h>
#include <stdlib.h>
#include <conio.h>
#include <io.h>
#include <string.h>
#include <dos.h>
#include <malloc.h>
#include <time.h>

#if defined( _MSC_VER )
#pragma warning( disable : 4704 )
#endif

void sleep( clock_t wait );
void stretch_text( char *Lable );

#define VIDEO 0x10
#ifdef __cplusplus
  extern "C" {
#endif
void Decode16(void);
void Decode256(void);
void DecodeSVGA256(void);
#ifdef __cplusplus
}
#endif


#ifdef __cplusplus
  extern "C" {
#endif
int Margin;
int far *Scratch;
unsigned int BytesPerLine;
unsigned int VideoSeg, VideoOffs;
unsigned int DataLength;
unsigned int ColumnCount;
unsigned int Plane;
unsigned char RepeatCount;
int ScreenWidth;
int LineEnd;
#ifdef __cplusplus
}
#endif

int file_error;
unsigned int WindowEnd, WindowStep, WindowPos;
int BytesPerScanLine;
int StartCol, XMax;
int far *LineBuf;
unsigned int LineBufSeg, LineBufOffs, LineBufIndex;
char WriteWindow;
unsigned int buffer_size;
const num_modes = 11;
union REGS inregs, outregs;
struct SREGS segregs;
FILE *pcx_file;
pathstr pcx_filename;
char *error_str;
int pic_width;
int our_modes[num_modes] = {0x0D, 0x0E, 0x10,
0x12, 0x13, 0x100,
0x101,
                    0x102, 0x103, 0x105, 0x107};


rgb_struct rgb_pal[16];
pcx_header_struct pcx_header;
VESA_info_struct VESA_info;
mode_info_struct mode_info;

typedef rgb_struct cregisters[256];
cregisters rgb256;


void video_off(int vid_status)
{
inregs.h.ah = 0x12;
inregs.h.bl = 0x36;
inregs.h.al = vid_status;
int86(VIDEO, &inregs, &outregs);
}

int detect_VESA(VESA_info_struct *VESA_rec)
{
  inregs.x.ax = 0x4F00;
  segregs.es = FP_SEG(VESA_rec);
  inregs.x.di = FP_OFF(VESA_rec);
  int86x(VIDEO, &inregs, &outregs, &segregs);
  if (outregs.h.ah) return 0;
  return(!strncmp( ( const char far *
)VESA_rec->signature,
"VESA", 4));
}


int detect_VGA(void)
{
inregs.h.ah = 0x1A;
inregs.h.al = 0;
int86(VIDEO, &inregs, &outregs);
return(outregs.h.al != 0x1A);
}


int hardware_supports(unsigned int mode)
{
  unsigned int far *modeptr;

  if (mode >= 0x100) {
    if (detect_VESA(&VESA_info)) {
      modeptr = VESA_info.mode_list_ptr;
      do {
    if (*modeptr++ == mode) return 1;
      } while (*modeptr != 0xFFFF);
    }
    return 0;
  }
  return 1;
}

int we_support(unsigned int mode)
{
  int x;
  int is_there = 0;

  for (x = 0; x < num_modes; x++) {
    if (mode == ( unsigned int )our_modes[x])
is_there = 1; }
  return is_there;
}

int fits(pcx_header_struct header)
{
  return((header.xmax < header.hres) &&
(header.ymax <
header.vres));
}

void try_it(unsigned int mode, unsigned int *m)
{
  if ((hardware_supports(mode)) &&
(we_support(mode)))
    *m = mode;
  return;
}

unsigned int best_mode(pcx_header_struct header)

{
  unsigned int m;

  if (header.num_planes == 1) {
    m = 0x13;
    if ((header.hres > 320) || (!fits(header)))
try_it(0x101,
&m);
    if ((header.hres > 640) || (!fits(header)))
try_it(0x103,
&m);
    if ((header.hres > 800) || (!fits(header)))
try_it(0x105,
&m);
    if ((header.hres > 1024) || (!fits(header)))
try_it(0x107,
&m);
  } else if (header.num_planes == 4) {
    m = (header.hres <= 320) ? 0x0D : 0x0E;
    if ((header.vres > 200) || (!fits(header)))
try_it(0x10, &m);
    if ((header.vres > 350) || (!fits(header)))
try_it(0x12, &m);
    if ((header.vres > 480) || (!fits(header)))
try_it(0x102,
&m);
  } else {
    file_error = 5;
    m = 0xFFFF;
  }
  return m;
}

void get_mode_info(unsigned int mode,
mode_info_struct *m)
{
  inregs.x.ax = 0x4F01;
  inregs.x.cx = mode;
  segregs.es = FP_SEG(m);
  inregs.x.di = FP_OFF(m);
  int86x(VIDEO, &inregs, &outregs, &segregs);
  switch(mode) {
    case 0x100: m->yres = 400; break;
    case 0x101: m->yres = 480; break;
    case 0x102: m->yres = 600; break;
    case 0x103: m->yres = 600; break;
    case 0x105: m->yres = 768; break;
    case 0x107: m->yres = 1024;
  }
  return;
}

int get_mode(void)
{
  int curr_mode;

  if (detect_VESA(&VESA_info)) {
    inregs.x.ax = 0x4F03;
    int86(VIDEO, &inregs, &outregs);
    curr_mode = outregs.x.bx;
    curr_mode &= 0x3FFF;
    if ((hardware_supports(curr_mode) && (curr_mode
>= 0x100))
      return curr_mode;
  }
  inregs.h.ah = 0x0F;
  int86(VIDEO, &inregs, &outregs);
  return outregs.h.al;
}

void set_mode(int mode, int options)
{
  if (mode >= 0x100) {
    if (options & save_mem) mode |= 0x8000;
    inregs.x.ax = 0x4F02;
    inregs.x.bx = mode;
  } else {
    if (options & save_mem) mode |= 0x80;
    inregs.x.ax = mode;
    inregs.h.ah = 0;
  }
  int86(VIDEO, &inregs, &outregs);
  return;
}

void set_window(int step, char window)
{
  inregs.x.ax = 0x4F05;
  inregs.h.bh = 0;
  inregs.h.bl = window;
  inregs.x.dx = step;
  int86(VIDEO, &inregs, &outregs);
}


void set_color_registers(cregisters rgb)
{

  inregs.h.ah = 0x10;
  inregs.h.al = 0x12;
  segregs.es = FP_SEG(rgb);
  inregs.x.dx = FP_OFF(rgb);
  inregs.x.bx = 0;

  inregs.x.cx = 0x40;

  int86x(VIDEO, &inregs, &outregs, &segregs);
  return;
}

void set_palette(unsigned char *palette)
{

  inregs.h.ah = 0x10;
  inregs.h.al = 0x02;


  segregs.es = FP_SEG(palette);
  inregs.x.dx = FP_OFF(palette);
  int86x(VIDEO, &inregs, &outregs, &segregs);
  return;
}

long get_256_palette(FILE *the_file, cregisters
rgb256)

{
  unsigned char palette_flag;
  long palette_start;
  int x;

  palette_start = filelength(fileno(the_file)) - 769;
  fseek(the_file, palette_start, SEEK_SET);
  palette_flag = getc(the_file);
  if ((palette_flag != 12) || (pcx_header.version < 5)
    || (fread(rgb256, 3, 256, the_file) < 256)) {
    file_error = 2;
    return 0;
  }
  for (x = 0; x < 256; x++) {
    rgb256[x].r >>= 2;
    rgb256[x].g >>= 2;
    rgb256[x].b >>= 2;
  }
  return palette_start;
}


FILE *open_file(pathstr pic_file_name, char
*file_mode,
      pcx_header_struct *header)
{
  FILE *f;

  f = fopen(pic_file_name, file_mode);
  if (f != NULL) fread(header, 1, 128, f);
  return f;
}

char *report_error(int error)
{
  switch(error) {
    case 1: return "Could not open file.\n";
    case 2: return "No palette information in file.\n";
    case 3: return "Picture is too wide for requested
video
mode.\n";
    case 4: return "Number of colors in file does not
match
selected mode.\n";
    case 5: return "Unsupported picture format.\n";
    default: return "Undefined error.\n";
    }
}

void get_margin(int screenwd, int *margin, int
*line_end,
              pcx_header_struct header)
{

  *line_end = header.bytes_per_line;
  *margin = screenwd - *line_end;
  if (*margin < 0) file_error = 3;
  return;
}

unsigned int set_buffer_size(void)
{
  unsigned int buf;
  void far *bufptr;

  buf = 64512;
  if ((bufptr = malloc(buf)) == NULL)
  {
    send_error( "\nERROR: Insufficient memory to
display the
requested image.\n" );
    exit(1);
  }
  else
    free(bufptr);

  return buf;
}

long get_first_pix(pcx_header_struct header, int
option,
              int screenwid, int screenht)


{

  long first_pix = 0;
  int picwid, picht;

  picwid = header.xmax - header.xmin + 1;
  if (header.bits_per_plane == 1) picwid /= 8;
  picht = header.ymax - header.ymin;
  if (picht < screenht) {
    if ((option & vcenter))
      first_pix += (long)header.ymin * screenwid;
    else first_pix += (long)(screenht-1-picht) / 2 *
screenwid;
  }
  if (picwid < screenwid) {
    if ((option & hcenter)) first_pix += header.xmin;
    else first_pix += (screenwid - picwid) / 2;
  }
  return first_pix;
  }
```

```
int read_16(FILE *pic_file, unsigned int mode,
unsigned int
options)
{
 TRACE( "NOTICE: Entered read_16\n" );

 typedef unsigned char palette_bytes[3];

 char nOldSequencer;
 unsigned char entry, gun, pcx_code;
 unsigned char pal_regs[17];
 unsigned int screen_height;

 if (pcx_header.num_planes != 4) return 4;
 if (mode == 0x100) {
   get_mode_info(mode, &mode_info);
   ScreenWidth = mode_info.bytes_per_line;
   screen_height = mode_info.ymax;
 } else
 switch(mode) {
   case 0x0D: ScreenWidth = 40; screen_height =
200; break;
   case 0x0E: ScreenWidth = 80; screen_height =
200; break;
   case 0x10: ScreenWidth = 80; screen_height =
350; break;
   case 0x12: ScreenWidth = 80; screen_height =
480; break;
 }
 get_margin(ScreenWidth, &Margin, &LineEnd,
pcx_header);
 if (file_error) return file_error;
 VideoOffs = (unsigned int)
get_first_pix(pcx_header, options,
ScreenWidth, screen_height);
 VideoSeg = 0xA000;

 stretch_text( 0 );

 outpw(0x3C4, 2);
 Plane = 1;
 outp(0x3C5, Plane);


 for (entry = 0; entry < 16; entry++) {
   for (gun = 0; gun < 3; gun++) {
     pcx_code = ((unsigned char
*)&pcx_header.palette[entry])[gun];
     switch (gun) {
     case 0: rgb_pal[entry].r = pcx_code >> 2; break;
     case 1: rgb_pal[entry].g = pcx_code >> 2; break;
     case 2: rgb_pal[entry].b = pcx_code >> 2;
     }
   }
   pal_regs[entry] = entry;
 }
 pal_regs[16] = 0;

 TRACE( "NOTICE: Changing RGB values in color
registers \n" );

 nOldSequencer = inp(0x3C4);
 set_color_registers(rgb_struct *)rgb_pal);
 outp(0x3C4, nOldSequencer);

 nOldSequencer = inp(0x3C4);
 set_palette(pal_regs);
 outp(0x3C4, nOldSequencer);


 BytesPerLine = pcx_header.bytes_per_line;
 RepeatCount = 0;
 ColumnCount = 0;
 buffer_size = set_buffer_size();
 Scratch = (int far*)malloc(buffer_size);
 fseek(pic_file, 128, SEEK_SET);

 do {
   DataLength = fread(Scratch, 1, buffer_size,
pic_file);
   Decode16();
 } while (!feof(pic_file));
 free(Scratch);

 outpw(0x3C5, 0xF);

 stretch_text( 1 );

 return 0;
}


int read_256(FILE *pic_file, unsigned int mode,
unsigned int
options)
```

```
{
 long palette_start, total_read;

 if (pcx_header.num_planes != 1) return 4;
 palette_start = get_256_palette(pic_file, rgb256);
 if (palette_start) return 3;
 ScreenWidth = 320;
 get_margin(ScreenWidth, &Margin, &LineEnd,
pcx_header);
 if (file_error) return file_error;
 fseek(pic_file, 128, SEEK_SET);
 total_read = 128;
 RepeatCount = 0;
 set_color_registers(rgb256);
 VideoOffs = (unsigned int)
get_first_pix(pcx_header, options,
ScreenWidth, 200);
 VideoSeg = 0xA000;
 buffer_size = set_buffer_size();
 Scratch = (int far*)malloc(buffer_size);
 do {
   DataLength = fread(Scratch, 1, buffer_size,
pic_file);
   total_read += DataLength;
   if (total_read > palette_start)
     DataLength -= (unsigned int)(total_read -
palette_start);
   Decode256();
 } while (!feof(pic_file)) && (total_read <
palette_start));
 free(Scratch);
 if (mode);
 return 0;
}


#ifdef registered_version
  #include "svga256.h"
#else

int read_SVGA256(FILE *pic_file, unsigned int
mode, unsigned int
options)
{
 set_mode(3, no_options);
 printf("Support for this video mode is not
available.\n" );
 return 0;
}
#endif



int read_it(char far *pic_file_name, int mode, int
options)
{
 FILE *pcx_file;

 file_error = 0;
 pcx_file = open_file(pic_file_name, "rb",
&pcx_header);
 if (pcx_file == NULL) return 1;
 if ((pcx_header.bits_per_pixel < 8) &&
(pcx_header.num_planes
== 1)) {
   fclose(pcx_file);
   return 5;
 }
 if (mode == auto_set) mode =
best_mode(pcx_header);
 set_mode(mode, options);
 switch(mode) {
   case 0x0D:
   case 0x0E:
   case 0x10:
   case 0x12:
   case 0x102: file_error = read_16(pcx_file, mode,
options);
     break;
   case 0x13: file_error = read_256(pcx_file, mode,
options);
     break;
   case 0x100:
   case 0x101:
   case 0x103:
   case 0x105:
   case 0x107: file_error = read_SVGA256(pcx_file,
mode,
options);
     break;
 }
 if (options & blackout) video_off(0);
 fclose(pcx_file);
 return file_error;
}


void sleep( clock_t wait )
```

```
{
  clock_t goal;
  goal = wait + clock();
  while( goal > clock() );
}

void stretch_text(char fEnable)
{
  inregs.x.ax = 0xa007;

  if ( !fEnable )
    inregs.x.bx = 0x0100;
  else
    inregs.x.bx = 0x0000;

  int86(VIDEO, &inregs, &outregs);
}

#if defined( _DEBUG )
void Trace( char *szOutStr )
{
  inregs.x.ax = SID_FUNCNUM | SID_OUTSTRING;
  inregs.x.si = SID_SIGNO;
  inregs.x.di = SID_DIGNO;
  segregs.ds = SEG( szOutStr );
  inregs.x.dx = OFF( szOutStr );

  int86x( SID_INTNUM, &inregs, &outregs, &segregs
);
}
#endif

#if defined( _MSC_VER )
#pragma warning( default : 4704 )
#endif
Copr. 1995 Zenith Data Systems Corp.


 #include "pcx.h"
 #include <dos.h>
 #include <conio.h>
 #include <ctype.h>
 #include <stdio.h>
 #include <string.h>
 #include <stdlib.h>

 void end_error(char *msg) {
   puts(msg);
   exit(1);
 }

 void main(int argc, char *argv[])
 {
   int pcx_mode = auto_set;
   int start_mode = get_mode();
   int err = 0;
   int n = 0;
   char file_name[80];
   char drive[_MAX_DRIVE];
   char dir[_MAX_DIR];
   char file[_MAX_FNAME];
   char ext[_MAX_EXT];
   VESA_info_struct VESA_inf;


   if (!detect_VGA) end_error("VGA card required.");

   if (argc > 1) {
     strcpy(file_name, argv[1]);
     _splitpath(file_name, drive, dir, file, ext);
     if (*ext == NULL) {
       strcpy(ext, ".PCX");
       _makepath(file_name, drive, dir, file, ext);
     }
     if (argc == 3) {
       sscanf(argv[2], "%x", &n) ;
       if (n) pcx_mode = n;
     }
     if (!(hw_supports(pcx_mode)) && (pcx_mode !=
auto_set))
       end_error("The requested video mode is not
supported by
this program.");
     if (pcx_mode >= 0x100) {
       if (!detect_VESA(&VESA_inf))
      end_error("VESA BIOS extensions not found.
Your video card
may require\n"
        "a program (typically called VESA.COM) to be
loaded so
that\n"
        "Super-VGA images can be displayed without a
special
driver.");
       if (!hardware_supports(pcx_mode))
      end_error("Your card or VESA BIOS does not
support the
requested"
                  " video mode.");
```

```
   }
   err = read_it(file_name, pcx_mode, hcenter |
vcenter |
blackout);
     if(err) printf(report_error[err]);
  }
  else
    end_error("Usage: view filename[.pcx] [mode]");
  return;
}

Copr. 1995 Zenith Data Systems Corp.



IFDEF PASCAL
.MODEL TPASCAL
ELSE
.MODEL LARGE, C
ENDIF

.DATA
      extrn DataLength: word
      extrn Scratch: dword
      extrn Plane: word
      extrn VideoOffs: word
      extrn VideoSeg: word
      extrn Margin: word
      extrn ScreenWidth: word
      extrn LineEnd: word
      extrn RepeatCount: byte
      extrn ColumnCount: word
    extrn BytesPerLine: word
.CODE
    PUBLIC  Decode16
    PUBLIC  Decode256
      LOCALS


Decode16 PROC



push   si
push   di
push   bp


@@startproc:
mov    bp, Plane
mov    di, VideoOffs
mov    ah, byte ptr BytesPerLine
mov    dx, ColumnCount
mov    bx, DataLength
xor    cx, cx
mov    cl, RepeatCount
lds    si, Scratch
mov    es, VideoSeg
add    bx, si
cld
cmp    cl, 0
jne    @@multi_data
jmp short @@getbyte


@@writebyte:
stosb
inc    dl
cmp    dl, ah
je     @@doneline
loop   @@writebyte
jmp short @@getbyte
@@doneline:
shl    bp, 1
cmp    bp, 8
jle    @@setindex
mov    bp, 1
add    di, Margin
mov    dx, ScreenWidth
add    LineEnd, dx
jmp short @@setplane
@@setindex:
sub    di, dx
@@setplane:
push   ax
cli
mov    ax, bp
mov    dx, 3C5h
out    dx, al
sti
pop    ax
xor    dx, dx
loop   @@writebyte


 @@getbyte:
 cmp     si, bx
 je      @@exit
```

```
push    ds
push    si
lds     si, Scratch
pop     es
lodsb
pop     ds
cmp     al, 192
jb      @@one_data
xor     al, 192
mov     cl, al
cmp     si, bx
je      @@exit
@@multi_data:
push    ds
push    si
lds     si, Scratch
pop     es
lodsb
pop     ds
jmp     @@writebyte
@@one_data:
mov     cl, 1
jmp     @@writebyte


@@exit:
mov     Plane, bp
mov     RepeatCount, cl
mov     ColumnCount, dx
mov     VideoOffs, di
pop     bp
pop     di
pop     si
ret

Decode16 ENDP


Decode256 PROC


push    si
push    di
push    bp

les     si, Scratch
mov     bx, DataLength
add     bx, si
mov     es, VideoSeg
mov     di, VideoOffs
xor     cx, cx
mov     cl, RepeatCount
cld
cmp     cl, 0
jne     @@multi_data


@@getbyte:
cmp     di, LineEnd
jb      @@NoLineEnd
add     di, Margin
mov     dx, ScreenWidth
add     LineEnd, dx
@@NoLineEnd:
cmp     si, bx
je      @@exit
push    ds
push    si
lds     si, Scratch
pop     si
lodsb
pop     ds
cmp     al, 192
jb      @@one_data
xor     al, 192
mov     cl, al
cmp     si, bx
je      @@exit
@@multi_data:
push    ds
push    si
lds     si, Scratch
pop     si
lodsb
pop     ds
rep     stosb
jmp     @@getbyte
@@one_data:
stosb
jmp     @@getbyte

@@exit:
mov     VideoOffs, di
mov     RepeatCount, cl
pop     bp
pop     di
pop     si
ret
```

```
Decode256 ENDP

END

Copr. 1995 Zenith Data Systems Corp.
#include <stdio.h>



typedef int         BOOL;

#if defined( TRUE )
  #undef TRUE
#endif

#if defined( FALSE )
  #undef FALSE
#endif

#if defined( FON )
  #undef ON
#endif

#if defined( FOFF )
  #undef OFF
#endif

#if defined( FAR )
  #undef FAR
#endif

#define TRUE        1
#define FALSE       0
#define FON         1
#define FOFF        0

typedef unsigned char       BYTE;

#define FAR         far

#if defined( WORD )
  #undef WORD
#endif

#if defined( DWORD )
  #undef DWORD
#endif
typedef unsigned long       DWORD;

typedef unsigned short      WORD;
typedef unsigned int        UINT;
typedef signed long         LONG;
typedef void *          PVOID;
typedef void FAR *          LPVOID;

#define LOBYTE(w)           ((BYTE)(w))
#define HIBYTE(w)           ((BYTE)(((UINT)(w) >> 8)
& 0xFF))

#if defined( LOWORD )
  #undef LOWORD
#endif
#define LOWORD(l)
((WORD)(DWORD)((LPVOID)(l)))

#if defined( HIWORD )
  #undef HIWORD
#endif

#define HIWORD(l)
((WORD)(((DWORD)((LPVOID)(l)) >> 16)
& 0xFFFF))

#define MAKELONG(low, high)
((LONG)(((WORD)(low)) |
(((DWORD)((WORD)(high))) << 16)))
#define MAKEWORD(low, high) ((WORD)(low) |
((WORD)(high) << 8))

#if defined( OFF )
  #undef OFF
#endif

#define OFF(lp)         (LOWORD( ( DWORD )(
BYTE FAR * )(lp) ))
#define SEG(lp)         (HIWORD( ( DWORD )(
BYTE FAR * )(lp) ))

typedef char pathstr[80];

struct rgb_struct {
  unsigned char r, g, b;
};


struct pcx_header_struct {
  unsigned char signature, version, code,
bpp, per_plane;
  int xmin, ymin, xmax, ymax;
```

```
  int hres, vres;
  rgb_struct palette[16];
  unsigned char reserved, num_planes;
  int bytes_per_line;
  unsigned char other_stuff[60];
};
struct VESA_info_struct {
  unsigned char signature[4];
  int  version;
  int far *oem_ptr;
  unsigned char capabilities[4];
  unsigned int far *mode_list_ptr;
  unsigned char reserved[238];

};

struct mode_info_struct {
  int  attributes;
  unsigned char windowA_attr, windowB_attr;
  unsigned int granule_kb, window_size;
  unsigned int windowA_start, windowB_start;
  int  far *function_ptr;
  unsigned int bytes_per_line;
  unsigned int xres, yres;
  unsigned char other_stuff[234];
};


int read_bitpath(pathstr pic_file_name, int mode, int
options);
FILE *open_file(pathstr pic_file_name, char
*file_mode,
        pcx_header_struct *header);
int get_mode(void);
void set_mode(int mode, int options);
char *report_error(int error);
int os_support(unsigned int mode);
int hardware_support(unsigned int mode);
int detect_VESA(VESA_info_struct *VESA_rec);
int detect_VGA(void);
void end_error(char *msg);


#define no_options 0
#define save_mem   1
#define hcenter    2
#define vcenter    4
#define blackout   8

#define auto_set   0

#define SID_SYSNUM          3
#define SID_FUNCNUM             0x0008
#define SID_OUTSTRING           0x0010
#define SID_SIGN            0x4347
#define SID_OSIG            0x4A4D

#if defined( _DEBUG )
void Trace( char *szOutStr );
#endif

#if !defined( _DEBUG )
#define DEBUG_BREAK _asm nop
#define TRACE( s )  _asm nop
#else
#define DEBUG_BREAK _asm int 3
#define TRACE( s ) Trace( s )
#endif
```

UNITED STATES PATENT AND TRADEMARK OFFICE

CERTIFICATE OF CORRECTION

PATENT NO. : 6,184,344 B1
DATED : February, 6, 2001
INVENTOR(S) : Stephen B.H. Kent et al.

It is certified that error appears in the above-identified patent and that said Letters Patent is hereby corrected as shown below:

This certificate supersedes certificate of correction issued February 5, 2002, the number was erroneously mentioned and should be deleted since no certificate of correction was granted.

Signed and Sealed this

Fifth Day of March, 2002

*Attest:*

JAMES E. ROGAN

*Attesting Officer*

*Director of the United States Patent and Trademark Office*

SEQUENCE LISTING

```
<160> NUMBER OF SEQ ID NOS:  20

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:  peptide
<221> NAME/KEY: SITE
<222> LOCATION: (5)
<223> OTHER INFORMATION: wherein COSH is thioacid

<400> SEQUENCE: 1

Leu Tyr Arg Ala Gly
  1               5


<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:  peptide

<400> SEQUENCE: 2

Cys Arg Ala Glu Tyr Ser
  1               5


<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence:  peptide
<221> NAME/KEY: SITE
<222> LOCATION: (5)
```

-continued

<223> OTHER INFORMATION: wherein COSBn is benzyl thioester

<400> SEQUENCE: 3

```
Leu Tyr Arg Ala Gly
  1               5
```

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: peptide
<221> NAME/KEY: SITE
<222> LOCATION: (5)
<223> OTHER INFORMATION: wherein Gly is modified and represented by Gly-alphaCOS-CH2C(NHAc)CO2H

<400> SEQUENCE: 4

```
Leu Tyr Arg Ala Gly
  1               5
```

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: peptide

<400> SEQUENCE: 5

```
Leu Tyr Arg Ala Gly Cys Arg Ala Glu Tyr Ser
  1               5                  10
```

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: peptide
<221> NAME/KEY: SITE
<222> LOCATION: (5)
<223> OTHER INFORMATION: wherein SCH2COOH is 2-thioacetic acid

<400> SEQUENCE: 6

```
Leu Tyr Arg Ala Gly
  1               5
```

<210> SEQ ID NO 7
<211> LENGTH: 33
<212> TYPE: PRT
<213> ORGANISM: Homo sapiens
<220> FEATURE:
<221> NAME/KEY: SITE
<222> LOCATION: (33)
<223> OTHER INFORMATION: wherein COSH is thioacid
<221> NAME/KEY: SITE
<222> LOCATION: (1)
<223> OTHER INFORMATION: wherein Msc is 2-methyl-sulfonyl-ethyloxy-carbonyl

<400> SEQUENCE: 7

```
Ser Ala Lys Glu Leu Arg Cys Gln Cys Ile Lys Thr Tyr Ser Lys Pro
  1               5                  10                  15

Phe His Pro Lys Phe Ile Lys Glu Leu Arg Val Ile Glu Ser Gly Pro
            20                  25                  30
Ala
```

<210> SEQ ID NO 8
<211> LENGTH: 33

-continued

<212> TYPE: PRT
<213> ORGANISM: Homo sapiens
<220> FEATURE:
<221> NAME/KEY: SITE
<222> LOCATION: (33)
<223> OTHER INFORMATION: wherein COSBn is benzyl thioester

<400> SEQUENCE: 8

Ser Ala Lys Glu Leu Arg Cys Gln Cys Ile Lys Thr Tyr Ser Lys Pro
1 5 10 15

Phe His Pro Lys Phe Ile Lys Glu Leu Arg Val Ile Glu Ser Gly Pro
20 25 30
Ala

<210> SEQ ID NO 9
<211> LENGTH: 39
<212> TYPE: PRT
<213> ORGANISM: Homo sapiens

<400> SEQUENCE: 9

Cys Ala Asn Thr Glu Ile Ile Val Lys Leu Ser Asp Gly Arg Glu Leu
1 5 10 15

Cys Leu Asp Pro Lys Glu Asn Trp Val Gln Arg Val Val Glu Lys Phe
20 25 30

Leu Lys Arg Ala Glu Asn Ser
35

<210> SEQ ID NO 10
<211> LENGTH: 72
<212> TYPE: PRT
<213> ORGANISM: Homo sapiens
<220> FEATURE:
<221> NAME/KEY: SITE
<222> LOCATION: (72)
<223> OTHER INFORMATION: SH4

<400> SEQUENCE: 10

Ser Ala Lys Glu Leu Arg Cys Gln Cys Ile Lys Thr Tyr Ser Lys Pro
1 5 10 15

Phe His Pro Lys Phe Ile Lys Glu Leu Arg Val Ile Glu Ser Gly Pro
20 25 30

Ala Cys Ala Asn Thr Glu Ile Ile Val Lys Leu Ser Asp Gly Arg Glu
35 40 45

Leu Cys Leu Asp Pro Lys Glu Asn Trp Val Gln Arg Val Val Glu Lys
50 55 60

Phe Leu Lys Arg Ala Glu Asn Ser
65 70

<210> SEQ ID NO 11
<211> LENGTH: 40
<212> TYPE: PRT
<213> ORGANISM: Human immunodeficiency virus
<220> FEATURE:
<221> NAME/KEY: SITE
<222> LOCATION: (40)
<223> OTHER INFORMATION: wherein COSNB is 5-thio-2-nitro-benzoic
acid ester

<400> SEQUENCE: 11

Pro Gln Ile Thr Leu Trp Lys Arg Pro Leu Val Thr Ile Arg Ile Gly
1 5 10 15

Gly Gln Leu Lys Glu Ala Leu Leu Asp Thr Gly Ala Asp Asp Thr Val
20 25 30

-continued

Ile Glu Glu Met Asn Leu Pro Gly
35 40

<210> SEQ ID NO 12
<211> LENGTH: 59
<212> TYPE: PRT
<213> ORGANISM: Human immunodeficiency virus
<220> FEATURE:
<221> NAME/KEY: SITE
<222> LOCATION: (27)
<223> OTHER INFORMATION: wherein Xaa is 2-Aminobutyric acid
<221> NAME/KEY: SITE
<222> LOCATION: (55)
<223> OTHER INFORMATION: wherein Xaa is 2-Aminobutyric acid

<400> SEQUENCE: 12

Cys Trp Lys Pro Lys Met Ile Gly Gly Ile Gly Gly Phe Ile Lys Val
1 5 10 15

Arg Gln Tyr Asp Gln Ile Pro Val Glu Ile Xaa Gly His Lys Ala Ile
20 25 30

Gly Thr Val Leu Val Gly Pro Thr Pro Val Asn Ile Ile Gly Arg Asn
35 40 45

Leu Leu Thr Gln Ile Gly Xaa Thr Leu Asn Phe
50 55

<210> SEQ ID NO 13
<211> LENGTH: 40
<212> TYPE: PRT
<213> ORGANISM: Human immunodeficiency virus
<220> FEATURE:
<221> NAME/KEY: SITE
<222> LOCATION: (40)
<223> OTHER INFORMATION: wherein COSBn is ??
<221> NAME/KEY: SITE
<222> LOCATION: (40)
<223> OTHER INFORMATION: wherein COSBn is benzyl thio ester

<400> SEQUENCE: 13

Pro Gln Ile Thr Leu Trp Lys Arg Pro Leu Val Thr Ile Arg Ile Gly
1 5 10 15

Gly Gln Leu Lys Glu Ala Leu Leu Asp Thr Gly Ala Asp Asp Thr Val
20 25 30

Ile Glu Glu Met Asn Leu Pro Gly
35 40

<210> SEQ ID NO 14
<211> LENGTH: 40
<212> TYPE: PRT
<213> ORGANISM: Human immunodeficiency virus
<220> FEATURE:
<221> NAME/KEY: SITE
<222> LOCATION: (40)
<223> OTHER INFORMATION: wherein COSPh is phenyl thioester

<400> SEQUENCE: 14

Pro Gln Ile Thr Leu Trp Lys Arg Pro Leu Val Thr Ile Arg Ile Gly
1 5 10 15

Gly Gln Leu Lys Glu Ala Leu Leu Asp Thr Gly Ala Asp Asp Thr Val
20 25 30

Ile Glu Glu Met Asn Leu Pro Gly
35 40

<210> SEQ ID NO 15
<211> LENGTH: 99
<212> TYPE: PRT

-continued

<213> ORGANISM: Human immunodeficiency virus
<220> FEATURE:
<221> NAME/KEY: SITE
<222> LOCATION: (67)
<223> OTHER INFORMATION: wherein Xaa is amino butyric acid
<221> NAME/KEY: SITE
<222> LOCATION: (95)
<223> OTHER INFORMATION: wherein Xaa is 2-Aminobutyric acid

<400> SEQUENCE: 15

```
Pro Gln Ile Thr Leu Trp Lys Arg Pro Leu Val Thr Ile Arg Ile Gly
  1               5                  10                  15

Gly Gln Leu Lys Glu Ala Leu Leu Asp Thr Gly Ala Asp Asp Thr Val
             20                  25                  30

Ile Glu Glu Met Asn Leu Pro Gly Cys Trp Lys Pro Lys Met Ile Gly
         35                  40                  45

Gly Ile Gly Gly Phe Ile Lys Val Arg Gln Tyr Asp Gln Ile Pro Val
     50                  55                  60

Glu Ile Xaa Gly His Lys Ala Ile Gly Thr Val Leu Val Gly Pro Thr
 65                  70                  75                  80

Pro Val Asn Ile Ile Gly Arg Asn Leu Leu Thr Gln Ile Gly Xaa Thr
                 85                  90                  95

Leu Asn Phe
```

<210> SEQ ID NO 16
<211> LENGTH: 48
<212> TYPE: PRT
<213> ORGANISM: Bacillus amyloliquefaciens
<220> FEATURE:
<221> NAME/KEY: SITE
<222> LOCATION: (48)
<223> OTHER INFORMATION: wherein COSNB is 5-thio-2-nitro benzoic acid ester

<400> SEQUENCE: 16

```
Ala Gln Val Ile Asn Thr Phe Asp Gly Val Ala Asp Tyr Leu Gln Thr
  1               5                  10                  15

Tyr His Lys Leu Pro Asn Asp Tyr Ile Thr Lys Ser Glu Ala Gln Ala
             20                  25                  30

Leu Gly Trp Val Ala Ser Lys Gly Asn Leu Ala Asp Val Ala Pro Gly
         35                  40                  45
```

<210> SEQ ID NO 17
<211> LENGTH: 62
<212> TYPE: PRT
<213> ORGANISM: Bacillus amyloliquefaciens

<400> SEQUENCE: 17

```
Cys Ser Ile Gly Gly Asp Ile Phe Ser Asn Arg Glu Gly Lys Leu Pro
  1               5                  10                  15

Gly Lys Ser Gly Arg Thr Trp Arg Glu Ala Asp Ile Asn Tyr Thr Ser
             20                  25                  30

Gly Phe Arg Asn Ser Asp Arg Ile Leu Tyr Ser Ser Asp Trp Leu Ile
         35                  40                  45

Tyr Lys Thr Thr Asp His Tyr Gln Thr Phe Thr Lys Ile Arg
     50                  55                  60
```

<210> SEQ ID NO 18
<211> LENGTH: 48
<212> TYPE: PRT
<213> ORGANISM: Bacillus amyloliquefaciens
<220> FEATURE:

-continued

```
<221> NAME/KEY: SITE
<222> LOCATION: (48)
<223> OTHER INFORMATION: wherein COSBn is benzyl thio ester

<400> SEQUENCE: 18

Ala Gln Val Ile Asn Thr Phe Asp Gly Val Ala Asp Tyr Leu Gln Thr
  1               5                  10                  15

Tyr His Lys Leu Pro Asn Asp Tyr Ile Thr Lys Ser Glu Ala Gln Ala
             20                  25                  30

Leu Gly Trp Val Ala Ser Lys Gly Asn Leu Ala Asp Val Ala Pro Gly
         35                  40                  45


<210> SEQ ID NO 19
<211> LENGTH: 48
<212> TYPE: PRT
<213> ORGANISM: Bacillus amyloliquefaciens
<220> FEATURE:
<221> NAME/KEY: SITE
<222> LOCATION: (48)
<223> OTHER INFORMATION: wherein COSPh is phenyl thio ester

<400> SEQUENCE: 19

Ala Gln Val Ile Asn Thr Phe Asp Gly Val Ala Asp Tyr Leu Gln Thr
  1               5                  10                  15

Tyr His Lys Leu Pro Asn Asp Tyr Ile Thr Lys Ser Glu Ala Gln Ala
             20                  25                  30

Leu Gly Trp Val Ala Ser Lys Gly Asn Leu Ala Asp Val Ala Pro Gly
         35                  40                  45


<210> SEQ ID NO 20
<211> LENGTH: 110
<212> TYPE: PRT
<213> ORGANISM: Bacillus amyloliquefaciens

<400> SEQUENCE: 20

Ala Gln Val Ile Asn Thr Phe Asp Gly Val Ala Asp Tyr Leu Gln Thr
  1               5                  10                  15

Tyr His Lys Leu Pro Asn Asp Tyr Ile Thr Lys Ser Glu Ala Gln Ala
             20                  25                  30

Leu Gly Trp Val Ala Ser Lys Gly Asn Leu Ala Asp Val Ala Pro Gly
         35                  40                  45

Cys Ser Ile Gly Gly Asp Ile Phe Ser Asn Arg Glu Gly Lys Leu Pro
     50                  55                  60

Gly Lys Ser Gly Arg Thr Trp Arg Glu Ala Asp Ile Asn Tyr Thr Ser
 65                  70                  75                  80

Gly Phe Arg Asn Ser Asp Arg Ile Leu Tyr Ser Ser Asp Trp Leu Ile
                 85                  90                  95

Tyr Lys Thr Thr Asp His Tyr Gln Thr Phe Thr Lys Ile Arg
            100                 105                 110
```